US006897053B1

(12) United States Patent
O'Donnell et al.

(10) Patent No.: US 6,897,053 B1

(45) Date of Patent: May 24, 2005

(54) ENZYMES DERIVED FROM THERMOPHILIC ORGANISMS THAT FUNCTION AS A CHROMOSOMAL REPLICASE, PREPARATION AND USE THEREOF

(75) Inventors: Michael E. O'Donnell, Hastings-on-Hudson, NY (US); Olga Yurieva, New York, NY (US)

(73) Assignee: Rockefeller University, New York, NY (US)

(*) Notice: Subject to any disclaimer, the term of this patent is extended or adjusted under 35 U.S.C. 154(b) by 67 days.

(21) Appl. No.: 09/716,964

(22) Filed: Nov. 21, 2000

Related U.S. Application Data

(63) Continuation-in-part of application No. 09/642,218, filed on Aug. 18, 2000, which is a continuation of application No. 09/057,416, filed on Apr. 8, 1998, now abandoned.

(60) Provisional application No. 60/043,202, filed on Apr. 8, 1997.

(51) Int. Cl.[7] .......................... C12N 9/12; C07H 21/04

(52) U.S. Cl. .......................... 435/194; 435/183; 435/6; 435/320.1; 435/252.3; 536/23.1; 536/23.2; 536/23.7

(58) Field of Search .......................... 536/23.1, 23.2, 536/23.7; 435/194, 320.1, 252.3

(56) References Cited

U.S. PATENT DOCUMENTS 5,192,674 A 3/1993 Oshima et al. ............. 435/194
5,242,818 A 9/1993 Oshima et al. ............. 435/194
5,322,785 A 6/1994 Comb et al. ................ 435/199
5,352,778 A 10/1994 Comb et al. ................ 536/237
5,374,553 A 12/1994 Gelfand et al. .......... 435/252.3
5,413,926 A 5/1995 Oshima et al. ............. 435/194
5,500,363 A 3/1996 Comb et al. ................ 435/194
5,545,552 A 8/1996 Mathur .................... 435/252.3
5,583,026 A 12/1996 O'Donnell .................. 435/194
5,618,711 A 4/1997 Gelfand et al. ............. 435/194
5,624,833 A 4/1997 Gelfand et al. ............. 435/194
5,633,159 A 5/1997 Pearson et al. ............. 435/194
5,736,373 A 4/1998 Hamilton .................... 435/194
5,744,312 A 4/1998 Mamone et al. ............... 435/6
5,789,224 A 8/1998 Gelfand et al. ............. 435/194
5,830,714 A 11/1998 Swaminathan et al. ..... 435/91.2
5,834,285 A 11/1998 Comb et al. ................ 435/194
6,066,483 A 5/2000 Riggs et al. ................ 435/194
6,100,078 A 8/2000 Riggs et al. ................ 435/194
6,238,905 B1 5/2001 McHenry et al. ........ 435/252.3
6,395,526 B1 5/2002 Uemori et al. .............. 435/194

FOREIGN PATENT DOCUMENTS

WO WO 91/09950 7/1991
WO WO 93/15115 8/1993

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*

Rudinger, "Characteristics of the Amino Acids as Components of a Peptide Hormone Sequence," In: Peptide Hormones, Ed. J.A. Parsons. University Park Press, Baltimore, MD, pp. 1–7 (1976).

Ngo et al., "Computational Complexity, Protein Structure Prediction, and the Ilevinthal Paradox," In: The Protein Folding Problem and Tertiary Structure Prediction, Eds. Merz et al., Birkhauser et al., Boston, MA, pp. 491–495 (1994).

Thornton et al., *Current Opinion in Biotechnology* 6(4):367–369 (1995).

Wallace, *FASEB Journal* 7:505–515 (1993).

McHenry et al., *J. Mol. Biol.* 272:178–189 (1997).

Yurieva et al., *J. Biol. Chem.* 272(43):27131–27139 (1997).

Bukhrashvili et al., *Biochimica et Biophysica Acta* 1008:102–107 (1989).

Elie et al., *Biochimica et Biophysica Acta* 951:261–267 (1988).

Pluthero, *Nucleic Acids Research* 21(20):4850–4851 (1993).

Alonso et al., *Nucl. Acids Res.* 18:6771–6777 (1990).

Blinkowa et al., *Nucleic Acids Research* 18:1725–1729 (1990).

Carter et al., *J. Bacteriol* 175:3812–3822 (1993).

Chen et al., *Proc. Natl. Acad. Sci USA* 5211–5215 (1992).

Cullman et al., *Mol. Cell Biol.* 150:4661–4671 (1995).

Dong et al., *J. Biol. Chem.* 11758–11766 (1993).

Flower et al., *Proc. Natl. Acad. Sci. USA* 87:3713–3717 (1990).

Guibus et al., *Cell* 87:297–306 (1996).

Jack et al., *Cell* 55:447–458 (1988).

Kelman et al., *Curr Opin Gen & Dev* 4:185–195 (1994).

Kong et al., *Cell* 69:425–437 (1992).

(Continued)

*Primary Examiner*—Richard Hutson
(74) *Attorney, Agent, or Firm*—Nixon Peabody LLP

(57) ABSTRACT

The present invention relates to an isolated DNA molecule from a thermophilic bacterium which encodes a DNA polymerase III-type enzyme subunit. Also encompassed by the present invention are host cells and expression system including the heterologous DNA molecule of the present invention, as well as isolated replication enzyme subunits encoded by such DNA molecules. Also disclosed is a method of producing a recombinant thermostable DNA polymerase III-type enzyme, or subunit thereof, from a thermophilic bacterium, which is carried out by transforming a host cell with at least one heterologous DNA molecule of the present invention under conditions suitable for expression of the DNA polymerase III-type enzyme, or subunit thereof, and then isolating the DNA polymerase III-type enzyme, or subunit thereof.

6 Claims, 82 Drawing Sheets

OTHER PUBLICATIONS

Kornberg et al., *DNA Replication*, $2^{nd}$ ed. New York: W.H. Freeman com, pp. 165–194 (1992).
Krishna et al., *Cell* 79:1233–1243 (1994).
Kuriyan et al., *J. Mol. Biol.* 234:915–925 (1993).
Larsen et al., *J. Bact.* 176:6842–6851 (1994).
Lee et al., *Proc. Natl. Acad. Sci. USA* 84:2713–2717 (1987).
Maki et al., *J. Biol. Chem.* 263:6570–6578 (1988).
McHenry et al., *J. Biol. Chem.* 257:1657–1663 (1982).
O'Donnell et al., *Mol. Cell Biol.* 3:953–957 (1992).
O'Donnell et al., *Nucl. Acids Res.* 21:1–3 (1993).
Onrust et al., *J. Biol. Chem.* 270:13366–13377 (1995).
Onrust et al., *J. Biol. Chem.* 266:21681–21686 (1991).
Perrino et al., *Biochemistry* 29:5226–5231 (1990).
Studwell–Vaughan, *J. Biol. Chem.* 266:19833–19841 (1991).
Stukenberg et al., *J. Biol. Chem.* 266:11328–11334 (1991).
Tsuchihashi et al., *Proc. Natl. Acad. Sci. USA* 87:2516–2520 (1990).
Tsuchihashi et al., *Gen. & Dev.* 6:511–519 (1992).
Tsuchihashi et al., *J. Biol. Chem.* 264:17790–17795 (1989).
Weiss et al., Cold Spring Harbor Symposia on Quantitative Biology, 52:687–693 (1987).
Yin et al., *Nucl. Acids Res.* 14:6541–6549 (1986).
Yuzhakov et al., *Cell* 86:877–886 (1996).

* cited by examiner

ATP binding

E. coli
MSYQVLARKWRPQTFADVVGQEHVLTALANGLSLGRIHHAYLFSGTRGVGKTSIARLLAK
B. subtilis
MSYQALYRVFRPQRFEDVVGQEHITKTLQNALLQKKFSHAYLFSGPRGTGKTSAAKIFAK
**** * * *** * *******. .* * * . ******  *** ..

E. coli
GLNCETGITATPCGVCDNCREIEQGRFVDLIEIDAASRTKVEDTRDLLDNVQYAPARGRF
B. subtilis
AVNCEHAPVDEPCNECAACKGITNGSISDVIEIDAASNNGVDEIRDIRDKVKFAPSAVTY
.* . * *. * .* *.******* . *.. **. * *..**. .

E. coli
KVYLIDEVHMLSRHSFNALLKTLEEPPEHVKFLLATTDPQKLPVTILSRCLQFHLKALDV
B. subtilis
KVYIIDEVHMLSIGAFNALLKTLEEPPEHCIFILATTEPHKIPLTIISRCQRFDFKRITS
*.**** .************ *.****.*.*.*..* .* * .

FIG. 2

```
TCCGGGGGTG   GGGTTCCCAG   GTAGACCCCG   GCCCCTCCCG   TGAGCCCCTT   TACCCAGGCC   60

GCCACCTCCT   CCAGGGGGGC   CAAGGCGTGC   AAGGAGAGGA   ACGTCCGCAC   CACGCCCTAT   120
                                                                   S.D.
ACTAGCCTT  GTG AGC GCC CTC TAC CGC CGC TTC CGC CCC CTC ACC TTC CAG GAG GTG GTG   180
           met ser ala leu tyr arg arg phe arg pro leu thr phe gln glu val val   (17)

                                                                          CAC
GGG CAG GAG CAC GTG AAG GAG CCC CTC CTC AAG GCC ATC CGG GAG GGG AGG CTC GCC CAG   240
gly gln glu his val lys glu pro leu leu lys ala ile arg glu gly arg leu ala gln   (37)

GCS TAC CTS TTC TCC GGS AC
GCC TAC CTC TTC TCC GGG CCC AGG GGC GTG GGC AAG ACC ACC ACG GCG AGG CTC CTC GCC   300
ala tyr leu phe ser gly pro arg gly val gly lys thr thr thr ala arg leu leu ala   (57)

ATG GCG GTG GGG TGC CAG GGG GAA GAC CCC CCT TGC GGG GTC TGC CCC CAC TGC CAG GCG   360
met ala val gly cys gln gly glu asp pro pro cys gly val cys pro his cys gln ala   (77)

GtG CAG AGG GGC GCC CAC CCG GAC GTG GTG GAC ATT GAC GCC GCC AGC AAC AAC TCC GTG   420
val gln arg gly ala his pro asp val val asp ile asp ala ala ser asn asn ser val   (97)

GAG GAC GTG CGG GAG CTG AGG GAA AGG ATC CAC CTC GCC CCC CTC TCT GCC CCC AGG AAG   480
glu asp val arg glu leu arg glu arg ile his leu ala pro leu ser ala pro arg lys   (117)

                                                                            C
GTC TTC ATC CTG GAC GAG GCC CAC ATG CTC TCC AAA AGC GCC TTC AAC GCC CTC CTC AAG   540
val phe ile leu asp Glu ala his met leu ser lys ser ala phe asn ala leu leu lys   (137)
```

FIG. 4A-1

*TGS CTS CTC CTC GGS GGS CTC GTG*
ACC CTG GAG GAG CCC CCG CCC CAC GTC CTC TTC GTC TTC GCC ACC ACC GAG CCC GAG AGG 600
thr leu glu glu pro pro pro his val leu phe val phe ala thr thr glu pro glu arg (157)

ATG CCC CCC ACC ATC CTC TCC CGC ACC CAG CAC TTC CGC TTC CGC CGC CTC ACG GAG GAG 660
met pro pro thr ile leu ser arg thr gln his phe arg phe arg arg leu thr glu glu (177)

GAG ATC GCC TTT AAG CTC CGG CGC ATC CTG GAG GCC GTG GGG CGG GAG GCG GAG GAG GAG 720
glu ile ala phe lys leu arg arg ile leu glu ala val gly arg glu ala glu glu glu (197)

GCC CTC CTC CTC CTC GCC CGC CTG GCG GAC GGG GCC CTT AGG GAC GCG GAA AGC CTC CTG 780
ala leu leu leu leu ala arg leu ala asp gly ala leu arg asp ala glu ser leu leu (217)

GAG CGC TTC CTC CTC CTG GAA GGC CCC CTC ACC CGG AAG GAG GTG GAG CGC GCC CTA GGC 840
glu arg phe leu leu leu glu gly pro leu thr arg lys glu val glu arg ala leu gly (237)

TCC CCC CCA GGG ACC GGG GTG GCC GAG ATC GCC GCC TCC CTC GCG AGG GGG AAA ACG GCG 900
ser pro pro gly thr gly val ala glu ile ala ala ser leu ala arg gly lys thr ala (257)

GAG GCC CTG GGC CTC GCC CGG CGC CTC TAC GGG GAA GGG TAC GCC CCG AGG AGC CTG GTC 960
glu ala leu gly leu ala arg arg leu tyr gly glu gly tyr ala pro arg ser leu val (277)

TCG GGC CTT TTG GAG GTG TTC CGG GAA GGC CTC TAC GCC GCC TTC GGC CTC GCG GGA ACC 1020
ser gly leu leu glu val phe arg glu gly leu tyr ala ala phe gly leu ala gly thr (297)

CCC CTT CCC GCC CCG CCC CAG GCC CTG ATC GCC GCC ATG ACC GCC CTG GAC GAG GCC ATG 1080
pro leu pro ala pro pro gln ala leu ile ala ala met thr ala leu asp glu ala met (317)

FIG.4A-2

```
GAG CGC CTC GCC CGC CGC TCC GAC GCC TTA AGC CTG GAG GTG GCC CTC CTG GAG GCG GGA  1140
glu arg leu ala arg arg ser asp ala leu ser leu glu val ala leu leu glu ala gly  (337)

AGG GCC CTG GCC GCC GAG GCC CTA CCC CAG CCC ACG GGC GCT CCT TCC CCA GAG GTC GGC  1200
arg ala leu ala ala glu ala leu pro gln pro thr gly ala pro ser pro glu val gly  (357)

CCC AAG CCG GAA AGC CCC CCG ACC CCG GAA CCC CCA AGG CCC GAG GAG GCG CCC GAC CTG  1260
pro lys pro glu ser pro pro thr pro glu pro pro arg pro glu glu ala pro asp leu  (377)

CGG GAG CGG TGG CGG GCC TTC CTC GAG GCC CTC AGG CCC ACC CTA CGG GCC TTC GTG CGG  1320
arg glu arg trp arg ala phe leu glu ala leu arg pro thr leu arg ala phe val arg  (397)

GAG GCC CGC CCG GAG GTC CGG GAA GGC CAG CTC TGC CTC GCT TTC CCC GAG GAC AAG GCC  1380
glu ala arg pro glu val arg glu gly gln leu cys leu ala phe pro glu asp lys ala  (417)

TTC CAC TAC CGC AAG GCC TCG GAA CAG AAG GTG AGG CTC CTC CCC CTG GCC CAG GCC CAT  1440
phe his tyr arg lys ala ser glu gln lys val arg leu leu pro leu ala gln ala his  (437)

                                                frameshift site
TTC GGG GTG GAG GAG GTC GTC CTC GTC CTG GAG GGA GAA AAA AAA AGC CTG AGC CCA AGG  1500
phe gly val glu glu val val leu val leu glu gly glu lys lys ser leu ser pro arg  (457)
```

FIG.4B-1

```
CCC CGC CCG GCC CCA CCT CCT GAA GCG CCC GCA CCC CCG GGC CCT CCC GAG GAG GAG GTA  1560
pro arg pro ala pro pro pro glu ala pro ala pro pro gly pro pro glu glu glu val  (477)

GAG GCG GAG GAA GCG GCG GAG GAG GCC CCG GAG GAG GCC TTG AGG CGG GTG GTC CGC CTC  1620
glu ala glu glu ala ala glu glu ala pro glu glu ala leu arg arg val val arg leu  (497)

CTG GGG GGG CGG GTG CTC TGG GTG CGG CGG CCC AGG ACC CGG GAG GCG CCG GAG GAG GAA  1680
leu gly gly arg val leu trp val arg arg pro arg thr arg glu ala pro glu glu glu  (517)

CCC CTG AGC CAA GAC GAG ATA GGG GGT ACT GGT ATA TAA   TGGGGGCATG   ACGCGGACCAC  1740
pro leu ser gln asp glu ile gly gly thr gly ile  *                                (529)

CGACCTCGGA   CAAGAGACCG   TGGACAACAT   CCTCAAGCGC   CTCCGCCGTA   TTGAGGGCCA  1820

GGTGCGGGGG   CTCCAGAAGA   TGGTGGCCGA   GGGCCGCCCC   TGCGACGAGG   TCCTCACCCA  1880

GATGACCGCC   ACCAAGAAGG   CCATGGAGGC   GGCGGCCACC   CTGATCCTCC   ACGAGTTCCT  1940

GAACGTCTGC   GCCGCCGAGG   TCTCCGAGGG   CAAGGTGAAC   CCCAAGAAGC   CCGAGGAGAT  2000

CGCCACCATG   CTGAAGAACT   TCATCTA                                           2027
```

FIG.4B-2

```
            GTG AGC GCC CTC TAC CGC CGC TTC CGC CCC CTC ACC TTC CAG GAG GTG GTG   51
GGG CAG GAG CAC GTG AAG GAG CCC CTC CTC AAG GCC ATC CGG GAG GGG AGG CTC GCC CAG  111
GCC TAC CTC TTC TCC GGG CCC AGG GGC GTG GGC AAG ACC ACC ACG GCG AGG CTC CTC GCC  171
ATG GCG GTG GGG TGC CAG GGG GAA GAC CCC CCT TGC GGG GTC TGC CCC CAC TGC CAG GCG  231
GtG CAG AGG GGC GCC CAC CCG GAC GTG GTG GAC ATT GAC GCC GCC AGC AAC AAC TCC GTG  291
GAG GAC GTG CGG GAG CTG AGG GAA AGG ATC CAC CTC GCC CCC CTC TCT GCC CCC AGG AAG  351
GTC TTC ATC CTG GAC GAG GCC CAC ATG CTC TCC AAA AGC GCC TTC AAC GCC CTC CTC AAG  411
ACC CTG GAG GAG CCC CCG CCC CAC GTC CTC TTC GTC TTC GCC ACC ACC GAG CCC GAG AGG  471
ATG CCC CCC ACC ATC CTC TCC CGC ACC CAG CAC TTC CGC TTC CGC CGC CTC ACG GAG GAG  531
GAG ATC GCC TTT AAG CTC CGG CGC ATC CTG GAG GCC GTG GGG CGG GAG GCG GAG GAG GAG  591
GCC CTC CTC CTC CTC GCC CGC CTG GCG GAC GGG GCC CTT AGG GAC GCG GAA AGC CTC CTG  651
GAG CGC TTC CTC CTC CTG GAA GGC CCC CTC ACC CGG AAG GAG GTG GAG CGC GCC CTA GGC  711
TCC CCC CCA GGG ACC GGG GTG GCC GAG ATC GCC GCC TCC CTC GCG AGG GGG AAA ACG GCG  771
GAG GCC CTG GGC CTC GCC CGG CGC CTC TAC GGG GAA GGG TAC GCC CCG AGG AGC CTG GTC  831
TCG GGC CTT TTG GAG GTG TTC CGG GAA GGC CTC TAC GCC GCC TTC GGC CTC GCG GGA ACC  891
CCC CTT CCC GCC CCG CCC CAG GCC CTG ATC GCC GCC ATG ACC GCC CTG GAC GAG GCC ATG  951
GAG CGC CTC GCC CGC CGC TCC GAC GCC TTA AGC CTG GAG GTG GCC CTC CTG GAG GCG GGA 1011
AGG GCC CTG GCC GCC GAG GCC CTA CCC CAG CCC ACG GGC GCT CCT TCC CCA GAG GTC GGC 1071
CCC AAG CCG GAA AGC CCC CCG ACC CCG GAA CCC CCA AGG CCC GAG GAG GCG CCC GAC CTG 1131
CGG GAG CGG TGG CGG GCC TTC CTC GAG GCC CTC AGG CCC ACC CTA CGG GCC TTC GTG CGG 1191
GAG GCC CGC CCG GAG GTC CGG GAA GGC CAG CTC TGC CTC GCT TTC CCC GAG GAC AAG GCC 1251
TTC CAC TAC CGC AAG GCC TCG GAA CAG AAG GTG AGG CTC CTC CCC CTG GCC CAG GCC CAT 1311
TTC GGG GTG GAG GAG GTC GTC CTC GTC CTG GAG GGA GAA AAA AAA AGC CTG AGC CCA AGG 1371
CCC CGC CCG GCC CCA CCT CCT GAA GCG CCC GCA CCC CCG GGC CCT CCC GAG GAG GAG GTA 1431
GAG GCG GAG GAA GCG GCG GAG GAG GCC CCG GAG GAG GCC TTG AGG CGG GTG GTC CGC CTC 1491
CTG GGG GGG CGG GTG CTC TGG GTG CGG CGG CCC AGG ACC CGG GAG GCG CCG GAG GAG GAA 1551
            CCC CTG AGC CAA GAC GAG ATA GGG GGT ACT GGT ATA TAA  (1590)
```

FIG.4C

```
Met ser ala leu tyr arg arg phe arg pro leu thr phe gln glu val val gly gln glu  20
his val lys glu pro leu leu lys ala ile arg glu gly arg leu ala gln ala tyr leu  40
phe ser gly pro arg gly val gly lys thr thr thr ala arg leu leu ala met ala val  60
gly cys gln gly glu asp pro pro cys gly val cys pro his cys gln ala val gln arg  80
gly ala his pro asp val val asp ile asp ala ala ser asn asn ser val glu asp val 100
arg glu leu arg glu arg ile his leu ala pro leu ser ala pro arg lys val phe ile 120
leu asp glu ala his met leu ser lys ser ala phe asn ala leu leu lys thr leu glu 140
glu pro pro pro his val leu phe val phe ala thr thr glu pro glu arg met pro pro 160
thr ile leu ser arg thr gln his phe arg phe arg arg leu thr glu glu glu ile ala 180
phe lys leu arg arg ile leu glu ala val gly arg glu ala glu glu glu ala leu leu 200
leu leu ala arg leu ala asp gly ala leu arg asp ala glu ser leu leu glu arg phe 220
leu leu leu glu gly pro leu thr arg lys glu val glu arg ala leu gly ser pro pro 240
gly thr gly val ala glu ile ala ala ser leu ala arg gly lys thr ala glu ala leu 260
gly leu ala arg arg leu tyr gly glu gly tyr ala pro arg ser leu val ser gly leu 280
leu glu val phe arg glu gly leu tyr ala ala phe gly leu ala gly thr pro leu pro 300
ala pro pro gln ala leu ile ala ala met thr ala leu asp glu ala met glu arg leu 320
ala arg arg ser asp ala leu ser leu glu val ala leu leu glu ala gly arg ala leu 340
ala ala glu ala leu pro gln pro thr gly ala pro ser pro glu val gly pro lys pro 360
glu ser pro pro thr pro glu pro pro arg pro glu glu ala pro asp leu arg glu arg 380
trp arg ala phe leu glu ala leu arg pro thr leu arg ala phe val arg glu ala arg 400
pro glu val arg glu gly gln leu cys leu ala phe pro glu asp lys ala phe his tyr 420
arg lys ala ser glu gln lys val arg leu leu pro leu ala gln ala his phe gly val 440
glu glu val val leu val leu glu gly glu lys lys ser leu ser pro arg pro arg pro 460
ala pro pro pro glu ala pro ala pro pro gly pro pro glu glu glu val glu ala glu 480
glu ala ala glu glu ala pro glu glu ala leu arg arg val val arg leu leu gly gly 500
arg val leu trp val arg arg pro arg thr arg glu ala pro glu glu glu pro leu ser 520
gln asp glu ile gly gly thr gly ile                                             529
```

FIG. 4D

```
Met ser ala leu tyr arg arg phe arg pro leu thr phe gln glu val val gly gln glu  20
his val lys glu pro leu leu lys ala ile arg glu gly arg leu ala gln ala tyr leu  40
phe ser gly pro arg gly val gly lys thr thr thr ala arg leu leu ala met ala val  60
gly cys gln gly glu asp pro pro cys gly val cys pro his cys gln ala val gln arg  80
gly ala his pro asp val val asp ile asp ala ala ser asn asn ser val glu asp val 100
arg glu leu arg glu arg ile his leu ala pro leu ser ala pro arg lys val phe ile 120
leu asp glu ala his met leu ser lys ser ala phe asn ala leu leu lys thr leu glu 140
glu pro pro pro his val leu phe val phe ala thr thr glu pro glu arg met pro pro 160
thr ile leu ser arg thr gln his phe arg phe arg arg leu thr glu glu glu ile ala 180
phe lys leu arg arg ile leu glu ala val gly arg glu ala glu glu glu ala leu leu 200
leu leu ala arg leu ala asp gly ala leu arg asp ala glu ser leu leu glu arg phe 220
leu leu leu glu gly pro leu thr arg lys glu val glu arg ala leu gly ser pro pro 240
gly thr gly val ala glu ile ala ala ser leu ala arg gly lys thr ala glu ala leu 260
gly leu ala arg arg leu tyr gly glu gly tyr ala pro arg ser leu val ser gly leu 280
leu glu val phe arg glu gly leu tyr ala ala phe gly leu ala gly thr pro leu pro 300
ala pro pro gln ala leu ile ala ala met thr ala leu asp glu ala met glu arg leu 320
ala arg arg ser asp ala leu ser leu glu val ala leu leu glu ala gly arg ala leu 340
ala ala glu ala leu pro gln pro thr gly ala pro ser pro glu val gly pro lys pro 360
glu ser pro pro thr pro glu pro pro arg pro glu glu ala pro asp leu arg glu arg 380
trp arg ala phe leu glu ala leu arg pro thr leu arg ala phe val arg glu ala arg 400
pro glu val arg glu gly gln leu cys leu ala phe pro glu asp lys ala phe his tyr 420
arg lys ala ser glu gln lys val arg leu leu pro leu ala gln ala his phe gly val 440
glu glu val val leu val leu glu gly glu lys lys lys pro asp pro lys ala pro pro 460
gly pro thr ser                                                                 464
```

FIG.4E

```
Met ser ala leu tyr arg arg phe arg pro leu thr phe gln glu val val gly gln glu  20
his val lys glu pro leu leu lys ala ile arg glu gly arg leu ala gln ala tyr leu  40
phe ser gly pro arg gly val gly lys thr thr thr ala arg leu leu ala met ala val  60
gly cys gln gly glu asp pro pro cys gly val cys pro his cys gln ala val gln arg  80
gly ala his pro asp val val asp ile asp ala ala ser asn asn ser val glu asp val 100
arg glu leu arg glu arg ile his leu ala pro leu ser ala pro arg lys val phe ile 120
leu asp glu ala his met leu ser lys ser ala phe asn ala leu leu lys thr leu glu 140
glu pro pro pro his val leu phe val phe ala thr thr glu pro glu arg met pro pro 160
thr ile leu ser arg thr gln his phe arg phe arg arg leu thr glu glu glu ile ala 180
phe lys leu arg arg ile leu glu ala val gly arg glu ala glu glu glu ala leu leu 200
leu leu ala arg leu ala asp gly ala leu arg asp ala glu ser leu leu glu arg phe 220
leu leu leu glu gly pro leu thr arg lys glu val glu arg ala leu gly ser pro pro 240
gly thr gly val ala glu ile ala ala ser leu ala arg gly lys thr ala glu ala leu 260
gly leu ala arg arg leu tyr gly glu gly tyr ala pro arg ser leu val ser gly leu 280
leu glu val phe arg glu gly leu tyr ala ala phe gly leu ala gly thr pro leu pro 300
ala pro pro gln ala leu ile ala ala met thr ala leu asp glu ala met glu arg leu 320
ala arg arg ser asp ala leu ser leu glu val ala leu leu glu ala gly arg ala leu 340
ala ala glu ala leu pro gln pro thr gly ala pro ser pro glu val gly pro lys pro 360
glu ser pro pro thr pro glu pro pro arg pro glu glu ala pro asp leu arg glu arg 380
trp arg ala phe leu glu ala leu arg pro thr leu arg ala phe val arg glu ala arg 400
pro glu val arg glu gly gln leu cys leu ala phe pro glu asp lys ala phe his tyr 420
arg lys ala ser glu gln lys val arg leu leu pro leu ala gln ala his phe gly val 440
glu glu val val leu val leu glu gly glu lys lys lys ala                          454
```

FIG.4F

```
                                                          ATP site
E.coli    MSYQVLARKWRPQTFADVVGQEHVLTALANGLSLGRIHHAYLFSGTRGVGKTSIARLLAK   60
H.inf.    ............K..........II.......KDN.L....................F..   60
B.sub.    ....A.Y.VF...R.E.......ITKT.Q.A.LQKKFS.......P..T....A.KIF..   60
C.cres.   DA.T.....Y..R..E.LI...AMVRT...AF.T...A..FMLT.V......TT.....R  113
M.gen.    -MH..FYQ.Y..IN.KQTL...SIRKI.V.AINRDKLPNG.I...E..T...TF.KII..   59
T.th.     --VSA.Y.RF..L..QE.......KEP.LKAIRE..LAQ.......P......TT.....M   58

                   Zn++ finger
            *                 *   *   *
E.coli    GLNCET----GITATPCGVCDNCREIEQGRFVDLIEIDAASRTKVEDTRDLLDNVQYAPA  116
H.inf.    ....VH----.V......E.E..KA....N.I..................E.......K.V  116
B.sub.    AV...H----APVDE..NE.AA.KG.TN.SIS.V.......NNG.DEI..IR.K.KF..S  116
C.cres.   A..Y..DTVK.PSVDLTTEGYH..S.IE..HM.VL.L........DEM.E...G.R...V  173
M.gen.    AI..LN----WDQIDV.NS..V.KS.NTNSAI.IV......KNGIN.I.E.VE..FNH.F  115
T.th      AVG.QG------EDP.....PH.QAVQR.AHP.VVD.....NNS...V.E.RERIHL..L  112

E.coli    RGRFKVYLIDEVHMLSRHSFNALLKTLEEPPEHVKFLLATTDPQKLPVTILSRCLQFHLK  176
H.inf.    V..............................Y..........................  176
B.sub.    AVTY...I.......IGA.............CI.I....E.H.I.L..I...QR.DF.  176
C.cres.   EA.Y...I.......TAA............P.A..IF...EIR.V........QR.D.R  233
M.gen.    TFKK...IL..A...TTQ.WGG........S.PY.L.IFT..EFN.I.L......QS.FF.  175
T.th.     SAPR..FIL..A....KSA.............P..L.VF...E.ERM.P.....TQH.RFR  172
```

FIG.5A

```
E.coli   ALDVEQIRHQLEHILNEEHIAHEPRALQLLARAAEGSLRDALSLTDQAIASGDGQ--VST  234
H.inf.   ...ET..SQH.A...TQ.N.PF.DP..VK..K..Q..I..S.........M..R.--.TN  234
B.sub.   RITSQA.VGRMNK.VDA.QLQV.EGS.EII.S..H.GM......L....SFSGDI--LKV  234
C.cres.  RVEPDVLVKHFDR.SAK.GARI.MD..A.I.......V..G...L....VQTERGQT.TS  293
M.gen.   KITSDL.LER.ND.AKK.K.KI.KD..IKI.DLSQ.....G...L..LAI.LIVKKL.LL  235
T.th.    R.TE.E.AFK.RR..EAVGREA.EE..L....L.D.A....E..LERFLLLEGP---LTR  229

E.coli   QAVSAMLGTLDDDQALSLVEAMVEANGERVMALINEAAARGIEWEALLVEMLGLLHRIAM  294
H.inf.   NV..N...L...NYSVDILY.LHQG...LL.RTLQRV.DAAGD.DK..G.CAEK..Q..L  294
B.sub.   EDALLIT.AVSQLYIGK.AKSLHDK.VSDALETL..LLQQ.KDPAK.IED.IFYFRDMLL  294
C.cres.  TV.RD...LA.RS.TIA.Y.HVMAGKTKDALEGFRALWGF.ADPAVVMLDV.DHC.AS.V  353
M.gen.   MLKKHLISLIEMQNL.L.KQFYQ.I                                    260
T.th.    KE.ERA..SPPGTGVAEIAASLARGKTAEALG.ARRLYGE.YAPRS.VSGL.EVFREGLY  289
```

FIG.5B

| | Reading frame | Blue | White |
|---|---|---|---|
| Shifty sequence | 0 | + | |
| | - 1 | + | |
| | - 2 | + | |
| Mutant sequence | 0 | ++ | |
| | - 1 | | + |
| | - 2 | | + |

ATP Agarose Step Column

Alignment of TTH1 with alphas subunits of other organisms.

| | | | |
|---|---|---|---|
| E.coli | DRYFLELIRTGRPDEESYLHAAVELAEARGLPVV | 197 | (ID#72) |
| V.chol. | DHFYLELIRTGRADEESYLHFALDVAEQYDLPVV | 197 | (ID#73) |
| H.inf. | DHFYLALSRTGRPNEERYIQAALKLAERCDLPLV | 197 | (ID#74) |
| R.prow. | DRFYFEIMRHDLPEEQFIENSYIQIASELSIPIV | 195 | (ID#75) |
| H.pyl. | DDFYLEIMRHGILDQRFIDEQVIKMSLETGLKII | 213 | (ID#76) |
| S.sp. | DDYYLEIQDHGSVEDRLVNINLVKIAQELDIKIV | 202 | (ID#77) |
| M.tub. | DNYFLELMDHGLTIERRVRDGLLEIGRALNIPPL | 220 | (ID#78) |
| T.th. | FFIEIQNHGLSEQK | | (ID#61) |

FIG.15A

Alignment of TTH2 with alphas subunits of other organisms.

| | | | |
|---|---|---|---|
| E.coli | NKRRAKNGEPPLDIAAIPLDDKKSFDMLQRSETTAVFQLESRGMKD | 618 | (ID#79) |
| V.chol. | NPRLKKAGKPPVRIEAIPLDDARSFRNLQDAKTTAVFQLESRGMKE | 618 | (ID#80) |
| H.inf. | NVRMVREGKPRVDIAAIPLDDPESFELLKRSETTAVFQLESRGMKD | 618 | (ID#81) |
| R.prow. | CKKLLKEQGIKIDFDDMTFDDKKTYQMLCKGKGVGVFQFESIGMKD | 624 | (ID#82) |
| H.pyl. | LKIIKTQHKISVDFLSLDMDDPKVYKTIQSGDTVGIFQIES-GMFQ | 648 | (ID#83) |
| S.sp. | QERKALQIRARTGSKKLPDDVKKTHKLLEAGDLEGIFQLESQGMKQ | 643 | (ID#84) |
| M.tub. | IDNVRANRGIDLDLESVPLDDKATYELLGRGDTLGVFQLDGGPMRD | 646 | (ID#85) |
| T.th. | RVELDYDALTLDD | | (ID#60) |

FIG.15B

```
ATGGGCCGGGAGCTCCGCTTCGCCCACCTCCACCAGCACA
CCCAGTTCTCCCTCCTGGACGGGGCGGCGAAGCTTTCCGA
CCTCCTCAAGTGGGTCAAGGAGACGACCCCCGAGGACCCC    120
GCCTTGGCCATGACCGACCACGGCAACCTCTTCGGGGCCG
TGGAGTTCTACAAGAAGGCCACCGAAATGGGCATCAAGCC
CATCCTGGGCTACGAGGCCTACGTGGCGGCGGAAAGCCGC    240
TTTGACCGCAAGCGGGGAAAGGGCCTAGACGGGGGCTACT
TTCACCTCACCCTCCTCGCCAAGGACTTCACGGGGTACCA
GAACCTGGTGCGCCTGGCGAGCCGGGCTTACCTGGAGGGG    360
TTTTACGAAAAGCCCCGGATTGACCGGGAGATCCTGCGCG
AGCACGCCGAGGGCCTCATCGCCCTCTCGGGGTGCCTCGG
GGCGGAGATCCCCCAGTTCATCCTCCAGGACCGTCTGGAC    480
CTGGCCGAGGCCCGGCTCAACGAGTACCTCTCCATCTTCA
AGGACCGCTTCTTCATCGAGATCCAGAACCACGGCCTCCC
CGAGCAGAAAAAGGTCAACGAGGTCCTCAAGGAGTTCGCC    600
CGAAAGTACGGCCTGGGGATGGTGGCCACCAACGACGGCC
ATTACGTGAGGAAGGAGGACGCCCGCGCCCACGAGGTCCT
CCTCGCCATCCAGTCCAAGAGCACCCTGGACGACCCCGGG    720
CGCTGGCGCTTCCCCTGCGACGAGTTCTACGTGAAGACCC
CCGAGGAGATGCGGGCCATGTTCCCCGAGGAGGAGTGGGG
GGACGAGCCCTTTGACAACACCGTGGAGATCGCCCGCATG    840
TGCAACGTGGAGCTGCCCATCGGGGACAAGATGGTCTACC
GAATCCCCCGCTTCCCCCTCCCCGAGGGGCGGACCGAGGC
CCAGTACCTCATGGAGCTCACCTTCAAGGGGCTCCTCCGC    960
CGCTACCCGGACCGGATCACCGAGGGCTTCTACCGGGAGG
TCTTCCGCCTTTTGGGGAAGCTTCCCCCCCACGGGGACGG
GGAGGCCTTGGCCGAGGCCTTGGCCCAGGTGGAGCGGGAG    1080
GCTTGGGAGAGGCTCATGAAGAGCCTCCCCCCTTTGGCCG
GGGTCAAGGAGTGGACGGCGGAGGCCATTTTCCACCGGGC
CCTTTACGAGCTTTCCGTGATAGAGCGCATGGGGTTTCCC    1200
GGCTACTTCCTCATCGTCCAGGACTACATCAACTGGGCCC
GGAGAAACGGCGTCTCCGTGGGGCCCGGCAGGGGGAGCGC
CGCCGGGAGCCTGGTGGCCTACGCCGTGGGGATCACCAAC    1320
ATTGACCCCCTCCGCTTCGGCCTCCTCTTTGAGCGCTTCC
TGAACCCGGAGAGGGTCTCCATGCCCGACATTGACACGGA
CTTCTCCGACCGGGAGCGGGACCGGGTGATCCAGTACGTG    1440
CGGGAGCGCTACGGCGAGGACAAGGTGGCCCAGATCGGCA
CCCTGGGAAGCCTCGCCTCCAAGGCCGCCCTCAAGGACGT
GGCCCGGGTCTACGGCATCCCCCACAAGAAGGCGGAGGAA    1560
TTGGCCAAGCTCATCCCGGTGCAGTTCGGGAAGCCCAAGC
CCCTGCAGGAGGCCATCCAGGTGGTGCCGGAGCTTAGGGC
GGAGATGGAGAAGGACCCCAAGGTGCGGGAGGTCCTCGAG    1680
GTGGCCATGCGCCTGGAGGGCCTGAACCGCCACGCCTCCG
TCCACGCCGCCGGGGTGGTGATCGCCGCCGAGCCCCTCAC
GGACCTCGTCCCCCTCATGCGCGACCAGGAAGGGCGGCCC    1800
GTCACCCAGTACGACATGGGGGCGGTGGAGGCCTTGGGGC
TTTTGAAGATGGACTTTTTGGGCCTCCGCACCCTCACCTT
```

FIG. 16A

CCTGGACGAGGTCAAGCGCATCGTCAAGGCGTCCCAGGGG 1920
GTGGAGCTGGACTACGATGCCCTCCCCCTGGACGACCCCA
AGACCTTCGCCCTCCTCTCCCGGGGGAGACCAAGGGGGT
CTTCCAGCTGGAGTCGGGGGGGATGACCGCCACGCTCCGC 2040
GGCCTCAAGCCGCGGCGCTTTGAGGACCTGATCGCCATCC
TCTCCCTCTACCGCCCCGGGCCCATGGAGCACATCCCCAC
CTACATCCGCCGCCACCACGGGCTGGAGCCCGTGAGCTAC 2160
AGCGAGTTTCCCCACGCCGAGAAGTACCTAAAGCCCATCC
TGGACGAGACCTACGGCATCCCCGTCTACCAGGAGCAGAT
CATGCAGATCGCCTCGGCCGTGGCGGGGTACTCCCTGGGC 2280
GAGGCGGACCTCCTGCGGCGGTCCATGGGCAAGAAGAAGG
TGGAGGAGATGAAGTCCCACCGGGAGCGCTTCGTCCAGGG
GGCCAAGGAAAGGGGCGTGCCCGAGGAGGAGGCCAACCGC 2400
CTCTTTGACATGCTGGAGGCCTTCGCCAACTACGGCTTCA
ACAAATCCCACGCTGCCGCCTACAGCCTCCTCTCCTACCA
GACCGCCTACGTGAAGGCCCACTACCCCGTGGAGTTCATG 2520
GCCGCCCTCCTCTCCGTGGAGCGGCACGACTCCGACAAGG
TGGCCGAGTACATCCGCGACGCCCGGGCCATGGGCATAGA
GGTCCTTCCCCCGGACGTCAACCGCTCCGGGTTTGACTTC 2640
CTGGTCCAGGGCCGGCAGATCCTTTTCGGCCTCTCCGCGG
TGAAGAACGTGGGCGAGGCGGCGGCGGAGGCCATTCTCCG
GGAGCGGGAGCGGGGCGGCCCCTACCGGAGCCTCGGCGAC 2760
TTCCTCAAGCGGCTGGACGAGAAGGTGCTCAACAAGCGGA
CCCTGGAGTCCCTCATCAAGGCGGGCGCCCTGGACGGCTT
CGGGGAAAGGGCGCGGCTCCTCGCCTCCCTGGAAGGGCTC 2880
CTCAAGTGGGCGGCCGAGAACCGGGAGAAGGCCCGCTCGG
GCATGATGGGCCTCTTCAGCGAAGTGGAGGAGCCGCCTTT
GGCCGAGGCCGCCCCCCTGGACGAGATCACCCGGCTCCGC 3000
TACGAGAAGGAGGCCCTGGGGATCTACGTCTCCGGCCACC
CCATCTTGCGGTACCCCGGGCTCCGGGAGACGGCCACCTG
CACCCTGGAGGAGCTTCCCCACCTGGCCCGGGACCTGCCG 3120
CCCCGGTCTAGGGTCCTCCTTGCCGGGATGGTGGAGGAGG
TGGTGCGCAAGCCCACAAAGAGCGGCGGGATGATGGCCCG
CTTCGTCCTCTCCGACGAGACGGGGGCGCTTGAGGCGGTG 3240
GCATTCGGCCGGGCCTACGACCAGGTCTCCCCGAGGCTCA
AGGAGGACACCCCCGTGCTCGTCCTCGCCGAGGTGGAGCG
GGAGGAGGGGGGCGTGCGGGTGCTGGCCCAGGCCGTTTGG 3360
ACCTACGAGGAGCTGGAGCAGGTCCCCCGGGCCCTCGAGG
TGGAGGTGGAGGCCTCCCTCCTGGACGACCGGGGGGTGGC
CCACCTGAAAAGCCTCCTGGACGAGCACGCGGGGACCCTC 3480
CCCCTGTACGTCCGGGTCCAGGGCGCCTTCGGCGAGGCCC
TCCTCGCCCTGAGGGAGGTGCGGGTGGGGGAGGAGGCTGT
AGGCGGCCGCGTGGTTCCGGGCCTACCTCCTGCCCGACCG 3600
GGAGGTCCTTCTCCAGGGCGGCCAGGCGGGGGAGGCCCAG
GAGGCGGTGCCCTTCTAGGGGGTGGGCCGTGAGACCTAGC
GCCATCGTTCTCGCCGGGGGCAAGGAGGCCTGGCCCCGAC 3720
CCCTTTTGG

FIG. 16B

MGRELRFAHLHQHTQFSLLDGAPKLSDLLKWVEETTPEDP
ALAMTDHGNLFGAVEFYKKATEMGIKPILGYEAYVAAESR
FDRKRGKGLDGGYFHLTLLAKDFTGYQNLVRLASRAYLEG 120
FYEKPRIDREILREHAEGLIALSGCLGAEIPQFILQDRLD
LAEARLNEYLSIFKDRFFIEIQNHGLPEQKKVNEVLKEFA
RKYGLGMVATNDGHYVRKEDARAHEVLLAIQSKSTLDDPG 240
ALALPCEEFYVKTPEEMRAMFPEEEVGGRSPLTTPWRSPH
VQRGAAIGTRWSTRIPRFPLPEGRTEAQYLMELTFKGLLR
RYPDRITEGFYREVFRLSGKLPPHGDGEALAEALAQVERE 360
AWERLMKSLPPLAGVKEWTAEAIFHRALYELSAIERMGFP
GLLPHRPGLHQLGPEKGVSVGPGRGGAAGSLVAYAVGITN
IDPLRFGLLFERFLNPERVSMPDIDTDFSDRERDRVIQYV 480
RERYGEDKVAQIGTLGSLASKAALKEVARVYGIPRKKAEE
LAKLIPVQFGKPKPLQEAIQVVPELRAEMEKDPKVREVLE
VAMRLEGLNRHASVHAGRGGVFSEPLTDLVPLCATRKGGP 600
YTQYDMGAVEALGLLKMDFLGLRTLTFLDEVKRIVKASQG
VELDYDALPLDDPKTFALLSRGETKGVFQLESGGMTATLR
GLKPRRFEDLIAILSLYRPGPMEHIPTYIRRHHGLEPVSY 720
SEFPHAEKYLKPILDETYGIPVYQEQIMQIASAVAGYSLG
EADLLRRSMGKKKVEEMKSHRERFVQGAKERGVPEEEANR
LFDMLEAFANYGFNKSHAAAYSLLSYQTAYVKAHYPVEFM 840
AALLSVERHDSDKVAEYIRDARAMGIEVLPPDVNRSGFDF
LVQGRQILFGLSAVKNVGEAAAEAILRERERGGPYRSLGD
FLKRLDEKVLNKRTLESLIKAGALDGFGERARLLASLEGL 960
LKWAAENREKARSGMMGLFSEVEEPPLAEAAPLDEITRLR
YEKEALGIYVSGHPILRYPGLRETATCTLEELPHLARDLP
PRSRVLLAGMVEEVVRKPTKSGGMMARFVLSDETGALEAV 1080
AFGRAYDQVSPRLKEDTPVLVLAEVEREEGGVRVLAQAVW
TYQELEQVPRALEVEVEASLPDDRGVAHLKSLLDEHAGTL
PLYVRVQGAFGEALLALREVRVGEEALGALEAAGFPAYLL 1200
PNREVSPRLTGSGGPRGRALSTGLALKTYPIALPGGNEAL
ARPLL

FIG. 16C

```
          Start1           Start2           3'-Exo I
T.th.     VERVVRTLLDGRFLLEEGVGLWEWRYPFPLEGEAVVVLDLETTGLAG------LDEVIEVGLLRLEGG---RRLPF
D.rad.                                PWPQDVVVFDLETTGFSPA-----SAAIVEIGAVRIVGGQIDETLKF
Bac.sub.  HGIKMIYGMEANLVDDGVPIAYNAAHRLLEEETYVVFDVETTGLSAV-----YDTIIELAAVKVKGGE--IIDKF
H.inf.                               MINPNRQIVLDTETTGMNQLGAHYEGHCIIEIGAVELINRR-YTGNNX
E.c.                                 MSTAITRQIVLDTETTGMNQIGAHSEGHKIIEIGAVEVVNRR-LTGNNF
H.pyl.    NLEYLKACGLNFIETSENLITLKNLKTPLKDEVFSFIDLETTGSCPI-----KHEILEIGAVQVKGGE--IINRF

                                                                 3'-Exo II
T.th.     QSLVR-PLPP---AEARSWNLT---GIPREALEEAPSLEEVLEKAYPLRGDATLVIHNAAFDLGFL-RPALEGLG
D.rad.    ETLVR-PTRPDGSMLSIPWQAQRVHGISDEMVRRAPAXKDVLPDFFDFVDGSAVVAHNVSFDGGFM-RAGAERLG
Bac.sub.  EAFAN-PHRP---LSATIIELT---GITDDMLQDAPDVVDVIRDFREWIGDDILVAHNASFDMGFL-NVAYKKLL
H.inf.    HIYIK-PDRP---XDPDAIKVH---GITDEMLADKPEFKEVAQDFLDYINGAELLIHNAPFDVGFM-DYEFRKLN
E.c.      HVYLK-DRLV----DPEAFGVH---GIAVDFLLDKPTFAEVAVEFMDYIRGAELVIHNAAFDIGFM-DYEFSLLK
H.pyl.    ETLVKVKSVP-----DYIAELT---GITYEDTLNAPSAHEALQELRLFLGNSVFVAHNANFDYNFLGRYFVEKLH

                                                        3'-Exo IIIC
T.th.     -----YRLENPVVDSLRLARRGLPGLRRYGLDALSEVLELPRRT--CHRALEDVERTLAVVHEVYYMLT-----SG
D.rad.    ----LSWAPERELCTMQLSRRAFPRERTHNLTVLAERLGLEFAPGGRHRSYGDVQVTAQAYLRLLELLG-----ER
Bac.sub.  E---VEKAKNPVIDTLELGRFLYPEFKNHRLNTLCKKFDIELTQ--HHRAIYDTEATAYLLLKMLKDAA-----EK
H.inf.    -LNVKTDDICLVTDTLQMARQMYPGKRN-NLDALCDRLGIDNSKRTLHGALLDAEILADVYLMMTGGQTNLFDEEE
E.c.      RDIAKTNTFCKVTDSLAVARKMFPGKRN-SLDALCARYEIDNSKRTLHGALLDAQILAEVYLAMTGGQTSMAFAME
H.pyl.    -----CPLLNLKLCTLDLSKRAILSMRY-SLSFLKELLGFGIEV--SHRAYADALASYKLFEICLLNLP--SYIKT
```

ATGGTGGAGCGGGTGGTGCGGACCCTTCTGGACGGGAGGT 40
TCCTCCTGGAGGAGGGGGTGGGGCTTTGGGAGTGGCGCTA
CCCCTTTCCCCTGGAGGGGGAGGCGGTGGTGGTCCTGGAC 120
CTGGAGACCACGGGGCTTGCCGGCCTGGACGAGGTGATTG
AGGTGGGCCTCCTCCGCCTGGAGGGGGGGAGGCGCCTCCC 200
CTTCCAGAGCCTCGTCCGGCCCCTCCCGCCCGCCGAAGCC
CGTTCGTGGAACCTCACCGGCATCCCCCGGGAGGCCCTGG 280
AGGAGGCCCCCTCCCTGGAGGAGGTTCTGGAGAAGGCCTA
CCCCCTCCGCGGCGACGCCACCTTGGTGATCCACAACGCC 360
GCCTTTGACCTGGGCTTCCTCCGCCCGGCCTTGGAGGGCC
TGGGCTACCGCCTGGAAAACCCCGTGGTGGACTCCCTGCG 440
CTTGGCCAGACGGGGCTTACCAGGCCTTAGGCGCTACGGC
CTGGACGCCCTCTCCGAGGTCCTGGAGCTTCCCCGAAGGA 520
CCTGCCACCGGGCCCTCGAGGACGTGGAGCGCACCCTCGC
CGTGGTGCACGAGGTATACTATATGCTTACGTCCGGCCGT 600
CCCCGCACGCTTTGGGAACTCGGGAGGTAG

MVERVVRTLLDGRFLLEEGVGLWEWRYPFPLEGEAVVVLD 40
LETTGLAGLDEVIEVGLLRLEGGRRLPFQSLVRPLPPAEA
RSWNLTGIPREALEEAPSLEEVLEKAYPLRGDATLVIHNA 120
AFDLGFLRPALEGLGYRLENPVVDSLRLARRGLPGLRRYG
LDALSEVLELPRRTCHRALEDVERTLAVVHEVYYMLTSGR 200
PRTLWELGRZ

FIG.18B

Alignment of dnaA genes.

```
P.mar.          MLEASWEK VQSSL--KQNLSK-- -----------PSYE TWIRPTEFSG--FKN GELTLIAPNSFSSAW LKNNYSQTIQETAE-  65
Syn.sp.       MVSCENLWQQ ALAIL--ATQLTK-- -----------PAFD TWIKASVLIS--LGD GVATIQVENGFVLNH LQKSYGPLLMEVLT-  67
B.sut.        MENILDLWNQ ALAQI--EKKLSK-- -----------PSFE TWMKSTKAHS--LQG DTLTITAPNEFARDW LESRYLHLIADTIY-  67
M.tub.  MTDDPGSGFTTVWNA VVSELNGDPKVDDGP SSDANLSAPLTPQQR AWLNLVQPLT--IVE GFALLSVPSSFVQNE IERHLRAPITDALS-  87
T.th.          MSHEAVWQH VLEHI--RRSITE-- -----------VEFH TWFERIRPLG--IRD GVLELAVPTSFALDW IRRHYAGLIQEGPR-  66
E.coli          MSLSLWQQ CLARL--QDELPA-- -----------TEFS MWIRPLQAE---LSD NTLALYAPNRFVLDW VRDKYLNNINGLLT-  64
T.mar.              MKER ILQEI--KTRVNR-- -----------KSWE LWFSSFDVKS--IEG NKVVFSVGNLFIKEW LEKKYYSVLSKAVK-  61
H.pyl.        MDTNNNIEKE ILALVKQNPKVSL-- -----------IEYE NYFSQLKYNPNASKS DIAFFYAPNQVLCTT ITAKYGALLKEILSQ  72

P.mar.  EIFG---EPVTVHVK VKANAESSDEHYSSA P-------------- ---ITPPLEASPGSV DSSGSSLRLSK---- -KTLPLLNLRYVFNR  130
Syn.sp. DLTG---QEITVKLI TDGLEPHS---LIGQ E-------------- ---SSLPMETTP--- --------------- -KNATALNGKYTFSR  115
B.sut.  ELTG---EELSIKFV IPQNQDVEDFMPKPQ VKKAVKEDTSDFPQN --------------- --------------- -----MLNPKYTFDT  119
M.tub.  RRLGH-QIQLGVRIA PPATDEADDTTVPPS ENPATTSPDTTTDND EIDDSAAARGDNQHS WPSYFTERPHNTDSA TAGVTSLNRRYTFDT  176
T.th.   LLGAQ-APRFELRVV PGVVVQEDIFQPPPS PPAQAQP-------- --------------- --------------- ---------EDTFKT  108
E.coli  SFCGADAPQLRFEVG TKPVTQTPQAAVTSN VAAPAQVAQTQPQRA APSTRSGWDNVPAPA EP------------- -TYRSNVNVKHTFDN  140
T.mar.  VVLG---NDATFEIT YEAFEPHSSYSEPLV KKRAVLLTP------ --------------- --------------- ------LNPDYTFEN  106
H.pyl.  NKVG-MHLAHSVDVR IEVAPKIQINAQSNI NYKAIKTS------- --------------- --------------- ------VKDSYTFEN  118

P.mar.  FVVGPNSRMAHAAAM AVAESPGREFNPLFI CGGVGLGKTHLMQAI GHYRLEIDPGAKVSY VSTETFTNDLIL--A IRQDRMQAFRDRYR-  217
Syn.sp. FVVGPTNRMAHAASL AVAESPGREFNPLFL CGGVGLGKTHLMQAI AHYRLEMYPNAKVYY VSTERFTNDLIT--A IRQDNMEDFRSYYR-  202
B.sut.  FVIGSGNRFAHAASL AVAEAPAKAYNPLFI YGGVGLGKTHLMHAI GHYVIDHNPSAKVVY LSSEKFTNEFIN--S IRDNKAVDFRNRYR-  206
M.tub.  FVIGASNRFAHAAAL AIAEAPARAYNPLFI WGESGLGKTHLLHAA GNYAQRLFPGMRVKY VSTEEFTNDFIN--S LRDDRKVAFKRSYR-  263
T.th.   SWWGPTTPWPHGGAV AVAESPGRAYNPLFI YGGRGLGKTYLMHAV GPLRAKRFPHMRLEY VSTETFTNELINRPS AR-DRMTEFRERYR-  196
E.coli  FVEGKSNQLARAAAR QVADNPGGAYNPLFL YGGTGLGKTHLLHAV GNGIMARKPNAKVVY MHSERFVQDMVK--A LQNNAIEEFKRYYR-  227
T.mar.  FVVGPGNSFAYHAAL EVAKHPGR-YNPLFI YGGVGLGKTHLLQSI GNYVVQNEPDLRVMY ITSEKFLNDLVD--S MKEGKLNEFREKYRK  193
H.pyl.  FVVGSCNNTVYEIAK KVAQSDTPPYNPVLF YGGTGLGKTHILNAI GNHALEK--HKKVVL VTSEDFLTDFLK--H LDNKTMDSFKAKYR-  203
```

FIG.19A

```
P.mar.   AADLILVDDIQFIEG KEYTQEEFFHTFNAL HDAGSQIVLASDRPP SQIPRLQERLMSRFS MGLIADVQAPDLETR MAILQKKAEHERVGL  307
Syn.sp.  SADFLLIDDIQFIKG KEYTQEEFFHTFNSL HEAGKQVVVASDRAP QRIPGLQDRLISRFS MGLIADIQVPDLETR MAILQKKAEYDRIRL  292
B.sut.   NVDVLLIDDIQFLAG KEQTQEEFFHTFNTL HEESKQIVISSDRPP KEIPTLEDRLRSRFE WGLITDITPPDLETR IAILRKKAKAEGLDI  296
M.tub.   DVDVLLVDDIQFIEG KEGIQEEFFHTFNTL HNANKQIVISSDRPP KQLATLEDRLRTRFE WGLITDVQPPELETR IAILRKKAQMERLAV  353
T.th.    SVDLLLVDDVQFIAG KERTQEEFFHTFNAL YEAHKQIILSSDRPP KDILTLEARLRSRFE WGLITDNPAPDLETR IAILKMNAS-SGPED  285
E.coli   SVDALLIDDIQFFAN KERSQEEFFHTFNAL LEGNQQIILTSDRYP KEINGVEDRLKSRFG WGLTVAIEPPELETR VAILMKKADENDIRL  317
T.mar.   KVDILLIDDVQFLIG KTGVQTELFHTFNEL HDSGKQIVICSDREP QKLSEFQDRLVSRFQ MGLVAKLEPPDEETR KSIARKMLEIEHGEL  283
H.pyl.   HCDFFLLDDAQFLQG KPKLEEEFFHTFNEL HANSKQIVLISDRSP KNIAGLEDRLKSRFE WGITAKVMPPDLETK LSIVKQKCQLNQITL  293

P.mar.   PRDLIQFIAGRFTSN IRELEGALTRAIAFA SITGLPMTVDSIAPM LD----PNGQGVEVT PKQVLDKVAEVFKVT PDEMRSASRRR-PVS  392
Syn.sp.  PKEVIEYIASHYTSN IRELEGALIRAIAYT SLSNVAMTVENIAPV LN----PPVEKVAAA PETIITIVAQHYQLK VEELLSNSRRR-EVS  377
B.sut.   PNEVMLYIANQIDSN IRELEGALIRVVAYS SLINKDINADLAAEA LKDII-PSSKPKVIT IKEIQRVVGQQFNIK LEDFKAKKRTK-SVA  384
M.tub.   PDDVLELIASSIERN IRELEGALIRVTAFA SLNKTPIDKALAEIV LRDLI-ADANTMQIS AATIMAATAEYFDTT VEELRGPGKTR-ALA  441
T.th.    PEDALEYIARQVTSN IREWEGALMRASPFA SLNGVELTRAVAAKA LRHLR-P--RELEAD PLEIIRKAAGPVRPE TPGGAHGERRKKEVV  372
E.coli   PGEVAFFIAKRLRSN VRELEGALNRVIANA NFTGRAITIDFVREA LRDLL-A-LQEKLVT IDNIQKTVAEYYKIK VADLLSKRRSR-SVA  404
T.mar.   PEEVLNFVAENVDDN LRRLRGAIIKLLVYK ETTGKEVDLKEAILL LKDFIKPNRVKAMDP IDELIEIVAKVTGVP REEILSNSRNV-KAL  372
H.pyl.   PEEVMEYIAQHISDN IRQMEGAIIKISVNA NLMNASIDLNLAKTV LEDL--QKDHAEGSS LENILLAVAQSLNLK SSEIKVSSRQK-NVA  380

P.mar.   QARQVGMYLMRQGTN LSLPRIGDTFGGKDH TTVMYAIEQVEKKLS S---------DPQIA SQVQKIRDLLQIDSR RKR----    461
Syn.sp.  LARQVGMYLMRQHTD LSLPRIGEAFGGKDH TTVMYSCDKITQLQQ K---------DWETS QTLTSLSHRINIAGQ APES---    447
B.sut.   FPRQIAMYLSREMTD SSLPKIGEEFGGRDH TTVIHAHEKISKLLA D---------DEQLQ QHVKEIKEQLK---- -------    446
M.tub.   QSRQIAMYLCRELTD LSLPKIGQAFG-RDH TTVMYAQRKILSEMA E---------RREVF DHVKELTTRIRQRSK R------    507
T.th.    LPRQLAMYLVRELTP ASLPEIGQLFGGRDH TTVRYAIQKVQELAG KP--------DREVQ GLLRTLREACTDPVD NLWITCG    446
E.coli   RPRQMAMALAKELTN HSLPEIGDAFGGRDH TTVLHACRKIEQLRE E---------SHDIK EDFSNLIRTLSS--- -------    467
T.mar.   TARRIGMYVAKNYLK SSLRTIAEKFN-RSH PVVVDSVKKVKDSLL KG--------NKQLK ALIDEVIGEISRRAL SG-----    440
H.pyl.   LARKLVVYFARLYTP NPTLSLAQFLDLKDH SSISKMYSGVKKMLE EEKSPFVLSLREEIK NRLNELNDKKTAFNS SE-----    457
```

FIG.19B

GTGTCGCACGAGGCCGTCTGGCAACACGTTCTGGAGCACA
TCCGCCGCAGCATCACCGAGGTGGAGTTCCACACCTGGTT
TGAAAGGATCCGCCCCTTGGGGATCCGGACGGGGTGCTG 120
GAGCTCGCCGTGCCCACCTCCTTTGCCCTGGACTGGATCC
GGCGCCACTACGCCGGCCTCATCCAGGAGGGCCCTCGGCT
CCTCGGGGCCCAGGCGCCCCGGTTTGAGCTCCGGGTGGTG 240
CCCGGGGTCGTAGTCCAGGAGGACATCTTCCAGCCCCCGC
CGAGCCCCCCGGCCCAAGCTCAACCCGAAGATACCTTTAA
AACTTCGTGGTGGGGCCCAACAACTCCATGGCCCCACGGC 360
GGCGCCGTGGCCGTGGCCGAGTCCCCCGGCCGGGCCTACA
ACCCCCTCTTCATCTACGGGGGCCGTGGCCTGGGAAAGAC
CTACCTGATGCACGCCGTGGGCCCACTCCGTGCGAAGCGC 480
TTCCCCCACATGAGATTAGAGTACGTTTCCACGGAAACTT
TCACCAACGAGCTCATCAACCGGCCATCCGCGAGGGACCG
GATGACGGAGTTCCGGGAGCGGTACCGCTCCGTGGACCTC 600
CTGCTGGTGGACGACGTCCAGTTCATCGCCGGAAAGGAGC
GCACCCAGGAGGAGTTTTTCCACACCTTCAACGCCCTTTA
CGAGGCCCACAAGCAGATCATCCTCTCCTCCGACCGGCCG 720
CCCAAGGACATCCTCACCCTGGAGGCGCGCCTGCGGAGCC
GCTTTGAGTGGGGCCTGATCACCGACAATCCAGCCCCCGA
CCTGGAAACCCGGATCGCCATCCTGAAGATGAACGCCAGC 840
AGCGGGCCTGAGGATCCCGAGGACGCCCTGGAGTACATCG
CCCGGCAGGTCACCTCCAACATCCGGGAGTGGGAAGGGGC
CCTCATGCGGGCATCGCCTTTCGCCTCCCTCAACGGCGTT 960
GAGCTGACCCGCGCCGTGGCGGCCAAGGCTCTCCGACATC
TTCGCCCCAGGGAGCTGGAGGCGGACCCCTTGGAGATCAT
CCGCAAAGCGGCGGACCAGTTCGGCCTGAAACCCCGGGA 1080
GGAGCTCACGGGGAGCGCCGCAAGAAGGAGGTGGTCCTCC
CCCGGCAGCTCGCCATGTACCTGGTGCGGGAGCTCACCCC
GGCCTCCCTGCCCGAGATCGACCAGCTCAACGACGACCGG 1200
GACCACACCACGGTCCTCTACGCCATCCAGAAGGTCCAGG
AGCTCGCGGAAAGCGACCGGGAGGTGCAGGGCCTCCTCCG
CACCCTCCGGGAGGCGTGCACATGA

FIG.20A

```
VSHEAVWQHVLEHIRRSITEVEFHTWFERIRPLGIRDGVL
ELAVPTSFALDWIRRHYAGLIQEGPRLLGAQAPRFELRVV
PGVVVQEDIFQPPPSPPAQAQPEDTFKTSWWGPTTPWPHG 120
GAVAVAESPGRAYNPLFIYGGRGLGKTYLMHAVGPLRAKR
FPHMRLEYVSTETFTNELINRPSARDRMTEFRERYRSVDL
LLVDDVQFIAGKERTQEEFFHTFNALYEAHKQIILSSDRP 240
PKDILTLEARLRSRFEWGLITDNPAPDLETRIAILKMNAS
SGPEDPEDALEYIARQVTSNIREWEGALMRASPFASLNGV
ELTRAVAAKALRHLRPRELEADPLEIIRKAAGPVRPETPG 360
GAHGERRKKEVVLPRQLAMYLVRELTPASLPEIDQLNDDR
DHTTVLYAIQKVQELAESDREVQGLLRTLREACT
```

FIG.20B

ATGAACATAACGGTTCCCAAAAAACTCCTCTCGGACCAGC 40
TTTCCCTCCTGGAGCGCATCGTCCCCTCTAGAAGCGCCAA
CCCCCTCTACACCTACCTGGGGCTTTACGCCGAGGAAGGG 120
GCCTTGATCCTCTTCGGGACCAACGGGGAGGTGGACCTCG
AGGTCCGCCTCCCCGCCGAGGCCCAAAGCCTTCCCCGGGT 200
GCTCGTCCCCGCCCAGCCCTTCTTCCAGCTGGTGCGGAGC
CTTCCTGGGGACCTCGTGGCCCTCGGCCTCGCCTCGGAGC 280
CGGGCCAGGGGGGGCAGCTGGAGCTCTCCTCCGGGCGTTT
CCGCACCCGGCTCAGCCTGGCCCCTGCCGAGGGCTACCCC 360
GAGCTTCTGGTGCCCGAGGGGGAGGACAAGGGGGCCTTCC
CCCTCCGGACGCGGATGCCCTCCGGGGAGCTCGTCAAGGC 440
CTTGACCCACGTGCGCTACGCCGCGAGCAACGAGGAGTAC
CGGGCCATCTTCCGCGGGGTGCAGCTGGAGTTCTCCCCCC 520
AGGGCTTCCGGGCGGTGGCCTCCGACGGGTACCGCCTCGC
CCTCTACGACCTGCCCCTGCCCCAAGGGTTCCAGGCCAAG 600
GCCGTGGTCCCCGCCCGGAGCGTGGACGAGATGGTGCGGG
TCCTGAAGGGGGCGGACGGGGCCGAGGCCGTCCTCGCCCT 680
GGGCGAGGGGGTGTTGGCCCTGGCCCTCGAGGGCGGAAGC
GGGGTCCGGATGGCCCTCCGCCTCATGGAAGGGGAGTTCC 760
CCGACTACCAGAGGGTCATCCCCCAGGAGTTCGCCCTCAA
GGTCCAGGTGGAGGGGGAGGCCCTCAGGGAGGCGGTGCGC 840
CGGGTGAGCGTCCTCTCCGACCGGCAGAACCACCGGGTGG
ACCTCCTTTTGGAGGAAGGCCGGATCCTCCTCTCCGCCGA 920
GGGGGACTACGGCAAGGGGCAGGAGGAGGTGCCCGCCCAG
GTGGAGGGGCCGGACATGGCCGTGGCCTACAACGCCCGCT 1000
ACCTCCTCGAGGCCCTCGCCCCCGTGGGGGACCGGGCCCA
CCTGGGCATCTCCGGGCCCACGAGCCCGAGCCTCATCTGG 1080
GGGGACGGGGAGGGGTACCGGGCGGTGGTGGTGCCCCTCA
GGGTCTAG 1128

FIG.21A

MNITVPKKLLSDQLSLLERIVPSRSANPLYTYLGLYAEEG 40
ALILFGTNGEVDLEVRLPAEAQSLPRVLVPAQPFFQLVRS
LPGDLVALGLASEPGQGGQLELSSGRFRTRLSLAPAEGYP 120
ELLVPEGEDKGAFPLRTRMPSGELVKALTHVRYAASNEEY
RAIFRGVQLEFSPQGFRAVASDGYRLALYDLPLPQGFQAK 200
AVVPARSVDEMVRVLKGADGAEAVLALGEGVLALALEGGS
GVRMALRLMEGEFPDYQRVIPQEFALKVQVEGEALREAVR 280
RVSVLSDRQNHRVDLLLEEGRILLSAEGDYGKGQEEVPAQ
VEGPDMAVAYNARYLLEALAPVGDRAHLGISGPTSPSLIW 360
GDGEGYRAVVVPLRVZ

FIG.21B

```
T.th.beta     MNITVPKKLLSDQLSLLERIVPSRSANPLYTYLGLYAEEGALILFGTNGEVDLEVRLPAE
E.coli.bet    MKFTVEREHLLKPLQQVSGPLGGRPTLPILGNLLLQVADGTLSLTGTDLEMEMVARVALV
P.mirab.be    MKFIIEREQLLKPLQQVSGPLGGRPTLPILGNLLLKVTENTLSLTGTDLEMEMMARVSLS
H.infl.bet    MQFSISRENLLKPLQQVCGVLSNRPNIPVLNNVLLQIEDYRLTITGTDLEVELSSQTQLS
P.put.beta    MHFTIQREALLKPLQLVAGVVERRQTLPVLSNVLLVVQGQQLSLTGTDLEVELVGRVQLE
B.cap.beta    MKFTIQNDILTKNLKKITRVLVKNISFPILENILIQVEDGTLSLTTTNLEIELISKIEII
              *   .   *   *  .   .     *.  . .     * .  *  *... .

T.th.beta     AQSLP-RVLVPAQPFFQLVRSLPGDLVALGLASEPGQGGQLELSSGRFRTRLSLAPAEGY
E.coli.bet    QPHEPGATTVPARKFFDICRGLP-EGAEIAVQLE---GERMLVRSGRSRFSLSTLPAADF
P.mirab.be    QSHEIGATTVPARKFFDIWRGLP-EGAEISVELD---GDRLLVRSGRSRFSLSTLPASDF
H.infl.bet    SSSENGTFTIPAKKFLDICRTLS-DDSEITVTFE---QDRALVQSGRSRFTLATQPAEEY
P.put.beta    EPAEPGEITVPARKLMDICKSLP-NDALIDIKVD---EQKLLVKAGRSRFTLSTLPANDF
B.cap.beta    TKYIPGKTTISGRKILNICRTLS-EKSKIKMQLK---NKKMYISSENSNYILSTLSADTF
                  .  .  .  . *    . .       . . .       *.   *  .

T.th.beta     PELLVPEGEDKGAFPLRTRMPSGELVKALTHVRYAASNEEYRAIFRGVQLEFSPQGFRAV
E.coli.bet    PNLDD--WQSEVEFTLPQAT----MKRLIEATQFSMAHQDVRYYLNGMLFETEGEELRTV
P.mirab.be    PNLDD--WQSEVEFTLPQAT----LKRLIESTQFSMAHQDVRYYLNGMLFETENTELRTV
H.infl.bet    PNLTD--WQSEVDFELPQNT----LRRLIEATQFSMANQDARYFLNGMKFETEGNLLRTV
P.put.beta    PTVEE--GPGSLTCNLEQSK----LRRLIERTSFAMAQQDVRYYLNGMLLEVSRNTLRAV
B.cap.beta    PNHQN--FDYISKFDISSNI----LKEMIEKTEFSMGKQDVRYYLNGMLLEKKDKFLRSV
              *      .          .  .    ..   .. *    *.  *      *.*

T.th.beta     ASDGYRLALYDLPLPQGFQA--KAVVPARSVDEMVRVLKGADGAEAVLALGEGVLALALE
E.coli.bet    ATDGHRLAVCSMPIGQSLPS-HSVIVPRKGVIELMRMLDG-GDNPLRVQIGSNNIRAHVG
P.mirab.be    ATDGHRLAVCAMDIGQSLPG-HSVIVPRKGVIELMRLLDGSGESLLQLQIGSNNLRAHVG
H.infl.bet    ATDGHRLAVCTISLEQELQN-HSVILPRKGVLELVRLLET-NDEPARLQIGTNNLRVHLK
P.put.beta    STDGHRLALCSMSAPIEQEDRHQVIVPRKGILELARLLTD-PEGMVSIVLGQHHIRATTG
B.cap.beta    ATDGYRLAISYTQLKKDINF-FSIIIPNKAVMELLKLLNT-QPQLLNILIGSNSIRIYTK
              ..** ***.             ..*  . .*. ..*    . .*   .
```

FIG.22A

```
T.th.beta      GGSGVRMALRLMEGEFPDYQRVIPQEFALKVQVEGEALREAVRRVSVLSDRQNHRVDLLL
E.coli.bet     ---DFIFTSKLVDGRFPDYRRVLPKNPDKHLEAGCDLLKQAFARAAILSNEKFRGVRLYV
P.mirab.be     ---DFIFTSKLVDGRFPDYRRVLPKNPTKTVIAGCDILKQAFSRAAILSNEKFRGVRINL
H.infl.bet     ---NTVFTSKLIDGRFPDYRRVLPRNATKIVEGNWEMLKQAFARASILSNERARSVRLSL
P.put.beta     ---EFTFTSKLVDGKFPDYERVLPKGGDKLVVGDRQALREAFSRTAILSNEKYRGIRLQL
B.cap.beta     ---NLIFTTQLIEGEYPDYKSVLFKEKKNPIITNSILLKKSLLRVAILAHEKFCGIEIKI
                   . .*..* .***  *. .     .       *. .   * ..*.  .   . . .

T.th.beta      EEGRILLSAEGDYGK-GQEEVPAQVEGPDMAVAYNARYLLEALAPVG-DRAHLGISGPTS
E.coli.bet     SENQLKITANNPEQEEAEEILDVTYSGAEMEIGFNVSYVLDVLNALKCENVRMMLTDSVS
P.mirab.be     TNGQLKITANNPEQEEAEEIVDVQYQGEEMEIGFNVSYLLDVLNTLKCEEVKLLLTDAVS
H.infl.bet     KENQLKITASNTEHEEAEEIVDVNYNGEELEVGFNVTYILDVLNALKCNQVRMCLTDAFS
P.put.beta     AAGQLKIQANNPEQEEAEEEISVDYEGSSLEIGFNVSYLLDVLGVMTTEQVRLILSDSNS
B.cap.beta     ENGKFKVLSDNQEEETAEDLFEIDYFGEKIEISINVYYLLDVINNIKSENIALFLNKSKS
                ..  . . .      ..        *  . .  *  *.*. . .     . .     *

T.th.beta      PSLIWGDG-EGYRAVVVPLRVZ    (ID#108)
E.coli.bet     SVQIEDAASQSAAYVVMPMRLZ    (ID#109)
P.mirab.be     SVQVENVASAAAAYVVMPMRL-    (ID#110)
H.infl.bet     SCLIENCEDSSCEYVIMPMRL-    (ID#111)
P.put.beta     SALLQEAGNDDSSYVVMPMRL-    (ID#112)
B.cap.beta     SIQIEAENNSSNAYVVMLLKR-    (ID#113)
                         *.. ..
```

FIG.22B

FIG.24A Induction
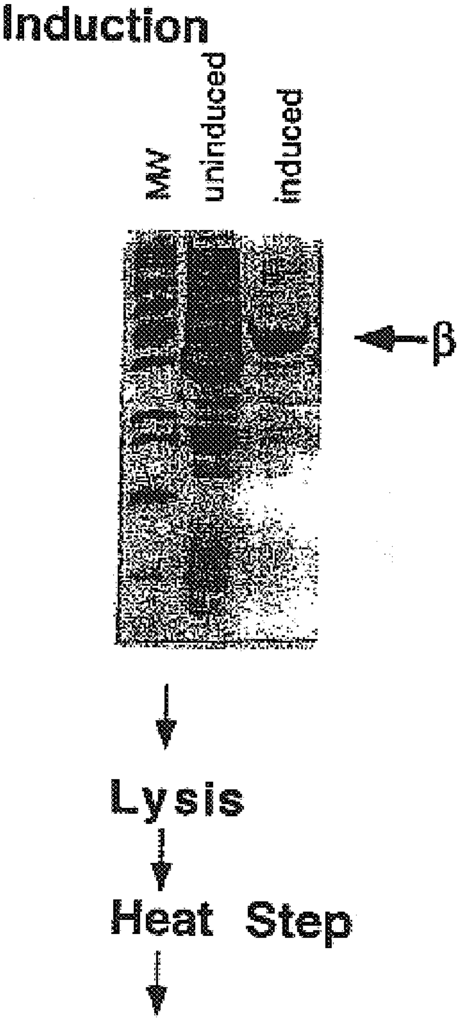
FIG.24B MonoQ Column
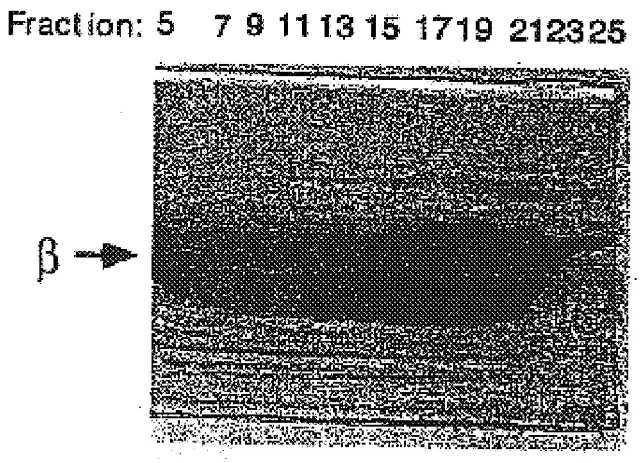

FIG.25A
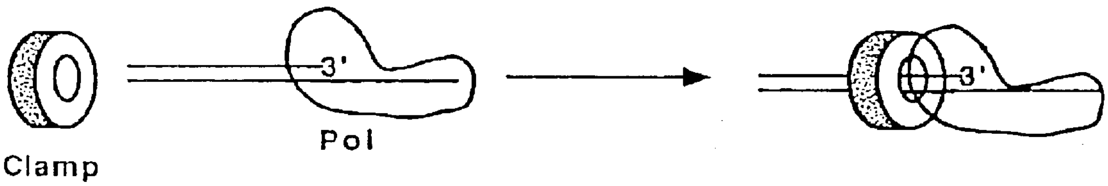
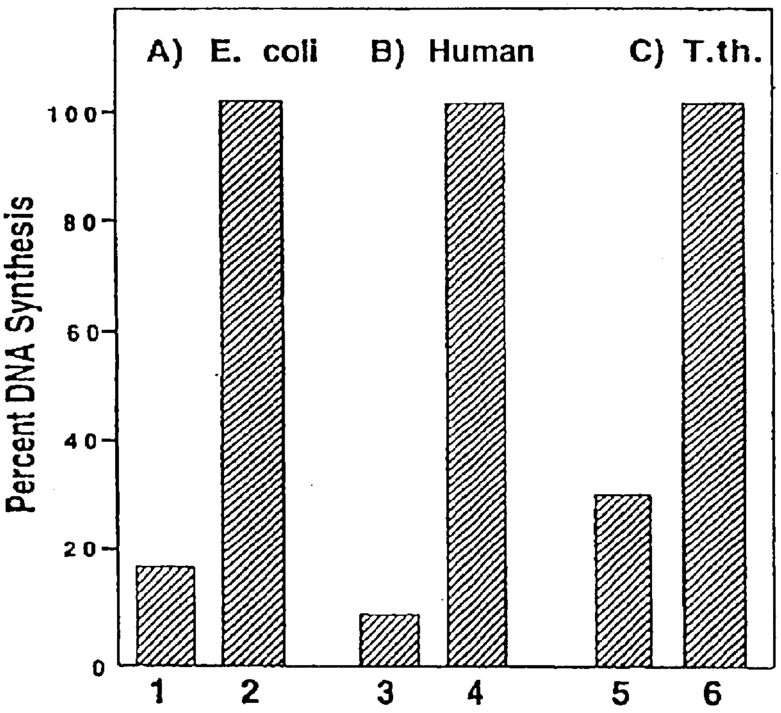
FIG.25B

FIG. 26A
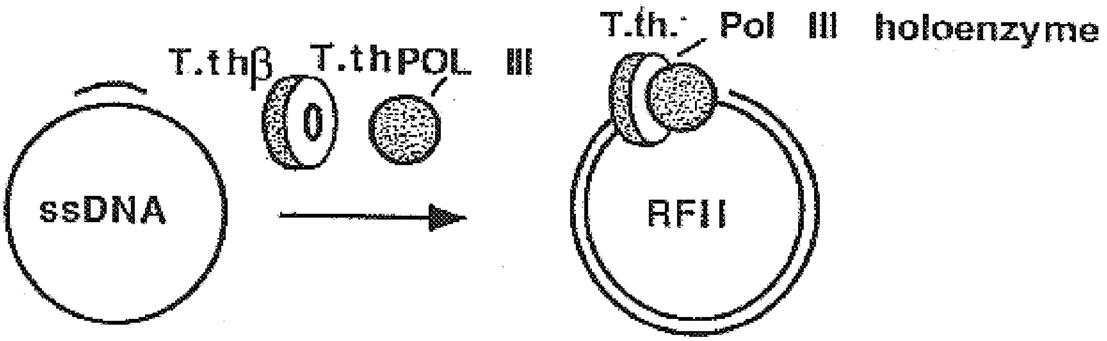
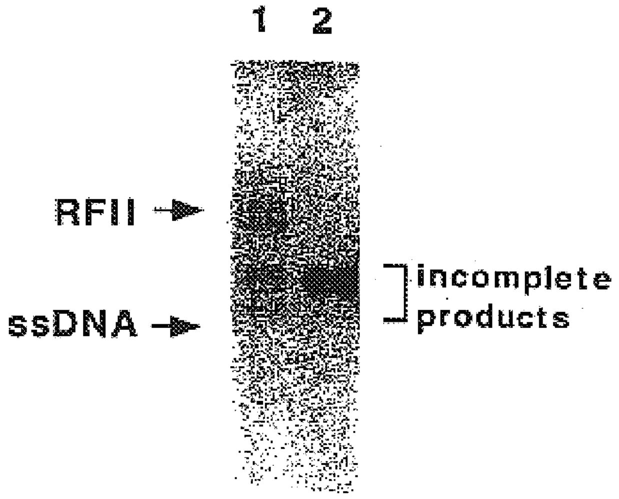
FIG. 26B

ATGAGTAAGGATTTCGTCCACCTTCACCTGCACACCCAGTTCTCACTCCT
GGACGGGGCTATAAAGATAGACGAGCTCGTGAAAAAGGCAAAGGAGTATG 100
GATACAAAGCTGTCGGAATGTCAGACCACGGAAACCTCTTCGGTTCGTAT
AAATTCTACAAAGCCCTGAAGGCGGAAGGAATTAAGCCCATAATCGGCAT 200
GGAAGCCTACTTTACCACGGGTTCGAGGTTTGACAGAAAGACTAAAACGA
GCGAGGACAACATAACCGACAAGTACAACCACCACCTCATACTTATAGCA 300
AAGGACGAAAAGGTCTAAAGAACTTAATGAAGCTCTCAACCCTCGCCTAC
AAAGAAGGTTTTTACTACAAACCCAGAATTGATTACGAACTCCTTGAAAA 400
GTACGGGGAGGGCCTAATAGCCCTTACCGCATGCCTGAAAGGTGTTCCCA
CCTACTACGCTTCTATAAACGAAGTGAAAAAGGCGGAGGAATGGGTAAAG 500
AAGTTCAAGGATATATTCGGAGATGACCTTTATTTAGAACTTCAAGCGAA
CAACATTCCAGAACAGGAAGTGGCAAACAGGAACTTAATAGAGATAGCCA 600
AAAAGTACGATGTGAAACTCATAGCGACGCAGGACGCCCACTACCTCAAT
CCCGAAGACAGGTACGCCCACACGGTTCTTATGGCACTTCAAATGAAAAA 700
GACCATTCACGAACTGAGTTCGGGAAACTTCAAGTGTTCAAACGAAGACC
TTCACTTTGCTCCACCCGAGTACATGTGGAAAAAGTTTGAAGGTAAGTTC 800
GAAGGCTGGGAAAAGGCACTCCTGAACACTCTCGAGGTAATGGAAAAGAC
AGCGGACAGCTTTGAGATATTTGAAAACTCCACCTACCTCCTTCCCAAGT 900
ACGACGTTCCGCCCGACAAAACCCTTGAGGAATACCTCAGAGAACTCGCG
TACAAAGGTTTAAGACAGAGGATAGAAAGGGGACAAGCTAAGGATACTAA 1000
AGAGTACTGGAGAGGCTCGAGTACGAACTGGAAGTTATAAACAAAATGG
GCTTTGCGGGATACTTCTTGATAGTTCAGGACTTCATAAACTGGGCTAAG 1100
AAAAACGACATACCTGTTGGACCCGGAAGGGGAAGTGCTGGAGGTTCCCT
CGTCGCATACGCCATCGGAATAACGGACGTTGACCCTATAAAGCACGGAT 1200
TCCTTTTTGAGAGGTTCTTAAACCCCGAAAGGGTTTCCATGCCGGATATA
GACGTGGATTTCTGTCAGGACAACAGGGAAAAGGTCATAGAGTACGTAAG 1300
GAACAAGTACGGACACGACAACGTAGCTCAGATAATCACCTACAACGTAA
TGAAGGCGAAGCAAACACTGAGAGACGTCGCAAGGGCCATGGGACTCCCC 1400
TACTCCACCGCGGACAAACTCGCAAAACTCATTCCTCAGGGGGACGTTCA
GGGAACGTGGCTCAGTCTGGAAGAGATGTACAAAACGCCTGTGGAGGAAC 1500
TCCTTCAGAAGTACGGAGAACACAGAACGGACATAGAGGACAACGTAAAG
AAGTTCAGACAGATATGCGAAGAAAGTCCGGAGATAAAACAGCTCGTTGA 1600
GACGGCCCTGAAGCTTGAAGGTCTCACGAGACACACCTCCCTCCACGCCG
CGGGAGTGGTTATAGCACCAAAGCCCTTGAGCGAGCTCGTTCCCCTCTAC 1700
TACGATAAAGAGGGCGAAGTCGCAACCCAGTACGACATGGTTCAGCTCGA
AGAACTCGGTCTCCTGAAGATGGACTTCCTCGGACTCAAAACCCTCACAG 1800
AACTGAAACTCATGAAAGAACTCATAAAGGAAAGACACGGAGTGGATATA
AACTTCCTTGAACTTCCCCTTGACGACCCGAAAGTTTACAAACTCCTTCA 1900
GGAAGGAAAAACCACGGGAGTGTTCCAGCTCGAAAGCAGGGGAATGAAAG
AACTCCTGAAGAAACTAAAGCCCGACAGCTTTGACGACATCGTTGCGGTC 2000
CTCGCACTCTACAGACCCGGACCTCTAAAGAGCGGACTCGTTGACACATA
CATTAAGAGAAAGCACGGAAAAGAACCCGTTGAGTACCCCTTCCCGGAGC 2100
TTGAACCCGTCCTTAAGGAAACCTACGGAGTAATCGTTTATCAGGAACAG
GTGATGAAGATGTCTCAGATACTTTCCGGCTTTACTCCCGGAGAGGCGGA 2200
TACCCTCAGAAAGGCGATAGGTAAGAAGAAAGCGGATTTAATGGCTCAGA
TGAAAGACAAGTTCATACAGGGAGCGGTGGAAAGGGGATACCCTGAAGAA 2300
AAGATAAGGAAGCTCTGGGAAGACATAGAGAAGTTCGCTTCCTACTCCTT
CAACAAGTCTCACTCGGTAGCTTACGGGTACATCTCCTACTGGACCGCCT 2400

FIG. 34A

```
ACGTTAAAGCCCACTATCCCGCGGAGTTCTTCGCGGTAAAACTCACAACT
GAAAAGAACGACAACAAGTTCCTCAACCTCATAAAAGACGCTAAACTCTT   2500
CGGATTTGAGATACTTCCCCCCGACATAAACAAGAGTGATGTAGGATTTA
CGATAGAAGGTGAAAACAGGATAAGGTTCGGGCTTGCGAGGATAAAGGGA   2600
GTGGGAGAGGAAACTGCTAAGATAATCGTTGAAGCTAGAAAGAAGTATAA
GCAGTTCAAAGGGCTTGCGGACTTCATAAACAAAACCAAGAACAGCAAGA   2700
TAAACAAGAAAGTCGTGGAAGCACTCGTAAAGGCAGGGGCTTTTGACTTT
ACTAAGAAAAAGAGGAAAGAACTACTCGCTAAAGTGGCAAACTCTGAAAA   2800
AGCATTAATGGCTACACAAAACTCCCTTTTCGGTGCACCGAAAGAAGAAG
TGGAAGAACTCGACCCCTTAAAGCTTGAAAAGGAAGTTCTCGGTTTTTAC   2900
ATTTCAGGGCACCCCCTTGACAACTACGAAAAGCTCCTCAAGAACCGCTA
CACACCCATTGAAGATTTAGAAGAGTGGGACAAGGAAAGCGAAGCGGTGC   3000
TTACAGGAGTTATCACGGAACTCAAAGTAAAAAAGACGAAAAACGGAGAT
TACATGGCGGTCTTCAACCTCGTTGACAAGACGGGACTAATAGAGTGTGT   3100
CGTCTTCCCGGGAGTTTACGAAGAGGCAAAGGAACTGATAGAAGAGGACA
GAGTAGTGGTAGTCAAAGGTTTTCTGGACGAGGACCTTGAAACGGAAAAT   3200
GTCAAGTTCGTGGTGAAAGAGGTTTTCTCCCCTGAGGAGTTCGCAAAGGA
GATGAGGAATACCCTTTATATATTCTTAAAAAGAGAGCAAGCCCTAAACG   3300
GCGTTGCCGAAAAACTAAAGGGAATTATTGAAAACAACAGGACGGAGGAC
GGATACAACTTGGTTCTCACGGTTGATCTGGGAGACTACTTCGTTGATTT   3400
AGCACTCCCACAAGATATGAAACTAAAGGCTGACAGAAAGGTTGTAGAGG
AGATAGAAAAACTGGGAGTGAAGGTCATAATTTAGTAAATAACCCTTACT   3500
TCCGAGTAGTCCCC
```

FIG. 34B

MSKDFVHLHLHTQFSLLDGAIKIDELVKKAKEYGYKAVGMSDHGNLFGSY
KFYKALKAEGIKPIIGMEAYFTTGSRFDRKTKTSEDNITDKYNHHLILIA 100
KDDKGLKNLMKLSTLAYKEGFYYKPRIDYELLEKYGEGLIALTACLKGVP
TYYASINEVKKAEEWVKKFKDIFGDDLYLELQANNIPEQEVANRNLIEIA 200
KKYDVKLIATQDAHYLNPEDRYAHTVLMALQMKKTIHELSSGNFKCSNED
LHFAPPEYMWKKFEGKFEGWEKALLNTLEVMEKTADSFEIFENSTYLLPK 300
YDVPPDKTLEEYLRELAYKGLRQRIERGQAKDTKEYWERLEYELEVINKM
GFAGYFLIVQDFINWAKKNDIPVGPGRGSAGGSLVAYAIGITDVDPIKHG 400
FLFERFLNPERVSMPDIDVDFCQDNREKVIEYVRNKYGHDNVAQIITYNV
MKAKQTLRDVARAMGLPYSTADKLAKLIPQGDVQGTWLSLEEMYKTPVEE 500
LLQKYGEHRTDIEDNVKKFRQICEESPEIKQLVETALKLEGLTRHTSLHA
AGVVIAPKPLSELVPLYYDKEGEVATQYDMVQLEELGLLKMDFLGLKTLT 600
ELKLMKELIKERHGVDINFLELPLDDPKVYKLLQEGKTTGVFQLESRGMK
ELLKKLKPDSFDDIVAVLALYRPGPLKSGLVDTYIKRKHGKEPVEYPFPE 700
LEPVLKETYGVIVYQEQVMKMSQILSGFTPGEADTLRKAIGKKKADLMAQ
MKDKFIQGAVERGYPEEKIRKLWEDIEKFASYSFNKSHSVAYGYISYWTA 800
YVKAHYPAEFFAVKLTTEKNDNKFLNLIKDAKLFGFEILPPDINKSDVGF
TIEGENRIRFGLARIKGVGEETAKIIVEARKKYKQFKGLADFINKTKNRK 900
INKKVVEALVKAGAFDFTKKKRKELLAKVANSEKALMATQNSLFGAPKEE
VEELDPLKLEKEVLGFYISGHPLDNYEKLLKNRYTPIEDLEEWDKESEAV 1000
LTGVITELKVKKTKNGDYMAVFNLVDKTGLIECVVFPGVYEEAKELIEED
RVVVVKGFLDEDLETENVKFVVKEVFSPEEFAKEMRNTLYIFLKREQALN 1100
GVAEKLKGIIENNRTEDGYNLVLTVDLGDYFVDLALPQDMKLKADRKVVE
EIEKLGVKVII 1161

FIG. 35

```
ATGAACTACGTTCCCTTCGCGAGAAAGTACAGACCGAAATTCTTCAGGGA
AGTAATAGGACAGGAAGCTCCCGTAAGGATACTCAAAAACGCTATAAAAA   100
ACGACAGAGTGGCTCACGCCTACCTCTTTGCCGGACCGAGGGGGGTTGGG
AAGACGACTATTGCAAGAATTCTCGCAAAAGCTTTGAACTGTAAAAATCC   200
CTCCAAACGGTGAGCCCTGCGGTGAGTGCGAAAACTGCAGGGAGATAGACA
GGGGTGTGTTCCCTGACTTAATTGAAATGGATGCCGCCTCAAACAGGGGT   300
ATAGACGACGTAAGGGCATTAAAAGAAGCGGTCAATTACAAACCTATAAA
AGGAAAGTACAAGGTTTACATAATAGACGAAGCTCACATGCTCACGAAAG   400
AAGCTTTCAACGCTCTCTTAAAAACCCTCGAAGAGCCCCCTCCCAGAACT
GTTTTCGTCCTTTGTACCACGGAGTACGACAAAATTCTTCCCACGATACT   500
CTCAAGGTGTCAGAGGATAATCTTCTCAAAGGTAAGAAAGGAAAAAGTAA
TAGAGTATCTAAAAAAGATATGTGAAAAGGAAGGGATTGAGTGCGAAGAC   600
GGAGCCCTTGAGGTTCTGGCTCATGCCTCTGAAGGGTGCATGAGGGATGC
AGCCTCTCTCCTGGACCAGGCGAGCGTTTACGGGGAAGGCAGGGTAACAA   700
AAGAAGTAGTGGAGAACTTCCTCGGAATTCTCAGTCAGGAAAGCGTTAGG
AGTTTTCTGAAATTGCTTCTGAACTCAGAAGTGGACGAAGCTATAAAGTT   800
CCTCAGAGAACTCTCAGAAAAGGGCTACAACCTGACCAAGTTTTGGGAGA
TGTTAGAAGAGGAAGTGAGAAACGCAATTTTAGTAAAGAGCCTGAAAAAT   900
CCCGAAAGCGTGGTTCAGAACTGGCAGGATTACGAAGACTTCAAAGACTA
CCCTCTGGAAGCCCTCCTCTACGTTGAGAACCTGATAAACAGGGGTAAAG  1000
TTGAAGCGAGAACGAGAGAACCCTTAAGAGCCTTTGAACTCGCGGTAATA
AAGAGCCTTATAGTCAAAGACATAATTCCCGTATCCCAGCTCGGAAGTGT  1100
GGTAAAGGAAACCAAAAAGGAAGAAAAGAAAGTTGAAGTAAAAGAAGAGC
CAAAAGTAAAAGAAGAAAAACCAAAGGAGCAGGAAGAGGACAGGTTCCAG  1200
AAAGTTTTAAACGCTGTGGACGGCAAAATCCTTAAAAGAATACTTGAAGG
GGCAAAAAGGGAAGAAAGAGACGGAAAAATCGTCCTAAAGATAGAAGCCT  1300
CTTATCTGAGAACCATGAAAAAGGAATTTGACTCACTAAAGGAGACTTTT
CCTTTTTTAGAGTTTGAACCCGTGGAGGATAAAAAAAAACCTCAGAAGTC  1400
CAGCGGGACGAGGCTGTTTTAAAGGTAAAGGAGCTCTTCAATGCAAAAAT
ACTCAAAGTACGAAGTAAAAGCTAAGGTCATAAAGGTGAGAATGCCCCGTG  1500
GAAGAGATAGGGCTGTTTAACGCACTAATAGACGGCTTGCCCAGGTACGC
ACTCACGAGGACGAAGGAAAAGGGAAAGGGAGAAGTTTTCGTTTTAGCGA  1600
CTCCTTATAAAGTCAAGGAATTGATGGAAGCTATGGAGGGTATGAAAAAA
CACATAAAGGATTTAGAAATCCTCGGAGAGACGGATGAGGATTTAACTTT  1700
TTAAAGTATGGGTGTATCTGAGCAAAGGTTTAAGCTAAAAACAAACCTGA
AACCCGCAGGGGACCAGCCGAAAGCCATAAAAAAACTCCTTGAAAACCTA  1800
AGGAAAGGCGTAAAAGAACAAACACTTCTCGGAGTCACGGGAAGCGGAAA
GACTTTTACTCTAGCAAACGTAATAGCGAAGTACAACAAACCAACTCTTG  1900
TGGTAGTTCACAACAAAATTCTCGCGGCACAGCTATACAGGGAGTTTAAA
GAACTATTCCCTGAAAACGCTGTAGAGTACTTTGTCTCTTACTACGACTA  2000
TTACCAACCTGAAGCCTACATTCCCGAAAAAGATTTATACATAGAAAAGG
ACGCGAGTATAAACGAAAGCTGGAACGTTTCAGACACTCCGCCACGATAT  2100
CCGTTCTAGAAAGGAGGGACGTTATAGTAGTTGCTTCAGTTTCTTGCATA
TACGGACTCGGGAAACCTGAGCACTACGAAAACCTGAGGATAAAACTCCA  2200
AAGGGGAATAAGACTGAACTTGAGTAAGCTCCTGAGGAAACTCGTTGAGC
TAGGATATCAGAGAAATGACTTTGCCATAAAGAGGGCTACCTTCTCGGTT  2300
AGGGGAGACGTGGTTGAGATAGTCCCTTCTCACACGGAAGATTACCTCGT
GAGGGTAGAGTTCTGGGACGACGAAGTTGAAAGAATAGTCCTCATGGACG  2400
CTCTGAAC
```

FIG. 36

MNYVPFARKYRPKFFREVIGQEAPVRILKNAIKNDRVAHAYLFAGPRGVG
KTTIARILAKALNCKNPSKGEPCGECENCREIDRGVFPDLIEMDAASNRG 100
IDDVRALKEAVNYKPIKGKYKVYIIDEAHMLTKEAFNALLKTLEEPPPRT
VFVLCTTEYDKILPTILSRCQRIIFSKVRKEKVIEYLKKICEKEGIECEE 200
GALEVLAHASEGCMRDAASLLDQASVYGEGRVTKEVVENFLGILSQESVR
SFLKLLLNSEVDEAIKFLRELSEKGYNLTKFWEMLEEEVRNAILVKSLKN 300
PESVVQNWQDYEDFKDYPLEALLYVENLINRGKVEARTREPLRAFELAVI
KSLIVKDIIPVSQLGSVVKETKKEEKKVEVKEEPKVKEEKPKEQEEDRFQ 400
KVLNAVDGKILKRILEGAKREERDGKIVLKIEASYLRTMKKEFDSLKETF
PFLEFEPVEDKKKPQKSSGTRLF 473

FIG. 37

ATGCGCGTTAAGGTGGACAGGGAGGAGCTTGAAGAGGTTCTTAAAAAAGC
AAGAGAAAGCACGGAAAAAAAAGCCGCACTCCCGATACTCGCGAACTTCT 100
TACTCTCCGCAAAAGAGGAAAACTTAATCGTAAGGGCAACGGACTTGGAA
AACTACCTTGTAGTCTCCGTAAAGGGGGAGGTTGAAGAGGAAGGAGAGGT 200
TTGCGTCCACTCTCAAAAACTCTACGATATAGTCAAGAACTTAAATTCCG
CTTACGTTTACCTTCATACGGAAGGTGAAAAACTCGTCATAACGGGAGGA 300
AAGAGTACGTACAAACTTCCGACAGCTCCCGCGGAGGACTTTCCCGAATT
TCCAGAAATCGTAGAAGGAGGAGAAACACTTTCGGGAAACCTTCTCGTTA 400
ACGGAATAGAAAAGGTAGAGTACGCCATAGCGAAGGAAGAAGCGAACATA
GCCCTTCAGGGAATGTATCTGAGAGGATACGAGGACAGAATTCACTTTGT 500
GTTCGGACGGTCACAGGCTTGCACTTTATGAACCTCTACGTAAACATTGA
AAAGAGTGAAGACGAGTCTTTTGCTTACTTCTCCACTCCCGAGTGGAAAC 600
TCGCCGTTAGCTCCTGGAAGGAGAATTCCCGGACTACATGAGTGTCATCC
CTGAGGAGTTTTCGGCGGAAGTCTTGTTTGAGACAGAGGAAGTCTTAAAG 700
GTTTTAAAGAGGTTGAAGGCTTTAAGCGAAGGAAAAGTTTTTCCCGTGAA
GATTACCTTAAGCGAAAACCTTGCCATCTTTGAGTTCGCGGATCCGGAGT 800
TCGGAGAAGCGAGAGAGGAAATTGAAGTGGAGTACACGGGAGAGCCCTTT
GAGATAGGATTCAACGGAAATACCTTATGGAGGCGCTTGACGCCTACGAC 900
AGCGAAAGAGTGTGGTTCAAGTTCACAACCCCCGACACGGCCACTTTATT
GGAGGCTGAAGATTACGAAAAGGAACCTTACAAGTGCATAATAATGCCGA 1000
TGAGGGTGTAGCCATGAAAAAAGCTTTAATCTTTTATTGAGCTTGAGCC
TTTTAATTCCTGCGTTTAGCGAAGCCAAACCCAAGTCTTC 1090

FIG. 38

MRVKVDREELEEVLKKARESTEKKAALPILANFLLSAKEENLIVRATDLE
NYLVVSVKGEVEEEGEVCVHSQKLYDIVKNLNSAYVYLHTEGEKLVITGG 100
KSTYKLPTAPAEDFPEFPEIVEGGETLSGNLLVNGIEKVEYAIAKEEANI
ALQGMYLRGYEDRIHFVGSDGHRLALYEPLGEFSKELLIPRKSLKVLKKL 200
ITGIEDVNIEKSEDESFAYFSTPEWKLAVRLLEGEFPDYMSVIPEEFSAE
VLFETEEVLKVLKRLKALSEGKVFPVKITLSENLAIFEFADPEFGEAREE 300
IEVEYTGEPFEIGFNGKYLMEALDAYDSERVWFKFTTPDTATLLEAEDYE
KEPYKCIIMPMRV 363

FIG. 39

```
GTGGAAACCACAATATTCCAGTTCCAGAAAACTTTTTTCACAAAACCTCC
GAAGGAGAGGGTCTTCGTCCTTCATGGAGAAGAGCAGTATCTCATAAGAA    100
CCTTTTTGTCTAAGCTGAAGGAAAAGTACGGGGAGAATTACACGGTTCTG
TGGGGGGATGAGATAAGCGAGGAGGAATTCTACACTGCCCTTTCCGAGAC    200
CAGTATATTCGGCGGTTCAAAGGAAAAAGCGGTGGTCATTTACAACTTCG
GGGATTTCCTGAAGAAGCTCGGAAGGAAGAAAAAGGAAAAAGAAAGGCTT    300
ATAAAAGTCCTCAGAAACGTAAAGAGTAACTACGTATTTATAGTGTACGA
TGCGAAACTCCAGAAACAGGAACTTTCTTCGGAACCTCTGAAATCCGTAG    400
CGTCTTTCGGCGGTATAGTGGTAGCAAACAGGCTGAGCAAGGAGAGGATA
AAACAGCTCGTCCTTAAGAAGTTCAAAGAAAAAGGGATAAACGTAGAAAA    500
CGATGCCCTTGAATACCTTCTCCAGCTCACGGGTTACAACTTGATGGAGC
TCAAACTTGAGGTTGAAAAACTGATAGATTACGCAAGTGAAAAGAAAATT    600
TTAACACTCGATGAGGTAAAGAGAGTAGCCTTCTCAGTCTCAGAAAACGT
AAACGTATTTGAGTTCGTTGATTTACTCCTCTTAAAAGATTACGAAAAGG    700
CTCTTAAAGTTTTGGACTCCCTCATTTCCTTCGGAATACACCCCCTCCAG
ATTATGAAAATCCTGTCCTCCTATGCTCTAAAACTTTACACCCTCAAGAG    800
GCTTGAAGAGAAGGGAGAGGACCTGAATAAGGCGATGGAAAGCGTGGGAA
TAAAGAACAACTTTCTCAAGATGAAGTTCAAATCTTACTTAAAGGCAAAC    900
TCTAAAGAGGACTTGAAGAACCTAATCCTCTCCCTCCAGAGGATAGACGC
TTTTTCTAAACTTTACTTTCAGGACACAGTGCAGTTGCTGGGGATTTCTT   1000
GACCTCAAGACTGGAGAGGGAAGTTGTGAAAAATACTTCTCATGGTGGAT
AATCTTTTTTATGAAGTTTGCGGTTTGCGTTTTTCCCGGTTCT          1093
```

FIG. 40

```
VETTIFQFQKTFFTKPPKERVFVLHGEEQYLIRTFLSKLKEKYGENYTVL
WGDEISEEEFYTALSETSIFGGSKEKAVVIYNFGDFLKKLGRKKKEKERL    100
IKVLRNVKSNYVFIVYDAKLQKQELSSEPLKSVASFGGIVVANRLSKERI
KQLVLKKFKEKGINVENDALEYLLQLTGYNLMELKLEVEKLIDYASEKKI    200
LTLDEVKRVAFSVSENVNVFEFVDLLLLKDYEKALKVLDSLISFGIHPLQ
IMKILSSYALKLYTLKRLEEKGEDLNKAMESVGIKNNFLKMKFKSYLKAN    300
SKEDLKNLILSLQRIDAFSKLYFQDTVQLLRDFLTSRLEREVVKNTSHGG
```

FIG. 41

```
ATGGAAAAAGTTTTTTTGGAAAAACTCCAGAAAACCTTGCACATACCCGG
AGGACTCCTTTTTTACGGCAAAGAAGGAAGCGGAAAGACGAAAACAGCTT    100
TTGAATTTGCAAAAGGTATTTTATGTAAGGAAAACGTACCTGGGGATGCG
GAAGTTGTCCCTCCTGCAAACACGTAAACGAGCTGGAGGAAGCCTTCTTT    200
AAAGGAGAAATAGAAGACTTTAAAGTTTATAAGACAAGGACGGTAAAAAG
CACTTCGTTTACCTTATGGGCGAACATCCCGACTTTGTGGTAATAATCCC    300
GAGCGGACATTACATAAAGATAGAACAGATAAGGGAAGTTAAGAACTTTG
CCTATGTGAAGCCCGCACTAAGCAGGAGAAAAGTAATTATAATAGACGAC    400
GCCCACGCGATGACCTCTCAGGCGGCAAACGCTCTTTTAAAGGTATTGGA
AGAGCCACCTGCGGACACCACCTTTATCTTGACCACGAACAGGCGTTCTG    500
CAATCCTGCCGACTATCCTCTCCAGAACTTTTCAAGTGGAGTTCAAGGGC
TTTTCAGTAAAAGAGGTTATGGAAATAGCGAAAGTAGACGAGGAAATAGC    600
GAAACTCTCTGGAGGCAGTCTAAAAAGGGCTATCTTACTAAAGGAAAACA
AAGATATCCTAAACAAAGTAAAGGAATTCTTGGAAAACGAGCCGTTAAAA    700
GTTTACAAGCTTGCAAGTGAATTCGAAAAGTGGGAACCTGAAAAGCAAAA
ACTCTTCCTTGAAATTATGGAAGAATTGGTATCTCAAAAATTGACCGAAG    800
AGAAAAAAGACAATTACACCTACCTTCTTGATACGATCAGACTCTTTAAA
GACGGACTCGCAAGGGGTGTAAACGAACCTCTGTGGCTGTTTACGTTAGC    900
CGTTCAGGCGGATTAATAAACCGTTATTGATTCCGTAACATTTAAACCTT
AATCTAAATTATGAGAGCCTTTGAAGGAGGTCTGGTATGGAAAATTTGAA   1000
GATTAGATATATAGATACGAGGAAGATAGGAACCGTGAGCGGTGTAAAAG
T                                                    1051
```

FIG. 42

```
MEKVFLEKLQKTLHIPGGLLFYGKEGSGKTKTAFEFAKGILCKENVPWGC
GSCPSCKHVNELEEAFFKGEIEDFKVYKDKDGKKHFVYLMGEHPDFVVII    100
PSGHYIKIEQIREVKNFAYVKPALSRRKVIIIDDAHAMTSQAANALLKVL
EEPPADTTFILTTNRRSAILPTILSRTFQVEFKGFSVKEVMEIAKVDEEI    200
AKLSGGSLKRAILLKENKDILNKVKEFLENEPLKVYKLASEFEKWEPEKQ
KLFLEIMEELVSQKLTEEKKDNYTYLLDTIRLFKDGLARGVNEPLWLFTL    300
AVQAD
```

FIG. 43

ATGAACTTCCTGAAAAAGTTCCTTTTACTGAGAAAAGCTCAAAAGTCTCC
TTACTTCGAAGAGTTCTACGAAGAAATCGATTTGAACCAGAAGGTGAAAG 100
ATGCAAGGTTTGTAGTTTTTGACTGCGAAGCCACAGAACTCGACGTAAAG
AAGGCAAAACTCCTTTCAATAGGTGCGGTTGAGGTTAAAAACCTGGAAAT 200
AGACCTCTCTAAATCTTTTTACGAGATACTCAAAAGTGACGAGATAAAGG
CGGCGGAGATACATGGAATAACCAGGGAAGACGTTGAAAAGTACGGAAAG 300
GAACCAAAGGAAGTAATATACGACTTTCTGAAGTACATAAAGGGAAGCGT
TCTCGTTGGCTACTACGTGAAGTTTGACGTCTCACTCGTTGAGAAGTACT 400
CCATAAAGTACTTCCAGTATCCAATCATCAACTACAAGTTAGACCTGTTT
AGTTTCGTGAAGAGAGAGTACCAGAGTGGCAGGAGTCTTGACGACCTTAT 500
GAAGGAACTCGGTGTAGAAATAAGGGCAAGGCACAACGCCCTTGAAGATG
CCTACATAACCGCTCTTCTTTTCCTAAAGTACGTTTACCCGAACAGGGAG 600
TACAGACTAAAGGATCTCCCGATTTTCCTT

FIG. 44

MNFLKKFLLLRKAQKSPYFEEFYEEIDLNQKVKDARFVVFDCEATELDVK
KAKLLSIGAVEVKNLEIDLSKSFYEILKSDEIKAAEIHGITREDVEKYGK 100
EPKEVIYDFLKYIKGSVLVGYYVKFDVSLVEKYSIKYFQYPIINYKLDLF
SFVKREYQSGRSLDDLMKELGVEIRARHNALEDAYITALLFLKYVYPNRE 200
YRLKDLPIFL

FIG. 45

ATGCTCAATAAGGTTTTTATAATAGGAAGACTTACGGGTGACCCCGTTAT
AACTTATCTACCGAGCGGAACGCCCGTAGTAGAGTTTACTCTGGCTTACA 100
ACAGAAGGTATAAAAACCAGAACGGTGAATTTCAGGAGGAAAGTCACTTC
TTTGACGTAAAGGCGTACGGAAAAATGGCTGAAGACTGGGCTACACGCTT 200
CTCGAAAGGATACCTCGTACTCGTAGAGGGAAGACTCTCCCAGGAAAAGT
GGGAGAAAGAAGGAAAGAAGTTCTCAAAGGTCAGGATAATAGCGGAAAAC 300
GTAAGATTAATAAACAGGCCGAAAGGTGCTGAACTTCAAGCAGAAGAAGA
GGAGGAAGTTCCTCCCATTGAGGAGGAAATTGAAAAACTCGGTAAAGAGG 400
AAGAGAAGCCTTTTACCGATGAAGAGGACGAAATACCTTTTTAATTTTGA
GGAGGTTAAAGTATGGTAGTGAGAGCTCCTAAGAAGAAAGTTTGTATGTA 500
CTGTGAACAAAAGAGAGAGCCAGATT

FIG. 46

MLNKVFIIGRLTGDPVITYLPSGTPVVEFTLAYNRRYKNQNGEFQEESHF
FDVKAYGKMAEDWATRFSKGYLVLVEGRLSQEKWEKEGKKFSKVRIIAEN 100
VRLINRPKGAELQAEEEEEVPPIEEEIEKLGKEEEKPFTDEEDEIPF

FIG. 47

```
ATGCAATTTGTGGATAAACTTCCCTGTGACGAATCCGCCGAGAGGGCGGT
TCTTGGCAGTATGCTTGAAGACCCCGAAAACATACCTCTGGTACTTGAAT      100
ACCTTAAAGAAGAAGACTTCTGCATAGACGAGCACAAGCTACTTTTCAGG
GTTCTTACAAACCTCTGGTCCGAGTACGGCAATAAGCTCGATTTCGTATT      200
AATAAAGGATCACCTTGAAAAGAAAAACTTACTCCAGAAAATACCTATAG
ACTGGCTCGAAGAACTCTACGAGGAGGCGGTATCCCCTGACACGCTTGAG      300
GAAGTCTGCAAAATAGTAAAACAACGTTCCGCACAGAGGGCGATAATTCA
ACTCGGTATAGAACTCATTCACAAAGGAAAGGAAAACAAAGACTTTCACA      400
CATTAATCGAGGAAGCCCAGAGCAGGATATTTTCCATAGCGGAAAGTGCT
ACATCTACGCAGTTTTACCATGTGAAAGACGTTGCGGAAGAAGTTATAGA      500
ACTCATTTATAAATTCAAAAGCTCTGACAGGCTAGTCACGGGACTCCCAA
GCGGTTTCACGGAACTCGATCTAAAGACGACGGGATTCCACCCTGGAGAC      600
TTAATAATACTCGCCGCAAGACCCGGTATGGGGAAAACCGCCTTTATGCT
CTCCATAATCTACAATCTCGCAAAAGACGAGGGAAAACCCTCAGCTGTAT      700
TTTCCTTGGAAATGAGCAAGGAACAGCTCGTTATGAGACTCCTCTCTATG
ATGTCGGAGGTCCCACTTTTCAAGATAAGGTCTGGAAGTATATCGAATGA      800
AGATTTAAAGAAGCTTGAAGCAAGCGCAATAGAACTCGCAAAGTACGACA
TATACCTCGACGACACACCCGCTCTCACTACAACGGATTTAAGGATAAGG      900
GCAAGAAAGCTCAGAAAGGAAAAGGAAGTTGAGTTCGTGGCGGTGGACTA
CTTGCAACTTCTGAGACCGCCAGTCCGAAAGAGTTCAAGACAGGAGGAAG      1000
TGGCAGAGGTTTCAAGAAACTTAAAAGCCCTTGCAAAGGAACTTCACATT
CCCGTTATGGCACTTGCGCAGCTCTCCCGTGAGGTGGAAAAGAGGAGTGA      1100
TAAAAGACCCCAGCTTGCGGACCTCAGAGAATCCGGACAGATAGAACAGG
ACGCAGACCTAATCCTTTTCCTCCACAGACCCGAGTACTACAAGAAAAAG      1200
CCAAATCCCGAAGAGCAGGGTATAGCGGAAGTGATAATAGCCAAGCAAAG
GCAAGGACCCACGGACATTGTGAAGCTCGCATTTATTAAGGAGTACACTA      1300
AGTTTGCAAACCTAGAAGCCCTTCCTGAACAACCTCCTGAAGAAGAGGAA
CTTTCCGAAATTATTGAAACACAGGAGGATGAAGGATTCGAAGATATTGA      1400
CTTCTGAAAATTAAGGTTTTATAATTTTATCTTGGCTATCCGGGGTAGCT
CAATCGGCAGAGCGGGTGGCTG                                  1472
```

FIG. 48

```
MQFVDKLPCDESAERAVLGSMLEDPENIPLVLEYLKEEDFCIDEHKLLFR
VLTNLWSEYGNKLDFVLIKDHLEKKNLLQKIPIDWLEELYEEAVSPDTLE      100
EVCKIVKQRSAQRAIIQLGITSTQFYHVKDVAEEVIELIYKFKSSDRLVT
GLPSGFTELDLKTTGFHPGDLIILAARPGMGKTAFMLSIIYNLAKDEGKP      200
SAVFSLEMSKEQLVMRLLSMMSEVPLFKIRSGSISNEDLKKLEASAIELA
KYDIYLDDTPALTTTDLRIRARKLRKEKEVEFVAVDYLQLLRPPVRKSSR      300
QEEVAEVSRNLKALAKELHIPVMALAQLSREVEKRSDKRPQLADLRESGQ
IEQDADLILFLHRPEYYKKKPNPEEQGIAEVIIAKQRQGPTDIVKLAFIK      400
EYTKFANLEALPEQPPEEEELSEIIETQEDEGFEDIDF
```

FIG. 49

ATGTCCTCGGACATAGACGAACTTAGACGGGAAATAGATATAGTAGACGT
CATTTCCGAATACTTAAACTTAGAGAAGGTAGGTTCCAATTACAGAACGA 100
ACTGTCCCTTTCACCCTGACGATACACCCTCCTTTTACGTGTCTCCAAGT
AAACAAATATTCAAGTGTTTCGGTTGCGGGGTAGGGGGAGACGCGATAAA 200
GTTCGTTTCCCTTTACGAGGACATCTCCTATTTTGAAGCCGCCCTTGAAC
TCGCAAAACGCTACGGAAAGAAATTAGACCTTGAAAAGATATCAAAAGAC 300
GAAAAGGTATACGTGGCTCTTGACAGGGTTTGTGATTTCTACAGGGAAAG
CCTTCTCAAAAACAGAGAGGCAAGTGAGTACGTAAAGAGTAGGGGAATAG 400
ACCCTAAAGTAGCGAGGAAGTTTGATCTTGGGTACGCACCTTCCAGTGAA
GCACTCGTAAAAGTCTTAAAAGAGAACGATCTTTTAGAGGCTTACCTTGA 500
AACTAAAAACCTCCTTTCTCCTACGAAGGGTGTTTACAGGGATCTCTTTC
TTCGGCGTGTCGTGATCCCGATAAAGGATCCGAGGGGAAGAGTTATAGGT 600
TTCGGTGGAAGGAGGATAGTAGAGGACAAATCTCCCAAGTACATAAACTC
TCCAGACAGCAGGGTATTTAAAAAGGGGGAGAACTTATTCGGTCTTTACG 700
AGGCAAAGGAGTATATAAAGGAAGAAGGATTTGCGATACTTGTGGAAGGG
TACTTTGACCTTTTGAGACTTTTTTCCGAGGGAATAAGGAACGTTGTTGC 800
ACCCCTCGGTACAGCCCTGACCCAAAATCAGGCAAACCTCCTTTCCAAGT
TCACAAAAAAGGTCTACATCCTTTACGACGGAGATGATGCGGGAAGAAAG 900
GCTATGAAAAGTGCCATTCCCCTACTCCTCAGTGCAGGAGTGGAAGTTTA
TCCCGTTTACCTCCCCGAAGGATACGATCCCGACGAGTTTATAAAGGAAT 1000
TCGGGAAAGAGGAATTAAGAAGACTGATAAACAGCTCAGGGGAGCTCTTT
GAAACGCTCATAAAAACCGCAAGGGAAAACTTAGAGGAGAAAACGCGTGA 1100
GTTCAGGTATTATCTGGGCTTTATTTCCGATGGAGTAAGGCGCTTTGCTC
TGGCTTCGGAGTTTCACACCAAGTACAAAGTTCCTATGGAAATTTTATTA 1200
ATGAAAATTGAAAAAAATTCTCAAGAAAAAGAAATTAAACTCTCCTTTAA
GGAAAAAATCTTCCTGAAAGGACTGATAGAATTAAAACCAAAAATAGACC 1300
TTGAAGTCCTGAACTTAAGTCCTGAGTTAAAGGAACTCGCAGTTAACGCC
TTAAACGGAGAGGAGCATTTACTTCCAAAAGAAGTTCTCGAGTACCAGGT 1400
GGATAACTTGGAGAAACTTTTTAACAACATCCTTAGGGATTTACAAAAAT
CTGGGAAAAAGAGGAAGAAAAGAGGGTTGAAAAATGTAAATACTTAATTA 1500
ACTTTAATAAATTTTTAGAGTTAGGA

FIG. 50

MSSDIDELRREIDIVDVISEYLNLEKVGSNYRTNCPFHPDDTPSFYVSPS
KQIFKCFGCGVGGDAIKFVSLYEDISYFEAALELAKRYGKKLDLEKISKD 100
EKVYVALDRVCDFYRESLLKNREASEYVKSRGIDPKVARKFDLGYAPSSE
ALVKVLKENDLLEAYLETKNLLSPTKGVYRDLFLRRVVIPIKDPRGRVIG 200
FGGRRIVEDKSPKYINSPDSRVFKKGENLFGLYEAKEYIKEEGFAILVEG
YFDLLRLFSEGIRNVVAPLGTALTQNQANLLSKFTKKVYILYDGDDAGRK 300
AMKSAIPLLLSAGVEVYPVYLPEGYDPDEFIKEFGKEELRRLINSSGELF
ETLIKTARENLEEKTREFRYYLGFISDGVRRFALASEFHTKYKVPMEILL 400
MKIEKNSQEKEIKLSFKEKIFLKGLIELKPKIDLEVLNLSPELKELAVNA
LNGEEHLLPKEVLEYQVDNLEKLFNNILRDLQKSGKKRKKRGLKNVNT 498

FIG. 51

ATGCAAGATACCGCTACCTGCAGTATTTGTCAGGGGACGGGATTCGTAAA
GACCGAAGACAACAAGGTAAGGCTCTGCGAATGCAGGTTCAAGAAAAGGG 100
ATGTAAACAGGGAACTAAACATCCCAAAGAGGTACTGGAACGCCAACTTA
GACACTTACCACCCCAAGAACGTATCCCAGAACAGGGCACTTTTGACGAT 200
AAGGGTCTTCGTCCACAACTTCAATCCCGAGGAAGGGAAAGGGCTTACCT
TTGTAGGATCTCCTGGAGTCGGCAAAACTCACCTTGCGGTTGCAACATTA 300
AAAGCGATTTATGAGAAGAAGGGAATCAGAGGATACTTCTTCGATACGAA
GGATCTAATATTCAGGTTAAAACACTTAATGGACGAGGGAAAGGATACAA 400
AGTTTTTAAAAACTGTCTTAAACTCACCGGTTTTGGTTCTCGACGACCTC
GGTTCTGAGAGGCTCAGTGACTGGCAGAGGGAACTCATCTCTTACATAAT 500
CACTTACAGGTATAACAACCTTAAGAGCACGATAATAACCACGAATTACT
CACTCCAGAGGGAAGAAGAGAGTAGCGTGAGGATAAGTGCGGATCTTGCA 600
AGCAGACTCGGAGAAAACGTAGTTTCAAAAATTTACGAGATGAACGAGTT
GCTCGTTATAAAGGGTTCCGACCTCAGGAAGTCTAAAAAGCTATCAACCC 700
CATCT

FIG. 52

MQDTATCSICQGTGFVKTEDNKVRLCECRFKKRDVNRELNIPKRYWNANL
DTYHPKNVSQNRALLTIRVFVHNFNPEEGKGLTFVGSPGVGKTHLAVATL 100
KAIYEKKGIRGYFFDTKDLIFRLKHLMDEGKDTKFLKTVLNSPVLVLDDL
GSERLSDWQRELISYIITYRYNNLKSTIITTNYSLQREEESSVRISADLA 200
SRLGENVVSKIYEMNELLVIKGSDLRKSKKLSTPS

FIG. 53

```
ATGAAAAAGATTGAAAATTTGAAGTGGAAAAATGTCTCGTTTAAAAGCCT
GGAAATAGATCCCGATGCAGGTGTGGTTCTCGTTTCCGTGGAAAAATTCT    100
CCGAAGAGATAGAAGACCTTGTGCGTTTACTGGAGAAGAAGACGCGGTTT
CGAGTCATCGTGAACGGTGTTCAAAAAAGTAACGGGGATCTAAGGGGAAA    200
GATACTTTCCCTTCTCAACGGTAATGTGCCTTACATAAAAGATGTTGTTT
TCGAAGGAAACAGGCTGATTCTGAAAGTGCTTGGAGATTTCGCGCGGGAC    300
AGGATCGCCTCCAAACTCAGAAGCACGAAAAAACAGCTCGATGAACTGCT
GCCTCCCGGAACAGAGATCATGCTGGAGGTTGTGGAGCCTCCGGAAGATC    400
TTTTGAAAAAGGAAGTACCACAACCAGAAAAGAGAGAAGAACCAAAGGGT
GAAGAATTGAAGATCGAGGATGAAAACCACATCTTTGGACAGAAACCCAG    500
AAAGATCGTCTTCACCCCCTCAAAAATCTTTGAGTACAACAAAAAGACAT
CGGTGAAGGGCAAGATCTTCAAAATAGAGAAGATCGAGGGGAAAAGAACG    600
GTCCTTCTGATTTACCTGACAGACGGAGAAGATTCTCTGATCTGCAAAGT
CTTCAACGACGTTGAAAAGGTCGAAGGGAAAGTATCGGTGGGAGACGTGA    700
TCGTTGCCACAGGAGACCTCCTTCTCGAAAACGGGGAGCCCACCCTTTAC
GTGAAGGGAATCACAAAACTTCCCGAAGCGAAAAGGATGGACAAATCTCC    800
GGTTAAGAGGGTGGAGCTCCACGCCCATACCAAGTTCAGCGATCAGGACG
CAATAACAGATGTGAACGAATATGTGAAACGAGCCAAGGAATGGGGCTTT    900
CCCGCGATAGCCCTCACGGATCATGGGAACGTTCAGGCCATACCTTACTT
CTACGACGCGGCGAAAGAAGCTGGAATAAAGCCCATTTTCGGTATCGAAG   1000
CGTATCTGGTGAGTGACGTGGAGCCCGTCATAAGGAATCTCTCCGACGAT
TCGACGTTTGGAGATGCCACGTTCGTCGTCCTCGACTTCGAGACGACGGG   1100
TCTCGACCCGCAGGTGGATGAGATCATCGAGATAGCAGCGGTGAAGATAC
AGGGTGGCCAGATAGTGGACGAGTACCACACTCTCATAAAGCCTTCCAGG   1200
GAGATCTCAAGAAAAAGTTCGGAGATCACCGGAATCACTCAAGAGATGCT
GGAAAACAAGAGAAGCATCGAGGAAGTTCTGCCGGAGTTCCTCGGTTTTC   1300
TGGAAGATTCCATCATCGTAGCACACAACGCCAACTTCGACTACAGATTT
CTGAGGCTGTGGATCAAAAAAGTGATGGGATTGGACTGGAAAGACCCTA   1400
CATAGATACGCTCGCCCTCGCAAAGTCCCTTCTCAAACTGAGAAGCTACT
CTCTGGATTCCGTTGTGGAAAAGCTCGGATTGGGTCCCTTCCGGCACCAC   1500
AGGGCCCTGGATGACGCGAGGGTCACCGCTCAGGTTTTCCTCAGGTTCGT
TGAGATGATGAAGAAGATCGGTATCACGAAGCTTTCAGAAATGGAGAAGT   1600
TGAAGGATACGATAGACTACACCGCGTTGAAACCCTTCCACTGCACGATC
CTCGTTCAGAACAAAAAGGGATTGAAAAACCTATACAAACTGGTTTCTGA   1700
TTCCTATATAAAGTACTTCTACGGTGTTCCGAGGATCCTCAAAAGTGAGC
TCATCGAGAACAGAGAAGGACTGCTCGTGGGTAGCGCGTGTATCTCCGGT   1800
GAGCTCGGACGTGCCGCCCTCGAAGGAGCGAGTGATTCAGAACTCGAAGA
GATCGCGAAGTTCTACGACTACATAGAAGTCATGCCGCTCGACGTTATAG   1900
CCGAAGATGAAGAAGACCTAGACAGAGAAAGACTGAAAGAAGTGTACCGA
AAACTCTACAGAATAGCGAAAAAATTGAACAAGTTCGTCGTCATGACCGG   2000
TGATGTTCATTTCCTCGATCCCGAAGATGCCAGGGGCAGAGCTGCACTTC
TGGCACCTCAGGGAAACAGAAACTTCGAGAATCAGCCCGCACTCTACCTC   2100
AGAACGACCGAAGAAATGCTCGAGAAGGCGATAGAGATATTCGAAGATGA
AGAGATCGCGAGGGAAGTCGTGATAGAGAATCCCAACAGAATAGCCGATA   2200
TGATCGAGGAAGTGCAGCCGCTCGAGAAAAAACTTCACCCGCCGATCATA
GAGAACGCCGATGAAATAGTGAGAAACCTCACCATGAAGCGGCGTACGA   2300
GATCTACGGTGATCCGCTTCCCGAAATCGTCCAGAAGCGTGTGGAAAAGG
```

FIG. 54A

AACTGAACGCCATCATAAATCATGGATACGCCGTTCTCTATCTCATCGCT 2400
CAGGAGCTCGTTCAGAAATCTATGAGCGATGGTTACGTGGTTGGATCCAG
AGGATCCGTCGGGTCTTCACTCGTGGCCAATCTCCTCGGAATAACAGAGG 2500
TGAATCCCCTACCACCACATTACAGGTGTCCAGAGTGCAAATACTTTGAA
GTTGTCGAAGACGACAGATACGGAGCGGGTTACGACCTTCCCAACAAGAA 2600
CTGTCCAAGATGTGGGGCTCCTCTCAGAAAAGACGGCCACGGCATACCGT
TTGAAACGTTCATGGGGTTCGAGGGTGACAAGGTCCCCGACATAGATCTC 2700
AACTTCTCAGGAGAGTATCAGGAACGTGCTCATCGTTTTGTGGAAGAACT
CTTCGGTAAAGACCACGTCTATAGGGCGGGAACCATAAACACCATCGCGG 2800
AAAGAAGTGCGGTGGGTTACGTGAGAAGCTACGAAGAGAAAACCGGAAAG
AAGCTCAGAAAGGCGGAAATGGAAAGACTCGTTTCCATGATCACGGGAGT 2900
GAAGAGAACGACGGGTCAGCACCCAGGGGGGCTCATGATCATACCGAAAG
ACAAAGAAGTCTACGATTTCACTCCCATACAGTATCCAGCCAACGATAGA 3000
AACGCAGGTGTGTTCACCACGCACTTCGCATACGAGACGATCCATGATGA
CCTGGTGAAGATAGATGCGCTCGGCCACGATGATCCCACTTTCATCAAGA 3100
TGCTCAAGGACCTCACCGGAATCGATCCCATGACGATTCCCATGGATGAC
CCCGATACGCTCGCCATATTCAGTTCTGTGAAGCCTCTTGGTGTGGATCC 3200
CGTTGAGCTGGAAAGCGATGTGGGAACGTACGGAATTCCGGAGTTCGGAA
CCGAGTTTGTGAGGGGAATGCTCGTTGAAACGAGACCAAAGAGTTTCGCC 3300
GAGCTTGTGAGAATCTCAGGACTGTCACACGGTACGGACGTCTGGTTGAA
CAACGCACGTGATTGGATAAACCTCGGCTACGCCAAGCTCTCCGAGGTTA 3400
TCTCGTGTAGGGACGACATCATGAACTTCCTCATACACAAAGGAATGGAA
CCGTCACTTGCCTTCAAGATCATGGAAAACGTCAGGAAGGGAAAGGGTAT 3500
CACAGAAGAGATGGAGAGCGAGATGAGAAGGCTGAAGGTTCCAGAATGGT
TCATCGAATCCTGTAAAAGGATCAAATATCTCTTCCCGAAAGCTCACGCT 3600
GTGGCTTACGTGAGTATGGCCTTCAGAATTGCTTACTTCAAGGTTCACTA
TCCTCTTCAGTTTTACGCGGCGTACTTCACGATAAAAGGTGATCAGTTCG 3700
ATCCGGTTCTCGTACTCAGGGGAAAAGAAGCCATAAAGAGGCGCTTGAGA
GAACTCAAAGCGATGCCTGCCAAAGACGCCCAGAAGAAAAACGAAGTGAG 3800
TGTTCTGGAGGTTGCCCTGGAAATGATACTGAGAGGTTTTTCCTTCCTAC
CGCCCGACATCTTCAAATCCGACGCGAAGAAATTTCTGATAGAAGGAAAC 3900
TCGCTGAGAATTCCGTTCAACAAACTTCCAGGACTGGGTGACAGCGTTGC
CGAGTCGATAATCAGAGCCAGGGAAGAAAAGCCGTTCACTTCGGTGGAAG 4000
ATCTCATGAAGAGGACCAAGGTCAACAAAAATCACATAGAGCTGATGAAA
AGCCTGGGTGTTCTCGGGGACCTTCCAGAGACGGAACAGTTCACGCTTTT 4100
C

FIG. 54B

MKKIENLKWKNVSFKSLEIDPDAGVVLVSVEKFSEEIEDLVRLLEKKTRF
RVIVNGVQKSNGDLRGKILSLLNGNVPYIKDVVFEGNRLILKVLGDFARD 100
RIASKLRSTKKQLDELLPPGTEIMLEVVEPPEDLLKKEVPQPEKREEPKG
EELKIEDENHIFGQKPRKIVFTPSKIFEYNKKTSVKGKIFKIEKIEGKRT 200
VLLIYLTDGEDSLICKVFNDVEKVEGKVSVGDVIVATGDLLLENGEPTLY
VKGITKLPEAKRMDKSPVKRVELHAHTKFSDQDAITDVNEYVKRAKEWGF 300
PAIALTDHGNVQAIPYFYDAAKEAGIKPIFGIEAYLVSDVEPVIRNLSDD
STFGDATFVVLDFETTGLDPQVDEIIEIGAVKIQGGQIVDEYHTLIKPSR 400
EISRKSSEITGITQEMLENKRSIEEVLPEFLGFLEDSIIVAHNANFDYRF
LRLWIKKVMGLDWERPYIDTLALAKSLLKLRSYSLDSVVEKLGLGPFRHH 500
RALDDARVTAQVFLRFVEMMKKIGITKLSEMEKLKDTIDYTALKPFHCTI
LVQNKKGLKNLYKLVSDSYIKYFYGVPRILKSELIENREGLLVGSACISG 600
ELGRAALEGASDSELEEIAKFYDYIEVMPLDVIAEDEEDLDRERLKEVYR
KLYRIAKKLNKFVVMTGDVHFLDPEDARGRAALLAPQGNRNFENQPALYL 700
RTTEEMLEKAIEIFEDEEIAREVVIENPNRIADMIEEVQPLEKKLHPPII
ENADEIVRNLTMKRAYEIYGDPLPEIVQKRVEKELNAIINHGYAVLYLIA 800
QELVQKSMSDGYVVGSRGSVGSSLVANLLGITEVNPLPPHYRCPECKYFE
VVEDDRYGAGYDLPNKNCPRCGAPLRKDGHGIPFETFMGFEGDKVPDIDL 900
NFSGEYQERAHRFVEELFGKDHVYRAGTINTIAERSAVGYVRSYEEKTGK
KLRKAEMERLVSMITGVKRTTGQHPGGLMIIPKDKEVYDFTPIQYPANDR 1000
NAGVFTTHFAYETIHDDLVKIDALGHDDPTFIKMLKDLTGIDPMTIPMDD
PDTLAIFSSVKPLGVDPVELESDVGTYGIPEFGTEFVRGMLVETRPKSFA 1100
ELVRISGLSHGTDVWLNNARDWINLGYAKLSEVISCRDDIMNFLIHKGME
PSLAFKIMENVRKGKGITEEMESEMRRLKVPEWFIESCKRIKYLFPKAHA 1200
VAYVSMAFRIAYFKVHYPLQFYAAYFTIKGDQFDPVLVLRGKEAIKRRLR
ELKAMPAKDAQKKNEVSVLEVALEMILRGFSFLPPDIFKSDAKKFLIEGN 1300
SLRIPFNKLPGLGDSVAESIIRAREEKPFTSVEDLMKRTKVNKNHIELMK
SLGVLGDLPETEQFTLF 1367

FIG. 55

```
GTGCTCGCCATGATATGGAACGACACCGTTTTTTGCGTCGTAGACACAGA
AACCACGGGAACCGATCCCTTTGCCGGAGACCGGATAGTTGAAATAGCCG   100
CTGTTCCTGTCTTCAAGGGGAAGATCTACAGAAACAAAGCGTTTCACTCT
CTCGTGAATCCCAGAATAAGAATCCCTGCGCTGATTCAGAAAGTTCACGG   200
TATCAGCAACATGGACATCGTGGAAGCGCCAGACATGGACACAGTTTACG
ATCTTTTCAGGGATTACGTGAAGGGAACGGTGCTCGTGTTTCACAACGCC   300
AACTTCGACCTCACTTTTCTGGATATGATGGCAAAGGAAACGGGAAACTT
TCCAATAACGAATCCCTACATCGACACACTCGATCTTTCAGAAGAGATCT   400
TTGGAAGGCCTCATTCTCTCAAATGGCTCTCCGAAAGACTTGGAATAAAA
ACCACGATACGGCACCGTGCTCTTCCAGATGCCCTGGTGACCGCAAGAGT   500
TTTTGTGAAGCTTGTTGAATTTCTTGGTGAAAACAGGGTCAACGAATTCA
TACGTGGAAAACGGGGG                                    567
```

FIG. 56

```
MLAMIWNDTVFCVVDTETTGTDPFAGDRIVEIAAVPVFKGKIYRNKAFHS
LVNPRIRIPALIQKVHGISNMDIVEAPDMDTVYDLFRDYVKGTVLVFHNA   100
NFDLTFLDMMAKETGNFPITNPYIDTLDLSEEIFGRPHSLKWLSERLGIK
TTIRHRALPDALVTARVFVKLVEFLGENRVNEFIRGKRG              189
```

FIG. 57

```
GTGGAAGTTCTTTACAGGAAGTACAGGCCAAAGACTTTTTCTGAGGTTGT
CAATCAGGATCATGTGAAGAAGGCAATAATCGGTGCTATTCAGAAGAACA   100
GCGTGGCCCACGGATACATATTCGCCGGTCCGAGGGGAACGGGGAAGACT
ACTCTTGCCAGAATTCTCGCAAAATCCCTGAACTGTGAGAACAGAAAGGG   200
AGTTGAACCCTGCAATTCCTGCAGAGCCTGCAGAGAGATAGACGAGGGAA
CCTTCATGGACGTGATAGAGCTCGACGCGGCCTCCAACAGAGGAATAGAC   300
GAGATCAGAAGAATCAGAGACGCCGTTGGATACAGGCCGATGGAAGGTAA
ATACAAAGTCTACATAATAGACGAAGTTCACATGCTCACGAAAGAAGCCT   400
TCAACGCGCTCCTCAAAACACTCGAAGAACCTCCTTCCCACGTCGTGTTC
GTGCTGGCAACGACAAACCTTGAGAAGGTTCCTCCCACGATTATCTCGAG   500
ATGTCAGGTTTTCGAGTTCAGAAACATTCCCGACGAGCTCATCGAAAAGA
GGCTCCAGGAAGTTGCGGAGGCTGAAGGAATAGAGATAGACAGGGAAGCT   600
CTGAGCTTCATCGCAAAAAGAGCCTCTGGAGGCTTGAGAGACGCGCTCAC
CATGCTCGAGCAGGTGTGGAAGTTCTCGGAAGGAAAGATAGATCTCGAGA   700
CGGTACACAGGGCGCTCGGGTTGATACCGATACAGGTTGTTCGCGATTAC
GTGAACGCTATCTTTTCTGGTGATGTGAAAAGGGTCTTCACCGTTCTCGA   800
CGACGTCTATTACAGCGGGAAGGACTACGAGGTGCTCATTCAGGAAGCAG
TCGAGGATCTGGTCGAAGACCTGGAAAGGGAGAGAGGGGTTTACCAGGTT   900
TCAGCGAACGATATAGTTCAGGTTTCGAGACAACTTCTGAATCTTCTGAG
AGAGATAAAGTTCGCCGAAGAAAAACGACTCGTCTGTAAAGTGGGTTCGG  1000
CTTACATAGCGACGAGGTTCTCCACCACAAACGTTCAGGAAAACGATGTC
AGAGAAAAAAACGATAATTCAAATGTACAGCAGAAAGAAGAGAAGAAAGA  1100
AACGGTGAAGGCAAAAGAAGAAAAACAGGAAGACAGCGAGTTCGAGAAAC
GCTTCAAAGAACTCATGGAAGAACTGAAAGAAAAGGGCGATCTCTCTATC  1200
TTTGTCGCTCTCAGCCTCTCAGAGGTGCAGTTTGACGGAGAAAAGGTGAT
TATTTCTTTTGATTCATCGAAAGCTATGCATTACGAGTTGATGAAGAAAA  1300
AACTGCCTGAGCTGGAAAACATTTTTTCTAGAAAACTCGGGAAAAAAGTA
GAAGTTGAACTTCGACTGATGGGAAAAGAAGAAACAATCGAGAAGGTTTC  1400
TCAGAAGATCCTGAGATTGTTTGAACAGGAGGGA
```

FIG. 58

```
MEVLYRKYRPKTFSEVVNQDHVKKAIIGAIQKNSVAHGYIFAGPRGTGKT
TLARILAKSLNCENRKGVEPCNSCRACREIDEGTFMDVIELDAASNRGID   100
EIRRIRDAVGYRPMEGKYKVYIIDEVHMLTKEAFNALLKTLEEPPSHVVF
VLATTNLEKVPPTIISRCQVFEFRNIPDELIEKRLQEVAEAEGIEIDREA   200
LSFIAKRASGGLRDALTMLEQVWKFSEGKIDLETVHRALGLIPIQVVRDY
VNAIFSGDVKRVFTVLDDVYYSGKDYEVLIQEAVEDLVEDLERERGVYQV   300
SANDIVQVSRQLLNLLREIKFAEEKRLVCKVGSAYIATRFSTTNVQENDV
REKNDNSNVQQKEEKKETVKAKEEKQEDSEFEKRFKELMEELKEKGDLSI   400
FVALSLSEVQFDGEKVIISFDSSKAMHYELMKKKLPELENIFSRKLGKKV
EVELRLMGKEETIEKVSQKILRLFEQEG                         478
```

FIG. 59

```
ATGAAAGTAACCGTCACGACTCTTGAATTGAAAGACAAAATAACCATCGC
CTCAAAAGCGCTCGCAAAGAAATCCGTGAAACCCATTCTTGCTGGATTTC    100
TTTTCGAAGTGAAAGATGGAAATTTCTACATCTGCGCGACCGATCTCGAG
ACCGGAGTCAAAGCAACCGTGAATGCCGCTGAAATCTCCGGTGAGGCACG    200
TTTTGTGGTACCAGGAGATGTCATTCAGAAGATGGTCAAGGTTCTCCCAG
ATGAGATAACGGAACTTTCTTTAGAGGGGGATGCTCTTGTTATAAGTTCT    300
GGAAGCACCGTTTTCAGGATCACCACCATGCCCGCGGACGAATTTCCAGA
GATAACGCCTGCCGAGTCTGGAATAACCTTCGAAGTTGACACTTCGCTCC    400
TCGAGGAAATGGTTGAAAAGGTCATCTTCGCCGCTGCCAAAGACGAGTTC
ATGCGAAATCTGAATGGAGTTTTCTGGGAACTCCACAAGAATCTTCTCAG    500
GCTGGTTGCAAGTGATGGTTTCAGACTTGCACTTGCTGAAGAGCAGATAG
AAAACGAGGAAGAGGCGAGTTTCTTGCTCTCTTTGAAGAGCATGAAAGAA    600
GTTCAAAACGTGCTGGACAACACAACGGAGCCGACTATAACGGTGAGGTA
CGATGGAAGAAGGGTTTCTCTGTCGACAAATGATGTAGAAACGGTGATGA    700
GAGTGGTCGACGCTGAATTTCCCGATTACAAAAGGGTGATCCCCGAAACT
TTCAAAACGAAAGTGGTGGTTTCCAGAAAAGAACTCAGGGAATCTTTGAA    800
GAGGGTGATGGTGATTGCCAGCAAGGGAAGCGAGTCCGTGAAGTTCGAAA
TAGAAGAAAACGTTATGAGACTTGTGAGCAAGAGCCCGGATTATGGAGAA    900
GTGGTCGATGAAGTTGAAGTTCAAAAAGAAGGGGAAGATCTCGTGATCGC
TTTCAACCCGAAGTTCATCGAGGACGTTTTGAAGCACATTGAGACTGAAG   1000
AAATCGAAATGAACTTCGTTGATTCTACCAGTCCATGTCAGATAAATCCA
CTCGATATTTCTGGATACCTTTACATAGTGATGCCCATCAGACTGGCA     1098
```

FIG. 60

```
MKVTVTTLELKDKITIASKALAKKSVKPILAGFLFEVKDGNFYICATDLE
TGVKATVNAAEISGEARFVVPGDVIQKMVKVLPDEITELSLEGDALVISS    100
GSTVFRITTMPADEFPEITPAESGITFEVDTSLLEEMVEKVIFAAAKDEF
MRNLNGVFWELHKNLLRLVASDGFRLALAEEQIENEEEASFLLSLKSMKE    200
VQNVLDNTTEPTITVRYDGRRVSLSTNDVETVMRVVDAEFPDYKRVIPET
FKTKVVVSRKELRESLKRVMVIASKGSESVKFEIEENVMRLVSKSPDYGE    300
VVDEVEVQKEGEDLVIAFNPKFIEDVLKHIETEEIEMNFVDSTSPCQINP
LDISGYLYIVMPIRLA                                      366
```

FIG. 61

```
ATGCCAGTCACGTTTCTCACAGGTACTGCAGAAACTCAGAAGGAAGAATT
GATAAAGAAACTCCTGAAGGATGGTAACGTGGAGTACATAAGGATCCATC     100
CGGAGGATCCCGACAAGATCGATTTCATAAGGTCTTTACTCAGGACAAAG
ACGATCTTTTCCAACAAGACGATCATTGACATCGTCAATTTCGATGAGTG     200
GAAAGCACAGGAGCAGAAGCGTCTCGTTGAACTTTTGAAAAACGTACCGG
AAGACGTTCATATCTTCATCCGTTCTCAAAAAACAGGTGGAAAGGGAGTA     300
GCGCTGGAGCTTCCGAAGCCATGGGAAACGGACAAGTGGCTTGAGTGGAT
AGAAAAGCGCTTCAGGGAGAATGGTTTGCTCATCGATAAAGATGCCCTTC     400
AGCTGTTTTTCTCCAAGGTTGGAACGAACGACCTGATCATAGAAAGGGAG
ATTGAAAAACTGAAAGCTTATTCCGAGGACAGAAAGATAACGGTAGAAGA     500
CGTGGAAGAGGTCGTTTTTACCTATCAGACTCCGGGATACGATGATTTTT
GCTTTGCTGTTTCCGAAGGAAAAAGGAAGCTCGCTCACTCTCTTCTGTCG     600
CAGCTGTGGAAAACCACAGAGTCCGTGGTGATTGCCACTGTCCTTGCGAA
TCACTTCTTGGATCTCTTCAAAATCCTCGTTCTTGTGACAAAGAAAAGAT     700
ACTACACCTGGCCTGATGTGTCCAGGGTGTCCAAAGAGCTGGGAATTCCC
GTTCCTCGTGTGGCTCGTTTCCTCGGTTTCTCCTTTAAGACCTGGAAATT     800
CAAGGTGATGAACCACCTCCTCTACTACGATGTGAAGAAGGTTAGAAAGA
TACTGAGGGATCTCTACGATCTGGACAGAGCCGTGAAAAGCGAAGAAGAT     900
CCAAAACCGTTCTTCCACGAGTTCATAGAAGAGGTGGCACTGGATGTATA
TTCTCTTCAGAGAGATGAAGAA                                 972
```

FIG. 62

```
MPVTFLTGTAETQKEELIKKLLKDGNVEYIRIHPEDPDKIDFIRSLLRTK
TIFSNKTIIDIVNFDEWKAQEQKRLVELLKNVPEDVHIFIRSQKTGGKGV     100
ALELPKPWETDKWLEWIEKRFRENGLLIDKDALQLFFSKVGTNDLIIERE
IEKLKAYSEDRKITVEDVEEVVFTYQTPGYDDFCFAVSEGKRKLAHSLLS     200
QLWKTTESVVIATVLANHFLDLFKILVLVTKKRYYTWPDVSRVSKELGIP
VPRVARFLGFSFKTWKFKVMNHLLYYDVKKVRKILRDLYDLDRAVKSEED     300
PKPFFHEFIEEVALDVYSLQRDEE
```

FIG. 63

```
ATGAACGATTTGATCAGAAAGTACGCTAAAGATCAACTGGAAACTTTGAA
AAGGATCATAGAAAAGTCTGAAGGAATATCCATCCTCATAAATGGAGAAG   100
ATCTCTCGTATCCGAGAGAAGTATCCCTTGAACTTCCCGAGTACGTGGAG
AAATTTCCCCCGAAGGCCTCGGATGTTCTGGAGATAGATCCCGAGGGGGA   200
GAACATAGGCATAGACGACATCAGAACGATAAAGGACTTCCTGAACTACA
GCCCCGAGCTCTACACGAGAAAGTACGTGATAGTCCACGACTGTGAAAGA   300
ATGACCCAGCAGGCGGCGAACGCGTTTCTGAAGGCCCTTGAAGAACCACC
AGAATACGCTGTGATCGTTCTGAACACTCGCCGCTGGCATTATCTACTGC   400
CGACGATAAAGAGCCGAGTGTTCAGAGTGGTTGTGAACGTTCCAAAGGAG
TTCAGAGATCTCGTGAAAGAGAAAATAGGAGATCTCTGGGAGGAACTTCC   500
ACTTCTTGAGAGAGACTTCAAAACGGCTCTCGAAGCCTACAAACTTGGTG
CGGAAAAACTTTCTGGATTGATGGAAAGTCTCAAAGTTTTGGAGACGGAA   600
AAACTCTTGAAAAAGGTCCTTTCAAAAGGCCTCGAAGGTTATCTCGCATG
TAGGGAGCTCCTGGAGAGATTTTCAAAGGTGGAATCGAAGGAATTCTTTG   700
CGCTTTTTGATCAGGTGACTAACACGATAACAGGAAAAGACGCGTTTCTT
TTGATCCAGAGACTGACAAGAATCATTCTCCACGAAAACACATGGGAAAG   800
CGTTGAAGATCAAAAAAGCGTGTCTTTCCTCGATTCAATTCTCAGGGTGA
AGATAGCGAATCTGAACAACAAACTCACTCTGATGAACATCCTCGCGATA   900
CACAGAGAGAGAAAGAGAGGTGTCAACGCTTGGAGC
```

FIG. 64

```
MNDLIRKYAKDQLETLKRIIEKSEGISILINGEDLSYPREVSLELPEYVE
KFPPKASDVLEIDPEGENIGIDDIRTIKDFLNYSPELYTRKYVIVHDCER   100
MTQQAANAFLKALEEPPEYAVIVLNTRRWHYLLPTIKSRVFRVVVNVPKE
FRDLVKEKIGDLWEELPLLERDFKTALEAYKLGAEKLSGLMESLKVLETE   200
KLLKKVLSKGLEGYLACRELLERFSKVESKEFFALFDQVTNTITGKDAFL
LIQRLTRIILHENTWESVEDKSVSFLDSILRVKIANLNNKLTLMNILAIH   300
RERKRGVNAWS
```

FIG. 65

ATGTCTTTCTTCAACAAGATCATACTCATAGGAAGACTCGTGAGAGATCC
CGAAGAGAGATACACGCTCAGCGGAACTCCAGTCACCACCTTCACCATAG 100
CGGTGGACAGGGTTCCCAGAAAGAACGCGCCGGACGACGCTCAAACGACT
GATTTCTTCAGGATCGTCACCTTTGGAAGACTGGCAGAGTTCGCTAGAAC 200
CTATCTCACCAAAGGAAGGCTCGTTCTCGTCGAAGGTGAAATGAGAATGA
GAAGATGGGAAACACCCACTGGAGAAAAGAGGGTATCTCCGGAGGTTGTC 300
GCAAACGTTGTTAGATTCATGGACAGAAAACCTGCTGAAACAGTTAGCGA
GACTGAAGAGGAGCTGGAAATACCGGAAGAAGACTTTTCCAGCGATACCT 400
TCAGTGAAGATGAACCACCATTT

FIG. 66

MSFFNKIILIGRLVRDPEERYTLSGTPVTTFTIAVDRVPRKNAPDDAQTT
DFFRIVTFGRLAEFARTYLTKGRLVLVEGEMRMRRWETPTGEKRVSPEVV 100
ANVVRFMDRKPAETVSETEEELEIPEEDFSSDTFSEDEPPF

FIG. 67

ATGCGTGTTCCCCCGCACAACTTAGAGGCCGAAGTTGCTGTGCTCGGAAG
CATATTGATAGATCCGTCGGTAATAAACGACGTTCTTGAAATTTTGAGCC 100
ACGAAGATTTCTATCTGAAAAAACACCAACACATCTTCAGAGCGATGGAA
GAGCTTTACGACGAAGGAAAACCGGTGGACGTGGTTTCCGTCTGTGACAA 200
GCTTCAAAGCATGGGAAAACTCGAGGAAGTAGGTGGAGATCTGGAAGTGG
CCCAGCTCGCTGAGGCTGTGCCCAGTTCTGCACACGCACTTCACTACGCG 300
GAGATCGTCAAGGAAAAATCCATTCTGAGGAAACTCATTGAGATCTCCAG
AAAAATCTCAGAAAGTGCCTACATGGAAGAAGATGTGGAGATCCTGCTCG 400
ACAACGCAGAAAAGATGATCTTCGAGATCTCAGAGATGAAAACGACAAAA
TCCTACGATCATCTGAGAGGCATCATGCACCGGGTGTTTGAAAACCTGGA 500
GAACTTCAGGGAAAGAGCCAACCTTATAGAACCCGGTGTGCTCATAACGG
GACTACCAACGGGATTCAAAAGTCTGGACAAACAGACCACAGGGTTCCAC 600
AGCTCCGATCTGGTGATAATAGCAGCGAGACCCTCCATGGGAAAAACCTC
CTTCGCACTCTCAATAGCGAGGAACATGGCTGTCAATTTCGAAATCCCCG 700
TCGGAATATTCAGTCTCGAGATGTCCAAGGAACAGCTCGCTCAAAGACTA
CTCAGCATGGAGTCCGGTGTGGATCTTTACAGCATCAGAACAGGATACCT 800
GGATCAGGAGAAGTGGGAAAGACTCACAATAGCGGCTTCTAAACTCTACA
AAGCACCCATAGTTGTGGACGATGAGTCACTCCTCGATCCGCGATCGTTG 900
AGGGCAAAAGCGAGAAGGATGAAAAAAGAATACGATGTAAAAGCCATTTT
TGTCGACTATCTCCAGCTCATGCACCTGAAAGGAAGAAAAGAAAGCAGAC 1000
AGCAGGAGATATCCGAGATCTCGAGATCTCTGAAGCTCCTTGCGAGGGAA
CTCGACATAGTGGTGATAGCGCTTTCACAGCTTTCGAGGGCCGTAGAACA 1100
GAGAGAAGACAAAAGACCGAGGCTGAGTGACCTCAGGGAATCCGGTGCGA
TAGAACAGGACGCAGACACAGTCATCTTCATCTACAGGGAGGAATATTAC 1200
AGGAGCAAAAAATCCAAAGAGGAAAGCAAGCTTCACGAACCTCACGAAGC
TGAAATCATAATAGGTAAACAGAGAAACGGTCCCGTTGGAACGATCACTC 1300
TGATCTTCGACCCCAGAACGGTTACGTTCCATGAAGTCGATGTGGTGCAT
TCA 1353

FIG. 68

MRVPPHNLEAEVAVLGSILIDPSVINDVLEILSHEDFYLKKHQHIFRAME
ELYDEGKPVDVVSVCDKLQSMGKLEEVGGDLEVAQLAEAVPSSAHALHYA 100
EIVKEKSILRKLIEISRKISESAYMEEDVEILLDNAEKMIFEISEMKTTK
SYDHLRGIMHRVFENLENFRERANLIEPGVLITGLPTGFKSLDKQTTGFH 200
SSDLVIIAARPSMGKTSFALSIARNMAVNFEIPVGIFSLEMSKEQLAQRL
LSMESGVDLYSIRTGYLDQEKWERLTIAASKLYKAPIVVDDESLLDPRSL 300
RAKARRMKKEYDVKAIFVDYLQLMHLKGRKESRQQEISEISRSLKLLARE
LDIVVIALSQLSRAVEQREDKRPRLSDLRESGAIEQDADTVIFIYREEYY 400
RSKKSKEESKLHEPHEAEIIIGKQRNGPVGTITLIFDPRTVTFHEVDVVH
S 451

FIG. 69

```
GTGATTCCTCGAGAGGTCATCGAGGAAATAAAAGAAAAGGTTGACATCGT
AGAGGTCATTTCCGAGTACGTGAATCTTACCCGGGTAGGTTCCTCCTACA    100
GGGCTCTCTGTCCCTTTCATTCAGAAACCAATCCTTCTTTCTACGTTCAT
CCGGGTTTGAAGATATACCATTGTTTCGGCTGCGGTGCGAGTGGAGACGT    200
CATCAAATTTCTTCAAGAAATGGAAGGGATCAGTTTCCAGGAAGCGCTGG
AAAGACTTGCCAAAAGAGCTGGGATTGATCTTTCTCTCTACAGAACAGAA    300
GGGACTTCTGAATACGGAAAATACATTCGTTTGTACGAAGAAACGTGGAA
AAGGTACGTCAAAGAGCTGGAGAAATCGAAAGAGGCAAAAGACTATTTAA    400
AAAGCAGAGGCTTCTCTGAAGAAGATATAGCAAAGTTCGGCTTTGGGTAC
GTCCCCAAGAGATCCAGCATCTCTATAGAAGTTGCAGAAGGCATGAACAT    500
AACACTGGAAGAACTTGTCAGATACGGTATCGCGCTGAAAAAGGGTGATC
GATTCGTTGATAGATTCGAAGGAAGAATCGTTGTTCCAATAAAGAACGAC    600
AGTGGTCATATTGTGGCTTTTGGTGGGCGTGCTCTCGGCAACGAAGAACC
GAAGTATTTGAACTCTCCAGAGACCAGGTATTTTTCGAAGAAGAAGACCC    700
TTTTTCTCTTCGATGAGGCGAAAAAAGTGGCAAAAGAGGTTGGTTTTTTC
GTCATCACCGAAGGCTACTTCGACGCGCTCGCATTCAGAAAGGATGGAAT    800
ACCAACGGCGGTCGCTGTTCTTGGGGCGAGTCTTTCAAGAGAGGCGATTC
TAAAACTTTCGGCGTATTCGAAAAACGTCATACTGTGTTTCGATAATGAC    900
AAAGCAGGCTTCAGAGCCACTCTCAAATCCCTCGAGGATCTCCTAGACTA
CGAATTCAACGTGCTTGTGGCAACCCCCTCTCCTTACAAAGACCCAGATG   1000
AACTCTTTCAGAAAGAAGGAGAAGGTTCATTGAAAAAGATGCTGAAAAAC
TCGCGTTCGTTCGAATATTTTCTGGTGACGGCTGGTGAGGTCTTCTTTGA   1100
CAGGAACAGCCCCGCGGGTGTGAGATCCTACCTTTCTTTCCTCAAAGGTT
GGGTCCAAAAGATGAGAAGGAAAGGATATTTGAAACACATAGAAAATCTC   1200
GTGAATGAGGTTTCATCTTCTCTCCAGATACCAGAAAACCAGATTTTGAA
CTTTTTTGAAAGCGACAGGTCTAACACTATGCCTGTTCATGAGACCAAGT   1300
CGTCAAAGGTTTACGATGAGGGGAGAGGACTGGCTTATTTGTTTTTGAAC
TACGAGGATTTGAGGGAAAAGATTCTGGAACTGGACTTAGAGGTACTGGA   1400
AGATAAAAACGCGAGGGAGTTTTTCAAGAGAGTCTCACTGGGAGAAGATT
TGAACAAAGTCATAGAAAACTTCCCAAAAGAGCTGAAAGACTGGATTTTT   1500
GAGACAATAGAAAGCATTCCTCCTCCAAAGGATCCCGAGAAATTCCTCGG
TGACCTCTCCGAAAAGTTGAAAATCCGACGGATAGAGAGACGTATCGCAG   1600
AAATAGATGATATGATAAAGAAAGCTTCAAACGATGAAGAAAGGCGTCTT
CTTCTCTCTATGAAAGTGGATCTCCTCAGAAAAATAAAGAGGAG         1695
```

FIG. 70

MIPREVIEEIKEKVDIVEVISEYVNLTRVGSSYRALCPFHSETNPSFYVH
PGLKIYHCFGCGASGDVIKFLQEMEGISFQEALERLAKRAGIDLSLYRTE 100
GTSEYGKYIRLYEETWKRYVKELEKSKEAKDYLKSRGFSEEDIAKFGFGY
VPKRSSISIEVAEGMNITLEELVRYGIALKKGDRFVDRFEGRIVVPIKND 200
SGHIVAFGGRALGNEEPKYLNSPETRYFSKKKTLFLFDEAKKVAKEVGFF
VITEGYFDALAFRKDGIPTAVAVLGASLSREAILKLSAYSKNVILCFDND 300
KAGFRATLKSLEDLLDYEFNVLVATPSPYKDPDELFQKEGEGSLKKMLKN
SRSFEYFLVTAGEVFFDRNSPAGVRSYLSFLKGWVQKMRRKGYLKHIENL 400
VNEVSSSLQIPENQILNFFESDRSNTMPVHETKSSKVYDEGRGLAYLFLN
YEDLREKILELDLEVLEDKNAREFFKRVSLGEDLNKVIENFPKELKDWIF 500
ETIESIPPPKDPEKFLGDLSEKLKIRRIERRIAEIDDMIKKASNDEERRL
LLSMKVDLLRKIKRR 565

FIG. 71

ATGGCTCTACACCCGGCTCACCCTGGGGCAATAATCGGGCACGAGGCCGT
TCTCGCCCTCCTTCCCCGCCTCACCGCCCAGACCCTGCTCTTCTCCGGCC 100
CCGAGGGGGTGGGGCGGCGCACCGTGGCCCGCTGGTACGCCTGGGGGCTC
AACCGCGGCTTCCCCCCGCCCTCCCTGGGGGAGCACCCGGACGTCCTCGA 200
GGTGGGGCCCAAGGCCCGGGACCTCCGGGGCCGGGCCGAGGTGCGGCTGG
AGGAGGTGGCGCCCCTCTTGGAGTGGTGCTCCAGCCACCCCCGGGAGCGG 300
GTGAAGGTGGCCATCCTGGACTCGGCCCACCTCCTCACCGAGGCCGCCGC
CAACGCCCTCCTCAAGCTCCTGGAGGAGCCCCCTTCCTACGCCCGCATCG 400
TCCTCATCGCCCCAAGCCGCGCCACCCTCCTCCCCACCCTGGCCTCCCGG
GCCACGGAGGTGGCATTCGCCCCCGTGCCCGAGGAGGCCCTGCGCGCCCT 500
CACCCAGGACCCGGAGCTCCTCCGCTACGCCGCCGGGGCCCCGGGCCGCC
TCCTTAGGGCCCTCCAGGACCCGGAGGGGTACCGGGCCCGCATGGCCAGG 600
GCGCAAAGGGTCCTGAAAGCCCCGCCCCTGGAGCGCCTCGCTTTGCTTCG
GGAGCTTTTGGCCGAGGAGGAGGGGGTCCACGCCCTCCACGCCGTCCTAA 700
AGCGCCCGGAGCACCTCCTTGCCCTGGAGCGGGCGCGGGAGGCCCTGGAG
GGGTACGTGAGCCCCGAGCTGGTCCTCGCCCGGCTGGCCTTAGACTTAGA 800
GACA

FIG. 72

MALHPAHPGAIIGHEAVLALLPRLTAQTLLFSGPEGVGRRTVARWYAWGL
NRGFPPPSLGEHPDVLEVGPKARDLRGRAEVRLEEVAPLLEWCSSHPRER 100
VKVAILDSAHLLTEAAANALLKLLEEPPSYARIVLIAPSRATLLPTLASR
ATEVAFAPVPEEALRALTQDPELLRYAAGAPGRLLRALQDPEGYRARMAR 200
AQRVLKAPPLERLALLRELLAEEEGVHALHAVLKRPEHLLALERAREALE
GYVSPELVLARLALDLET 268

FIG. 73

```
ATGCTGGACCTGAGGGAGGTGGGGGAGGCGGAGTGGAAGGCCCTAAAGCC
CCTTTTGGAAAGCGTGCCCGAGGGCGTCCCCGTCCTCCTCCTGGACCCTA      100
AGCCAAGCCCCTCCCGGGCGGCCTTCTACCGGAACCGGGAAAGGCGGGAC
TTCCCCACCCCCAAGGGGAAGGACCTGGTGCGGCACCTGGAAAACCGGGC      200
CAAGCGCCTGGGGCTCAGGCTCCCGGGCGGGGTGGCCCAGTACCTGGCCT
CCCTGGAGGGGGACCTCGAGGCCCTGGAGCGGGAGCTGGAGAAGCTTGCC      300
CTCCTCTCCCCACCCCTCACCCTGGAGAAGGTGGAGAAGGTGGTGGCCCT
GAGGCCCCCCCTCACGGGCTTTGACCTGGTGCGCTCCGTCCTGGAGAAGG      400
ACCCCAAGGAGGCCCTCCTGCGCCTAGGCGGCCTCAAGGAGGAGGGGGAG
GAGCCCCTCAGGCTCCTCGGGGCCCTCTCCTGGCAGTTCGCCCTCCTCGC      500
CCGGGCCTTCTTCCTCCTCCGGGAAAACCCCAGGCCCAAGGAGGAGGACC
TCGCCCGCCTCGAGGCCCACCCCTACGCCGCCCGCCGCGCCCTGGAGGCG      600
GCGAAGCGCCTCACGGAAGAGGCCCTCAAGGAGGCCCTGGACGCCCTCAT
GGAGGCGGAAAAGAGGGCCAAGGGGGGGAAAGACCCGTGGCTCGCCCTGG      700
AGGCGGCGGTCCTCCGCCTCGCCCGTTGA
```

FIG. 74

```
MVIAFTGDPFLAREALLEEARLRGLSRFTEPTPEALAQALAPGLFGGGGA
MLDLREVGEAEWKALKPLLESVPEGVPVLLLDPKPSPSRAAFYRNRERRD      100
FPTPKGKDLVRHLENRAKRLGLRLPGGVAQYLASLEGDLEALERELEKLA
LLSPPLTLEKVEKVVALRPPLTGFDLVRSVLEKDPKEALLRLGGLKEEGE      200
EPLRLLGALSWQFALLARAFFLLRENPRPKEEDLARLEAHPYAARRALEA
AKRLTEEALKEALDALMEAEKRAKGGKDPWLALEAAVLRLAR            292
```

FIG. 75

```
ATGGCTCGAGGCCTGAACCGCGTTTTCCTCATCGGCGCCCTCGCCACCCG
GCCGGACATGCGCTACACCCCGGCGGGCTCGCCATTTTGGACCTGACCC    100
TCGCCGGTCAGGACCTGCTTCTTTCCGATAACGGGGGGAACCGGAGGTG
TCCTGGTACCACCGGGTGAGGCTCTTAGGCCGCCAGGCGGAGATGTGGGG    200
CGACCTCTTGGACCAAGGGCAGCTCGTCTTCGTGGAGGGCCGCCTGGAGT
ACCGCCAGTGGGAAAGGGAGGGGGAGAAGCGGAGCGAGCTCCAGATCCGG    300
GCCGACTTCCGGACCCCCTGGACGACCGGGGGAAGAAGCGGGCGGAGGAC
AGCCGGGGCCAGCCCAGGCTCCGCGCCGCCCTGAACCAGGTCTTCCTCAT    400
GGGCAACCTGACCCGGGACCCGGAACTCCGCTACACCCCCCAGGGCACCG
CGGTGGCCCGGCTGGGCCTGGCGGTGAACGAGCGCCGCCAGGGGGCGGAG    500
GAGCGCACCCACTTCGTGGAGGTTCAGGCCTGGCGCGACCTGGCGGAGTG
GGCCGCCGAGCTGAGGAAGGGCGACGGCCTTTTCGTGATCGGCAGGTTGG    600
TGAACGACTCCTGGACCAGCTCCAGCGGCGAGCGGCGCTTCCAGACCCGT
GTGGAGGCCCTCAGGCTGGAGCGCCCCACCCGTGGACCTGCCCAGGCCTG    700
CCCAGGCCGGCGGAACAGGTCCCGCGAAGTCCAGACGGGTGGGGTGGACA
TTGACGAAGGCTTGGAAGACTTTCCGCCGGAGGAGGATTTGCCGTTTTGA    800
GCACGAA
```

FIG. 76

```
MARGLNRVFLIGALATRPDMRYTPAGLAILDLTLAGQDLLLSDNGGEPEV
SWYHRVRLLGRQAEMWGDLLDQGQLVFVEGRLEYRQWEREGEKRSELQIR    100
ADFLDPLDDRGKKRAEDSRGQPRLRAALNQVFLMGNLTRDPELRYTPQGT
AVARLGLAVNERRQGAEERTHFVEVQAWRDLAEWAAELRKGDGLFVIGRL    200
VNDSWTSSSGERRFQTRVEALRLERPTRGPAQACPGRRNRSREVQTGGVD
IDEGLEDFPPEEDLPF                                      266
```

FIG. 77

```
AATTCCGACATTTCAATTGAATCGTTTATTCCGCTTGAAAAAGAAGGCAA
GTTGCTCGTTGATGTGAAAAGACCGGGGAGCATCGTACTGCAGGCGCGCT   100
TTTTCTCTGAAATCGTGAAAAAACTGCCGCAACAAACGGTGGAAATCGAA
ACGGAAGACAACTTTTTGACGATCATCCGCTCGGGGCACTCAGAATTCCG   200
CCTCAATGGGCTAAACGCCGACGAATATCCGCGCCTGCCGCAAATTGAAG
AAGAAAACGTGTTTCAAATCCCGGCTGATTTATTGAAAACCGTGATTCGG   300
CAAACGGTGTTCGCCGTTTCTACATCGGAAACGCGCCCAATCTTGACAGG
TGTCAACTGGAAAGTTGAACATGGCGAGCTTGTCTGCACAGCGACCGACA   400
GTCATCGCTTAGCCATGCGCAAAGTGAAAATTGAGTCGGAAAATGAAGTA
TCATACAACGTCGTCATCCCTGGAAAAAGTCTTAATGAGCTCAGCAAAAT   500
TTTGGATGACGGCAACCACCCGGTGGACATCGTCATGACAGCCAATCAAG
TGCTATTTAAGGCCGAGCACCTTCTCTTCTTTTCCCGGCTGCTTGACGGC   600
AACTATCCGGAGACGGCCCGCTTGATTCCAACAGAAAGCAAAACGACCAT
GATCGTCAATGCAAAAGAGTTTCTGCAGGCAATCGACCGAGCGTCCTTGC   700
TTGCTCGAGAAGGAAGGAACAACGTTGTGAAACTGACGACGCTTCCTGGA
GGAATGCTCGAAATTTCTTCGATTTCTCCGAGATCGGGAAAGTGACGGAG   800
CAGCTGCAAACGGAGTCTCTTGAAGGGGAAGAGTTGAACATTTCGTTCAG
CGCGAAATATATGATGGACGCGTTGCGGGCGCTTGATGGAACAGACATTT   900
CAAATCAGCTTCACTGGGGCCATGCGGCCGTTCCTGTTGCGCCCGCTTCA
ACCGATTCGATGCTTCAGCTCATTTTGCCGGTGAGAACATAT           992
```

FIG. 78

```
NSDISIIESFIPLEKEGKLLVDVKRPGSIVLQARFFSEIVKKLPQQTVEI
ETEDNFLTIIRSGHSEFRLNGLNADEYPRLPQIEEENVFQIPADLLKTVI   100
RQTVFAVSTSETRPILTGVNWKVEHGELVCTATDSHRLAMRKVKIIESEN
EVSYNVVIPGKSLNELSKIILDDGNHPVDIVMTANQVLFKAEHLLFFSRL   200
LDGNYPETARLIPTESKTTMIVNAKEFLQAIDRASLLAREGRNNVVKLTT
LPGGMLEISSISPEIGKVTEQLQTESLEGEELNISFSAKYMMDALRALDG   300
TDIQISFTGAMRPFLLRPLHTDSMLQLILPVRTY
```

FIG. 79

```
ATGATTAACCGCGTCATTTTGGTCGGCAGGTTAACGAGAGATCCGGAGTT
GCGTTACACTCCAAGCGGAGTGGCTGTTGCCACGTTTACGCTCGCGGTCA     100
ACCGTCCGTTTACAAATCAGCAGGGCGAGCGGGAAACGGATTTTATTCAA
TGTGTCGTTTGGCGCCGCCAGGCGGAAAACGTCGCCAACTTTTTGAAAAA     200
GGGGAGCTTGGCTGGTGTCGATGGCCGACTGCAAACCCGCAGCTATGAAA
ATCAAGAAGGTCGGCGTGTGTACGTGACGGAAGTGGTGGCTGATAGCGTC     300
CAATTTCTTGAGCCGAAAGGAACGAGCGAGCAGCGAGGGGCGACAGCAGG
CGGCTACTATGGGGATCCATTCCCATTCGGGCAAGATCAGAACCACCAAT     400
ATCCGAACGAAAAAGGGTTTGGCCGCATCGATGACGATCCTTTCGCCAAT
GACGGCCAGCCGATCGATATTTCTGATGATGATTTGCCGTTT             492
```

FIG. 80

```
MINRVILVGRLTRDPELRYTPSGVAVATFTLAVNRPFTNQSYENQEGRRV
YVTEVVADSVQFLEPKGTSEQRGATAGGYYQGERETDFIQCVVWRRQAEN     100
VANFLKKGSLAGVDGRLQTRGDPFPFGQDQNHQYPNEKGFGRIDDDPFAN
DGQPIDISDDDLPF                                         164
```

FIG. 81

```
ATGCTGGAACGCGTATGGGGAAACATTGAAAAACGGCGTTTTTCTCCCCT
TTATTTATTATACGGCAATGAGCCGTTTTTATTAACGGAAACGTATGAGC   100
GATTGGTGAACGCAGCGCTTGGCCCCGAGGAGCGGGAGTGGAACTTGGCT
GTGTACGACTGCGAGGAAACGCCGATCGAGGCGGCGCTTGAGGAGGCCGA   200
GACGGTGCCGTTTTTCGGCGAGCGGCGTGTCATTCTCATCAAGCATCCAT
ATTTTTTTACGTCTGAAAAAGAGAAGGAGATCGAACATGATTTGGCGAAG   300
CTGGAGGCGTACTTGAAGGCGCCGTCGCCGTTTTCGATCGTCGTCTTTTT
CGCGCCGTACGAGAAGCTTGATGAGCGAAAAAAAATTACGAAGCTCGCCA   400
AAGAGCAAAGCGAAGTCGTCATCGCCGCCCCGCTCGCCGAAGCGGAGCTG
CGTGCCTGGGTGCGGCGCCGCATCGAGAGCCAAGGGGCGCAAGCAAGCGA   500
CGAGGCGATTGATGTCCTGTTGCGGCGGGCCGGGACGCAGCTTTCCGCCT
TGGCGAATGAAATCGATAAATTGGCCCTGTTTGCCGGATCGGGCGGAACC   600
ATCGAGGCGGCGGCGGTTGAGCGGCTTGTCGCCCGCACGCCGGAAGAAAA
CGTATTTGTGCTTGTCGAGCAAGTGGCGAAGCGCGACATTCCAGCAGCGT   700
TGCAGACGTTTTATGATCTGCTTGAAAACAATGAAGAGCCGATCAAAATT
TTGGCGTTGCTCGCCGCCCATTTCCGCTTGCTTTCGCAAGTGAAATGGCT   800
TGCCTCCTTAGGCTACGGACAGGCGCAAATTGCTGCGGCGCTCAAGGTGC
ACCCGTTCCGCGTCAAGCTCGCTCTTGCTCAAGCGGCCCGCTTCGCTGAC   900
GGAGAGCTTGCTGAGGCGATCAACGAGCTCGCTGACGCCGATTACGAAGT
CAAAAGCGGGGCGGTCGATCGCCGGTTGGCCGTTGAGCTGCTTCTGATGC   1000
GCTGGGGCGCCCGCCCGGCGCAAGCGGGGCGCCACGGCCGGCGG
```

FIG. 82

```
MLERVWGNIEKRRFSPLYLLYGNEPFLLTETYERLVNAALGPEEREWNLA
VYDCEETPIEAALEEAETVPFFGERRVILIKHPYFFTSEKEKEIEHDLAK   100
LEAYLKAPSPFSIVVFFAPYEKLDERKKITKLAKEQSEVVIAAPLAEAEL
RAWVRRRIESQGAQASDEAIDVLLRRAGTQLSALANEIDKLALFAGSGGT   200
IEAAAVERLVARTPEENVFVLVEQVAKRDIPAALQTFYDLLENNEEPIKI
LALLAAHFRLLSQVKWLASLGYGQAQIAAALKVHPFRVKLALAQAARFAD   300
GELAEAINELADADYEVKSGAVDRRLAVELLLMRWGARPAQAGRHGRR
```

FIG. 83

ATGCGATGGGAACAGCTAGCGAAACGCCAGCCGGTGGTGGCGAAAATGCT
GCAAAGCGGCTTGGAAAAAGGGCGGATTTCTCATGCGTACTTGTTTGAGG 100
GGCAGCGGGGGACGGGCAAAAAAGCGGCCAGTTTGTTGTTGGCGAAACGT
TTGTTTTGTCTGTCCCCAATCGGAGTTTCCCCGTGTCTAGAGTGCCGCAA 200
CTGCCGGCGCATCGACTCCGGCAACCACCCTGACGTCCGGGTGATCGGCC
CAGATGGAGGATCAATCAAAAAGGAACAAATCGAATGGCTGCAGCAAGAG 300
TTCTCGAAAACAGCGGTCGAGTCGGATAAAAAAATGTACATCGTTGAGCA
CGCCGATCAAATGACGACAAGCGCTGCCAACAGCCTTCTGAAATTTTTGG 400
AAGAGCCGCATCCGGGGACGGTGGCGGTATTGCTGACTGAGCAATACCAC
CGCCTGCTAGGGACGATCGTTTCCCGCTGTCAAGTGCTTTCGTTCCGGCC 500
GTTGCCGCCGGCAGAGCTCGCCCAGGGACTTGTCGAGGAGCACGTGCCGT
TGCCGTTGGCGCTGTTGGCTGCCCATTTGACAAACAGCTTCGAGGAAGCA 600
CTGGCGCTTGCCAAAGATAGTTGGTTTGCCGAGGCGCGAACATTAGTGCT
ACAATGGTATGAGATGCTGGGCAAGCCGGAGCTGCAGCTTTTGTTTTTCA 700
TCCACGACCGCTTGTTTCCGCATTTTTTGGAAAGCCATCAGCTTGACCTT
GGACTTG 757

FIG. 84

MRWEQLAKRQPVVAKMLQSGLEKGRISHAYLFEGQRGTGKKAASLLLAKR
LFCLSPIGVSPCLECRNCRRIDSGNHPDVRVIGPDGGSIKKEQIEWLQQE 100
FSKTAVESDKKMYIVEHADQMTTSAANSLLKFLEEPHPGTVAVLLTEQYH
RLLGTIVSRCQVLSFRPLPPAELAQGLVEEHVPLPLALLAAHLTNSFEEA 200
LALAKDSWFAEARTLVLQWYEMLGKPELQLLFFIHDRLFPHFLESHQLDL
GL 252

FIG. 85

GTGGCATACCAAGCGTTATATCGCGTGTTTCGGCCGCAGCGCTTTGCGGA
CATGGTCGGCCAAGAACACGTGACCAAGACGTTGCAAAGCGCCCTGCTTC 100
AACATAAAATATCGCACGCTTACTTATTTTCCGGCCCGCGCGGTACAGGA
AAAACGAGCGCAGCGAAAATTTTCGCCAAGGCGGTCAACTGTGAACAGGC 200
GCCAGCGGCGGAGCCATGCAATGAGTGTCCAGCTTGCCTCGGCATTACGA
ATGGAACGGTTCCCGATGTGCTGGAAATTGACGCTGCTTCCAACAACCGC 300
GTCGATGAAATTCGTGATATCCGTGAGAAGGTGAAATTTGCGCCAACGTC
GGCCCGCTACAAAGTGTATATCATCGACGAGGTGCATATGCTGTCGATCG 400
GTGCGTTTAACGCGCTGTTGAAAACGTTGGAGGAGCCGCCGAAACACGTC
ATTTTCATTTTGGCCACGACCGAGCCGCACAAAATTCCGGCGACGATCAT 500
TTCCCGCTGCCAACGGTTCGATTTTCGCCGCATCCCGCTTCAGGCGATCG
TTTCACGGCTAAAGTACGTCGCAAGCGCCCAAGGTGTCGAGGCGTCAGAT 600
GAGGCATTGTCCGCCATCGCCCGTGCTGCAGACGGGGGGATGCGCGATGC
GCTCAGCTTGCTTGATCAAGCCATTTCGTTCAGCGACGGGAAACTTCGGC 700
TCGACGACGTGCTGGCGATGACCGGGGCTGCATCATTTGCCGCCTTATCG
AGCTTCATCGAAGCCATCCACCGCAAAGATACAGCGGCGGTTCTTCAGCA 800
CTTGGAAACGATGATGGCGCAAGGGAAAGATCCGCATCGTTTGGTTGAAG
ACTTGATTTTGTACTATCGCGATTTATTGCTGTACAAAACCGCTCCCTAT 900
GTGGAGGGAGCGATTCAAATTGCTGTCGTTGACGAAGCGTTCACTTCACT
GTCGGAAATGATTCCGGTTTCCAATTTATACGAGGCCATCGAGTTGCTGA 1000
ACAAAAGCCAGCAAGAGATGAAGTGGACAAACCACCCGCGCCTTCTGTTG
GAAGTGGCGCTTGTGAAACTTTGCCATCCATCAGCCGCCGCCCCGTCGCT 1100
GTCGGCTTCCGAGTTGGAACCGTTGATAAAGCGGATTGAAACGCTGGAGG
CGGAATTGCGGCGCCTGAAGGAACAACCGCCTGCCCCTCCGTCGACCGCC 1200
GCGCCGGTGAAAAAACTGTCCAAACCGATGAAAACGGGGGGATATAAAGC
CCCGGTTGGCCGCATTTACGAGCTGTTGAAACAGGCGACGCATGAAGATT 1300
TAGCTTTGGTGAAAGGATGCTGGGCGGATGTGCTCGACACGTTGAAACGG
CAGCATAAAGTGTCGCACGCTGCCTTGCTGCAAGAGAGCGAGCCGGTTGC 1400
AGCGAGCGCCTCAGCGTTTGTATTAAAATTCAAATACGAAATCCACTGCA
AAATGGCGACCGATCCCACAAGTTCGGTCAAAGAAAACGTCGAAGCGATT 1500
TTGTTTGAGCTGACAAACCGCCGCTTTGAAATGGTAGCCATTCCGGAGGG
AGAATGGGGAAAAATAAGAGAAGAGTTCATCCGCAATAAGGACGCCATGG 1600
TGGAAAAAAGCGAAGAAGATCCGTTAATCGCCGAAGCGAAGCGGCTGTTT
GGCGAAGAGCTGATCGAAATTAAAGAA 1677

FIG. 86

```
VAYQALYRVFRPQRFADMVGQEHVTKTLQSALLQHKISHAYLFSGPRGTG
KTSAAKIFAKAVNCEQAPAAEPCNECPACLGITNGTVPDVLEIDAASNNR    100
VDEIRDIREKVKFAPTSARYKVYIIDEVHMLSIGAFNALLKTLEEPPKHV
IFILATTEPHKIPATIISRCQRFDFRRIPLQAIVSRLKYVASAQGVEASD    200
EALSAIARAADGGMRDALSLLDQAISFSDGKLRLDDVLAMTGAASFAALS
SFIEAIHRKDTAAVLQHLETMMAQGKDPHRLVEDLILYYRDLLLYKTAPY    300
VEGAIQIAVVDEAFTSLSEMIPVSNLYEAIELLNKSQQEMKWTNHPRLLL
EVALVKLCHPSAAAPSLSASELEPLIKRIETLEAELRRLKEQPPAPPSTA    400
APVKKLSKPMKTGGYKAPVGRIYELLKQATHEDLALVKGCWADVLDTLKR
QHKVSHAALLQESEPVAASASAFVLKFKYEIHCKMATDPTSSVKENVEAI    500
LFELTNRRFEMVAIPEGEWGKIREEFIRNKDAMVEKSEEDPLIAEAKRLF
GEELIEIKE                                             559
```

FIG. 87

ATGGTGACAAAAGAGCAAAAAGAGCGGTTTCTCATCCTGCTTGAGCAGCT
GAAGATGACGTCGGACGAATGGATGCCGCATTTTCGTGAGGCAGCCATTC 100
GCAAAGTCGTGATCGATAAAGAGGAGAAAAGCTGGCATTTTTATTTTCAG
TTCGACAACGTGCTGCCGGTTCATGTATACAAAACGTTTGCCGATCGGCT 200
GCAGACGGCGTTCCGCCATATCGCCGCCGTCCGCCATACGATGGAGGTCG
AAGCGCCGCGCGTAACTGAGGCGGATGTGCAGGCGTATTGGCCGCTTTGC 300
CTTGCCGAGCTGCAAGAAGGCATGTCGCCGCTTGTCGATTGGCTCAGCCG
GCAGACGCCTGAGCTGAAAGGAAACAAGCTGCTTGTCGTTGCCCGCCATG 400
AAGCGGAAGCGCTGGCGATCAAACGGCGGTTCGCCAAAAAAATCGCTGAT
GTGTACGCTTCGTTTGGGTTTCCCCCCCTTCAGCTTGACGTCAGCGTCGA 500
GCCGTCCAAGCAAGAAATGGAACAGTTTTTGGCGCAAAAACAGCAAGAGG
ACGAAGAGCGAGCGCTTGCTGTACTGACCGATTTAGCGAGGGAAGAAGAA 600
AAGGCCGCGTCTGCGCCGCCGTCCGGTCCGCTTGTCATCGGCTATCCGAT
CCGCGACGAGGAGCCGGTGCGGCGGCTTGAAACGATCGTCGAAGAAGAGC 700
GGCGCGTCGTTGTGCAAGGCTATGTATTTGACGCCGAAGTGAGCGAATTA
AAAAGCGGCCGCACGCTGTTGACCATGAAAATCACAGATTACACGAACTC 800
GATTTTAGTCAAAATGTTCTCGCGCGACAAAGAGGACGCCGAGCTTATGA
GCGGCGTCAAAAAAGGCATGTGGGTGAAAGTGCGCGGCAGCGTGCAAAAC 900
GATACGTTCGTCCGTGATTTGGTCATCATCGCCAACGATTTGAACGAAAT
CGCCGCAAACGAACGGCAAGATACGGCGCCGGAAGGGGAAAAGAGGGTCG 1000
AGCTCCATTTGCATACCCCGATGAGCCAAATGGACGCGGTCACCTCGGTG
ACAAAACTCATTGAGCAAGCGAAAAAATGGGGGCATCCGGCGATCGCCGT 1100
CACCGACCATGCCGTTGTTCAGTCGTTTCCGGAGGCCTACAGCGCGGCGA
AAAAACACGGCATGAAGGTCATTTACGGCCTTGAGGCGAACATCGTCGAC 1200
GATGGCGTGCCGATCGCCTACAATGAGACGCACCGCCGTCTTTCGGAGGA
AACGTACGTCGTCTTTGACGTCGAGACGACGGGCCTGTCGGCTGTGTACA 1300
ATACGATCATTGAGCTGGCGGCGGTGAAAGTGAAAGACGGCGAGATCATC
GACCGATTCATGTCGTTTGCCAACCCTGGACATCCGTTGTCGGTGACAAC 1400
GATGGAGCTGACTGGGATCACCGATGAGATGGTGAAAGACGCCCCGAAGC
CGGACGAGGTGCTAGCCCGTTTTGTTGACTGGGCCGGCGATGCGACGCTT 1500
GTTGCCCACAACGCCAGCTTTGACATCGGTTTTTAAACGCGGGCCTCGC
TCGCATGGGGCGCGGCAAAATCGCGAATCCAGTCATCGATACGCTCGAGC 1600
TGGCCCGTTTTTTATACCCGGATTTGAAAAACCATCGGCTCAATACATTG
TGCAAAAAATTTGACATTGAATTGACGCAGCATCACCGCGCCATCTACGA 1700
CGCGGAGGCGACCGGGCATTTGCTTATGCGGCTGTTGAAGGAAGCGGAAG
AGCGCGGCATACTGTTTCATGACGAATTAAACAGCCGCACGCACAGCGAA 1800
GCGTCCTATCGGCTTGCGCGCCCGTTCCATGTGACGCTGTTGGCGCAAAA
CGAGACTGGATTGAAAAATTTGTTCAAGCTTGTGTCATTGTCGCACATTC 1900
AATATTTTCACCGTGTGCCGCGCATCCCGCGCTCCGTGCTCGTCAAGCAC
CGCGACGGCCTGCTTGTCGGCTCGGGCTGCGACAAAGGAGAGCTGTTTGA 2000
CAACTTGATCCAAAAGGCGCCGGAAGAAGTCGAAGACATCGCCCGTTTTT
ACGATTTTCTTGAAGTGCATCCGCCGGACGTGTACAAGCCGCTCATCGAG 2100
ATGGATTATGTGAAAGACGAAGAGATGATCAAAAACATCATCCGCAGCAT
CGTCGCCCTTGGTGAGAAGCTTGACATCCCGGTTGTCGCCACTGGCAACG 2200

FIG. 88A

TCCATTACTTGAACCCAGAAGATAAAATTTACCGGAAAATCTTAATCCAT
TCGCAAGGCGGGGCGAATCCGCTCAACCGCCATGAACTGCCGGATGTATA 2300
TTTCCGTACGACGAATGAAATGCTTGACTGCTTCTCGTTTTAGGGCCGG
AAAAAGCGAAGGAAATCGTCGTTGACAACACGCAAAAAATCGCTTCGTTA 2400
ATCGGCGATGTCAAGCCGATCAAAGATGAGCTGTATACGCCGCGCATTGA
AGGGGCGGACGAGGAAATCAGGGAAATGAGCTACCGGCGGGCGAAGGAAA 2500
TTTACGGCGACCCGTTGCCGAAACTTGTTGAAGAGCGGCTTGAGAAGGAG
CTAAAAAGCATCATCGGCCATGGCTTTGCCGTCATTTATTTGATCTCGCA 2600
CAAGCTTGTGAAAAAATCGCTCGATGACGGCTACCTTGTCGGGTCGCGCG
GATCGGTCGGCTCGTCGTTTGTCGCGACGATGACGGAAATCACCGAGGTC 2700
AATCCGCTGCCGCCGCATTACGTTTGCCCGAACTGCAAGCATTCGGAGTT
CTTTAACGACGGTTCAGTCGGCTCAGGGTTTGATTTGCCGGATAAAAACT 2800
GCCCGCGATGTGGGACGAAATACAAGAAAGACGGGCACGACATCCCGTTT
GAGACGTTTCTCGGCTTTAAAGGCGACAAAGTGCCGGATATCGACTTGAA 2900
CTTTTCCGGCGAATACCAGCCGCGCGCCCACAACTATACGAAAGTGCTGT
TTGGCGAAGACAACGTCTACCGCGCCGGGACGATTGGCACGGTCGCTGAC 3000
AAAACGGCGTACGGATTTGTCAAAGCGTATGCGAGCGACCATAACTTAGA
GCTGCGCGGCGCGGAAATCGACGGCTCGCGGCTGGCTGCACCGGGGTGAA 3100
GCGGACGACCGGGCAGCATCCGGCGCGCATCATCGTCGTCCCGGATTATA
TGGAAATTTACGATTTTACGCCGATTCAATATCCGGCCGATGACACGTCC 3200
TCTGAATGGCGGACGACCCATTTCGACTTCCATTCGATCCACGACAATTT
GTTGAAGCTCGATATTCTCGGGCACGACGATCCGACGGTCATTCGCATGC 3300
TGCAAGATTTAAGCGGCATCGATCCGAAAACGATCCCGACCGACGACCCG
GATGTGATGGGCATTTTCAGCAGCACCGAGCCGCTTGGCGTTACGCCGGA 3400
GCAAATCATGTGCAATGTCGGCACGATCGGCATTCCGGAGTTTGGCACGC
GCTTCGTTCGGCAAATGTTGGAAGAGACAAGGCCAAAAACGTTTTCCGAA 3500
CTCGTGCAAATTTCCGGCTTGTCGCACGGCACCGATGTGTGGCTCGGCAA
CGCGCAAGAGCTCATTCAAAACGGCACGTGTACGTTATCGGAAGTCATCG 3600
GCTGCCGCGACGACATTATGGTCTATTTGATTTACCGCGGGCTCGAGCCG
TCGCTCGCTTTTAAAATCATGGAATCCGTGCGCAAAGGAAAAGGCTTAAC 3700
GCCGGAGTTTGAAGCAGAAATGCGCAAACATGACGTGCCGGAGTGGTACA
TCGATTCATGCAAAAAAATCAAGTACATGTTCCCGAAAGCGCACGCCGCC 3800
GCCTACGTGTTAATGGCGGTGCGCATCGCCTACTTTAAGGTGCACCATCC
GCTTTTGTATTACGCGTCGTACTTTACGGTGCGGGCGGAGGACTTTGACC 3900
TTGACGCCATGATCAAAGGATCACCCGCCATTCGCAAGCGGATTGAGGAA
ATCAACGCCAAAGGCATTCAGGCGACGGCGAAAGAAAAAAGCTTGCTCAC 4000
GGTTCTTGAGGTGGCCTTAGAGATGTGCGAGCGCGGCTTTTCCTTTAAAA
ATATCGATTTGTACCGCTCGCAGGCGACGGAATTCGTCATTGACGGCAAT 4100
TCTCTCATTCCGCCGTTCAACGCCATTCCGGGGCTTGGGACGAACGTGGC
GCAGGCGATCGTGCGCGCCCGCGAGGAAGGCGAGTTTTTGTCGAAGGAGG 4200
ATTTGCAACAGCGCGGCAAATTGTCGAAAACGCTGCTCGAGTATCTAGAA
AGCCGCGGCTGCCTTGACTCGCTTCCAGACCATAACCAGCTGTCGCTGTT 4300
T

FIG. 88B

MVTKEQKERFLILLEQLKMTSDEWMPHFREAAIRKVVIDKEEKSWHFYFQ
FDNVLPVHVYKTFADRLQTAFRHIAAVRHTMEVEAPRVTEADVQAYWPLC 100
LAELQEGMSPLVDWLSRQTPELKGNKLLVVARHEAEALAIKRRFAKKIAD
VYASFGFPPLQLDVSVEPSKQEMEQFLAQKQQEDEERALAVLTDLAREEE 200
KAASAPPSGPLVIGYPIRDEEPVRRLETIVEEERRVVVQGYVFDAEVSEL
KSGRTLLTMKITDYTNSILVKMFSRDKEDAELMSGVKKGMWVKVRGSVQN 300
DTFVRDLVIIANDLNEIAANERQDTAPEGEKRVELHLHTPMSQMDAVTSV
TKLIEQAKKWGHPAIAVTDHAVVQSFPEAYSAAKKHGMKVIYGLEANIVD 400
DGVPIAYNETHRRLSEETYVVFDVETTGLSAVYNTIIELAAVKVKDGEII
DRFMSFANPGHPLSVTTMELTGITDEMVKDAPKPDEVLARFVDWAGDATL 500
VAHNASFDIGFLNAGLARMGRGKIANPVIDTLELARFLYPDLKNHRLNTL
CKKFDIELTQHHRAIYDAEATGHLLMRLLKEAEERGILFHDELNSRTHSE 600
ASYRLARPFHVTLLAQNETGLKNLFKLVSLSHIQYFHRVPRIPRSVLVKH
RDGLLVGSGCDKGELFDNLIQKAPEEVEDIARFYDFLEVHPPDVYKPLIE 700
MDYVKDEEMIKNIIRSIVALGEKLDIPVVATGNVHYLNPEDKIYRKILIH
SQGGANPLNRHELPDVYFRTTNEMLDCFSFLGPEKAKEIVVDNTQKIASL 800
IGDVKPIKDELYTPRIEGADEEIREMSYRRAKEIYGDPLPKLVEERLEKE
LKSIIGHGFAVIYLISHKLVKKSLDDGYLVGSRGSVGSSFVATMTEITEV 900
NPLPPHYVCPNCKHSEFFNDGSVGSGFDLPDKNCPRCGTKYKKDGHDIPF
ETFLGFKGDKVPDIDLNFSGEYQPRAHNYTKVLFGEDNVYRAGTIGTVAD 1000
KTAYGFVKAYASDHNLELRGAEIDLAAGCTGVKRTTGQHPGGIIVVPDYM
EIYDFTPIQYPADDTSSEWRTTHFDFHSIHDNLLKLDILGHDDPTVIRML 1100
QDLSGIDPKTIPTDDPDVMGIFSSTEPLGVTPEQIMCNVGTIGIPEFGTR
FVRQMLEETRPKTFSELVQISGLSHGTDVWLGNAQELIQNGTCTLSEVIC 1200
CRDDIMVYLIYRGLEPSLAFKIMESVRKGKGLTPEFEAEMRKHDVPEWYI
DSCKKIKYMFPKAHAAAYVLMAVRIAYFKVHHPLLYYASYFTVRAEDFDL 1300
DAMIKGSPAIRKRIEEINAKGIQATAKEKSLLTVLEVALEMCERGFSFKN
IDLYRSQATEFVIDGNSLIPPFNAIPGLGTNVAQAIVRAREEGEFLSKED 1400
LQQRGKLSKTLLEYLESRGCLDSLPDHNQLSLF

FIG. 89

SEQUENCE LISTING

<160> NUMBER OF SEQ ID NOS: 212

<210> SEQ ID NO 1
<211> LENGTH: 2007
<212> TYPE: DNA
<213> ORGANISM: Thermus thermophilus

<400> SEQUENCE: 1
tccgggggtg gggttcccag gtagaccccg gcccctcccg tgagcccctt tacccaggcc 60
gccacctcct ccagggggggc caaggcgtgc aaggagagga acgtccgcac cacgccctat 120
actagccttg tgagcgccct ctaccgccgc ttccgccccc tcaccttcca ggaggtggtg 180
gggcaggagc acgtgaagga gcccctcctc aaggccatcc gggaggggag gctcgcccag 240
gcctacctct tctccgggcc caggggcgtg ggcaagacca ccacggcgag gctcctcgcc 300
atggcggtgg ggtgccaggg ggaagacccc ccttgcgggg tctgccccca ctgccaggcg 360
gtgcagaggg gcgcccaccc ggacgtggtg gacattgacg ccgccagcaa caactccgtg 420
gaggacgtgc gggagctgag ggaaaggatc cacctcgccc ccctctctgc ccccaggaag 480
gtcttcatcc tggacgaggc ccacatgctc tccaaaagcg ccttcaacgc cctcctcaag 540
accctggagg agcccccgcc ccacgtcctc ttcgtcttcg ccaccaccga gcccgagagg 600 atgccccccca ccatcctctc ccgcacccag cacttccgct tccgccgcct cacggaggag 660
gagatcgcct ttaagctccg gcgcatcctg gaggccgtgg ggcgggaggc ggaggaggag 720
gccctcctcc tcctcgcccg cctggcggac ggggccctta gggacgcgga aagcctcctg 780
gagcgcttcc tcctcctgga aggcccctc acccggaagg aggtggagcg cgccctaggc 840 tccccccag ggaccggggt ggccgagatc gccgcctccc tcgcgagggg gaaaacggcg 900
gaggccctgg gcctcgcccg gcgcctctac ggggaagggt acgccccgag gagcctggtc 960
tcgggccttt tggaggtgtt ccgggaaggc ctctacgccg ccttcggcct cgcgggaacc 1020
ccccttcccg ccccgcccca ggccctgatc gccgccatga ccgccctgga cgaggccatg 1080
gagcgcctcg cccgccgctc cgacgcctta agcctggagg tggccctcct ggaggcggga 1140
agggccctgg ccgccgaggc cctaccccag cccacgggcg ctccttcccc agaggtcggc 1200
cccaagccgg aaagccccc gaccccggaa cccccaaggc ccgaggaggc gcccgacctg 1260
cgggagcggt ggcgggcctt cctcgaggcc ctcaggccca ccctacgggc cttcgtgcgg 1320

-continued

```
gaggcccgcc cggaggtccg ggaaggccag ctctgcctcg ctttccccga ggacaaggcc   1380

ttccactacc gcaaggcctc ggaacagaag gtgaggctcc tccccctggc ccaggcccat   1440

ttcggggtgg aggaggtcgt cctcgtcctg gagggagaaa aaaaaagcct gagcccaagg   1500

ccccgcccgg ccccacctcc tgaagcgccc gcacccccgg gccctcccga ggaggaggta   1560

gaggcggagg aagcggcgga ggaggccccg gaggaggcct tgaggcgggt ggtccgcctc   1620

ctgggggggc gggtgctctg ggtgcggcgg cccaggaccc gggaggcgcc ggaggaggaa   1680

cccctgagcc aagacgagat agggggtact ggtatataat gggggcatga cgcggaccac   1740

cgacctcgga caagagaccg tggacaacat cctcaagcgc ctccgccgta ttgagggcca   1800

ggtgcggggg ctccagaaga tggtggccga gggccgcccc tgcgacgagg tcctcaccca   1860

gatgaccgcc accaagaagg ccatggaggc ggcggccacc ctgatcctcc acgagttcct   1920

gaacgtctgc gccgccgagg tctccgaggg caaggtgaac cccaagaagc ccgaggagat   1980

cgccaccatg ctgaagaact tcatcta                                       2007


<210> SEQ ID NO 2
<211> LENGTH: 529
<212> TYPE: PRT
<213> ORGANISM: Thermus thermophilus

<400> SEQUENCE: 2

Met Ser Ala Leu Tyr Arg Arg Phe Arg Pro Leu Thr Phe Gln Glu Val
1               5                   10                  15

Val Gly Gln Glu His Val Lys Glu Pro Leu Leu Lys Ala Ile Arg Glu
            20                  25                  30

Gly Arg Leu Ala Gln Ala Tyr Leu Phe Ser Gly Pro Arg Gly Val Gly
        35                  40                  45

Lys Thr Thr Thr Ala Arg Leu Leu Ala Met Ala Val Gly Cys Gln Gly
    50                  55                  60

Glu Asp Pro Pro Cys Gly Val Cys Pro His Cys Gln Ala Val Gln Arg
65                  70                  75                  80

Gly Ala His Pro Asp Val Val Asp Ile Asp Ala Ala Ser Asn Asn Ser
                85                  90                  95

Val Glu Asp Val Arg Glu Leu Arg Glu Arg Ile His Leu Ala Pro Leu
            100                 105                 110

Ser Ala Pro Arg Lys Val Phe Ile Leu Asp Glu Ala His Met Leu Ser
        115                 120                 125

Lys Ser Ala Phe Asn Ala Leu Leu Lys Thr Leu Glu Glu Pro Pro Pro
    130                 135                 140

His Val Leu Phe Val Phe Ala Thr Thr Glu Pro Glu Arg Met Pro Pro
145                 150                 155                 160

Thr Ile Leu Ser Arg Thr Gln His Phe Arg Phe Arg Arg Leu Thr Glu
                165                 170                 175

Glu Glu Ile Ala Phe Lys Leu Arg Arg Ile Leu Glu Ala Val Gly Arg
            180                 185                 190

Glu Ala Glu Glu Glu Ala Leu Leu Leu Leu Ala Arg Leu Ala Asp Gly
        195                 200                 205

Ala Leu Arg Asp Ala Glu Ser Leu Leu Glu Arg Phe Leu Leu Leu Glu
    210                 215                 220

Gly Pro Leu Thr Arg Lys Glu Val Glu Arg Ala Leu Gly Ser Pro Pro
225                 230                 235                 240

Gly Thr Gly Val Ala Glu Ile Ala Ala Ser Leu Ala Arg Gly Lys Thr
```

-continued

```
                245                 250                 255

Ala Glu Ala Leu Gly Leu Ala Arg Arg Leu Tyr Gly Glu Gly Tyr Ala
            260                 265                 270

Pro Arg Ser Leu Val Ser Gly Leu Leu Glu Val Phe Arg Glu Gly Leu
        275                 280                 285

Tyr Ala Ala Phe Gly Leu Ala Gly Thr Pro Leu Pro Ala Pro Pro Gln
    290                 295                 300

Ala Leu Ile Ala Ala Met Thr Ala Leu Asp Glu Ala Met Glu Arg Leu
305                 310                 315                 320

Ala Arg Arg Ser Asp Ala Leu Ser Leu Glu Val Ala Leu Leu Glu Ala
                325                 330                 335

Gly Arg Ala Leu Ala Ala Glu Ala Leu Pro Gln Pro Thr Gly Ala Pro
            340                 345                 350

Ser Pro Glu Val Gly Pro Lys Pro Glu Ser Pro Pro Thr Pro Glu Pro
        355                 360                 365

Pro Arg Pro Glu Glu Ala Pro Asp Leu Arg Glu Arg Trp Arg Ala Phe
    370                 375                 380

Leu Glu Ala Leu Arg Pro Thr Leu Arg Ala Phe Val Arg Glu Ala Arg
385                 390                 395                 400

Pro Glu Val Arg Glu Gly Gln Leu Cys Leu Ala Phe Pro Glu Asp Lys
                405                 410                 415

Ala Phe His Tyr Arg Lys Ala Ser Glu Gln Lys Val Arg Leu Leu Pro
            420                 425                 430

Leu Ala Gln Ala His Phe Gly Val Glu Glu Val Val Leu Val Leu Glu
        435                 440                 445

Gly Glu Lys Lys Ser Leu Ser Pro Arg Pro Arg Pro Ala Pro Pro Pro
    450                 455                 460

Glu Ala Pro Ala Pro Pro Gly Pro Pro Glu Glu Glu Val Glu Ala Glu
465                 470                 475                 480

Glu Ala Ala Glu Glu Ala Pro Glu Glu Ala Leu Arg Arg Val Val Arg
                485                 490                 495

Leu Leu Gly Gly Arg Val Leu Trp Val Arg Arg Pro Arg Thr Arg Glu
            500                 505                 510

Ala Pro Glu Glu Glu Pro Leu Ser Gln Asp Glu Ile Gly Gly Thr Gly
        515                 520                 525

Ile


<210> SEQ ID NO 3
<211> LENGTH: 1590
<212> TYPE: DNA
<213> ORGANISM: Thermus thermophilus

<400> SEQUENCE: 3

gtgagcgccc tctaccgccg cttccgcccc ctcaccttcc aggaggtggt ggggcaggag      60

cacgtgaagg agcccctcct caaggccatc cgggaggga ggctcgccca ggcctacctc     120

ttctccgggc ccaggggcgt gggcaagacc accacggcga ggctcctcgc catggcggtg     180

gggtgccagg gggaagaccc cccttgcggg gtctgccccc actgccaggc ggtgcagagg     240

ggcgcccacc cggacgtggt ggacattgac gccgccagca acaactccgt ggaggacgtg     300

cgggagctga gggaaaggat ccacctcgcc cccctctctg cccccaggaa ggtcttcatc     360

ctggacgagg cccacatgct ctccaaaagc gccttcaacg ccctcctcaa gaccctggag     420

gagcccccgc cccacgtcct cttcgtcttc gccaccaccg agcccgagag gatgcccccc     480
```

-continued

```
accatcctct cccgcaccca gcacttccgc ttccgccgcc tcacggagga ggagatcgcc    540

tttaagctcc ggcgcatcct ggaggccgtg gggcgggagg cggaggagga ggccctcctc    600

ctcctcgccc gcctggcgga cggggccctt agggacgcgg aaagcctcct ggagcgcttc    660

ctcctcctgg aaggccccct cacccggaag gaggtggagc gcgccctagg ctcccccccca    720

gggaccgggg tggccgagat cgccgcctcc ctcgcgaggg ggaaaacggc ggaggccctg    780

ggcctcgccc ggcgcctcta cggggaaggg tacgccccga ggagcctggt ctcgggcctt    840

ttggaggtgt tccgggaagg cctctacgcc gccttcggcc tcgcgggaac ccccccttccc    900

gccccgcccc aggccctgat cgccgccatg accgccctgg acgaggccat ggagcgcctc    960

gcccgccgct ccgacgcctt aagcctggag gtggccctcc tggaggcggg aagggccctg   1020

gccgccgagg ccctacccca gcccacgggc gctccttccc cagaggtcgg ccccaagccg   1080

gaaagccccc cgaccccgga acccccaagg cccgaggagg cgcccgacct gcgggagcgg   1140

tggcgggcct tcctcgaggc cctcaggccc accctacggg ccttcgtgcg ggaggcccgc   1200

ccggaggtcc gggaaggcca gctctgcctc gctttccccg aggacaaggc cttccactac   1260

cgcaaggcct cggaacagaa ggtgaggctc ctccccctgg cccaggccca tttcggggtg   1320

gaggaggtcg tcctcgtcct ggagggagaa aaaaaaagcc tgagcccaag gccccgcccg   1380

gccccacctc ctgaagcgcc cgcacccccg ggccctcccg aggaggaggt agaggcggag   1440

gaagcggcgg aggaggcccc ggaggaggcc ttgaggcggg tggtccgcct cctgggggg    1500

cgggtgctct gggtgcggcg gcccaggacc cgggaggcgc cggaggagga acccctgagc   1560

caagacgaga taggggtac tggtatataa                                     1590
```

<210> SEQ ID NO 4
<211> LENGTH: 464
<212> TYPE: PRT
<213> ORGANISM: Thermus thermophilus

<400> SEQUENCE: 4

```
Met Ser Ala Leu Tyr Arg Arg Phe Arg Pro Leu Thr Phe Gln Glu Val
  1               5                  10                  15

Val Gly Gln Glu His Val Lys Glu Pro Leu Leu Lys Ala Ile Arg Glu
             20                  25                  30

Gly Arg Leu Ala Gln Ala Tyr Leu Phe Ser Gly Pro Arg Gly Val Gly
         35                  40                  45

Lys Thr Thr Thr Ala Arg Leu Leu Ala Met Ala Val Gly Cys Gln Gly
     50                  55                  60

Glu Asp Pro Pro Cys Gly Val Cys Pro His Cys Gln Ala Val Gln Arg
 65                  70                  75                  80

Gly Ala His Pro Asp Val Val Asp Ile Asp Ala Ala Ser Asn Asn Ser
                 85                  90                  95

Val Glu Asp Val Arg Glu Leu Arg Glu Arg Ile His Leu Ala Pro Leu
            100                 105                 110

Ser Ala Pro Arg Lys Val Phe Ile Leu Asp Glu Ala His Met Leu Ser
        115                 120                 125

Lys Ser Ala Phe Asn Ala Leu Leu Lys Thr Leu Glu Glu Pro Pro Pro
    130                 135                 140

His Val Leu Phe Val Phe Ala Thr Thr Glu Pro Glu Arg Met Pro Pro
145                 150                 155                 160

Thr Ile Leu Ser Arg Thr Gln His Phe Arg Phe Arg Arg Leu Thr Glu
                165                 170                 175
```

-continued

```
Glu Glu Ile Ala Phe Lys Leu Arg Arg Ile Leu Glu Ala Val Gly Arg
            180                 185                 190

Glu Ala Glu Glu Glu Ala Leu Leu Leu Leu Ala Arg Leu Ala Asp Gly
        195                 200                 205

Ala Leu Arg Asp Ala Glu Ser Leu Leu Glu Arg Phe Leu Leu Leu Glu
    210                 215                 220

Gly Pro Leu Thr Arg Lys Glu Val Glu Arg Ala Leu Gly Ser Pro Pro
225                 230                 235                 240

Gly Thr Gly Val Ala Glu Ile Ala Ala Ser Leu Ala Arg Gly Lys Thr
                245                 250                 255

Ala Glu Ala Leu Gly Leu Ala Arg Arg Leu Tyr Gly Glu Gly Tyr Ala
            260                 265                 270

Pro Arg Ser Leu Val Ser Gly Leu Leu Glu Val Phe Arg Glu Gly Leu
        275                 280                 285

Tyr Ala Ala Phe Gly Leu Ala Gly Thr Pro Leu Pro Ala Pro Pro Gln
    290                 295                 300

Ala Leu Ile Ala Ala Met Thr Ala Leu Asp Glu Ala Met Glu Arg Leu
305                 310                 315                 320

Ala Arg Arg Ser Asp Ala Leu Ser Leu Glu Val Ala Leu Leu Glu Ala
                325                 330                 335

Gly Arg Ala Leu Ala Ala Glu Ala Leu Pro Gln Pro Thr Gly Ala Pro
            340                 345                 350

Ser Pro Glu Val Gly Pro Lys Pro Glu Ser Pro Pro Thr Pro Glu Pro
        355                 360                 365

Pro Arg Pro Glu Glu Ala Pro Asp Leu Arg Glu Arg Trp Arg Ala Phe
    370                 375                 380

Leu Glu Ala Leu Arg Pro Thr Leu Arg Ala Phe Val Arg Glu Ala Arg
385                 390                 395                 400

Pro Glu Val Arg Glu Gly Gln Leu Cys Leu Ala Phe Pro Glu Asp Lys
                405                 410                 415

Ala Phe His Tyr Arg Lys Ala Ser Glu Gln Lys Val Arg Leu Leu Pro
            420                 425                 430

Leu Ala Gln Ala His Phe Gly Val Glu Glu Val Val Leu Val Leu Glu
        435                 440                 445

Gly Glu Lys Lys Lys Pro Glu Pro Lys Ala Pro Pro Gly Pro Thr Ser
    450                 455                 460


<210> SEQ ID NO 5
<211> LENGTH: 454
<212> TYPE: PRT
<213> ORGANISM: Thermus thermophilus

<400> SEQUENCE: 5

Met Ser Ala Leu Tyr Arg Arg Phe Arg Pro Leu Thr Phe Gln Glu Val
  1               5                  10                  15

Val Gly Gln Glu His Val Lys Glu Pro Leu Leu Lys Ala Ile Arg Glu
             20                  25                  30

Gly Arg Leu Ala Gln Ala Tyr Leu Phe Ser Gly Pro Arg Gly Val Gly
         35                  40                  45

Lys Thr Thr Thr Ala Arg Leu Leu Ala Met Ala Val Gly Cys Gln Gly
     50                  55                  60

Glu Asp Pro Pro Cys Gly Val Cys Pro His Cys Gln Ala Val Gln Arg
 65                  70                  75                  80

Gly Ala His Pro Asp Val Val Asp Ile Asp Ala Ala Ser Asn Asn Ser
                 85                  90                  95
```

-continued

```
Val Glu Asp Val Arg Glu Leu Arg Glu Arg Ile His Leu Ala Pro Leu
            100                 105                 110

Ser Ala Pro Arg Lys Val Phe Ile Leu Asp Glu Ala His Met Leu Ser
        115                 120                 125

Lys Ser Ala Phe Asn Ala Leu Leu Lys Thr Leu Glu Glu Pro Pro Pro
    130                 135                 140

His Val Leu Phe Val Phe Ala Thr Thr Glu Pro Glu Arg Met Pro Pro
145                 150                 155                 160

Thr Ile Leu Ser Arg Thr Gln His Phe Arg Phe Arg Arg Leu Thr Glu
                165                 170                 175

Glu Glu Ile Ala Phe Lys Leu Arg Arg Ile Leu Glu Ala Val Gly Arg
            180                 185                 190

Glu Ala Glu Glu Glu Ala Leu Leu Leu Leu Ala Arg Leu Ala Asp Gly
        195                 200                 205

Ala Leu Arg Asp Ala Glu Ser Leu Leu Glu Arg Phe Leu Leu Leu Glu
    210                 215                 220

Gly Pro Leu Thr Arg Lys Glu Val Glu Arg Ala Leu Gly Ser Pro Pro
225                 230                 235                 240

Gly Thr Gly Val Ala Glu Ile Ala Ala Ser Leu Ala Arg Gly Lys Thr
                245                 250                 255

Ala Glu Ala Leu Gly Leu Ala Arg Arg Leu Tyr Gly Glu Gly Tyr Ala
            260                 265                 270

Pro Arg Ser Leu Val Ser Gly Leu Leu Glu Val Phe Arg Glu Gly Leu
        275                 280                 285

Tyr Ala Ala Phe Gly Leu Ala Gly Thr Pro Leu Pro Ala Pro Pro Gln
    290                 295                 300

Ala Leu Ile Ala Ala Met Thr Ala Leu Asp Glu Ala Met Glu Arg Leu
305                 310                 315                 320

Ala Arg Arg Ser Asp Ala Leu Ser Leu Glu Val Ala Leu Leu Glu Ala
                325                 330                 335

Gly Arg Ala Leu Ala Ala Glu Ala Leu Pro Gln Pro Thr Gly Ala Pro
            340                 345                 350

Ser Pro Glu Val Gly Pro Lys Pro Glu Ser Pro Pro Thr Pro Glu Pro
        355                 360                 365

Pro Arg Pro Glu Glu Ala Pro Asp Leu Arg Glu Arg Trp Arg Ala Phe
    370                 375                 380

Leu Glu Ala Leu Arg Pro Thr Leu Arg Ala Phe Val Arg Glu Ala Arg
385                 390                 395                 400

Pro Glu Val Arg Glu Gly Gln Leu Cys Leu Ala Phe Pro Glu Asp Lys
                405                 410                 415

Ala Phe His Tyr Arg Lys Ala Ser Glu Gln Lys Val Arg Leu Leu Pro
            420                 425                 430

Leu Ala Gln Ala His Phe Gly Val Glu Glu Val Val Leu Val Leu Glu
        435                 440                 445

Gly Glu Lys Lys Lys Ala
    450
```

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 6

-continued cgcaagcttc acgcstacct sttctccggs ac 32

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: peptide

<400> SEQUENCE: 7

His Ala Tyr Leu Phe Ser Gly Thr
1 5

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 8
cgcgaattcg tgctcsggsg gctcctcsag sgtc 34

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 9

Lys Thr Leu Glu Glu Pro Pro Glu His
1 5

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 10
gcgcggatcc ggagggagaa aaaaaaagcc tcagccca 38

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 11
gcgcggatcc ggagggagag aagaaaagcc tcagccca 38

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 12
gaattaaatt cgcgcttcgg gaggtggg 28

<210> SEQ ID NO 13

-continued

<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 13
gcgcgaattc gcgcttcggg aggtggg 27

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 14
gcgcgaattc gggcgcttca ggaggtggg 29

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 15
gtggtgcata tggtgagcgc cctctaccgc c 31

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 16
gtggtggtcg acccaggagg gccacctcca g 31

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (2)
<223> OTHER INFORMATION: X is any aa at position 2
<220> FEATURE:
<221> NAME/KEY: PEPTIDE
<222> LOCATION: (3)
<223> OTHER INFORMATION: X is any aa at position 3
<220> FEATURE:
<221> NAME/KEY: PEPTIDE
<222> LOCATION: (5)
<223> OTHER INFORMATION: X is any aa at position 5

<400> SEQUENCE: 17

Gly Xaa Xaa Gly Xaa Gly Lys Thr
1 5

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: peptide -continued

<400> SEQUENCE: 18

```
Lys Pro Asp Pro Lys Ala Pro Pro Gly Pro Thr Ser
  1               5                  10
```

<210> SEQ ID NO 19
<211> LENGTH: 180
<212> TYPE: PRT
<213> ORGANISM: Escherichia coli

<400> SEQUENCE: 19

```
Met Ser Tyr Gln Val Leu Ala Arg Lys Trp Arg Pro Gln Thr Phe Ala
  1               5                  10                  15

Asp Val Val Gly Gln Glu His Val Leu Thr Ala Leu Ala Asn Gly Leu
             20                  25                  30

Ser Leu Gly Arg Ile His His Ala Tyr Leu Phe Ser Gly Thr Arg Gly
         35                  40                  45

Val Gly Lys Thr Ser Ile Ala Arg Leu Leu Ala Lys Gly Leu Asn Cys
     50                  55                  60

Glu Thr Gly Ile Thr Ala Thr Pro Cys Gly Val Cys Asp Asn Cys Arg
 65                  70                  75                  80

Glu Ile Glu Gln Gly Arg Phe Val Asp Leu Ile Glu Ile Asp Ala Ala
                 85                  90                  95

Ser Arg Thr Lys Val Glu Asp Thr Arg Asp Leu Leu Asp Asn Val Gln
            100                 105                 110

Tyr Ala Pro Ala Arg Gly Arg Phe Lys Val Tyr Leu Ile Asp Glu Val
        115                 120                 125

His Met Leu Ser Arg His Ser Phe Asn Ala Leu Leu Lys Thr Leu Glu
    130                 135                 140

Glu Pro Pro Glu His Val Lys Phe Leu Leu Ala Thr Thr Asp Pro Gln
145                 150                 155                 160

Lys Leu Pro Val Thr Ile Leu Ser Arg Cys Leu Gln Phe His Leu Lys
                165                 170                 175

Ala Leu Asp Val
            180
```

<210> SEQ ID NO 20
<211> LENGTH: 180
<212> TYPE: PRT
<213> ORGANISM: Bacillus subtilis

<400> SEQUENCE: 20

```
Met Ser Tyr Gln Ala Leu Tyr Arg Val Phe Arg Pro Gln Arg Phe Glu
  1               5                  10                  15

Asp Val Val Gly Gln Glu His Ile Thr Lys Thr Leu Gln Asn Ala Leu
             20                  25                  30

Leu Gln Lys Lys Phe Ser His Ala Tyr Leu Phe Ser Gly Pro Arg Gly
         35                  40                  45

Thr Gly Lys Thr Ser Ala Ala Lys Ile Phe Ala Lys Ala Val Asn Cys
     50                  55                  60

Glu His Ala Pro Val Asp Glu Pro Cys Asn Glu Cys Ala Ala Cys Lys
 65                  70                  75                  80

Gly Ile Thr Asn Gly Ser Ile Ser Asp Val Ile Glu Ile Asp Ala Ala
                 85                  90                  95

Ser Asn Asn Gly Val Asp Glu Ile Arg Asp Ile Arg Asp Lys Val Lys
            100                 105                 110

Phe Ala Pro Ser Ala Val Thr Tyr Lys Val Tyr Ile Ile Asp Glu Val
```

-continued

```
        115                 120                 125

His Met Leu Ser Ile Gly Ala Phe Asn Ala Leu Leu Lys Thr Leu Glu
    130                 135                 140

Glu Pro Pro Glu His Cys Ile Phe Ile Leu Ala Thr Thr Glu Pro His
145                 150                 155                 160

Lys Ile Pro Leu Thr Ile Ile Ser Arg Cys Gln Arg Phe Asp Phe Lys
                165                 170                 175

Arg Ile Thr Ser
            180


<210> SEQ ID NO 21
<211> LENGTH: 294
<212> TYPE: PRT
<213> ORGANISM: Escherichia coli

<400> SEQUENCE: 21

Met Ser Tyr Gln Val Leu Ala Arg Lys Trp Arg Pro Gln Thr Phe Ala
  1               5                  10                  15

Asp Val Val Gly Gln Glu His Val Leu Thr Ala Leu Ala Asn Gly Leu
             20                  25                  30

Ser Leu Gly Arg Ile His His Ala Tyr Leu Phe Ser Gly Thr Arg Gly
         35                  40                  45

Val Gly Lys Thr Ser Ile Ala Arg Leu Leu Ala Lys Gly Leu Asn Cys
     50                  55                  60

Glu Thr Gly Ile Thr Ala Thr Pro Cys Gly Val Cys Asp Asn Cys Arg
 65                  70                  75                  80

Glu Ile Glu Gln Gly Arg Phe Val Asp Leu Ile Glu Ile Asp Ala Ala
                 85                  90                  95

Ser Arg Thr Lys Val Glu Asp Thr Arg Asp Leu Leu Asp Asn Val Gln
            100                 105                 110

Tyr Ala Pro Ala Arg Gly Arg Phe Lys Val Tyr Leu Ile Asp Glu Val
        115                 120                 125

His Met Leu Ser Arg His Ser Phe Asn Ala Leu Leu Lys Thr Leu Glu
    130                 135                 140

Glu Pro Pro Glu His Val Lys Phe Leu Leu Ala Thr Thr Asp Pro Gln
145                 150                 155                 160

Lys Leu Pro Val Thr Ile Leu Ser Arg Cys Leu Gln Phe His Leu Lys
                165                 170                 175

Ala Leu Asp Val Glu Gln Ile Arg His Gln Leu Glu His Ile Leu Asn
            180                 185                 190

Glu Glu His Ile Ala His Glu Pro Arg Ala Leu Gln Leu Leu Ala Arg
        195                 200                 205

Ala Ala Glu Gly Ser Leu Arg Asp Ala Leu Ser Leu Thr Asp Gln Ala
    210                 215                 220

Ile Ala Ser Gly Asp Gly Gln Val Ser Thr Gln Ala Val Ser Ala Met
225                 230                 235                 240

Leu Gly Thr Leu Asp Asp Asp Gln Ala Leu Ser Leu Val Glu Ala Met
                245                 250                 255

Val Glu Ala Asn Gly Glu Arg Val Met Ala Leu Ile Asn Glu Ala Ala
            260                 265                 270

Ala Arg Gly Ile Glu Trp Glu Ala Leu Leu Val Glu Met Leu Gly Leu
        275                 280                 285

Leu His Arg Ile Ala Met
    290
```

-continued

<210> SEQ ID NO 22
<211> LENGTH: 294
<212> TYPE: PRT
<213> ORGANISM: Haemophilus influenzae

<400> SEQUENCE: 22

```
Met Ser Tyr Gln Val Leu Ala Arg Lys Trp Arg Pro Lys Thr Phe Ala
  1               5                  10                  15

Asp Val Val Gly Gln Glu His Ile Ile Thr Ala Leu Ala Asn Gly Leu
             20                  25                  30

Lys Asp Asn Arg Leu His His Ala Tyr Leu Phe Ser Gly Thr Arg Gly
         35                  40                  45

Val Gly Lys Thr Ser Ile Ala Arg Leu Phe Ala Lys Gly Leu Asn Cys
     50                  55                  60

Val His Gly Val Thr Ala Thr Pro Cys Gly Glu Cys Glu Asn Cys Lys
 65                  70                  75                  80

Ala Ile Glu Gln Gly Asn Phe Ile Asp Leu Ile Glu Ile Asp Ala Ala
                 85                  90                  95

Ser Arg Thr Lys Val Glu Asp Thr Arg Glu Leu Leu Asp Asn Val Gln
            100                 105                 110

Tyr Lys Pro Val Val Gly Arg Phe Lys Val Tyr Leu Ile Asp Glu Val
        115                 120                 125

His Met Leu Ser Arg His Ser Phe Asn Ala Leu Leu Lys Thr Leu Glu
    130                 135                 140

Glu Pro Pro Glu Tyr Val Lys Phe Leu Leu Ala Thr Thr Asp Pro Gln
145                 150                 155                 160

Lys Leu Pro Val Thr Ile Leu Ser Arg Cys Leu Gln Phe His Leu Lys
                165                 170                 175

Ala Leu Asp Glu Thr Gln Ile Ser Gln His Leu Ala His Ile Leu Thr
            180                 185                 190

Gln Glu Asn Ile Pro Phe Glu Asp Pro Ala Leu Val Lys Leu Ala Lys
        195                 200                 205

Ala Ala Gln Gly Ser Ile Arg Asp Ser Leu Ser Leu Thr Asp Gln Ala
    210                 215                 220

Ile Ala Met Gly Asp Arg Gln Val Thr Asn Asn Val Val Ser Asn Met
225                 230                 235                 240

Leu Gly Leu Leu Asp Asp Asn Tyr Ser Val Asp Ile Leu Tyr Ala Leu
                245                 250                 255

His Gln Gly Asn Gly Glu Leu Leu Met Arg Thr Leu Gln Arg Val Ala
            260                 265                 270

Asp Ala Ala Gly Asp Trp Asp Lys Leu Leu Gly Glu Cys Ala Glu Lys
        275                 280                 285

Leu His Gln Ile Ala Leu
    290
```

<210> SEQ ID NO 23
<211> LENGTH: 294
<212> TYPE: PRT
<213> ORGANISM: Bacillus subtilis

<400> SEQUENCE: 23

```
Met Ser Tyr Gln Ala Leu Tyr Arg Val Phe Arg Pro Gln Arg Phe Glu
  1               5                  10                  15

Asp Val Val Gly Gln Glu His Ile Thr Lys Thr Leu Gln Asn Ala Leu
             20                  25                  30
```

-continued

```
Leu Gln Lys Lys Phe Ser His Ala Tyr Leu Phe Ser Gly Pro Arg Gly
        35                  40                  45

Thr Gly Lys Thr Ser Ala Ala Lys Ile Phe Ala Lys Ala Val Asn Cys
    50                  55                  60

Glu His Ala Pro Val Asp Glu Pro Cys Asn Glu Cys Ala Ala Cys Lys
65                  70                  75                  80

Gly Ile Thr Asn Gly Ser Ile Ser Asp Val Ile Glu Ile Asp Ala Ala
                85                  90                  95

Ser Asn Asn Gly Val Asp Glu Ile Arg Asp Ile Arg Asp Lys Val Lys
            100                 105                 110

Phe Ala Pro Ser Ala Val Thr Tyr Lys Val Tyr Ile Ile Asp Glu Val
        115                 120                 125

His Met Leu Ser Ile Gly Ala Phe Asn Ala Leu Leu Lys Thr Leu Glu
    130                 135                 140

Glu Pro Pro Glu His Cys Ile Phe Ile Leu Ala Thr Thr Glu Pro His
145                 150                 155                 160

Lys Ile Pro Leu Thr Ile Ile Ser Arg Cys Gln Arg Phe Asp Phe Lys
                165                 170                 175

Arg Ile Thr Ser Gln Ala Ile Val Gly Arg Met Asn Lys Ile Val Asp
            180                 185                 190

Ala Glu Gln Leu Gln Val Glu Glu Gly Ser Leu Glu Ile Ile Ala Ser
        195                 200                 205

Ala Ala His Gly Gly Met Arg Asp Ala Leu Ser Leu Leu Asp Gln Ala
    210                 215                 220

Ile Ser Phe Ser Gly Asp Ile Leu Lys Val Glu Asp Ala Leu Leu Ile
225                 230                 235                 240

Thr Gly Ala Val Ser Gln Leu Tyr Ile Gly Lys Leu Ala Lys Ser Leu
                245                 250                 255

His Asp Lys Asn Val Ser Asp Ala Leu Glu Thr Leu Asn Glu Leu Leu
            260                 265                 270

Gln Gln Gly Lys Asp Pro Ala Lys Leu Ile Glu Asp Met Ile Phe Tyr
        275                 280                 285

Phe Arg Asp Met Leu Leu
    290


<210> SEQ ID NO 24
<211> LENGTH: 300
<212> TYPE: PRT
<213> ORGANISM: Caulobacter crescentus

<400> SEQUENCE: 24

Asp Ala Tyr Thr Val Leu Ala Arg Lys Tyr Arg Pro Arg Thr Phe Glu
1               5                   10                  15

Asp Leu Ile Gly Gln Glu Ala Met Val Arg Thr Leu Ala Asn Ala Phe
            20                  25                  30

Ser Thr Gly Arg Ile Ala His Ala Phe Met Leu Thr Gly Val Arg Gly
        35                  40                  45

Val Gly Lys Thr Thr Thr Ala Arg Leu Leu Ala Arg Ala Leu Asn Tyr
    50                  55                  60

Glu Thr Asp Thr Val Lys Gly Pro Ser Val Asp Leu Thr Thr Glu Gly
65                  70                  75                  80

Tyr His Cys Arg Ser Ile Ile Glu Gly Arg His Met Asp Val Leu Glu
                85                  90                  95

Leu Asp Ala Ala Ser Arg Thr Lys Val Asp Glu Met Arg Glu Leu Leu
            100                 105                 110
```

-continued

```
Asp Gly Val Arg Tyr Ala Pro Val Glu Ala Arg Tyr Lys Val Tyr Ile
        115                 120                 125

Ile Asp Glu Val His Met Leu Ser Thr Ala Ala Phe Asn Ala Leu Leu
    130                 135                 140

Lys Thr Leu Glu Glu Pro Pro Pro His Ala Lys Phe Ile Phe Ala Thr
145                 150                 155                 160

Thr Glu Ile Arg Lys Val Pro Val Thr Ile Leu Ser Arg Cys Gln Arg
                165                 170                 175

Phe Asp Leu Arg Arg Val Glu Pro Asp Val Leu Val Lys His Phe Asp
            180                 185                 190

Arg Ile Ser Ala Lys Glu Gly Ala Arg Ile Glu Met Asp Ala Leu Ala
        195                 200                 205

Leu Ile Ala Arg Ala Ala Glu Gly Ser Val Arg Asp Gly Leu Ser Leu
    210                 215                 220

Leu Asp Gln Ala Ile Val Gln Thr Glu Arg Gly Gln Thr Val Thr Ser
225                 230                 235                 240

Thr Val Val Arg Asp Met Leu Gly Leu Ala Asp Arg Ser Gln Thr Ile
                245                 250                 255

Ala Leu Tyr Glu His Val Met Ala Gly Lys Thr Lys Asp Ala Leu Glu
            260                 265                 270

Gly Phe Arg Ala Leu Trp Gly Phe Gly Ala Asp Pro Ala Val Val Met
        275                 280                 285

Leu Asp Val Leu Asp His Cys His Ala Ser Ala Val
    290                 295                 300


<210> SEQ ID NO 25
<211> LENGTH: 260
<212> TYPE: PRT
<213> ORGANISM: Mycoplasma genitalium

<400> SEQUENCE: 25

Met His Gln Val Phe Tyr Gln Lys Tyr Arg Pro Ile Asn Phe Lys Gln
  1               5                  10                  15

Thr Leu Gly Gln Glu Ser Ile Arg Lys Ile Leu Val Asn Ala Ile Asn
             20                  25                  30

Arg Asp Lys Leu Pro Asn Gly Tyr Ile Phe Ser Gly Glu Arg Gly Thr
         35                  40                  45

Gly Lys Thr Thr Phe Ala Lys Ile Ile Ala Lys Ala Ile Asn Cys Leu
     50                  55                  60

Asn Trp Asp Gln Ile Asp Val Cys Asn Ser Cys Asp Val Cys Lys Ser
 65                  70                  75                  80

Ile Asn Thr Asn Ser Ala Ile Asp Ile Val Glu Ile Asp Ala Ala Ser
                 85                  90                  95

Lys Asn Gly Ile Asn Asp Ile Arg Glu Leu Val Glu Asn Val Phe Asn
            100                 105                 110

His Pro Phe Thr Phe Lys Lys Lys Val Tyr Ile Leu Asp Glu Ala His
        115                 120                 125

Met Leu Thr Thr Gln Ser Trp Gly Gly Leu Leu Lys Thr Leu Glu Glu
    130                 135                 140

Ser Pro Pro Tyr Val Leu Phe Ile Phe Thr Thr Thr Glu Phe Asn Lys
145                 150                 155                 160

Ile Pro Leu Thr Ile Leu Ser Arg Cys Gln Ser Phe Phe Phe Lys Lys
                165                 170                 175

Ile Thr Ser Asp Leu Ile Leu Glu Arg Leu Asn Asp Ile Ala Lys Lys
```

-continued

```
            180                 185                 190

Glu Lys Ile Lys Ile Glu Lys Asp Ala Leu Ile Lys Ile Ala Asp Leu
        195                 200                 205

Ser Gln Gly Ser Leu Arg Asp Gly Leu Ser Leu Leu Asp Gln Leu Ala
    210                 215                 220

Ile Ser Leu Ile Val Lys Lys Leu Val Leu Leu Met Leu Lys Lys His
225                 230                 235                 240

Leu Ile Ser Leu Ile Glu Met Gln Asn Leu Leu Leu Leu Lys Gln Phe
                245                 250                 255

Tyr Gln Glu Ile
            260


<210> SEQ ID NO 26
<211> LENGTH: 289
<212> TYPE: PRT
<213> ORGANISM: Thermus thermophilus

<400> SEQUENCE: 26

Val Ser Ala Leu Tyr Arg Arg Phe Arg Pro Leu Thr Phe Gln Glu Val
  1               5                  10                  15

Val Gly Gln Glu His Val Lys Glu Pro Leu Leu Lys Ala Ile Arg Glu
             20                  25                  30

Gly Arg Leu Ala Gln Ala Tyr Leu Phe Ser Gly Pro Arg Gly Val Gly
         35                  40                  45

Lys Thr Thr Thr Ala Arg Leu Leu Ala Met Ala Val Gly Cys Gln Gly
     50                  55                  60

Glu Asp Pro Pro Cys Gly Val Cys Pro His Cys Gln Ala Val Gln Arg
 65                  70                  75                  80

Gly Ala His Pro Asp Val Val Asp Ile Asp Ala Ala Ser Asn Asn Ser
                 85                  90                  95

Val Glu Asp Val Arg Glu Leu Arg Glu Arg Ile His Leu Ala Pro Leu
            100                 105                 110

Ser Ala Pro Arg Lys Val Phe Ile Leu Asp Glu Ala His Met Leu Ser
        115                 120                 125

Lys Ser Ala Phe Asn Ala Leu Leu Lys Thr Leu Glu Glu Pro Pro Pro
    130                 135                 140

His Val Leu Phe Val Phe Ala Thr Thr Glu Pro Glu Arg Met Pro Pro
145                 150                 155                 160

Thr Ile Leu Ser Arg Thr Gln His Phe Arg Phe Arg Arg Leu Thr Glu
                165                 170                 175

Glu Glu Ile Ala Phe Lys Leu Arg Arg Ile Leu Glu Ala Val Gly Arg
            180                 185                 190

Glu Ala Glu Glu Glu Ala Leu Leu Leu Leu Ala Arg Leu Ala Asp Gly
        195                 200                 205

Ala Leu Arg Asp Ala Glu Ser Leu Leu Glu Arg Phe Leu Leu Leu Glu
    210                 215                 220

Gly Pro Leu Thr Arg Lys Glu Val Glu Arg Ala Leu Gly Ser Pro Pro
225                 230                 235                 240

Gly Thr Gly Val Ala Glu Ile Ala Ala Ser Leu Ala Arg Gly Lys Thr
                245                 250                 255

Ala Glu Ala Leu Gly Leu Ala Arg Arg Leu Tyr Gly Glu Gly Tyr Ala
            260                 265                 270

Pro Arg Ser Leu Val Ser Gly Leu Leu Glu Val Phe Arg Glu Gly Leu
        275                 280                 285
```

-continued

Tyr

<210> SEQ ID NO 27
<211> LENGTH: 101
<212> TYPE: RNA
<213> ORGANISM: Thermus thermophilus

<400> SEQUENCE: 27
guccuggagg gagaaaaaaa aagccugagc ccaaggcccc gcccggcccc accuccugaa 60
gcgcccgcac ccccgggccc ucccgaggag gagguagagg c 101

<210> SEQ ID NO 28
<211> LENGTH: 11
<212> TYPE: PRT
<213> ORGANISM: Thermus thermophilus

<400> SEQUENCE: 28

Val Leu Glu Gly Glu Lys Lys Ser Leu Ser Pro
1 5 10

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: unsure
<222> LOCATION: (6)
<223> OTHER INFORMATION: N at position 6 is either G or C
<220> FEATURE:
<221> NAME/KEY: unsure
<222> LOCATION: (12)
<223> OTHER INFORMATION: N at position 12 is either G or C
<220> FEATURE:
<221> NAME/KEY: unsure
<222> LOCATION: (21)
<223> OTHER INFORMATION: N at position 21 is either G or C

<400> SEQUENCE: 29
cacgcntacc tnttctccgg nac 23

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: unsure
<222> LOCATION: (7)
<223> OTHER INFORMATION: N at position 7 is either G or C
<220> FEATURE:
<221> NAME/KEY: unsure
<222> LOCATION: (10)
<223> OTHER INFORMATION: N at position 10 is either G or C
<220> FEATURE:
<221> NAME/KEY: unsure
<222> LOCATION: (19)
<223> OTHER INFORMATION: N at position 19 is either G or C
<220> FEATURE:
<221> NAME/KEY: unsure
<222> LOCATION: (22)
<223> OTHER INFORMATION: N at position 22 is either G or C

<400> SEQUENCE: 30
gtgctcnggn ggctcctcnt cngtc 25

<210> SEQ ID NO 31

-continued

<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 31
gtgggatccg tggttctgga tctcgatgaa gaa 33

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 32
gtgggatcca cggsctstcs gagcagaag 29

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 33
gcgggatcct caacgaggac ctctccatct tcaa 34

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 34
gcgggatcct tgtcgtcsag sgtsagsgcg tcgta 35

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 35
gggaaggacc agcgcgtact ccccctgctc ctaggtgtg 39

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 36
gtgtggatcc ttcttcttsc ccatsgc 27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 37

-continued caccgattcc agtggtgcct aggtgtg 27

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 38
caacacctgg tgttccagga gcctgtgctt 30

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 39
ccagaatcgt ctgctggtcg tag 23

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 40
agcaccctgg aggagcttc 19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 41
catgtcgtac tgggtgtac 19

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: unsure
<222> LOCATION: (7)
<223> OTHER INFORMATION: N at position 7 is A, C, G, or T
<220> FEATURE:
<221> NAME/KEY: unsure
<222> LOCATION: (8)
<223> OTHER INFORMATION: N at position 8 is A, C, G, or T
<220> FEATURE:
<221> NAME/KEY: unsure
<222> LOCATION: (13)
<223> OTHER INFORMATION: N at position 13 is A, C, G, or T
<220> FEATURE:
<221> NAME/KEY: unsure
<222> LOCATION: (14)
<223> OTHER INFORMATION: N at position 14 is A, C, G, or T

<400> SEQUENCE: 42
gtsgtsnnsg acnnsgagac sacsggg 27

-continued

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: unsure
<222> LOCATION: (8)
<223> OTHER INFORMATION: N at position 8 is A, C, G, or T
<220> FEATURE:
<221> NAME/KEY: unsure
<222> LOCATION: (9)
<223> OTHER INFORMATION: N at position 9 is A, C, G, or T
<220> FEATURE:
<221> NAME/KEY: unsure
<222> LOCATION: (17)
<223> OTHER INFORMATION: N at position 17 is A, C, G, or T
<220> FEATURE:
<221> NAME/KEY: unsure
<222> LOCATION: (18)
<223> OTHER INFORMATION: N at position 18 is A, C, G, or T

<400> SEQUENCE: 43
gaasccsnng tcgaasnngg cgttgtg 27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 44
cggggatcca cctcaatcac ctcgtgg 27

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 45
cggggatccg ccaccttgcg gctccgggtg 30

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 46
gcgctctaga cgagttccca aagcgtgcgg t 31

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 47
cgcgtctaga tcacctgtat ccaga 25

<210> SEQ ID NO 48
<211> LENGTH: 33

-continued

<212> TYPE: DNA
<213> ORGANISM: Artificial Sequence
<220> FEATURE:
<223> OTHER INFORMATION: Description of Artificial Sequence: primer

<400> SEQUENCE: 48
gcggcgcata tggtggtggt cctggacctg gag 33

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 49
cgcgtctaga tcacctgtat ccaga 25

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 50
gtsctsgtsa agacscactt 20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 51
sagsagsgcg ttgaasgtgt g 21

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 52
ctcgttggtg aaagtttccg tg 22

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 53
cgtccagttc atcgccggaa agga 24

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 54

-continued

```
tctggcaaca cgttctggag cacatcc                                          27


<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence:  primer

<400> SEQUENCE: 55

tgctggcgtt catcttcagg atg                                              23


<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence:  primer

<400> SEQUENCE: 56

catcctgaag atgaacgcca gca                                              23


<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence:  primer

<400> SEQUENCE: 57

aggttatcca caggggtcat gtgca                                            25


<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence:  primer

<400> SEQUENCE: 58

gtgtgtcata tgaacataac ggttcccaa                                        29


<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence:  primer

<400> SEQUENCE: 59

gcgcgaattc tcccttgtgg aaggcttag                                        29


<210> SEQ ID NO 60
<211> LENGTH: 13
<212> TYPE: PRT
<213> ORGANISM: Thermus thermophilus

<400> SEQUENCE: 60

Arg Val Glu Leu Asp Tyr Asp Ala Leu Thr Leu Asp Asp
  1               5                  10


<210> SEQ ID NO 61
<211> LENGTH: 14
<212> TYPE: PRT
<213> ORGANISM: Thermus thermophilus
```

-continued

<400> SEQUENCE: 61

```
Phe Phe Ile Glu Ile Gln Asn His Gly Leu Ser Glu Gln Lys
  1               5                  10
```

<210> SEQ ID NO 62
<211> LENGTH: 8
<212> TYPE: PRT
<213> ORGANISM: Thermus thermophilus

<400> SEQUENCE: 62

```
Phe Phe Ile Glu Ile Gln Asn His
  1               5
```

<210> SEQ ID NO 63
<211> LENGTH: 8
<212> TYPE: PRT
<213> ORGANISM: Thermus thermophilus

<400> SEQUENCE: 63

```
Tyr Asp Ala Leu Thr Leu Asp Asp
  1               5
```

<210> SEQ ID NO 64
<211> LENGTH: 6
<212> TYPE: PRT
<213> ORGANISM: Thermus thermophilus

<400> SEQUENCE: 64

```
Ala Met Gly Lys Lys Lys
  1               5
```

<210> SEQ ID NO 65
<211> LENGTH: 9
<212> TYPE: PRT
<213> ORGANISM: Thermus thermophilus

<400> SEQUENCE: 65

```
Phe Asn Lys Ser His Ser Ala Ala Tyr
  1               5
```

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is undefined
<220> FEATURE:
<221> NAME/KEY: PEPTIDE
<222> LOCATION: (5)
<223> OTHER INFORMATION: Xaa at position 5 is undefined

<400> SEQUENCE: 66

```
Val Val Xaa Asp Xaa Glu Thr Thr Gly
  1               5
```

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE -continued
<222> LOCATION: (4)
<223> OTHER INFORMATION: Xaa at position 4 is undefined
<220> FEATURE:
<221> NAME/KEY: PEPTIDE
<222> LOCATION: (7)
<223> OTHER INFORMATION: Xaa at position 7 is undefined

<400> SEQUENCE: 67

His Asn Ala Xaa Phe Asp Xaa Gly Phe
1 5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is undefined
<220> FEATURE:
<221> NAME/KEY: PEPTIDE
<222> LOCATION: (5)
<223> OTHER INFORMATION: Xaa at position 5 is undefined

<400> SEQUENCE: 68

Val Val Xaa Asp Xaa Glu Thr Thr Gly
1 5

<210> SEQ ID NO 69
<211> LENGTH: 7
<212> TYPE: PRT
<213> ORGANISM: Thermus thermophilus

<400> SEQUENCE: 69

Val Leu Val Lys Thr His Leu
1 5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: peptide

<400> SEQUENCE: 70

His Arg Ala Leu Tyr Asp
1 5

<210> SEQ ID NO 71
<211> LENGTH: 7
<212> TYPE: PRT
<213> ORGANISM: Thermus thermophilus

<400> SEQUENCE: 71

His Thr Phe Asn Ala Leu Leu
1 5

<210> SEQ ID NO 72
<211> LENGTH: 34
<212> TYPE: PRT
<213> ORGANISM: Escherichia coli

<400> SEQUENCE: 72

Asp Arg Tyr Phe Leu Glu Leu Ile Arg Thr Gly Arg Pro Asp Glu Glu
1 5 10 15

-continued

```
Ser Tyr Leu His Ala Ala Val Glu Leu Ala Glu Ala Arg Gly Leu Pro
            20                  25                  30

Val Val


<210> SEQ ID NO 73
<211> LENGTH: 34
<212> TYPE: PRT
<213> ORGANISM: Vibrio cholerae

<400> SEQUENCE: 73

Asp His Phe Tyr Leu Glu Leu Ile Arg Thr Gly Arg Ala Asp Glu Glu
  1               5                  10                  15

Ser Tyr Leu His Phe Ala Leu Asp Val Ala Glu Gln Tyr Asp Leu Pro
            20                  25                  30

Val Val


<210> SEQ ID NO 74
<211> LENGTH: 34
<212> TYPE: PRT
<213> ORGANISM: Haemophilus influenzae

<400> SEQUENCE: 74

Asp His Phe Tyr Leu Ala Leu Ser Arg Thr Gly Arg Pro Asn Glu Glu
  1               5                  10                  15

Arg Tyr Ile Gln Ala Ala Leu Lys Leu Ala Glu Arg Cys Asp Leu Pro
            20                  25                  30

Leu Val


<210> SEQ ID NO 75
<211> LENGTH: 34
<212> TYPE: PRT
<213> ORGANISM: Rickettsia prowazekii

<400> SEQUENCE: 75

Asp Arg Phe Tyr Phe Glu Ile Met Arg His Asp Leu Pro Glu Glu Gln
  1               5                  10                  15

Phe Ile Glu Asn Ser Tyr Ile Gln Ile Ala Ser Glu Leu Ser Ile Pro
            20                  25                  30

Ile Val


<210> SEQ ID NO 76
<211> LENGTH: 34
<212> TYPE: PRT
<213> ORGANISM: Helicobacter pylori

<400> SEQUENCE: 76

Asp Asp Phe Tyr Leu Glu Ile Met Arg His Gly Ile Leu Asp Gln Arg
  1               5                  10                  15

Phe Ile Asp Glu Gln Val Ile Lys Met Ser Leu Glu Thr Gly Leu Lys
            20                  25                  30

Ile Ile


<210> SEQ ID NO 77
<211> LENGTH: 34
<212> TYPE: PRT
<213> ORGANISM: Synechocystis sp.

<400> SEQUENCE: 77

Asp Asp Tyr Tyr Leu Glu Ile Gln Asp His Gly Ser Val Glu Asp Arg
  1               5                  10                  15
```

```
Leu Val Asn Ile Asn Leu Val Lys Ile Ala Gln Glu Leu Asp Ile Lys
            20                  25                  30

Ile Val


<210> SEQ ID NO 78
<211> LENGTH: 34
<212> TYPE: PRT
<213> ORGANISM: Mycobacterium tuberculosis

<400> SEQUENCE: 78

Asp Asn Tyr Phe Leu Glu Leu Met Asp His Gly Leu Thr Ile Glu Arg
  1               5                  10                  15

Arg Val Arg Asp Gly Leu Leu Glu Ile Gly Arg Ala Leu Asn Ile Pro
            20                  25                  30

Pro Leu


<210> SEQ ID NO 79
<211> LENGTH: 46
<212> TYPE: PRT
<213> ORGANISM: Escherichia coli

<400> SEQUENCE: 79

Asn Lys Arg Arg Ala Lys Asn Gly Glu Pro Pro Leu Asp Ile Ala Ala
  1               5                  10                  15

Ile Pro Leu Asp Asp Lys Lys Ser Phe Asp Met Leu Gln Arg Ser Glu
            20                  25                  30

Thr Thr Ala Val Phe Gln Leu Glu Ser Arg Gly Met Lys Asp
        35                  40                  45


<210> SEQ ID NO 80
<211> LENGTH: 46
<212> TYPE: PRT
<213> ORGANISM: Vibrio cholerae

<400> SEQUENCE: 80

Asn Pro Arg Leu Lys Lys Ala Gly Lys Pro Pro Val Arg Ile Glu Ala
  1               5                  10                  15

Ile Pro Leu Asp Asp Ala Arg Ser Phe Arg Asn Leu Gln Asp Ala Lys
            20                  25                  30

Thr Thr Ala Val Phe Gln Leu Glu Ser Arg Gly Met Lys Glu
        35                  40                  45


<210> SEQ ID NO 81
<211> LENGTH: 46
<212> TYPE: PRT
<213> ORGANISM: Haemophilus influenzae

<400> SEQUENCE: 81

Asn Val Arg Met Val Arg Glu Gly Lys Pro Arg Val Asp Ile Ala Ala
  1               5                  10                  15

Ile Pro Leu Asp Asp Pro Glu Ser Phe Glu Leu Leu Lys Arg Ser Glu
            20                  25                  30

Thr Thr Ala Val Phe Gln Leu Glu Ser Arg Gly Met Lys Asp
        35                  40                  45


<210> SEQ ID NO 82
<211> LENGTH: 46
<212> TYPE: PRT
<213> ORGANISM: Rickettsia prowazekii
```

-continued

<400> SEQUENCE: 82

Cys Lys Lys Leu Leu Lys Glu Gln Gly Ile Lys Ile Asp Phe Asp Asp
1               5                   10                  15

Met Thr Phe Asp Asp Lys Lys Thr Tyr Gln Met Leu Cys Lys Gly Lys
            20                  25                  30

Gly Val Gly Val Phe Gln Phe Glu Ser Ile Gly Met Lys Asp
        35                  40                  45

<210> SEQ ID NO 83
<211> LENGTH: 45
<212> TYPE: PRT
<213> ORGANISM: Helicobacter pylori

<400> SEQUENCE: 83

Leu Lys Ile Ile Lys Thr Gln His Lys Ile Ser Val Asp Phe Leu Ser
1               5                   10                  15

Leu Asp Met Asp Asp Pro Lys Val Tyr Lys Thr Ile Gln Ser Gly Asp
            20                  25                  30

Thr Val Gly Ile Phe Gln Ile Glu Ser Gly Met Phe Gln
        35                  40                  45

<210> SEQ ID NO 84
<211> LENGTH: 46
<212> TYPE: PRT
<213> ORGANISM: Synechocystis sp.

<400> SEQUENCE: 84

Gln Glu Arg Lys Ala Leu Gln Ile Arg Ala Arg Thr Gly Ser Lys Lys
1               5                   10                  15

Leu Pro Asp Asp Val Lys Lys Thr His Lys Leu Leu Glu Ala Gly Asp
            20                  25                  30

Leu Glu Gly Ile Phe Gln Leu Glu Ser Gln Gly Met Lys Gln
        35                  40                  45

<210> SEQ ID NO 85
<211> LENGTH: 46
<212> TYPE: PRT
<213> ORGANISM: Mycobacterium tuberculosis

<400> SEQUENCE: 85

Ile Asp Asn Val Arg Ala Asn Arg Gly Ile Asp Leu Asp Leu Glu Ser
1               5                   10                  15

Val Pro Leu Asp Asp Lys Ala Thr Tyr Glu Leu Leu Gly Arg Gly Asp
            20                  25                  30

Thr Leu Gly Val Phe Gln Leu Asp Gly Gly Pro Met Arg Asp
        35                  40                  45

<210> SEQ ID NO 86
<211> LENGTH: 3729
<212> TYPE: DNA
<213> ORGANISM: Thermus thermophilus

<400> SEQUENCE: 86
atgggccggg agctccgctt cgcccacctc caccagcaca cccagttctc cctcctggac 60
ggggcggcga agctttccga cctcctcaag tgggtcaagg agacgacccc cgaggacccc 120
gccttggcca tgaccgacca cggcaacctc ttcggggccg tggagttcta caagaaggcc 180
accgaaatgg gcatcaagcc catcctgggc tacgaggcct acgtggcggc ggaaagccgc 240
tttgaccgca agcggggaaa gggcctagac gggggctact ttcacctcac cctcctcgcc 300

-continued

```
aaggacttca cggggtacca gaacctggtg cgcctggcga gccgggctta cctggagggg    360
ttttacgaaa agccccggat tgaccgggag atcctgcgcg agcacgccga gggcctcatc    420
gccctctcgg ggtgcctcgg ggcggagatc ccccagttca tcctccagga ccgtctggac    480
ctggccgagg cccggctcaa cgagtacctc tccatcttca aggaccgctt cttcatcgag    540
atccagaacc acggcctccc cgagcagaaa aaggtcaacg aggtcctcaa ggagttcgcc    600
cgaaagtacg gcctggggat ggtggccacc aacgacggcc attacgtgag gaaggaggac    660
gcccgcgccc acgaggtcct cctcgccatc cagtccaaga gcaccctgga cgaccccggg    720
cgctggcgct tcccctgcga cgagttctac gtgaagaccc ccgaggagat gcgggccatg    780
ttccccgagg aggagtgggg ggacgagccc tttgacaaca ccgtggagat cgcccgcatg    840
tgcaacgtgg agctgcccat cggggacaag atggtctacc gaatccccccg cttcccccctc   900
cccgaggggc ggaccgaggc ccagtacctc atggagctca ccttcaaggg gctcctccgc    960
cgctacccgg accggatcac cgagggcttc taccgggagg tcttccgcct tttggggaag   1020
cttccccccc acggggacgg ggaggccttg gccgaggcct tggcccaggt ggagcgggag   1080
gcttgggaga ggctcatgaa gagcctcccc cctttggccg gggtcaagga gtggacggcg   1140
gaggccattt tccaccgggc cctttacgag ctttccgtga tagagcgcat ggggtttccc   1200
ggctacttcc tcatcgtcca ggactacatc aactgggccc ggagaaacgg cgtctccgtg   1260
gggcccggca gggggagcgc cgccgggagc ctggtggcct acgccgtggg gatcaccaac   1320
attgaccccc tccgcttcgg cctcctcttt gagcgcttcc tgaacccgga gagggtctcc   1380
atgcccgaca ttgacacgga cttctccgac cgggagcggg accgggtgat ccagtacgtg   1440
cgggagcgct acggcgagga caaggtggcc cagatcggca ccctgggaag cctcgcctcc   1500
aaggccgccc tcaaggacgt ggcccgggtc tacggcatcc cccacaagaa ggcggaggaa   1560
ttggccaagc tcatcccggt gcagttcggg aagcccaagc ccctgcagga ggccatccag   1620
gtggtgccgg agcttagggc ggagatggag aaggacccca aggtgcggga ggtcctcgag   1680
gtggccatgc gcctggaggg cctgaaccgc cacgcctccg tccacgccgc cggggtggtg   1740
atcgccgccg agcccctcac ggacctcgtc cccctcatgc gcgaccagga agggcggccc   1800
gtcacccagt acgacatggg ggcggtggag gccttggggc ttttgaagat ggactttttg   1860
ggcctccgca ccctcacctt cctggacgag gtcaagcgca tcgtcaaggc gtcccagggg   1920
gtggagctgg actacgatgc cctcccccctg gacgacccca agaccttcgc cctcctctcc   1980
cgggggggaga ccaagggggt cttccagctg gagtcggggg ggatgaccgc cacgctccgc   2040
ggcctcaagc cgcggcgctt tgaggacctg atcgccatcc tctccctcta ccgccccggg   2100
cccatggagc acatccccac ctacatccgc cgccaccacg ggctggagcc cgtgagctac   2160
agcgagtttc cccacgccga gaagtaccta aagcccatcc tggacgagac ctacggcatc   2220
cccgtctacc aggagcagat catgcagatc gcctcggccg tggcggggta ctccctgggc   2280
gaggcggacc tcctgcggcg gtccatgggc aagaagaagg tggaggagat gaagtcccac   2340
cgggagcgct tcgtccaggg ggccaaggaa aggggcgtgc ccgaggagga ggccaaccgc   2400
ctctttgaca tgctggaggc cttcgccaac tacggcttca acaaatccca cgctgccgcc   2460
tacagcctcc tctcctacca gaccgcctac gtgaaggccc actaccccgt ggagttcatg   2520
gccgccctcc tctccgtgga gcggcacgac tccgacaagg tggccgagta catccgcgac   2580
gcccgggcca tgggcataga ggtccttccc ccggacgtca accgctccgg gtttgacttc   2640
```

-continued

```
ctggtccagg gccggcagat ccttttcggc ctctccgcgg tgaagaacgt gggcgaggcg   2700

gcggcggagg ccattctccg ggagcgggag cggggcggcc cctaccggag cctcggcgac   2760

ttcctcaagc ggctggacga gaaggtgctc aacaagcgga ccctggagtc cctcatcaag   2820

gcgggcgccc tggacggctt cggggaaagg gcgcggctcc tcgcctccct ggaagggctc   2880

ctcaagtggg cggccgagaa ccgggagaag gcccgctcgg gcatgatggg cctcttcagc   2940

gaagtggagg agccgccttt ggccgaggcc gccccccctgg acgagatcac ccggctccgc   3000

tacgagaagg aggccctggg gatctacgtc tccggccacc ccatcttgcg gtaccccggg   3060

ctccgggaga cggccacctg caccctggag gagcttcccc acctggcccg ggacctgccg   3120

ccccggtcta gggtcctcct tgccgggatg gtggaggagg tggtgcgcaa gcccacaaag   3180

agcggcggga tgatggcccg cttcgtcctc tccgacgaga cgggggcgct tgaggcggtg   3240

gcattcggcc gggcctacga ccaggtctcc ccgaggctca aggaggacac ccccgtgctc   3300

gtcctcgccg aggtggagcg ggaggagggg ggcgtgcggg tgctggccca ggccgtttgg   3360

acctacgagg agctggagca ggtcccccgg gccctcgagg tggaggtgga ggcctccctc   3420

ctggacgacc ggggggtggc ccacctgaaa agcctcctgg acgagcacgc ggggaccctc   3480

cccctgtacg tccgggtcca gggcgccttc ggcgaggccc tcctcgccct gagggaggtg   3540

cgggtggggg aggaggctgt aggcggccgc gtggttccgg gcctacctcc tgcccgaccg   3600

ggaggtcctt ctccagggcg gccaggcggg ggaggcccag gaggcggtgc ccttctaggg   3660

ggtgggccgt gagacctagc gccatcgttc tcgccggggg caaggaggcc tgggcccgac   3720

cccttttgg                                                           3729
```

```
<210> SEQ ID NO 87
<211> LENGTH: 1245
<212> TYPE: PRT
<213> ORGANISM: Thermus thermophilus

<400> SEQUENCE: 87

Met Gly Arg Glu Leu Arg Phe Ala His Leu His Gln His Thr Gln Phe
  1               5                  10                  15

Ser Leu Leu Asp Gly Ala Pro Lys Leu Ser Asp Leu Leu Lys Trp Val
             20                  25                  30

Glu Glu Thr Thr Pro Glu Asp Pro Ala Leu Ala Met Thr Asp His Gly
         35                  40                  45

Asn Leu Phe Gly Ala Val Glu Phe Tyr Lys Lys Ala Thr Glu Met Gly
     50                  55                  60

Ile Lys Pro Ile Leu Gly Tyr Glu Ala Tyr Val Ala Ala Glu Ser Arg
 65                  70                  75                  80

Phe Asp Arg Lys Arg Gly Lys Gly Leu Asp Gly Gly Tyr Phe His Leu
                 85                  90                  95

Thr Leu Leu Ala Lys Asp Phe Thr Gly Tyr Gln Asn Leu Val Arg Leu
            100                 105                 110

Ala Ser Arg Ala Tyr Leu Glu Gly Phe Tyr Glu Lys Pro Arg Ile Asp
        115                 120                 125

Arg Glu Ile Leu Arg Glu His Ala Glu Gly Leu Ile Ala Leu Ser Gly
    130                 135                 140

Cys Leu Gly Ala Glu Ile Pro Gln Phe Ile Leu Gln Asp Arg Leu Asp
145                 150                 155                 160

Leu Ala Glu Ala Arg Leu Asn Glu Tyr Leu Ser Ile Phe Lys Asp Arg
                165                 170                 175
```

-continued

```
Phe Phe Ile Glu Ile Gln Asn His Gly Leu Pro Glu Gln Lys Lys Val
            180                 185                 190

Asn Glu Val Leu Lys Glu Phe Ala Arg Lys Tyr Gly Leu Gly Met Val
        195                 200                 205

Ala Thr Asn Asp Gly His Tyr Val Arg Lys Glu Asp Ala Arg Ala His
    210                 215                 220

Glu Val Leu Leu Ala Ile Gln Ser Lys Ser Thr Leu Asp Asp Pro Gly
225                 230                 235                 240

Ala Leu Ala Leu Pro Cys Glu Glu Phe Tyr Val Lys Thr Pro Glu Glu
                245                 250                 255

Met Arg Ala Met Phe Pro Glu Glu Glu Val Gly Gly Arg Ser Pro Leu
            260                 265                 270

Thr Thr Pro Trp Arg Ser Pro His Val Gln Arg Gly Ala Ala Ile Gly
        275                 280                 285

Thr Arg Trp Ser Thr Arg Ile Pro Arg Phe Pro Leu Pro Glu Gly Arg
    290                 295                 300

Thr Glu Ala Gln Tyr Leu Met Glu Leu Thr Phe Lys Gly Leu Leu Arg
305                 310                 315                 320

Arg Tyr Pro Asp Arg Ile Thr Glu Gly Phe Tyr Arg Glu Val Phe Arg
                325                 330                 335

Leu Ser Gly Lys Leu Pro Pro His Gly Asp Gly Glu Ala Leu Ala Glu
            340                 345                 350

Ala Leu Ala Gln Val Glu Arg Glu Ala Trp Glu Arg Leu Met Lys Ser
        355                 360                 365

Leu Pro Pro Leu Ala Gly Val Lys Glu Trp Thr Ala Glu Ala Ile Phe
    370                 375                 380

His Arg Ala Leu Tyr Glu Leu Ser Ala Ile Glu Arg Met Gly Phe Pro
385                 390                 395                 400

Gly Leu Leu Pro His Arg Pro Gly Leu His Gln Leu Gly Pro Glu Lys
                405                 410                 415

Gly Val Ser Val Gly Pro Gly Arg Gly Gly Ala Ala Gly Ser Leu Val
            420                 425                 430

Ala Tyr Ala Val Gly Ile Thr Asn Ile Asp Pro Leu Arg Phe Gly Leu
        435                 440                 445

Leu Phe Glu Arg Phe Leu Asn Pro Glu Arg Val Ser Met Pro Asp Ile
    450                 455                 460

Asp Thr Asp Phe Ser Asp Arg Glu Arg Asp Arg Val Ile Gln Tyr Val
465                 470                 475                 480

Arg Glu Arg Tyr Gly Glu Asp Lys Val Ala Gln Ile Gly Thr Leu Gly
                485                 490                 495

Ser Leu Ala Ser Lys Ala Ala Leu Lys Glu Val Ala Arg Val Tyr Gly
            500                 505                 510

Ile Pro Arg Lys Lys Ala Glu Glu Leu Ala Lys Leu Ile Pro Val Gln
        515                 520                 525

Phe Gly Lys Pro Lys Pro Leu Gln Glu Ala Ile Gln Val Val Pro Glu
    530                 535                 540

Leu Arg Ala Glu Met Glu Lys Asp Pro Lys Val Arg Glu Val Leu Glu
545                 550                 555                 560

Val Ala Met Arg Leu Glu Gly Leu Asn Arg His Ala Ser Val His Ala
                565                 570                 575

Gly Arg Gly Gly Val Phe Ser Glu Pro Leu Thr Asp Leu Val Pro Leu
            580                 585                 590

Cys Ala Thr Arg Lys Gly Gly Pro Tyr Thr Gln Tyr Asp Met Gly Ala
```

-continued

```
        595                 600                 605

Val Glu Ala Leu Gly Leu Leu Lys Met Asp Phe Leu Gly Leu Arg Thr
    610                 615                 620

Leu Thr Phe Leu Asp Glu Val Lys Arg Ile Val Lys Ala Ser Gln Gly
625                 630                 635                 640

Val Glu Leu Asp Tyr Asp Ala Leu Pro Leu Asp Asp Pro Lys Thr Phe
                645                 650                 655

Ala Leu Leu Ser Arg Gly Glu Thr Lys Gly Val Phe Gln Leu Glu Ser
            660                 665                 670

Gly Gly Met Thr Ala Thr Leu Arg Gly Leu Lys Pro Arg Arg Phe Glu
        675                 680                 685

Asp Leu Ile Ala Ile Leu Ser Leu Tyr Arg Pro Gly Pro Met Glu His
    690                 695                 700

Ile Pro Thr Tyr Ile Arg Arg His His Gly Leu Glu Pro Val Ser Tyr
705                 710                 715                 720

Ser Glu Phe Pro His Ala Glu Lys Tyr Leu Lys Pro Ile Leu Asp Glu
                725                 730                 735

Thr Tyr Gly Ile Pro Val Tyr Gln Glu Gln Ile Met Gln Ile Ala Ser
            740                 745                 750

Ala Val Ala Gly Tyr Ser Leu Gly Glu Ala Asp Leu Leu Arg Arg Ser
        755                 760                 765

Met Gly Lys Lys Lys Val Glu Glu Met Lys Ser His Arg Glu Arg Phe
    770                 775                 780

Val Gln Gly Ala Lys Glu Arg Gly Val Pro Glu Glu Glu Ala Asn Arg
785                 790                 795                 800

Leu Phe Asp Met Leu Glu Ala Phe Ala Asn Tyr Gly Phe Asn Lys Ser
                805                 810                 815

His Ala Ala Ala Tyr Ser Leu Leu Ser Tyr Gln Thr Ala Tyr Val Lys
            820                 825                 830

Ala His Tyr Pro Val Glu Phe Met Ala Ala Leu Leu Ser Val Glu Arg
        835                 840                 845

His Asp Ser Asp Lys Val Ala Glu Tyr Ile Arg Asp Ala Arg Ala Met
    850                 855                 860

Gly Ile Glu Val Leu Pro Pro Asp Val Asn Arg Ser Gly Phe Asp Phe
865                 870                 875                 880

Leu Val Gln Gly Arg Gln Ile Leu Phe Gly Leu Ser Ala Val Lys Asn
                885                 890                 895

Val Gly Glu Ala Ala Ala Glu Ala Ile Leu Arg Glu Arg Glu Arg Gly
            900                 905                 910

Gly Pro Tyr Arg Ser Leu Gly Asp Phe Leu Lys Arg Leu Asp Glu Lys
        915                 920                 925

Val Leu Asn Lys Arg Thr Leu Glu Ser Leu Ile Lys Ala Gly Ala Leu
    930                 935                 940

Asp Gly Phe Gly Glu Arg Ala Arg Leu Leu Ala Ser Leu Glu Gly Leu
945                 950                 955                 960

Leu Lys Trp Ala Ala Glu Asn Arg Glu Lys Ala Arg Ser Gly Met Met
                965                 970                 975

Gly Leu Phe Ser Glu Val Glu Glu Pro Pro Leu Ala Glu Ala Ala Pro
            980                 985                 990

Leu Asp Glu Ile Thr Arg Leu Arg Tyr Glu Lys Glu Ala Leu Gly Ile
        995                 1000                1005

Tyr Val Ser Gly His Pro Ile Leu Arg Tyr Pro Gly Leu Arg Glu Thr
   1010                1015                1020
```

-continued

```
Ala Thr Cys Thr Leu Glu Glu Leu Pro His Leu Ala Arg Asp Leu Pro
1025                1030                1035                1040

Pro Arg Ser Arg Val Leu Leu Ala Gly Met Val Glu Glu Val Val Arg
                1045                1050                1055

Lys Pro Thr Lys Ser Gly Gly Met Met Ala Arg Phe Val Leu Ser Asp
            1060                1065                1070

Glu Thr Gly Ala Leu Glu Ala Val Ala Phe Gly Arg Ala Tyr Asp Gln
       1075                1080                1085

Val Ser Pro Arg Leu Lys Glu Asp Thr Pro Val Leu Val Leu Ala Glu
   1090                1095                1100

Val Glu Arg Glu Glu Gly Gly Val Arg Val Leu Ala Gln Ala Val Trp
1105                1110                1115                1120

Thr Tyr Gln Glu Leu Glu Gln Val Pro Arg Ala Leu Glu Val Glu Val
                1125                1130                1135

Glu Ala Ser Leu Pro Asp Asp Arg Gly Val Ala His Leu Lys Ser Leu
            1140                1145                1150

Leu Asp Glu His Ala Gly Thr Leu Pro Leu Tyr Val Arg Val Gln Gly
       1155                1160                1165

Ala Phe Gly Glu Ala Leu Leu Ala Leu Arg Glu Val Arg Val Gly Glu
   1170                1175                1180

Glu Ala Leu Gly Ala Leu Glu Ala Ala Gly Phe Pro Ala Tyr Leu Leu
1185                1190                1195                1200

Pro Asn Arg Glu Val Ser Pro Arg Leu Thr Gly Ser Gly Gly Pro Arg
                1205                1210                1215

Gly Arg Ala Leu Ser Thr Gly Leu Ala Leu Lys Thr Tyr Pro Ile Ala
            1220                1225                1230

Leu Pro Gly Gly Asn Glu Ala Leu Ala Arg Pro Leu Leu
       1235                1240                1245


<210> SEQ ID NO 88
<211> LENGTH: 198
<212> TYPE: PRT
<213> ORGANISM: Thermus thermophilus

<400> SEQUENCE: 88

Val Glu Arg Val Val Arg Thr Leu Leu Asp Gly Arg Phe Leu Leu Glu
  1               5                  10                  15

Glu Gly Val Gly Leu Trp Glu Trp Arg Tyr Pro Phe Pro Leu Glu Gly
             20                  25                  30

Glu Ala Val Val Val Leu Asp Leu Glu Thr Thr Gly Leu Ala Gly Leu
         35                  40                  45

Asp Glu Val Ile Glu Val Gly Leu Leu Arg Leu Glu Gly Gly Arg Arg
     50                  55                  60

Leu Pro Phe Gln Ser Leu Val Arg Pro Leu Pro Pro Ala Glu Ala Arg
 65                  70                  75                  80

Ser Trp Asn Leu Thr Gly Ile Pro Arg Glu Ala Leu Glu Glu Ala Pro
                 85                  90                  95

Ser Leu Glu Glu Val Leu Glu Lys Ala Tyr Pro Leu Arg Gly Asp Ala
            100                 105                 110

Thr Leu Val Ile His Asn Ala Ala Phe Asp Leu Gly Phe Leu Arg Pro
        115                 120                 125

Ala Leu Glu Gly Leu Gly Tyr Arg Leu Glu Asn Pro Val Val Asp Ser
    130                 135                 140

Leu Arg Leu Ala Arg Arg Gly Leu Pro Gly Leu Arg Arg Tyr Gly Leu
```

-continued 145 150 155 160

Asp Ala Leu Ser Glu Val Leu Glu Leu Pro Arg Arg Thr Cys His Arg
165 170 175

Ala Leu Glu Asp Val Glu Arg Thr Leu Ala Val Val His Glu Val Tyr
180 185 190

Tyr Met Leu Thr Ser Gly
195

<210> SEQ ID NO 89
<211> LENGTH: 182
<212> TYPE: PRT
<213> ORGANISM: Deinococcus radiodurans
<220> FEATURE:
<221> NAME/KEY: PEPTIDE
<222> LOCATION: (79)
<223> OTHER INFORMATION: X at position 79 is undefined

<400> SEQUENCE: 89

Pro Trp Pro Gln Asp Val Val Val Phe Asp Leu Glu Thr Thr Gly Phe
1 5 10 15

Ser Pro Ala Ser Ala Ala Ile Val Glu Ile Gly Ala Val Arg Ile Val
20 25 30

Gly Gly Gln Ile Asp Glu Thr Leu Lys Phe Glu Thr Leu Val Arg Pro
35 40 45

Thr Arg Pro Asp Gly Ser Met Leu Ser Ile Pro Trp Gln Ala Gln Arg
50 55 60

Val His Gly Ile Ser Asp Glu Met Val Arg Arg Ala Pro Ala Xaa Lys
65 70 75 80

Asp Val Leu Pro Asp Phe Phe Asp Phe Val Asp Gly Ser Ala Val Val
85 90 95

Ala His Asn Val Ser Phe Asp Gly Gly Phe Met Arg Ala Gly Ala Glu
100 105 110

Arg Leu Gly Leu Ser Trp Ala Pro Glu Arg Glu Leu Cys Thr Met Gln
115 120 125

Leu Ser Arg Arg Ala Phe Pro Arg Glu Arg Thr His Asn Leu Thr Val
130 135 140

Leu Ala Glu Arg Leu Gly Leu Glu Phe Ala Pro Gly Gly Arg His Arg
145 150 155 160

Ser Tyr Gly Asp Val Gln Val Thr Ala Gln Ala Tyr Leu Arg Leu Leu
165 170 175

Glu Leu Leu Gly Glu Arg
180

<210> SEQ ID NO 90
<211> LENGTH: 201
<212> TYPE: PRT
<213> ORGANISM: Bacillus subtilis

<400> SEQUENCE: 90

His Gly Ile Lys Met Ile Tyr Gly Met Glu Ala Asn Leu Val Asp Asp
1 5 10 15

Gly Val Pro Ile Ala Tyr Asn Ala Ala His Arg Leu Leu Glu Glu Glu
20 25 30

Thr Tyr Val Val Phe Asp Val Glu Thr Thr Gly Leu Ser Ala Val Tyr
35 40 45

Asp Thr Ile Ile Glu Leu Ala Ala Val Lys Val Lys Gly Gly Glu Ile
50 55 60

-continued

```
Ile Asp Lys Phe Glu Ala Phe Ala Asn Pro His Arg Pro Leu Ser Ala
 65                  70                  75                  80

Thr Ile Ile Glu Leu Thr Gly Ile Thr Asp Asp Met Leu Gln Asp Ala
                 85                  90                  95

Pro Asp Val Val Asp Val Ile Arg Asp Phe Arg Glu Trp Ile Gly Asp
            100                 105                 110

Asp Ile Leu Val Ala His Asn Ala Ser Phe Asp Met Gly Phe Leu Asn
        115                 120                 125

Val Ala Tyr Lys Lys Leu Leu Glu Val Glu Lys Ala Lys Asn Pro Val
    130                 135                 140

Ile Asp Thr Leu Glu Leu Gly Arg Phe Leu Tyr Pro Glu Phe Lys Asn
145                 150                 155                 160

His Arg Leu Asn Thr Leu Cys Lys Lys Phe Asp Ile Glu Leu Thr Gln
                165                 170                 175

His His Arg Ala Ile Tyr Asp Thr Glu Ala Thr Ala Tyr Leu Leu Leu
            180                 185                 190

Lys Met Leu Lys Asp Ala Ala Glu Lys
        195                 200


<210> SEQ ID NO 91
<211> LENGTH: 188
<212> TYPE: PRT
<213> ORGANISM: Haemophilus influenzae
<220> FEATURE:
<221> NAME/KEY: PEPTIDE
<222> LOCATION: (47)
<223> OTHER INFORMATION: X at position 47 is undefined
<220> FEATURE:
<221> NAME/KEY: PEPTIDE
<222> LOCATION: (57)
<223> OTHER INFORMATION: X at position 57 is undefined

<400> SEQUENCE: 91

Met Ile Asn Pro Asn Arg Gln Ile Val Leu Asp Thr Glu Thr Thr Gly
  1               5                  10                  15

Met Asn Gln Leu Gly Ala His Tyr Glu Gly His Cys Ile Ile Glu Ile
             20                  25                  30

Gly Ala Val Glu Leu Ile Asn Arg Arg Tyr Thr Gly Asn Asn Xaa His
         35                  40                  45

Ile Tyr Ile Lys Pro Asp Arg Pro Xaa Asp Pro Asp Ala Ile Lys Val
     50                  55                  60

His Gly Ile Thr Asp Glu Met Leu Ala Asp Lys Pro Glu Phe Lys Glu
 65                  70                  75                  80

Val Ala Gln Asp Phe Leu Asp Tyr Ile Asn Gly Ala Glu Leu Leu Ile
                 85                  90                  95

His Asn Ala Pro Phe Asp Val Gly Phe Met Asp Tyr Glu Phe Arg Lys
            100                 105                 110

Leu Asn Leu Asn Val Lys Thr Asp Asp Ile Cys Leu Val Thr Asp Thr
        115                 120                 125

Leu Gln Met Ala Arg Gln Met Tyr Pro Gly Lys Arg Asn Asn Leu Asp
    130                 135                 140

Ala Leu Cys Asp Arg Leu Gly Ile Asp Asn Ser Lys Arg Thr Leu His
145                 150                 155                 160

Gly Ala Leu Leu Asp Ala Glu Ile Leu Ala Asp Val Tyr Leu Met Met
                165                 170                 175

Thr Gly Gly Gln Thr Asn Leu Phe Asp Glu Glu Glu
            180                 185
```

<210> SEQ ID NO 92
<211> LENGTH: 189
<212> TYPE: PRT
<213> ORGANISM: Escherichia coli

<400> SEQUENCE: 92

```
Met Ser Thr Ala Ile Thr Arg Gln Ile Val Leu Asp Thr Glu Thr Thr
  1               5                  10                  15

Gly Met Asn Gln Ile Gly Ala His Ser Glu Gly His Lys Ile Ile Glu
             20                  25                  30

Ile Gly Ala Val Glu Val Val Asn Arg Arg Leu Thr Gly Asn Asn Phe
         35                  40                  45

His Val Tyr Leu Lys Asp Arg Leu Val Asp Pro Glu Ala Phe Gly Val
     50                  55                  60

His Gly Ile Ala Val Asp Phe Leu Leu Asp Lys Pro Thr Phe Ala Glu
 65                  70                  75                  80

Val Ala Val Glu Phe Met Asp Tyr Ile Arg Gly Ala Glu Leu Val Ile
                 85                  90                  95

His Asn Ala Ala Phe Asp Ile Gly Phe Met Asp Tyr Glu Phe Ser Leu
            100                 105                 110

Leu Lys Arg Asp Ile Ala Lys Thr Asn Thr Phe Cys Lys Val Thr Asp
        115                 120                 125

Ser Leu Ala Val Ala Arg Lys Met Phe Pro Gly Lys Arg Asn Ser Leu
    130                 135                 140

Asp Ala Leu Cys Ala Arg Tyr Glu Ile Asp Asn Ser Lys Arg Thr Leu
145                 150                 155                 160

His Gly Ala Leu Leu Asp Ala Gln Ile Leu Ala Glu Val Tyr Leu Ala
                165                 170                 175

Met Thr Gly Gly Gln Thr Ser Met Ala Phe Ala Met Glu
            180                 185
```

<210> SEQ ID NO 93
<211> LENGTH: 201
<212> TYPE: PRT
<213> ORGANISM: Helicobacter pylori

<400> SEQUENCE: 93

```
Asn Leu Glu Tyr Leu Lys Ala Cys Gly Leu Asn Phe Ile Glu Thr Ser
  1               5                  10                  15

Glu Asn Leu Ile Thr Leu Lys Asn Leu Lys Thr Pro Leu Lys Asp Glu
             20                  25                  30

Val Phe Ser Phe Ile Asp Leu Glu Thr Thr Gly Ser Cys Pro Ile Lys
         35                  40                  45

His Glu Ile Leu Glu Ile Gly Ala Val Gln Val Lys Gly Gly Glu Ile
     50                  55                  60

Ile Asn Arg Phe Glu Thr Leu Val Lys Val Lys Ser Val Pro Asp Tyr
 65                  70                  75                  80

Ile Ala Glu Leu Thr Gly Ile Thr Tyr Glu Asp Thr Leu Asn Ala Pro
                 85                  90                  95

Ser Ala His Glu Ala Leu Gln Glu Leu Arg Leu Phe Leu Gly Asn Ser
            100                 105                 110

Val Phe Val Ala His Asn Ala Asn Phe Asp Tyr Asn Phe Leu Gly Arg
        115                 120                 125

Tyr Phe Val Glu Lys Leu His Cys Pro Leu Leu Asn Leu Lys Leu Cys
    130                 135                 140
```

-continued

```
Thr Leu Asp Leu Ser Lys Arg Ala Ile Leu Ser Met Arg Tyr Ser Leu
145                 150                 155                 160

Ser Phe Leu Lys Glu Leu Leu Gly Phe Gly Ile Glu Val Ser His Arg
                165                 170                 175

Ala Tyr Ala Asp Ala Leu Ala Ser Tyr Lys Leu Phe Glu Ile Cys Leu
            180                 185                 190

Leu Asn Leu Pro Ser Tyr Ile Lys Thr
        195                 200


<210> SEQ ID NO 94
<211> LENGTH: 630
<212> TYPE: DNA
<213> ORGANISM: Thermus thermophilus

<400> SEQUENCE: 94

atggtggagc gggtggtgcg gacccttctg gacgggaggt tcctcctgga ggagggggtg      60

gggctttggg agtggcgcta cccctttccc ctggaggggg aggcggtggt ggtcctggac     120

ctggagacca cggggcttgc cggcctggac gaggtgattg aggtgggcct cctccgcctg     180

gaggggggga ggcgcctccc cttccagagc ctcgtccggc ccctcccgcc cgccgaagcc     240

cgttcgtgga acctcaccgg catcccccgg gaggccctgg aggaggcccc ctccctggag     300

gaggttctgg agaaggccta ccccctccgc ggcgacgcca ccttggtgat ccacaacgcc     360

gcctttgacc tgggcttcct ccgcccggcc ttggagggcc tgggctaccg cctggaaaac     420

cccgtggtgg actccctgcg cttggccaga cggggcttac caggccttag gcgctacggc     480

ctggacgccc tctccgaggt cctggagctt ccccgaagga cctgccaccg ggccctcgag     540

gacgtggagc gcaccctcgc cgtggtgcac gaggtatact atatgcttac gtccggccgt     600

ccccgcacgc tttgggaact cgggaggtag                                      630


<210> SEQ ID NO 95
<211> LENGTH: 210
<212> TYPE: PRT
<213> ORGANISM: Thermus thermophilus

<400> SEQUENCE: 95

Met Val Glu Arg Val Val Arg Thr Leu Leu Asp Gly Arg Phe Leu Leu
  1               5                  10                  15

Glu Glu Gly Val Gly Leu Trp Glu Trp Arg Tyr Pro Phe Pro Leu Glu
            20                  25                  30

Gly Glu Ala Val Val Val Leu Asp Leu Glu Thr Thr Gly Leu Ala Gly
        35                  40                  45

Leu Asp Glu Val Ile Glu Val Gly Leu Leu Arg Leu Glu Gly Gly Arg
     50                  55                  60

Arg Leu Pro Phe Gln Ser Leu Val Arg Pro Leu Pro Pro Ala Glu Ala
 65                  70                  75                  80

Arg Ser Trp Asn Leu Thr Gly Ile Pro Arg Glu Ala Leu Glu Glu Ala
                 85                  90                  95

Pro Ser Leu Glu Glu Val Leu Glu Lys Ala Tyr Pro Leu Arg Gly Asp
            100                 105                 110

Ala Thr Leu Val Ile His Asn Ala Ala Phe Asp Leu Gly Phe Leu Arg
        115                 120                 125

Pro Ala Leu Glu Gly Leu Gly Tyr Arg Leu Glu Asn Pro Val Val Asp
    130                 135                 140

Ser Leu Arg Leu Ala Arg Arg Gly Leu Pro Gly Leu Arg Arg Tyr Gly
145                 150                 155                 160
```

-continued

Leu Asp Ala Leu Ser Glu Val Leu Glu Leu Pro Arg Arg Thr Cys His
165 170 175

Arg Ala Leu Glu Asp Val Glu Arg Thr Leu Ala Val Val His Glu Val
180 185 190

Tyr Tyr Met Leu Thr Ser Gly Arg Pro Arg Thr Leu Trp Glu Leu Gly
195 200 205

Arg Glx
210

<210> SEQ ID NO 96
<211> LENGTH: 461
<212> TYPE: PRT
<213> ORGANISM: Pseudomonas marcesans

<400> SEQUENCE: 96

Met Leu Glu Ala Ser Trp Glu Lys Val Gln Ser Ser Leu Lys Gln Asn
1 5 10 15

Leu Ser Lys Pro Ser Tyr Glu Thr Trp Ile Arg Pro Thr Glu Phe Ser
20 25 30

Gly Phe Lys Asn Gly Glu Leu Thr Leu Ile Ala Pro Asn Ser Phe Ser
35 40 45

Ser Ala Trp Leu Lys Asn Asn Tyr Ser Gln Thr Ile Gln Glu Thr Ala
50 55 60

Glu Glu Ile Phe Gly Glu Pro Val Thr Val His Val Lys Val Lys Ala
65 70 75 80

Asn Ala Glu Ser Ser Asp Glu His Tyr Ser Ser Ala Pro Ile Thr Pro
85 90 95

Pro Leu Glu Ala Ser Pro Gly Ser Val Asp Ser Ser Gly Ser Ser Leu
100 105 110

Arg Leu Ser Lys Lys Thr Leu Pro Leu Leu Asn Leu Arg Tyr Val Phe
115 120 125

Asn Arg Phe Val Val Gly Pro Asn Ser Arg Met Ala His Ala Ala Ala
130 135 140

Met Ala Val Ala Glu Ser Pro Gly Arg Glu Phe Asn Pro Leu Phe Ile
145 150 155 160

Cys Gly Gly Val Gly Leu Gly Lys Thr His Leu Met Gln Ala Ile Gly
165 170 175

His Tyr Arg Leu Glu Ile Asp Pro Gly Ala Lys Val Ser Tyr Val Ser
180 185 190

Thr Glu Thr Phe Thr Asn Asp Leu Ile Leu Ala Ile Arg Gln Asp Arg
195 200 205

Met Gln Ala Phe Arg Asp Arg Tyr Arg Ala Ala Asp Leu Ile Leu Val
210 215 220

Asp Asp Ile Gln Phe Ile Glu Gly Lys Glu Tyr Thr Gln Glu Glu Phe
225 230 235 240

Phe His Thr Phe Asn Ala Leu His Asp Ala Gly Ser Gln Ile Val Leu
245 250 255

Ala Ser Asp Arg Pro Pro Ser Gln Ile Pro Arg Leu Gln Glu Arg Leu
260 265 270

Met Ser Arg Phe Ser Met Gly Leu Ile Ala Asp Val Gln Ala Pro Asp
275 280 285

Leu Glu Thr Arg Met Ala Ile Leu Gln Lys Lys Ala Glu His Glu Arg
290 295 300

Val Gly Leu Pro Arg Asp Leu Ile Gln Phe Ile Ala Gly Arg Phe Thr

-continued

```
305                 310                 315                 320

Ser Asn Ile Arg Glu Leu Glu Gly Ala Leu Thr Arg Ala Ile Ala Phe
                325                 330                 335

Ala Ser Ile Thr Gly Leu Pro Met Thr Val Asp Ser Ile Ala Pro Met
            340                 345                 350

Leu Asp Pro Asn Gly Gln Gly Val Glu Val Thr Pro Lys Gln Val Leu
        355                 360                 365

Asp Lys Val Ala Glu Val Phe Lys Val Thr Pro Asp Glu Met Arg Ser
    370                 375                 380

Ala Ser Arg Arg Arg Pro Val Ser Gln Ala Arg Gln Val Gly Met Tyr
385                 390                 395                 400

Leu Met Arg Gln Gly Thr Asn Leu Ser Leu Pro Arg Ile Gly Asp Thr
                405                 410                 415

Phe Gly Gly Lys Asp His Thr Thr Val Met Tyr Ala Ile Glu Gln Val
            420                 425                 430

Glu Lys Lys Leu Ser Ser Asp Pro Gln Ile Ala Ser Gln Val Gln Lys
        435                 440                 445

Ile Arg Asp Leu Leu Gln Ile Asp Ser Arg Arg Lys Arg
    450                 455                 460


<210> SEQ ID NO 97
<211> LENGTH: 447
<212> TYPE: PRT
<213> ORGANISM: Synechocystis sp.

<400> SEQUENCE: 97

Met Val Ser Cys Glu Asn Leu Trp Gln Gln Ala Leu Ala Ile Leu Ala
  1               5                  10                  15

Thr Gln Leu Thr Lys Pro Ala Phe Asp Thr Trp Ile Lys Ala Ser Val
             20                  25                  30

Leu Ile Ser Leu Gly Asp Gly Val Ala Thr Ile Gln Val Glu Asn Gly
         35                  40                  45

Phe Val Leu Asn His Leu Gln Lys Ser Tyr Gly Pro Leu Leu Met Glu
     50                  55                  60

Val Leu Thr Asp Leu Thr Gly Gln Glu Ile Thr Val Lys Leu Ile Thr
 65                  70                  75                  80

Asp Gly Leu Glu Pro His Ser Leu Ile Gly Gln Glu Ser Ser Leu Pro
                 85                  90                  95

Met Glu Thr Thr Pro Lys Asn Ala Thr Ala Leu Asn Gly Lys Tyr Thr
            100                 105                 110

Phe Ser Arg Phe Val Val Gly Pro Thr Asn Arg Met Ala His Ala Ala
        115                 120                 125

Ser Leu Ala Val Ala Glu Ser Pro Gly Arg Glu Phe Asn Pro Leu Phe
    130                 135                 140

Leu Cys Gly Gly Val Gly Leu Gly Lys Thr His Leu Met Gln Ala Ile
145                 150                 155                 160

Ala His Tyr Arg Leu Glu Met Tyr Pro Asn Ala Lys Val Tyr Tyr Val
                165                 170                 175

Ser Thr Glu Arg Phe Thr Asn Asp Leu Ile Thr Ala Ile Arg Gln Asp
            180                 185                 190

Asn Met Glu Asp Phe Arg Ser Tyr Tyr Arg Ser Ala Asp Phe Leu Leu
        195                 200                 205

Ile Asp Asp Ile Gln Phe Ile Lys Gly Lys Glu Tyr Thr Gln Glu Glu
    210                 215                 220
```

-continued

```
Phe Phe His Thr Phe Asn Ser Leu His Glu Ala Gly Lys Gln Val Val
225                 230                 235                 240

Val Ala Ser Asp Arg Ala Pro Gln Arg Ile Pro Gly Leu Gln Asp Arg
                245                 250                 255

Leu Ile Ser Arg Phe Ser Met Gly Leu Ile Ala Asp Ile Gln Val Pro
            260                 265                 270

Asp Leu Glu Thr Arg Met Ala Ile Leu Gln Lys Lys Ala Glu Tyr Asp
        275                 280                 285

Arg Ile Arg Leu Pro Lys Glu Val Ile Glu Tyr Ile Ala Ser His Tyr
    290                 295                 300

Thr Ser Asn Ile Arg Glu Leu Glu Gly Ala Leu Ile Arg Ala Ile Ala
305                 310                 315                 320

Tyr Thr Ser Leu Ser Asn Val Ala Met Thr Val Glu Asn Ile Ala Pro
                325                 330                 335

Val Leu Asn Pro Pro Val Glu Lys Val Ala Ala Ala Pro Glu Thr Ile
            340                 345                 350

Ile Thr Ile Val Ala Gln His Tyr Gln Leu Lys Val Glu Glu Leu Leu
        355                 360                 365

Ser Asn Ser Arg Arg Arg Glu Val Ser Leu Ala Arg Gln Val Gly Met
    370                 375                 380

Tyr Leu Met Arg Gln His Thr Asp Leu Ser Leu Pro Arg Ile Gly Glu
385                 390                 395                 400

Ala Phe Gly Gly Lys Asp His Thr Thr Val Met Tyr Ser Cys Asp Lys
                405                 410                 415

Ile Thr Gln Leu Gln Gln Lys Asp Trp Glu Thr Ser Gln Thr Leu Thr
            420                 425                 430

Ser Leu Ser His Arg Ile Asn Ile Ala Gly Gln Ala Pro Glu Ser
        435                 440                 445


<210> SEQ ID NO 98
<211> LENGTH: 446
<212> TYPE: PRT
<213> ORGANISM: Bacillus subtilis

<400> SEQUENCE: 98

Met Glu Asn Ile Leu Asp Leu Trp Asn Gln Ala Leu Ala Gln Ile Glu
  1               5                  10                  15

Lys Lys Leu Ser Lys Pro Ser Phe Glu Thr Trp Met Lys Ser Thr Lys
             20                  25                  30

Ala His Ser Leu Gln Gly Asp Thr Leu Thr Ile Thr Ala Pro Asn Glu
         35                  40                  45

Phe Ala Arg Asp Trp Leu Glu Ser Arg Tyr Leu His Leu Ile Ala Asp
     50                  55                  60

Thr Ile Tyr Glu Leu Thr Gly Glu Glu Leu Ser Ile Lys Phe Val Ile
 65                  70                  75                  80

Pro Gln Asn Gln Asp Val Glu Asp Phe Met Pro Lys Pro Gln Val Lys
                 85                  90                  95

Lys Ala Val Lys Glu Asp Thr Ser Asp Phe Pro Gln Asn Met Leu Asn
            100                 105                 110

Pro Lys Tyr Thr Phe Asp Thr Phe Val Ile Gly Ser Gly Asn Arg Phe
        115                 120                 125

Ala His Ala Ala Ser Leu Ala Val Ala Glu Ala Pro Ala Lys Ala Tyr
    130                 135                 140

Asn Pro Leu Phe Ile Tyr Gly Gly Val Gly Leu Gly Lys Thr His Leu
145                 150                 155                 160
```

-continued

```
Met His Ala Ile Gly His Tyr Val Ile Asp His Asn Pro Ser Ala Lys
                165                 170                 175

Val Val Tyr Leu Ser Ser Glu Lys Phe Thr Asn Glu Phe Ile Asn Ser
            180                 185                 190

Ile Arg Asp Asn Lys Ala Val Asp Phe Arg Asn Arg Tyr Arg Asn Val
        195                 200                 205

Asp Val Leu Leu Ile Asp Asp Ile Gln Phe Leu Ala Gly Lys Glu Gln
    210                 215                 220

Thr Gln Glu Glu Phe Phe His Thr Phe Asn Thr Leu His Glu Glu Ser
225                 230                 235                 240

Lys Gln Ile Val Ile Ser Ser Asp Arg Pro Pro Lys Glu Ile Pro Thr
                245                 250                 255

Leu Glu Asp Arg Leu Arg Ser Arg Phe Glu Trp Gly Leu Ile Thr Asp
            260                 265                 270

Ile Thr Pro Pro Asp Leu Glu Thr Arg Ile Ala Ile Leu Arg Lys Lys
        275                 280                 285

Ala Lys Ala Glu Gly Leu Asp Ile Pro Asn Glu Val Met Leu Tyr Ile
    290                 295                 300

Ala Asn Gln Ile Asp Ser Asn Ile Arg Glu Leu Glu Gly Ala Leu Ile
305                 310                 315                 320

Arg Val Val Ala Tyr Ser Ser Leu Ile Asn Lys Asp Ile Asn Ala Asp
                325                 330                 335

Leu Ala Ala Glu Ala Leu Lys Asp Ile Ile Pro Ser Ser Lys Pro Lys
            340                 345                 350

Val Ile Thr Ile Lys Glu Ile Gln Arg Val Val Gly Gln Gln Phe Asn
        355                 360                 365

Ile Lys Leu Glu Asp Phe Lys Ala Lys Lys Arg Thr Lys Ser Val Ala
    370                 375                 380

Phe Pro Arg Gln Ile Ala Met Tyr Leu Ser Arg Glu Met Thr Asp Ser
385                 390                 395                 400

Ser Leu Pro Lys Ile Gly Glu Glu Phe Gly Gly Arg Asp His Thr Thr
                405                 410                 415

Val Ile His Ala His Glu Lys Ile Ser Lys Leu Leu Ala Asp Asp Glu
            420                 425                 430

Gln Leu Gln Gln His Val Lys Glu Ile Lys Glu Gln Leu Lys
        435                 440                 445


<210> SEQ ID NO 99
<211> LENGTH: 507
<212> TYPE: PRT
<213> ORGANISM: Mycobacterium tuberculosis

<400> SEQUENCE: 99

Met Thr Asp Asp Pro Gly Ser Gly Phe Thr Thr Val Trp Asn Ala Val
  1               5                  10                  15

Val Ser Glu Leu Asn Gly Asp Pro Lys Val Asp Asp Gly Pro Ser Ser
             20                  25                  30

Asp Ala Asn Leu Ser Ala Pro Leu Thr Pro Gln Gln Arg Ala Trp Leu
         35                  40                  45

Asn Leu Val Gln Pro Leu Thr Ile Val Glu Gly Phe Ala Leu Leu Ser
     50                  55                  60

Val Pro Ser Ser Phe Val Gln Asn Glu Ile Glu Arg His Leu Arg Ala
 65                  70                  75                  80

Pro Ile Thr Asp Ala Leu Ser Arg Arg Leu Gly His Gln Ile Gln Leu
```

-continued

```
                85                  90                  95

Gly Val Arg Ile Ala Pro Pro Ala Thr Asp Glu Ala Asp Asp Thr Thr
            100                 105                 110

Val Pro Pro Ser Glu Asn Pro Ala Thr Thr Ser Pro Asp Thr Thr Thr
        115                 120                 125

Asp Asn Asp Glu Ile Asp Asp Ser Ala Ala Ala Arg Gly Asp Asn Gln
    130                 135                 140

His Ser Trp Pro Ser Tyr Phe Thr Glu Arg Pro His Asn Thr Asp Ser
145                 150                 155                 160

Ala Thr Ala Gly Val Thr Ser Leu Asn Arg Arg Tyr Thr Phe Asp Thr
                165                 170                 175

Phe Val Ile Gly Ala Ser Asn Arg Phe Ala His Ala Ala Ala Leu Ala
            180                 185                 190

Ile Ala Glu Ala Pro Ala Arg Ala Tyr Asn Pro Leu Phe Ile Trp Gly
        195                 200                 205

Glu Ser Gly Leu Gly Lys Thr His Leu Leu His Ala Ala Gly Asn Tyr
    210                 215                 220

Ala Gln Arg Leu Phe Pro Gly Met Arg Val Lys Tyr Val Ser Thr Glu
225                 230                 235                 240

Glu Phe Thr Asn Asp Phe Ile Asn Ser Leu Arg Asp Asp Arg Lys Val
                245                 250                 255

Ala Phe Lys Arg Ser Tyr Arg Asp Val Asp Val Leu Leu Val Asp Asp
            260                 265                 270

Ile Gln Phe Ile Glu Gly Lys Glu Gly Ile Gln Glu Glu Phe Phe His
        275                 280                 285

Thr Phe Asn Thr Leu His Asn Ala Asn Lys Gln Ile Val Ile Ser Ser
    290                 295                 300

Asp Arg Pro Pro Lys Gln Leu Ala Thr Leu Glu Asp Arg Leu Arg Thr
305                 310                 315                 320

Arg Phe Glu Trp Gly Leu Ile Thr Asp Val Gln Pro Pro Glu Leu Glu
                325                 330                 335

Thr Arg Ile Ala Ile Leu Arg Lys Lys Ala Gln Met Glu Arg Leu Ala
            340                 345                 350

Val Pro Asp Asp Val Leu Glu Leu Ile Ala Ser Ser Ile Glu Arg Asn
        355                 360                 365

Ile Arg Glu Leu Glu Gly Ala Leu Ile Arg Val Thr Ala Phe Ala Ser
    370                 375                 380

Leu Asn Lys Thr Pro Ile Asp Lys Ala Leu Ala Glu Ile Val Leu Arg
385                 390                 395                 400

Asp Leu Ile Ala Asp Ala Asn Thr Met Gln Ile Ser Ala Ala Thr Ile
                405                 410                 415

Met Ala Ala Thr Ala Glu Tyr Phe Asp Thr Thr Val Glu Glu Leu Arg
            420                 425                 430

Gly Pro Gly Lys Thr Arg Ala Leu Ala Gln Ser Arg Gln Ile Ala Met
        435                 440                 445

Tyr Leu Cys Arg Glu Leu Thr Asp Leu Ser Leu Pro Lys Ile Gly Gln
    450                 455                 460

Ala Phe Gly Arg Asp His Thr Thr Val Met Tyr Ala Gln Arg Lys Ile
465                 470                 475                 480

Leu Ser Glu Met Ala Glu Arg Arg Glu Val Phe Asp His Val Lys Glu
                485                 490                 495

Leu Thr Thr Arg Ile Arg Gln Arg Ser Lys Arg
            500                 505
```

-continued

<210> SEQ ID NO 100
<211> LENGTH: 446
<212> TYPE: PRT
<213> ORGANISM: Thermus thermophilus

<400> SEQUENCE: 100

```
Met Ser His Glu Ala Val Trp Gln His Val Leu Glu His Ile Arg Arg
  1               5                  10                  15

Ser Ile Thr Glu Val Glu Phe His Thr Trp Phe Glu Arg Ile Arg Pro
             20                  25                  30

Leu Gly Ile Arg Asp Gly Val Leu Glu Leu Ala Val Pro Thr Ser Phe
         35                  40                  45

Ala Leu Asp Trp Ile Arg Arg His Tyr Ala Gly Leu Ile Gln Glu Gly
     50                  55                  60

Pro Arg Leu Leu Gly Ala Gln Ala Pro Arg Phe Glu Leu Arg Val Val
 65                  70                  75                  80

Pro Gly Val Val Val Gln Glu Asp Ile Phe Gln Pro Pro Pro Ser Pro
                 85                  90                  95

Pro Ala Gln Ala Gln Pro Glu Asp Thr Phe Lys Thr Ser Trp Trp Gly
            100                 105                 110

Pro Thr Thr Pro Trp Pro His Gly Gly Ala Val Ala Val Ala Glu Ser
        115                 120                 125

Pro Gly Arg Ala Tyr Asn Pro Leu Phe Ile Tyr Gly Gly Arg Gly Leu
    130                 135                 140

Gly Lys Thr Tyr Leu Met His Ala Val Gly Pro Leu Arg Ala Lys Arg
145                 150                 155                 160

Phe Pro His Met Arg Leu Glu Tyr Val Ser Thr Glu Thr Phe Thr Asn
                165                 170                 175

Glu Leu Ile Asn Arg Pro Ser Ala Arg Asp Arg Met Thr Glu Phe Arg
            180                 185                 190

Glu Arg Tyr Arg Ser Val Asp Leu Leu Leu Val Asp Asp Val Gln Phe
        195                 200                 205

Ile Ala Gly Lys Glu Arg Thr Gln Glu Glu Phe Phe His Thr Phe Asn
    210                 215                 220

Ala Leu Tyr Glu Ala His Lys Gln Ile Ile Leu Ser Ser Asp Arg Pro
225                 230                 235                 240

Pro Lys Asp Ile Leu Thr Leu Glu Ala Arg Leu Arg Ser Arg Phe Glu
                245                 250                 255

Trp Gly Leu Ile Thr Asp Asn Pro Ala Pro Asp Leu Glu Thr Arg Ile
            260                 265                 270

Ala Ile Leu Lys Met Asn Ala Ser Ser Gly Pro Glu Asp Pro Glu Asp
        275                 280                 285

Ala Leu Glu Tyr Ile Ala Arg Gln Val Thr Ser Asn Ile Arg Glu Trp
    290                 295                 300

Glu Gly Ala Leu Met Arg Ala Ser Pro Phe Ala Ser Leu Asn Gly Val
305                 310                 315                 320

Glu Leu Thr Arg Ala Val Ala Ala Lys Ala Leu Arg His Leu Arg Pro
                325                 330                 335

Arg Glu Leu Glu Ala Asp Pro Leu Glu Ile Ile Arg Lys Ala Ala Gly
            340                 345                 350

Pro Val Arg Pro Glu Thr Pro Gly Gly Ala His Gly Glu Arg Arg Lys
        355                 360                 365

Lys Glu Val Val Leu Pro Arg Gln Leu Ala Met Tyr Leu Val Arg Glu
```

-continued

```
    370                 375                 380

Leu Thr Pro Ala Ser Leu Pro Glu Ile Gly Gln Leu Phe Gly Gly Arg
385                 390                 395                 400

Asp His Thr Thr Val Arg Tyr Ala Ile Gln Lys Val Gln Glu Leu Ala
                405                 410                 415

Gly Lys Pro Asp Arg Glu Val Gln Gly Leu Leu Arg Thr Leu Arg Glu
            420                 425                 430

Ala Cys Thr Asp Pro Val Asp Asn Leu Trp Ile Thr Cys Gly
        435                 440                 445


<210> SEQ ID NO 101
<211> LENGTH: 467
<212> TYPE: PRT
<213> ORGANISM: Escherichia coli

<400> SEQUENCE: 101

Met Ser Leu Ser Leu Trp Gln Gln Cys Leu Ala Arg Leu Gln Asp Glu
  1               5                  10                  15

Leu Pro Ala Thr Glu Phe Ser Met Trp Ile Arg Pro Leu Gln Ala Glu
            20                  25                  30

Leu Ser Asp Asn Thr Leu Ala Leu Tyr Ala Pro Asn Arg Phe Val Leu
        35                  40                  45

Asp Trp Val Arg Asp Lys Tyr Leu Asn Asn Ile Asn Gly Leu Leu Thr
    50                  55                  60

Ser Phe Cys Gly Ala Asp Ala Pro Gln Leu Arg Phe Glu Val Gly Thr
 65                  70                  75                  80

Lys Pro Val Thr Gln Thr Pro Gln Ala Ala Val Thr Ser Asn Val Ala
                85                  90                  95

Ala Pro Ala Gln Val Ala Gln Thr Gln Pro Gln Arg Ala Ala Pro Ser
            100                 105                 110

Thr Arg Ser Gly Trp Asp Asn Val Pro Ala Pro Ala Glu Pro Thr Tyr
        115                 120                 125

Arg Ser Asn Val Asn Val Lys His Thr Phe Asp Asn Phe Val Glu Gly
    130                 135                 140

Lys Ser Asn Gln Leu Ala Arg Ala Ala Ala Arg Gln Val Ala Asp Asn
145                 150                 155                 160

Pro Gly Gly Ala Tyr Asn Pro Leu Phe Leu Tyr Gly Gly Thr Gly Leu
                165                 170                 175

Gly Lys Thr His Leu Leu His Ala Val Gly Asn Gly Ile Met Ala Arg
            180                 185                 190

Lys Pro Asn Ala Lys Val Val Tyr Met His Ser Glu Arg Phe Val Gln
        195                 200                 205

Asp Met Val Lys Ala Leu Gln Asn Asn Ala Ile Glu Glu Phe Lys Arg
    210                 215                 220

Tyr Tyr Arg Ser Val Asp Ala Leu Leu Ile Asp Asp Ile Gln Phe Phe
225                 230                 235                 240

Ala Asn Lys Glu Arg Ser Gln Glu Glu Phe Phe His Thr Phe Asn Ala
                245                 250                 255

Leu Leu Glu Gly Asn Gln Gln Ile Ile Leu Thr Ser Asp Arg Tyr Pro
            260                 265                 270

Lys Glu Ile Asn Gly Val Glu Asp Arg Leu Lys Ser Arg Phe Gly Trp
        275                 280                 285

Gly Leu Thr Val Ala Ile Glu Pro Pro Glu Leu Glu Thr Arg Val Ala
    290                 295                 300
```

-continued

```
Ile Leu Met Lys Lys Ala Asp Glu Asn Asp Ile Arg Leu Pro Gly Glu
305                 310                 315                 320

Val Ala Phe Phe Ile Ala Lys Arg Leu Arg Ser Asn Val Arg Glu Leu
                325                 330                 335

Glu Gly Ala Leu Asn Arg Val Ile Ala Asn Ala Asn Phe Thr Gly Arg
            340                 345                 350

Ala Ile Thr Ile Asp Phe Val Arg Glu Ala Leu Arg Asp Leu Leu Ala
        355                 360                 365

Leu Gln Glu Lys Leu Val Thr Ile Asp Asn Ile Gln Lys Thr Val Ala
    370                 375                 380

Glu Tyr Tyr Lys Ile Lys Val Ala Asp Leu Leu Ser Lys Arg Arg Ser
385                 390                 395                 400

Arg Ser Val Ala Arg Pro Arg Gln Met Ala Met Ala Leu Ala Lys Glu
                405                 410                 415

Leu Thr Asn His Ser Leu Pro Glu Ile Gly Asp Ala Phe Gly Gly Arg
            420                 425                 430

Asp His Thr Thr Val Leu His Ala Cys Arg Lys Ile Glu Gln Leu Arg
        435                 440                 445

Glu Glu Ser His Asp Ile Lys Glu Asp Phe Ser Asn Leu Ile Arg Thr
    450                 455                 460

Leu Ser Ser
465


<210> SEQ ID NO 102
<211> LENGTH: 440
<212> TYPE: PRT
<213> ORGANISM: Thermatoga maritima

<400> SEQUENCE: 102

Met Lys Glu Arg Ile Leu Gln Glu Ile Lys Thr Arg Val Asn Arg Lys
  1               5                  10                  15

Ser Trp Glu Leu Trp Phe Ser Ser Phe Asp Val Lys Ser Ile Glu Gly
            20                  25                  30

Asn Lys Val Val Phe Ser Val Gly Asn Leu Phe Ile Lys Glu Trp Leu
        35                  40                  45

Glu Lys Lys Tyr Tyr Ser Val Leu Ser Lys Ala Val Lys Val Val Leu
     50                  55                  60

Gly Asn Asp Ala Thr Phe Glu Ile Thr Tyr Glu Ala Phe Glu Pro His
 65                  70                  75                  80

Ser Ser Tyr Ser Glu Pro Leu Val Lys Lys Arg Ala Val Leu Leu Thr
                 85                  90                  95

Pro Leu Asn Pro Asp Tyr Thr Phe Glu Asn Phe Val Val Gly Pro Gly
            100                 105                 110

Asn Ser Phe Ala Tyr His Ala Ala Leu Glu Val Ala Lys His Pro Gly
        115                 120                 125

Arg Tyr Asn Pro Leu Phe Ile Tyr Gly Gly Val Gly Leu Gly Lys Thr
    130                 135                 140

His Leu Leu Gln Ser Ile Gly Asn Tyr Val Val Gln Asn Glu Pro Asp
145                 150                 155                 160

Leu Arg Val Met Tyr Ile Thr Ser Glu Lys Phe Leu Asn Asp Leu Val
                165                 170                 175

Asp Ser Met Lys Glu Gly Lys Leu Asn Glu Phe Arg Glu Lys Tyr Arg
            180                 185                 190

Lys Lys Val Asp Ile Leu Leu Ile Asp Asp Val Gln Phe Leu Ile Gly
        195                 200                 205
```

-continued

Lys Thr Gly Val Gln Thr Glu Leu Phe His Thr Phe Asn Glu Leu His
    210                 215                 220

Asp Ser Gly Lys Gln Ile Val Ile Cys Ser Asp Arg Glu Pro Gln Lys
225                 230                 235                 240

Leu Ser Glu Phe Gln Asp Arg Leu Val Ser Arg Phe Gln Met Gly Leu
                245                 250                 255

Val Ala Lys Leu Glu Pro Pro Asp Glu Glu Thr Arg Lys Ser Ile Ala
            260                 265                 270

Arg Lys Met Leu Glu Ile Glu His Gly Glu Leu Pro Glu Glu Val Leu
        275                 280                 285

Asn Phe Val Ala Glu Asn Val Asp Asp Asn Leu Arg Arg Leu Arg Gly
    290                 295                 300

Ala Ile Ile Lys Leu Leu Val Tyr Lys Glu Thr Thr Gly Lys Glu Val
305                 310                 315                 320

Asp Leu Lys Glu Ala Ile Leu Leu Leu Lys Asp Phe Ile Lys Pro Asn
                325                 330                 335

Arg Val Lys Ala Met Asp Pro Ile Asp Glu Leu Ile Glu Ile Val Ala
            340                 345                 350

Lys Val Thr Gly Val Pro Arg Glu Glu Ile Leu Ser Asn Ser Arg Asn
        355                 360                 365

Val Lys Ala Leu Thr Ala Arg Arg Ile Gly Met Tyr Val Ala Lys Asn
    370                 375                 380

Tyr Leu Lys Ser Ser Leu Arg Thr Ile Ala Glu Lys Phe Asn Arg Ser
385                 390                 395                 400

His Pro Val Val Val Asp Ser Val Lys Lys Val Lys Asp Ser Leu Leu
                405                 410                 415

Lys Gly Asn Lys Gln Leu Lys Ala Leu Ile Asp Glu Val Ile Gly Glu
            420                 425                 430

Ile Ser Arg Arg Ala Leu Ser Gly
        435                 440

<210> SEQ ID NO 103
<211> LENGTH: 457
<212> TYPE: PRT
<213> ORGANISM: Helicobacter pylori

<400> SEQUENCE: 103

Met Asp Thr Asn Asn Asn Ile Glu Lys Glu Ile Leu Ala Leu Val Lys
  1               5                  10                  15

Gln Asn Pro Lys Val Ser Leu Ile Glu Tyr Glu Asn Tyr Phe Ser Gln
             20                  25                  30

Leu Lys Tyr Asn Pro Asn Ala Ser Lys Ser Asp Ile Ala Phe Phe Tyr
         35                  40                  45

Ala Pro Asn Gln Val Leu Cys Thr Thr Ile Thr Ala Lys Tyr Gly Ala
     50                  55                  60

Leu Leu Lys Glu Ile Leu Ser Gln Asn Lys Val Gly Met His Leu Ala
 65                  70                  75                  80

His Ser Val Asp Val Arg Ile Glu Val Ala Pro Lys Ile Gln Ile Asn
                 85                  90                  95

Ala Gln Ser Asn Ile Asn Tyr Lys Ala Ile Lys Thr Ser Val Lys Asp
            100                 105                 110

Ser Tyr Thr Phe Glu Asn Phe Val Val Gly Ser Cys Asn Asn Thr Val
        115                 120                 125

Tyr Glu Ile Ala Lys Lys Val Ala Gln Ser Asp Thr Pro Pro Tyr Asn

-continued

```
    130                 135                 140

Pro Val Leu Phe Tyr Gly Gly Thr Gly Leu Gly Lys Thr His Ile Leu
145                 150                 155                 160

Asn Ala Ile Gly Asn His Ala Leu Glu Lys His Lys Lys Val Val Leu
                165                 170                 175

Val Thr Ser Glu Asp Phe Leu Thr Asp Phe Leu Lys His Leu Asp Asn
            180                 185                 190

Lys Thr Met Asp Ser Phe Lys Ala Lys Tyr Arg His Cys Asp Phe Phe
        195                 200                 205

Leu Leu Asp Asp Ala Gln Phe Leu Gln Gly Lys Pro Lys Leu Glu Glu
    210                 215                 220

Glu Phe Phe His Thr Phe Asn Glu Leu His Ala Asn Ser Lys Gln Ile
225                 230                 235                 240

Val Leu Ile Ser Asp Arg Ser Pro Lys Asn Ile Ala Gly Leu Glu Asp
                245                 250                 255

Arg Leu Lys Ser Arg Phe Glu Trp Gly Ile Thr Ala Lys Val Met Pro
            260                 265                 270

Pro Asp Leu Glu Thr Lys Leu Ser Ile Val Lys Gln Lys Cys Gln Leu
        275                 280                 285

Asn Gln Ile Thr Leu Pro Glu Glu Val Met Glu Tyr Ile Ala Gln His
    290                 295                 300

Ile Ser Asp Asn Ile Arg Gln Met Glu Gly Ala Ile Ile Lys Ile Ser
305                 310                 315                 320

Val Asn Ala Asn Leu Met Asn Ala Ser Ile Asp Leu Asn Leu Ala Lys
                325                 330                 335

Thr Val Leu Glu Asp Leu Gln Lys Asp His Ala Glu Gly Ser Ser Leu
            340                 345                 350

Glu Asn Ile Leu Leu Ala Val Ala Gln Ser Leu Asn Leu Lys Ser Ser
        355                 360                 365

Glu Ile Lys Val Ser Ser Arg Gln Lys Asn Val Ala Leu Ala Arg Lys
    370                 375                 380

Leu Val Val Tyr Phe Ala Arg Leu Tyr Thr Pro Asn Pro Thr Leu Ser
385                 390                 395                 400

Leu Ala Gln Phe Leu Asp Leu Lys Asp His Ser Ser Ile Ser Lys Met
                405                 410                 415

Tyr Ser Gly Val Lys Lys Met Leu Glu Glu Glu Lys Ser Pro Phe Val
            420                 425                 430

Leu Ser Leu Arg Glu Glu Ile Lys Asn Arg Leu Asn Glu Leu Asn Asp
        435                 440                 445

Lys Lys Thr Ala Phe Asn Ser Ser Glu
    450                 455
```

<210> SEQ ID NO 104
<211> LENGTH: 1305
<212> TYPE: DNA
<213> ORGANISM: Thermus thermophilus

<400> SEQUENCE: 104

```
gtgtcgcacg aggccgtctg gcaacacgtt ctggagcaca tccgccgcag catcaccgag      60

gtggagttcc acacctggtt tgaaaggatc cgcccccttgg ggatccggga cggggtgctg    120

gagctcgccg tgcccacctc ctttgccctg gactggatcc ggcgccacta cgccggcctc    180

atccaggagg gccctcggct cctcggggcc caggcgcccc ggtttgagct ccgggtggtg    240

cccggggtcg tagtccagga ggacatcttc cagcccccgc cgagcccccc ggcccaagct    300
```

-continued

```
caacccgaag ataccttaa aacttcgtgg tggggcccaa caactccatg gccccacggc    360
ggcgccgtgg ccgtggccga gtcccccggc cgggcctaca accccctctt catctacggg    420
ggccgtggcc tgggaaagac ctacctgatg cacgccgtgg gcccactccg tgcgaagcgc    480
ttcccccaca tgagattaga gtacgtttcc acggaaactt tcaccaacga gctcatcaac    540
cggccatccg cgagggaccg gatgacggag ttccgggagc ggtaccgctc cgtggacctc    600
ctgctggtgg acgacgtcca gttcatcgcc ggaaaggagc gcacccagga ggagtttttc    660
cacaccttca acgcccttta cgaggcccac aagcagatca tcctctcctc cgaccggccg    720
cccaaggaca tcctcaccct ggaggcgcgc ctgcggagcc gctttgagtg gggcctgatc    780
accgacaatc cagcccccga cctggaaacc cggatcgcca tcctgaagat gaacgccagc    840
agcgggcctg aggatcccga ggacgccctg gagtacatcg cccggcaggt cacctccaac    900
atccgggagt gggaaggggc cctcatgcgg gcatcgcctt tcgcctccct caacggcgtt    960
gagctgaccc gcgccgtggc ggccaaggct ctccgacatc ttcgccccag ggagctggag   1020
gcggacccct tggagatcat ccgcaaagcg gcgggaccag ttcggcctga aaccccggga   1080
ggagctcacg gggagcgccg caagaaggag gtggtcctcc cccggcagct cgccatgtac   1140
ctggtgcggg agctcacccc ggcctccctg cccgagatcg accagctcaa cgacgaccgg   1200
gaccacacca cggtcctcta cgccatccag aaggtccagg agctcgcgga aagcgaccgg   1260
gaggtgcagg gcctcctccg caccctccgg gaggcgtgca catga                   1305
```

<210> SEQ ID NO 105
<211> LENGTH: 434
<212> TYPE: PRT
<213> ORGANISM: Thermus thermophilus

<400> SEQUENCE: 105

```
Val Ser His Glu Ala Val Trp Gln His Val Leu Glu His Ile Arg Arg
  1               5                  10                  15

Ser Ile Thr Glu Val Glu Phe His Thr Trp Phe Glu Arg Ile Arg Pro
             20                  25                  30

Leu Gly Ile Arg Asp Gly Val Leu Glu Leu Ala Val Pro Thr Ser Phe
         35                  40                  45

Ala Leu Asp Trp Ile Arg Arg His Tyr Ala Gly Leu Ile Gln Glu Gly
     50                  55                  60

Pro Arg Leu Leu Gly Ala Gln Ala Pro Arg Phe Glu Leu Arg Val Val
 65                  70                  75                  80

Pro Gly Val Val Val Gln Glu Asp Ile Phe Gln Pro Pro Pro Ser Pro
                 85                  90                  95

Pro Ala Gln Ala Gln Pro Glu Asp Thr Phe Lys Thr Ser Trp Trp Gly
            100                 105                 110

Pro Thr Thr Pro Trp Pro His Gly Gly Ala Val Ala Val Ala Glu Ser
        115                 120                 125

Pro Gly Arg Ala Tyr Asn Pro Leu Phe Ile Tyr Gly Gly Arg Gly Leu
    130                 135                 140

Gly Lys Thr Tyr Leu Met His Ala Val Gly Pro Leu Arg Ala Lys Arg
145                 150                 155                 160

Phe Pro His Met Arg Leu Glu Tyr Val Ser Thr Glu Thr Phe Thr Asn
                165                 170                 175

Glu Leu Ile Asn Arg Pro Ser Ala Arg Asp Arg Met Thr Glu Phe Arg
            180                 185                 190
```

-continued

```
Glu Arg Tyr Arg Ser Val Asp Leu Leu Leu Val Asp Asp Val Gln Phe
        195                 200                 205

Ile Ala Gly Lys Glu Arg Thr Gln Glu Glu Phe Phe His Thr Phe Asn
    210                 215                 220

Ala Leu Tyr Glu Ala His Lys Gln Ile Ile Leu Ser Ser Asp Arg Pro
225                 230                 235                 240

Pro Lys Asp Ile Leu Thr Leu Glu Ala Arg Leu Arg Ser Arg Phe Glu
                245                 250                 255

Trp Gly Leu Ile Thr Asp Asn Pro Ala Pro Asp Leu Glu Thr Arg Ile
            260                 265                 270

Ala Ile Leu Lys Met Asn Ala Ser Ser Gly Pro Glu Asp Pro Glu Asp
        275                 280                 285

Ala Leu Glu Tyr Ile Ala Arg Gln Val Thr Ser Asn Ile Arg Glu Trp
    290                 295                 300

Glu Gly Ala Leu Met Arg Ala Ser Pro Phe Ala Ser Leu Asn Gly Val
305                 310                 315                 320

Glu Leu Thr Arg Ala Val Ala Ala Lys Ala Leu Arg His Leu Arg Pro
                325                 330                 335

Arg Glu Leu Glu Ala Asp Pro Leu Glu Ile Ile Arg Lys Ala Ala Gly
            340                 345                 350

Pro Val Arg Pro Glu Thr Pro Gly Gly Ala His Gly Glu Arg Arg Lys
        355                 360                 365

Lys Glu Val Val Leu Pro Arg Gln Leu Ala Met Tyr Leu Val Arg Glu
    370                 375                 380

Leu Thr Pro Ala Ser Leu Pro Glu Ile Asp Gln Leu Asn Asp Asp Arg
385                 390                 395                 400

Asp His Thr Thr Val Leu Tyr Ala Ile Gln Lys Val Gln Glu Leu Ala
                405                 410                 415

Glu Ser Asp Arg Glu Val Gln Gly Leu Leu Arg Thr Leu Arg Glu Ala
            420                 425                 430

Cys Thr
```

<210> SEQ ID NO 106
<211> LENGTH: 1128
<212> TYPE: DNA
<213> ORGANISM: Thermus thermophilus

<400> SEQUENCE: 106

```
atgaacataa cggttcccaa aaaactcctc tcggaccagc tttccctcct ggagcgcatc     60

gtcccctcta gaagcgccaa ccccctctac acctacctgg ggctttacgc cgaggaaggg    120

gccttgatcc tcttcgggac caacggggag gtggacctcg aggtccgcct ccccgccgag    180

gcccaaagcc ttccccgggt gctcgtcccc gcccagccct tcttccagct ggtgcggagc    240

cttcctgggg acctcgtggc cctcggcctc gcctcggagc cgggccaggg ggggcagctg    300

gagctctcct ccgggcgttt ccgcacccgg ctcagcctgg cccctgccga gggctacccc    360

gagcttctgg tgcccgaggg ggaggacaag gggggccttcc ccctccggac gcggatgccc    420

tccggggagc tcgtcaaggc cttgacccac gtgcgctacg ccgcgagcaa cgaggagtac    480

cgggccatct tccgcggggt gcagctggag ttctcccccc agggcttccg ggcggtggcc    540

tccgacgggt accgcctcgc cctctacgac ctgcccctgc cccaagggtt ccaggccaag    600

gccgtggtcc ccgcccggag cgtggacgag atggtgcggg tcctgaaggg ggcggacggg    660

gccgaggccg tcctcgccct gggcgagggg gtgttggccc tggccctcga gggcggaagc    720
```

-continued

```
ggggtccgga tggccctccg cctcatggaa ggggagttcc ccgactacca gagggtcatc    780

ccccaggagt tcgccctcaa ggtccaggtg gagggggagg ccctcaggga ggcggtgcgc    840

cgggtgagcg tcctctccga ccggcagaac caccgggtgg acctcctttt ggaggaaggc    900

cggatcctcc tctccgccga gggggactac ggcaaggggc aggaggaggt gcccgcccag    960

gtggaggggc cggacatggc cgtggcctac aacgcccgct acctcctcga ggccctcgcc   1020

cccgtggggg accgggccca cctgggcatc tccgggccca cgagcccgag cctcatctgg   1080

ggggacgggg aggggtaccg ggcggtggtg gtgcccctca gggtctag                1128
```

<210> SEQ ID NO 107
<211> LENGTH: 376
<212> TYPE: PRT
<213> ORGANISM: Thermus thermophilus

<400> SEQUENCE: 107

```
Met Asn Ile Thr Val Pro Lys Lys Leu Leu Ser Asp Gln Leu Ser Leu
  1               5                  10                  15

Leu Glu Arg Ile Val Pro Ser Arg Ser Ala Asn Pro Leu Tyr Thr Tyr
             20                  25                  30

Leu Gly Leu Tyr Ala Glu Glu Gly Ala Leu Ile Leu Phe Gly Thr Asn
         35                  40                  45

Gly Glu Val Asp Leu Glu Val Arg Leu Pro Ala Glu Ala Gln Ser Leu
     50                  55                  60

Pro Arg Val Leu Val Pro Ala Gln Pro Phe Phe Gln Leu Val Arg Ser
 65                  70                  75                  80

Leu Pro Gly Asp Leu Val Ala Leu Gly Leu Ala Ser Glu Pro Gly Gln
                 85                  90                  95

Gly Gly Gln Leu Glu Leu Ser Ser Gly Arg Phe Arg Thr Arg Leu Ser
            100                 105                 110

Leu Ala Pro Ala Glu Gly Tyr Pro Glu Leu Leu Val Pro Glu Gly Glu
        115                 120                 125

Asp Lys Gly Ala Phe Pro Leu Arg Thr Arg Met Pro Ser Gly Glu Leu
    130                 135                 140

Val Lys Ala Leu Thr His Val Arg Tyr Ala Ala Ser Asn Glu Glu Tyr
145                 150                 155                 160

Arg Ala Ile Phe Arg Gly Val Gln Leu Glu Phe Ser Pro Gln Gly Phe
                165                 170                 175

Arg Ala Val Ala Ser Asp Gly Tyr Arg Leu Ala Leu Tyr Asp Leu Pro
            180                 185                 190

Leu Pro Gln Gly Phe Gln Ala Lys Ala Val Val Pro Ala Arg Ser Val
        195                 200                 205

Asp Glu Met Val Arg Val Leu Lys Gly Ala Asp Gly Ala Glu Ala Val
    210                 215                 220

Leu Ala Leu Gly Glu Gly Val Leu Ala Leu Ala Leu Glu Gly Gly Ser
225                 230                 235                 240

Gly Val Arg Met Ala Leu Arg Leu Met Glu Gly Glu Phe Pro Asp Tyr
                245                 250                 255

Gln Arg Val Ile Pro Gln Glu Phe Ala Leu Lys Val Gln Val Glu Gly
            260                 265                 270

Glu Ala Leu Arg Glu Ala Val Arg Arg Val Ser Val Leu Ser Asp Arg
        275                 280                 285

Gln Asn His Arg Val Asp Leu Leu Leu Glu Glu Gly Arg Ile Leu Leu
    290                 295                 300
```

-continued

```
Ser Ala Glu Gly Asp Tyr Gly Lys Gly Gln Glu Glu Val Pro Ala Gln
305                 310                 315                 320

Val Glu Gly Pro Asp Met Ala Val Ala Tyr Asn Ala Arg Tyr Leu Leu
                325                 330                 335

Glu Ala Leu Ala Pro Val Gly Asp Arg Ala His Leu Gly Ile Ser Gly
            340                 345                 350

Pro Thr Ser Pro Ser Leu Ile Trp Gly Asp Gly Glu Gly Tyr Arg Ala
        355                 360                 365

Val Val Val Pro Leu Arg Val Glx
    370                 375


<210> SEQ ID NO 108
<211> LENGTH: 376
<212> TYPE: PRT
<213> ORGANISM: Thermus thermophilus

<400> SEQUENCE: 108

Met Asn Ile Thr Val Pro Lys Lys Leu Leu Ser Asp Gln Leu Ser Leu
  1               5                  10                  15

Leu Glu Arg Ile Val Pro Ser Arg Ser Ala Asn Pro Leu Tyr Thr Tyr
            20                  25                  30

Leu Gly Leu Tyr Ala Glu Glu Gly Ala Leu Ile Leu Phe Gly Thr Asn
        35                  40                  45

Gly Glu Val Asp Leu Glu Val Arg Leu Pro Ala Glu Ala Gln Ser Leu
     50                  55                  60

Pro Arg Val Leu Val Pro Ala Gln Pro Phe Phe Gln Leu Val Arg Ser
 65                  70                  75                  80

Leu Pro Gly Asp Leu Val Ala Leu Gly Leu Ala Ser Glu Pro Gly Gln
                 85                  90                  95

Gly Gly Gln Leu Glu Leu Ser Ser Gly Arg Phe Arg Thr Arg Leu Ser
            100                 105                 110

Leu Ala Pro Ala Glu Gly Tyr Pro Glu Leu Leu Val Pro Glu Gly Glu
        115                 120                 125

Asp Lys Gly Ala Phe Pro Leu Arg Thr Arg Met Pro Ser Gly Glu Leu
    130                 135                 140

Val Lys Ala Leu Thr His Val Arg Tyr Ala Ala Ser Asn Glu Glu Tyr
145                 150                 155                 160

Arg Ala Ile Phe Arg Gly Val Gln Leu Glu Phe Ser Pro Gln Gly Phe
                165                 170                 175

Arg Ala Val Ala Ser Asp Gly Tyr Arg Leu Ala Leu Tyr Asp Leu Pro
            180                 185                 190

Leu Pro Gln Gly Phe Gln Ala Lys Ala Val Val Pro Ala Arg Ser Val
        195                 200                 205

Asp Glu Met Val Arg Val Leu Lys Gly Ala Asp Gly Ala Glu Ala Val
    210                 215                 220

Leu Ala Leu Gly Glu Gly Val Leu Ala Leu Ala Leu Glu Gly Gly Ser
225                 230                 235                 240

Gly Val Arg Met Ala Leu Arg Leu Met Glu Gly Glu Phe Pro Asp Tyr
                245                 250                 255

Gln Arg Val Ile Pro Gln Glu Phe Ala Leu Lys Val Gln Val Glu Gly
            260                 265                 270

Glu Ala Leu Arg Glu Ala Val Arg Arg Val Ser Val Leu Ser Asp Arg
        275                 280                 285

Gln Asn His Arg Val Asp Leu Leu Leu Glu Glu Gly Arg Ile Leu Leu
    290                 295                 300
```

-continued

```
Ser Ala Glu Gly Asp Tyr Gly Lys Gly Gln Glu Glu Val Pro Ala Gln
305                 310                 315                 320

Val Glu Gly Pro Asp Met Ala Val Ala Tyr Asn Ala Arg Tyr Leu Leu
                325                 330                 335

Glu Ala Leu Ala Pro Val Gly Asp Arg Ala His Leu Gly Ile Ser Gly
            340                 345                 350

Pro Thr Ser Pro Ser Leu Ile Trp Gly Asp Gly Glu Gly Tyr Arg Ala
        355                 360                 365

Val Val Val Pro Leu Arg Val Glx
    370                 375


<210> SEQ ID NO 109
<211> LENGTH: 367
<212> TYPE: PRT
<213> ORGANISM: Escherichia coli

<400> SEQUENCE: 109

Met Lys Phe Thr Val Glu Arg Glu His Leu Leu Lys Pro Leu Gln Gln
  1               5                  10                  15

Val Ser Gly Pro Leu Gly Gly Arg Pro Thr Leu Pro Ile Leu Gly Asn
             20                  25                  30

Leu Leu Leu Gln Val Ala Asp Gly Thr Leu Ser Leu Thr Gly Thr Asp
         35                  40                  45

Leu Glu Met Glu Met Val Ala Arg Val Ala Leu Val Gln Pro His Glu
     50                  55                  60

Pro Gly Ala Thr Thr Val Pro Ala Arg Lys Phe Phe Asp Ile Cys Arg
 65                  70                  75                  80

Gly Leu Pro Glu Gly Ala Glu Ile Ala Val Gln Leu Glu Gly Glu Arg
                 85                  90                  95

Met Leu Val Arg Ser Gly Arg Ser Arg Phe Ser Leu Ser Thr Leu Pro
            100                 105                 110

Ala Ala Asp Phe Pro Asn Leu Asp Asp Trp Gln Ser Glu Val Glu Phe
        115                 120                 125

Thr Leu Pro Gln Ala Thr Met Lys Arg Leu Ile Glu Ala Thr Gln Phe
    130                 135                 140

Ser Met Ala His Gln Asp Val Arg Tyr Tyr Leu Asn Gly Met Leu Phe
145                 150                 155                 160

Glu Thr Glu Gly Glu Glu Leu Arg Thr Val Ala Thr Asp Gly His Arg
                165                 170                 175

Leu Ala Val Cys Ser Met Pro Ile Gly Gln Ser Leu Pro Ser His Ser
            180                 185                 190

Val Ile Val Pro Arg Lys Gly Val Ile Glu Leu Met Arg Met Leu Asp
        195                 200                 205

Gly Gly Asp Asn Pro Leu Arg Val Gln Ile Gly Ser Asn Asn Ile Arg
    210                 215                 220

Ala His Val Gly Asp Phe Ile Phe Thr Ser Lys Leu Val Asp Gly Arg
225                 230                 235                 240

Phe Pro Asp Tyr Arg Arg Val Leu Pro Lys Asn Pro Asp Lys His Leu
                245                 250                 255

Glu Ala Gly Cys Asp Leu Leu Lys Gln Ala Phe Ala Arg Ala Ala Ile
            260                 265                 270

Leu Ser Asn Glu Lys Phe Arg Gly Val Arg Leu Tyr Val Ser Glu Asn
        275                 280                 285

Gln Leu Lys Ile Thr Ala Asn Asn Pro Glu Gln Glu Glu Ala Glu Glu
```

-continued

```
    290                 295                 300

Ile Leu Asp Val Thr Tyr Ser Gly Ala Glu Met Glu Ile Gly Phe Asn
305                 310                 315                 320

Val Ser Tyr Val Leu Asp Val Leu Asn Ala Leu Lys Cys Glu Asn Val
                325                 330                 335

Arg Met Met Leu Thr Asp Ser Val Ser Ser Val Gln Ile Glu Asp Ala
            340                 345                 350

Ala Ser Gln Ser Ala Ala Tyr Val Val Met Pro Met Arg Leu Glx
        355                 360                 365


<210> SEQ ID NO 110
<211> LENGTH: 367
<212> TYPE: PRT
<213> ORGANISM: Proteus mirabilis

<400> SEQUENCE: 110

Met Lys Phe Ile Ile Glu Arg Glu Gln Leu Leu Lys Pro Leu Gln Gln
  1               5                  10                  15

Val Ser Gly Pro Leu Gly Gly Arg Pro Thr Leu Pro Ile Leu Gly Asn
             20                  25                  30

Leu Leu Leu Lys Val Thr Glu Asn Thr Leu Ser Leu Thr Gly Thr Asp
         35                  40                  45

Leu Glu Met Glu Met Met Ala Arg Val Ser Leu Ser Gln Ser His Glu
     50                  55                  60

Ile Gly Ala Thr Thr Val Pro Ala Arg Lys Phe Phe Asp Ile Trp Arg
 65                  70                  75                  80

Gly Leu Pro Glu Gly Ala Glu Ile Ser Val Glu Leu Asp Gly Asp Arg
                 85                  90                  95

Leu Leu Val Arg Ser Gly Arg Ser Arg Phe Ser Leu Ser Thr Leu Pro
            100                 105                 110

Ala Ser Asp Phe Pro Asn Leu Asp Asp Trp Gln Ser Glu Val Glu Phe
        115                 120                 125

Thr Leu Pro Gln Ala Thr Leu Lys Arg Leu Ile Glu Ser Thr Gln Phe
    130                 135                 140

Ser Met Ala His Gln Asp Val Arg Tyr Tyr Leu Asn Gly Met Leu Phe
145                 150                 155                 160

Glu Thr Glu Asn Thr Glu Leu Arg Thr Val Ala Thr Asp Gly His Arg
                165                 170                 175

Leu Ala Val Cys Ala Met Asp Ile Gly Gln Ser Leu Pro Gly His Ser
            180                 185                 190

Val Ile Val Pro Arg Lys Gly Val Ile Glu Leu Met Arg Leu Leu Asp
        195                 200                 205

Gly Ser Gly Glu Ser Leu Leu Gln Leu Gln Ile Gly Ser Asn Asn Leu
    210                 215                 220

Arg Ala His Val Gly Asp Phe Ile Phe Thr Ser Lys Leu Val Asp Gly
225                 230                 235                 240

Arg Phe Pro Asp Tyr Arg Arg Val Leu Pro Lys Asn Pro Thr Lys Thr
                245                 250                 255

Val Ile Ala Gly Cys Asp Ile Leu Lys Gln Ala Phe Ser Arg Ala Ala
            260                 265                 270

Ile Leu Ser Asn Glu Lys Phe Arg Gly Val Arg Ile Asn Leu Thr Asn
        275                 280                 285

Gly Gln Leu Lys Ile Thr Ala Asn Asn Pro Glu Gln Glu Glu Ala Glu
    290                 295                 300
```

-continued

```
Glu Ile Val Asp Val Gln Tyr Gln Gly Glu Glu Met Glu Ile Gly Phe
305                 310                 315                 320

Asn Val Ser Tyr Leu Leu Asp Val Leu Asn Thr Leu Lys Cys Glu Glu
                325                 330                 335

Val Lys Leu Leu Leu Thr Asp Ala Val Ser Ser Val Gln Val Glu Asn
            340                 345                 350

Val Ala Ser Ala Ala Ala Ala Tyr Val Val Met Pro Met Arg Leu
        355                 360                 365


<210> SEQ ID NO 111
<211> LENGTH: 366
<212> TYPE: PRT
<213> ORGANISM: Haemophilus influenzae

<400> SEQUENCE: 111

Met Gln Phe Ser Ile Ser Arg Glu Asn Leu Leu Lys Pro Leu Gln Gln
  1               5                  10                  15

Val Cys Gly Val Leu Ser Asn Arg Pro Asn Ile Pro Val Leu Asn Asn
             20                  25                  30

Val Leu Leu Gln Ile Glu Asp Tyr Arg Leu Thr Ile Thr Gly Thr Asp
         35                  40                  45

Leu Glu Val Glu Leu Ser Ser Gln Thr Gln Leu Ser Ser Ser Ser Glu
     50                  55                  60

Asn Gly Thr Phe Thr Ile Pro Ala Lys Lys Phe Leu Asp Ile Cys Arg
 65                  70                  75                  80

Thr Leu Ser Asp Asp Ser Glu Ile Thr Val Thr Phe Glu Gln Asp Arg
                 85                  90                  95

Ala Leu Val Gln Ser Gly Arg Ser Arg Phe Thr Leu Ala Thr Gln Pro
            100                 105                 110

Ala Glu Glu Tyr Pro Asn Leu Thr Asp Trp Gln Ser Glu Val Asp Phe
        115                 120                 125

Glu Leu Pro Gln Asn Thr Leu Arg Arg Leu Ile Glu Ala Thr Gln Phe
    130                 135                 140

Ser Met Ala Asn Gln Asp Ala Arg Tyr Phe Leu Asn Gly Met Lys Phe
145                 150                 155                 160

Glu Thr Glu Gly Asn Leu Leu Arg Thr Val Ala Thr Asp Gly His Arg
                165                 170                 175

Leu Ala Val Cys Thr Ile Ser Leu Glu Gln Glu Leu Gln Asn His Ser
            180                 185                 190

Val Ile Leu Pro Arg Lys Gly Val Leu Glu Leu Val Arg Leu Leu Glu
        195                 200                 205

Thr Asn Asp Glu Pro Ala Arg Leu Gln Ile Gly Thr Asn Asn Leu Arg
    210                 215                 220

Val His Leu Lys Asn Thr Val Phe Thr Ser Lys Leu Ile Asp Gly Arg
225                 230                 235                 240

Phe Pro Asp Tyr Arg Arg Val Leu Pro Arg Asn Ala Thr Lys Ile Val
                245                 250                 255

Glu Gly Asn Trp Glu Met Leu Lys Gln Ala Phe Ala Arg Ala Ser Ile
            260                 265                 270

Leu Ser Asn Glu Arg Ala Arg Ser Val Arg Leu Ser Leu Lys Glu Asn
        275                 280                 285

Gln Leu Lys Ile Thr Ala Ser Asn Thr Glu His Glu Glu Ala Glu Glu
    290                 295                 300

Ile Val Asp Val Asn Tyr Asn Gly Glu Glu Leu Glu Val Gly Phe Asn
305                 310                 315                 320
```

-continued

```
Val Thr Tyr Ile Leu Asp Val Leu Asn Ala Leu Lys Cys Asn Gln Val
                325                 330                 335

Arg Met Cys Leu Thr Asp Ala Phe Ser Ser Cys Leu Ile Glu Asn Cys
            340                 345                 350

Glu Asp Ser Ser Cys Glu Tyr Val Ile Met Pro Met Arg Leu
        355                 360                 365
```

<210> SEQ ID NO 112
<211> LENGTH: 367
<212> TYPE: PRT
<213> ORGANISM: Pseudomonas putida

<400> SEQUENCE: 112

```
Met His Phe Thr Ile Gln Arg Glu Ala Leu Leu Lys Pro Leu Gln Leu
  1               5                  10                  15

Val Ala Gly Val Val Glu Arg Arg Gln Thr Leu Pro Val Leu Ser Asn
            20                  25                  30

Val Leu Leu Val Val Gln Gly Gln Gln Leu Ser Leu Thr Gly Thr Asp
        35                  40                  45

Leu Glu Val Glu Leu Val Gly Arg Val Gln Leu Glu Glu Pro Ala Glu
    50                  55                  60

Pro Gly Glu Ile Thr Val Pro Ala Arg Lys Leu Met Asp Ile Cys Lys
 65                  70                  75                  80

Ser Leu Pro Asn Asp Ala Leu Ile Asp Ile Lys Val Asp Glu Gln Lys
                85                  90                  95

Leu Leu Val Lys Ala Gly Arg Ser Arg Phe Thr Leu Ser Thr Leu Pro
            100                 105                 110

Ala Asn Asp Phe Pro Thr Val Glu Glu Gly Pro Gly Ser Leu Thr Cys
        115                 120                 125

Asn Leu Glu Gln Ser Lys Leu Arg Arg Leu Ile Glu Arg Thr Ser Phe
    130                 135                 140

Ala Met Ala Gln Gln Asp Val Arg Tyr Tyr Leu Asn Gly Met Leu Leu
145                 150                 155                 160

Glu Val Ser Arg Asn Thr Leu Arg Ala Val Ser Thr Asp Gly His Arg
                165                 170                 175

Leu Ala Leu Cys Ser Met Ser Ala Pro Ile Glu Gln Glu Asp Arg His
            180                 185                 190

Gln Val Ile Val Pro Arg Lys Gly Ile Leu Glu Leu Ala Arg Leu Leu
        195                 200                 205

Thr Asp Pro Glu Gly Met Val Ser Ile Val Leu Gly Gln His His Ile
    210                 215                 220

Arg Ala Thr Thr Gly Glu Phe Thr Phe Thr Ser Lys Leu Val Asp Gly
225                 230                 235                 240

Lys Phe Pro Asp Tyr Glu Arg Val Leu Pro Lys Gly Gly Asp Lys Leu
                245                 250                 255

Val Val Gly Asp Arg Gln Ala Leu Arg Glu Ala Phe Ser Arg Thr Ala
            260                 265                 270

Ile Leu Ser Asn Glu Lys Tyr Arg Gly Ile Arg Leu Gln Leu Ala Ala
        275                 280                 285

Gly Gln Leu Lys Ile Gln Ala Asn Asn Pro Glu Gln Glu Glu Ala Glu
    290                 295                 300

Glu Glu Ile Ser Val Asp Tyr Glu Gly Ser Ser Leu Glu Ile Gly Phe
305                 310                 315                 320

Asn Val Ser Tyr Leu Leu Asp Val Leu Gly Val Met Thr Thr Glu Gln
```

-continued

```
                325                 330                 335

Val Arg Leu Ile Leu Ser Asp Ser Asn Ser Ser Ala Leu Leu Gln Glu
            340                 345                 350

Ala Gly Asn Asp Asp Ser Ser Tyr Val Val Met Pro Met Arg Leu
        355                 360                 365


<210> SEQ ID NO 113
<211> LENGTH: 366
<212> TYPE: PRT
<213> ORGANISM: Buchnera aphidicola

<400> SEQUENCE: 113

Met Lys Phe Thr Ile Gln Asn Asp Ile Leu Thr Lys Asn Leu Lys Lys
  1               5                  10                  15

Ile Thr Arg Val Leu Val Lys Asn Ile Ser Phe Pro Ile Leu Glu Asn
            20                  25                  30

Ile Leu Ile Gln Val Glu Asp Gly Thr Leu Ser Leu Thr Thr Thr Asn
        35                  40                  45

Leu Glu Ile Glu Leu Ile Ser Lys Ile Glu Ile Ile Thr Lys Tyr Ile
     50                  55                  60

Pro Gly Lys Thr Thr Ile Ser Gly Arg Lys Ile Leu Asn Ile Cys Arg
 65                  70                  75                  80

Thr Leu Ser Glu Lys Ser Lys Ile Lys Met Gln Leu Lys Asn Lys Lys
                85                  90                  95

Met Tyr Ile Ser Ser Glu Asn Ser Asn Tyr Ile Leu Ser Thr Leu Ser
            100                 105                 110

Ala Asp Thr Phe Pro Asn His Gln Asn Phe Asp Tyr Ile Ser Lys Phe
        115                 120                 125

Asp Ile Ser Ser Asn Ile Leu Lys Glu Met Ile Glu Lys Thr Glu Phe
    130                 135                 140

Ser Met Gly Lys Gln Asp Val Arg Tyr Tyr Leu Asn Gly Met Leu Leu
145                 150                 155                 160

Glu Lys Lys Asp Lys Phe Leu Arg Ser Val Ala Thr Asp Gly Tyr Arg
                165                 170                 175

Leu Ala Ile Ser Tyr Thr Gln Leu Lys Lys Asp Ile Asn Phe Phe Ser
            180                 185                 190

Ile Ile Ile Pro Asn Lys Ala Val Met Glu Leu Leu Lys Leu Leu Asn
        195                 200                 205

Thr Gln Pro Gln Leu Leu Asn Ile Leu Ile Gly Ser Asn Ser Ile Arg
    210                 215                 220

Ile Tyr Thr Lys Asn Leu Ile Phe Thr Thr Gln Leu Ile Glu Gly Glu
225                 230                 235                 240

Tyr Pro Asp Tyr Lys Ser Val Leu Phe Lys Glu Lys Lys Asn Pro Ile
                245                 250                 255

Ile Thr Asn Ser Ile Leu Leu Lys Lys Ser Leu Leu Arg Val Ala Ile
            260                 265                 270

Leu Ala His Glu Lys Phe Cys Gly Ile Glu Ile Lys Ile Glu Asn Gly
        275                 280                 285

Lys Phe Lys Val Leu Ser Asp Asn Gln Glu Glu Glu Thr Ala Glu Asp
    290                 295                 300

Leu Phe Glu Ile Asp Tyr Phe Gly Glu Lys Ile Glu Ile Ser Ile Asn
305                 310                 315                 320

Val Tyr Tyr Leu Leu Asp Val Ile Asn Asn Ile Lys Ser Glu Asn Ile
                325                 330                 335
```

-continued

Ala Leu Phe Leu Asn Lys Ser Lys Ser Ser Ile Gln Ile Glu Ala Glu
340 345 350

Asn Asn Ser Ser Asn Ala Tyr Val Val Met Leu Leu Lys Arg
355 360 365

<210> SEQ ID NO 114
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 114
gtgtggatcc tcgtcccct catgcgcgac caggaaggg 39

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 115
gtgtggatcc gtggtgacct tagccac 27

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 116
ttcgtgtccg aggaccttgt ggtccacaac 30

<210> SEQ ID NO 117
<211> LENGTH: 3514
<212> TYPE: DNA
<213> ORGANISM: Aquifex aeolicus

<400> SEQUENCE: 117
atgagtaagg atttcgtcca ccttcacctg cacacccagt tctcactcct ggacggggct 60
ataaagatag acgagctcgt gaaaaaggca aaggagtatg gatacaaagc tgtcggaatg 120
tcagaccacg gaaacctctt cggttcgtat aaattctaca aagccctgaa ggcggaagga 180
attaagccca taatcggcat ggaagcctac tttaccacgg gttcgaggtt tgacagaaag 240
actaaaacga gcgaggacaa cataaccgac aagtacaacc accacctcat acttatagca 300
aaggacgaaa aggtctaaag aacttaatga agctctcaac cctcgcctac aaagaaggtt 360
tttactacaa acccagaatt gattacgaac tccttgaaaa gtacggggag ggcctaatag 420
cccttaccgc atgcctgaaa ggtgttccca cctactacgc ttctataaac gaagtgaaaa 480
aggcggagga atgggtaaag aagttcaagg atatattcgg agatgacctt tatttagaac 540
ttcaagcgaa caacattcca gaacaggaag tggcaaacag gaacttaata gagatagcca 600
aaaagtacga tgtgaaactc atagcgacgc aggacgccca ctacctcaat cccgaagaca 660
ggtacgccca cacggttctt atggcacttc aaatgaaaaa gaccattcac gaactgagtt 720
cgggaaactt caagtgttca aacgaagacc ttcactttgc tccacccgag tacatgtgga 780
aaaagtttga aggtaagttc gaaggctggg aaaaggcact cctgaacact ctcgaggtaa 840
tggaaaagac agcggacagc tttgagatat ttgaaaactc cacctacctc cttcccaagt 900

-continued

```
acgacgttcc gcccgacaaa acccttgagg aatacctcag agaactcgcg tacaaaggtt    960
taagacagag gatagaaagg ggacaagcta aggatactaa agagtactgg gagaggctcg   1020
agtacgaact ggaagttata aacaaaatgg gctttgcggg atacttcttg atagttcagg   1080
acttcataaa ctgggctaag aaaaacgaca tacctgttgg acccggaagg ggaagtgctg   1140
gaggttccct cgtcgcatac gccatcggaa taacggacgt tgaccctata aagcacggat   1200
tcctttttga gaggttctta aaccccgaaa gggtttccat gccggatata gacgtggatt   1260
tctgtcagga caacagggaa aaggtcatag agtacgtaag gaacaagtac ggacacgaca   1320
acgtagctca gataatcacc tacaacgtaa tgaaggcgaa gcaaacactg agagacgtcg   1380
caagggccat gggactcccc tactccaccg cggacaaact cgcaaaactc attcctcagg   1440
gggacgttca gggaacgtgg ctcagtctgg aagagatgta caaaacgcct gtggaggaac   1500
tccttcagaa gtacggagaa cacagaacgg acatagagga caacgtaaag aagttcagac   1560
agatatgcga agaaagtccg gagataaaac agctcgttga gacggccctg aagcttgaag   1620
gtctcacgag acacacctcc ctccacgccg cgggagtggt tatagcacca aagcccttga   1680
gcgagctcgt tcccctctac tacgataaag agggcgaagt cgcaacccag tacgacatgg   1740
ttcagctcga agaactcggt ctcctgaaga tggacttcct cggactcaaa accctcacag   1800
aactgaaact catgaaagaa ctcataaagg aaagacacgg agtggatata aacttccttg   1860
aacttcccct tgacgacccg aaagtttaca aactccttca ggaaggaaaa accacgggag   1920
tgttccagct cgaaagcagg ggaatgaaag aactcctgaa gaaactaaag cccgacagct   1980
ttgacgacat cgttgcggtc ctcgcactct acagacccgg acctctaaag agcggactcg   2040
ttgacacata cattaagaga aagcacggaa aagaacccgt tgagtacccc ttcccggagc   2100
ttgaacccgt ccttaaggaa acctacggag taatcgttta tcaggaacag gtgatgaaga   2160
tgtctcagat actttccggc tttactcccg gagaggcgga taccctcaga aaggcgatag   2220
gtaagaagaa agcggattta atggctcaga tgaaagacaa gttcatacag ggagcggtgg   2280
aaaggggata ccctgaagaa aagataagga agctctggga agacatagag aagttcgctt   2340
cctactcctt caacaagtct cactcggtag cttacgggta catctcctac tggaccgcct   2400
acgttaaagc ccactatccc gcggagttct tcgcggtaaa actcacaact gaaaagaacg   2460
acaacaagtt cctcaacctc ataaaagacg ctaaactctt cggatttgag atacttcccc   2520
ccgacataaa caagagtgat gtaggattta cgatagaagg tgaaaacagg ataaggttcg   2580
ggcttgcgag gataaaggga gtgggagagg aaactgctaa gataatcgtt gaagctagaa   2640
agaagtataa gcagttcaaa gggcttgcgg acttcataaa caaaaccaag aacaggaaga   2700
taaacaagaa agtcgtggaa gcactcgtaa aggcaggggc ttttgacttt actaagaaaa   2760
agaggaaaga actactcgct aaagtggcaa actctgaaaa agcattaatg gctacacaaa   2820
actccctttt cggtgcaccg aaagaagaag tggaagaact cgacccctta aagcttgaaa   2880
aggaagttct cggtttttac atttcagggc accccttga caactacgaa aagctcctca    2940
agaaccgcta cacacccatt gaagatttag aagagtggga caaggaaagc gaagcggtgc   3000
ttacaggagt tatcacggaa ctcaaagtaa aaaagacgaa aaacggagat tacatggcgg   3060
tcttcaacct cgttgacaag acgggactaa tagagtgtgt cgtcttcccg ggagtttacg   3120
aagaggcaaa ggaactgata gaagaggaca gagtagtggt agtcaaaggt tttctggacg   3180
aggaccttga aacggaaaat gtcaagttcg tggtgaaaga ggttttctcc cctgaggagt   3240
```

-continued

```
tcgcaaagga gatgaggaat accctttata tattcttaaa aagagagcaa gccctaaacg   3300

gcgttgccga aaaactaaag ggaattattg aaaacaacag gacggaggac ggatacaact   3360

tggttctcac ggttgatctg ggagactact tcgttgattt agcactccca caagatatga   3420

aactaaaggc tgacagaaag gttgtagagg agatagaaaa actgggagtg aaggtcataa   3480

tttagtaaat aacccttact tccgagtagt cccc                               3514
```

```
<210> SEQ ID NO 118
<211> LENGTH: 1161
<212> TYPE: PRT
<213> ORGANISM: Aquifex aeolicus

<400> SEQUENCE: 118

Met Ser Lys Asp Phe Val His Leu His Leu His Thr Gln Phe Ser Leu
  1               5                  10                  15

Leu Asp Gly Ala Ile Lys Ile Asp Glu Leu Val Lys Lys Ala Lys Glu
             20                  25                  30

Tyr Gly Tyr Lys Ala Val Gly Met Ser Asp His Gly Asn Leu Phe Gly
         35                  40                  45

Ser Tyr Lys Phe Tyr Lys Ala Leu Lys Ala Glu Gly Ile Lys Pro Ile
     50                  55                  60

Ile Gly Met Glu Ala Tyr Phe Thr Thr Gly Ser Arg Phe Asp Arg Lys
 65                  70                  75                  80

Thr Lys Thr Ser Glu Asp Asn Ile Thr Asp Lys Tyr Asn His His Leu
                 85                  90                  95

Ile Leu Ile Ala Lys Asp Asp Lys Gly Leu Lys Asn Leu Met Lys Leu
            100                 105                 110

Ser Thr Leu Ala Tyr Lys Glu Gly Phe Tyr Tyr Lys Pro Arg Ile Asp
        115                 120                 125

Tyr Glu Leu Leu Glu Lys Tyr Gly Glu Gly Leu Ile Ala Leu Thr Ala
    130                 135                 140

Cys Leu Lys Gly Val Pro Thr Tyr Tyr Ala Ser Ile Asn Glu Val Lys
145                 150                 155                 160

Lys Ala Glu Glu Trp Val Lys Lys Phe Lys Asp Ile Phe Gly Asp Asp
                165                 170                 175

Leu Tyr Leu Glu Leu Gln Ala Asn Asn Ile Pro Glu Gln Glu Val Ala
            180                 185                 190

Asn Arg Asn Leu Ile Glu Ile Ala Lys Lys Tyr Asp Val Lys Leu Ile
        195                 200                 205

Ala Thr Gln Asp Ala His Tyr Leu Asn Pro Glu Asp Arg Tyr Ala His
    210                 215                 220

Thr Val Leu Met Ala Leu Gln Met Lys Lys Thr Ile His Glu Leu Ser
225                 230                 235                 240

Ser Gly Asn Phe Lys Cys Ser Asn Glu Asp Leu His Phe Ala Pro Pro
                245                 250                 255

Glu Tyr Met Trp Lys Lys Phe Glu Gly Lys Phe Glu Gly Trp Glu Lys
            260                 265                 270

Ala Leu Leu Asn Thr Leu Glu Val Met Glu Lys Thr Ala Asp Ser Phe
        275                 280                 285

Glu Ile Phe Glu Asn Ser Thr Tyr Leu Leu Pro Lys Tyr Asp Val Pro
    290                 295                 300

Pro Asp Lys Thr Leu Glu Glu Tyr Leu Arg Glu Leu Ala Tyr Lys Gly
305                 310                 315                 320

Leu Arg Gln Arg Ile Glu Arg Gly Gln Ala Lys Asp Thr Lys Glu Tyr
```

-continued

```
            325                 330                 335

Trp Glu Arg Leu Glu Tyr Glu Leu Glu Val Ile Asn Lys Met Gly Phe
        340                 345                 350

Ala Gly Tyr Phe Leu Ile Val Gln Asp Phe Ile Asn Trp Ala Lys Lys
    355                 360                 365

Asn Asp Ile Pro Val Gly Pro Gly Arg Gly Ser Ala Gly Gly Ser Leu
    370                 375                 380

Val Ala Tyr Ala Ile Gly Ile Thr Asp Val Asp Pro Ile Lys His Gly
385                 390                 395                 400

Phe Leu Phe Glu Arg Phe Leu Asn Pro Glu Arg Val Ser Met Pro Asp
                405                 410                 415

Ile Asp Val Asp Phe Cys Gln Asp Asn Arg Glu Lys Val Ile Glu Tyr
            420                 425                 430

Val Arg Asn Lys Tyr Gly His Asp Asn Val Ala Gln Ile Ile Thr Tyr
        435                 440                 445

Asn Val Met Lys Ala Lys Gln Thr Leu Arg Asp Val Ala Arg Ala Met
    450                 455                 460

Gly Leu Pro Tyr Ser Thr Ala Asp Lys Leu Ala Lys Leu Ile Pro Gln
465                 470                 475                 480

Gly Asp Val Gln Gly Thr Trp Leu Ser Leu Glu Glu Met Tyr Lys Thr
                485                 490                 495

Pro Val Glu Glu Leu Leu Gln Lys Tyr Gly Glu His Arg Thr Asp Ile
            500                 505                 510

Glu Asp Asn Val Lys Lys Phe Arg Gln Ile Cys Glu Glu Ser Pro Glu
        515                 520                 525

Ile Lys Gln Leu Val Glu Thr Ala Leu Lys Leu Glu Gly Leu Thr Arg
    530                 535                 540

His Thr Ser Leu His Ala Ala Gly Val Val Ile Ala Pro Lys Pro Leu
545                 550                 555                 560

Ser Glu Leu Val Pro Leu Tyr Tyr Asp Lys Glu Gly Glu Val Ala Thr
                565                 570                 575

Gln Tyr Asp Met Val Gln Leu Glu Glu Leu Gly Leu Leu Lys Met Asp
            580                 585                 590

Phe Leu Gly Leu Lys Thr Leu Thr Glu Leu Lys Leu Met Lys Glu Leu
        595                 600                 605

Ile Lys Glu Arg His Gly Val Asp Ile Asn Phe Leu Glu Leu Pro Leu
    610                 615                 620

Asp Asp Pro Lys Val Tyr Lys Leu Leu Gln Glu Gly Lys Thr Thr Gly
625                 630                 635                 640

Val Phe Gln Leu Glu Ser Arg Gly Met Lys Glu Leu Leu Lys Lys Leu
                645                 650                 655

Lys Pro Asp Ser Phe Asp Asp Ile Val Ala Val Leu Ala Leu Tyr Arg
            660                 665                 670

Pro Gly Pro Leu Lys Ser Gly Leu Val Asp Thr Tyr Ile Lys Arg Lys
        675                 680                 685

His Gly Lys Glu Pro Val Glu Tyr Pro Phe Pro Glu Leu Glu Pro Val
    690                 695                 700

Leu Lys Glu Thr Tyr Gly Val Ile Val Tyr Gln Glu Gln Val Met Lys
705                 710                 715                 720

Met Ser Gln Ile Leu Ser Gly Phe Thr Pro Gly Glu Ala Asp Thr Leu
                725                 730                 735

Arg Lys Ala Ile Gly Lys Lys Lys Ala Asp Leu Met Ala Gln Met Lys
            740                 745                 750
```

-continued

```
Asp Lys Phe Ile Gln Gly Ala Val Glu Arg Gly Tyr Pro Glu Glu Lys
        755                 760                 765

Ile Arg Lys Leu Trp Glu Asp Ile Glu Lys Phe Ala Ser Tyr Ser Phe
    770                 775                 780

Asn Lys Ser His Ser Val Ala Tyr Gly Tyr Ile Ser Tyr Trp Thr Ala
785                 790                 795                 800

Tyr Val Lys Ala His Tyr Pro Ala Glu Phe Phe Ala Val Lys Leu Thr
                805                 810                 815

Thr Glu Lys Asn Asp Asn Lys Phe Leu Asn Leu Ile Lys Asp Ala Lys
            820                 825                 830

Leu Phe Gly Phe Glu Ile Leu Pro Pro Asp Ile Asn Lys Ser Asp Val
        835                 840                 845

Gly Phe Thr Ile Glu Gly Glu Asn Arg Ile Arg Phe Gly Leu Ala Arg
    850                 855                 860

Ile Lys Gly Val Gly Glu Glu Thr Ala Lys Ile Ile Val Glu Ala Arg
865                 870                 875                 880

Lys Lys Tyr Lys Gln Phe Lys Gly Leu Ala Asp Phe Ile Asn Lys Thr
                885                 890                 895

Lys Asn Arg Lys Ile Asn Lys Lys Val Val Glu Ala Leu Val Lys Ala
            900                 905                 910

Gly Ala Phe Asp Phe Thr Lys Lys Lys Arg Lys Glu Leu Leu Ala Lys
        915                 920                 925

Val Ala Asn Ser Glu Lys Ala Leu Met Ala Thr Gln Asn Ser Leu Phe
    930                 935                 940

Gly Ala Pro Lys Glu Glu Val Glu Glu Leu Asp Pro Leu Lys Leu Glu
945                 950                 955                 960

Lys Glu Val Leu Gly Phe Tyr Ile Ser Gly His Pro Leu Asp Asn Tyr
                965                 970                 975

Glu Lys Leu Leu Lys Asn Arg Tyr Thr Pro Ile Glu Asp Leu Glu Glu
            980                 985                 990

Trp Asp Lys Glu Ser Glu Ala Val Leu Thr Gly Val Ile Thr Glu Leu
        995                 1000                1005

Lys Val Lys Lys Thr Lys Asn Gly Asp Tyr Met Ala Val Phe Asn Leu
   1010                1015                1020

Val Asp Lys Thr Gly Leu Ile Glu Cys Val Val Phe Pro Gly Val Tyr
1025                1030                1035                1040

Glu Glu Ala Lys Glu Leu Ile Glu Glu Asp Arg Val Val Val Val Lys
               1045                1050                1055

Gly Phe Leu Asp Glu Asp Leu Glu Thr Glu Asn Val Lys Phe Val Val
           1060                1065                1070

Lys Glu Val Phe Ser Pro Glu Glu Phe Ala Lys Glu Met Arg Asn Thr
       1075                1080                1085

Leu Tyr Ile Phe Leu Lys Arg Glu Gln Ala Leu Asn Gly Val Ala Glu
   1090                1095                1100

Lys Leu Lys Gly Ile Ile Glu Asn Asn Arg Thr Glu Asp Gly Tyr Asn
1105                1110                1115                1120

Leu Val Leu Thr Val Asp Leu Gly Asp Tyr Phe Val Asp Leu Ala Leu
               1125                1130                1135

Pro Gln Asp Met Lys Leu Lys Ala Asp Arg Lys Val Val Glu Glu Ile
           1140                1145                1150

Glu Lys Leu Gly Val Lys Val Ile Ile
       1155                1160
```

-continued

<210> SEQ ID NO 119
<211> LENGTH: 2408
<212> TYPE: DNA
<213> ORGANISM: Aquifex aeolicus

<400> SEQUENCE: 119
atgaactacg ttcccttcgc gagaaagtac agaccgaaat tcttcaggga agtaatagga 60
caggaagctc ccgtaaggat actcaaaaac gctataaaaa acgacagagt ggctcacgcc 120
tacctctttg ccggaccgag gggggttggg aagacgacta ttgcaagaat tctcgcaaaa 180
gctttgaact gtaaaaatcc ctccaaaggt gagccctgcg gtgagtgcga aaactgcagg 240
gagatagaca ggggtgtgtt ccctgactta attgaaatgg atgccgcctc aaacaggggt 300
atagacgacg taagggcatt aaaagaagcg gtcaattaca aacctataaa aggaaagtac 360
aaggtttaca taatagacga agctcacatg ctcacgaaag aagctttcaa cgctctctta 420
aaaaccctcg aagagccccc tcccagaact gttttcgtcc tttgtaccac ggagtacgac 480
aaaattcttc ccacgatact ctcaaggtgt cagaggataa tcttctcaaa ggtaagaaag 540
gaaaaagtaa tagagtatct aaaaaagata tgtgaaaagg aagggattga gtgcgaagag 600
ggagcccttg aggttctggc tcatgcctct gaagggtgca tgagggatgc agcctctctc 660
ctggaccagg cgagcgttta cggggaaggc agggtaacaa aagaagtagt ggagaacttc 720
ctcggaattc tcagtcagga aagcgttagg agttttctga aattgcttct gaactcagaa 780
gtggacgaag ctataaagtt cctcagagaa ctctcagaaa agggctacaa cctgaccaag 840
ttttgggaga tgttagaaga ggaagtgaga aacgcaattt tagtaaagag cctgaaaaat 900
cccgaaagcg tggttcagaa ctggcaggat tacgaagact tcaaagacta ccctctggaa 960
gccctcctct acgttgagaa cctgataaac aggggtaaag ttgaagcgag aacgagagaa 1020
cccttaagag cctttgaact cgcggtaata aagagcctta tagtcaaaga cataattccc 1080
gtatcccagc tcggaagtgt ggtaaaggaa accaaaaagg aagaaaagaa agttgaagta 1140
aaagaagagc caaaagtaaa agaagaaaaa ccaaaggagc aggaagagga caggttccag 1200
aaagttttaa acgctgtgga cggcaaaatc cttaaaagaa tacttgaagg ggcaaaaagg 1260
gaagaaagag acggaaaaat cgtcctaaag atagaagcct cttatctgag aaccatgaaa 1320
aaggaatttg actcactaaa ggagactttt ccttttttag agtttgaacc cgtggaggat 1380
aaaaaaaaac ctcagaagtc cagcgggacg aggctgtttt aaaggtaaag gagctcttca 1440
atgcaaaaat actcaaagta cgaagtaaaa gctaaggtca taaaggtgag aatgcccgtg 1500
gaagagatag ggctgtttaa cgcactaata gacggcttgc ccaggtacgc actcacgagg 1560
acgaaggaaa agggaaaggg agaagttttc gttttagcga ctccttataa agtcaaggaa 1620
ttgatggaag ctatggaggg tatgaaaaaa cacataaagg atttagaaat cctcggagag 1680
acggatgagg atttaacttt ttaaagtatg ggtgtatctg agcaaaggtt taagctaaaa 1740
acaaacctga aacccgcagg ggaccagccg aaagccataa aaaaactcct tgaaaaccta 1800
aggaaaggcg taaaagaaca aacacttctc ggagtcacgg gaagcggaaa gacttttact 1860
ctagcaaacg taatagcgaa gtacaacaaa ccaactcttg tggtagttca caacaaaatt 1920
ctcgcggcac agctatacag ggagtttaaa gaactattcc ctgaaaacgc tgtagagtac 1980
tttgtctctt actacgacta ttaccaacct gaagcctaca ttcccgaaaa agatttatac 2040
atagaaaagg acgcgagtat aaacgaaagc tggaacgttt cagacactcc gccacgatat 2100
ccgttctaga aaggagggac gttatagtag ttgcttcagt ttcttgcata tacggactcg 2160

-continued

```
ggaaacctga gcactacgaa aacctgagga taaaactcca aaggggaata agactgaact   2220

tgagtaagct cctgaggaaa ctcgttgagc taggatatca gagaaatgac tttgccataa   2280

agagggctac cttctcggtt aggggagacg tggttgagat agtcccttct cacacggaag   2340

attacctcgt gagggtagag ttctgggacg acgaagttga aagaatagtc ctcatggacg   2400

ctctgaac                                                             2408


<210> SEQ ID NO 120
<211> LENGTH: 473
<212> TYPE: PRT
<213> ORGANISM: Aquifex aeolicus

<400> SEQUENCE: 120

Met Asn Tyr Val Pro Phe Ala Arg Lys Tyr Arg Pro Lys Phe Phe Arg
  1               5                  10                  15

Glu Val Ile Gly Gln Glu Ala Pro Val Arg Ile Leu Lys Asn Ala Ile
             20                  25                  30

Lys Asn Asp Arg Val Ala His Ala Tyr Leu Phe Ala Gly Pro Arg Gly
         35                  40                  45

Val Gly Lys Thr Thr Ile Ala Arg Ile Leu Ala Lys Ala Leu Asn Cys
     50                  55                  60

Lys Asn Pro Ser Lys Gly Glu Pro Cys Gly Glu Cys Glu Asn Cys Arg
 65                  70                  75                  80

Glu Ile Asp Arg Gly Val Phe Pro Asp Leu Ile Glu Met Asp Ala Ala
                 85                  90                  95

Ser Asn Arg Gly Ile Asp Asp Val Arg Ala Leu Lys Glu Ala Val Asn
            100                 105                 110

Tyr Lys Pro Ile Lys Gly Lys Tyr Lys Val Tyr Ile Ile Asp Glu Ala
        115                 120                 125

His Met Leu Thr Lys Glu Ala Phe Asn Ala Leu Leu Lys Thr Leu Glu
    130                 135                 140

Glu Pro Pro Pro Arg Thr Val Phe Val Leu Cys Thr Thr Glu Tyr Asp
145                 150                 155                 160

Lys Ile Leu Pro Thr Ile Leu Ser Arg Cys Gln Arg Ile Ile Phe Ser
                165                 170                 175

Lys Val Arg Lys Glu Lys Val Ile Glu Tyr Leu Lys Lys Ile Cys Glu
            180                 185                 190

Lys Glu Gly Ile Glu Cys Glu Glu Gly Ala Leu Glu Val Leu Ala His
        195                 200                 205

Ala Ser Glu Gly Cys Met Arg Asp Ala Ala Ser Leu Leu Asp Gln Ala
    210                 215                 220

Ser Val Tyr Gly Glu Gly Arg Val Thr Lys Glu Val Val Glu Asn Phe
225                 230                 235                 240

Leu Gly Ile Leu Ser Gln Glu Ser Val Arg Ser Phe Leu Lys Leu Leu
                245                 250                 255

Leu Asn Ser Glu Val Asp Glu Ala Ile Lys Phe Leu Arg Glu Leu Ser
            260                 265                 270

Glu Lys Gly Tyr Asn Leu Thr Lys Phe Trp Glu Met Leu Glu Glu Glu
        275                 280                 285

Val Arg Asn Ala Ile Leu Val Lys Ser Leu Lys Asn Pro Glu Ser Val
    290                 295                 300

Val Gln Asn Trp Gln Asp Tyr Glu Asp Phe Lys Asp Tyr Pro Leu Glu
305                 310                 315                 320
```

-continued

```
Ala Leu Leu Tyr Val Glu Asn Leu Ile Asn Arg Gly Lys Val Glu Ala
                325                 330                 335

Arg Thr Arg Glu Pro Leu Arg Ala Phe Glu Leu Ala Val Ile Lys Ser
            340                 345                 350

Leu Ile Val Lys Asp Ile Ile Pro Val Ser Gln Leu Gly Ser Val Val
        355                 360                 365

Lys Glu Thr Lys Lys Glu Glu Lys Lys Val Glu Val Lys Glu Glu Pro
    370                 375                 380

Lys Val Lys Glu Glu Lys Pro Lys Glu Gln Glu Glu Asp Arg Phe Gln
385                 390                 395                 400

Lys Val Leu Asn Ala Val Asp Gly Lys Ile Leu Lys Arg Ile Leu Glu
                405                 410                 415

Gly Ala Lys Arg Glu Glu Arg Asp Gly Lys Ile Val Leu Lys Ile Glu
            420                 425                 430

Ala Ser Tyr Leu Arg Thr Met Lys Lys Glu Phe Asp Ser Leu Lys Glu
        435                 440                 445

Thr Phe Pro Phe Leu Glu Phe Glu Pro Val Glu Asp Lys Lys Lys Pro
    450                 455                 460

Gln Lys Ser Ser Gly Thr Arg Leu Phe
465                 470

<210> SEQ ID NO 121
<211> LENGTH: 1090
<212> TYPE: DNA
<213> ORGANISM: Aquifex aeolicus

<400> SEQUENCE: 121

atgcgcgtta aggtggacag ggaggagctt gaagaggttc ttaaaaaagc aagagaaagc      60

acggaaaaaa aagccgcact cccgatactc gcgaacttct tactctccgc aaaagaggaa     120

aacttaatcg taagggcaac ggacttggaa aactaccttg tagtctccgt aaagggggag     180

gttgaagagg aaggagaggt ttgcgtccac tctcaaaaac tctacgatat agtcaagaac     240

ttaaattccg cttacgttta ccttcatacg gaaggtgaaa aactcgtcat aacgggagga     300

aagagtacgt acaaacttcc gacagctccc gcggaggact ttcccgaatt tccagaaatc     360

gtagaaggag gagaaacact ttcgggaaac cttctcgtta acggaataga aaaggtagag     420

tacgccatag cgaaggaaga agcgaacata gcccttcagg gaatgtatct gagaggatac     480

gaggacagaa ttcactttgt gttcggacgg tcacaggctt gcactttatg aacctctacg     540

taaacattga aaagagtgaa gacgagtctt ttgcttactt ctccactccc gagtggaaac     600

tcgccgttag ctcctggaag gagaattccc ggactacatg agtgtcatcc ctgaggagtt     660

ttcggcggaa gtcttgtttg agacagagga agtcttaaag gttttaaaga ggttgaaggc     720

tttaagcgaa ggaaaagttt ttcccgtgaa gattacctta agcgaaaacc ttgccatctt     780

tgagttcgcg gatccggagt tcggagaagc gagagaggaa attgaagtgg agtacacggg     840

agagcccttt gagataggat tcaacggaaa taccttatgg aggcgcttga cgcctacgac     900

agcgaaagag tgtggttcaa gttcacaacc cccgacacgg ccactttatt ggaggctgaa     960

gattacgaaa aggaacctta caagtgcata ataatgccga tgagggtgta gccatgaaaa    1020

aagctttaat ctttttattg agcttgagcc ttttaattcc tgcgtttagc gaagccaaac    1080

ccaagtcttc                                                           1090

<210> SEQ ID NO 122
<211> LENGTH: 363
```

-continued

<212> TYPE: PRT
<213> ORGANISM: Aquifex aeolicus

<400> SEQUENCE: 122

Met Arg Val Lys Val Asp Arg Glu Glu Leu Glu Glu Val Leu Lys Lys
1               5                   10                  15

Ala Arg Glu Ser Thr Glu Lys Lys Ala Ala Leu Pro Ile Leu Ala Asn
            20                  25                  30

Phe Leu Leu Ser Ala Lys Glu Glu Asn Leu Ile Val Arg Ala Thr Asp
        35                  40                  45

Leu Glu Asn Tyr Leu Val Val Ser Val Lys Gly Glu Val Glu Glu Glu
    50                  55                  60

Gly Glu Val Cys Val His Ser Gln Lys Leu Tyr Asp Ile Val Lys Asn
65                  70                  75                  80

Leu Asn Ser Ala Tyr Val Tyr Leu His Thr Glu Gly Glu Lys Leu Val
                85                  90                  95

Ile Thr Gly Gly Lys Ser Thr Tyr Lys Leu Pro Thr Ala Pro Ala Glu
            100                 105                 110

Asp Phe Pro Glu Phe Pro Glu Ile Val Glu Gly Gly Glu Thr Leu Ser
        115                 120                 125

Gly Asn Leu Leu Val Asn Gly Ile Glu Lys Val Glu Tyr Ala Ile Ala
    130                 135                 140

Lys Glu Glu Ala Asn Ile Ala Leu Gln Gly Met Tyr Leu Arg Gly Tyr
145                 150                 155                 160

Glu Asp Arg Ile His Phe Val Gly Ser Asp Gly His Arg Leu Ala Leu
                165                 170                 175

Tyr Glu Pro Leu Gly Glu Phe Ser Lys Glu Leu Leu Ile Pro Arg Lys
            180                 185                 190

Ser Leu Lys Val Leu Lys Lys Leu Ile Thr Gly Ile Glu Asp Val Asn
        195                 200                 205

Ile Glu Lys Ser Glu Asp Glu Ser Phe Ala Tyr Phe Ser Thr Pro Glu
    210                 215                 220

Trp Lys Leu Ala Val Arg Leu Leu Glu Gly Glu Phe Pro Asp Tyr Met
225                 230                 235                 240

Ser Val Ile Pro Glu Glu Phe Ser Ala Glu Val Leu Phe Glu Thr Glu
                245                 250                 255

Glu Val Leu Lys Val Leu Lys Arg Leu Lys Ala Leu Ser Glu Gly Lys
            260                 265                 270

Val Phe Pro Val Lys Ile Thr Leu Ser Glu Asn Leu Ala Ile Phe Glu
        275                 280                 285

Phe Ala Asp Pro Glu Phe Gly Glu Ala Arg Glu Glu Ile Glu Val Glu
    290                 295                 300

Tyr Thr Gly Glu Pro Phe Glu Ile Gly Phe Asn Gly Lys Tyr Leu Met
305                 310                 315                 320

Glu Ala Leu Asp Ala Tyr Asp Ser Glu Arg Val Trp Phe Lys Phe Thr
                325                 330                 335

Thr Pro Asp Thr Ala Thr Leu Leu Glu Ala Glu Asp Tyr Glu Lys Glu
            340                 345                 350

Pro Tyr Lys Cys Ile Ile Met Pro Met Arg Val
        355                 360

<210> SEQ ID NO 123
<211> LENGTH: 1093
<212> TYPE: DNA
<213> ORGANISM: Aquifex aeolicus

<400> SEQUENCE: 123
gtggaaacca caatattcca gttccagaaa actttttca caaaacctcc gaaggagagg 60
gtcttcgtcc ttcatggaga agagcagtat ctcataagaa cctttttgtc taagctgaag 120
gaaaagtacg gggagaatta cacggttctg tggggggatg agataagcga ggaggaattc 180
tacactgccc tttccgagac cagtatattc ggcggttcaa aggaaaaagc ggtggtcatt 240
tacaacttcg ggatttcct gaagaagctc ggaaggaaga aaaaggaaaa agaaaggctt 300
ataaaagtcc tcagaaacgt aaagagtaac tacgtattta tagtgtacga tgcgaaactc 360
cagaaacagg aactttcttc ggaacctctg aaatccgtag cgtctttcgg cggtatagtg 420
gtagcaaaca ggctgagcaa ggagaggata aaacagctcg tccttaagaa gttcaaagaa 480
aaagggataa acgtagaaaa cgatgccctt gaataccttc tccagctcac gggttacaac 540
ttgatggagc tcaaacttga ggttgaaaaa ctgatagatt acgcaagtga aaagaaaatt 600
ttaacactcg atgaggtaaa gagagtagcc ttctcagtct cagaaaacgt aaacgtattt 660
gagttcgttg atttactcct cttaaaagat tacgaaaagg ctcttaaagt tttggactcc 720
ctcatttcct tcggaataca ccccctccag attatgaaaa tcctgtcctc ctatgctcta 780
aaactttaca ccctcaagag gcttgaagag aagggagagg acctgaataa ggcgatggaa 840
agcgtgggaa taaagaacaa ctttctcaag atgaagttca aatcttactt aaaggcaaac 900
tctaaagagg acttgaagaa cctaatcctc tccctccaga ggatagacgc tttttctaaa 960
ctttactttc aggacacagt gcagttgctg ggatttctt gacctcaaga ctggagaggg 1020
aagttgtgaa aaatacttct catggtggat aatcttttt atgaagtttg cggtttgcgt 1080
ttttcccggt tct 1093

<210> SEQ ID NO 124
<211> LENGTH: 350
<212> TYPE: PRT
<213> ORGANISM: Aquifex aeolicus

<400> SEQUENCE: 124

Val Glu Thr Thr Ile Phe Gln Phe Gln Lys Thr Phe Phe Thr Lys Pro
1 5 10 15

Pro Lys Glu Arg Val Phe Val Leu His Gly Glu Glu Gln Tyr Leu Ile
20 25 30

Arg Thr Phe Leu Ser Lys Leu Lys Glu Lys Tyr Gly Glu Asn Tyr Thr
35 40 45

Val Leu Trp Gly Asp Glu Ile Ser Glu Glu Glu Phe Tyr Thr Ala Leu
50 55 60

Ser Glu Thr Ser Ile Phe Gly Gly Ser Lys Glu Lys Ala Val Val Ile
65 70 75 80

Tyr Asn Phe Gly Asp Phe Leu Lys Lys Leu Gly Arg Lys Lys Lys Glu
85 90 95

Lys Glu Arg Leu Ile Lys Val Leu Arg Asn Val Lys Ser Asn Tyr Val
100 105 110

Phe Ile Val Tyr Asp Ala Lys Leu Gln Lys Gln Glu Leu Ser Ser Glu
115 120 125

Pro Leu Lys Ser Val Ala Ser Phe Gly Gly Ile Val Val Ala Asn Arg
130 135 140

Leu Ser Lys Glu Arg Ile Lys Gln Leu Val Leu Lys Lys Phe Lys Glu
145 150 155 160

-continued

```
Lys Gly Ile Asn Val Glu Asn Asp Ala Leu Glu Tyr Leu Leu Gln Leu
                165                 170                 175

Thr Gly Tyr Asn Leu Met Glu Leu Lys Leu Glu Val Glu Lys Leu Ile
            180                 185                 190

Asp Tyr Ala Ser Glu Lys Lys Ile Leu Thr Leu Asp Glu Val Lys Arg
        195                 200                 205

Val Ala Phe Ser Val Ser Glu Asn Val Asn Val Phe Glu Phe Val Asp
    210                 215                 220

Leu Leu Leu Leu Lys Asp Tyr Glu Lys Ala Leu Lys Val Leu Asp Ser
225                 230                 235                 240

Leu Ile Ser Phe Gly Ile His Pro Leu Gln Ile Met Lys Ile Leu Ser
                245                 250                 255

Ser Tyr Ala Leu Lys Leu Tyr Thr Leu Lys Arg Leu Glu Glu Lys Gly
            260                 265                 270

Glu Asp Leu Asn Lys Ala Met Glu Ser Val Gly Ile Lys Asn Asn Phe
        275                 280                 285

Leu Lys Met Lys Phe Lys Ser Tyr Leu Lys Ala Asn Ser Lys Glu Asp
    290                 295                 300

Leu Lys Asn Leu Ile Leu Ser Leu Gln Arg Ile Asp Ala Phe Ser Lys
305                 310                 315                 320

Leu Tyr Phe Gln Asp Thr Val Gln Leu Leu Arg Asp Phe Leu Thr Ser
                325                 330                 335

Arg Leu Glu Arg Glu Val Val Lys Asn Thr Ser His Gly Gly
            340                 345                 350


<210> SEQ ID NO 125
<211> LENGTH: 1051
<212> TYPE: DNA
<213> ORGANISM: Aquifex aeolicus

<400> SEQUENCE: 125

atggaaaaag ttttttgga aaaactccag aaaaccttgc acatacccgg aggactcctt      60

ttttacggca aagaaggaag cggaaagacg aaaacagctt ttgaatttgc aaaaggtatt     120

ttatgtaagg aaaacgtacc tggggatgcg gaagttgtcc ctcctgcaaa cacgtaaacg     180

agctggagga agccttcttt aaaggagaaa tagaagactt taaagtttat aagacaagga     240

cggtaaaaag cacttcgttt accttatggg cgaacatccc gactttgtgg taataatccc     300

gagcggacat tacataaaga tagaacagat aagggaagtt aagaactttg cctatgtgaa     360

gcccgcacta agcaggagaa aagtaattat aatagacgac gcccacgcga tgacctctca     420

ggcggcaaac gctcttttaa aggtattgga agagccacct gcggacacca cctttatctt     480

gaccacgaac aggcgttctg caatcctgcc gactatcctc tccagaactt ttcaagtgga     540

gttcaagggc ttttcagtaa aagaggttat ggaaatagcg aaagtagacg aggaaatagc     600

gaaactctct ggaggcagtc taaaaagggc tatcttacta aaggaaaaca aagatatcct     660

aaacaaagta aaggaattct tggaaaacga gccgttaaaa gtttacaagc ttgcaagtga     720

attcgaaaag tgggaacctg aaaagcaaaa actcttcctt gaaattatgg aagaattggt     780

atctcaaaaa ttgaccgaag agaaaaaaga caattacacc taccttcttg atacgatcag     840

actctttaaa gacggactcg caaggggtgt aaacgaacct ctgtggctgt ttacgttagc     900

cgttcaggcg gattaataaa ccgttattga ttccgtaaca tttaaacctt aatctaaatt     960

atgagagcct ttgaaggagg tctggtatgg aaaatttgaa gattagatat atagatacga    1020

ggaagatagg aaccgtgagc ggtgtaaaag t                                   1051
```

-continued

<210> SEQ ID NO 126
<211> LENGTH: 305
<212> TYPE: PRT
<213> ORGANISM: Aquifex aeolicus

<400> SEQUENCE: 126

```
Met Glu Lys Val Phe Leu Glu Lys Leu Gln Lys Thr Leu His Ile Pro
  1               5                  10                  15

Gly Gly Leu Leu Phe Tyr Gly Lys Glu Gly Ser Gly Lys Thr Lys Thr
             20                  25                  30

Ala Phe Glu Phe Ala Lys Gly Ile Leu Cys Lys Glu Asn Val Pro Trp
         35                  40                  45

Gly Cys Gly Ser Cys Pro Ser Cys Lys His Val Asn Glu Leu Glu Glu
     50                  55                  60

Ala Phe Phe Lys Gly Glu Ile Glu Asp Phe Lys Val Tyr Lys Asp Lys
 65                  70                  75                  80

Asp Gly Lys Lys His Phe Val Tyr Leu Met Gly Glu His Pro Asp Phe
                 85                  90                  95

Val Val Ile Ile Pro Ser Gly His Tyr Ile Lys Ile Glu Gln Ile Arg
            100                 105                 110

Glu Val Lys Asn Phe Ala Tyr Val Lys Pro Ala Leu Ser Arg Arg Lys
        115                 120                 125

Val Ile Ile Ile Asp Asp Ala His Ala Met Thr Ser Gln Ala Ala Asn
    130                 135                 140

Ala Leu Leu Lys Val Leu Glu Glu Pro Pro Ala Asp Thr Thr Phe Ile
145                 150                 155                 160

Leu Thr Thr Asn Arg Arg Ser Ala Ile Leu Pro Thr Ile Leu Ser Arg
                165                 170                 175

Thr Phe Gln Val Glu Phe Lys Gly Phe Ser Val Lys Glu Val Met Glu
            180                 185                 190

Ile Ala Lys Val Asp Glu Glu Ile Ala Lys Leu Ser Gly Gly Ser Leu
        195                 200                 205

Lys Arg Ala Ile Leu Leu Lys Glu Asn Lys Asp Ile Leu Asn Lys Val
    210                 215                 220

Lys Glu Phe Leu Glu Asn Glu Pro Leu Lys Val Tyr Lys Leu Ala Ser
225                 230                 235                 240

Glu Phe Glu Lys Trp Glu Pro Glu Lys Gln Lys Leu Phe Leu Glu Ile
                245                 250                 255

Met Glu Glu Leu Val Ser Gln Lys Leu Thr Glu Glu Lys Lys Asp Asn
            260                 265                 270

Tyr Thr Tyr Leu Leu Asp Thr Ile Arg Leu Phe Lys Asp Gly Leu Ala
        275                 280                 285

Arg Gly Val Asn Glu Pro Leu Trp Leu Phe Thr Leu Ala Val Gln Ala
    290                 295                 300

Asp
305
```

<210> SEQ ID NO 127
<211> LENGTH: 630
<212> TYPE: DNA
<213> ORGANISM: Aquifex aeolicus

<400> SEQUENCE: 127

```
atgaacttcc tgaaaaagtt ccttttactg agaaaagctc aaaagtctcc ttacttcgaa      60
```

-continued

```
gagttctacg aagaaatcga tttgaaccag aaggtgaaag atgcaaggtt tgtagttttt    120

gactgcgaag ccacagaact cgacgtaaag aaggcaaaac tcctttcaat aggtgcggtt    180

gaggttaaaa acctggaaat agacctctct aaatcttttt acgagatact caaaagtgac    240

gagataaagg cggcggagat acatggaata accagggaag acgttgaaaa gtacggaaag    300

gaaccaaagg aagtaatata cgactttctg aagtacataa agggaagcgt tctcgttggc    360

tactacgtga agtttgacgt ctcactcgtt gagaagtact ccataaagta cttccagtat    420

ccaatcatca actacaagtt agacctgttt agtttcgtga agagagagta ccagagtggc    480

aggagtcttg acgaccttat gaaggaactc ggtgtagaaa taagggcaag gcacaacgcc    540

cttgaagatg cctacataac cgctcttctt ttcctaaagt acgtttaccc gaacagggag    600

tacagactaa aggatctccc gattttcctt                                      630


<210> SEQ ID NO 128
<211> LENGTH: 210
<212> TYPE: PRT
<213> ORGANISM: Aquifex aeolicus

<400> SEQUENCE: 128

Met Asn Phe Leu Lys Lys Phe Leu Leu Leu Arg Lys Ala Gln Lys Ser
  1               5                  10                  15

Pro Tyr Phe Glu Glu Phe Tyr Glu Glu Ile Asp Leu Asn Gln Lys Val
             20                  25                  30

Lys Asp Ala Arg Phe Val Val Phe Asp Cys Glu Ala Thr Glu Leu Asp
         35                  40                  45

Val Lys Lys Ala Lys Leu Leu Ser Ile Gly Ala Val Glu Val Lys Asn
     50                  55                  60

Leu Glu Ile Asp Leu Ser Lys Ser Phe Tyr Glu Ile Leu Lys Ser Asp
 65                  70                  75                  80

Glu Ile Lys Ala Ala Glu Ile His Gly Ile Thr Arg Glu Asp Val Glu
                 85                  90                  95

Lys Tyr Gly Lys Glu Pro Lys Glu Val Ile Tyr Asp Phe Leu Lys Tyr
            100                 105                 110

Ile Lys Gly Ser Val Leu Val Gly Tyr Tyr Val Lys Phe Asp Val Ser
        115                 120                 125

Leu Val Glu Lys Tyr Ser Ile Lys Tyr Phe Gln Tyr Pro Ile Ile Asn
    130                 135                 140

Tyr Lys Leu Asp Leu Phe Ser Phe Val Lys Arg Glu Tyr Gln Ser Gly
145                 150                 155                 160

Arg Ser Leu Asp Asp Leu Met Lys Glu Leu Gly Val Glu Ile Arg Ala
                165                 170                 175

Arg His Asn Ala Leu Glu Asp Ala Tyr Ile Thr Ala Leu Leu Phe Leu
            180                 185                 190

Lys Tyr Val Tyr Pro Asn Arg Glu Tyr Arg Leu Lys Asp Leu Pro Ile
        195                 200                 205

Phe Leu
    210


<210> SEQ ID NO 129
<211> LENGTH: 526
<212> TYPE: DNA
<213> ORGANISM: Aquifex aeolicus

<400> SEQUENCE: 129

atgctcaata aggtttttat aataggaaga cttacgggtg accccgttat aacttatcta     60
```

-continued

```
ccgagcggaa cgcccgtagt agagtttact ctggcttaca acagaaggta taaaaaccag    120

aacggtgaat ttcaggagga aagtcacttc tttgacgtaa aggcgtacgg aaaaatggct    180

gaagactggg ctacacgctt ctcgaaagga tacctcgtac tcgtagaggg aagactctcc    240

caggaaaagt gggagaaaga aggaaagaag ttctcaaagg tcaggataat agcggaaaac    300

gtaagattaa taaacaggcc gaaaggtgct gaacttcaag cagaagaaga ggaggaagtt    360

cctcccattg aggaggaaat tgaaaaactc ggtaaagagg aagagaagcc ttttaccgat    420

gaagaggacg aaataccttt ttaattttga ggaggttaaa gtatggtagt gagagctcct    480

aagaagaaag tttgtatgta ctgtgaacaa aagagagagc cagatt                   526
```

<210> SEQ ID NO 130
<211> LENGTH: 147
<212> TYPE: PRT
<213> ORGANISM: Aquifex aeolicus

<400> SEQUENCE: 130

```
Met Leu Asn Lys Val Phe Ile Ile Gly Arg Leu Thr Gly Asp Pro Val
  1               5                  10                  15

Ile Thr Tyr Leu Pro Ser Gly Thr Pro Val Val Glu Phe Thr Leu Ala
             20                  25                  30

Tyr Asn Arg Arg Tyr Lys Asn Gln Asn Gly Glu Phe Gln Glu Glu Ser
         35                  40                  45

His Phe Phe Asp Val Lys Ala Tyr Gly Lys Met Ala Glu Asp Trp Ala
     50                  55                  60

Thr Arg Phe Ser Lys Gly Tyr Leu Val Leu Val Glu Gly Arg Leu Ser
 65                  70                  75                  80

Gln Glu Lys Trp Glu Lys Glu Gly Lys Lys Phe Ser Lys Val Arg Ile
                 85                  90                  95

Ile Ala Glu Asn Val Arg Leu Ile Asn Arg Pro Lys Gly Ala Glu Leu
            100                 105                 110

Gln Ala Glu Glu Glu Glu Glu Val Pro Pro Ile Glu Glu Glu Ile Glu
        115                 120                 125

Lys Leu Gly Lys Glu Glu Glu Lys Pro Phe Thr Asp Glu Glu Asp Glu
    130                 135                 140

Ile Pro Phe
145
```

<210> SEQ ID NO 131
<211> LENGTH: 1472
<212> TYPE: DNA
<213> ORGANISM: Aquifex aeolicus

<400> SEQUENCE: 131

```
atgcaatttg tggataaact tccctgtgac gaatccgccg agagggcggt tcttggcagt     60

atgcttgaag accccgaaaa catacctctg gtacttgaat accttaaaga agaagacttc    120

tgcatagacg agcacaagct acttttcagg gttcttacaa acctctggtc cgagtacggc    180

aataagctcg atttcgtatt aataaaggat caccttgaaa agaaaaactt actccagaaa    240

atacctatag actggctcga agaactctac gaggaggcgg tatcccctga cacgcttgag    300

gaagtctgca aaatagtaaa acaacgttcc gcacagaggg cgataattca actcggtata    360

gaactcattc acaaaggaaa ggaaaacaaa gactttcaca cattaatcga ggaagcccag    420

agcaggatat tttccatagc ggaaagtgct acatctacgc agttttacca tgtgaaagac    480
```

```
gttgcggaag aagttataga actcatttat aaattcaaaa gctctgacag gctagtcacg    540
ggactcccaa gcggtttcac ggaactcgat ctaaagacga cgggattcca ccctggagac    600
ttaataatac tcgccgcaag acccggtatg gggaaaaccg cctttatgct ctccataatc    660
tacaatctcg caaaagacga gggaaaaccc tcagctgtat tttccttgga aatgagcaag    720
gaacagctcg ttatgagact cctctctatg atgtcggagg tcccactttt caagataagg    780
tctggaagta tatcgaatga agatttaaag aagcttgaag caagcgcaat agaactcgca    840
aagtacgaca tatacctcga cgacacaccc gctctcacta caacggattt aaggataagg    900
gcaagaaagc tcagaaagga aaaggaagtt gagttcgtgg cggtggacta cttgcaactt    960
ctgagaccgc cagtccgaaa gagttcaaga caggaggaag tggcagaggt ttcaagaaac   1020
ttaaaagccc ttgcaaagga acttcacatt cccgttatgg cacttgcgca gctctcccgt   1080
gaggtggaaa agaggagtga taaaagaccc cagcttgcgg acctcagaga atccggacag   1140
atagaacagg acgcagacct aatccttttc ctccacagac ccgagtacta caagaaaaag   1200
ccaaatcccg aagagcaggg tatagcggaa gtgataatag ccaagcaaag gcaaggaccc   1260
acggacattg tgaagctcgc atttattaag gagtacacta agtttgcaaa cctagaagcc   1320
cttcctgaac aacctcctga agaagaggaa ctttccgaaa ttattgaaac acaggaggat   1380
gaaggattcg aagatattga cttctgaaaa ttaaggtttt ataattttat cttggctatc   1440
cggggtagct caatcggcag agcgggtggc tg                                  1472

<210> SEQ ID NO 132
<211> LENGTH: 438
<212> TYPE: PRT
<213> ORGANISM: Aquifex aeolicus

<400> SEQUENCE: 132

Met Gln Phe Val Asp Lys Leu Pro Cys Asp Glu Ser Ala Glu Arg Ala
 1               5                  10                  15

Val Leu Gly Ser Met Leu Glu Asp Pro Glu Asn Ile Pro Leu Val Leu
                20                  25                  30

Glu Tyr Leu Lys Glu Glu Asp Phe Cys Ile Asp Glu His Lys Leu Leu
            35                  40                  45

Phe Arg Val Leu Thr Asn Leu Trp Ser Glu Tyr Gly Asn Lys Leu Asp
        50                  55                  60

Phe Val Leu Ile Lys Asp His Leu Glu Lys Lys Asn Leu Leu Gln Lys
    65                  70                  75                  80

Ile Pro Ile Asp Trp Leu Glu Glu Leu Tyr Glu Glu Ala Val Ser Pro
                85                  90                  95

Asp Thr Leu Glu Glu Val Cys Lys Ile Val Lys Gln Arg Ser Ala Gln
               100                 105                 110

Arg Ala Ile Ile Gln Leu Gly Ile Thr Ser Thr Gln Phe Tyr His Val
           115                 120                 125

Lys Asp Val Ala Glu Glu Val Ile Glu Leu Ile Tyr Lys Phe Lys Ser
       130                 135                 140

Ser Asp Arg Leu Val Thr Gly Leu Pro Ser Gly Phe Thr Glu Leu Asp
145                 150                 155                 160

Leu Lys Thr Thr Gly Phe His Pro Gly Asp Leu Ile Ile Leu Ala Ala
               165                 170                 175

Arg Pro Gly Met Gly Lys Thr Ala Phe Met Leu Ser Ile Ile Tyr Asn
           180                 185                 190

Leu Ala Lys Asp Glu Gly Lys Pro Ser Ala Val Phe Ser Leu Glu Met
```

-continued

```
        195                 200                 205

Ser Lys Glu Gln Leu Val Met Arg Leu Leu Ser Met Met Ser Glu Val
    210                 215                 220

Pro Leu Phe Lys Ile Arg Ser Gly Ser Ile Ser Asn Glu Asp Leu Lys
225                 230                 235                 240

Lys Leu Glu Ala Ser Ala Ile Glu Leu Ala Lys Tyr Asp Ile Tyr Leu
                245                 250                 255

Asp Asp Thr Pro Ala Leu Thr Thr Thr Asp Leu Arg Ile Arg Ala Arg
            260                 265                 270

Lys Leu Arg Lys Glu Lys Glu Val Glu Phe Val Ala Val Asp Tyr Leu
        275                 280                 285

Gln Leu Leu Arg Pro Pro Val Arg Lys Ser Ser Arg Gln Glu Glu Val
    290                 295                 300

Ala Glu Val Ser Arg Asn Leu Lys Ala Leu Ala Lys Glu Leu His Ile
305                 310                 315                 320

Pro Val Met Ala Leu Ala Gln Leu Ser Arg Glu Val Glu Lys Arg Ser
                325                 330                 335

Asp Lys Arg Pro Gln Leu Ala Asp Leu Arg Glu Ser Gly Gln Ile Glu
            340                 345                 350

Gln Asp Ala Asp Leu Ile Leu Phe Leu His Arg Pro Glu Tyr Tyr Lys
        355                 360                 365

Lys Lys Pro Asn Pro Glu Glu Gln Gly Ile Ala Glu Val Ile Ile Ala
    370                 375                 380

Lys Gln Arg Gln Gly Pro Thr Asp Ile Val Lys Leu Ala Phe Ile Lys
385                 390                 395                 400

Glu Tyr Thr Lys Phe Ala Asn Leu Glu Ala Leu Pro Glu Gln Pro Pro
                405                 410                 415

Glu Glu Glu Glu Leu Ser Glu Ile Ile Glu Thr Gln Glu Asp Glu Gly
            420                 425                 430

Phe Glu Asp Ile Asp Phe
        435
```

<210> SEQ ID NO 133
<211> LENGTH: 1526
<212> TYPE: DNA
<213> ORGANISM: Aquifex aeolicus

<400> SEQUENCE: 133

```
atgtcctcgg acatagacga acttagacgg gaaatagata tagtagacgt catttccgaa      60

tacttaaact tagagaaggt aggttccaat tacagaacga actgtccctt tcaccctgac     120

gatacaccct ccttttacgt gtctccaagt aaacaaatat tcaagtgttt cggttgcggg     180

gtagggggag acgcgataaa gttcgtttcc ctttacgagg acatctccta ttttgaagcc     240

gcccttgaac tcgcaaaacg ctacggaaag aaattagacc ttgaaaagat atcaaaagac     300

gaaaaggtat acgtggctct tgacagggtt tgtgatttct acagggaaag ccttctcaaa     360

aacagagagg caagtgagta cgtaaagagt aggggaatag accctaaagt agcgaggaag     420

tttgatcttg ggtacgcacc ttccagtgaa gcactcgtaa aagtcttaaa agagaacgat     480

cttttagagg cttaccttga aactaaaaac ctcctttctc ctacgaaggg tgtttacagg     540

gatctctttc ttcggcgtgt cgtgatcccg ataaaggatc cgaggggaag agttataggt     600

ttcggtggaa ggaggatagt agaggacaaa tctcccaagt acataaactc tccagacagc     660

agggtattta aaaaggggga gaacttattc ggtctttacg aggcaaagga gtatataaag     720
```

-continued

```
gaagaaggat ttgcgatact tgtggaaggg tactttgacc ttttgagact tttttccgag    780

ggaataagga acgttgttgc acccctcggt acagccctga cccaaaatca ggcaaacctc    840

ctttccaagt tcacaaaaaa ggtctacatc ctttacgacg gagatgatgc gggaagaaag    900

gctatgaaaa gtgccattcc cctactcctc agtgcaggag tggaagttta tcccgtttac    960

ctcccccgaag gatacgatcc cgacgagttt ataaaggaat tcgggaaaga ggaattaaga   1020

agactgataa acagctcagg ggagctcttt gaaacgctca taaaaaccgc aagggaaaac   1080

ttagaggaga aaacgcgtga gttcaggtat tatctgggct ttatttccga tggagtaagg   1140

cgctttgctc tggcttcgga gtttcacacc aagtacaaag ttcctatgga aattttatta   1200

atgaaaattg aaaaaaattc tcaagaaaaa gaaattaaac tctcctttaa ggaaaaaatc   1260

ttcctgaaag gactgataga attaaaacca aaaatagacc ttgaagtcct gaacttaagt   1320

cctgagttaa aggaactcgc agttaacgcc ttaaacggag aggagcattt acttccaaaa   1380

gaagttctcg agtaccaggt ggataacttg gagaaacttt ttaacaacat ccttagggat   1440

ttacaaaaat ctgggaaaaa gaggaagaaa agagggttga aaaatgtaaa tacttaatta   1500

actttaataa atttttagag ttagga                                         1526
```

<210> SEQ ID NO 134
<211> LENGTH: 498
<212> TYPE: PRT
<213> ORGANISM: Aquifex aeolicus

<400> SEQUENCE: 134

```
Met Ser Ser Asp Ile Asp Glu Leu Arg Arg Glu Ile Asp Ile Val Asp
  1               5                  10                  15

Val Ile Ser Glu Tyr Leu Asn Leu Glu Lys Val Gly Ser Asn Tyr Arg
             20                  25                  30

Thr Asn Cys Pro Phe His Pro Asp Asp Thr Pro Ser Phe Tyr Val Ser
         35                  40                  45

Pro Ser Lys Gln Ile Phe Lys Cys Phe Gly Cys Gly Val Gly Gly Asp
     50                  55                  60

Ala Ile Lys Phe Val Ser Leu Tyr Glu Asp Ile Ser Tyr Phe Glu Ala
 65                  70                  75                  80

Ala Leu Glu Leu Ala Lys Arg Tyr Gly Lys Lys Leu Asp Leu Glu Lys
                 85                  90                  95

Ile Ser Lys Asp Glu Lys Val Tyr Val Ala Leu Asp Arg Val Cys Asp
            100                 105                 110

Phe Tyr Arg Glu Ser Leu Leu Lys Asn Arg Glu Ala Ser Glu Tyr Val
        115                 120                 125

Lys Ser Arg Gly Ile Asp Pro Lys Val Ala Arg Lys Phe Asp Leu Gly
    130                 135                 140

Tyr Ala Pro Ser Ser Glu Ala Leu Val Lys Val Leu Lys Glu Asn Asp
145                 150                 155                 160

Leu Leu Glu Ala Tyr Leu Glu Thr Lys Asn Leu Leu Ser Pro Thr Lys
                165                 170                 175

Gly Val Tyr Arg Asp Leu Phe Leu Arg Arg Val Val Ile Pro Ile Lys
            180                 185                 190

Asp Pro Arg Gly Arg Val Ile Gly Phe Gly Gly Arg Arg Ile Val Glu
        195                 200                 205

Asp Lys Ser Pro Lys Tyr Ile Asn Ser Pro Asp Ser Arg Val Phe Lys
    210                 215                 220

Lys Gly Glu Asn Leu Phe Gly Leu Tyr Glu Ala Lys Glu Tyr Ile Lys
```

-continued

```
225                 230                 235                 240

Glu Glu Gly Phe Ala Ile Leu Val Glu Gly Tyr Phe Asp Leu Leu Arg
                245                 250                 255

Leu Phe Ser Glu Gly Ile Arg Asn Val Val Ala Pro Leu Gly Thr Ala
            260                 265                 270

Leu Thr Gln Asn Gln Ala Asn Leu Leu Ser Lys Phe Thr Lys Lys Val
        275                 280                 285

Tyr Ile Leu Tyr Asp Gly Asp Asp Ala Gly Arg Lys Ala Met Lys Ser
    290                 295                 300

Ala Ile Pro Leu Leu Leu Ser Ala Gly Val Glu Val Tyr Pro Val Tyr
305                 310                 315                 320

Leu Pro Glu Gly Tyr Asp Pro Asp Glu Phe Ile Lys Glu Phe Gly Lys
                325                 330                 335

Glu Glu Leu Arg Arg Leu Ile Asn Ser Ser Gly Glu Leu Phe Glu Thr
            340                 345                 350

Leu Ile Lys Thr Ala Arg Glu Asn Leu Glu Glu Lys Thr Arg Glu Phe
        355                 360                 365

Arg Tyr Tyr Leu Gly Phe Ile Ser Asp Gly Val Arg Arg Phe Ala Leu
    370                 375                 380

Ala Ser Glu Phe His Thr Lys Tyr Lys Val Pro Met Glu Ile Leu Leu
385                 390                 395                 400

Met Lys Ile Glu Lys Asn Ser Gln Glu Lys Glu Ile Lys Leu Ser Phe
                405                 410                 415

Lys Glu Lys Ile Phe Leu Lys Gly Leu Ile Glu Leu Lys Pro Lys Ile
            420                 425                 430

Asp Leu Glu Val Leu Asn Leu Ser Pro Glu Leu Lys Glu Leu Ala Val
        435                 440                 445

Asn Ala Leu Asn Gly Glu Glu His Leu Leu Pro Lys Glu Val Leu Glu
    450                 455                 460

Tyr Gln Val Asp Asn Leu Glu Lys Leu Phe Asn Asn Ile Leu Arg Asp
465                 470                 475                 480

Leu Gln Lys Ser Gly Lys Lys Arg Lys Lys Arg Gly Leu Lys Asn Val
                485                 490                 495

Asn Thr


<210> SEQ ID NO 135
<211> LENGTH: 705
<212> TYPE: DNA
<213> ORGANISM: Aquifex aeolicus

<400> SEQUENCE: 135

atgcaagata ccgctacctg cagtatttgt caggggacgg gattcgtaaa gaccgaagac      60

aacaaggtaa ggctctgcga atgcaggttc aagaaaaggg atgtaaacag ggaactaaac     120

atcccaaaga ggtactggaa cgccaactta gacacttacc accccaagaa cgtatcccag     180

aacagggcac ttttgacgat aagggtcttc gtccacaact tcaatcccga ggaagggaaa     240

gggcttacct ttgtaggatc tcctggagtc ggcaaaactc accttgcggt tgcaacatta     300

aaagcgattt atgagaagaa gggaatcaga ggatacttct tcgatacgaa ggatctaata     360

ttcaggttaa aacacttaat ggacgaggga aaggatacaa agtttttaaa aactgtctta     420

aactcaccgg ttttggttct cgacgacctc ggttctgaga ggctcagtga ctggcagagg     480

gaactcatct cttacataat cacttacagg tataacaacc ttaagagcac gataataacc     540

acgaattact cactccagag ggaagaagag agtagcgtga ggataagtgc ggatcttgca     600
```

-continued

```
agcagactcg gagaaaacgt agtttcaaaa atttacgaga tgaacgagtt gctcgttata    660

aagggttccg acctcaggaa gtctaaaaag ctatcaaccc catct                    705


<210> SEQ ID NO 136
<211> LENGTH: 235
<212> TYPE: PRT
<213> ORGANISM: Aquifex aeolicus

<400> SEQUENCE: 136

Met Gln Asp Thr Ala Thr Cys Ser Ile Cys Gln Gly Thr Gly Phe Val
  1               5                  10                  15

Lys Thr Glu Asp Asn Lys Val Arg Leu Cys Glu Cys Arg Phe Lys Lys
             20                  25                  30

Arg Asp Val Asn Arg Glu Leu Asn Ile Pro Lys Arg Tyr Trp Asn Ala
         35                  40                  45

Asn Leu Asp Thr Tyr His Pro Lys Asn Val Ser Gln Asn Arg Ala Leu
     50                  55                  60

Leu Thr Ile Arg Val Phe Val His Asn Phe Asn Pro Glu Glu Gly Lys
 65                  70                  75                  80

Gly Leu Thr Phe Val Gly Ser Pro Gly Val Gly Lys Thr His Leu Ala
                 85                  90                  95

Val Ala Thr Leu Lys Ala Ile Tyr Glu Lys Lys Gly Ile Arg Gly Tyr
            100                 105                 110

Phe Phe Asp Thr Lys Asp Leu Ile Phe Arg Leu Lys His Leu Met Asp
        115                 120                 125

Glu Gly Lys Asp Thr Lys Phe Leu Lys Thr Val Leu Asn Ser Pro Val
    130                 135                 140

Leu Val Leu Asp Asp Leu Gly Ser Glu Arg Leu Ser Asp Trp Gln Arg
145                 150                 155                 160

Glu Leu Ile Ser Tyr Ile Ile Thr Tyr Arg Tyr Asn Asn Leu Lys Ser
                165                 170                 175

Thr Ile Ile Thr Thr Asn Tyr Ser Leu Gln Arg Glu Glu Glu Ser Ser
            180                 185                 190

Val Arg Ile Ser Ala Asp Leu Ala Ser Arg Leu Gly Glu Asn Val Val
        195                 200                 205

Ser Lys Ile Tyr Glu Met Asn Glu Leu Leu Val Ile Lys Gly Ser Asp
    210                 215                 220

Leu Arg Lys Ser Lys Lys Leu Ser Thr Pro Ser
225                 230                 235


<210> SEQ ID NO 137
<211> LENGTH: 4101
<212> TYPE: DNA
<213> ORGANISM: Thermatoga maritima

<400> SEQUENCE: 137

atgaaaaaga ttgaaaattt gaagtggaaa aatgtctcgt ttaaaagcct ggaaatagat     60

cccgatgcag gtgtggttct cgtttccgtg gaaaaattct ccgaagagat agaagacctt    120

gtgcgtttac tggagaagaa gacgcggttt cgagtcatcg tgaacggtgt tcaaaaaagt    180

aacggggatc taaggggaaa gatactttcc cttctcaacg gtaatgtgcc ttacataaaa    240

gatgttgttt tcgaaggaaa caggctgatt ctgaaagtgc ttggagattt cgcgcgggac    300

aggatcgcct ccaaactcag aagcacgaaa aaacagctcg atgaactgct gcctcccgga    360

acagagatca tgctggaggt tgtggagcct ccggaagatc ttttgaaaaa ggaagtacca    420
```

-continued

```
caaccagaaa agagagaaga accaaagggt gaagaattga agatcgagga tgaaaaccac    480
atctttggac agaaacccag aaagatcgtc ttcaccccct caaaaatctt tgagtacaac    540
aaaaagacat cggtgaaggg caagatcttc aaaatagaga agatcgaggg gaaaagaacg    600
gtccttctga tttacctgac agacggagaa gattctctga tctgcaaagt cttcaacgac    660
gttgaaaagg tcgaagggaa agtatcggtg ggagacgtga tcgttgccac aggagacctc    720
cttctcgaaa acggggagcc caccctttac gtgaagggaa tcacaaaact tcccgaagcg    780
aaaaggatgg acaaatctcc ggttaagagg gtggagctcc acgcccatac caagttcagc    840
gatcaggacg caataacaga tgtgaacgaa tatgtgaaac gagccaagga atggggcttt    900
cccgcgatag ccctcacgga tcatgggaac gttcaggcca taccttactt ctacgacgcg    960
gcgaaagaag ctggaataaa gcccattttc ggtatcgaag cgtatctggt gagtgacgtg   1020
gagcccgtca taaggaatct ctccgacgat tcgacgtttg gagatgccac gttcgtcgtc   1080
ctcgacttcg agacgacggg tctcgacccg caggtggatg agatcatcga gataggagcg   1140
gtgaagatac agggtggcca gatagtggac gagtaccaca ctctcataaa gccttccagg   1200
gagatctcaa gaaaaagttc ggagatcacc ggaatcactc aagagatgct ggaaaacaag   1260
agaagcatcg aggaagttct gccggagttc ctcggttttc tggaagattc catcatcgta   1320
gcacacaacg ccaacttcga ctacagattt ctgaggctgt ggatcaaaaa agtgatggga   1380
ttggactggg aaagacccta catagatacg ctcgccctcg caaagtccct tctcaaactg   1440
agaagctact ctctggattc cgttgtggaa aagctcggat tgggtccctt ccggcaccac   1500
agggccctgg atgacgcgag ggtcaccgct caggttttcc tcaggttcgt tgagatgatg   1560
aagaagatcg gtatcacgaa gctttcagaa atggagaagt tgaaggatac gatagactac   1620
accgcgttga aacccttcca ctgcacgatc ctcgttcaga acaaaaaggg attgaaaaac   1680
ctatacaaac tggtttctga ttcctatata aagtacttct acggtgttcc gaggatcctc   1740
aaaagtgagc tcatcgagaa cagagaagga ctgctcgtgg gtagcgcgtg tatctccggt   1800
gagctcggac gtgccgccct cgaaggagcg agtgattcag aactcgaaga gatcgcgaag   1860
ttctacgact acatagaagt catgccgctc gacgttatag ccgaagatga agaagaccta   1920
gacagagaaa gactgaaaga agtgtaccga aaactctaca gaatagcgaa aaaattgaac   1980
aagttcgtcg tcatgaccgg tgatgttcat ttcctcgatc ccgaagatgc caggggcaga   2040
gctgcacttc tggcacctca gggaaacaga aacttcgaga atcagcccgc actctacctc   2100
agaacgaccg aagaaatgct cgagaaggcg atagagatat tcgaagatga agagatcgcg   2160
agggaagtcg tgatagagaa tcccaacaga atagccgata tgatcgagga agtgcagccg   2220
ctcgagaaaa aacttcaccc gccgatcata gagaacgccg atgaaatagt gagaaacctc   2280
accatgaagc gggcgtacga gatctacggt gatccgcttc ccgaaatcgt ccagaagcgt   2340
gtggaaaagg aactgaacgc catcataaat catggatacg ccgttctcta tctcatcgct   2400
caggagctcg ttcagaaatc tatgagcgat ggttacgtgg ttggatccag aggatccgtc   2460
gggtcttcac tcgtggccaa tctcctcgga ataacagagg tgaatcccct accaccacat   2520
tacaggtgtc cagagtgcaa atactttgaa gttgtcgaag acgacagata cggagcgggt   2580
tacgaccttc ccaacaagaa ctgtccaaga tgtggggctc ctctcagaaa agacggccac   2640
ggcataccgt ttgaaacgtt catggggttc gagggtgaca aggtccccga catagatctc   2700
aacttctcag gagagtatca ggaacgtgct catcgttttg tggaagaact cttcggtaaa   2760
```

-continued

```
gaccacgtct atagggcggg aaccataaac accatcgcgg aaagaagtgc ggtgggttac   2820

gtgagaagct acgaagagaa aaccggaaag aagctcagaa aggcggaaat ggaaagactc   2880

gtttccatga tcacgggagt gaagagaacg acgggtcagc acccaggggg gctcatgatc   2940

ataccgaaag acaaagaagt ctacgatttc actcccatac agtatccagc caacgataga   3000

aacgcaggtg tgttcaccac gcacttcgca tacgagacga tccatgatga cctggtgaag   3060

atagatgcgc tcggccacga tgatcccact ttcatcaaga tgctcaagga cctcaccgga   3120

atcgatccca tgacgattcc catggatgac cccgatacgc tcgccatatt cagttctgtg   3180

aagcctcttg gtgtggatcc cgttgagctg gaaagcgatg tgggaacgta cggaattccg   3240

gagttcggaa ccgagtttgt gaggggaatg ctcgttgaaa cgagaccaaa gagtttcgcc   3300

gagcttgtga gaatctcagg actgtcacac ggtacggacg tctggttgaa caacgcacgt   3360

gattggataa acctcggcta cgccaagctc tccgaggtta tctcgtgtag ggacgacatc   3420

atgaacttcc tcatacacaa aggaatggaa ccgtcacttg ccttcaagat catggaaaac   3480

gtcaggaagg gaaagggtat cacagaagag atggagagcg agatgagaag gctgaaggtt   3540

ccagaatggt tcatcgaatc ctgtaaaagg atcaaatatc tcttcccgaa agctcacgct   3600

gtggcttacg tgagtatggc cttcagaatt gcttacttca aggttcacta tcctcttcag   3660

ttttacgcgg cgtacttcac gataaaaggt gatcagttcg atccggttct cgtactcagg   3720

ggaaaagaag ccataaagag gcgcttgaga gaactcaaag cgatgcctgc caaagacgcc   3780

cagaagaaaa acgaagtgag tgttctggag gttgccctgg aaatgatact gagaggtttt   3840

tccttcctac cgcccgacat cttcaaatcc gacgcgaaga aatttctgat agaaggaaac   3900

tcgctgagaa ttccgttcaa caaacttcca ggactgggtg acagcgttgc cgagtcgata   3960

atcagagcca gggaagaaaa gccgttcact tcggtggaag atctcatgaa gaggaccaag   4020

gtcaacaaaa atcacataga gctgatgaaa agcctgggtg ttctcgggga ccttccagag   4080

acggaacagt tcacgctttt c                                             4101
```

<210> SEQ ID NO 138
<211> LENGTH: 1367
<212> TYPE: PRT
<213> ORGANISM: Thermatoga maritima

<400> SEQUENCE: 138

```
Met Lys Lys Ile Glu Asn Leu Lys Trp Lys Asn Val Ser Phe Lys Ser
  1               5                  10                  15

Leu Glu Ile Asp Pro Asp Ala Gly Val Val Leu Val Ser Val Glu Lys
             20                  25                  30

Phe Ser Glu Glu Ile Glu Asp Leu Val Arg Leu Leu Glu Lys Lys Thr
         35                  40                  45

Arg Phe Arg Val Ile Val Asn Gly Val Gln Lys Ser Asn Gly Asp Leu
     50                  55                  60

Arg Gly Lys Ile Leu Ser Leu Leu Asn Gly Asn Val Pro Tyr Ile Lys
 65                  70                  75                  80

Asp Val Val Phe Glu Gly Asn Arg Leu Ile Leu Lys Val Leu Gly Asp
                 85                  90                  95

Phe Ala Arg Asp Arg Ile Ala Ser Lys Leu Arg Ser Thr Lys Lys Gln
            100                 105                 110

Leu Asp Glu Leu Leu Pro Pro Gly Thr Glu Ile Met Leu Glu Val Val
        115                 120                 125

Glu Pro Pro Glu Asp Leu Leu Lys Lys Glu Val Pro Gln Pro Glu Lys
```

-continued

```
    130                 135                 140

Arg Glu Glu Pro Lys Gly Glu Glu Leu Lys Ile Glu Asp Glu Asn His
145                 150                 155                 160

Ile Phe Gly Gln Lys Pro Arg Lys Ile Val Phe Thr Pro Ser Lys Ile
                165                 170                 175

Phe Glu Tyr Asn Lys Lys Thr Ser Val Lys Gly Lys Ile Phe Lys Ile
            180                 185                 190

Glu Lys Ile Glu Gly Lys Arg Thr Val Leu Leu Ile Tyr Leu Thr Asp
        195                 200                 205

Gly Glu Asp Ser Leu Ile Cys Lys Val Phe Asn Asp Val Glu Lys Val
    210                 215                 220

Glu Gly Lys Val Ser Val Gly Asp Val Ile Val Ala Thr Gly Asp Leu
225                 230                 235                 240

Leu Leu Glu Asn Gly Glu Pro Thr Leu Tyr Val Lys Gly Ile Thr Lys
                245                 250                 255

Leu Pro Glu Ala Lys Arg Met Asp Lys Ser Pro Val Lys Arg Val Glu
            260                 265                 270

Leu His Ala His Thr Lys Phe Ser Asp Gln Asp Ala Ile Thr Asp Val
        275                 280                 285

Asn Glu Tyr Val Lys Arg Ala Lys Glu Trp Gly Phe Pro Ala Ile Ala
    290                 295                 300

Leu Thr Asp His Gly Asn Val Gln Ala Ile Pro Tyr Phe Tyr Asp Ala
305                 310                 315                 320

Ala Lys Glu Ala Gly Ile Lys Pro Ile Phe Gly Ile Glu Ala Tyr Leu
                325                 330                 335

Val Ser Asp Val Glu Pro Val Ile Arg Asn Leu Ser Asp Asp Ser Thr
            340                 345                 350

Phe Gly Asp Ala Thr Phe Val Val Leu Asp Phe Glu Thr Thr Gly Leu
        355                 360                 365

Asp Pro Gln Val Asp Glu Ile Ile Glu Ile Gly Ala Val Lys Ile Gln
    370                 375                 380

Gly Gly Gln Ile Val Asp Glu Tyr His Thr Leu Ile Lys Pro Ser Arg
385                 390                 395                 400

Glu Ile Ser Arg Lys Ser Ser Glu Ile Thr Gly Ile Thr Gln Glu Met
                405                 410                 415

Leu Glu Asn Lys Arg Ser Ile Glu Glu Val Leu Pro Glu Phe Leu Gly
            420                 425                 430

Phe Leu Glu Asp Ser Ile Ile Val Ala His Asn Ala Asn Phe Asp Tyr
        435                 440                 445

Arg Phe Leu Arg Leu Trp Ile Lys Lys Val Met Gly Leu Asp Trp Glu
    450                 455                 460

Arg Pro Tyr Ile Asp Thr Leu Ala Leu Ala Lys Ser Leu Leu Lys Leu
465                 470                 475                 480

Arg Ser Tyr Ser Leu Asp Ser Val Val Glu Lys Leu Gly Leu Gly Pro
                485                 490                 495

Phe Arg His His Arg Ala Leu Asp Asp Ala Arg Val Thr Ala Gln Val
            500                 505                 510

Phe Leu Arg Phe Val Glu Met Met Lys Lys Ile Gly Ile Thr Lys Leu
        515                 520                 525

Ser Glu Met Glu Lys Leu Lys Asp Thr Ile Asp Tyr Thr Ala Leu Lys
    530                 535                 540

Pro Phe His Cys Thr Ile Leu Val Gln Asn Lys Lys Gly Leu Lys Asn
545                 550                 555                 560
```

-continued

```
Leu Tyr Lys Leu Val Ser Asp Ser Tyr Ile Lys Tyr Phe Tyr Gly Val
                565                 570                 575

Pro Arg Ile Leu Lys Ser Glu Leu Ile Glu Asn Arg Glu Gly Leu Leu
            580                 585                 590

Val Gly Ser Ala Cys Ile Ser Gly Glu Leu Gly Arg Ala Ala Leu Glu
        595                 600                 605

Gly Ala Ser Asp Ser Glu Leu Glu Glu Ile Ala Lys Phe Tyr Asp Tyr
    610                 615                 620

Ile Glu Val Met Pro Leu Asp Val Ile Ala Glu Asp Glu Glu Asp Leu
625                 630                 635                 640

Asp Arg Glu Arg Leu Lys Glu Val Tyr Arg Lys Leu Tyr Arg Ile Ala
                645                 650                 655

Lys Lys Leu Asn Lys Phe Val Val Met Thr Gly Asp Val His Phe Leu
            660                 665                 670

Asp Pro Glu Asp Ala Arg Gly Arg Ala Ala Leu Leu Ala Pro Gln Gly
        675                 680                 685

Asn Arg Asn Phe Glu Asn Gln Pro Ala Leu Tyr Leu Arg Thr Thr Glu
    690                 695                 700

Glu Met Leu Glu Lys Ala Ile Glu Ile Phe Glu Asp Glu Glu Ile Ala
705                 710                 715                 720

Arg Glu Val Val Ile Glu Asn Pro Asn Arg Ile Ala Asp Met Ile Glu
                725                 730                 735

Glu Val Gln Pro Leu Glu Lys Lys Leu His Pro Pro Ile Ile Glu Asn
            740                 745                 750

Ala Asp Glu Ile Val Arg Asn Leu Thr Met Lys Arg Ala Tyr Glu Ile
        755                 760                 765

Tyr Gly Asp Pro Leu Pro Glu Ile Val Gln Lys Arg Val Glu Lys Glu
    770                 775                 780

Leu Asn Ala Ile Ile Asn His Gly Tyr Ala Val Leu Tyr Leu Ile Ala
785                 790                 795                 800

Gln Glu Leu Val Gln Lys Ser Met Ser Asp Gly Tyr Val Val Gly Ser
                805                 810                 815

Arg Gly Ser Val Gly Ser Ser Leu Val Ala Asn Leu Leu Gly Ile Thr
            820                 825                 830

Glu Val Asn Pro Leu Pro Pro His Tyr Arg Cys Pro Glu Cys Lys Tyr
        835                 840                 845

Phe Glu Val Val Glu Asp Asp Arg Tyr Gly Ala Gly Tyr Asp Leu Pro
    850                 855                 860

Asn Lys Asn Cys Pro Arg Cys Gly Ala Pro Leu Arg Lys Asp Gly His
865                 870                 875                 880

Gly Ile Pro Phe Glu Thr Phe Met Gly Phe Glu Gly Asp Lys Val Pro
                885                 890                 895

Asp Ile Asp Leu Asn Phe Ser Gly Glu Tyr Gln Glu Arg Ala His Arg
            900                 905                 910

Phe Val Glu Glu Leu Phe Gly Lys Asp His Val Tyr Arg Ala Gly Thr
        915                 920                 925

Ile Asn Thr Ile Ala Glu Arg Ser Ala Val Gly Tyr Val Arg Ser Tyr
    930                 935                 940

Glu Glu Lys Thr Gly Lys Lys Leu Arg Lys Ala Glu Met Glu Arg Leu
945                 950                 955                 960

Val Ser Met Ile Thr Gly Val Lys Arg Thr Thr Gly Gln His Pro Gly
                965                 970                 975
```

-continued

```
Gly Leu Met Ile Ile Pro Lys Asp Lys Glu Val Tyr Asp Phe Thr Pro
            980                 985                 990

Ile Gln Tyr Pro Ala Asn Asp Arg Asn Ala Gly Val Phe Thr Thr His
        995                 1000                1005

Phe Ala Tyr Glu Thr Ile His Asp Asp Leu Val Lys Ile Asp Ala Leu
    1010                1015                1020

Gly His Asp Asp Pro Thr Phe Ile Lys Met Leu Lys Asp Leu Thr Gly
1025                1030                1035                1040

Ile Asp Pro Met Thr Ile Pro Met Asp Asp Pro Asp Thr Leu Ala Ile
                1045                1050                1055

Phe Ser Ser Val Lys Pro Leu Gly Val Asp Pro Val Glu Leu Glu Ser
            1060                1065                1070

Asp Val Gly Thr Tyr Gly Ile Pro Glu Phe Gly Thr Glu Phe Val Arg
        1075                1080                1085

Gly Met Leu Val Glu Thr Arg Pro Lys Ser Phe Ala Glu Leu Val Arg
    1090                1095                1100

Ile Ser Gly Leu Ser His Gly Thr Asp Val Trp Leu Asn Asn Ala Arg
1105                1110                1115                1120

Asp Trp Ile Asn Leu Gly Tyr Ala Lys Leu Ser Glu Val Ile Ser Cys
                1125                1130                1135

Arg Asp Asp Ile Met Asn Phe Leu Ile His Lys Gly Met Glu Pro Ser
            1140                1145                1150

Leu Ala Phe Lys Ile Met Glu Asn Val Arg Lys Gly Lys Gly Ile Thr
        1155                1160                1165

Glu Glu Met Glu Ser Glu Met Arg Arg Leu Lys Val Pro Glu Trp Phe
    1170                1175                1180

Ile Glu Ser Cys Lys Arg Ile Lys Tyr Leu Phe Pro Lys Ala His Ala
1185                1190                1195                1200

Val Ala Tyr Val Ser Met Ala Phe Arg Ile Ala Tyr Phe Lys Val His
                1205                1210                1215

Tyr Pro Leu Gln Phe Tyr Ala Ala Tyr Phe Thr Ile Lys Gly Asp Gln
            1220                1225                1230

Phe Asp Pro Val Leu Val Leu Arg Gly Lys Glu Ala Ile Lys Arg Arg
        1235                1240                1245

Leu Arg Glu Leu Lys Ala Met Pro Ala Lys Asp Ala Gln Lys Lys Asn
    1250                1255                1260

Glu Val Ser Val Leu Glu Val Ala Leu Glu Met Ile Leu Arg Gly Phe
1265                1270                1275                1280

Ser Phe Leu Pro Pro Asp Ile Phe Lys Ser Asp Ala Lys Lys Phe Leu
                1285                1290                1295

Ile Glu Gly Asn Ser Leu Arg Ile Pro Phe Asn Lys Leu Pro Gly Leu
            1300                1305                1310

Gly Asp Ser Val Ala Glu Ser Ile Ile Arg Ala Arg Glu Glu Lys Pro
        1315                1320                1325

Phe Thr Ser Val Glu Asp Leu Met Lys Arg Thr Lys Val Asn Lys Asn
    1330                1335                1340

His Ile Glu Leu Met Lys Ser Leu Gly Val Leu Gly Asp Leu Pro Glu
1345                1350                1355                1360

Thr Glu Gln Phe Thr Leu Phe
                1365


<210> SEQ ID NO 139
<211> LENGTH: 567
<212> TYPE: DNA
```

-continued

<213> ORGANISM: Thermatoga maritima

<400> SEQUENCE: 139
gtgctcgcca tgatatggaa cgacaccgtt ttttgcgtcg tagacacaga aaccacggga 60
accgatccct ttgccggaga ccggatagtt gaaatagccg ctgttcctgt cttcaagggg 120
aagatctaca gaaacaaagc gtttcactct ctcgtgaatc ccagaataag aatccctgcg 180
ctgattcaga aagttcacgg tatcagcaac atggacatcg tggaagcgcc agacatggac 240
acagtttacg atcttttcag ggattacgtg aagggaacgg tgctcgtgtt tcacaacgcc 300
aacttcgacc tcacttttct ggatatgatg gcaaaggaaa cgggaaactt tccaataacg 360
aatccctaca tcgacacact cgatctttca gaagagatct ttggaaggcc tcattctctc 420
aaatggctct ccgaaagact tggaataaaa accacgatac ggcaccgtgc tcttccagat 480
gccctggtga ccgcaagagt ttttgtgaag cttgttgaat ttcttggtga aaacagggtc 540
aacgaattca tacgtggaaa acggggg 567

<210> SEQ ID NO 140
<211> LENGTH: 189
<212> TYPE: PRT
<213> ORGANISM: Thermatoga maritima

<400> SEQUENCE: 140

Met Leu Ala Met Ile Trp Asn Asp Thr Val Phe Cys Val Val Asp Thr
1 5 10 15

Glu Thr Thr Gly Thr Asp Pro Phe Ala Gly Asp Arg Ile Val Glu Ile
20 25 30

Ala Ala Val Pro Val Phe Lys Gly Lys Ile Tyr Arg Asn Lys Ala Phe
35 40 45

His Ser Leu Val Asn Pro Arg Ile Arg Ile Pro Ala Leu Ile Gln Lys
50 55 60

Val His Gly Ile Ser Asn Met Asp Ile Val Glu Ala Pro Asp Met Asp
65 70 75 80

Thr Val Tyr Asp Leu Phe Arg Asp Tyr Val Lys Gly Thr Val Leu Val
85 90 95

Phe His Asn Ala Asn Phe Asp Leu Thr Phe Leu Asp Met Met Ala Lys
100 105 110

Glu Thr Gly Asn Phe Pro Ile Thr Asn Pro Tyr Ile Asp Thr Leu Asp
115 120 125

Leu Ser Glu Glu Ile Phe Gly Arg Pro His Ser Leu Lys Trp Leu Ser
130 135 140

Glu Arg Leu Gly Ile Lys Thr Thr Ile Arg His Arg Ala Leu Pro Asp
145 150 155 160

Ala Leu Val Thr Ala Arg Val Phe Val Lys Leu Val Glu Phe Leu Gly
165 170 175

Glu Asn Arg Val Asn Glu Phe Ile Arg Gly Lys Arg Gly
180 185

<210> SEQ ID NO 141
<211> LENGTH: 1434
<212> TYPE: DNA
<213> ORGANISM: Thermatoga maritima

<400> SEQUENCE: 141
gtggaagttc tttacaggaa gtacaggcca aagacttttt ctgaggttgt caatcaggat 60
catgtgaaga aggcaataat cggtgctatt cagaagaaca gcgtggccca cggatacata 120

-continued

```
ttcgccggtc cgaggggaac ggggaagact actcttgcca gaattctcgc aaaatccctg    180
aactgtgaga acagaaaggg agttgaaccc tgcaattcct gcagagcctg cagagagata    240
gacgagggaa ccttcatgga cgtgatagag ctcgacgcgg cctccaacag aggaatagac    300
gagatcagaa gaatcagaga cgccgttgga tacaggccga tggaaggtaa atacaaagtc    360
tacataatag acgaagttca catgctcacg aaagaagcct tcaacgcgct cctcaaaaca    420
ctcgaagaac ctccttccca cgtcgtgttc gtgctggcaa cgacaaacct tgagaaggtt    480
cctcccacga ttatctcgag atgtcaggtt ttcgagttca gaaacattcc cgacgagctc    540
atcgaaaaga ggctccagga agttgcggag gctgaaggaa tagagataga cagggaagct    600
ctgagcttca tcgcaaaaag agcctctgga ggcttgagag acgcgctcac catgctcgag    660
caggtgtgga agttctcgga aggaaagata gatctcgaga cggtacacag ggcgctcggg    720
ttgataccga tacaggttgt tcgcgattac gtgaacgcta tcttttctgg tgatgtgaaa    780
agggtcttca ccgttctcga cgacgtctat tacagcggga aggactacga ggtgctcatt    840
caggaagcag tcgaggatct ggtcgaagac ctggaaaggg agagaggggt ttaccaggtt    900
tcagcgaacg atatagttca ggtttcgaga caacttctga atcttctgag agagataaag    960
ttcgccgaag aaaaacgact cgtctgtaaa gtgggttcgg cttacatagc gacgaggttc   1020
tccaccacaa acgttcagga aaacgatgtc agagaaaaaa acgataattc aaatgtacag   1080
cagaaagaag agaagaaaga aacggtgaag gcaaaagaag aaaaacagga agacagcgag   1140
ttcgagaaac gcttcaaaga actcatggaa gaactgaaag aaaagggcga tctctctatc   1200
tttgtcgctc tcagcctctc agaggtgcag tttgacggag aaaaggtgat tatttctttt   1260
gattcatcga aagctatgca ttacgagttg atgaagaaaa aactgcctga gctggaaaac   1320
attttttcta gaaaactcgg gaaaaaagta gaagttgaac ttcgactgat gggaaaagaa   1380
gaaacaatcg agaaggtttc tcagaagatc ctgagattgt ttgaacagga ggga         1434
```

<210> SEQ ID NO 142
<211> LENGTH: 478
<212> TYPE: PRT
<213> ORGANISM: Thermatoga maritima

<400> SEQUENCE: 142

```
Met Glu Val Leu Tyr Arg Lys Tyr Arg Pro Lys Thr Phe Ser Glu Val
  1               5                  10                  15

Val Asn Gln Asp His Val Lys Lys Ala Ile Ile Gly Ala Ile Gln Lys
             20                  25                  30

Asn Ser Val Ala His Gly Tyr Ile Phe Ala Gly Pro Arg Gly Thr Gly
         35                  40                  45

Lys Thr Thr Leu Ala Arg Ile Leu Ala Lys Ser Leu Asn Cys Glu Asn
     50                  55                  60

Arg Lys Gly Val Glu Pro Cys Asn Ser Cys Arg Ala Cys Arg Glu Ile
 65                  70                  75                  80

Asp Glu Gly Thr Phe Met Asp Val Ile Glu Leu Asp Ala Ala Ser Asn
                 85                  90                  95

Arg Gly Ile Asp Glu Ile Arg Arg Ile Arg Asp Ala Val Gly Tyr Arg
            100                 105                 110

Pro Met Glu Gly Lys Tyr Lys Val Tyr Ile Ile Asp Glu Val His Met
        115                 120                 125

Leu Thr Lys Glu Ala Phe Asn Ala Leu Leu Lys Thr Leu Glu Glu Pro
    130                 135                 140
```

-continued

```
Pro Ser His Val Val Phe Val Leu Ala Thr Thr Asn Leu Glu Lys Val
145                 150                 155                 160

Pro Pro Thr Ile Ile Ser Arg Cys Gln Val Phe Glu Phe Arg Asn Ile
                165                 170                 175

Pro Asp Glu Leu Ile Glu Lys Arg Leu Gln Glu Val Ala Glu Ala Glu
            180                 185                 190

Gly Ile Glu Ile Asp Arg Glu Ala Leu Ser Phe Ile Ala Lys Arg Ala
        195                 200                 205

Ser Gly Gly Leu Arg Asp Ala Leu Thr Met Leu Glu Gln Val Trp Lys
    210                 215                 220

Phe Ser Glu Gly Lys Ile Asp Leu Glu Thr Val His Arg Ala Leu Gly
225                 230                 235                 240

Leu Ile Pro Ile Gln Val Val Arg Asp Tyr Val Asn Ala Ile Phe Ser
                245                 250                 255

Gly Asp Val Lys Arg Val Phe Thr Val Leu Asp Asp Val Tyr Tyr Ser
            260                 265                 270

Gly Lys Asp Tyr Glu Val Leu Ile Gln Glu Ala Val Glu Asp Leu Val
        275                 280                 285

Glu Asp Leu Glu Arg Glu Arg Gly Val Tyr Gln Val Ser Ala Asn Asp
    290                 295                 300

Ile Val Gln Val Ser Arg Gln Leu Leu Asn Leu Leu Arg Glu Ile Lys
305                 310                 315                 320

Phe Ala Glu Glu Lys Arg Leu Val Cys Lys Val Gly Ser Ala Tyr Ile
                325                 330                 335

Ala Thr Arg Phe Ser Thr Thr Asn Val Gln Glu Asn Asp Val Arg Glu
            340                 345                 350

Lys Asn Asp Asn Ser Asn Val Gln Gln Lys Glu Glu Lys Lys Glu Thr
        355                 360                 365

Val Lys Ala Lys Glu Glu Lys Gln Glu Asp Ser Glu Phe Glu Lys Arg
    370                 375                 380

Phe Lys Glu Leu Met Glu Glu Leu Lys Glu Lys Gly Asp Leu Ser Ile
385                 390                 395                 400

Phe Val Ala Leu Ser Leu Ser Glu Val Gln Phe Asp Gly Glu Lys Val
                405                 410                 415

Ile Ile Ser Phe Asp Ser Ser Lys Ala Met His Tyr Glu Leu Met Lys
            420                 425                 430

Lys Lys Leu Pro Glu Leu Glu Asn Ile Phe Ser Arg Lys Leu Gly Lys
        435                 440                 445

Lys Val Glu Val Glu Leu Arg Leu Met Gly Lys Glu Glu Thr Ile Glu
    450                 455                 460

Lys Val Ser Gln Lys Ile Leu Arg Leu Phe Glu Gln Glu Gly
465                 470                 475
```

<210> SEQ ID NO 143
<211> LENGTH: 1098
<212> TYPE: DNA
<213> ORGANISM: Thermatoga maritima

<400> SEQUENCE: 143

```
atgaaagtaa ccgtcacgac tcttgaattg aaagacaaaa taaccatcgc ctcaaaagcg     60

ctcgcaaaga aatccgtgaa acccattctt gctggatttc ttttcgaagt gaaagatgga    120

aatttctaca tctgcgcgac cgatctcgag accggagtca aagcaaccgt gaatgccgct    180

gaaatctccg gtgaggcacg ttttgtggta ccaggagatg tcattcagaa gatggtcaag    240
```

-continued

```
gttctcccag atgagataac ggaactttct ttagaggggg atgctcttgt tataagttct    300

ggaagcaccg ttttcaggat caccaccatg cccgcggacg aatttccaga gataacgcct    360

gccgagtctg gaataacctt cgaagttgac acttcgctcc tcgaggaaat ggttgaaaag    420

gtcatcttcg ccgctgccaa agacgagttc atgcgaaatc tgaatggagt tttctgggaa    480

ctccacaaga atcttctcag gctggttgca agtgatggtt tcagacttgc acttgctgaa    540

gagcagatag aaaacgagga agaggcgagt ttcttgctct ctttgaagag catgaaagaa    600

gttcaaaacg tgctggacaa cacaacggag ccgactataa cggtgaggta cgatggaaga    660

agggtttctc tgtcgacaaa tgatgtagaa acggtgatga gagtggtcga cgctgaattt    720

cccgattaca aaagggtgat ccccgaaact ttcaaaacga aagtggtggt ttccagaaaa    780

gaactcaggg aatctttgaa gagggtgatg gtgattgcca gcaagggaag cgagtccgtg    840

aagttcgaaa tagaagaaaa cgttatgaga cttgtgagca agagcccgga ttatggagaa    900

gtggtcgatg aagttgaagt tcaaaaagaa ggggaagatc tcgtgatcgc tttcaacccg    960

aagttcatcg aggacgtttt gaagcacatt gagactgaag aaatcgaaat gaacttcgtt   1020

gattctacca gtccatgtca gataaatcca ctcgatattt ctggatacct ttacatagtg   1080

atgcccatca gactggca                                                 1098
```

<210> SEQ ID NO 144
<211> LENGTH: 366
<212> TYPE: PRT
<213> ORGANISM: Thermatoga maritima

<400> SEQUENCE: 144

```
Met Lys Val Thr Val Thr Thr Leu Glu Leu Lys Asp Lys Ile Thr Ile
  1               5                  10                  15

Ala Ser Lys Ala Leu Ala Lys Lys Ser Val Lys Pro Ile Leu Ala Gly
             20                  25                  30

Phe Leu Phe Glu Val Lys Asp Gly Asn Phe Tyr Ile Cys Ala Thr Asp
         35                  40                  45

Leu Glu Thr Gly Val Lys Ala Thr Val Asn Ala Ala Glu Ile Ser Gly
     50                  55                  60

Glu Ala Arg Phe Val Val Pro Gly Asp Val Ile Gln Lys Met Val Lys
 65                  70                  75                  80

Val Leu Pro Asp Glu Ile Thr Glu Leu Ser Leu Glu Gly Asp Ala Leu
                 85                  90                  95

Val Ile Ser Ser Gly Ser Thr Val Phe Arg Ile Thr Thr Met Pro Ala
            100                 105                 110

Asp Glu Phe Pro Glu Ile Thr Pro Ala Glu Ser Gly Ile Thr Phe Glu
        115                 120                 125

Val Asp Thr Ser Leu Leu Glu Glu Met Val Glu Lys Val Ile Phe Ala
    130                 135                 140

Ala Ala Lys Asp Glu Phe Met Arg Asn Leu Asn Gly Val Phe Trp Glu
145                 150                 155                 160

Leu His Lys Asn Leu Leu Arg Leu Val Ala Ser Asp Gly Phe Arg Leu
                165                 170                 175

Ala Leu Ala Glu Glu Gln Ile Glu Asn Glu Glu Glu Ala Ser Phe Leu
            180                 185                 190

Leu Ser Leu Lys Ser Met Lys Glu Val Gln Asn Val Leu Asp Asn Thr
        195                 200                 205

Thr Glu Pro Thr Ile Thr Val Arg Tyr Asp Gly Arg Arg Val Ser Leu
```

-continued

```
    210                 215                 220

Ser Thr Asn Asp Val Glu Thr Val Met Arg Val Val Asp Ala Glu Phe
225                 230                 235                 240

Pro Asp Tyr Lys Arg Val Ile Pro Glu Thr Phe Lys Thr Lys Val Val
                245                 250                 255

Val Ser Arg Lys Glu Leu Arg Glu Ser Leu Lys Arg Val Met Val Ile
            260                 265                 270

Ala Ser Lys Gly Ser Glu Ser Val Lys Phe Glu Ile Glu Glu Asn Val
        275                 280                 285

Met Arg Leu Val Ser Lys Ser Pro Asp Tyr Gly Glu Val Val Asp Glu
    290                 295                 300

Val Glu Val Gln Lys Glu Gly Glu Asp Leu Val Ile Ala Phe Asn Pro
305                 310                 315                 320

Lys Phe Ile Glu Asp Val Leu Lys His Ile Glu Thr Glu Glu Ile Glu
                325                 330                 335

Met Asn Phe Val Asp Ser Thr Ser Pro Cys Gln Ile Asn Pro Leu Asp
            340                 345                 350

Ile Ser Gly Tyr Leu Tyr Ile Val Met Pro Ile Arg Leu Ala
        355                 360                 365
```

<210> SEQ ID NO 145
<211> LENGTH: 972
<212> TYPE: DNA
<213> ORGANISM: Thermatoga maritima

<400> SEQUENCE: 145

```
atgccagtca cgtttctcac aggtactgca gaaactcaga aggaagaatt gataaagaaa     60

ctcctgaagg atggtaacgt ggagtacata aggatccatc cggaggatcc cgacaagatc    120

gatttcataa ggtctttact caggacaaag acgatctttt ccaacaagac gatcattgac    180

atcgtcaatt tcgatgagtg gaaagcacag gagcagaagc gtctcgttga acttttgaaa    240

aacgtaccgg aagacgttca tatcttcatc cgttctcaaa aacaggtgg aaagggagta    300

gcgctggagc ttccgaagcc atgggaaacg gacaagtggc ttgagtggat agaaaagcgc    360

ttcagggaga atggtttgct catcgataaa gatgcccttc agctgttttt ctccaaggtt    420

ggaacgaacg acctgatcat agaaagggag attgaaaaac tgaaagctta ttccgaggac    480

agaaagataa cggtagaaga cgtggaagag gtcgttttta cctatcagac tccgggatac    540

gatgattttt gctttgctgt ttccgaagga aaaaggaagc tcgctcactc tcttctgtcg    600

cagctgtgga aaaccacaga gtccgtggtg attgccactg tccttgcgaa tcacttcttg    660

gatctcttca aaatcctcgt tcttgtgaca aagaaaagat actacacctg gcctgatgtg    720

tccagggtgt ccaaagagct gggaattccc gttcctcgtg tggctcgttt cctcggtttc    780

tcctttaaga cctggaaatt caaggtgatg aaccacctcc tctactacga tgtgaagaag    840

gttagaaaga tactgaggga tctctacgat ctggacagag ccgtgaaaag cgaagaagat    900

ccaaaaccgt tcttccacga gttcatagaa gaggtggcac tggatgtata ttctcttcag    960

agagatgaag aa                                                        972
```

<210> SEQ ID NO 146
<211> LENGTH: 324
<212> TYPE: PRT
<213> ORGANISM: Thermatoga maritima

<400> SEQUENCE: 146

-continued

```
Met Pro Val Thr Phe Leu Thr Gly Thr Ala Glu Thr Gln Lys Glu Glu
  1               5                  10                  15

Leu Ile Lys Lys Leu Leu Lys Asp Gly Asn Val Glu Tyr Ile Arg Ile
             20                  25                  30

His Pro Glu Asp Pro Asp Lys Ile Asp Phe Ile Arg Ser Leu Leu Arg
         35                  40                  45

Thr Lys Thr Ile Phe Ser Asn Lys Thr Ile Ile Asp Ile Val Asn Phe
     50                  55                  60

Asp Glu Trp Lys Ala Gln Glu Gln Lys Arg Leu Val Glu Leu Leu Lys
 65                  70                  75                  80

Asn Val Pro Glu Asp Val His Ile Phe Ile Arg Ser Gln Lys Thr Gly
                 85                  90                  95

Gly Lys Gly Val Ala Leu Glu Leu Pro Lys Pro Trp Glu Thr Asp Lys
            100                 105                 110

Trp Leu Glu Trp Ile Glu Lys Arg Phe Arg Glu Asn Gly Leu Leu Ile
        115                 120                 125

Asp Lys Asp Ala Leu Gln Leu Phe Phe Ser Lys Val Gly Thr Asn Asp
    130                 135                 140

Leu Ile Ile Glu Arg Glu Ile Glu Lys Leu Lys Ala Tyr Ser Glu Asp
145                 150                 155                 160

Arg Lys Ile Thr Val Glu Asp Val Glu Glu Val Val Phe Thr Tyr Gln
                165                 170                 175

Thr Pro Gly Tyr Asp Asp Phe Cys Phe Ala Val Ser Glu Gly Lys Arg
            180                 185                 190

Lys Leu Ala His Ser Leu Leu Ser Gln Leu Trp Lys Thr Thr Glu Ser
        195                 200                 205

Val Val Ile Ala Thr Val Leu Ala Asn His Phe Leu Asp Leu Phe Lys
    210                 215                 220

Ile Leu Val Leu Val Thr Lys Lys Arg Tyr Tyr Thr Trp Pro Asp Val
225                 230                 235                 240

Ser Arg Val Ser Lys Glu Leu Gly Ile Pro Val Pro Arg Val Ala Arg
                245                 250                 255

Phe Leu Gly Phe Ser Phe Lys Thr Trp Lys Phe Lys Val Met Asn His
            260                 265                 270

Leu Leu Tyr Tyr Asp Val Lys Lys Val Arg Lys Ile Leu Arg Asp Leu
        275                 280                 285

Tyr Asp Leu Asp Arg Ala Val Lys Ser Glu Glu Asp Pro Lys Pro Phe
    290                 295                 300

Phe His Glu Phe Ile Glu Glu Val Ala Leu Asp Val Tyr Ser Leu Gln
305                 310                 315                 320

Arg Asp Glu Glu
```

```
<210> SEQ ID NO 147
<211> LENGTH: 936
<212> TYPE: DNA
<213> ORGANISM: Thermatoga maritima

<400> SEQUENCE: 147

atgaacgatt tgatcagaaa gtacgctaaa gatcaactgg aaactttgaa aaggatcata     60

gaaaagtctg aaggaatatc catcctcata aatggagaag atctctcgta tccgagagaa    120

gtatcccttg aacttcccga gtacgtggag aaatttcccc cgaaggcctc ggatgttctg    180

gagatagatc ccgaggggga gaacataggc atagacgaca tcagaacgat aaaggacttc    240

ctgaactaca gccccgagct ctacacgaga aagtacgtga tagtccacga ctgtgaaaga    300
```

-continued

```
atgacccagc aggcggcgaa cgcgtttctg aaggcccttg aagaaccacc agaatacgct    360

gtgatcgttc tgaacactcg ccgctggcat tatctactgc cgacgataaa gagccgagtg    420

ttcagagtgg ttgtgaacgt tccaaaggag ttcagagatc tcgtgaaaga gaaaatagga    480

gatctctggg aggaacttcc acttcttgag agagacttca aaacggctct cgaagcctac    540

aaacttggtg cggaaaaact ttctggattg atggaaagtc tcaaagtttt ggagacggaa    600

aaactcttga aaaaggtcct ttcaaaaggc ctcgaaggtt atctcgcatg tagggagctc    660

ctggagagat tttcaaaggt ggaatcgaag gaattctttg cgctttttga tcaggtgact    720

aacacgataa caggaaaaga cgcgtttctt ttgatccaga gactgacaag aatcattctc    780

cacgaaaaca catgggaaag cgttgaagat caaaaaagcg tgtctttcct cgattcaatt    840

ctcagggtga agatagcgaa tctgaacaac aaactcactc tgatgaacat cctcgcgata    900

cacagagaga gaaagagagg tgtcaacgct tggagc                              936
```

<210> SEQ ID NO 148
<211> LENGTH: 311
<212> TYPE: PRT
<213> ORGANISM: Thermatoga maritima

<400> SEQUENCE: 148

```
Met Asn Asp Leu Ile Arg Lys Tyr Ala Lys Asp Gln Leu Glu Thr Leu
  1               5                  10                  15

Lys Arg Ile Ile Glu Lys Ser Glu Gly Ile Ser Ile Leu Ile Asn Gly
             20                  25                  30

Glu Asp Leu Ser Tyr Pro Arg Glu Val Ser Leu Glu Leu Pro Glu Tyr
         35                  40                  45

Val Glu Lys Phe Pro Pro Lys Ala Ser Asp Val Leu Glu Ile Asp Pro
     50                  55                  60

Glu Gly Glu Asn Ile Gly Ile Asp Asp Ile Arg Thr Ile Lys Asp Phe
 65                  70                  75                  80

Leu Asn Tyr Ser Pro Glu Leu Tyr Thr Arg Lys Tyr Val Ile Val His
                 85                  90                  95

Asp Cys Glu Arg Met Thr Gln Gln Ala Ala Asn Ala Phe Leu Lys Ala
            100                 105                 110

Leu Glu Glu Pro Pro Glu Tyr Ala Val Ile Val Leu Asn Thr Arg Arg
        115                 120                 125

Trp His Tyr Leu Leu Pro Thr Ile Lys Ser Arg Val Phe Arg Val Val
    130                 135                 140

Val Asn Val Pro Lys Glu Phe Arg Asp Leu Val Lys Glu Lys Ile Gly
145                 150                 155                 160

Asp Leu Trp Glu Glu Leu Pro Leu Leu Glu Arg Asp Phe Lys Thr Ala
                165                 170                 175

Leu Glu Ala Tyr Lys Leu Gly Ala Glu Lys Leu Ser Gly Leu Met Glu
            180                 185                 190

Ser Leu Lys Val Leu Glu Thr Glu Lys Leu Leu Lys Lys Val Leu Ser
        195                 200                 205

Lys Gly Leu Glu Gly Tyr Leu Ala Cys Arg Glu Leu Leu Glu Arg Phe
    210                 215                 220

Ser Lys Val Glu Ser Lys Glu Phe Phe Ala Leu Phe Asp Gln Val Thr
225                 230                 235                 240

Asn Thr Ile Thr Gly Lys Asp Ala Phe Leu Leu Ile Gln Arg Leu Thr
                245                 250                 255
```

-continued

```
Arg Ile Ile Leu His Glu Asn Thr Trp Glu Ser Val Glu Asp Lys Ser
            260                 265                 270

Val Ser Phe Leu Asp Ser Ile Leu Arg Val Lys Ile Ala Asn Leu Asn
        275                 280                 285

Asn Lys Leu Thr Leu Met Asn Ile Leu Ala Ile His Arg Glu Arg Lys
    290                 295                 300

Arg Gly Val Asn Ala Trp Ser
305                 310


<210> SEQ ID NO 149
<211> LENGTH: 423
<212> TYPE: DNA
<213> ORGANISM: Thermatoga maritima

<400> SEQUENCE: 149

atgtctttct tcaacaagat catactcata ggaagactcg tgagagatcc cgaagagaga      60

tacacgctca gcggaactcc agtcaccacc ttcaccatag cggtggacag ggttcccaga     120

aagaacgcgc cggacgacgc tcaaacgact gatttcttca ggatcgtcac ctttggaaga     180

ctggcagagt tcgctagaac ctatctcacc aaaggaaggc tcgttctcgt cgaaggtgaa     240

atgagaatga gaagatggga aacacccact ggagaaaaga gggtatctcc ggaggttgtc     300

gcaaacgttg ttagattcat ggacagaaaa cctgctgaaa cagttagcga gactgaagag     360

gagctggaaa taccggaaga agacttttcc agcgatacct tcagtgaaga tgaaccacca     420

ttt                                                                   423


<210> SEQ ID NO 150
<211> LENGTH: 141
<212> TYPE: PRT
<213> ORGANISM: Thermatoga maritima

<400> SEQUENCE: 150

Met Ser Phe Phe Asn Lys Ile Ile Leu Ile Gly Arg Leu Val Arg Asp
  1               5                  10                  15

Pro Glu Glu Arg Tyr Thr Leu Ser Gly Thr Pro Val Thr Thr Phe Thr
             20                  25                  30

Ile Ala Val Asp Arg Val Pro Arg Lys Asn Ala Pro Asp Asp Ala Gln
         35                  40                  45

Thr Thr Asp Phe Phe Arg Ile Val Thr Phe Gly Arg Leu Ala Glu Phe
     50                  55                  60

Ala Arg Thr Tyr Leu Thr Lys Gly Arg Leu Val Leu Val Glu Gly Glu
 65                  70                  75                  80

Met Arg Met Arg Arg Trp Glu Thr Pro Thr Gly Glu Lys Arg Val Ser
                 85                  90                  95

Pro Glu Val Val Ala Asn Val Val Arg Phe Met Asp Arg Lys Pro Ala
            100                 105                 110

Glu Thr Val Ser Glu Thr Glu Glu Glu Leu Glu Ile Pro Glu Glu Asp
        115                 120                 125

Phe Ser Ser Asp Thr Phe Ser Glu Asp Glu Pro Pro Phe
    130                 135                 140


<210> SEQ ID NO 151
<211> LENGTH: 1353
<212> TYPE: DNA
<213> ORGANISM: Thermatoga maritima

<400> SEQUENCE: 151
```

-continued

```
atgcgtgttc ccccgcacaa cttagaggcc gaagttgctg tgctcggaag catattgata     60

gatccgtcgg taataaacga cgttcttgaa attttgagcc acgaagattt ctatctgaaa    120

aaacaccaac acatcttcag agcgatggaa gagctttacg acgaaggaaa accggtggac    180

gtggtttccg tctgtgacaa gcttcaaagc atgggaaaac tcgaggaagt aggtggagat    240

ctggaagtgg cccagctcgc tgaggctgtg cccagttctg cacacgcact tcactacgcg    300

gagatcgtca aggaaaaatc cattctgagg aaactcattg agatctccag aaaaatctca    360

gaaagtgcct acatggaaga agatgtggag atcctgctcg acaacgcaga aaagatgatc    420

ttcgagatct cagagatgaa aacgacaaaa tcctacgatc atctgagagg catcatgcac    480

cgggtgtttg aaaacctgga gaacttcagg gaaagagcca accttataga acccggtgtg    540

ctcataacgg gactaccaac gggattcaaa agtctggaca aacagaccac agggttccac    600

agctccgatc tggtgataat agcagcgaga ccctccatgg gaaaaacctc cttcgcactc    660

tcaatagcga ggaacatggc tgtcaatttc gaaatccccg tcggaatatt cagtctcgag    720

atgtccaagg aacagctcgc tcaaagacta ctcagcatgg agtccggtgt ggatctttac    780

agcatcagaa caggatacct ggatcaggag aagtgggaaa gactcacaat agcggcttct    840

aaactctaca aagcacccat agttgtggac gatgagtcac tcctcgatcc gcgatcgttg    900

agggcaaaag cgagaaggat gaaaaaagaa tacgatgtaa aagccatttt tgtcgactat    960

ctccagctca tgcacctgaa aggaagaaaa gaaagcagac agcaggagat atccgagatc   1020

tcgagatctc tgaagctcct tgcgagggaa ctcgacatag tggtgatagc gctttcacag   1080

ctttcgaggg ccgtagaaca gagagaagac aaaagaccga ggctgagtga cctcagggaa   1140

tccggtgcga tagaacagga cgcagacaca gtcatcttca tctacaggga ggaatattac   1200

aggagcaaaa aatccaaaga ggaaagcaag cttcacgaac ctcacgaagc tgaaatcata   1260

ataggtaaac agagaaacgg tcccgttgga acgatcactc tgatcttcga ccccagaacg   1320

gttacgttcc atgaagtcga tgtggtgcat tca                                1353
```

<210> SEQ ID NO 152
<211> LENGTH: 451
<212> TYPE: PRT
<213> ORGANISM: Thermatoga maritima

<400> SEQUENCE: 152

```
Met Arg Val Pro Pro His Asn Leu Glu Ala Glu Val Ala Val Leu Gly
  1               5                  10                  15

Ser Ile Leu Ile Asp Pro Ser Val Ile Asn Asp Val Leu Glu Ile Leu
             20                  25                  30

Ser His Glu Asp Phe Tyr Leu Lys Lys His Gln His Ile Phe Arg Ala
         35                  40                  45

Met Glu Glu Leu Tyr Asp Glu Gly Lys Pro Val Asp Val Val Ser Val
     50                  55                  60

Cys Asp Lys Leu Gln Ser Met Gly Lys Leu Glu Glu Val Gly Gly Asp
 65                  70                  75                  80

Leu Glu Val Ala Gln Leu Ala Glu Ala Val Pro Ser Ser Ala His Ala
                 85                  90                  95

Leu His Tyr Ala Glu Ile Val Lys Glu Lys Ser Ile Leu Arg Lys Leu
            100                 105                 110

Ile Glu Ile Ser Arg Lys Ile Ser Glu Ser Ala Tyr Met Glu Glu Asp
        115                 120                 125

Val Glu Ile Leu Leu Asp Asn Ala Glu Lys Met Ile Phe Glu Ile Ser
```

-continued

```
    130                 135                 140

Glu Met Lys Thr Thr Lys Ser Tyr Asp His Leu Arg Gly Ile Met His
145                 150                 155                 160

Arg Val Phe Glu Asn Leu Glu Asn Phe Arg Glu Arg Ala Asn Leu Ile
                165                 170                 175

Glu Pro Gly Val Leu Ile Thr Gly Leu Pro Thr Gly Phe Lys Ser Leu
            180                 185                 190

Asp Lys Gln Thr Thr Gly Phe His Ser Ser Asp Leu Val Ile Ile Ala
        195                 200                 205

Ala Arg Pro Ser Met Gly Lys Thr Ser Phe Ala Leu Ser Ile Ala Arg
    210                 215                 220

Asn Met Ala Val Asn Phe Glu Ile Pro Val Gly Ile Phe Ser Leu Glu
225                 230                 235                 240

Met Ser Lys Glu Gln Leu Ala Gln Arg Leu Leu Ser Met Glu Ser Gly
                245                 250                 255

Val Asp Leu Tyr Ser Ile Arg Thr Gly Tyr Leu Asp Gln Glu Lys Trp
            260                 265                 270

Glu Arg Leu Thr Ile Ala Ala Ser Lys Leu Tyr Lys Ala Pro Ile Val
        275                 280                 285

Val Asp Asp Glu Ser Leu Leu Asp Pro Arg Ser Leu Arg Ala Lys Ala
    290                 295                 300

Arg Arg Met Lys Lys Glu Tyr Asp Val Lys Ala Ile Phe Val Asp Tyr
305                 310                 315                 320

Leu Gln Leu Met His Leu Lys Gly Arg Lys Glu Ser Arg Gln Gln Glu
                325                 330                 335

Ile Ser Glu Ile Ser Arg Ser Leu Lys Leu Leu Ala Arg Glu Leu Asp
            340                 345                 350

Ile Val Val Ile Ala Leu Ser Gln Leu Ser Arg Ala Val Glu Gln Arg
        355                 360                 365

Glu Asp Lys Arg Pro Arg Leu Ser Asp Leu Arg Glu Ser Gly Ala Ile
    370                 375                 380

Glu Gln Asp Ala Asp Thr Val Ile Phe Ile Tyr Arg Glu Glu Tyr Tyr
385                 390                 395                 400

Arg Ser Lys Lys Ser Lys Glu Glu Ser Lys Leu His Glu Pro His Glu
                405                 410                 415

Ala Glu Ile Ile Ile Gly Lys Gln Arg Asn Gly Pro Val Gly Thr Ile
            420                 425                 430

Thr Leu Ile Phe Asp Pro Arg Thr Val Thr Phe His Glu Val Asp Val
        435                 440                 445

Val His Ser
    450
```

<210> SEQ ID NO 153
<211> LENGTH: 1695
<212> TYPE: DNA
<213> ORGANISM: Thermatoga maritima

<400> SEQUENCE: 153

```
gtgattcctc gagaggtcat cgaggaaata aaagaaaagg ttgacatcgt agaggtcatt      60

tccgagtacg tgaatcttac ccgggtaggt tcctcctaca gggctctctg tccctttcat     120

tcagaaacca atccttcttt ctacgttcat ccgggtttga agatatacca ttgtttcggc     180

tgcggtgcga gtggagacgt catcaaattt cttcaagaaa tggaagggat cagtttccag     240

gaagcgctgg aaagacttgc caaaagagct gggattgatc tttctctcta cagaacagaa     300
```

-continued

```
gggacttctg aatacggaaa atacattcgt ttgtacgaag aaacgtggaa aaggtacgtc    360
aaagagctgg agaaatcgaa agaggcaaaa gactatttaa aaagcagagg cttctctgaa    420
gaagatatag caaagttcgg ctttgggtac gtccccaaga gatccagcat ctctatagaa    480
gttgcagaag gcatgaacat aacactggaa gaacttgtca gatacggtat cgcgctgaaa    540
aagggtgatc gattcgttga tagattcgaa ggaagaatcg ttgttccaat aaagaacgac    600
agtggtcata ttgtggcttt tggtgggcgt gctctcggca acgaagaacc gaagtatttg    660
aactctccag agaccaggta tttttcgaag aagaagaccc tttttctctt cgatgaggcg    720
aaaaaagtgg caaaagaggt tggttttttc gtcatcaccg aaggctactt cgacgcgctc    780
gcattcagaa aggatggaat accaacggcg gtcgctgttc ttggggcgag tctttcaaga    840
gaggcgattc taaaactttc ggcgtattcg aaaaacgtca tactgtgttt cgataatgac    900
aaagcaggct tcagagccac tctcaaatcc ctcgaggatc tcctagacta cgaattcaac    960
gtgcttgtgg caacccccctc tccttacaaa gacccagatg aactctttca gaaagaagga   1020
gaaggttcat tgaaaaagat gctgaaaaac tcgcgttcgt tcgaatattt tctggtgacg   1080
gctggtgagg tcttctttga caggaacagc cccgcgggtg tgagatccta cctttctttc   1140
ctcaaaggtt gggtccaaaa gatgagaagg aaaggatatt tgaaacacat agaaaatctc   1200
gtgaatgagg tttcatcttc tctccagata ccagaaaacc agattttgaa ctttttttgaa   1260
agcgacaggt ctaacactat gcctgttcat gagaccaagt cgtcaaaggt ttacgatgag   1320
gggagaggac tggcttattt gtttttgaac tacgaggatt tgagggaaaa gattctggaa   1380
ctggacttag aggtactgga agataaaaac gcgagggagt ttttcaagag agtctcactg   1440
ggagaagatt tgaacaaagt catagaaaac ttcccaaaag agctgaaaga ctggattttt   1500
gagacaatag aaagcattcc tcctccaaag gatcccgaga aattcctcgg tgacctctcc   1560
gaaaagttga aaatccgacg gatagagaga cgtatcgcag aaatagatga tatgataaag   1620
aaagcttcaa acgatgaaga aaggcgtctt cttctctcta tgaaagtgga tctcctcaga   1680
aaaataaaga ggagg                                                     1695
```

<210> SEQ ID NO 154
<211> LENGTH: 565
<212> TYPE: PRT
<213> ORGANISM: Thermatoga maritima

<400> SEQUENCE: 154

```
Met Ile Pro Arg Glu Val Ile Glu Glu Ile Lys Glu Lys Val Asp Ile
  1               5                  10                  15

Val Glu Val Ile Ser Glu Tyr Val Asn Leu Thr Arg Val Gly Ser Ser
             20                  25                  30

Tyr Arg Ala Leu Cys Pro Phe His Ser Glu Thr Asn Pro Ser Phe Tyr
         35                  40                  45

Val His Pro Gly Leu Lys Ile Tyr His Cys Phe Gly Cys Gly Ala Ser
     50                  55                  60

Gly Asp Val Ile Lys Phe Leu Gln Glu Met Glu Gly Ile Ser Phe Gln
 65                  70                  75                  80

Glu Ala Leu Glu Arg Leu Ala Lys Arg Ala Gly Ile Asp Leu Ser Leu
                 85                  90                  95

Tyr Arg Thr Glu Gly Thr Ser Glu Tyr Gly Lys Tyr Ile Arg Leu Tyr
            100                 105                 110

Glu Glu Thr Trp Lys Arg Tyr Val Lys Glu Leu Glu Lys Ser Lys Glu
```

-continued

```
        115                 120                 125

Ala Lys Asp Tyr Leu Lys Ser Arg Gly Phe Ser Glu Glu Asp Ile Ala
    130                 135                 140

Lys Phe Gly Phe Gly Tyr Val Pro Lys Arg Ser Ser Ile Ser Ile Glu
145                 150                 155                 160

Val Ala Glu Gly Met Asn Ile Thr Leu Glu Glu Leu Val Arg Tyr Gly
                165                 170                 175

Ile Ala Leu Lys Lys Gly Asp Arg Phe Val Asp Arg Phe Glu Gly Arg
            180                 185                 190

Ile Val Val Pro Ile Lys Asn Asp Ser Gly His Ile Val Ala Phe Gly
        195                 200                 205

Gly Arg Ala Leu Gly Asn Glu Glu Pro Lys Tyr Leu Asn Ser Pro Glu
    210                 215                 220

Thr Arg Tyr Phe Ser Lys Lys Lys Thr Leu Phe Leu Phe Asp Glu Ala
225                 230                 235                 240

Lys Lys Val Ala Lys Glu Val Gly Phe Phe Val Ile Thr Glu Gly Tyr
                245                 250                 255

Phe Asp Ala Leu Ala Phe Arg Lys Asp Gly Ile Pro Thr Ala Val Ala
            260                 265                 270

Val Leu Gly Ala Ser Leu Ser Arg Glu Ala Ile Leu Lys Leu Ser Ala
        275                 280                 285

Tyr Ser Lys Asn Val Ile Leu Cys Phe Asp Asn Asp Lys Ala Gly Phe
    290                 295                 300

Arg Ala Thr Leu Lys Ser Leu Glu Asp Leu Leu Asp Tyr Glu Phe Asn
305                 310                 315                 320

Val Leu Val Ala Thr Pro Ser Pro Tyr Lys Asp Pro Asp Glu Leu Phe
                325                 330                 335

Gln Lys Glu Gly Glu Gly Ser Leu Lys Lys Met Leu Lys Asn Ser Arg
            340                 345                 350

Ser Phe Glu Tyr Phe Leu Val Thr Ala Gly Glu Val Phe Phe Asp Arg
        355                 360                 365

Asn Ser Pro Ala Gly Val Arg Ser Tyr Leu Ser Phe Leu Lys Gly Trp
    370                 375                 380

Val Gln Lys Met Arg Arg Lys Gly Tyr Leu Lys His Ile Glu Asn Leu
385                 390                 395                 400

Val Asn Glu Val Ser Ser Ser Leu Gln Ile Pro Glu Asn Gln Ile Leu
                405                 410                 415

Asn Phe Phe Glu Ser Asp Arg Ser Asn Thr Met Pro Val His Glu Thr
            420                 425                 430

Lys Ser Ser Lys Val Tyr Asp Glu Gly Arg Gly Leu Ala Tyr Leu Phe
        435                 440                 445

Leu Asn Tyr Glu Asp Leu Arg Glu Lys Ile Leu Glu Leu Asp Leu Glu
    450                 455                 460

Val Leu Glu Asp Lys Asn Ala Arg Glu Phe Phe Lys Arg Val Ser Leu
465                 470                 475                 480

Gly Glu Asp Leu Asn Lys Val Ile Glu Asn Phe Pro Lys Glu Leu Lys
                485                 490                 495

Asp Trp Ile Phe Glu Thr Ile Glu Ser Ile Pro Pro Pro Lys Asp Pro
            500                 505                 510

Glu Lys Phe Leu Gly Asp Leu Ser Glu Lys Leu Lys Ile Arg Arg Ile
        515                 520                 525

Glu Arg Arg Ile Ala Glu Ile Asp Asp Met Ile Lys Lys Ala Ser Asn
    530                 535                 540
```

-continued

```
Asp Glu Glu Arg Arg Leu Leu Leu Ser Met Lys Val Asp Leu Leu Arg
545                 550                 555                 560

Lys Ile Lys Arg Arg
                565
```

<210> SEQ ID NO 155
<211> LENGTH: 804
<212> TYPE: DNA
<213> ORGANISM: Thermus thermophilus

<400> SEQUENCE: 155

```
atggctctac acccggctca ccctggggca ataatcgggc acgaggccgt tctcgccctc      60

cttccccgcc tcaccgccca gaccctgctc ttctccggcc ccgagggggt ggggcggcgc     120

accgtggccc gctggtacgc ctgggggctc aaccgcggct tccccccgcc ctccctgggg     180

gagcacccgg acgtcctcga ggtggggccc aaggcccggg acctccgggg ccgggccgag     240

gtgcggctgg aggaggtggc gcccctcttg gagtggtgct ccagccaccc ccgggagcgg     300

gtgaaggtgg ccatcctgga ctcggcccac ctcctcaccg aggccgccgc caacgccctc     360

ctcaagctcc tggaggagcc cccttcctac gcccgcatcg tcctcatcgc cccaagccgc     420

gccaccctcc tccccaccct ggcctcccgg gccacggagg tggcattcgc ccccgtgccc     480

gaggaggccc tgcgcgccct cacccaggac ccggagctcc tccgctacgc cgccggggcc     540

ccgggccgcc tccttagggc cctccaggac ccggaggggt accgggcccg catggccagg     600

gcgcaaaggg tcctgaaagc ccgcccctg gagcgcctcg ctttgcttcg ggagcttttg     660

gccgaggagg agggggtcca cgccctccac gccgtcctaa agcgcccgga gcacctcctt     720

gccctggagc gggcgcggga ggccctggag gggtacgtga gccccgagct ggtcctcgcc     780

cggctggcct tagacttaga gaca                                            804
```

<210> SEQ ID NO 156
<211> LENGTH: 268
<212> TYPE: PRT
<213> ORGANISM: Thermus thermophilus

<400> SEQUENCE: 156

```
Met Ala Leu His Pro Ala His Pro Gly Ala Ile Ile Gly His Glu Ala
  1               5                  10                  15

Val Leu Ala Leu Leu Pro Arg Leu Thr Ala Gln Thr Leu Leu Phe Ser
             20                  25                  30

Gly Pro Glu Gly Val Gly Arg Arg Thr Val Ala Arg Trp Tyr Ala Trp
         35                  40                  45

Gly Leu Asn Arg Gly Phe Pro Pro Pro Ser Leu Gly Glu His Pro Asp
     50                  55                  60

Val Leu Glu Val Gly Pro Lys Ala Arg Asp Leu Arg Gly Arg Ala Glu
 65                  70                  75                  80

Val Arg Leu Glu Glu Val Ala Pro Leu Leu Glu Trp Cys Ser Ser His
                 85                  90                  95

Pro Arg Glu Arg Val Lys Val Ala Ile Leu Asp Ser Ala His Leu Leu
            100                 105                 110

Thr Glu Ala Ala Ala Asn Ala Leu Leu Lys Leu Leu Glu Glu Pro Pro
        115                 120                 125

Ser Tyr Ala Arg Ile Val Leu Ile Ala Pro Ser Arg Ala Thr Leu Leu
    130                 135                 140

Pro Thr Leu Ala Ser Arg Ala Thr Glu Val Ala Phe Ala Pro Val Pro
```

-continued

```
145                 150                 155                 160

Glu Glu Ala Leu Arg Ala Leu Thr Gln Asp Pro Glu Leu Leu Arg Tyr
                165                 170                 175

Ala Ala Gly Ala Pro Gly Arg Leu Leu Arg Ala Leu Gln Asp Pro Glu
            180                 185                 190

Gly Tyr Arg Ala Arg Met Ala Arg Ala Gln Arg Val Leu Lys Ala Pro
        195                 200                 205

Pro Leu Glu Arg Leu Ala Leu Leu Arg Glu Leu Leu Ala Glu Glu Glu
    210                 215                 220

Gly Val His Ala Leu His Ala Val Leu Lys Arg Pro Glu His Leu Leu
225                 230                 235                 240

Ala Leu Glu Arg Ala Arg Glu Ala Leu Glu Gly Tyr Val Ser Pro Glu
                245                 250                 255

Leu Val Leu Ala Arg Leu Ala Leu Asp Leu Glu Thr
            260                 265
```

<210> SEQ ID NO 157
<211> LENGTH: 729
<212> TYPE: DNA
<213> ORGANISM: Thermus thermophilus

<400> SEQUENCE: 157

```
atgctggacc tgagggaggt gggggaggcg gagtggaagg ccctaaagcc ccttttggaa     60

agcgtgcccg agggcgtccc cgtcctcctc ctggacccta agccaagccc ctcccgggcg    120

gccttctacc ggaaccggga aaggcgggac ttccccaccc ccaaggggaa ggacctggtg    180

cggcacctgg aaaaccgggc caagcgcctg ggctcaggc  tcccgggcgg ggtggcccag    240

tacctggcct ccctggaggg ggacctcgag gccctggagc gggagctgga gaagcttgcc    300

ctcctctccc cacccctcac cctggagaag gtggagaagg tggtggccct gaggcccccc    360

ctcacgggct ttgacctggt gcgctccgtc ctggagaagg accccaagga ggccctcctg    420

cgcctaggcg gcctcaagga ggagggggag gagcccctca ggctcctcgg ggccctctcc    480

tggcagttcg ccctcctcgc ccgggccttc ttcctcctcc gggaaaaccc caggcccaag    540

gaggaggacc tcgcccgcct cgaggcccac ccctacgccg cccgccgcgc cctggaggcg    600

gcgaagcgcc tcacggaaga ggccctcaag gaggccctgg acgccctcat ggaggcggaa    660

aagagggcca agggggggaa agacccgtgg ctcgccctgg aggcggcggt cctccgcctc    720

gcccgttga                                                            729
```

<210> SEQ ID NO 158
<211> LENGTH: 292
<212> TYPE: PRT
<213> ORGANISM: Thermus thermophilus

<400> SEQUENCE: 158

```
Met Val Ile Ala Phe Thr Gly Asp Pro Phe Leu Ala Arg Glu Ala Leu
  1               5                  10                  15

Leu Glu Glu Ala Arg Leu Arg Gly Leu Ser Arg Phe Thr Glu Pro Thr
            20                  25                  30

Pro Glu Ala Leu Ala Gln Ala Leu Ala Pro Gly Leu Phe Gly Gly Gly
        35                  40                  45

Gly Ala Met Leu Asp Leu Arg Glu Val Gly Glu Ala Glu Trp Lys Ala
     50                  55                  60

Leu Lys Pro Leu Leu Glu Ser Val Pro Glu Gly Val Pro Val Leu Leu
 65                  70                  75                  80
```

-continued

```
Leu Asp Pro Lys Pro Ser Pro Ser Arg Ala Ala Phe Tyr Arg Asn Arg
                85                  90                  95

Glu Arg Arg Asp Phe Pro Thr Pro Lys Gly Lys Asp Leu Val Arg His
            100                 105                 110

Leu Glu Asn Arg Ala Lys Arg Leu Gly Leu Arg Leu Pro Gly Gly Val
        115                 120                 125

Ala Gln Tyr Leu Ala Ser Leu Glu Gly Asp Leu Glu Ala Leu Glu Arg
    130                 135                 140

Glu Leu Glu Lys Leu Ala Leu Leu Ser Pro Pro Leu Thr Leu Glu Lys
145                 150                 155                 160

Val Glu Lys Val Val Ala Leu Arg Pro Pro Leu Thr Gly Phe Asp Leu
                165                 170                 175

Val Arg Ser Val Leu Glu Lys Asp Pro Lys Glu Ala Leu Leu Arg Leu
            180                 185                 190

Gly Gly Leu Lys Glu Glu Gly Glu Glu Pro Leu Arg Leu Leu Gly Ala
        195                 200                 205

Leu Ser Trp Gln Phe Ala Leu Leu Ala Arg Ala Phe Phe Leu Leu Arg
    210                 215                 220

Glu Asn Pro Arg Pro Lys Glu Glu Asp Leu Ala Arg Leu Glu Ala His
225                 230                 235                 240

Pro Tyr Ala Ala Arg Arg Ala Leu Glu Ala Ala Lys Arg Leu Thr Glu
                245                 250                 255

Glu Ala Leu Lys Glu Ala Leu Asp Ala Leu Met Glu Ala Glu Lys Arg
            260                 265                 270

Ala Lys Gly Gly Lys Asp Pro Trp Leu Ala Leu Glu Ala Ala Val Leu
        275                 280                 285

Arg Leu Ala Arg
    290
```

<210> SEQ ID NO 159
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 159
gtgtgtcata tgagtaagga tttcgtccac cttcacc 37

<210> SEQ ID NO 160
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 160
gtgtgtggat ccggggacta ctcggaagta aggg 34

<210> SEQ ID NO 161
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 161
gtgtgtcata tggaaaccac aatattccag ttccag 36

<210> SEQ ID NO 162
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 162
gtgtgtggat ccttatccac catgagaagt atttttcac 39

<210> SEQ ID NO 163
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 163
gtgtgtcata tggaaaaagt ttttttgga aaaaactcca g 41

<210> SEQ ID NO 164
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 164
gtgtgtggat ccttaatccg cctgaacggc taacg 35

<210> SEQ ID NO 165
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 165
gtgtgtcata tgaactacgt tcccttcgcg agaaagtaca g 41

<210> SEQ ID NO 166
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 166
gtgtgtggat ccttaaaaca gcctcgtccc gctgga 36

<210> SEQ ID NO 167
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 167
gtgtgtcata tgcgcgttaa ggtggacagg gag 33

<210> SEQ ID NO 168
<211> LENGTH: 35
<212> TYPE: DNA
<213> ORGANISM: Artificial Sequence
<220> FEATURE:
<223> OTHER INFORMATION: Description of Artificial Sequence: primer -continued

<400> SEQUENCE: 168
tgtgtctcga gtcatggcta caccctcatc ggcat 35

<210> SEQ ID NO 169
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 169
gtgtgtcata tgctcaataa ggtttttata ataggaagac ttacggg 47

<210> SEQ ID NO 170
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 170
gtgtggatcc ttaaaaaggt atttcgtcct cttcatcgg 39

<210> SEQ ID NO 171
<211> LENGTH: 807
<212> TYPE: DNA
<213> ORGANISM: Thermus thermophilus

<400> SEQUENCE: 171
atggctcgag gcctgaaccg cgttttcctc atcggcgccc tcgccacccg gccggacatg 60
cgctacaccc cggcggggct cgccattttg gacctgaccc tcgccggtca ggacctgctt 120
ctttccgata acgggggga accggaggtg tcctggtacc accgggtgag gctcttaggc 180
cgccaggcgg agatgtgggg cgacctcttg gaccaagggc agctcgtctt cgtggagggc 240
cgcctggagt accgccagtg ggaaagggag ggggagaagc ggagcgagct ccagatccgg 300
gccgacttcc ggaccccctg gacgaccggg ggaagaagcg ggcggaggac agccggggcc 360
agcccaggct ccgcgccgcc ctgaaccagg tcttcctcat gggcaacctg acccgggacc 420
cggaactccg ctacaccccc cagggcaccg cggtggcccg gctgggcctg gcggtgaacg 480
agcgccgcca gggggcggag gagcgcaccc acttcgtgga ggttcaggcc tggcgcgacc 540
tggcggagtg ggccgccgag ctgaggaagg gcgacggcct tttcgtgatc ggcaggttgg 600
tgaacgactc ctggaccagc tccagcggcg agcggcgctt ccagacccgt gtggaggccc 660
tcaggctgga gcgccccacc cgtggacctg cccaggcctg cccaggccgg cggaacaggt 720
cccgcgaagt ccagacgggt ggggtggaca ttgacgaagg cttggaagac tttccgccgg 780
aggaggattt gccgttttga gcacgaa 807

<210> SEQ ID NO 172
<211> LENGTH: 266
<212> TYPE: PRT
<213> ORGANISM: Thermus thermophilus

<400> SEQUENCE: 172

Met Ala Arg Gly Leu Asn Arg Val Phe Leu Ile Gly Ala Leu Ala Thr
1 5 10 15

Arg Pro Asp Met Arg Tyr Thr Pro Ala Gly Leu Ala Ile Leu Asp Leu
20 25 30

-continued

```
Thr Leu Ala Gly Gln Asp Leu Leu Leu Ser Asp Asn Gly Gly Glu Pro
        35                  40                  45

Glu Val Ser Trp Tyr His Arg Val Arg Leu Leu Gly Arg Gln Ala Glu
    50                  55                  60

Met Trp Gly Asp Leu Leu Asp Gln Gly Gln Leu Val Phe Val Glu Gly
65                  70                  75                  80

Arg Leu Glu Tyr Arg Gln Trp Glu Arg Glu Gly Glu Lys Arg Ser Glu
                85                  90                  95

Leu Gln Ile Arg Ala Asp Phe Leu Asp Pro Leu Asp Asp Arg Gly Lys
            100                 105                 110

Lys Arg Ala Glu Asp Ser Arg Gly Gln Pro Arg Leu Arg Ala Ala Leu
        115                 120                 125

Asn Gln Val Phe Leu Met Gly Asn Leu Thr Arg Asp Pro Glu Leu Arg
    130                 135                 140

Tyr Thr Pro Gln Gly Thr Ala Val Ala Arg Leu Gly Leu Ala Val Asn
145                 150                 155                 160

Glu Arg Arg Gln Gly Ala Glu Glu Arg Thr His Phe Val Glu Val Gln
                165                 170                 175

Ala Trp Arg Asp Leu Ala Glu Trp Ala Ala Glu Leu Arg Lys Gly Asp
            180                 185                 190

Gly Leu Phe Val Ile Gly Arg Leu Val Asn Asp Ser Trp Thr Ser Ser
        195                 200                 205

Ser Gly Glu Arg Arg Phe Gln Thr Arg Val Glu Ala Leu Arg Leu Glu
    210                 215                 220

Arg Pro Thr Arg Gly Pro Ala Gln Ala Cys Pro Gly Arg Arg Asn Arg
225                 230                 235                 240

Ser Arg Glu Val Gln Thr Gly Gly Val Asp Ile Asp Glu Gly Leu Glu
                245                 250                 255

Asp Phe Pro Pro Glu Glu Asp Leu Pro Phe
            260                 265
```

<210> SEQ ID NO 173
<211> LENGTH: 992
<212> TYPE: DNA
<213> ORGANISM: Bacillus stearothermophilus

<400> SEQUENCE: 173

```
aattccgaca tttcaattga atcgtttatt ccgcttgaaa aagaaggcaa gttgctcgtt      60

gatgtgaaaa gaccggggag catcgtactg caggcgcgct tttctctga aatcgtgaaa      120

aaactgccgc aacaaacggt ggaaatcgaa acggaagaca actttttgac gatcatccgc     180

tcggggcact cagaattccg cctcaatggg ctaaacgccg acgaatatcc gcgcctgccg     240

caaattgaag aagaaaacgt gtttcaaatc ccggctgatt tattgaaaac cgtgattcgg     300

caaacggtgt tcgccgtttc tacatcggaa acgcgcccaa tcttgacagg tgtcaactgg     360

aaagttgaac atggcgagct tgtctgcaca gcgaccgaca gtcatcgctt agccatgcgc     420

aaagtgaaaa ttgagtcgga aaatgaagta tcatacaacg tcgtcatccc tggaaaaagt     480

cttaatgagc tcagcaaaat tttggatgac ggcaaccacc cggtggacat cgtcatgaca     540

gccaatcaag tgctatttaa ggccgagcac cttctcttct tttcccggct gcttgacggc     600

aactatccgg agacggcccg cttgattcca acagaaagca aaacgaccat gatcgtcaat     660

gcaaaagagt ttctgcaggc aatcgaccga gcgtccttgc ttgctcgaga aggaaggaac     720

aacgttgtga aactgacgac gcttcctgga ggaatgctcg aaatttcttc gatttctccg     780
```

-continued

```
agatcgggaa agtgacggag cagctgcaaa cggagtctct tgaaggggaa gagttgaaca    840

tttcgttcag cgcgaaatat atgatggacg cgttgcgggc gcttgatgga acagacattt    900

caaatcagct tcactggggc catgcggccg ttcctgttgc gcccgcttca accgattcga    960

tgcttcagct cattttgccg gtgagaacat at                                   992
```

<210> SEQ ID NO 174
<211> LENGTH: 334
<212> TYPE: PRT
<213> ORGANISM: Bacillus stearothermophilus

<400> SEQUENCE: 174

```
Asn Ser Asp Ile Ser Ile Ile Glu Ser Phe Ile Pro Leu Glu Lys Glu
  1               5                  10                  15

Gly Lys Leu Leu Val Asp Val Lys Arg Pro Gly Ser Ile Val Leu Gln
             20                  25                  30

Ala Arg Phe Phe Ser Glu Ile Val Lys Lys Leu Pro Gln Gln Thr Val
         35                  40                  45

Glu Ile Glu Thr Glu Asp Asn Phe Leu Thr Ile Ile Arg Ser Gly His
     50                  55                  60

Ser Glu Phe Arg Leu Asn Gly Leu Asn Ala Asp Glu Tyr Pro Arg Leu
 65                  70                  75                  80

Pro Gln Ile Glu Glu Glu Asn Val Phe Gln Ile Pro Ala Asp Leu Leu
                 85                  90                  95

Lys Thr Val Ile Arg Gln Thr Val Phe Ala Val Ser Thr Ser Glu Thr
            100                 105                 110

Arg Pro Ile Leu Thr Gly Val Asn Trp Lys Val Glu His Gly Glu Leu
        115                 120                 125

Val Cys Thr Ala Thr Asp Ser His Arg Leu Ala Met Arg Lys Val Lys
    130                 135                 140

Ile Ile Glu Ser Glu Asn Glu Val Ser Tyr Asn Val Val Ile Pro Gly
145                 150                 155                 160

Lys Ser Leu Asn Glu Leu Ser Lys Ile Ile Leu Asp Asp Gly Asn His
                165                 170                 175

Pro Val Asp Ile Val Met Thr Ala Asn Gln Val Leu Phe Lys Ala Glu
            180                 185                 190

His Leu Leu Phe Phe Ser Arg Leu Leu Asp Gly Asn Tyr Pro Glu Thr
        195                 200                 205

Ala Arg Leu Ile Pro Thr Glu Ser Lys Thr Thr Met Ile Val Asn Ala
    210                 215                 220

Lys Glu Phe Leu Gln Ala Ile Asp Arg Ala Ser Leu Leu Ala Arg Glu
225                 230                 235                 240

Gly Arg Asn Asn Val Val Lys Leu Thr Thr Leu Pro Gly Gly Met Leu
                245                 250                 255

Glu Ile Ser Ser Ile Ser Pro Glu Ile Gly Lys Val Thr Glu Gln Leu
            260                 265                 270

Gln Thr Glu Ser Leu Glu Gly Glu Glu Leu Asn Ile Ser Phe Ser Ala
        275                 280                 285

Lys Tyr Met Met Asp Ala Leu Arg Ala Leu Asp Gly Thr Asp Ile Gln
    290                 295                 300

Ile Ser Phe Thr Gly Ala Met Arg Pro Phe Leu Leu Arg Pro Leu His
305                 310                 315                 320

Thr Asp Ser Met Leu Gln Leu Ile Leu Pro Val Arg Thr Tyr
                325                 330
```

<210> SEQ ID NO 175
<211> LENGTH: 492
<212> TYPE: DNA
<213> ORGANISM: Bacillus stearothermophilus

<400> SEQUENCE: 175

| | | | | | |
|---|---|---|---|---|---|
| atgattaacc | gcgtcatttt | ggtcggcagg | ttaacgagag | atccggagtt | gcgttacact | 60 |
| ccaagcggag | tggctgttgc | cacgtttacg | ctcgcggtca | accgtccgtt | tacaaatcag | 120 |
| cagggcgagc | gggaaacgga | ttttattcaa | tgtgtcgttt | ggcgccgcca | ggcggaaaac | 180 |
| gtcgccaact | ttttgaaaaa | ggggagcttg | gctggtgtcg | atggccgact | gcaaacccgc | 240 |
| agctatgaaa | atcaagaagg | tcggcgtgtg | tacgtgacgg | aagtggtggc | tgatagcgtc | 300 |
| caatttcttg | agccgaaagg | aacgagcgag | cagcgagggg | cgacagcagg | cggctactat | 360 |
| ggggatccat | tcccattcgg | gcaagatcag | aaccaccaat | atccgaacga | aaaagggttt | 420 |
| ggccgcatcg | atgacgatcc | tttcgccaat | gacggccagc | cgatcgatat | ttctgatgat | 480 |
| gatttgccgt | tt | | | | | 492 |

<210> SEQ ID NO 176
<211> LENGTH: 164
<212> TYPE: PRT
<213> ORGANISM: Bacillus stearothermophilus

<400> SEQUENCE: 176

Met Ile Asn Arg Val Ile Leu Val Gly Arg Leu Thr Arg Asp Pro Glu
1               5                  10                  15

Leu Arg Tyr Thr Pro Ser Gly Val Ala Val Ala Thr Phe Thr Leu Ala
            20                  25                  30

Val Asn Arg Pro Phe Thr Asn Gln Ser Tyr Glu Asn Gln Glu Gly Arg
        35                  40                  45

Arg Val Tyr Val Thr Glu Val Val Ala Asp Ser Val Gln Phe Leu Glu
    50                  55                  60

Pro Lys Gly Thr Ser Glu Gln Arg Gly Ala Thr Ala Gly Gly Tyr Tyr
65                  70                  75                  80

Gln Gly Glu Arg Glu Thr Asp Phe Ile Gln Cys Val Val Trp Arg Arg
                85                  90                  95

Gln Ala Glu Asn Val Ala Asn Phe Leu Lys Lys Gly Ser Leu Ala Gly
            100                 105                 110

Val Asp Gly Arg Leu Gln Thr Arg Gly Asp Pro Phe Pro Phe Gly Gln
        115                 120                 125

Asp Gln Asn His Gln Tyr Pro Asn Glu Lys Gly Phe Gly Arg Ile Asp
    130                 135                 140

Asp Asp Pro Phe Ala Asn Asp Gly Gln Pro Ile Asp Ile Ser Asp Asp
145                 150                 155                 160

Asp Leu Pro Phe

<210> SEQ ID NO 177
<211> LENGTH: 1044
<212> TYPE: DNA
<213> ORGANISM: Bacillus stearothermophilus

<400> SEQUENCE: 177

| | | | | | |
|---|---|---|---|---|---|
| atgctggaac | gcgtatgggg | aaacattgaa | aaacggcgtt | tttctcccct | ttatttatta | 60 |
| tacggcaatg | agccgttttt | attaacggaa | acgtatgagc | gattggtgaa | cgcagcgctt | 120 |
| ggccccgagg | agcgggagtg | gaacttggct | gtgtacgact | gcgaggaaac | gccgatcgag | 180 |

-continued

```
gcggcgcttg aggaggccga gacggtgccg tttttcggcg agcggcgtgt cattctcatc    240

aagcatccat attttttac gtctgaaaaa gagaaggaga tcgaacatga tttggcgaag    300

ctggaggcgt acttgaaggc gccgtcgccg ttttcgatcg tcgtcttttt cgcgccgtac    360

gagaagcttg atgagcgaaa aaaaattacg aagctcgcca aagagcaaag cgaagtcgtc    420

atcgccgccc cgctcgccga agcggagctg cgtgcctggg tgcggcgccg catcgagagc    480

caaggggcgc aagcaagcga cgaggcgatt gatgtcctgt tgcggcgggc cgggacgcag    540

ctttccgcct tggcgaatga aatcgataaa ttggccctgt ttgccggatc gggcggaacc    600

atcgaggcgg cggcggttga gcggcttgtc gcccgcacgc cggaagaaaa cgtatttgtg    660

cttgtcgagc aagtggcgaa gcgcgacatt ccagcagcgt tgcagacgtt ttatgatctg    720

cttgaaaaca atgaagagcc gatcaaaatt ttggcgttgc tcgccgccca tttccgcttg    780

ctttcgcaag tgaaatggct tgcctcctta ggctacggac aggcgcaaat tgctgcggcg    840

ctcaaggtgc acccgttccg cgtcaagctc gctcttgctc aagcggcccg cttcgctgac    900

ggagagcttg ctgaggcgat caacgagctc gctgacgccg attacgaagt gaaaagcggg    960

gcggtcgatc gccggttggc cgttgagctg cttctgatgc gctggggcgc ccgcccggcg   1020

caagcggggc gccacggccg gcgg                                          1044
```

```
<210> SEQ ID NO 178
<211> LENGTH: 348
<212> TYPE: PRT
<213> ORGANISM: Bacillus stearothermophilus

<400> SEQUENCE: 178

Met Leu Glu Arg Val Trp Gly Asn Ile Glu Lys Arg Arg Phe Ser Pro
  1               5                  10                  15

Leu Tyr Leu Leu Tyr Gly Asn Glu Pro Phe Leu Leu Thr Glu Thr Tyr
             20                  25                  30

Glu Arg Leu Val Asn Ala Ala Leu Gly Pro Glu Glu Arg Glu Trp Asn
         35                  40                  45

Leu Ala Val Tyr Asp Cys Glu Glu Thr Pro Ile Glu Ala Ala Leu Glu
     50                  55                  60

Glu Ala Glu Thr Val Pro Phe Phe Gly Glu Arg Arg Val Ile Leu Ile
 65                  70                  75                  80

Lys His Pro Tyr Phe Phe Thr Ser Glu Lys Glu Lys Glu Ile Glu His
                 85                  90                  95

Asp Leu Ala Lys Leu Glu Ala Tyr Leu Lys Ala Pro Ser Pro Phe Ser
            100                 105                 110

Ile Val Val Phe Phe Ala Pro Tyr Glu Lys Leu Asp Glu Arg Lys Lys
        115                 120                 125

Ile Thr Lys Leu Ala Lys Glu Gln Ser Glu Val Val Ile Ala Ala Pro
    130                 135                 140

Leu Ala Glu Ala Glu Leu Arg Ala Trp Val Arg Arg Arg Ile Glu Ser
145                 150                 155                 160

Gln Gly Ala Gln Ala Ser Asp Glu Ala Ile Asp Val Leu Leu Arg Arg
                165                 170                 175

Ala Gly Thr Gln Leu Ser Ala Leu Ala Asn Glu Ile Asp Lys Leu Ala
            180                 185                 190

Leu Phe Ala Gly Ser Gly Gly Thr Ile Glu Ala Ala Ala Val Glu Arg
        195                 200                 205

Leu Val Ala Arg Thr Pro Glu Glu Asn Val Phe Val Leu Val Glu Gln
```

-continued

```
    210                 215                 220

Val Ala Lys Arg Asp Ile Pro Ala Ala Leu Gln Thr Phe Tyr Asp Leu
225                 230                 235                 240

Leu Glu Asn Asn Glu Glu Pro Ile Lys Ile Leu Ala Leu Leu Ala Ala
                245                 250                 255

His Phe Arg Leu Leu Ser Gln Val Lys Trp Leu Ala Ser Leu Gly Tyr
            260                 265                 270

Gly Gln Ala Gln Ile Ala Ala Ala Leu Lys Val His Pro Phe Arg Val
        275                 280                 285

Lys Leu Ala Leu Ala Gln Ala Ala Arg Phe Ala Asp Gly Glu Leu Ala
    290                 295                 300

Glu Ala Ile Asn Glu Leu Ala Asp Ala Asp Tyr Glu Val Lys Ser Gly
305                 310                 315                 320

Ala Val Asp Arg Arg Leu Ala Val Glu Leu Leu Leu Met Arg Trp Gly
                325                 330                 335

Ala Arg Pro Ala Gln Ala Gly Arg His Gly Arg Arg
            340                 345
```

<210> SEQ ID NO 179
<211> LENGTH: 757
<212> TYPE: DNA
<213> ORGANISM: Bacillus stearothermophilus

<400> SEQUENCE: 179

```
atgcgatggg aacagctagc gaaacgccag ccggtggtgg cgaaaatgct gcaaagcggc     60

ttggaaaaag gcggatttc tcatgcgtac ttgtttgagg ggcagcgggg gacgggcaaa    120

aaagcggcca gtttgttgtt ggcgaaacgt ttgttttgtc tgtccccaat cggagtttcc    180

ccgtgtctag agtgccgcaa ctgccggcgc atcgactccg gcaaccaccc tgacgtccgg    240

gtgatcggcc cagatggagg atcaatcaaa aaggaacaaa tcgaatggct gcagcaagag    300

ttctcgaaaa cagcggtcga gtcggataaa aaaatgtaca tcgttgagca cgccgatcaa    360

atgacgacaa gcgctgccaa cagccttctg aaatttttgg aagagccgca tccggggacg    420

gtggcggtat tgctgactga gcaataccac cgcctgctag ggacgatcgt ttcccgctgt    480

caagtgcttt cgttccggcc gttgccgccg gcagagctcg cccagggact tgtcgaggag    540

cacgtgccgt tgccgttggc gctgttggct gcccatttga caaacagctt cgaggaagca    600

ctggcgcttg ccaaagatag ttggtttgcc gaggcgcgaa cattagtgct acaatggtat    660

gagatgctgg gcaagccgga gctgcagctt ttgtttttca tccacgaccg cttgtttccg    720

catttttgg aaagccatca gcttgacctt ggacttg                              757
```

<210> SEQ ID NO 180
<211> LENGTH: 252
<212> TYPE: PRT
<213> ORGANISM: Bacillus stearothermophilus

<400> SEQUENCE: 180

```
Met Arg Trp Glu Gln Leu Ala Lys Arg Gln Pro Val Val Ala Lys Met
  1               5                  10                  15

Leu Gln Ser Gly Leu Glu Lys Gly Arg Ile Ser His Ala Tyr Leu Phe
             20                  25                  30

Glu Gly Gln Arg Gly Thr Gly Lys Lys Ala Ala Ser Leu Leu Leu Ala
         35                  40                  45

Lys Arg Leu Phe Cys Leu Ser Pro Ile Gly Val Ser Pro Cys Leu Glu
     50                  55                  60
```

-continued

```
Cys Arg Asn Cys Arg Arg Ile Asp Ser Gly Asn His Pro Asp Val Arg
 65                  70                  75                  80

Val Ile Gly Pro Asp Gly Gly Ser Ile Lys Lys Glu Gln Ile Glu Trp
                 85                  90                  95

Leu Gln Gln Glu Phe Ser Lys Thr Ala Val Glu Ser Asp Lys Lys Met
            100                 105                 110

Tyr Ile Val Glu His Ala Asp Gln Met Thr Thr Ser Ala Ala Asn Ser
        115                 120                 125

Leu Leu Lys Phe Leu Glu Glu Pro His Pro Gly Thr Val Ala Val Leu
    130                 135                 140

Leu Thr Glu Gln Tyr His Arg Leu Leu Gly Thr Ile Val Ser Arg Cys
145                 150                 155                 160

Gln Val Leu Ser Phe Arg Pro Leu Pro Pro Ala Glu Leu Ala Gln Gly
                165                 170                 175

Leu Val Glu Glu His Val Pro Leu Pro Leu Ala Leu Leu Ala Ala His
            180                 185                 190

Leu Thr Asn Ser Phe Glu Glu Ala Leu Ala Leu Ala Lys Asp Ser Trp
        195                 200                 205

Phe Ala Glu Ala Arg Thr Leu Val Leu Gln Trp Tyr Glu Met Leu Gly
    210                 215                 220

Lys Pro Glu Leu Gln Leu Leu Phe Phe Ile His Asp Arg Leu Phe Pro
225                 230                 235                 240

His Phe Leu Glu Ser His Gln Leu Asp Leu Gly Leu
                245                 250
```

<210> SEQ ID NO 181
<211> LENGTH: 1677
<212> TYPE: DNA
<213> ORGANISM: Bacillus stearothermophilus

<400> SEQUENCE: 181

```
gtggcatacc aagcgttata tcgcgtgttt cggccgcagc gctttgcgga catggtcggc     60

caagaacacg tgaccaagac gttgcaaagc gccctgcttc aacataaaat atcgcacgct    120

tacttatttt ccggcccgcg cggtacagga aaaacgagcg cagcgaaaat tttcgccaag    180

gcggtcaact gtgaacaggc gccagcggcg gagccatgca atgagtgtcc agcttgcctc    240

ggcattacga atggaacggt tcccgatgtg ctggaaattg acgctgcttc caacaaccgc    300

gtcgatgaaa ttcgtgatat ccgtgagaag gtgaaatttg cgccaacgtc ggcccgctac    360

aaagtgtata tcatcgacga ggtgcatatg ctgtcgatcg gtgcgtttaa cgcgctgttg    420

aaaacgttgg aggagccgcc gaaacacgtc attttcattt tggccacgac cgagccgcac    480

aaaattccgg cgacgatcat ttcccgctgc caacggttcg attttcgccg catcccgctt    540

caggcgatcg tttcacggct aaagtacgtc gcaagcgccc aaggtgtcga ggcgtcagat    600

gaggcattgt ccgccatcgc ccgtgctgca gacgggggga tgcgcgatgc gctcagcttg    660

cttgatcaag ccatttcgtt cagcgacggg aaacttcggc tcgacgacgt gctggcgatg    720

accggggctg catcatttgc cgccttatcg agcttcatcg aagccatcca ccgcaaagat    780

acagcggcgg ttcttcagca cttggaaacg atgatggcgc aagggaaaga tccgcatcgt    840

ttggttgaag acttgatttt gtactatcgc gatttattgc tgtacaaaac cgctccctat    900

gtggagggag cgattcaaat tgctgtcgtt gacgaagcgt tcacttcact gtcggaaatg    960

attccggttt ccaatttata cgaggccatc gagttgctga acaaaagcca gcaagagatg   1020
```

-continued

```
aagtggacaa accacccgcg ccttctgttg gaagtggcgc ttgtgaaact ttgccatcca   1080

tcagccgccg ccccgtcgct gtcggcttcc gagttggaac cgttgataaa gcggattgaa   1140

acgctggagg cggaattgcg gcgcctgaag gaacaaccgc ctgcccctcc gtcgaccgcc   1200

gcgccggtga aaaaactgtc caaaccgatg aaaacggggg gatataaagc cccggttggc   1260

cgcatttacg agctgttgaa acaggcgacg catgaagatt tagctttggt gaaaggatgc   1320

tgggcggatg tgctcgacac gttgaaacgg cagcataaag tgtcgcacgc tgccttgctg   1380

caagagagcg agccggttgc agcgagcgcc tcagcgtttg tattaaaatt caaatacgaa   1440

atccactgca aaatggcgac cgatcccaca agttcggtca aagaaaacgt cgaagcgatt   1500

ttgtttgagc tgacaaaccg ccgctttgaa atggtagcca ttccggaggg agaatgggga   1560

aaaataagag aagagttcat ccgcaataag gacgccatgg tggaaaaaag cgaagaagat   1620

ccgttaatcg ccgaagcgaa gcggctgttt ggcgaagagc tgatcgaaat taaagaa      1677
```

<210> SEQ ID NO 182
<211> LENGTH: 559
<212> TYPE: PRT
<213> ORGANISM: Bacillus stearothermophilus

<400> SEQUENCE: 182

```
Val Ala Tyr Gln Ala Leu Tyr Arg Val Phe Arg Pro Gln Arg Phe Ala
  1               5                  10                  15

Asp Met Val Gly Gln Glu His Val Thr Lys Thr Leu Gln Ser Ala Leu
             20                  25                  30

Leu Gln His Lys Ile Ser His Ala Tyr Leu Phe Ser Gly Pro Arg Gly
         35                  40                  45

Thr Gly Lys Thr Ser Ala Ala Lys Ile Phe Ala Lys Ala Val Asn Cys
     50                  55                  60

Glu Gln Ala Pro Ala Ala Glu Pro Cys Asn Glu Cys Pro Ala Cys Leu
 65                  70                  75                  80

Gly Ile Thr Asn Gly Thr Val Pro Asp Val Leu Glu Ile Asp Ala Ala
                 85                  90                  95

Ser Asn Asn Arg Val Asp Glu Ile Arg Asp Ile Arg Glu Lys Val Lys
            100                 105                 110

Phe Ala Pro Thr Ser Ala Arg Tyr Lys Val Tyr Ile Ile Asp Glu Val
        115                 120                 125

His Met Leu Ser Ile Gly Ala Phe Asn Ala Leu Leu Lys Thr Leu Glu
    130                 135                 140

Glu Pro Pro Lys His Val Ile Phe Ile Leu Ala Thr Thr Glu Pro His
145                 150                 155                 160

Lys Ile Pro Ala Thr Ile Ile Ser Arg Cys Gln Arg Phe Asp Phe Arg
                165                 170                 175

Arg Ile Pro Leu Gln Ala Ile Val Ser Arg Leu Lys Tyr Val Ala Ser
            180                 185                 190

Ala Gln Gly Val Glu Ala Ser Asp Glu Ala Leu Ser Ala Ile Ala Arg
        195                 200                 205

Ala Ala Asp Gly Gly Met Arg Asp Ala Leu Ser Leu Leu Asp Gln Ala
    210                 215                 220

Ile Ser Phe Ser Asp Gly Lys Leu Arg Leu Asp Asp Val Leu Ala Met
225                 230                 235                 240

Thr Gly Ala Ala Ser Phe Ala Ala Leu Ser Ser Phe Ile Glu Ala Ile
                245                 250                 255

His Arg Lys Asp Thr Ala Ala Val Leu Gln His Leu Glu Thr Met Met
```

-continued

```
            260                 265                 270

Ala Gln Gly Lys Asp Pro His Arg Leu Val Glu Asp Leu Ile Leu Tyr
        275                 280                 285

Tyr Arg Asp Leu Leu Leu Tyr Lys Thr Ala Pro Tyr Val Glu Gly Ala
    290                 295                 300

Ile Gln Ile Ala Val Val Asp Glu Ala Phe Thr Ser Leu Ser Glu Met
305                 310                 315                 320

Ile Pro Val Ser Asn Leu Tyr Glu Ala Ile Glu Leu Leu Asn Lys Ser
                325                 330                 335

Gln Gln Glu Met Lys Trp Thr Asn His Pro Arg Leu Leu Leu Glu Val
            340                 345                 350

Ala Leu Val Lys Leu Cys His Pro Ser Ala Ala Ala Pro Ser Leu Ser
        355                 360                 365

Ala Ser Glu Leu Glu Pro Leu Ile Lys Arg Ile Glu Thr Leu Glu Ala
    370                 375                 380

Glu Leu Arg Arg Leu Lys Glu Gln Pro Pro Ala Pro Pro Ser Thr Ala
385                 390                 395                 400

Ala Pro Val Lys Lys Leu Ser Lys Pro Met Lys Thr Gly Gly Tyr Lys
                405                 410                 415

Ala Pro Val Gly Arg Ile Tyr Glu Leu Leu Lys Gln Ala Thr His Glu
            420                 425                 430

Asp Leu Ala Leu Val Lys Gly Cys Trp Ala Asp Val Leu Asp Thr Leu
        435                 440                 445

Lys Arg Gln His Lys Val Ser His Ala Ala Leu Leu Gln Glu Ser Glu
    450                 455                 460

Pro Val Ala Ala Ser Ala Ser Ala Phe Val Leu Lys Phe Lys Tyr Glu
465                 470                 475                 480

Ile His Cys Lys Met Ala Thr Asp Pro Thr Ser Ser Val Lys Glu Asn
                485                 490                 495

Val Glu Ala Ile Leu Phe Glu Leu Thr Asn Arg Arg Phe Glu Met Val
            500                 505                 510

Ala Ile Pro Glu Gly Glu Trp Gly Lys Ile Arg Glu Glu Phe Ile Arg
        515                 520                 525

Asn Lys Asp Ala Met Val Glu Lys Ser Glu Glu Asp Pro Leu Ile Ala
    530                 535                 540

Glu Ala Lys Arg Leu Phe Gly Glu Glu Leu Ile Glu Ile Lys Glu
545                 550                 555
```

<210> SEQ ID NO 183
<211> LENGTH: 4301
<212> TYPE: DNA
<213> ORGANISM: Bacillus stearothermophilus

<400> SEQUENCE: 183

```
atggtgacaa aagagcaaaa agagcggttt ctcatcctgc ttgagcagct gaagatgacg      60

tcggacgaat ggatgccgca ttttcgtgag gcagccattc gcaaagtcgt gatcgataaa     120

gaggagaaaa gctggcattt ttattttcag ttcgacaacg tgctgccggt tcatgtatac     180

aaaacgtttg ccgatcggct gcagacggcg ttccgccata tcgccgccgt ccgccatacg     240

atggaggtcg aagcgccgcg cgtaactgag gcggatgtgc aggcgtattg gccgctttgc     300

cttgccgagc tgcaagaagg catgtcgccg cttgtcgatt ggctcagccg gcagacgcct     360

gagctgaaag gaaacaagct gcttgtcgtt gcccgccatg aagcggaagc gctggcgatc     420

aaacggcggt tcgccaaaaa aatcgctgat gtgtacgctt cgtttgggtt tcccccccctt     480
```

-continued

```
cagcttgacg tcagcgtcga gccgtccaag caagaaatgg aacagttttt ggcgcaaaaa    540
cagcaagagg acgaagagcg agcgcttgct gtactgaccg atttagcgag ggaagaagaa    600
aaggccgcgt ctgcgccgcc gtccggtccg cttgtcatcg gctatccgat ccgcgacgag    660
gagccggtgc ggcggcttga aacgatcgtc gaagaagagc ggcgcgtcgt tgtgcaaggc    720
tatgtatttg acgccgaagt gagcgaatta aaaagcggcc gcacgctgtt gaccatgaaa    780
atcacagatt acacgaactc gattttagtc aaaatgttct cgcgcgacaa agaggacgcc    840
gagcttatga gcggcgtcaa aaaaggcatg tgggtgaaag tgcgcggcag cgtgcaaaac    900
gatacgttcg tccgtgattt ggtcatcatc gccaacgatt tgaacgaaat cgccgcaaac    960
gaacggcaag atacggcgcc ggaaggggaa aagagggtcg agctccattt gcataccccg   1020
atgagccaaa tggacgcggt cacctcggtg acaaaactca ttgagcaagc gaaaaaatgg   1080
gggcatccgg cgatcgccgt caccgaccat gccgttgttc agtcgtttcc ggaggcctac   1140
agcgcggcga aaaaacacgg catgaaggtc atttacggcc ttgaggcgaa catcgtcgac   1200
gatggcgtgc cgatcgccta caatgagacg caccgccgtc tttcggagga aacgtacgtc   1260
gtctttgacg tcgagacgac gggcctgtcg gctgtgtaca atacgatcat tgagctggcg   1320
gcggtgaaag tgaaagacgg cgagatcatc gaccgattca tgtcgtttgc caaccctgga   1380
catccgttgt cggtgacaac gatggagctg actgggatca ccgatgagat ggtgaaagac   1440
gccccgaagc cggacgaggt gctagcccgt tttgttgact gggccggcga tgcgacgctt   1500
gttgcccaca acgccagctt tgacatcggt tttttaaacg cgggcctcgc tcgcatgggg   1560
cgcggcaaaa tcgcgaatcc agtcatcgat acgctcgagc tggcccgttt tttatacccg   1620
gatttgaaaa accatcggct caatacattg tgcaaaaaat ttgacattga attgacgcag   1680
catcaccgcg ccatctacga cgcggaggcg accgggcatt tgcttatgcg gctgttgaag   1740
gaagcggaag agcgcggcat actgtttcat gacgaattaa acagccgcac gcacagcgaa   1800
gcgtcctatc ggcttgcgcg cccgttccat gtgacgctgt tggcgcaaaa cgagactgga   1860
ttgaaaaatt tgttcaagct tgtgtcattg tcgcacattc aatattttca ccgtgtgccg   1920
cgcatcccgc gctccgtgct cgtcaagcac cgcgacggcc tgcttgtcgg ctcgggctgc   1980
gacaaaggag agctgtttga caacttgatc caaaaggcgc cggaagaagt cgaagacatc   2040
gcccgttttt acgattttct tgaagtgcat ccgccggacg tgtacaagcc gctcatcgag   2100
atggattatg tgaaagacga agagatgatc aaaaacatca tccgcagcat cgtcgccctt   2160
ggtgagaagc ttgacatccc ggttgtcgcc actggcaacg tccattactt gaacccagaa   2220
gataaaattt accggaaaat cttaatccat tcgcaaggcg ggcgaatcc gctcaaccgc   2280
catgaactgc cggatgtata tttccgtacg acgaatgaaa tgcttgactg cttctcgttt   2340
ttagggccgg aaaaagcgaa ggaaatcgtc gttgacaaca cgcaaaaaat cgcttcgtta   2400
atcggcgatg tcaagccgat caaagatgag ctgtatacgc cgcgcattga aggggcggac   2460
gaggaaatca gggaaatgag ctaccggcgg gcgaaggaaa tttacggcga cccgttgccg   2520
aaacttgttg aagagcggct tgagaaggag ctaaaaagca tcatcggcca tggctttgcc   2580
gtcatttatt tgatctcgca caagcttgtg aaaaaatcgc tcgatgacgg ctaccttgtc   2640
gggtcgcgcg gatcggtcgg ctcgtcgttt gtcgcgacga tgacggaaat caccgaggtc   2700
aatccgctgc cgccgcatta cgtttgcccg aactgcaagc attcggagtt ctttaacgac   2760
ggttcagtcg gctcagggtt tgatttgccg gataaaaact gcccgcgatg tgggacgaaa   2820
```

-continued

```
tacaagaaag acgggcacga catcccgttt gagacgtttc tcggctttaa aggcgacaaa   2880

gtgccggata tcgacttgaa cttttccggc gaataccagc cgcgcgccca caactatacg   2940

aaagtgctgt ttggcgaaga caacgtctac cgcgccggga cgattggcac ggtcgctgac   3000

aaaacggcgt acggatttgt caaagcgtat gcgagcgacc ataacttaga gctgcgcggc   3060

gcggaaatcg acggctcgcg gctggctgca ccggggtgaa gcggacgacc gggcagcatc   3120

cgggcggcat catcgtcgtc ccggattata tggaaattta cgattttacg ccgattcaat   3180

atccggccga tgacacgtcc tctgaatggc ggacgaccca tttcgacttc cattcgatcc   3240

acgacaattt gttgaagctc gatattctcg ggcacgacga tccgacggtc attcgcatgc   3300

tgcaagattt aagcggcatc gatccgaaaa cgatcccgac cgacgacccg gatgtgatgg   3360

gcattttcag cagcaccgag ccgcttggcg ttacgccgga gcaaatcatg tgcaatgtcg   3420

gcacgatcgg cattccggag tttggcacgc gcttcgttcg gcaaatgttg gaagagacaa   3480

ggccaaaaac gttttccgaa ctcgtgcaaa tttccggctt gtcgcacggc accgatgtgt   3540

ggctcggcaa cgcgcaagag ctcattcaaa acggcacgtg tacgttatcg gaagtcatcg   3600

gctgccgcga cgacattatg gtctatttga tttaccgcgg gctcgagccg tcgctcgctt   3660

ttaaaatcat ggaatccgtg cgcaaaggaa aaggcttaac gccggagttt gaagcagaaa   3720

tgcgcaaaca tgacgtgccg gagtggtaca tcgattcatg caaaaaaatc aagtacatgt   3780

tcccgaaagc gcacgccgcc gcctacgtgt taatggcggt gcgcatcgcc tactttaagg   3840

tgcaccatcc gcttttgtat tacgcgtcgt actttacggt gcgggcggag gactttgacc   3900

ttgacgccat gatcaaagga tcacccgcca ttcgcaagcg gattgaggaa atcaacgcca   3960

aaggcattca ggcgacggcg aaagaaaaaa gcttgctcac ggttcttgag gtggccttag   4020

agatgtgcga gcgcggcttt tcctttaaaa atatcgattt gtaccgctcg caggcgacgg   4080

aattcgtcat tgacggcaat tctctcattc cgccgttcaa cgccattccg gggcttggga   4140

cgaacgtggc gcaggcgatc gtgcgcgccc gcgaggaagg cgagtttttg tcgaaggagg   4200

atttgcaaca gcgcggcaaa ttgtcgaaaa cgctgctcga gtatctagaa agccgcggct   4260

gccttgactc gcttccagac cataaccagc tgtcgctgtt t                       4301
```

```
<210> SEQ ID NO 184
<211> LENGTH: 1433
<212> TYPE: PRT
<213> ORGANISM: Bacillus stearothermophilus

<400> SEQUENCE: 184

Met Val Thr Lys Glu Gln Lys Glu Arg Phe Leu Ile Leu Leu Glu Gln
  1               5                  10                  15

Leu Lys Met Thr Ser Asp Glu Trp Met Pro His Phe Arg Glu Ala Ala
             20                  25                  30

Ile Arg Lys Val Val Ile Asp Lys Glu Glu Lys Ser Trp His Phe Tyr
         35                  40                  45

Phe Gln Phe Asp Asn Val Leu Pro Val His Val Tyr Lys Thr Phe Ala
     50                  55                  60

Asp Arg Leu Gln Thr Ala Phe Arg His Ile Ala Ala Val Arg His Thr
 65                  70                  75                  80

Met Glu Val Glu Ala Pro Arg Val Thr Glu Ala Asp Val Gln Ala Tyr
                 85                  90                  95

Trp Pro Leu Cys Leu Ala Glu Leu Gln Glu Gly Met Ser Pro Leu Val
            100                 105                 110
```

-continued

```
Asp Trp Leu Ser Arg Gln Thr Pro Glu Leu Lys Gly Asn Lys Leu Leu
        115                 120                 125

Val Val Ala Arg His Glu Ala Glu Ala Leu Ala Ile Lys Arg Arg Phe
    130                 135                 140

Ala Lys Lys Ile Ala Asp Val Tyr Ala Ser Phe Gly Phe Pro Pro Leu
145                 150                 155                 160

Gln Leu Asp Val Ser Val Glu Pro Ser Lys Gln Glu Met Glu Gln Phe
                165                 170                 175

Leu Ala Gln Lys Gln Gln Glu Asp Glu Glu Arg Ala Leu Ala Val Leu
            180                 185                 190

Thr Asp Leu Ala Arg Glu Glu Glu Lys Ala Ala Ser Ala Pro Pro Ser
        195                 200                 205

Gly Pro Leu Val Ile Gly Tyr Pro Ile Arg Asp Glu Glu Pro Val Arg
    210                 215                 220

Arg Leu Glu Thr Ile Val Glu Glu Glu Arg Arg Val Val Val Gln Gly
225                 230                 235                 240

Tyr Val Phe Asp Ala Glu Val Ser Glu Leu Lys Ser Gly Arg Thr Leu
                245                 250                 255

Leu Thr Met Lys Ile Thr Asp Tyr Thr Asn Ser Ile Leu Val Lys Met
            260                 265                 270

Phe Ser Arg Asp Lys Glu Asp Ala Glu Leu Met Ser Gly Val Lys Lys
        275                 280                 285

Gly Met Trp Val Lys Val Arg Gly Ser Val Gln Asn Asp Thr Phe Val
    290                 295                 300

Arg Asp Leu Val Ile Ile Ala Asn Asp Leu Asn Glu Ile Ala Ala Asn
305                 310                 315                 320

Glu Arg Gln Asp Thr Ala Pro Glu Gly Glu Lys Arg Val Glu Leu His
                325                 330                 335

Leu His Thr Pro Met Ser Gln Met Asp Ala Val Thr Ser Val Thr Lys
            340                 345                 350

Leu Ile Glu Gln Ala Lys Lys Trp Gly His Pro Ala Ile Ala Val Thr
        355                 360                 365

Asp His Ala Val Val Gln Ser Phe Pro Glu Ala Tyr Ser Ala Ala Lys
    370                 375                 380

Lys His Gly Met Lys Val Ile Tyr Gly Leu Glu Ala Asn Ile Val Asp
385                 390                 395                 400

Asp Gly Val Pro Ile Ala Tyr Asn Glu Thr His Arg Arg Leu Ser Glu
                405                 410                 415

Glu Thr Tyr Val Val Phe Asp Val Glu Thr Thr Gly Leu Ser Ala Val
            420                 425                 430

Tyr Asn Thr Ile Ile Glu Leu Ala Ala Val Lys Val Lys Asp Gly Glu
        435                 440                 445

Ile Ile Asp Arg Phe Met Ser Phe Ala Asn Pro Gly His Pro Leu Ser
    450                 455                 460

Val Thr Thr Met Glu Leu Thr Gly Ile Thr Asp Glu Met Val Lys Asp
465                 470                 475                 480

Ala Pro Lys Pro Asp Glu Val Leu Ala Arg Phe Val Asp Trp Ala Gly
                485                 490                 495

Asp Ala Thr Leu Val Ala His Asn Ala Ser Phe Asp Ile Gly Phe Leu
            500                 505                 510

Asn Ala Gly Leu Ala Arg Met Gly Arg Gly Lys Ile Ala Asn Pro Val
        515                 520                 525

Ile Asp Thr Leu Glu Leu Ala Arg Phe Leu Tyr Pro Asp Leu Lys Asn
```

-continued

```
    530                 535                 540

His Arg Leu Asn Thr Leu Cys Lys Lys Phe Asp Ile Glu Leu Thr Gln
545                 550                 555                 560

His His Arg Ala Ile Tyr Asp Ala Glu Ala Thr Gly His Leu Leu Met
                565                 570                 575

Arg Leu Leu Lys Glu Ala Glu Glu Arg Gly Ile Leu Phe His Asp Glu
            580                 585                 590

Leu Asn Ser Arg Thr His Ser Glu Ala Ser Tyr Arg Leu Ala Arg Pro
        595                 600                 605

Phe His Val Thr Leu Leu Ala Gln Asn Glu Thr Gly Leu Lys Asn Leu
    610                 615                 620

Phe Lys Leu Val Ser Leu Ser His Ile Gln Tyr Phe His Arg Val Pro
625                 630                 635                 640

Arg Ile Pro Arg Ser Val Leu Val Lys His Arg Asp Gly Leu Leu Val
                645                 650                 655

Gly Ser Gly Cys Asp Lys Gly Glu Leu Phe Asp Asn Leu Ile Gln Lys
            660                 665                 670

Ala Pro Glu Glu Val Glu Asp Ile Ala Arg Phe Tyr Asp Phe Leu Glu
        675                 680                 685

Val His Pro Pro Asp Val Tyr Lys Pro Leu Ile Glu Met Asp Tyr Val
    690                 695                 700

Lys Asp Glu Glu Met Ile Lys Asn Ile Ile Arg Ser Ile Val Ala Leu
705                 710                 715                 720

Gly Glu Lys Leu Asp Ile Pro Val Val Ala Thr Gly Asn Val His Tyr
                725                 730                 735

Leu Asn Pro Glu Asp Lys Ile Tyr Arg Lys Ile Leu Ile His Ser Gln
            740                 745                 750

Gly Gly Ala Asn Pro Leu Asn Arg His Glu Leu Pro Asp Val Tyr Phe
        755                 760                 765

Arg Thr Thr Asn Glu Met Leu Asp Cys Phe Ser Phe Leu Gly Pro Glu
    770                 775                 780

Lys Ala Lys Glu Ile Val Val Asp Asn Thr Gln Lys Ile Ala Ser Leu
785                 790                 795                 800

Ile Gly Asp Val Lys Pro Ile Lys Asp Glu Leu Tyr Thr Pro Arg Ile
                805                 810                 815

Glu Gly Ala Asp Glu Glu Ile Arg Glu Met Ser Tyr Arg Arg Ala Lys
            820                 825                 830

Glu Ile Tyr Gly Asp Pro Leu Pro Lys Leu Val Glu Glu Arg Leu Glu
        835                 840                 845

Lys Glu Leu Lys Ser Ile Ile Gly His Gly Phe Ala Val Ile Tyr Leu
    850                 855                 860

Ile Ser His Lys Leu Val Lys Lys Ser Leu Asp Asp Gly Tyr Leu Val
865                 870                 875                 880

Gly Ser Arg Gly Ser Val Gly Ser Ser Phe Val Ala Thr Met Thr Glu
                885                 890                 895

Ile Thr Glu Val Asn Pro Leu Pro Pro His Tyr Val Cys Pro Asn Cys
            900                 905                 910

Lys His Ser Glu Phe Phe Asn Asp Gly Ser Val Gly Ser Gly Phe Asp
        915                 920                 925

Leu Pro Asp Lys Asn Cys Pro Arg Cys Gly Thr Lys Tyr Lys Lys Asp
    930                 935                 940

Gly His Asp Ile Pro Phe Glu Thr Phe Leu Gly Phe Lys Gly Asp Lys
945                 950                 955                 960
```

-continued

```
Val Pro Asp Ile Asp Leu Asn Phe Ser Gly Glu Tyr Gln Pro Arg Ala
                965                 970                 975

His Asn Tyr Thr Lys Val Leu Phe Gly Glu Asp Asn Val Tyr Arg Ala
            980                 985                 990

Gly Thr Ile Gly Thr Val Ala Asp Lys Thr Ala Tyr Gly Phe Val Lys
        995                 1000                1005

Ala Tyr Ala Ser Asp His Asn Leu Glu Leu Arg Gly Ala Glu Ile Asp
    1010                1015                1020

Leu Ala Ala Gly Cys Thr Gly Val Lys Arg Thr Thr Gly Gln His Pro
1025                1030                1035                1040

Gly Gly Ile Ile Val Val Pro Asp Tyr Met Glu Ile Tyr Asp Phe Thr
                1045                1050                1055

Pro Ile Gln Tyr Pro Ala Asp Asp Thr Ser Ser Glu Trp Arg Thr Thr
            1060                1065                1070

His Phe Asp Phe His Ser Ile His Asp Asn Leu Leu Lys Leu Asp Ile
        1075                1080                1085

Leu Gly His Asp Asp Pro Thr Val Ile Arg Met Leu Gln Asp Leu Ser
    1090                1095                1100

Gly Ile Asp Pro Lys Thr Ile Pro Thr Asp Asp Pro Asp Val Met Gly
1105                1110                1115                1120

Ile Phe Ser Ser Thr Glu Pro Leu Gly Val Thr Pro Glu Gln Ile Met
                1125                1130                1135

Cys Asn Val Gly Thr Ile Gly Ile Pro Glu Phe Gly Thr Arg Phe Val
            1140                1145                1150

Arg Gln Met Leu Glu Glu Thr Arg Pro Lys Thr Phe Ser Glu Leu Val
        1155                1160                1165

Gln Ile Ser Gly Leu Ser His Gly Thr Asp Val Trp Leu Gly Asn Ala
    1170                1175                1180

Gln Glu Leu Ile Gln Asn Gly Thr Cys Thr Leu Ser Glu Val Ile Gly
1185                1190                1195                1200

Cys Arg Asp Asp Ile Met Val Tyr Leu Ile Tyr Arg Gly Leu Glu Pro
                1205                1210                1215

Ser Leu Ala Phe Lys Ile Met Glu Ser Val Arg Lys Gly Lys Gly Leu
            1220                1225                1230

Thr Pro Glu Phe Glu Ala Glu Met Arg Lys His Asp Val Pro Glu Trp
        1235                1240                1245

Tyr Ile Asp Ser Cys Lys Lys Ile Lys Tyr Met Phe Pro Lys Ala His
    1250                1255                1260

Ala Ala Ala Tyr Val Leu Met Ala Val Arg Ile Ala Tyr Phe Lys Val
1265                1270                1275                1280

His His Pro Leu Leu Tyr Tyr Ala Ser Tyr Phe Thr Val Arg Ala Glu
                1285                1290                1295

Asp Phe Asp Leu Asp Ala Met Ile Lys Gly Ser Pro Ala Ile Arg Lys
            1300                1305                1310

Arg Ile Glu Glu Ile Asn Ala Lys Gly Ile Gln Ala Thr Ala Lys Glu
        1315                1320                1325

Lys Ser Leu Leu Thr Val Leu Glu Val Ala Leu Glu Met Cys Glu Arg
    1330                1335                1340

Gly Phe Ser Phe Lys Asn Ile Asp Leu Tyr Arg Ser Gln Ala Thr Glu
1345                1350                1355                1360

Phe Val Ile Asp Gly Asn Ser Leu Ile Pro Pro Phe Asn Ala Ile Pro
                1365                1370                1375
```

-continued

```
Gly Leu Gly Thr Asn Val Ala Gln Ala Ile Val Arg Ala Arg Glu Glu
          1380                1385                1390

Gly Glu Phe Leu Ser Lys Glu Asp Leu Gln Gln Arg Gly Lys Leu Ser
      1395                1400                1405

Lys Thr Leu Leu Glu Tyr Leu Glu Ser Arg Gly Cys Leu Asp Ser Leu
   1410                1415                1420

Pro Asp His Asn Gln Leu Ser Leu Phe
1425                1430
```

<210> SEQ ID NO 185
<211> LENGTH: 199
<212> TYPE: PRT
<213> ORGANISM: Thermus thermophilus

<400> SEQUENCE: 185

```
Thr Pro Lys Gly Lys Asp Leu Val Arg His Leu Glu Asn Arg Ala Lys
  1               5                  10                  15

Arg Leu Gly Leu Arg Leu Pro Gly Gly Val Ala Gln Tyr Leu Ala Ser
             20                  25                  30

Leu Glu Gly Asp Leu Glu Ala Leu Glu Arg Glu Leu Glu Lys Leu Ala
         35                  40                  45

Leu Leu Ser Pro Pro Leu Thr Leu Glu Lys Val Glu Lys Val Val Ala
     50                  55                  60

Leu Arg Pro Pro Leu Thr Gly Phe Asp Leu Val Arg Ser Val Leu Glu
 65                  70                  75                  80

Lys Asp Pro Lys Glu Ala Leu Leu Arg Leu Gly Arg Leu Lys Glu Glu
                 85                  90                  95

Gly Glu Glu Pro Leu Arg Leu Leu Gly Ala Leu Ser Trp Gln Phe Ala
            100                 105                 110

Leu Leu Ala Arg Ala Phe Phe Leu Leu Arg Glu Met Pro Arg Pro Lys
        115                 120                 125

Glu Glu Asp Leu Ala Arg Leu Glu Ala His Pro Tyr Ala Ala Lys Lys
    130                 135                 140

Ala Leu Leu Glu Ala Ala Arg Arg Leu Thr Glu Glu Ala Leu Lys Glu
145                 150                 155                 160

Ala Leu Asp Ala Leu Met Glu Ala Glu Lys Arg Ala Lys Gly Gly Lys
                165                 170                 175

Asp Pro Trp Leu Ala Leu Glu Ala Ala Val Leu Arg Leu Ala Arg Pro
            180                 185                 190

Ala Gly Gln Pro Arg Val Asp
        195
```

<210> SEQ ID NO 186
<211> LENGTH: 27
<212> TYPE: DNA
<213> ORGANISM: Artificial Sequence
<220> FEATURE:
<223> OTHER INFORMATION: Description of Artificial Sequence:  PCR primer

<400> SEQUENCE: 186
gcccagtacc tcgcctccct cgagggg 27

<210> SEQ ID NO 187
<211> LENGTH: 27
<212> TYPE: DNA
<213> ORGANISM: Artificial Sequence
<220> FEATURE:
<223> OTHER INFORMATION: Description of Artificial Sequence:  PCR primer

<400> SEQUENCE: 187 ggccccttg gccttctcgg cctccat 27

<210> SEQ ID NO 188
<211> LENGTH: 331
<212> TYPE: DNA
<213> ORGANISM: Thermus thermophilus

<400> SEQUENCE: 188
agactcgagg ccctggagcg ggagctggag aagcttgccc tcctctcccc acccctcacc 60
ctggagaagg tggagaaggt ggtggccctg aggccccccc tcacgggctt tgacctggtg 120
cgctccgtcc tggagaagga ccccaaggag gccctcctgc gcctcaggcg cctcagggag 180
gagggggagg agcccctcag gctcctcggg gccctctcct ggcagttcgc cctcctcgcc 240
cgggccttct tcctcctccg ggaaaacccc aggcccaagg aggaggacct cgcccgcctc 300
gaggcccacc cctacgccgc caagaaggcc a 331

<210> SEQ ID NO 189
<211> LENGTH: 110
<212> TYPE: PRT
<213> ORGANISM: Thermus thermophilus

<400> SEQUENCE: 189

Arg Leu Glu Ala Leu Glu Arg Glu Leu Glu Lys Leu Ala Leu Leu Ser
1 5 10 15

Pro Pro Leu Thr Leu Glu Lys Val Glu Lys Val Val Ala Leu Arg Pro
20 25 30

Pro Leu Thr Gly Phe Asp Leu Val Arg Ser Val Leu Glu Lys Asp Pro
35 40 45

Lys Glu Ala Leu Leu Arg Leu Arg Arg Leu Arg Glu Glu Gly Glu Glu
50 55 60

Pro Leu Arg Leu Leu Gly Ala Leu Ser Trp Gln Phe Ala Leu Leu Ala
65 70 75 80

Arg Ala Phe Phe Leu Leu Arg Glu Asn Pro Arg Pro Lys Glu Glu Asp
85 90 95

Leu Ala Arg Leu Glu Ala His Pro Tyr Ala Ala Lys Lys Ala
100 105 110

<210> SEQ ID NO 190
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 190
gtggtgtcta gacatcataa cggttctggc a 31

<210> SEQ ID NO 191
<211> LENGTH: 27
<212> TYPE: DNA
<213> ORGANISM: Artificial Sequence
<220> FEATURE:
<223> OTHER INFORMATION: Description of Artificial Sequence: PCR Primer

<400> SEQUENCE: 191
gagggccacc accttctcca ccttctc 27

<210> SEQ ID NO 192

-continued

<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 192
ctccgtcctg gagaaggacc ccaag 25

<210> SEQ ID NO 193
<211> LENGTH: 29
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: primer_bind
<222> LOCATION: (15)
<223> OTHER INFORMATION: S at position 15 can be either C or G
<220> FEATURE:
<221> NAME/KEY: primer_bind
<222> LOCATION: (27)
<223> OTHER INFORMATION: S at position 27 can be either C or G

<400> SEQUENCE: 193
cgcgaattca acgcsctcct caagacsct 29

<210> SEQ ID NO 194
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 194
gacacttaac atatggtcat cgccttcacc g 31

<210> SEQ ID NO 195
<211> LENGTH: 38
<212> TYPE: DNA
<213> ORGANISM: Artificial Sequence
<220> FEATURE:
<223> OTHER INFORMATION: Description of Artificial Sequence: PCR primer

<400> SEQUENCE: 195
gtgtgtgaat tcgggtcaac gggcgaggcg gaggaccg 38

<210> SEQ ID NO 196
<211> LENGTH: 10
<212> TYPE: PRT
<213> ORGANISM: Deinococcus radiodurans

<400> SEQUENCE: 196

Val Ile Leu Asn Pro Gly Ser Val Gly Gln
1 5 10

<210> SEQ ID NO 197
<211> LENGTH: 10
<212> TYPE: PRT
<213> ORGANISM: Methanococcus jannaschii

<400> SEQUENCE: 197

Tyr Leu Ile Asn Pro Gly Ser Val Gly Gln
1 5 10

<210> SEQ ID NO 198
<211> LENGTH: 10

-continued

<212> TYPE: PRT
<213> ORGANISM: Thermotoga maritima

<400> SEQUENCE: 198

Leu Val Leu Asn Pro Gly Ser Ala Gly Arg
1 5 10

<210> SEQ ID NO 199
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 199
ctggtgaacc cgggctccgt gggccagc 28

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence:
polypeptide

<400> SEQUENCE: 200

Leu Leu Val Asn Pro Gly Ser Val Gly Gln
1 5 10

<210> SEQ ID NO 201
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 201
ctcgaggagc ttgaggaggg tgttggc 27

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence:
polypeptide

<400> SEQUENCE: 202

Ala Asn Thr Leu Leu Lys Leu Leu Glu
1 5

<210> SEQ ID NO 203
<211> LENGTH: 32
<212> TYPE: PRT
<213> ORGANISM: Deinococcus radiodurans

<400> SEQUENCE: 203

Gly Phe Gly Gly Val Gln Leu His Ala Ala His Gly Tyr Leu Leu Ser
1 5 10 15

Gln Phe Leu Ser Pro Arg His Asn Val Arg Glu Asp Glu Tyr Gly Gly
20 25 30

<210> SEQ ID NO 204
<211> LENGTH: 32
<212> TYPE: PRT
<213> ORGANISM: Caenorhabditis elegans -continued

<400> SEQUENCE: 204

```
Gly Phe Asp Gly Ile Gln Leu His Gly Ala His Gly Tyr Leu Leu Ser
  1               5                  10                  15

Gln Phe Thr Ser Pro Thr Thr Asn Lys Arg Val Asp Lys Tyr Gly Gly
             20                  25                  30
```

<210> SEQ ID NO 205
<211> LENGTH: 32
<212> TYPE: PRT
<213> ORGANISM: Pseudomonas aeruginosa

<400> SEQUENCE: 205

```
Gly Phe Ser Gly Val Glu Ile His Ala Ala His Gly Tyr Leu Leu Ser
  1               5                  10                  15

Gln Phe Leu Ser Pro Leu Ser Asn Arg Arg Ser Asp Ala Trp Gly Gly
             20                  25                  30
```

<210> SEQ ID NO 206
<211> LENGTH: 32
<212> TYPE: PRT
<213> ORGANISM: Archaeoglobus fulgidus

<400> SEQUENCE: 206

```
Gly Phe Asp Ala Val Gln Leu His Ala Ala His Gly Tyr Leu Leu Ser
  1               5                  10                  15

Glu Phe Ile Ser Pro His Val Asn Arg Arg Lys Asp Glu Tyr Gly Gly
             20                  25                  30
```

<210> SEQ ID NO 207
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 207

```
catcctggac tcggcccacc tcctcaccga                                   30
```

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: polypeptide

<400> SEQUENCE: 208

```
Ile Leu Asp Ser Ala His Leu Leu Thr
  1               5
```

<210> SEQ ID NO 209
<211> LENGTH: 33
<212> TYPE: DNA
<213> ORGANISM: Artificial Sequence
<220> FEATURE:
<223> OTHER INFORMATION: Description of Artificial Sequence: PCR primer

<400> SEQUENCE: 209

```
gaggaggtag ccgtgggccg cgtggagctc cac                               33
```

<210> SEQ ID NO 210
<211> LENGTH: 11
<212> TYPE: PRT

-continued

```
<213> ORGANISM: Artificial Sequence
<220> FEATURE:
<223> OTHER INFORMATION: Description of Artificial Sequence:
      polypeptide

<400> SEQUENCE: 210

Val Glu Leu His Ala Ala His Gly Tyr Leu Leu
  1               5                   10


<210> SEQ ID NO 211
<211> LENGTH: 32
<212> TYPE: DNA
<213> ORGANISM: Artificial Sequence
<220> FEATURE:
<223> OTHER INFORMATION: Description of Artificial Sequence:  PCR primer

<400> SEQUENCE: 211

ggctttccca tatggctcta cacccggctc ac                                  32


<210> SEQ ID NO 212
<211> LENGTH: 29
<212> TYPE: DNA
<213> ORGANISM: Artificial Sequence
<220> FEATURE:
<223> OTHER INFORMATION: Description of Artificial Sequence:  PCR primer

<400> SEQUENCE: 212

gcgtggatcc acggtcatgt ctctaagtc                                      29
```

ENZYMES DERIVED FROM THERMOPHILIC ORGANISMS THAT FUNCTION AS A CHROMOSOMAL REPLICASE, PREPARATION AND USE THEREOF

The present application is a continuation-in-part of U.S. patent application Ser. No. 09/642,218, filed Aug. 18, 2000, as a continuation of U.S. patent application Ser. No. 09/057,416, filed Apr. 8, 1998, now abandoned, which claims the benefit of U.S. Provisional Patent Application Ser. No. 60/043,202 filed Apr. 8, 1997. Both the '416 application and the '202 provisional application are hereby incorporated by reference.

The present invention was made with funding from National Institutes of Health Grant No. GM38839. The United States Government may have certain rights in this invention.

FIELD OF THE INVENTION

The present invention relates to thermostable DNA polymerases and, more particularly, to such polymerases as can serve as chromosomal replicases and are derived from thermophilic bacteria More particularly, the invention extends to DNA polymerase III-type enzymes from thermophilic bacteria, including *Aquifex aeolicus, Thermus thermophilus, Thermotoga maritima*, and *Bacillus stearothermophilus*, as well as purified, recombinant or non-recombinant subunits thereof and their use, and to isolated DNA coding for such polymerases and their subunits. Such DNA is obtained from the respective genes (e.g., dnaX, holA, holB, dnaA, dnaN, dnaQ, dnaE, ssb, etc.) of various thermophilic eubacteria, including but not limited to *Thermus thermophilus, Aquifex aeolicus, Thermotoga maritima*, and *Bacillus stearothermophilus.*

BACKGROUND OF THE INVENTION

Thermostable DNA polymerases have been disclosed previously as set forth in U.S. Pat. No. 5,192,674 to Oshima et al., U.S. Pat. Nos. 5,322,785 and 5,352,778 to Comb et al., U.S. Pat. No. 5,545,552 to Mathur, and others. All of the noted references recite the use of polymerases as important catalytic tools in the practice of molecular cloning techniques such as polymerase chain reaction (PCR). Each of the references states that a drawback of the extant polymerases are their limited thermostability, and consequent useful life in the participation in PCR. Such limitations also manifest themselves in the inability to obtain extended lengths of nucleotides, and in the instance of Taq polymerase, the lack of 3' to 5' exonuclease activity, and the drawback of the inability to excise misinserted nucleotides (Perrino, 1990).

More generally, such polymerases, including those disclosed in the referenced patents, are of the Polymerase I variety as they are often 90–95 kDa in size and may have 5' to 3' exonuclease activity. They define a single subunit with concomitant limits on their ability to hasten the amplification process and to promote the rapid preparation of longer strands of DNA.

Chromosomal replicases are composed of several subunits in all organisms (Kornberg and Baker, 1992). In keeping with the need to replicate long chromosomes, replicases are rapid and highly processive multiprotein machines. Cellular replicases are classically comprised of three components: a clamp, a clamp loader, and the DNA polymerase (reviewed in Kelman and O'Donnell, 1995; McHenry, 1991). For purposes of the present invention, the foregoing components also serve as a broad definition of a "Pol III-type enzyme".

DNA polymerase III holoenzyme (Pol III holoenzyme) is the multi-subunit replicase of the *E. coli* chromosome. Pol III holoenzyme is distinguished from Pol I type DNA polymerases by its high processivity (>50 kbp) and rapid rate of synthesis (750 nts/s) (reviewed in Kornberg and Baker, 1992; Kelman and O'Donnell, 1995). The high processivity and speed is rooted in a ring shaped subunit, called β, that encircles DNA and slides along it while tethering the Pol III holoenzyme to the template (Stukenberg et al., 1991; Kong et al., 1992). The ring shaped β clamp is assembled around DNA by the multisubunit clamp loader, called γ complex. The γ complex couples the energy of ATP hydrolysis to the assembly of the β clamp onto DNA. This γ complex, which functions as a clamp loader, is an integral component of the Pol III holoenzyme particle. A brief overview of the organization of subunits within the holoenzyme and their function follows.

Pol III holoenzyme consists of 10 different subunits, some of which are present in multiple copies for a total of 18 polypeptide chains (Onrust et al., 1995). The organization of these subunits in the holoenzyme particle is illustrated in FIG. 1. As depicted in the diagram, the subunits of the holoenzyme can be grouped functionally into three components: 1) the DNA polymerase III core is the catalytic unit and consists of the α (DNA polymerase), ϵ (3'-5' exonuclease), and θ subunits (McHenry and Crow, 1979), 2) the β "sliding clamp" is the ring shaped protein that secures the core polymerase to DNA for processivity (Kong et al., 1992), and 3) the 5 protein γ complex (γδδ'χψ) is the "clamp loader" that couples ATP hydrolysis to assembly of β clamps around DNA (O'Donnell, 1987; Maki et al., 1988). A dimer of the τ subunit acts as a "macromolecular organizer" holding together two molecules of core (Studwell-Vaughan and O'Donnell, 1991; Low et al., 1976) and one molecule of γ complex forming the Pol III* subassembly (Onrust et al., 1995). This organizing role of τ to form Pol III* is indicated in the center of FIG. 1. Two β dimers associate with the two cores within Pol III* to form the holoenzyme, which is capable of replicating both strands of duplex DNA simultaneously (Maki et al., 1988).

The DNA polymerase III holoenzyme assembles onto a primed template in two distinct steps. In the first step, the γ complex assembles the β clamp onto the DNA. The γ complex and the core polymerase utilize the same surface of the β ring and they cannot both utilize it at the same time (Naktinis et al., 1996). Hence, in the second step the γ complex moves away from β thus allowing access of the core polymerase to the β clamp for processive DNA synthesis. The γ complex and core remain attached to each other during this switching process by the τ subunit organizer.

The γ complex consists of 5 different subunits ($\gamma_{2-4}\delta_1\delta'_1\chi_1\psi_1$). An overview of the mechanism of the clamp loading process follows. The δ subunit is the major touch point to the β clamp and leads to ring opening, but δ is buried within γ complex such that contact with β is prevented (Naktinis et al., 1995). The γ subunit is the ATP interactive protein but is not an ATPase by itself (Tsuchihashi and Kornberg, 1989). The δ' subunit bridges the δ and γ subunits resulting in a γδδ' complex that exhibits DNA dependent ATPase activity and is competent to assemble clamps on DNA (Onrust et al., 1991). Upon binding of ATP to γ, a change in the conformation of the complex exposes δ for interaction with β (Naktinis et al., 1995). The function of the smaller subunits, χ and ψ, is to contact SSB (through χ) thus promoting clamp assembly and high processivity during replication (Kelman and O'Donnell, 1995).

The three component Pol III-type enzyme in eukaryotes contains a clamp that has the same shape as *E. coli* β, but instead of a homodimer it is a heterotrimer. This heterotrimeric ring, called PCNA (proliferating cell nuclear antigen), has 6 domains like β, but instead of each PCNA monomer being composed of 3 domains and dimerizing to form a 6 domain ring (e.g., like β), the PCNA monomer has 2 domains and it trimerizes to form a 6 domain ring (Krishna et al., 1994; Kuriyan and O'Donnell, 1993). The chain fold of the domains are the same in prokaryotes (β) and eukaryotes (PCNA); thus, the rings have the same overall 6-domain ring shape. The clamp loader of the eukaryotic Pol III-type replicase is called RFC (Replication factor C) and it consists of subunits having homology to the γ and δ' subunits of the *E. coli* γ complex (Cullmann et al., 1995). The eukaryotic DNA polymerase III-type enzyme contains either of two DNA polymerases, DNA polymerase δ and DNA polymerase ϵ (Bambara and Jessee, 1991; Linn, 1991; Sugino, 1995). It is entirely conceivable that yet other types of DNA polymerases can function with either a PCNA or β clamp to form a Pol III-type enzyme (for example, DNA polymerase II of *E. coli* functions with the β subunit placed onto DNA by the γ complex clamp loader) (Hughes et al., 1991; Bonner et al., 1992). The bacteriophage T4 also utilizes a Pol III-type 3-component replicase. The clamp is a homotrimer like PCNA, called gene 45 protein (Young et al., 1992). The gene 45 protein forms the same 6-domain ring structure as β and PCNA (Moarefi et al., 2000). The clamp loader is a complex of two subunits called the gene 44/62 protein complex. The DNA polymerase is the gene 43 protein and it is stimulated by the gene 45 sliding clamp when it is assembled onto DNA by the 44/62 protein clamp loader. The Pol III-type enzyme may be either bound together into one particle (e.g., *E. coli* Pol III holoenzyme), or its three components may function separately (like the eukaryotic Pol III-type replicases).

There is an early report on separation of three DNA polymerases from *T.th.* cells, however each polymerase form was reminiscent of the preexisting types of DNA polymerase isolated from thermophiles in that each polymerase was in the 110,000–120,000 range and lacked 3'-5' exonuclease activity (Ruttimann et al., 1985). These are well below the molecular weight of Pol III-type complexes that contain in addition to the DNA polymerase subunit, other subunits such as γ and τ. Although the three polymerases displayed some differences in activity (column elution behavior, and optimum divalent cation, template, and temperatures) it seems likely that these three forms were either different repair type polymerases or derivatives of one repair enzyme (e.g., Pol I) that was modified by post translational modification(s) that altered their properties (e.g. phosphorylation, methylation, proteolytic clipping of residues that alter activity, or association with different ligands such as a small protein or contaminating DNA). Despite this previous work, it remained to be demonstrated that thermophiles harbor a Pol III-type enzyme that contain multiple subunits such as γ and/or τ, functioned with a sliding clamp accessory protein, or could extend a primer rapidly and processively over a long stretch (>5 kb) of ssDNA (Ruttimann et al., 1985).

Previously, it was not known what polymerase thermophilic bacteria used to replicate their chromosome since only Pol I type enzymes have been reported from thermophiles. By distinction, chromosomal replicases, such as Polymerase III, identified in *E. coli*, if available in a thermostable bacterium, with all its accessory subunits, could provide a great improvement over the Polymerase I type enzymes, in that they are generally much more efficient—about 5 times faster—and much more highly processive. Hence, one may expect faster and longer chain production in PCR, and higher quality of DNA sequencing ladders. Clearly, the ability to practice such synthetic techniques as PCR would be enhanced by these methods disclosed for how to obtain genes and subunits of DNA polymerase III holoenzyme from thermophilic sources.

The present invention is directed to achieving these objectives and overcoming the various deficiencies in the art.

SUMMARY OF THE INVENTION

In accordance with the present invention, DNA Polymerase III-type enzymes as defined herein are disclosed that may be isolated and purified from a thermophilic bacterial source, that display rapid synthesis characteristic of a chromosomal replicase, and that possesses all of the structural and processive advantages sought and recited above. More particularly, the invention extends to thermostable Polymerase III-type enzymes derived from thermophilic bacteria that exhibit the ability to extend a primer over a long stretch (>5 kb) of ssDNA at elevated temperature, the ability to be stimulated by a cognate sliding clamp (e.g., β) of the type that is assembled on DNA by a 'clamp' loader (e.g., γ complex), and have clamp loading subunits that show DNA stimulated ATPase activity at elevated temperature and/or ionic strength. Representative thermophile polymerases include those isolated from the thermophilic eubacteria *Aquifex aeolicus* (*A.ae.* polymerase) and other members of the Aquifex genus; *Thermus thermophilus* (*T.th.* polymerase), *Thermus favus* (*Tfl*/Tub polymerase), *Thermus ruber* (*Tru* polymerase), *Thermus brockianus* (DYNAZYME™ polymerase), and other members of the Thermus genus; *Bacillus stearothermophilus* (*B.st.* polymerase) and other members of the Bacillus genus; *Thermoplasma acidophilum* (*Tac* polymerase) and other members of the Thermoplasma genus; and *Thermotoga neapolitana* (*Tne* polymerase; see WO 96/10640 to Chatterjee et al.), *Thermotoga maritima* (*Tma* polymerase; see U.S. Pat. No. 5,374,553 to Gelfand et al.), and other species of the Thermotoga genus (Tsp polymerase). In a preferred embodiment, the thermophilic bacteria comprise species of Aquifex, Thermus, Bacillus, and Thermotoga, and particularly *A.ae., T.th., B.st.*, and *Tma.*

A particular Polymerase III-type enzyme in accordance with the invention may include at least one of the following subunits:

A. a γ subunit having an amino acid sequence corresponding to SEQ. ID. Nos. 4 or 5 (*T.th.*);

B. a τ subunit having an amino acid sequence corresponding to SEQ. ID. No. 2 (*T.th.*), SEQ. ID. No. 120 (*A.ae.*), SEQ. ID. No. 142 (*T.ma.*) or SEQ. ID. No. 182 (*B.st.*);

C. a ϵ subunit having an amino acid sequence corresponding to SEQ. ID. No. 95 (*T.th.*), SEQ. ID. No. 128 (*A.ae.*), or SEQ. ID. No. 140 (*T.ma.*);

D. a α subunit including an amino acid sequence corresponding to SEQ. ID. No. 87 (*T.th.*), SEQ. ID. No. 118 (*A.ae.*), SEQ. ID. No. 138 (*T.ma.*), or SEQ. ID. Nos. 184 (PolC which has both α and ϵ activity, *B.st.*);

E. a β subunit having an amino acid sequence corresponding to SEQ. ID. No. 107 (*T.th.*), SEQ. ID. No. 122 (*A.ae.*), SEQ. ID. No. 144 (*T.ma.*), or SEQ. ID. No. 174 (*B.st.*), F. a δ subunit having an amino acid sequence corresponding to SEQ. ID. No. 158 (*T.th.*), SEQ. ID. No. 124 (*A.ae.*), SEQ. ID. No. 146 (*T.ma.*) or SEQ. ID. No. 178 (*B.st.*);

G. a δ' subunit having an amino acid sequence corresponding to SEQ. ID. No. 156 (*T.th.*), SEQ. ID. No. 126 (*A.ae.*), SEQ. ID. No. 148 (*T.ma.*) or SEQ. ID. No. 180 (*B.st.*);

variants, including allelic variants, muteins, analogs and fragments of any of subparts (A) through (G), and compatible combinations thereof, capable of functioning in DNA amplification and sequencing.

The invention also extends to the genes that correspond to and can code on expression for the subunits set forth above, and accordingly includes the following: dnaX, holA, holB, dnaQ, dnaE, dnaN, and ssb, as well as conserved variants and active fragments thereof.

Accordingly, the Polymerase III-type enzyme of the present invention comprises at least one gene encoding a subunit thereof, which gene is selected from the group consisting of dnaX, holA, holB, dnaQ, dnaE and dnaN, and combinations thereof. More particularly, the invention extends to the nucleic acid molecule encoding the γ and τ subunits, and includes the dnaX gene which has a nucleotide sequence as set forth herein, as well as conserved variants, active fragments and analogs thereof. Likewise, the nucleotide sequences encoding the α subunit (dnaE gene), the ϵ subunit (dnaQ gene), the β subunit (dnaN gene), the δ subunit (holA gene), and the δ' subunit (holB gene) each comprise the nucleotide sequences as set forth herein, as well as conserved variants, active fragments and analogs thereof. Those nucleotide sequences for *T.th.* are as follows: dnaX (SEQ. ID. No. 3), dnaE (SEQ. ID. No. 86), dnaQ (SEQ. ID. No. 94), dnaN (SEQ. ID. No. 106), holA (SEQ. ID. No. 157), and holB (SEQ. ID. No. 155). Those nucleotide sequences for *A.ae.* are as follows: dnaX (SEQ. ID. No. 119), dnaE (SEQ. ID. No. 117), dnaQ (SEQ. ID. No. 127), dnaN (SEQ. ID. No. 121), holA (SEQ. ID. No. 123), and holB (SEQ. ID. No. 125). Those nucleotide sequences for *T.ma.* are as follows: dnaX (SEQ. ID. No. 141), dnaE (SEQ. ID. No. 137), dnaQ (SEQ. ID. No. 139), dnaN (SEQ. ID. No. 143), holA (SEQ. ID. No. 145), and holB (SEQ. ID. No. 147). Those nucleotide sequences for *B.st.* are as follows: dnaX (SEQ. ID. No. 181), polC (SEQ. ID. Nos. 183), dnaN (SEQ. ID. No. 173), holA (SEQ. ID. No. 177), and holB (SEQ. ID. No. 179).

The invention also provides methods and products for identifying, isolating and cloning DNA molecules which encode such accessory subunits encoded by the recited genes of the DNA polymerase III-type enzyme hereof.

Yet further, the invention extends to Polymerase III-type enzymes prepared by the purification of an extract taken from, e.g., the particular thermophile under examination, treated with appropriate solvents and then subjected to chromatographic separation on, e.g., an anion exchange column, followed by analysis of long chain synthetic ability or Western analysis of the respective peaks against antibody to at least one of the anticipated enzyme subunits to confirm presence of Pol III, and thereafter, peptide sequencing of subunits that co purify and amplification to obtain the putative gene and its encoded enzyme.

The present invention also relates to recombinant γ, τ, ϵ, α (as well as PolC), δ, δ' and β subunits and SSB from thermophiles. In the instance of the γ and τ subunits of *T.th.*, the invention includes the characterization of a frameshifting sequence that is internal to the gene and specifies relative abundance of the γ and τ gene products of *T.th.* dnaX. From this characterization, expression of either one of the subunits can be increased at the expense of the other (i.e. mutant frameshift could make all τ, simple recloning at the end of the frameshift could make exclusively γ and no τ).

In a further aspect of the present invention, DNA probes can be constructed from the DNA sequences coding for, e.g., the *T.th., A.ae., T.ma.*, or *B.st.* dnaX, dnaQ, dnaE, dnaA, dnaN, holA, holB, and ssb genes, conserved variants and active fragments thereof, all as defined herein, and may be used to identify and isolate the corresponding genes coding for the subunits of DNA polymerase III holoenzyme from other thermophiles, such as those listed earlier herein. Accordingly, all chromosomal replicases (DNA Polymerase III-type) from thermophilic sources are contemplated and included herein.

The invention also extends to methods for identifying Polymerase III-type enzymes by use of the techniques of long-chain extension and elucidation of subunits with antibodies, as described herein and with reference to the examples.

The invention further extends to the isolated and purified DNA Polymerase III from *T.th., A.ae., T.ma.*, and *B.st.*, the amino acid sequences of the γ, τ, ϵ, α (as well as PolC), δ, δ', and β subunits and SSB, as set forth herein, and the nucleotide sequences of the corresponding genes from *T.th., A.ae., T.ma.*, or *B.st.* set forth herein, as well as to active fragments thereof, oligonucleotides and probes prepared or derived therefrom and the transformed cells that may be likewise prepared. Accordingly, the invention comprises the individual subunits enumerated above and hereinafter, corresponding isolated polynucleotides and respective amino acid sequences for each of the γ, τ, ϵ, α (as well as PolC), δ, δ', and β subunits and SSB, and to conserved variants, fragments, and the like, as well as to methods of their preparation and use in DNA amplification and sequencing. In a particular embodiment, the invention extends to vectors for the expression of the subunit genes of the present invention.

The invention also includes methods for the preparation of the DNA Polymerase III-type enzymes and the corresponding subunit genes of the present invention, and to the use of the enzymes and constructs having active fragments thereof, in the preparation, reconstitution or modification of like enzymes, as well as in amplification and sequencing of DNA by methods such as PCR, and like protocols, and to the DNA molecules amplified and sequenced by such methods. In this regard, a Pol III-type enzyme that is reconstituted in the absence of ϵ, or using a mutated ϵ with less 3'-5' exonuclease activity, may be a superior enzyme in either PCR or DNA sequencing applications, (e.g. Tabor et al., 1995).

The invention is directed to methods for amplifying and sequencing a DNA molecule, particularly via the polymerase chain reaction (PCR), using the present DNA polymerase III-type enzymes or complexes. In particular, the invention extends to methods of amplifying and sequencing of DNA using thermostable pol III-type enzyme complexes isolated from thermophilic bacteria such as Thermotoga and Thermus species, or recombinant thermostable enzymes. The invention also provides amplified DNA molecules made by the methods of the invention, and kits for amplifying or sequencing a DNA molecule by the methods of the invention.

In this connection, the invention extends to methods for amplification of DNA that can achieve long chain extension of primed DNA, as by the application and use of Polymerase III-type enzymes of the present invention. An illustration of such methods is presented in Examples 15 and 16, infra.

Likewise, kits for amplification and sequencing of such DNA molecules are included, which kits contain the enzymes of the present invention, including subunits thereof, together with other necessary or desirable reagents and materials, and directions for use. The details of the practice of the invention as set forth above and later on herein, and with reference to the patents and literature cited herein, are all expressly incorporated herein by reference and made a part hereof.

As stated, and in accordance with a principal object of the present invention, Polymerase III-type enzymes and their sub-units are provided that are derived from thermophiles and that are adapted to participate in improved DNA amplification and sequencing techniques, and the consequent ability to prepare larger DNA strands more rapidly and accurately.

It is a further object of the present invention to provide DNA molecules that are amplified and sequenced using the Polymerase III-type enzymes hereof.

It is a still further object of the present invention to provide enzymes and corresponding methods for amplification and sequencing of DNA that can be practiced without the participation of the clamp-loading component of the enzyme.

It is a still further object of the present invention to provide kits and other assemblies of materials for the practice of the methods of amplification and sequencing as aforesaid, that include and use the DNA polymerase III-type enzymes herein as part thereof.

One goal of this invention is to fully reconstitute the rapid and processive replicase from an extreme thermophilic eubacterium from fully recombinant protein subunits. One might think that the extreme heat in which these bacteria grow may have resulted in a completely different solution to the problem of chromosome replication. Prior to filing of the previously-identified priority applications, it is believed that Pol III had not been identified in any thermophile until the present inventors found that *Thermus thermophilus*, which grows at a rather high temperature of 70–80° C., would appear to contain a Pol III. Subsequent to this invention, the genome sequence of *A. aeolicus* was published which shows dnaE, dnaN, and dnaX genes. However, previous work did not fully reconstitute the working replication machinery from fully recombinant subunits. A holA gene and holB has not been identified previously in *T. thermophilus* or *A. aeolicus*, and studies in the *E. coli* system show that delta and delta prime, encoded by holA and holB, respectively, are essential to loading the beta clamp onto DNA and, thus, is essential for rapid and processive holoenzyme function (U.S. Pat. Nos. 5,583,026 and 5,668,004 to O'Donnell, which are hereby incorporated by reference).

This invention fully reconstitutes a functional DNA polymerase III holoenzyme from the extreme thermophiles *Thermus thermophilus* and *Aquifex aeolicus*. *Aquifex aeolicus* grows at an even higher temperature than *Thermus thermophilus*, up to 85° C. In this invention, the genes of *Thermus thermophilus, Aquifex aeolicus, Thermotoga maritima*, and *Bacillus stearothermophilus* that are necessary to reconstitute the complete DNA polymerase III machinery, which acts as a rapid and processive polymerase, are identified. Indeed, a delta prime (holB) and delta (holA) subunits are needed.

The dnaE, dnaN, dnaX, dnaQ, holA, and holB genes are used to express and purify the protein "gears", and the proteins are used to reassemble the replication machine. The *T.th.* Pot III is similar to *E. coli*. The *A.ae.* Pol III is slightly dissimilar from the machinery of previously studied replicases. The *A.ae.* dnaX gene encoded only one protein, tau, and in this fashion is similar to the dnaX of the gram positive organism, *Staphylococcus aureus*. In contrast, the dnaX of the gram negative cell, *E. coli*, produces two proteins. The *Aquifex aeolicus* polymerase subunit, alpha (encoded by dnaE) does not contain the 3'-5' proofreading exonuclease. In this regard, *A. aeolicus* is similar to *E. coli*, but dissimilar to the replicase of the gram positive organisms. In Gram positive organisms, the PolC polymerase subunit of the replicase contains the exonuclease activity in the same polypeptide chain as the polymerase (Low et al., 1976; Barnes et al., 1994; Pacitti et al., 1995). Further, the polymerase III of thermophilic bacteria retains activity at high temperature.

Thermostable rapid and processive three component DNA polymerases can be applied to several important uses. DNA polymerases currently in use for DNA sequencing and DNA amplification use enzymes that are much slower and thus could be improved upon. This is especially true of amplification as the three component polymerase is capable of speed and high processivity making possible amplification of very long (tens of Kb to Mb) lengths of DNA in a time-efficient manner. These three component polymerases also function in conjunction with a replicative helicase (DnaB), and thus are capable of amplification at a single temperature, using the helicase to melt the DNA duplex. This property could be useful in some methods of amplification, and in polymerase chain reaction (PCR) methodology. For example, the $\alpha\tau\delta\delta'/\beta$ form of the *E. coli* DNA polymerase III holoenzyme has been shown to function in both DNA sequencing and PCR (U.S. Pat. Nos. 5,583,026 and 5,668,004 to O'Donnell).

Other objects and advantages will become apparent from a review of the ensuing description which proceeds with reference to the following illustrative drawings.

DESCRIPTION OF THE DRAWINGS

FIG. 2 is an alignment of the N-terminal regions of *E. coli* (SEQ. ID. No. 19) and *B. subtilis* (SEQ. ID. No. 20) dnaX gene product. Asterisks indicate identities. The ATP binding consensus sequence is indicated. The two regions used for PCR primer design are shown in bold.

FIGS. 4A and 4B depict the full sequence of the dnaX gene of *T. thermophilus*. DNA sequence (upper case, and corresponding to SEQ ID No. 1) and predicted amino acid sequence (lower case, and corresponding to SEQ ID No. 2) yields a 529 amino acid protein ($\tau$) of 58.0 kDa. A putative frameshifting sequence containing several A residues 1478–1486 (underlined) may produce a smaller protein ($\gamma$) of 49.8 kDa. The potential Shine-Dalgarno (S.D.) signal is bold and underlined. The start codon is in bold, and the stop codon for $\tau$ is marked by an asterisk. The potential stop codon for $\gamma$ is shown in bold after the frameshift site, and two potential Shine-Dalgarno sequences upstream of the frameshift site are indicated. Sequences of the primers used for PCR are shown in italics above the nucleotide sequence of dnaX. The ATP binding site is indicated, and the asterisks above the four Cys residues near the ATP site indicate the putative $Zn^{2+}$ finger. The proline rich area is indicated above the sequence. Numbering of the nucleotide sequence is presented to the right. Numbering of the amino acid sequence of τ is shown in parenthesis to the right.

FIG. 4C depicts the isolated DNA coding sequence for the dnaX gene (also present in FIGS. 4A and 4B) in accordance with the invention, which corresponds to SEQ. ID. No. 3.

FIG. 4D depicts the polypeptide sequence of the γ subunit of the Polymerase III of the present invention, which corresponds to SEQ. ID. No. 4.

FIG. 4E depicts the polypeptide sequence of the γ subunit of the Polymerase III of the present invention defined by a −1 frameshift, which corresponds to SEQ. ID. No. 4.

FIG. 4F depicts the polypeptide sequence of the γ subunit of the Polymerase III of the present invention defined by a −2 frameshift, which corresponds to SEQ. ID. No. 5.

FIGS. 5A–B are alignments of the γ/τ ATP binding domains for different bacteria. Dots indicate those residues that are identical to the *E. coli* dnaX sequence. The ATP consensus site is underlined, and the conserved cysteine residues that form the zinc finger are indicated with asterisks. *E. coli, Escherichia coli* (SEQ. ID. No. 21); *H. inf., Haemophilus influenzae* (SEQ. ID. No. 22); *B. sub., Bacillus subtilis* (SEQ. ID. No. 23); *C. cres., Caulobacter crescentus* (SEQ. ID. No. 24); *M. gen., Mycoplasma genitalium* (SEQ. ID. No. 25); *T.th., Thermus thermophilus* (SEQ. ID. No. 26). Alignments were produced using Clustal.

FIG. 14A is a 12% SDS polyacrylamide gel stained with Coomassie Blue of the MonoQ column. Load stands for the material loaded onto the column (ATP agarose bound fractions). FT stands for protein that flowed through the MonoQ column. Fractions are indicated above the gel. *T.th.* subunits in fractions 17–19 are indicated by the labels placed between fractions 18 and 19. Additional small subunits may be present but difficult to visualize, or may have run off the gel. *E. coli* γ,δ shows a mixture of the α,γ, and δ subunits of DNA polymerase III holoenzyme (they are labeled to the right in the figure). FIG. 14B shows the Western results of an SDS gel of the MonoQ fractions probed with rabbit antiserum raised against the *E. coli* α subunit. Load and FT are as described in Panel A. Fraction numbers are shown above the gel. The band that comigrates with *E coli* α, and the band in the Coomassie Blue stained gel in Panel A, is marked with an arrow. This band was analyzed for microsequence and the results are shown in FIG. 15.

FIGS. 15A–B show the alignments of the peptides obtained from *T.th.* α subunit, TTH1 (shown in A) and TTH2 (shown in B) with the amino acid sequences of the α subunits of other organisms. The amino acid number of these regions within each respective protein sequence are shown to the right. The abbreviations of the organisms are as follows. *E.coli—Escherichia coli* (SEQ ID NOS: 72 and 79 in 15A–B, respectively), *V.chol.—Vibrio cholerae* (SEQ ID NOS: 73 and 80 in 15A–B, respectively), *H. inf.—Haemophilus influenzae* (SEQ ID NOS: 74 and 81 in 15A–B, respectively), *R.prow.—Rickettsia prowazekii* (SEQ ID NOS: 75 and 82 in 15A–B, respectively), *H.pyl.—Helicobacter pylori* (SEQ ID NOS: 76 and 83 in 15A–B, respectively), S.sp.—Synechocystis sp. (SEQ ID NOS: 77 and 84 in 15A–B, respectively), *M.tub.—Mycobacterium tuberculosis* (SEQ ID NOS: 78 and 85 in 15A–B, respectively), *T.th.—Thermus thermophilus* (SEQ ID NOS: 61 and 60 in 15A–B, respectively).

FIGS. 16A–C show a nucleotide (Panels A–B, SEQ. ID. No. 86) and amino acid (Panel C, SEQ. ID. No. 87) sequence of the dnaE gene encoding the α subunit of DNA polymerase III replication enzyme.

FIG. 17 shows an alignment of the amino acid sequence of ε subunits encoded by dnaQ of several organisms. The amino acid sequence of the *Thermus thermophilus* ε subunit of dnaQ is also shown. *T.th., Thermus thermophilus* (SEQ. ID. No. 88); *D.rad., Deinococcus radiodurans* (SEQ. ID. No. 89); *Bac.sub., Bacillus subtilis* (SEQ. ID. No. 90); *H.inf., Haemophilus influenzae* (SEQ. ID. No. 91); *E.c., Escherichia coli* (SEQ. ID. No. 92); *H.pyl., Helicobacter pylori* (SEQ. ID. No. 93). The regions used to obtain the inner part of the dnaQ gene are shown in bold. The starts used for expression of the *T.th.* ε subunit are marked.

FIGS. 18A–B show the nucleotide (Panel A, SEQ. ID. No. 94) and amino acid (Panel B , SEQ. ID. No. 95) sequence of the dnaQ gene encoding the ε subunit of DNA polymerase III replication enzyme.

FIGS. 19A–B show an alignment of the DnaA protein of several organisms. The amino acid sequence of the *Thermus thermophilus* DnaA protein is also shown. *P.mar., Pseudomonas marcesans* (SEQ. ID. No. 96); Syn.sp., Synechocystis sp. (SEQ. ID. No. 97); *Bac.sub., Bacillus subtilis* (SEQ. ID. No. 98); *M. tub; Mycobacterium tuberculosis* (SEQ. ID. No. 99); *T.th., Thermus thermophilus* (SEQ. ID. No. 100); *E.coli., Escherichia coli* (SEQ. ID. No. 101); *T. mar., Thermaloga maritima* (SEQ. ID. No. 102); and *H.pyl., Helicobacter pylori* (SEQ. ID. No. 103).

FIGS. 20A–B show the nucleotide (Panel A, SEQ. ID. No. 104) and amino acid (Panel B , SEQ. ID. No. 105) sequence of the dnaA gene of *Thermus thermophilus.*

FIGS. 21A–B show the nucleotide (Panel A, SEQ. ID. No. 106) and amino acid (Panel B , SEQ. ID. No. 107) sequence of the dnaN gene encoding the β subunit of DNA polymerase III replication enzyme.

FIGS. 22A–B show an alignment of the β subunit of *T.th.* to the β subunits of other organisms. *T.th., Thermus thermophilus* (SEQ. ID. No. 108); *E. coli, Escherichia coli* (SEQ. ID. No. 109); *P. mirab, Proteus mirabilis* (SEQ. ID. No. 110); *H. infl, Haemophilus influenzae* (SEQ. ID. No. 111); *P. put., Pseudomonas putida* (SEQ. ID. No. 112); and *B. cap., Buchnera aphidicola* (SEQ. ID. No. 113).

Figure 23:
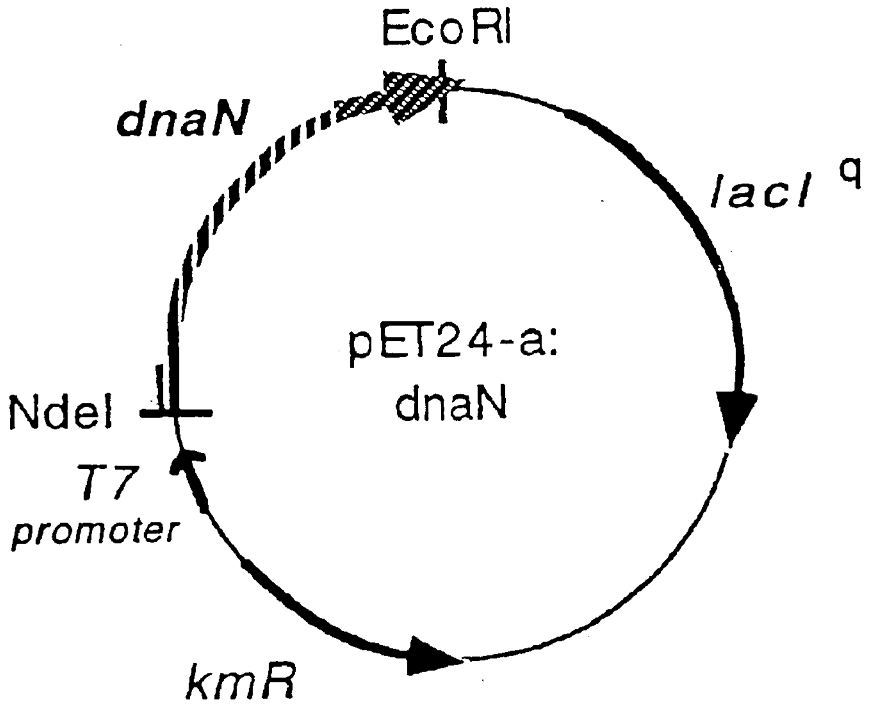

FIG. 23 is a map of the pET24:dnaN plasmid. The functional regions of the plasmid are indicated by arrows and italic, restriction sites are marked with bars and symbols. The hatched parts in the plasmid correspond to *T.th.* dnaN.

FIGS. 24A–B show the induction of *T.th.* β in *E. coli* cells harboring the *T.th.* β expression vector. Panel A is the cell induction. The first lane shows molecular weight markers (MW). The second lane shows uninduced *E. coli* cells, and the third lane shows induced *E. coli*. The induced *T.th.* β is indicated by the arrow shown to the left. Induced cells were lysed then treated with heat and the soluble portion was chromatographed on MonoQ. Panel B shows the results of MonoQ purification of *T.th.* β.

FIG. 25A is a schematic depiction of the use of the use of the enzymes of the present invention in accordance with an alternate embodiment hereof. In this scheme the clamp (β or PCNA) slides over the end of linear DNA to enhance the polymerase (Pol III-type such as Pol III, Polβ or Polδ.) In this fashion the clamp loader activity is not needed.

FIG. 25B graphically demonstrates the results of the practice of the alternate embodiment of the invention described and set forth in Example 15, infra. Lane 1*, E. coli* Pol III without β; Lane 2*, E. coli* with β; Lane 3, human Polδ without PCNA; Lane 4, human Polδ with PCNA; Lane 5*, T.th.* Pol III without *T.th.* β; Lane 6*, T.th.* Pol III with *T.th.* β. The respective pmol synthesis in lanes 1–6 are: 6, 35, 2, 24, 0.6 and 1.9.

FIGS. 26A–B show the use of *T.th.* Pol III in extending singly primed M13mp18 to an RFII form. The scheme in FIG. 26A shows the primed template in which a DNA 57mer was annealled to the M13mp18 ssDNA circle. Then *T.th.* β subunit (produced recombinantly) and *T.th.* Pol III were added to the DNA in the presence of radioactive nucleoside triphosphates. In FIG. 26B, the products of the reaction were analyzed in a 0.8% native agarose gel. The position of ssDNA starting material, the RFII product, and of intermediate species, are shown to the sides of the gel. Lane 1, use of Pol III. Lane 2, use of the non-Pol III DNA polymerase.

Figure 27:
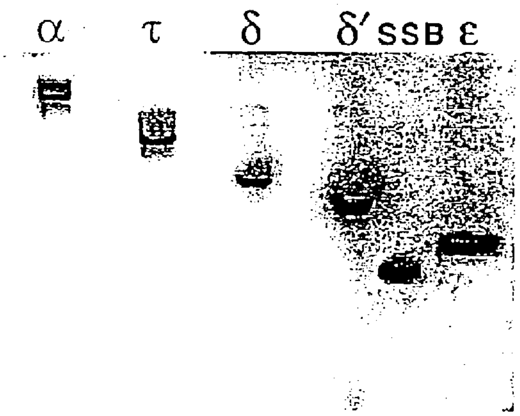

FIG. 27 is an SDS polyacrylamide gel of the proteins of the *A. aeolicus* replication machinery.

Figure 28:
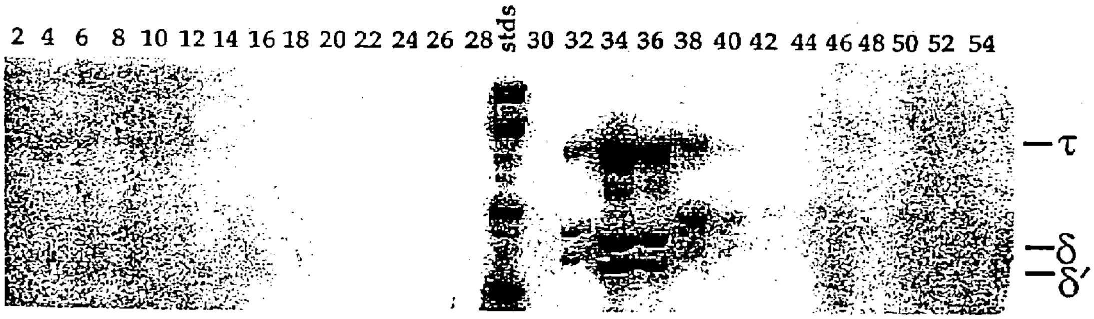

FIG. 28 is an SDS polyacrylamide gel analysis of the MonoQ fractions of the method used to reconstitute and purify the *A. aeolicus* τδδ' complex.

Figure 29:
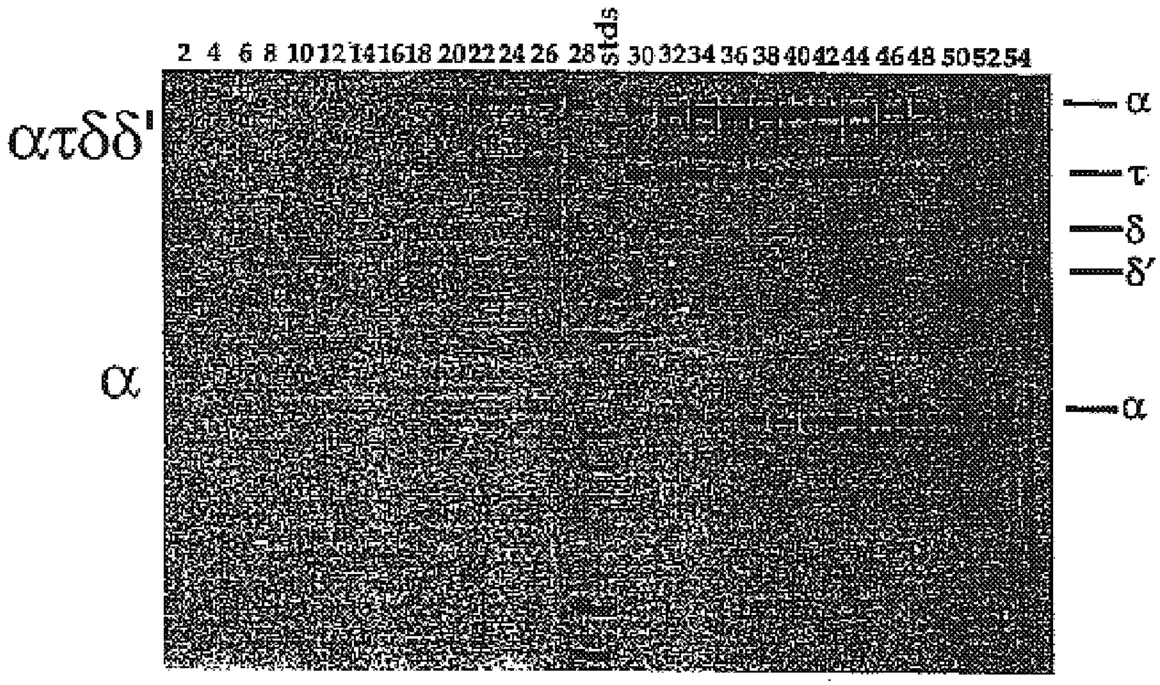

FIG. 29 is an SDS polyacrylamide gel analysis of the gel filtration column fractions used in the preparation of the *A. aeolicus* ατδδ' complex. The bottom gel analysis shows the profile obtained using the *A. aeolicus* α subunit (polymerase) in the absence of the other subunits.

Figure 30:
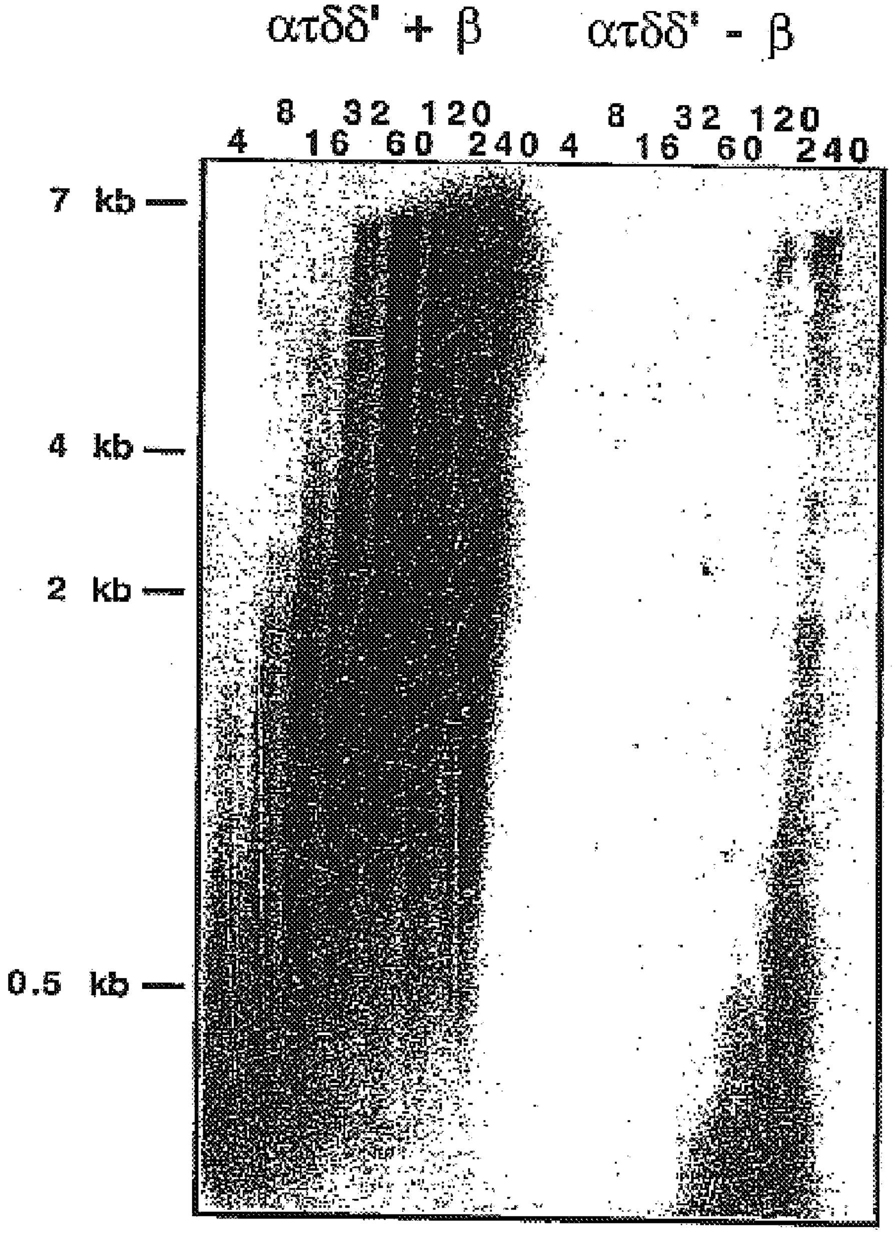

FIG. 30 is an alkaline agarose gel analysis of reaction products for extension of a single primer around a 7.2 kb M13mp18 circular ssDNA genome that has been coated with *A. aeolicus* SSB. The time course on the left are produced by ατδδ'/β, and the time course on the right is produced by ατδδ' in the absence of β.

Figure 31:
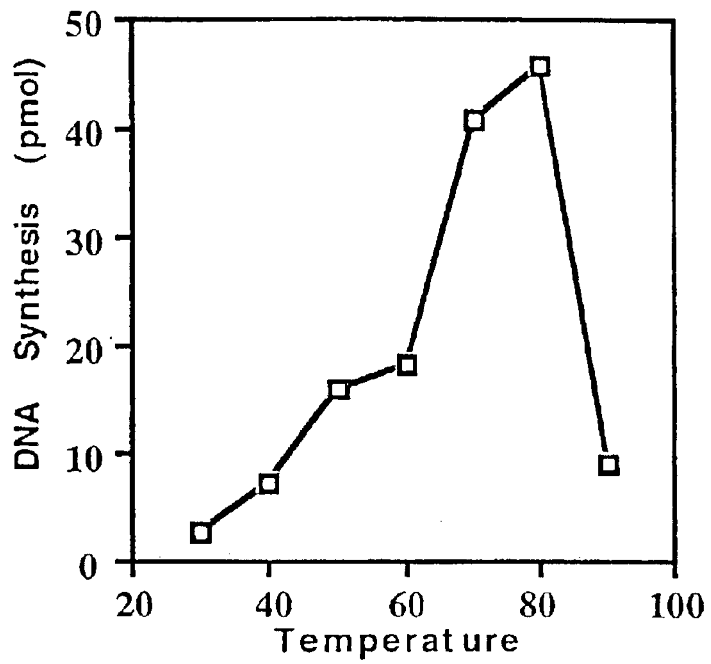

FIG. 31 is a graph illustrating the optimal temperature for activity of the alpha subunit of Thermus replicase using a calf thymus DNA replication assay. Reactions were shifted to the indicated temperature for 5 minutes before detecting the level of DNA synthesis activity.

Figure 32:
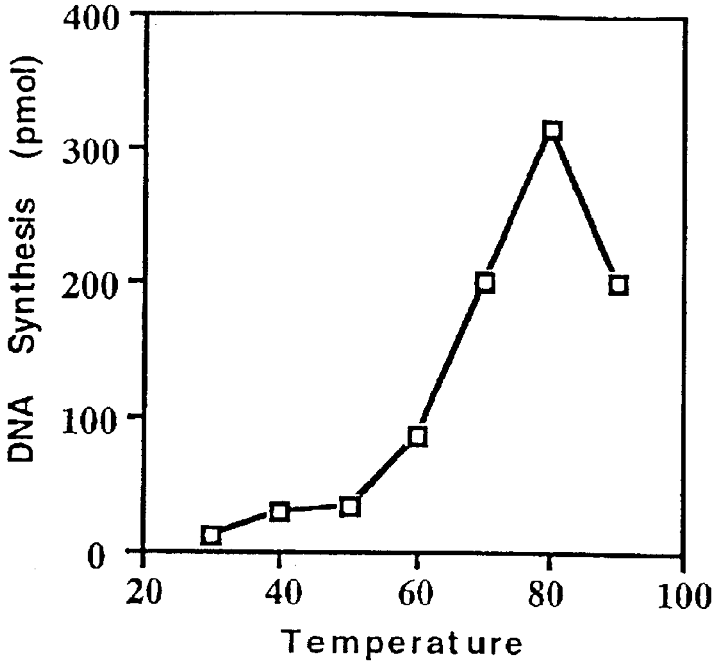

FIG. 32 is a graph illustrating the optimal temperature for activity of the alpha subunit of the Aquifex replicase using a calf thymus DNA replication assay. Reactions were shifted to the indicated temperature for 5 minutes before detecting the level of DNA synthesis activity.

FIGS. 33A–E illustrate the heat stability of Aquifex components. Assays of either α (FIG. 33A), β (FIG. 33B), τδδ' complex (FIG. 33C), SSB (FIG. 33D) and ατδδ' complex (FIG. 33E) were performed after heating samples at the indicated temperatures. Components were heated in buffer containing the following: 0.1% Triton X-100 (filled diamonds); 0.05% Tween-20 and 0.01% NP-40 (filled circles); 4 mM $CaCl_2$ (filled triangles); 40% Glycerol (inverted filled triangles); 0.01% Triton X-100, 0.05% Tween-20, 0.01% NP-40, 4 mM $CaCl_2$ (half-filled square); 40% Glycerol, 0.1% Triton X-100 (open diamonds); 40% Glycerol, 0.05% Tween-20, 0.01% NP-40 (open circles); 40% Glycerol, 4 mM $CaCl_2$ (open triangles); 40% Glycerol, 0.01% Triton X-100, 0.05% Tween-20, 0.01% NP-40, 4 mM $CaCl_2$ (half-filled diamonds).

FIGS. 34A–B show the nucleotide sequence (SEQ. ID. No. 117) of the dnaE gene of *A. aeolicus.*

FIG. 35 shows the amino acid sequence (SEQ. ID. No. 118) of the α subunit of *A. aeolicus.*

FIG. 36 shows the nucleotide sequence (SEQ. ID. No. 119) of the dnaX gene of *A. aeolicus.*

FIG. 37 shows the amino acid sequence (SEQ. ID. No. 120) of the tau subunit of *A. aeolicus.*

FIG. 38 shows the nucleotide sequence (SEQ. ID. No. 121) of the dnaN gene of *A. aeolicus.*

FIG. 39 shows the amino acid sequence (SEQ. ID. No. 122) of the β subunit of *A. aeolicus.*

FIG. 40 shows the partial nucleotide sequence (SEQ. ID. No. 123) of the holA gene of *A. aeolicus.*

FIG. 41 shows the partial amino acid sequence (SEQ. ID. No. 124) of the δ subunit of *A. aeolicus.*

FIG. 42 shows the nucleotide sequence (SEQ. ID. No. 125) of the holB gene of *A. aeolicus.*

FIG. 43 shows the amino acid sequence (SEQ. ID. No. 126) of the δ subunit of *A. aeolicus.*

FIG. 44 shows the nucleotide sequence (SEQ. ID. No. 127) of the dnaQ of *A. aeolicus.*

FIG. 45 shows the amino acid sequence (SEQ. ID. No. 128) of the ε subunit of *A. aeolicus.*

FIG. 46 shows the nucleotide sequence (SEQ. ID. No. 129) of the ssb gene of *A. aeolicus.*

FIG. 47 shows the amino acid sequence (SEQ. ID. No. 130) of the single-strand binding protein of *A. aeolicus.*

FIG. 48 shows the nucleotide sequence (SEQ. ID. No. 131) of the dnaB gene of *A. aeolicus.*

FIG. 49 shows the amino acid sequence (SEQ. ID. No. 132) of the DnaB helicase of *A. aeolicus.*

FIG. 50 shows the nucleotide sequence (SEQ. ID. No. 133) of the dnaG gene of *A. aeolicus.*

FIG. 51 shows the amino acid sequence (SEQ. ID. No. 134) of the DnaG primase of *A. aeolicus.*

FIG. 52 shows the nucleotide sequence (SEQ. ID. No. 135) of the dnaC gene of *A. aeolicus.*

FIG. 53 shows the amino acid sequence (SEQ. ID. No. 136) of the DnaC protein of *A. aeolicus.*

FIGS. 54A–B shows the nucleotide sequence (SEQ. ID. No. 137) of the dnaE gene of *T. maritima.*

FIG. 55 shows the amino acid sequence (SEQ. ID. No. 138) of the a subunit of *T. maritima.*

FIG. 56 shows the nucleotide sequence (SEQ. ID. No. 139) of the dnaQ gene of *T. maritima.*

FIG. 57 shows the amino acid sequence (SEQ. ID. No. 140) of the ε subunit of *T. maritima.*

FIG. 58 shows the nucleotide sequence (SEQ. ID. No. 141) of the dnaX gene of *T. maritima.*

FIG. 59 shows the amino acid sequence (SEQ. ID. No. 142) of the tau subunit of *T. maritima.*

FIG. 60 shows the nucleotide sequence (SEQ. ID. No. 143) of the dnaN gene of *T. maritima.*

FIG. 61 shows the amino acid sequence (SEQ. ID. No. 144) of the β subunit of *T. maritima.*

FIG. 62 shows the nucleotide sequence (SEQ. ID. No. 145) of the holA gene of *T. maritima.*

FIG. 63 shows the amino acid sequence (SEQ. ID. No. 146) of the δ subunit of *T. maritima.*

FIG. 64 shows the nucleotide sequence (SEQ. ID. No. 147) of the holB gene of *T. maritima.*

FIG. 65 shows the amino acid sequence (SEQ. ID. No. 148) of the δ' subunit of *T. maritima.*

FIG. 66 shows the nucleotide sequence (SEQ. ID. No. 149) of the ssb gene of *T. maritima.*

FIG. 67 shows the amino acid sequence (SEQ. ID. No. 150) of the single-strand binding protein of *T. maritima.*

FIG. 68 shows the nucleotide sequence (SEQ. ID. No. 151) of the dnaB gene of *T. maritima.*

FIG. 69 shows the amino acid sequence (SEQ. ID. No. 152) of the DnaB helicase of *T. maritima.*

FIG. 70 shows the nucleotide sequence (SEQ. ID. No. 153) of the dnaG gene of *T. maritima.*

FIG. 71 shows the amino acid sequence (SEQ. ID. No. 154) of the DnaG primase of *T. maritima.*

FIG. 72 shows the nucleotide sequence (SEQ. ID. No. 155) of the holB gene of *T. thermophilus.*

FIG. 73 shows the amino acid sequence (SEQ. ID. No. 156) of the δ' subunit of *T. thermophilus.*

FIG. 74 shows the nucleotide sequence (SEQ. ID. No. 157) of the holA gene of *T. thermophilus.*

FIG. 75 shows the amino acid sequence (SEQ. ID. No. 158) of the δ subunit of *T. thermophilus.*

FIG. 76 shows the nucleotide sequence (SEQ. ID. No. 171) of the ssb gene of *T. thermophilus.*

FIG. 77 shows the amino acid sequence (SEQ. ID. No. 172) of the single-strand binding protein of *T. thermophilus.*

FIG. 78 shows the partial nucleotide sequence (SEQ. ID. No. 173) of the dnaN gene of *B. stearothermophilus.*

FIG. 79 shows the partial amino acid sequence (SEQ. ID. No. 174) of the β subunit of *B. stearothermophilus.*

FIG. 80 shows the nucleotide sequence (SEQ. ID. No. 175) of the ssb gene of *B. stearothermophilus.*

FIG. 81 shows the amino acid sequence (SEQ. ID. No. 176) of the single-strand binding protein of *B. stearothermophilus.*

FIG. 82 shows the nucleotide sequence (SEQ. ID. No. 177) of the holA gene of *B. stearothermophilus.*

FIG. 83 shows the amino acid sequence (SEQ. ID. No. 178) of the δ subunit of *B. stearothermophilus.*

FIG. 84 shows the nucleotide sequence (SEQ. ID. No. 179) of the holB gene of *B. stearothermophilus.*

FIG. 85 shows the amino acid sequence (SEQ. ID. No. 180) of the δ' subunit of *B. stearothermophilus.*

FIG. 86 shows the partial nucleotide sequence (SEQ. ID. No. 181) of the dnaX gene of *B. stearothermophilus.*

FIG. 87 shows the partial amino acid sequence (SEQ. ID. No. 182) of the tau subunit of *B. stearothermophilus.*

FIGS. 88A–B show the nucleotide sequence (SEQ. ID. No. 183) of the polC gene of *B. stearothermophilus.*

FIG. 89 shows the amino acid sequence (SEQ. ID. No. 184) of the PolC or α-large subunit of *B. stearothermophilus.*

DETAILED DESCRIPTION OF THE INVENTION

In accordance with the present invention there may be employed conventional molecular biology, microbiology, and recombinant DNA techniques within the skill of the art. Such techniques are explained fully in the literature. See, e.g., Sambrook et al., "Molecular Cloning: A Laboratory Manual" (1989); "Current Protocols in Molecular Biology" Volumes I–III (Ausubel, R. M., ed.) (1994); "Cell Biology: A Laboratory Handbook" Volumes I–III (Celis, J. E., ed.) (1994); "Current Protocols in Immunology" Volumes I–III (Coligan, J. E., ed.) (1994); "Oligonucleotide Synthesis" (M. J. Gait, ed.) (1984); "Nucleic Acid Hybridization" (B. D. Hames & S. J. Higgins, eds.) (1985); "Transcription And Translation" (B. D. Hames & S. J. Higgins, eds.) (1984); "Animal Cell Culture" (R. I. Freshney, ed.) (1986); "Immobilized Cells And Enzymes" (IRL Press) (1986); B. Perbal, "A Practical Guide To Molecular Cloning" (1984), each of which is hereby incorporated by reference.

Therefore, if appearing herein, the following terms shall have the definitions set out below.

The terms "DNA Polymerase III," "Polymerase III-type enzyme(s)", "Polymerase III enzyme complex(s)", "*T.th.* DNA Polymerase III", "*A.ae.* DNA Polymerase III", "*T.ma.* DNA Polymerase III", and any variants not specifically listed, may be used herein interchangeably, as are β subunit and sliding clamp and clamp as are also γ complex, clamp loader, and RFC, as used throughout the present application and claims refer to proteinaceous material including single or multiple proteins, and extends to those proteins having the amino acid sequence data described herein and presented in the Figures and corresponding Sequence Listing entries, and the corresponding profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "DNA Polymerase III," "*T.th.* DNA Polymerase III," and "γ and τ subunits", "β subunit", "α subunit", "ϵ subunit", "δ subunit", "δ' subunit", "SSB protein", "sliding clamp" and "clamp loader" are intended to include within their scope proteins specifically recited herein as well as all substantially homologous analogs and allelic variations. As used herein γ complex refers to a particular type of clamp loader that includes a γ subunit.

Also as used herein, the term "thermolabile enzyme" refers to a DNA polymerase which is not resistant to inactivation by heat. For example, T5 DNA polymerase, the activity of which is totally inactivated by exposing the enzyme to a temperature of 90° C. for 30 seconds, is considered to be a thermolabile DNA polymerase. As used herein, a thermolabile DNA polymerase is less resistant to heat inactivation than in a thermostable DNA polymerase. A thermolabile DNA polymerase typically will also have a lower optimum temperature than a thermostable DNA polymerase. Thermolabile DNA polymerases are typically isolated from mesophilic organisms, for example mesophilic bacteria or eukaryotes, including certain animals.

As used herein, the term "thermostable enzyme" refers to an enzyme which is stable to heat and is heat resistant and catalyzes (facilitates) combination of the nucleotides in the proper manner to form the primer extension products that are complementary to each nucleic acid strand. Generally, the synthesis will be initiated at the 3' end of each primer and will proceed in the 5' direction along the template strand, until synthesis terminates, producing molecules of different lengths.

The thermostable enzyme herein must satisfy a single criterion to be effective for the amplification reaction, i.e., the enzyme must not become irreversibly denatured (inactivated) when subjected to the elevated temperatures for the time necessary to effect denaturation of double-stranded nucleic acids. Irreversible denaturation for purposes herein refers to permanent and complete loss of enzymatic activity. The heating conditions necessary for denaturation will depend, e.g., on the buffer salt concentration and the length and nucleotide composition of the nucleic acids being denatured, but typically range from about 90° C. to about 96° C. for a time depending mainly on the temperature and the nucleic acid length, typically about 0.5 to four minutes. Higher temperatures may be tolerated as the buffer salt concentration and/or GC composition of the nucleic acid is increased. Preferably, the enzyme will not become irreversibly denatured at about 90°–100° C.

The thermostable enzymes herein preferably have an optimum temperature at which they function that is higher than about 40° C., which is the temperature below which hybridization of primer to template is promoted, although, depending on (1) magnesium and salt concentrations and (2) composition and length of primer, hybridization can occur at higher temperature (e.g., 45°70° C.). The higher the temperature optimum for the enzyme, the greater the specificity and/or selectivity of the primer-directed extension process. However, enzymes that are active below 40° C., e.g., at 37° C., are also within the scope of this invention provided they are heat-stable. Preferably, the optimum temperature ranges from about 50° to about 90° C., more preferably about 60° to about 80° C. In this connection, the term "elevated temperature" as used herein is intended to cover sustained temperatures of operation of the enzyme that are equal to or higher than about 60° C.

The term "template" as used herein refers to a double-stranded or single-stranded DNA molecule which is to be amplified, synthesized, or sequenced. In the case of a double-stranded DNA molecule, denaturation of its strands to form a first and a second strand is performed before these molecules may be amplified, synthesized or sequenced. A primer, complementary to a portion of a DNA template is hybridized under appropriate conditions and the DNA polymerase of the invention may then synthesize a DNA molecule complementary to said template or a portion thereof. The newly synthesized DNA molecule, according to the invention, may be equal or shorter in length than the original DNA template. Mismatch incorporation during the synthesis or extension of the newly synthesized DNA molecule may result in one or a number of mismatched base pairs. Thus, the synthesized DNA molecule need not be exactly complementary to the DNA template.

The term "incorporating" as used herein means becoming a part of a DNA molecule or primer.

As used herein "amplification" refers to any in vitro method for increasing the number of copies of a nucleotide sequence, or its complimentary sequence, with the use of a DNA polymerase. Nucleic acid amplification results in the incorporation of nucleotides into a DNA molecule or primer thereby forming a new DNA molecule complementary to a DNA template. The formed DNA molecule and its template can be used as templates to synthesize additional DNA molecules. As used herein, one amplification reaction may consist of many rounds of DNA replication. DNA amplification reactions include, for example, polymerase chain reactions (PCR). One PCR reaction may consist of about 20 to 100 "cycles" of denaturation and synthesis of a DNA molecule. In this connection, the use of the term "long stretches of DNA" as it refers to the extension of primer along DNA is intended to cover such extensions of an average length exceeding 7 kilobases. Naturally, such length will vary, and all such variations are considered to be included within the scope of the invention.

As used herein, the term "holoenzyme" refers to a multi-subunit DNA polymerase activity comprising and resulting from various subunits which each may have distinct activities but which when contained in an enzyme reaction operate to carry out the function of the polymerase (typically DNA synthesis) and enhance its activity over use of the DNA polymerase subunit alone. For example, *E. coli* DNA polymerase III is a holoenzyme comprising three components of one or more subunits each: (1) a core component consisting of a heterotrimer of $\alpha,\epsilon$ and $\theta$ subunits; (2) a $\beta$ component consisting of a $\beta$ subunit dimer; and (3) a $\gamma$ complex component consisting of a heteropentamer of $\gamma$, $\delta$, $\delta'$, $\chi$ and $\psi$ subunits (see Studwell and O'Donnell, 1990). These three components, and the various subunits of which they consist, are linked non-covalently to form the DNA polymerase III holoenzyme complex. However, they also function when not linked in solution.

As used herein, "enzyme complex" refers to a protein structure consisting essentially of two or more subunits of a replication enzyme, which may or may not be identical, noncovalently linked to each other to form a multi-subunit structure. An enzyme complex according to this definition ideally will have a particular enzymatic activity, up to and including the activity of the replication enzyme. For example, a "DNA pol III enzyme complex" as used herein means a multi-subunit protein activity comprising two or more of the subunits of the DNA pol III replication enzyme as defined above, and having DNA polymerizing or synthesizing activity. Thus, this term encompasses the native replication enzyme, as well as an enzyme complex lacking one or more of the subunits of the replication enzyme (e.g., DNA pol III exo-, which lacks the $\epsilon$ subunit).

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

TABLE OF CORRESPONDENCE

| SYMBOLS | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used generally herein, such as in referring to probes prepared and used in the present invention, is defined as a molecule comprised of two or more (deoxy)ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Suitable conditions include those characterized by a hybridization buffer comprising 0.9M sodium citrate ("SSC") buffer at a temperature of about 37° C. and washing in SSC buffer at a temperature of about 37° C.; and preferably in a hybridization buffer comprising 20% formamide in 0.9M SSC buffer at a temperature of about 42° C. and washing with.0.2×SSC buffer at about 42° C. Stringency conditions can be further varied by modifying the temperature and/or salt content of the buffer, or by modifying the length of the hybridization probe as is known to those of skill in the art. Defining appropriate hybridization conditions is within the skill of the art. See, e.g., Maniatis et al., 1982; Glover, 1985; Hames and Higgins, 1984.

It should be appreciated that also within the scope of the present invention are degenerate DNA sequences. By "degenerate" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |

-continued

| | |
|---|---|
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made, e.g., in SEQ. ID. No. 1, or any of the nucleic acids set forth herein, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino acids with nonpolar R groups
Alanine
Valine
Leucine
Isoleucine
Proline
Phenylalanine
Tryptophan
Methionine Amino acids with uncharged polar R groups
Glycine
Serine
Threonine
Cysteine
Tyrosine
Asparagine
Glutamine Amino acids with charged polar R groups (negatively charged at pH 6.0)
Aspartic acid
Glutamic acid Basic amino acids (positively charged at pH 6.0)
Lysine
Arginine
Histidine (at pH 6.0)

Amino acids with phenyl groups:
Phenylalanine
Tryptophan
Tyrosine

Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced into a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces U-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. No. 4,816,397 to Boss et al. and U.S. Pat. No. 4,816,567 to Cabilly et al.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein. Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')2 portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10–20° C. below the predicted or determined $T_m$ with washes of higher stringency, if desired.

In its primary aspect, the present invention concerns the identification of a class of DNA Polymerase III-type enzymes or complexes found in thermophilic bacteria such as *Thermus thermophilus* (*T.th.*), *Aquifex aeolicus* (*A.ae.*), *Thermotoga maritima* (*T.ma.*), *Bacillus stearothermophilus* (*B.st.*) and other eubacteria which exhibit the following characteristics, among their properties: the ability to extend a primer over a long stretch of ssDNA at elevated temperature, stimulation by its cognate sliding clamp of the type that is assembled on DNA by a clamp loader, accessory subunits that exhibit DNA-stimulated ATPase activity at elevated temperature and/or ionic strength, and an associated 3'-5' exonuclease activity. In a particular aspect, the invention extends to Polymerase III-type enzymes derived from a broad class of thermophilic eubacteria that include polymerases isolated from the thermophilic bacteria *Aquifex aeolicus* (*A.ae.* polymerase) and other members of the Aquifex genus; *Thermus thermophilus* (*T.th.* polymerase), *Thermus favus* (*Tfl*/Tub polymerase), *Thermus ruber* (*Tru* polymerase), *Thermus brockianus* (DYNAZYME™ polymerase) and other members of the Thermus genus; *Bacillus stearothermophilus* (*Bst* polymerase) and other members of the Bacillus genus; *Thermoplasma acidophilum* (*Tac* polymerase) and other members of the Thermoplasma genus; and *Thermotoga neapolitana* (*Tne* polymerase; See WO 96/10640 to Chatterjee et al.), *Thermotoga maritima* (*Tma* polymerase; See U.S. Pat. No. 5,374,553 to Gelfand et al.), and other members of the Thermotoga genus. The particular polymerase discussed herein by way of illustration and not limitation, is the enzyme derived from *T.th., A.ae., T.ma.*, or *B.st.*

Polymerase III-type enzymes covered by the invention include those that may be prepared by purification from cellular material, as described in detail in the Examples infra, as well as enzyme assemblies or complexes that comprise the combination of individually prepared enzyme subunits or components. Accordingly, the entire enzyme may be prepared by purification from cellular material, or may be constructed by the preparation of the individual components and their assembly into the functional enzyme. A representative and non-limitative protocol for the preparation of an enzyme by this latter route is set forth in U.S. Pat. No. 5,583,026 to O'Donnell, and the disclosure thereof is incorporated herein in its entirety for such purpose.

Likewise, individual subunits may be modified, e.g. as by incorporation therein of single residue substitutions to create active sites therein, for the purpose of imparting new or enhanced properties to enzymes containing the modified subunits (see, e.g., Tabor, 1995). Likewise, individual subunits prepared in accordance with the invention, may be used individually and for example, may be substituted for their counterparts in other enzymes, to improve or particularize the properties of the resultant modified enzyme. Such modifications are within the skill of the art and are considered to be included within the scope of the present invention.

Accordingly, the invention includes the various subunits that may comprise the enzymes, and accordingly extends to the genes and corresponding proteins that may be encoded thereby, such as the $\alpha$ (as well as PolC), $\beta$, $\gamma$, $\epsilon$, $\tau$, $\delta$ and $\delta'$ subunits, respectively. More particularly, in *Thermus thermophilus* the $\alpha$ subunit corresponds to dnaE, the $\beta$ subunit corresponds to dnaN, the $\epsilon$ subunit corresponds to dnaQ, and the $\gamma$ and $\tau$ subunits correspond to dnaX, the $\delta$ subunit corresponds to holA, and the $\delta'$ subunit corresponds to holB. In *Aquifex aeolicus* and *Thermotoga maritima*, the $\alpha$ subunit corresponds to dnaE, the $\beta$ subunit corresponds to dnaN, the $\epsilon$ subunit corresponds to dnaQ, the $\tau$ subunit corresponds to dnaX, the $\delta$ subunit corresponds to holA, and the $\delta'$ subunit corresponds to holB. In *Bacillus stearothermophilus*, the PolC which has both $\alpha$ and $\epsilon$ activities corresponds to polC, the $\beta$ subunit corresponds to dnaN, the $\epsilon$ subunit corresponds to dnaQ, the $\tau$ subunit corresponds to dnaX, the $\delta$ subunit corresponds to holA, and the $\delta'$ subunit corresponds to holB.

Accordingly, the Polymerase III-type enzyme of the present invention comprises at least one gene encoding a subunit thereof, which gene is selected from the group consisting of dnaX, dnaQ, dnaE, dnaN, holA, holB, and combinations thereof. More particularly, the invention extends to the nucleic acid molecule encoding them and their encoded subunits.

In the *T.th.* Pol III enzyme, this includes the following nucleotide sequences: dnaX (SEQ. ID. No. 3), dnaE (SEQ. ID. No. 86), dnaQ (SEQ. ID. No. 94), dnaN (SEQ. ID. No. 106), holA (SEQ. ID. No. 157), and holB (SEQ. ID. No. 155).

In the *A.ae.* Pol III enzyme, this includes the following nucleotide sequences: dnaX (SEQ. ID. No. 119), dnaE (SEQ. ID. No. 117), dnaQ (SEQ. ID. No. 127), dnaN (SEQ. ID. No. 121), holA (SEQ. ID. No. 123), and holB (SEQ. ID. No. 125).

In the *T.ma.* Pol III enzyme, this includes the following nucleotide sequences: dnaX (SEQ. ID. No. 141), dnaE (SEQ. ID. No. 137), dnaQ (SEQ. ID. No. 139), dnaN (SEQ. ID. No. 143), holA (SEQ. ID. No. 145), and holB (SEQ. ID. No. 147).

In the *B.st.* Pol III enzyme, this includes the following nucleotide sequences: dnaX (SEQ. ID. No. 181), dnaN (SEQ. ID. No. 173), holA (SEQ. ID. No. 177), holB (SEQ. ID. No. 179), and polC (SEQ. ID. Nos. 183).

In each of the Pol III type enzymes of the present invention, not only are each of the above-identified coding sequences contemplated, but also conserved variants, active fragments and analogs thereof.

A particular *T.th.* Polymerase III-type enzyme in accordance with the invention may include at least one of the following sub-units: a γ subunit having an amino acid sequence corresponding to SEQ. ID. Nos. 4 and 5; a τ subunit having an amino acid sequence corresponding to SEQ. ID. No. 2; a ϵ subunit having an amino acid sequence corresponding to SEQ. ID. No. 95; a α subunit including an amino acid sequence corresponding SEQ. ID. No. 87; a β subunit having an amino acid sequence corresponding to SEQ. ID. No. 107; a δ subunit having an am amino acid sequence corresponding to SEQ. ID. No. 158; a δ' subunit having an amino acid sequence corresponding to SEQ. ID. No. 156; as well as variants, including allelic variants, muteins, analogs and fragments of any of the subunits, and compatible combinations thereof, capable of functioning in DNA amplification and sequencing.

A particular *A.ae.* Polymerase III-type enzyme in accordance with the invention may include at least one of the following subunits: a τ subunit having an amino acid sequence corresponding to SEQ. ID. No. 120; a ϵ subunit having an amino acid sequence corresponding to SEQ. ID. No. 128; a α subunit including an amino acid sequence corresponding to SEQ. ID. No. 118; a β subunit having an amino acid sequence corresponding to SEQ. ID. No. 122; a δ subunit having an amino acid sequence corresponding to SEQ. ID. No. 124; a δ' subunit having an amino acid sequence corresponding to SEQ. ID. No. 126; as well as variants, including allelic variants, muteins, analogs and fragments of any of the subunits, and compatible combinations thereof, capable of functioning in DNA amplification and sequencing.

A particular *T.ma.* Polymerase III-type enzyme in accordance with the invention may include at least one of the following subunits: a τ subunit having an amino acid sequence corresponding to SEQ. ID. No. 142; a ϵ subunit having an amino acid sequence corresponding to SEQ. ID. No. 140; a α subunit including an amino acid sequence corresponding to SEQ. ID. No. 138; a β subunit having an amino acid sequence corresponding to SEQ. ID. No. 144; a δ subunit having an amino acid sequence corresponding to SEQ. ID. No. 146; a δ' subunit having an amino acid sequence corresponding to SEQ. ID. No. 148; as well as variants, including allelic variants, muteins, analogs and fragments of any of the subunits, and compatible combinations thereof, capable of functioning in DNA amplification and sequencing.

A particular *B.st.* Polymerase III-type enzyme in accordance with the invention may include at least one of the following subunits: a τ subunit having a partial amino acid sequence corresponding to SEQ. ID. No. 182; a β subunit having an amino acid sequence corresponding to SEQ ID. No. 174; a δ subunit having an amino acid sequence corresponding to SEQ. ID. No. 178; a δ' subunit having an amino acid sequence corresponding to SEQ. ID. No. 180; a PolC subunit having an amino acid sequence corresponding to SEQ. ID. Nos. 184; as well as variants, including allelic variants, muteins, analogs and fragments of any of the subunits, and compatible combinations thereof, capable of functioning in DNA amplification and sequencing.

The invention also includes and extends to the use and application of the enzyme and/or one or more of its components for DNA molecule amplification and sequencing by the methods set forth hereinabove, and in greater detail later on herein.

One of the subunits of the invention is the *T.th.* γ/τ subunit encoded by a dnaX gene, which frameshifts as much as −2 with high efficiency, and that, upon frameshifting, leads to the addition of more than one extra amino acid residue to the C-terminus (to form the γ subunit). Further, the invention likewise extends to a dnaX gene derived from a thermophile such as *T.th.*, that possesses the frameshift defined herein and that codes for expression of the γ and τ subunits of DNA Polymerase III.

The present invention provides methods for amplifying or sequencing a nucleic acid molecule comprising contacting the nucleic acid molecule with a composition comprising a DNA polymerase III enzyme (DNA pol III) complex (for sequencing, preferably a DNA pol III complex that is substantially reduced in 3'-5' exonuclease activity). DNA pol III complexes used in the methods of the present invention are thermostable.

The invention also provides DNA molecules amplified by the present methods, methods of preparing a recombinant vector comprising inserting a DNA molecule amplified by the present methods into a vector, which is preferably an expression vector, and recombinant vectors prepared by these methods.

The invention also provides methods of preparing a recombinant host cell comprising inserting a DNA molecule amplified by the present methods into a host cell, which preferably a bacterial cell, most preferably an *Escherichia coli* cell; a yeast cell; or an animal cell, most preferably an insect cell, a nematode cell or a mammalian cell. The invention also provides and recombinant host cells prepared by these methods.

In additional preferred embodiments, the present invention provides kits for amplifying or sequencing a nucleic acid molecule. DNA amplification kits according to the invention comprise a carrier means having in close confinement therein two or more container means, wherein a first container means contains a DNA polymerase III enzyme complex and a second container means contains a deoxynucleoside triphosphate. DNA sequencing kits according to the present invention comprise a multi-protein Pol III-type enzyme complex and a second container means contains a dideoxynucleoside triphosphate. The DNA pol III contained in the container means of such kits is preferably substantially reduced in 5'-3' exonuclease activity, may be thermostable, and may be isolated from the thermophilic cellular sources described above.

DNA pol III-type enzyme complexes for use in the present invention may be isolated from any organism that produced the DNA pol III-type enzyme complexes naturally or recombinantly. Such enzyme complexes may be thermostable, isolated from a variety of thermophilic organisms.

The thermostable DNA polymerase III-type enzymes or complexes that are an important aspect of this invention, may be isolated from a variety of thermophilic bacteria that are available commercially (for example, from American Type Culture Collection, Rockville, Md.). Suitable for use as sources of thermostable enzymes are the thermophilic eubacteria *Aquifex aeolicus* and other species of the Aquifex genus; *Thermus aquaticus, Thermus thermophilus, Thermus flavus, Thermus ruber, Thermus brockianus*, and other species of the Thermus genus; *Bacillus stearothermophilus, Bacillus subtilis*, and other species of the Bacillus genus; *Thermoplasma acidophilum* and other species of the Thermoplasma genus; *Thermotoga neapolitana, Thermotoga maritima* and other species of the Thermotoga genus; and mutants of each of these species. It will be understood by one of ordinary skill in the art, however, that any thermophilic microorganism might be used as a source of thermostable DNA pol III-type enzymes and polypeptides for use in the methods of the present invention. Bacterial cells may be grown according to standard microbiological techniques, using culture media and incubation conditions suitable for growing active cultures of the particular thermophilic species that are well-known to one of ordinary skill in the art (see, e.g., Brock et al., 1969; Oshima et al., 1974). Thermostable DNA pol III complexes may then be isolated from such thermophilic cellular sources as described for thermolabile complexes above.

Several methods are available for identifying homologous nucleic acids and protein subunits in other thermophilic eubacteria, either those listed above or otherwise. These methods include the following:

(1) The following procedure was used to obtain the genes encoding *T.th.* $\epsilon$ (dnaQ), $\tau/\gamma$ (dnaX), DnaA (dnaA), and $\beta$ (dnaN). Protein sequences encoded by genes of non-thermophilic bacteria (i.e., mesophiles) are aligned to identify highly conserved amino acid sequences. PCR primers at conserved positions are designed using the codon usage of the organism of interest to amplify an internal section of the gene from genomic DNA extracted from the organism. The PCR product is sequenced. New primers are designed near the ends of the sequence to obtain new sequence that flanks the ends using circular PCR (also called inversed PCR) on genomic DNA that has been cut with the appropriate restriction enzyme and ligated into circles. These new PCR products are sequenced. The procedure is repeated until the entire gene sequence has been obtained. Also, dnaN (encoding $\beta$) is located next to dnaA in bacteria and, therefore, dnaN can be obtained by cloning DNA flanking the dnaA gene by the circular PCR procedure starting within dnaA. Once the gene is obtained, it is cloned into an expression vector for protein production.

(2) The following procedure was used to obtain the genes encoding *T.th.* $\alpha$ polymerase (dnaE gene). The DNA polymerase III can be purified directly from the organism of interest and amino acid sequence of the subunit(s) obtained directly. In the case of *T.th., T.th.* cells were lysed and proteins were fractionated. An antibody against *E. coli* $\alpha$ was used to probe column fractions by Western analysis, which reacted with *T.th.* $\alpha$. The *T.th.* $\alpha$ was transferred to a membrane, proteolyzed, and fragments were sequenced. The sequence was used to design PCR primers for amplification of an internal section of the dnaE gene. Remaining flanking sequences are then obtained by circular PCR.

(3) The following procedure can be used to identify published nucleictide sequences which have not yet been identified as to their function. This method was used to obtain *T.th.* $\delta$ (holA) and $\delta'$ (holB), although they could presumably also have been obtained via Methods 1 and 2 above. Discovery of *T.th.* dnaE ($\alpha$), dnaN ($\beta$) and dnaX ($\tau/\gamma$) indicates that thermophiles use a class III type of DNA polymerase ($\alpha$) that utilize a clamp ($\beta$) and must also use a clamp loader since they have $\tau/\gamma$. Also, the biochemical experiments in the Examples infra show that the *T.th.* polymerase functions with the *T.th.* $\beta$ clamp. Having demonstrated that a thermophile (e.g., *T.th.*) does indeed utilize a class III type of polymerase with a clamp and clamp loader, it can be assumed that they may have $\delta$ and $\delta'$ subunits needed to form a complex with $\tau/\gamma$ for functional clamp loading activity (i.e., as shown in *E. coli*, $\delta$ and $\delta'$ bind either $\tau$ or $\gamma$ to form $\tau\delta\delta'$ or $\gamma\delta\delta'$ complex, both of which are functional clamp loaders). The $\delta$ subunit is not very well conserved, but does give a match in the sequence databases for *A.ae., T.ma*, and *T.th.* The *T.th.* database provided limited information on the amino acid sequence of $\delta$ subunit, although one can easily obtain the complete sequence of *T.th.* holA by PCR and circular PCR as outlined above in Method 1. The *A.ae.* and *T.ma.* databases are complete and, therefore, the entire holA sequence from these genomes are identified. Neither database recognized these sequences as $\delta$ encoded by holA. The $\delta'$ subunit (holB) is fairly well conserved. Again the incomplete *T.th.* database provided limited $\delta$ sequence, but as with $\delta$, it is a straight forward process for anyone experienced in the area to obtain the rest of the holB sequence using PCR and circular PCR as described in Method 1. Neither the *A.ae.* nor *T.ma.* databases recognized holB encoding $\delta'$. Nevertheless, holB was identified as encoding $\delta'$ by searching the databases with $\delta'$ sequence. In each case, the *Thermatoga maritima* and *Aquifex aeolicus* holB gene and $\delta$ sequence were obtained in their entirety. Neither database had previously annotated holA or holB encoding $\delta$ and $\delta$40 .

As stated above and in accordance with the present invention, once nucleic acid molecules have been obtained, they may be amplified according to any of the literature-described manual or automated amplification methods. Such methods includes, but are not limited to, PCR (U.S. Pat. No. 4,683,195 to Mullis et al. and U.S. Pat. No. 4,683,202 to Mullis), Strand Displacement Amplification (SDA) (U.S. Pat. No. 5,455,166 to Walker), and Nucleic Acid Sequence-Based Amplification (NASBA) (U.S. Pat. No. 5,409,818 to Davey et al.; EP 329,822 to Davey et al.). Most preferably, nucleic acid molecules are amplified by the methods of the present invention using PCR-based amplification techniques.

In the initial steps of each of these amplification methods, the nucleic acid molecule to be amplified is contacted with a composition comprising a DNA polymerase belonging to the evolutionary "family A" class (e.g., Taq DNA pol I or *E. coli* pol I) or the "family "B" class (e.g., Vent and Pfu DNA polymerases—see Ito and Braithwaite, 1991). All of these DNA polymerases are present as single subunits and are primarily involved in DNA repair. In contrast, the DNA pol III-type enzymes are multisubunit complexes that mainly function in the replication of the chromosome, and the subunit containing the DNA polymerase activity is in the "family C" class.

Thus, in amplifying a nucleic acid molecule according to the methods of the present invention, the nucleic acid molecule is contacted with a composition comprising a thermostable DNA pol III-type enzyme complex.

Once the nucleic acid molecule to be amplified is contacted with the DNA pol III-type complex, the amplification reaction may proceed according to standard protocols for each of the above-described techniques. Since most of these techniques comprise a high-temperature denaturation step, if a thermolabile DNA pol III-type enzyme complex is used in nucleic acid amplification by any of these techniques the enzyme would need to be added at the start of each amplification cycle, since it would be heat-inactivated at the denaturation step. However, a thermostable DNA pol III-type complex used in these methods need only be added once at the start of the amplification (as for Taq DNA polymerase in traditional PCR amplifications), as its activity will be unaffected by the high temperature of the denaturation step. It should be noted, however, that because DNA pol III-type enzymes may have a much more rapid rate of nucleotide incorporation than the polymerases commonly used in these amplification techniques, the cycle times may need to be adjusted to shorter intervals than would be standard.

In an alternative preferred embodiment, the invention provides methods of extending primers for several kilobases, a reaction that is central to amplifying large nucleic acid molecules, by a technique commonly referred to as "long chain PCR" (Barnes, 1994; Cheng, 1994).

In such a method the target primed DNA can contain a single strand stretch of DNA to be copied into the double strand form of several or tens of kilobases. The reaction is performed in a suitable buffer, preferably Tris, at a pH of between 5.5–9.5, preferably 7.5. The reaction also contains $MgCl_2$ in the range 1 mM to 10 mM, preferably 8 mM, and may contain a suitable salt such as NaCl, KCl or sodium or potassium acetate. The reaction also contains ATP in the range of 20 $\mu$M to 1 mM, preferably 0.5 mM, that is needed for the clamp loader to assemble the clamp onto the primed template, and a sufficient concentration of deoxynucleoside triphosphates in the range of 50 $\mu$M to 0.5 mM, preferably 60 $\mu$M for chain extension. The reaction contains a sliding clamp, such as the β subunit, in the range of 20 ng to 200 ng, preferably 100 ng, for action as a clamp to stimulate the DNA polymerase. The chain extension reaction contains a DNA polymerase and a clamp loader, that could be added either separately or as a single Pol III*-like particle, preferably as a Pol III* like particle that contains the DNA polymerase and clamp loading activities. The Pol III-type enzyme is added preferably at a concentrations of about 0.0002–200 units per milliliter, about 0.002–100 units per milliliter, about 0.2–50 units per milliliter, and most preferably about 2–50 units per milliliter. The reaction is incubated at elevated temperature, preferably 60° C. or more, and could include other proteins to enhance activity such as a single strand DNA binding protein.

In another preferred embodiment, the invention provides methods of extending primers on linear templates in the absence of the clamp loader. In this reaction, the primers are annealled to the linear DNA, preferably at the ends such as in standard PCR applications. The reaction is performed in a suitable buffer, preferably Tris, at a pH of between 5.5–9.5, preferably 7.5. The reaction also contains $MgCl_2$ in the range of 1 mM to 10 mM, preferably 8 mM, and may contain a suitable salt such as NaCl, KCl or sodium or potassium acetate. The reaction also contains a sufficient concentration of deoxynucleoside triphosphates in the range of 50 $\mu$M to 0.5 mM, preferably 60 $\mu$M for chain extension. The reaction contains a sliding clamp, such as the β subunit, in the range of 20 ng to 20 $\mu$g, preferably about 2 $\mu$g, for ability to slide on the end of the DNA and associate with the polymerase for action as a clamp to stimulate the DNA polymerase. The chain extension reaction also contains a Pol III-type polymerase subunit such as α, core, or a Pol III*-like particle. The Pol III-type enzyme is added preferably at a concentrations of about 0.0002–200 units per milliliter, about 0.002–100 units per milliliter, about 0.2–50 units per milliliter, and most preferably about 2–50 units per milliliter. The reaction is incubated at elevated temperature, preferably 60° C. or more, and could include other proteins to enhance activity such as a single strand DNA binding protein.

The methods of the present invention thus will provide high-fidelity amplified copies of a nucleic acid molecule in a more rapid fashion than traditional amplification methods using the repair-type enzymes.

These amplified nucleic acid molecules may then be manipulated according to standard recombinant DNA techniques. For example, a nucleic acid molecule amplified according to the present methods may be inserted into a vector, which is preferably an expression vector, to produce a recombinant vector comprising the amplified nucleic acid molecule. This vector may then be inserted into a host cell, where it may, for example, direct the host cell to produce a recombinant polypeptide encoded by the amplified nucleic acid molecule. Methods for inserting nucleic acid molecules into vectors, and inserting these vectors into host cells, are well-known to one of ordinary skill in the art (see, e.g., Maniatis, 1992).

Alternatively, the amplified nucleic acid molecules may be directly inserted into a host cell, where it may be incorporated into the host cell genome or may exist as an extrachromosomal nucleic acid molecule, thereby producing a recombinant host cell. Methods for introduction of a nucleic acid molecule into a host cell, including calcium phosphate transfection, DEAE-dextran mediated transfection, cationic lipid-mediated transfection, electroporation, transduction, infection or other methods, are described in many standard laboratory manuals (see, e.g., Davis, 1986).

For each of the above techniques wherein an amplified nucleic acid molecule is introduced into a host cell via a vector or via direct introduction, preferred host cells include but are not limited to a bacterial cell, a yeast cell, or an animal cell. Bacterial host cells preferred in the present invention are *E. coli*, Bacillus spp., Streptomyces spp., Erwinia spp., Klebsiella spp. and *Salmonella typhimurium*. Preferred as a host cell is *E. coli* and particularly preferred are *E. coli* strains DH10B and Stb12, which are available commercially (Life Technologies, Inc. Gaithersburg, Md.). Preferred animal host cells are insect cells, nematode cells and mammalian cells. Insect host cells preferred in the present invention are Drosophila spp. cells, Spodoptera Sf9 and Sf21 cells, and Trichoplusa High-Five cells, each of which is available commercially (e.g., from Invitrogen; San Diego, Calif.). Preferred nematode host cells are those derived from *C. elegans*, and preferred mammalian host cells are those derived from rodents, particularly rats, mice or hamsters, and primates, particularly monkeys and humans. Particularly preferred as mammalian host cells are CHO cells, COS cells and VERO cells.

By the present invention, nucleic acid molecules may be sequenced according to any of the literature-described manual or automated sequencing methods. Such methods include, but are not limited to, dideoxy sequencing methods such as "Sanger sequencing" (Sanger and Coulson, 1975; Sanger et al., 1977; U.S. Pat. No. 4,962,022 to Fleming et al.; and U.S. Pat. No. 5,498,523 to Tabor et al.), as well as more complex PCR-based nucleic acid fingerprinting techniques such as Random Amplified Polymorphic DNA (RAPD) analysis (Williams et al., 1990). Arbitrarily Primed PCR (AP-PCR) (Welsh and McClelland, 1990), DNA Amplification Fingerprinting (DAF) (Caetano-Anollés, 1991), microsatellite PCR or Directed Amplification of Minisatellite-region DNA (DAMD) (Heath et al., 1993), and Amplification Fragment Length Polymorphism (AFLP) analysis (EP 534,858 to Vos et al.; Vos et al., 1995; Lin and Kuo, 1995).

As described above for amplification methods, the nucleic acid molecule to be sequenced by these methods is typically contacted with a composition comprising a type A or type B DNA polymerase. By contrast, in sequencing a nucleic acid molecule according to the methods of the present invention, the nucleic acid molecule is contacted with a composition comprising a thermostable DNA pol III-type enzyme complex instead of necessarily using a DNA polymerase of the family A or B classes. As for amplification methods, the DNA pol III-type complexes used in the nucleic acid sequencing methods of the present invention are preferably substantially reduced in 3'-5' exonuclease activity; most preferable for use in the present methods is a DNA polymerase III-type complex which lacks the $\epsilon$ subunit. DNA pol III-type complexes used for nucleic acid sequencing according to the present methods are used at the same preferred concentration ranges described above for long chain extension of primers.

Once the nucleic acid molecule to be sequenced is contacted with the DNA pol III complex, the sequencing reactions may proceed according to the protocols disclosed in the above-referenced techniques.

As discussed above, the invention extends to kits for use in nucleic acid amplification or sequencing utilizing DNA polymerase III-type enzymes according to the present methods. A DNA amplification kit according to the present invention may comprise a carrier means, such as vials, tubes, bottles and the like. A first such container means may contain a DNA polymerase III-type enzyme complex, and a second such container means may contain a deoxynucleoside triphosphate. The amplification kit encompassed by this aspect of the present invention may further comprise additional reagents and compounds necessary for carrying out standard nucleic amplification protocols (See U.S. Pat. No. 4,683,195 to Mullis et al. and U.S. Pat. No. 4,683,202 to Mullis, which are directed to methods of DNA amplification by PCR).

Similarly, a DNA sequencing kit according to the present invention comprises a carrier means having in close confinement therein two or more container means, such as vials, tubes, bottles and the like. A first such container means may contain a DNA polymerase III-type enzyme complex, and a second such container means may contain a dideoxynucleoside triphosphate. The sequencing kit may further comprise additional reagents and compounds necessary for carrying out standard nucleic sequencing protocols, such as pyrophosphatase, agarose or polyacrylamide media for formulating sequencing gels, and other components necessary for detection of sequenced nucleic acids (See U.S. Pat. No. 4,962,020 to Fleming et al. and U.S. Pat. No. 5,498,523 to Tabor et al., which are directed to methods of DNA sequencing).

The DNA polymerase III-type complex contained in the first container means of the amplification and sequencing kits provided by the invention is preferably a thermostable DNA polymerase III-type enzyme complex and more preferably a DNA polymerase III-type enzyme complex that is reduced in 3-5' exonuclease activity. Naturally, the foregoing methods and kits are presented as illustrative and not restrictive of the use and application of the enzymes of the invention for DNA molecule amplification and sequencing. Likewise, the applications of specific embodiments of the enzymes, including conserved variants and active fragments thereof are considered to be disclosed and included within the scope of the invention.

As discussed earlier, individual subunits could be modified to customize enzyme construction and corresponding use and activity. For example, the region of $\alpha$ that interacts with $\beta$ could be subcloned onto another DNA polymerase, thereby causing $\beta$ to enhance the activity of the recombinant polymerase. Alternatively, the $\beta$ clamp could be modified to function with another protein or enzyme thereby enhancing its activity or acting to localize its action to a particular targeted DNA. Finally, the polymerase active site could be modified to enhance its action, for example changing Tyrosine enabling more equal site stoppage with the four ddNTPs (Tabor et al., 1995). This represents a particular non-limiting illustration of the scope and practice of the present invention with reference to the utility of individual subunits hereof.

Accordingly and as stated above, the present invention also relates to a recombinant DNA molecule or cloned gene, or a degenerate variant thereof, which encodes any one or all of the subunits of the DNA Polymerase III-type enzymes of the present invention, or active fragments thereof. In the instance of the $\tau$ subunit, a predicted molecular weight of about 58 kD and an amino acid sequence set forth in SEQ ID Nos. 4 or 5 is comprehended; preferably a nucleic acid molecule, in particular a recombinant DNA molecule or cloned gene, encoding the 58 kD subunit of the Polymerase III of the invention, that has a nucleotide sequence or is complementary to a DNA sequence shown in FIGS. 4A and 4B (SEQ ID No. 1), and the coding region for dnaX set forth in FIG. 4C (SEQ ID No. 3). The $\gamma$ subunit is smaller, and is approximately 50 kD, depending upon the extent of the frameshift that occurs. More particularly, and as set forth in FIG. 4E (SEQ ID No. 4), the $\gamma$ subunit defined by a −1 frameshift possesses a molecular weight of 50.8 kD, while the $\gamma$ subunit defined by a −2 frameshift, set forth in FIG. 4F (SEQ ID No. 5), possesses a molecular weight of 49.8 kD.

As discussed above, the invention also extends to the genes including holA, holB, dnaX, dnaQ, dnaE, and dnaN from thermophilic eubacteria (i.e., *T.th.* and *A.ae.*) that have been isolated and/or purified, to corresponding vectors for the genes, and particularly, to the vectors disclosed herein, and to host cells including such vectors. In this connection, probes have been prepared which hybridize to the DNA polymerase III-type enzymes of the present invention, and which are selected from the various oligonucleotide probes or primers set forth in the present application. These include, without limitation, the oligonucleotide defined in SEQ ID No. 6 the oligonucleotide defined in SEQ ID No. 8 the oligonucleotide defined in SEQ ID No. 10 the oligonucleotide defined in SEQ ID No. 11 the oligonucleotide defined in SEQ ID No. 12 the oligonucleotide defined in SEQ ID No. 13 the oligonucleotide defined in SEQ ID No. 14 the oligonucleotide defined in SEQ ID No. 15, and the oligonucleotide defined in SEQ ID No. 16.

The methods of the invention include a method for producing a recombinant thermostable DNA polymerase III-type enzyme from a thermophilic bacterium, such as *T.th.*, *A.ae.*, *Th.ma.*, or *B.st.* which comprises culturing a host cell transformed with a vector of the invention under conditions suitable for the expression of the present DNA polymerase III. Another method includes a method for isolating a target DNA fragment consisting essentially of a DNA coding for a thermostable DNA polymerase III-type enzyme from a thermophilic bacterium comprising the steps of:

(a) forming a genomic library from the bacterium;

(b) transforming or transfecting an appropriate host cell with the library of step (a);

(c) contacting DNA from the transformed or transfected host cell with a DNA probe which hybridizes to a DNA fragment selected from the group consisting of the DNA fragments defined in SEQ ID No. 6 and the DNA fragments defined in SEQ ID No. 8 or the oligonucleotides set forth above; wherein hybridization is conducted under the following conditions:

i) hybridization: 1% crystalline BSA (fraction V) (Sigma), 1 mM EDTA, 0.5 M NaHPO4 (pH 7.2), 7% SDS at 65° C. for 12 hours and;

ii) wash: 5×20 minutes with wash buffer consisting of 0.5% BSA, fraction V), 1 mM Na2 EDTA, 40 mM NaHPO4 (pH 7.2), and 5% SDS;

(d) assaying the transformed or transfected cell of step (c) which hybridizes to the DNA probe for DNA polymerase III-type activity; and (e) isolating a target DNA fragment which codes for the thermostable DNA polymerase III-type enzyme.

Also, antibodies including both polyclonal and monoclonal antibodies, and the DNA Polymerase III-like enzyme complex and/or their $\gamma$ and $\tau$ subunits, $\alpha$ subunit(s), $\delta$ subunit, $\delta'$ subunit, $\beta$ subunit, $\epsilon$ subunit may be used in the preparation of the enzymes of the present invention as well as other enzymes of similar thermophilic origin. For example, the DNA Polymerase III-type complex or its subunits may be used to produce both polyclonal and monoclonal antibodies to themselves in a variety of cellular media, by known techniques such as the hybridoma technique utilizing, for example, fused mouse spleen lymphocytes and myeloma cells.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., Schreier et al., 1980; Hammerling et al., 1981; Kennett et al., 1980; see also U.S. Pat. No. 4,341,761 to Ganfield et al.; U.S. Pat. No. 4,399,121 to Albarella et al.; U.S. Pat. No. 4,427,783 to Newman et al.; U.S. Pat. No. 4,444,887 to Hoffman; U.S. Pat. No. 4,451,570 to Royston et al.; U.S. Pat. No. 4,466,917 to Nussenzweig et al.; U.S. Pat. No. 4,472,500 to Milstein et al.; U.S. Pat. No. 4,491,632 to Wands et al.; and U.S. Pat. No. 4,493,890 to Morris.

Methods for producing polyclonal anti-polypeptide antibodies are well-known in the art. See U.S. Pat. No. 4,493,795 to Nestor et al. A monoclonal antibody, typically containing Fab and/or $F(ab')_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with an elastin-binding portion thereof.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM) (Dulbecco et al., 1959) supplemented with 4.5 gm/l glucose, 20 mm glutamine, and 20% fetal calf serum. An exemplary inbred mouse strain is the Balb/c.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage $\lambda$, e.g., NM989, and other phage DNA, e.g., M13 and filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage $\lambda$, the control regions of fd coat protein, the promoter for 3-phosphoglycerate kinase or other glycolytic enzymes, the promoters of acid phosphatase (e.g., Pho5), the promoters of the yeast $\alpha$-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli*, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly with regard to potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that analogs may be prepared from nucleotide sequences of the protein complex/subunit derived within the scope of the present invention. Analogs, such as fragments, may be produced, for example, by pepsin digestion of bacterial material. Other analogs, such as muteins, can be produced by standard site-directed mutagenesis of dnaX, dnaE, dnaQ, dnaN, holA, or holB coding sequences. Especially useful may be a mutation in dnaE that provides the polymerase with the ability to incorporate all four ddNTPs with equal efficiency thereby producing an even binding pattern in sequencing gels, as discussed above and with reference to Tabor et al., 1995.

As mentioned above, a DNA sequence corresponding to dnaX, dnaQ, holA, holB, dnaE, or dnaN, or encoding the subunits of the DNA Polymerase III of the invention can be prepared synthetically rather than cloned. The DNA sequence can be designed with the appropriate codons for the amino acid sequence of the subunit(s) of interest. In general, one will select preferred codons for the intended host if the sequence will be used for expression. The complete sequence is assembled from overlapping oligonucleotides prepared by standard methods and assembled into a complete coding sequence (Edge, 1981; Nambair et al., 1984; Jay et al., 1984).

Synthetic DNA sequences allow convenient construction of genes which will express DNA Polymerase III analogs or "muteins". Alternatively, DNA encoding muteins can be made by site-directed mutagenesis of native dnaX, dnaQ, holA, holB, dnaE or dnaN genes or their corresponding cDNAs, and muteins can be made directly using conventional polypeptide synthesis.

A general method for site-specific incorporation of unnatural amino acids into proteins is described in Noren et al., 1989. This method may be used to create analogs with unnatural amino acids.

GENERAL DESCRIPTION OF THE INVENTION

As discussed above, the present invention has as one of its characterizing features, that a Polymerase III-type enzyme as defined hereinabove, has been discovered in a thermophile, that has the structure and function of a chromosomal replicase. This structure and function confers significant benefit when the enzyme is employed in procedures such as PCR where speed and accuracy of DNA reconstruction is crucial.

Chromosomal replicases are composed of several subunits in all organisms (Kornberg and Baker, 1992). In keeping with the need to replicate long chromosomes, replicases are rapid and highly processive multiprotein machines. All cellular replicases examined to date derive their processivity from one subunit that is shaped like a ring and completely encircles DNA (Kuriyan and O'Donnell, 1993; Kelman and O'Donnell, 1994). This "sliding clamp" subunit acts as a mobile tether for the polymerase machine (Stukenberg et al., 1991). The sliding clamp does not assemble onto the DNA by itself, but requires a complex of several proteins, called a "clamp loader" which couples ATP hydrolysis to the assembly of sliding clamps onto DNA (O'Donnell et al., 1992). Hence, Pol III-type cellular replicases are comprised of three components: a clamp, a clamp loader, and the DNA polymerase.

An overall goal is to identify and isolate all of the genes encoding the replicase subunits from a thermophile for expression and purification in large quantity. Following this, the replication apparatus can be reassembled from individual subunit components for use in kits, PCR, sequencing and diagnostic applications (Onrust et al., 1995).

As a beginning to identify and characterize the replicase of a thermophile, we started by looking for a homologue to the prokaryotic dnaX gene which encode subunits ($\gamma$ and $\tau$) of the replicase. The dnaX gene has another homologue, holB, which encodes yet another subunit ($\delta'$) of the replicase. The amino acid sequence of $\delta'$ (encoded by holA) and $\tau/\gamma$ subunits (encoded by dnaX) are particularly highly conserved in evolution from prokaryotes to eukaryotes (Chen et al., 1992; O'Donnell et al., 1993; Onrust et al., 1993; Carter et al., 1993; Cullman et al., 1995).

One organism chosen for study and exposition herein is the exemplary extreme thermophile *Thermus thermophilus* (*T.th.*). It is understood that other members of the class such as the eubacterium Thermatoga are expected to be analogous in both structure and function. Thus, the investigation of *T.th.* proceeded and initially, a *T.th.* homologue of dnaX was identified. The gene encodes a full length protein of 529 amino acids. The amino terminal third of the sequence shares over 50% homology to dnaX genes as divergent as *E. coli* (grain negative) and *B. subtilis* (gram positive). The *T.th.* dnaX gene contains a DNA sequence that provides a translational frameshift signal for production of two proteins from the same gene. Such frameshifting has been documented only in the case of *E. coli* (Tsuchihashi and Kornberg, 1990; Flower and McHenry, 1990; Blinkowa and Walker, 1990). No frameshifting has been documented to occur in the dnaX homologues (RFC subunit genes) of yeast and humans (Eukaryotic kingdom).

The presence of a dnaX gene that produces two subunits implies that *T.th.* has a clamp loader ($\gamma$) and may be organized by $\tau$ into a Pol III*-type replicase like the replicative DNA polymerase of *Escherichia coli*, DNA polymerase III holoenzyme. The *E. coli* DNA polymerase III holoenzyme contains 10 different subunits, some in copies of two or more for a total composition of 18 polypeptide chains (Kornberg and Baker, 1992; Onrust et al., 1995). The holoenzyme is composed of three major activities: the 3-subunit DNA polymerase core ($\alpha\epsilon\theta$), the $\beta$ subunit DNA sliding clamp, and the 5-subunit γ complex clamp loader (γδδ'χψ). This 3 component strategy generalizes to eukaryotes which utilize a clamp (PCNA) and a 5-subunit RFC clamp loader (RFC) which provide processivity to DNA polymerase δ (reviewed in Kelman and O'Donnell, 1994).

In *E. coli*, the polymerase and clamp loader components are organized into one Pol III* particle by the τ subunit, that acts as a "glue" protein (Onrust et al., 1995). One dimer of τ holds together two core polymerases in the particle which are utilized for the coordinated and simultaneous replication of both strands of duplex DNA (McHenry, 1982; Maki et al., 1988; Yuzhakov et al., 1996). The "glue" protein τ subunit also binds one clamp loader (called γ complex) thereby acting as a scaffold for a large superstructure assembly called DNA polymerase III*. The gene encoding τ, called dnaX, also encodes the γ subunit of DNA polymerase III. The β subunit then associates with Pol III* to form the DNA polymerase III holoenzyme. The γ subunit is approximately ⅔ the length of τ. γ shares the N-terminus of τ, but is truncated by a translational frameshifting mechanism that, after the shift, encounters a stop codon within two amino acids (Tsuchihashi and Kornberg, 1990; Flower and McHenry, 1990; Blinkowa and Walker, 1990). Hence, γ is the N-terminal 453 amino acids of τ, but contains one unique residue at the C-terminus (the penultimate codon encodes a Lys residue which is the same sequence as if the frameshift did not take place). This frameshift is highly efficient and occurs approximately 50% of the time.

The sequence of the γ and τ subunits encoded by the dnaX gene are homologous to the clamp loading subunits in all other organisms extending from gram negative bacteria through gram positive bacteria, the Archeae Kingdom and the Eukaryotic Kingdom from yeast to humans (O'Donnell et al., 1993). All of these organisms utilize a three component replicase (DNA polymerase, clamp and clamp loader) and in these cases the 3 components appear to behave as independent units in solution rather than forming a large holoenzyme superstructure. For example, in eukaryotes from yeast to humans, the clamp loader is the five subunit RFC, the clamp is PCNA, and the polymerases δ and ϵ are all stimulated by the PCNA clamp assembled onto primed DNA by RFC (reviewed in Kelman and O'Donnell 1994).

The discovery of a dnaX gene in *T.th.* provided confidence that thermophilic bacteria would contain a three component Pol III-type enzyme. Hence, we proceeded to identify the dnaQ and dnaN genes encoding, respectively, the proofreading 3'-5' exonuclease, and the β DNA sliding clamp subunits of a Pol III-type enzyme. Following this, we purified from extracts of *T.th.* cells, a Pol III-type enzyme. This enzyme preparation had the unique property of extending a single primer around a long 7.2 kb single strand DNA genome of M13mp18 bacteriophage. Such a primer extension assay serves as a tool to detect and identify the Pol III-type of enzyme in cell extracts. The enzyme was confirmed to be a Pol III-type enzyme based on its reactivity with antibody directed against the *E. coli* α subunit (the DNA polymerase subunit) and antibody directed against *E. coli* γ subunit. Proteins corresponding to α, τ, γ, δ and δ' were easily visible and lend themselves to identification of the genes through use of peptide microsequencing followed by primer design for PCR amplification. For example, from this DNA pol III-type preparation, the peptide sequence of the α subunit was obtained, which then allowed the dnaE gene encoding the α subunit (DNA polymerase) of the Pol III-type enzyme to be obtain.

These methods should be widely applicable to other thermophilic bacteria. Additional antibody reagents against other Pol III-type enzyme components, such as RFC subunits, DNA polymerase delta, epsilon or beta, and the PCNA clamp from known organisms can be made quite easily as polyclonal or monoclonal antibody preparations using as antigen either naturally purified sequence, recombinant sequence, or synthetic peptide sequence. Examples of known sequences of these Pol III-type enzymes are to be found in: DNA polymerases (Braithwaite and Ito, 1993), RFC clamp loaders (Cullman et al., 1995) and PCNA (Kelman and O'Donnell, 1995).

The remaining genes of *T.th.* Pol III needed for efficient extension of primed templates, holA and holB, are now identified. The holA coding sequence (SEQ. ID. No. 157) encodes the δ subunit (SEQ. ID. No. 158) and the holB coding sequence (SEQ. ID. No. 155) encodes the δ' subunit (SEQ. ID. No. 156). The holA and holB coding sequences and the δ and δ' subunits were identified via BLAST search (Altschul et al., 1997), and subsequently isolated following circular PCR. These genes will provide the subunit preparations through use of standard recombinant techniques and protein purification protocols. The protein subunits can then be used to reconstitute the enzyme complexes as they exist in the cell. This type of reconstitution of Pol III has been demonstrated using the protein subunits of DNA polymerase III holoenzyme from *E. coli* to assemble the entire particle. See, e.g., U.S. Pat. Nos. 5,583,026 and 5,668,004 to O'Donnell; and Onrust et al., 1995. The disclosures of these references are incorporated herein in their entireties.

Another organism chosen for study and exposition herein is the extreme thermophile *Aquifex aeolicus*. Thus, the present invention also relates to various isolated DNA molecules from *Aquifex aeolicus*, in particular the DNA molecules encoding various replication proteins. These include dnaE, dnaX, dnaN, holA, holB, ssb DNA molecules from *A. aeolicus*. These DNA molecules can be inserted into an expression system or used to transform host cells from which isolated proteins can be obtained. The isolated proteins encoded by these DNA molecules are also disclosed.

Unless otherwise indicated below, the *Aquifex aeolicus* sequences were obtained by sequence comparisons using the *Thermus thermophilus* counterparts as query against the genome of *Aquifex aeolicus* (Deckert et al., 1998).

The *A. aeolicus* dnaE gene has a nucleotide coding sequence according to SEQ. ID. No. 117 and encodes the α subunit of the of DNA Polymerase III, which has an amino acid sequence according to SEQ. ID. No. 1 18. The *A.ae.* α subunit has approximately 41% aa identity to the *T.th.* α subunit.

The *A. aeolicus* dnaX gene has a nucleotide coding sequence according to SEQ. ID. No. 119 and encodes the τ subunit of the of DNA Polymerase III, which has an amino acid sequence according to SEQ. ID. No. 120. The *A.ae.* τ subunit has approximately 51% aa identity to the *T.th.* τ subunit.

The *A. aeolicus* dnaN gene has a nucleotide coding sequence according to SEQ. ID. No. 121 and encodes the β subunit of DNA Polymerase III, which has an amino acid sequence according to SEQ. ID. No. 122. The *A.ae.* β subunit has approximately 27% aa identity to the *T.th.* β subunit.

The *A. aeolicus* dnaQ gene has a nucleotide coding sequence according to SEQ. ID. No. 127 and encodes the ϵ subunit of the of DNA Polymerase III, which has an amino acid sequence according to SEQ. ID. No. 128. The *A.ae.* ϵ subunit has approximately 26% aa identity to the *T.th.* ϵ subunit.

The *A. aeolicus* ssb gene has a nucleotide coding sequence according to SEQ. ID. No. 129 and encodes the SSB protein, which has an amino acid sequence according to SEQ. ID. No. 130. The *A.ae* SSB protein has approximately 22% aa identity to the *T.th.* SSB protein.

Further, the coding sequences of *A. aeolicus* genes encoding the helicase (dnaB), helicase loader (dnaC), and primase (dnaG) are also disclosed. The *A. aeolicus* dnaB gene has a nucleotide coding sequence according to SEQ. ID. No. 131 and encodes the DnaB protein, which functions as a helicase and has an amino acid sequence according to SEQ. ID. No. 132. The *A. aeolicus* dnaG gene has a nucleotide coding sequence according to SEQ. ID. No. 133 and encodes the DnaG protein, which functions as a primase and has an amino acid sequence according to SEQ. ID. No. 134. The *A. aeolicus* dnaC gene has a nucleotide coding sequence according to SEQ. ID. No. 135 and encodes the DnaC protein, which functions as a helicase loader and has an amino acid sequence according to SEQ. ID. No. 136.

The *A. aeolicus* holA and holB genes were previously unidentified by Deckert et al., 1998. Using *Thermus thermophilus* δ' subunit amino acid sequence and the *Thermatoga maritima* δ subunit amino acid sequence (SEQ. ID. No. 146 which itself was obtained using the *T.th.* δ subunit amino acid sequence of SEQ. ID. No. 158) in separate BLAST searches (Altschul et al., 1997), corresponding polypeptide products in *Aquifex aeolicus* were identified. The *A. aeolicus* holA gene has a nucleotide coding sequence according to SEQ. ID. No. 123 and encodes the δ subunit of the of DNA Polymerase III, which has an amino acid sequence according to SEQ. ID. No. 124. The *A.ae.* δ subunit has approximately 21% aa identity to the *T.m.* δ subunit. The *A. aeolicus* holB gene has a nucleotide coding sequence according to SEQ. ID. No. 125 and encodes the δ' subunit of the of DNA Polymerase III, which has an amino acid sequence according to SEQ. ID. No. 126. The *A.ae.* δ' subunit has approximately 24% aa identity to the *T.th.* δ' subunit.

This invention also clones at least the coding regions of a set of *A. aeolicus* genes which encode proteins that assemble into an *A. aeolicus* DNA polymerase III replication enzyme. These genes (dnaE, dnaN, dnaX, dnaQ, holA, holB, ssb) were cloned into expression vectors, the proteins were expressed in *E. coli*, and the corresponding protein subunits were purified (alpha, beta, tau, delta, delta prime, SSB). This invention identifies the major protein-protein contacts among these subunits, shows how these proteins can be assembled into higher order multiprotein complexes, and how to form a rapid and processive DNA polymerase III holoenzyme.

In contrast to the *E. coli* and *T. thermophilus* dnaX genes which encode both τ and γ subunits, the *A. aeolicus* dnaX gene produces only the full length τ subunit when expressed in *E. coli*. The *A. aeolicus* τ is intermediate in length between the γ and τ subunits of *E. coli* DNA polymerase III holoenzyme. The *E. coli* τ binds α, the γ subunit does not bind α. Due to the intermediate size of *A. aeolicus* τ, it was not known whether the *A. aeolicus* τ would bind the α subunit. This invention shows that indeed, the *A. aeolicus* τ binds to α, as well as δ and δ', thereby forming an *A. aeolicus* ατδδ' complex. Until the identification of the δ and δ' subunits by the present invention, their existence, let alone their interaction with τ and α, was not even known.

The *A. aeolicus* ατδδ'/β Pol III can be applied in several useful DNA handling techniques. For example, the thermophilic Pol III will be useful in DNA sequencing, especially at high temperature. Also, use of a thermal resistant rapid and processive Pol III is an important improvement to polymerase chain reaction technology. The ability of the *A. aeolicus* Pol III to extend primers for multiple kilobases makes possible the amplification of very long segments of DNA (long chain PCR).

Another organism chosen for study and exposition herein is the extreme thermophile *Thermotoga maritima*. Thus, the present invention also relates to various isolated DNA molecules from *Thermotoga maritima*, in particular the DNA molecules encoding various replication proteins. These include dnaE, dnaX, dnaN, dnaQ, holA, holB, ssb DNA molecules from *Thermotoga maritima*. These DNA molecules can be inserted into an expression system or used to transform host cells from which isolated proteins can be obtained. The isolated proteins encoded by these DNA molecules are also disclosed.

Unless otherwise indicated below, the *Thermotoga maritima* sequences were obtained by sequence comparisons using the *Thermus thermophilus* counterparts as query against the genome of *Thermotoga maritima* (Nelson et al., 1999).

The *T. maritima* dnaE gene has a nucleotide coding sequence according to SEQ. ID. No. 137 and encodes the α subunit of the of DNA Polymerase III, which has an amino acid sequence according to SEQ. ID. No. 138. The *T.m.* α subunit has approximately 33% aa identity to the *T.th.* α subunit.

The *T. maritima* dnaQ gene has a nucleotide coding sequence according to SEQ. ID. No. 139 and encodes the ε subunit of the of DNA Polymerase III, which has an amino acid sequence according to SEQ. ID. No. 140. The *T.m.* ε subunit has approximately 34% aa identity to the *T.th.* ε subunit.

The *T. maritima* dnaX gene has a nucleotide coding sequence according to SEQ. ID. No. 141 and encodes the τ subunit of the of DNA Polymerase III, which has an amino acid sequence according to SEQ. ID. No. 142. The *T.m.* τ subunit has approximately 48% aa identity to the *T.th.* τ subunit.

The *T. maritima* dnaN gene has a nucleotide coding sequence according to SEQ. ID. No. 143 and encodes the β subunit of DNA Polymerase III, which has an amino acid sequence according to SEQ. ID. No. 144. The *T.m.* β subunit has approximately 28% aa identity to the *T.th.* β subunit.

The *T. maritima* ssb gene has a nucleotide coding sequence according to SEQ. ID. No. 149 and encodes the SSB protein, which has an amino acid sequence according to SEQ. ID. No. 150. The *T.m.* SSB protein has approximately 18% aa identity to the *T.th.* SSB protein.

Further, the coding sequences of *T. maritima* genes encoding the helicase (dnaB) and primase (dnaG) are also disclosed. The *T. maritima* dnaB gene has a nucleotide coding sequence according to SEQ. ID. No. 151 and encodes the DnaB protein, which functions as a helicase and has an amino acid sequence according to SEQ. ID. No. 152. The *T. maritima* dnaG gene has a nucleotide coding sequence according to SEQ. ID. No. 153 and encodes the DnaG protein, which functions as a primase and has an amino acid sequence according to SEQ. ID. No. 154.

The *T. maritima* holA and holB genes were previously unidentified by Nelson et al., 1999). Using the *Thermus thermophilus* δ and δ' subunit amino acid sequences (SEQ. ID. Nos. 158 and 156, respectively) in separate BLAST searches (Altschul et al., 1997), corresponding polypeptide products in *T. maritima* were identified. The *T. maritima* holA gene has a nucleotide coding sequence according to SEQ. ID. No. 145 and encodes the o subunit of the of DNA Polymerase III, which has an amino acid sequence according to SEQ. ID. No. 146. The *T.m.* δ subunit has approximately 37% aa identity to the *T.th.* δ subunit. The *T.m.* holB gene has a nucleotide coding sequence according to SEQ. ID. No. 147 and encodes the δ' subunit which has an amino acid sequence according to SEQ. ID. No. 148. The *T.m.* δ' subunit has approximately 25% aa identity to the *T.th.* δ' subunit.

Yet another organism chosen for study and exposition herein is the extreme thermophile *Bacillus stearothermophilus*. Thus, the present invention also relates to various isolated DNA molecules from *Bacillus stearothermophilus*, in particular the DNA molecules encoding various replication proteins. These include dnaE, dnaX, dnaN, dnaQ, holA, holB, ssb DNA molecules from *Bacillus stearothermophilus*. These DNA molecules can be inserted into an expression system or used to transform host cells from which isolated proteins can be obtained. The isolated proteins encoded by these DNA molecules are also disclosed.

Unless otherwise indicated below, the *Bacillus stearothermophilus* sequences were obtained by searching the database of this organism (at http://www.genome.ou.edu).

The *B. stearothermophilus* polC gene has a nucleotide coding sequence according to SEQ. ID. No. 183 and encodes the PolC or α-large subunit of the DNA Polymerase III, which has an amino acid sequence according to SEQ. ID. No. 184. The *B.st.* PolC subunit, like the PolC subunits of other Gram positive organisms, contains both polymerase and 3'-5' exonuclease activity. This subunit, therefore, is essentially a fusion of α and ϵ.

The *B. stearothermophilus* dnaX gene has a partial nucleotide coding sequence according to SEQ. ID. No. 181 and encodes the τ subunit of the of DNA Polymerase III, which has a partial amino acid sequence according to SEQ. ID. No. 182. The *B.st.* τ subunit has approximately 31% aa identity to the *T.th.* τ subunit.

The *B. stearothermophilus* dnaN gene has a partial nucleotide coding sequence according to SEQ. ID. No. 173 and encodes the β subunit of DNA Polymerase III, which has a partial amino acid sequence according to SEQ. ID. No. 174. The *B.st.* β subunit has approximately 21% aa identity to the *T.th.* β subunit.

The *B. stearothermophilus* ssb gene has a nucleotide coding sequence according to SEQ. ID. No.175 and encodes the SSB protein, which has an amino acid sequence according to SEQ. ID. No. 176. The *B.st.* SSB protein has approximately 23% aa identity to the *T.th.* SSB protein.

The *B. stearothermophilus* holA gene has a nucleotide coding sequence according to SEQ. ID. No. 177 and encodes the δ subunit of DNA Polymerase III, which has an amino acid sequence according to SEQ. ID. No. 178. The *B.st.* δ subunit has approximately 26% aa identity to the *T.th.* δ subunit.

The *B. stearothermophilus* holB gene has a nucleotide coding sequence according to SEQ. ID. No. 179 and encodes the δ' subunit of DNA Polymerase III, which has an amino acid sequence according to SEQ. ID. No. 180. The *B.st.* δ' subunit has approximately 25% aa identity to the *T.th.* δ' subunit.

By conducting BLAST searches of unidentified genomic DNA from other thermophilic eubacteria, it is possible to identify coding regions which encode various functional subunits of other Pol III replicative machinery.

Although it is generally appreciated that proteins isolated from a thermophile should retain activity at high temperature, there is no guarantee that they will retain temperature resistance when isolated in pure form. This invention shows that the *A. aeolicus* Pol III, like the *T. thermophilus* Pol III, is resistant to high temperature. It is expected that the *Th. maritima* and *B. stearothermophilus* Pol III enzymes will similalry be resistant to high temperature.

The following experiments illustrate the identification and characterization of the enzymes and constructs of the present invention. Accordingly, in Examples 1–8 below, the identification and expression of the γ and τ is presented, as the first step in the elucidation of the *Thermus thermophilus* Polymerase III reflective of the present invention. Examples 9–12 which follow set forth the protocol for the purification of the remainder of the sub-units of the enzyme that represent substantial entirety of the functional replicative machinery of the enzyme. Examples 18–30 demonstrate the preparation of isolated *A. aeolicus* sequences Pol III subunits and their thermostable use.

EXAMPLE 1

Experimental Procedures

Materials

DNA modification enzymes were from New England Biolabs. Labelled nucleotides were from Amersham, and unlabeled nucleotides were from New England Biolabs The Alter-1 vector was from Promega. pET plasmids and *E. coli* strains, BL21(DE3) and BL21(DE3)pLysS were from Novagen. Oligonucleotides were from Operon. Buffer A is 20 mM Tris-HCl (pH 7.5), 0.1 mM EDTA, 5 mM DTT, and 10% glycerol.

Genomic DNA

*Thermus thermophilus* (strain HB8) was obtained from the American Type Tissue Collection. Genomic DNA was prepared from cells grown in 0.11 of Thermus medium N697 (ATCC: 4 g yeast extract, 8.0 g polypeptone (BBL 11910), 2.0 g NaCl, 30.0 g agar, 1.0 L distilled water) at 75° C. overnight. Cells were collected by centrifugation at 4° C. and the cell pellet was resuspended in 25 ml of 100 mM Tris-HCl (pH 8.0), 0.05 M EDTA, 2 mg/ml lysozyme and incubated at room temperature for 10 min. Then 25 ml 0.10 M EDTA (pH 8.0), 6% SDS was added and mixed followed by 60 ml of phenol. The mixture was shaken for 40 min. followed by centrifugation at 10,000×G for 10 min. at room temperature. The upper phase (50 ml) was removed and mixed with 50 ml of phenol:chloroform (50:50 v/v) for 30 min. followed by centrifugation for 10 min. at room temperature. The upper phase was decanted and the DNA was precipitated upon addition of 1/10 th volume 3 M sodium acetate (pH 6.5) and 1 volume ethanol. The precipitate was collected by centrifugation and washed twice with 2 ml of 80% ethanol, dried and resuspended in 1 ml T.E. buffer (10 mM Tris HCl (pH 7.5), 1 mM EDTA).

Cloning of dnaX

DNA oligonucleotides for amplification of *T.th.* genomic DNA were as follows. The upstream 32mer (5'-CGC AAGCTTCACGCSTACCTSTTCTCCGGSAC-3', S indicating a mixture of G and C) (SEQ. ID. No. 6) consists of a HindIII site within the first 9 nucleotides (underlined) followed by codons (SEQ. ID. No. 29) encoding the following amino acid sequence (HAYLFSGT) (SEQ. ID. No. 7). The downstream 34 mer (5'-CGC GAATTCGTGCTCSGGSGGCTCCTCSAGSGTC-3') (SEQ. ID. No. 8) consists of an EcoRI site (underlined) followed by codons (SEQ. ID. No. 30) encoding the sequence KTLEEPPEH (SEQ. ID. No. 9) on the complementary strand. The amplification reactions contained 10 ng *T.th.* genomic DNA, 0.5 mM of each primer, in a volume of 100 μl of Vent polymerase reaction mixture according to the manufacturers instructions (10 μl ThermoPol Buffer, 0.5 mM each dNTP and 0.5 mM $MgSO_4$). Amplification was performed using the following cycling scheme: 5 cycles of: 30 sec. at 95.5° C., 30 sec. at 40° C., 2 min. at 72° C.; 5 cycles of: 30 sec. at 95.5° C., 30 sec. at 45° C., and 2 min. at 72° C.; and 30 cycles of: 30 sec. at 95.5° C., 30 sec. at 50° C., and 30 sec. at 72° C. Products were visualized in a 1.5% native agarose gel.

Genomic DNA was digested with either XhoI, XbaI, StuI, PstI, NcoI, MluI, KpnI, HindIII, EcoRI, EagI, BglI, or BamHI, followed by Southern analysis in a native agarose gel (Maniatis et al., 1982). Approximately 0.5 μg of digest was analyzed in each lane of a 0.8% native agarose gel followed by transfer to an MSI filter (Micron Separations Inc.). The transfer included the following steps:

1. The agarose gel was soaked in 500 ml of 1% HCl with gentle shaking for 10 min.
2. Then the gel was soaked in 500 ml of 0.5 M NaOH+1.5 M NaCl for 40 min.
3. After that the gel was soaked in 500 ml of 1M ammonium acetate for 1 h.
4. The DNA was transferred to the MSI filter with the use of blotting paper for 4 h.
5. The filter was kept at 80° C. for 15 min. in the oven.
6. The pre-hybridization step was run in 10 ml of Hybridization solution (1% crystalline BSA (fraction V) (Sigma), 1 mM EDTA, 0.5 M NaHPO4 (pH 7.2), 7% SDS) at 65° C. for 30 min.
7. The probe, radiolabelled by the random priming method (see below), was added to the pre-hybridization solution and kept at 65° C. for 12 h.
8. The filter was washed with low stringency with 200 ml of the wash buffer (0.5% BSA, fraction V), 1 mM Na2 EDTA, 40 mM NaHPO4 (pH 7.2), 5% SDS with gentle shaking for 20 min. This step was repeated 5 times, followed by exposure to X-ray film (XAR-5, Kodak).

As a probe, the PCR product was radiolabelled by random as follows.

1. 14 ml of the mixture containing 0.2 μg of PCR product DNA, 1 μg of the pd(N6) (Promega) and 2.5 ml of the 10×Klenow reaction buffer (100 mM Tris-HCl (pH 7.5), 50 mM $MgCl_2$, 75 mM dithiothreitol) were boiled for 10 min. and then kept at 4° C.
2. The reaction volume was increased up to 25 μl, containing in addition 33 μM of each dNTP, except dATP, 10 μCi [α-$^{32}$P]dATP (800 Ci/mM), and 2 units of Klenow enzyme. The reaction mixture was incubated 1.5 h.
3. 2 mg of sonicated herring sperm DNA (GibcoBRL) was added to the reaction and the volume was increased to 2 ml using hybridization solution. The sample was then boiled for 10 min.

A genomic library of XbaI digested DNA was prepared upon treating 1 μg genomic *T.th.* DNA with 10 units of XbaI in 100 μl of NEBufferN2 (50 mM NaCl, 10 mM Tris-HCl (pH 7.9), 10 mM MgCl2, 1 mM DTT) for 2 h at 37° C. The digested DNA was purified by phenol chloroform extraction and ethanol precipitation. The Alter-1 vector (0.5 μg) (Promega) was digested with 1 unit of XbaI in NEBuffer N2 and then purified by phenol/chloroform extraction and ethanol precipitation. One microgram of genomic digest was incubated with 0.05 μg of digested Alter-1 and 20 U of T4 ligase in 30 μl of ligase buffer (50 mM Tris-HCl (pH 7.8), 10 mM MgCl2, 10 mM DTT and 1 mM ATP) at 15° C. for 12 h. The ligation reaction was transformed into the DH5α strain of *E. coli* and transformants were plated on LB plates containing ampicillin and screened for the dnaX insert using the radiolabelled PCR probe as follows:

1. The colonies tested were lifted onto MSI filters, approximately 100 colonies to each filter.
2. The filters, removed from the LB/Tc plates, were placed side up on a sheet of Whatman 3 MM paper soaked with 0.5 M NaOH for 5 min.
3. The filters were transferred to a sheet of paper soaked with 1 M Tris-HCl (pH 7.5) for 5 min.
4. The filters were placed on a sheet of paper soaked in 0.5 M Tris-HCl (pH 7.5), 1.25 M NaCl for 5 min.
5. After drying by air, the filters were heated in the oven 80° C. for 15 min. and then were analyzed by Southern hybridization.

Plasmid DNA was prepared from 20 positive colonies; of these 6 contained the expected 4 kb insert when digested with XbaI. Sequencing of the insert was performed by the Sanger method using the Vent polymerase sequencing kit according to the manufacturers instructions (New England Biolabs).

Identification of the dnaX Gene

Figure 1:
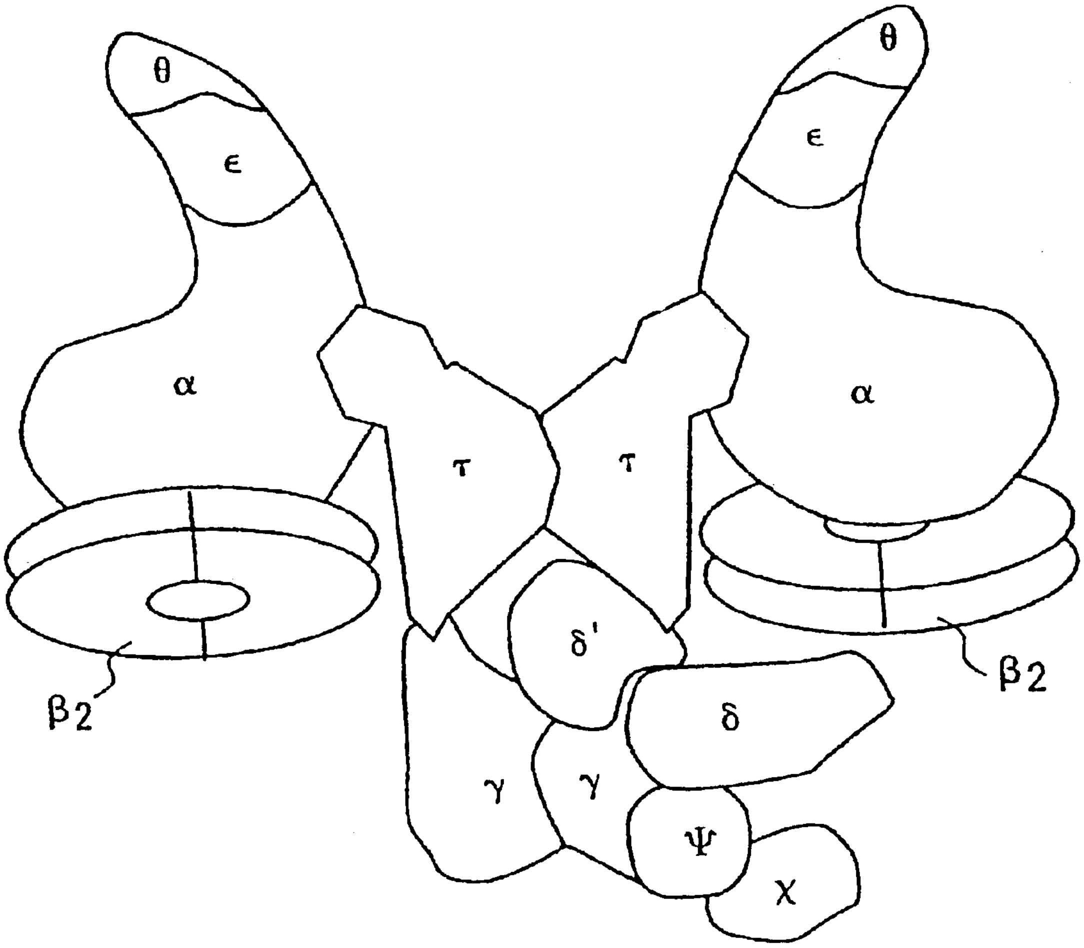
FIG. 1 is a schematic depiction of the structure and components of enzymes of the general family to which the enzymes of the present invention belong.
Figure 3:
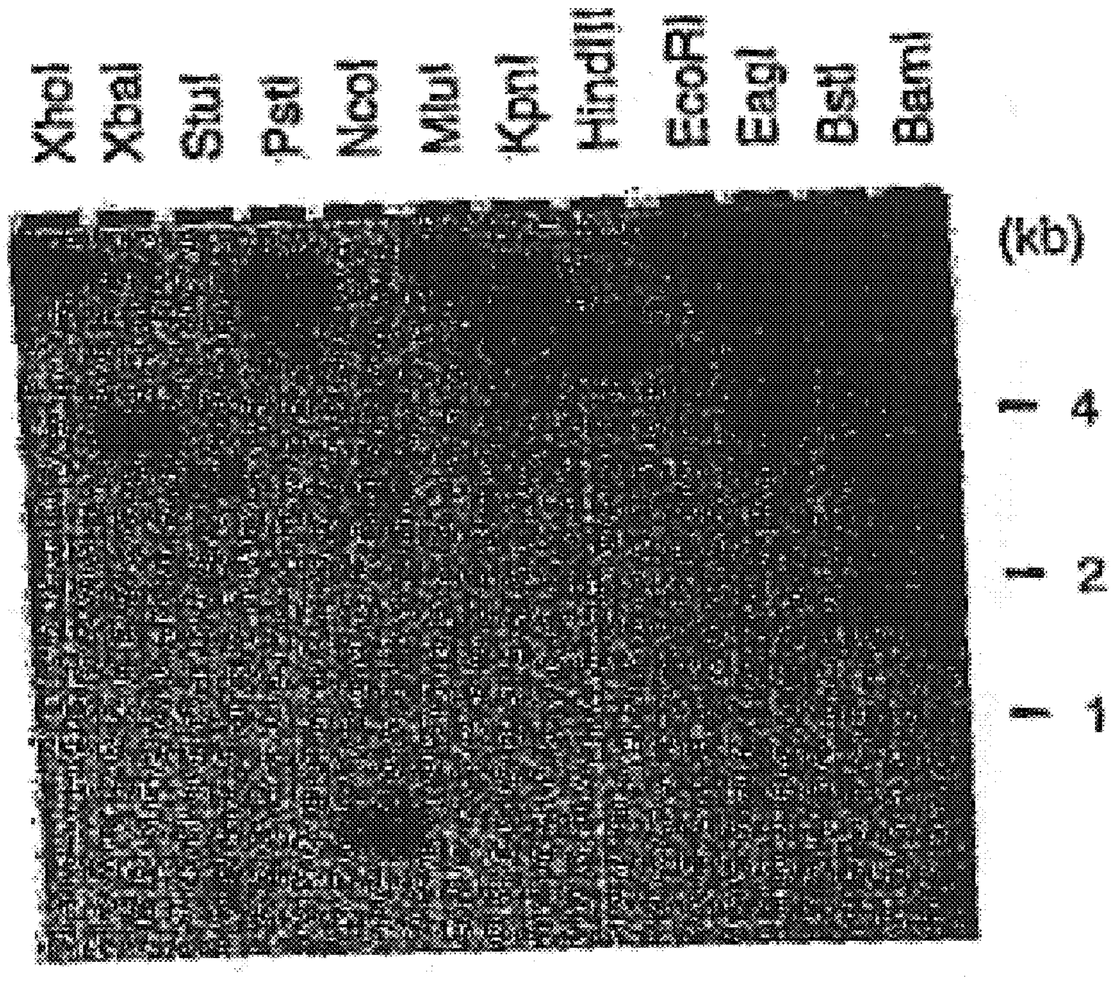
FIG. 3 is an image showing the Southern analysis of *T. thermophilus* genomic DNA. Genomic DNA was analyzed for presence of the dnaZ gene using the PCR radiolabeled probe. Enzymes used for digestion are shown above each lane. The numbering to the right corresponds to the length of DNA fragments (kb).
Figure 6:
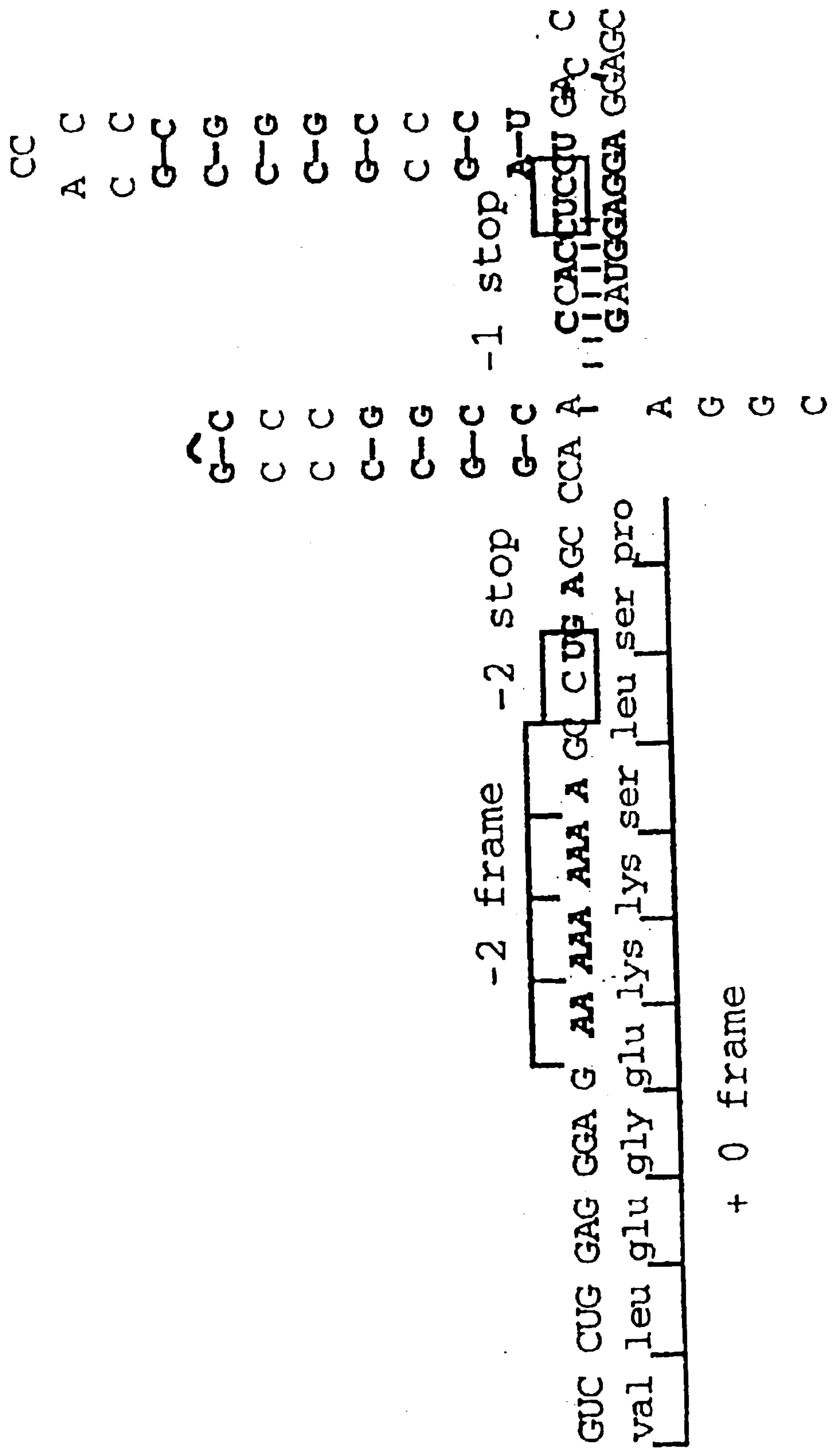
FIG. 6 is a diagram indicating a signal for ribosomal frameshifting in *T.th.* dnaX. The diagram shows part of the sequence of the RNA (SEQ. ID. No. 27) around the frameshifting site (SEQ. ID. No. 28), including the suspected slippery sequence A9 (bold italic). The stop codon in the −2 reading frame is indicated. Also indicated are potential step loop structures and the nearest stop codons in the −1 reading frame.

The dnaX genes of the gram negative *E. coli* and the gram positive *B. subtilis* share more than 50% identity in amino acid sequence within the N-terminal 180 residues containing the ATP-binding domain (FIG. 2). Two highly conserved regions (shown in bold in FIG. 2) were used to design oligonucleotide primers for application of the polymerase chain reaction to *T.th.* genomic DNA. The expected PCR product, including the restriction sites (i.e. before cutting) is 345 nucleotides. Use of these primers with genomic *T.th.* DNA resulted in a product of the expected size. The PCR product was then radiolabelled and used to probe genomic DNA in a Southern analysis (FIG. 3). Genomic DNA was digested with several different restriction endonucleases, electrophoresed in a native agarose gel and then probed with the PCR fragment. The Southern analysis showed an XbaI fragment of approximately 4 kb, more than sufficient length to encode the dnaX gene. Other restriction nucleases produced fragments that were significantly longer, or produced two or more fragments indicating presence of a site within the coding sequence of dnaX.

To obtain full length dnaX, genomic DNA was digested with XbaI and ligated into XbaI digested Alter-1 vector. Ligated DNA was transformed into DH5 alpha cells, and colonies were screened with the labeled PCR probe. Plasmid DNA was prepared from 20 positive colonies and analyzed for the appropriate sized insert using XbaI. Six of the twenty clones contained the expected 4 kb XbaI fragment as an insert, the sequence of which is shown in FIGS. 4A and 4B.

The Frameshift Site

The dnaX gene of *E. coli* produces two proteins, the γ and τ subunits, by a −1 frameshift (Tsuchihashi and Kornberg, 1990; Flower and McHenry, 1990; Blinkowa and Walker, 1990). The full length product yields τ, and the frameshift results in addition of one amino acid before encountering a stop codon to produce γ. The −1 frameshift site in the *E. coli* dnaX gene contains the sequence, A AAA AAG, which follows the X XXY YYZ rule found in retroviral genes (Jacks et al., 1988). This "slippery sequence" preserves the initial two residues of the tRNAs in the aminoacyl and peptidyl sites both before and after the frameshift. Mutagenesis of the *E. coli* dnaX frameshifting site has shown that the first three residues can be nucleotides other than A, but that A's in the second set of three nucleotides is important to frameshifting (Tsuchihashi and Brown, 1992).

Immediately downstream of the stop codon is a potential stem-loop structure which enhances frameshifting, presumably by causing the ribosome to pause. Further, the AAG codon lacks a cognate tRNA in *E. coli* and thus the G residue may facilitate the pause, and has been shown to aid the vigorous frameshifting observed in the *E. coli* dnaX gene (Tsuchihashi and Brown, 1992). A fourth component of frameshifting in the *E. coli* dnaX gene is presence of an upstream Shine-Dalgarno sequence which is thought to pair with the 16S rRNA to increase the frequency of frameshifting still further (Larsen et al., 1994).

Examination of the *T.th.* dnaX sequence reveals a single site that fulfills the X XXY YYZ rule in which positions 4–7 are A residues. The site is unique from that in *E. coli* as all seven residues are A, and the heptanucleotide sequence is flanked by another A residue on each side (i.e. A9). Surprisingly, the stop codon immediately downstream of this site is in the −2 frame, although there is a stop codon in the −1 frame 28 nucleotides downstream of the −2 stop codon. Indeed, a −2 frameshift would fulfill the requirement that the first two nucleotides of each codon in the peptidyl and aminoacyl sites be conserved during either a −1 or a −2 frameshift. As with the case of *E. coli* dnaX, there are secondary structure step loop structures immediately downstream. Finally, there is a Shine-Dalgarno sequence immediately adjacent to the frameshift site, as well as another Shine-Dalgarno sequence 22 nucleotides upstream of the frameshift site.

Figures 8A, 8B:
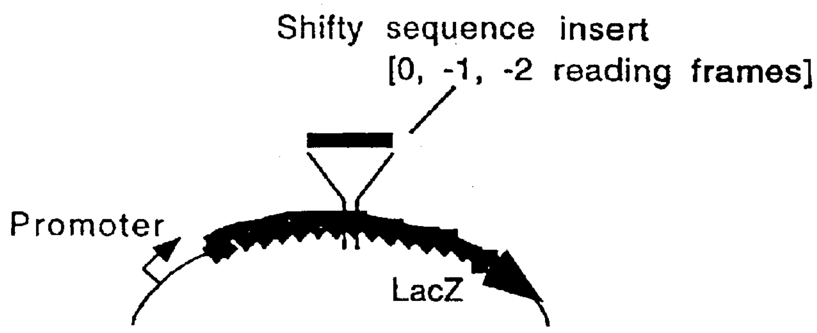
FIGS. 8A–B are images of *E. coli* colonies expressing *T.th.* dnaX −1 and −2 frameshifts. The region of the dnaX gene slippery sequence was cloned into the lacZ gene of pUC 19 in three reading frames, then transformed into *E. coli* cells and plated on LB plates containing X-gal. The slippery sequence was also mutated by inserting two G residues into the A9 sequence and then cloned into pUC19 in all three reading frames. Color of colonies observed are indicated by the plus signs. The picture shows the colonies, the type of frameshift required for readthrough (blue color) is indicted next to the sector.

Assuming the first stop codon is utilized (i.e. −2 frameshift), the predicted size of the γ subunit in *T.th.* is 454 amino acids for a mass of 49.8 kDa, over 2 kDa larger than the 431 residue γ subunit (47.5 kDa) of *E. coli*. This would result in 2 residues after the −2 frameshift (i.e. after the GluLysLys, the residues LysAla would be added) to be compared to the result of the −1 frameshift in *E. coli* which also results in 2 residues (LysGlu). In the event that a −1 frameshift were utilized in the *T.th.* dnaX gene, then an additional 12 residues would be added following the frameshift for a molecular mass of 50.8 kDa (i.e. after the GluLysLys, the residues LysProAspProLysAlaProProGlyProThrSer would be added at aa 453–464 of SEQ. ID. No. 4). As explained later, this nucleotide sequence was found to promote both −1 and −2 frameshifting in *E. coli* (FIG. 8). But first, we examined *T.th.* cells by Western analysis for the presence of two subunits homologous to *E. coli* γ and τ.

EXAMPLE 2

Frameshifting Analysis of the *T.th.* dnaX Gene

Frameshifting was analyzed by inserting the frameshift site into lacZ in the three different reading frames, followed by plating on X-gal and scoring for blue or white colony formation (Weiss et al., 1987). The frameshifting region within *T.th.* dnaX was subcloned into the EcoRI/BamHI sites of pUC19. These sites are within the polylinker inside of the β-galactosidase gene. Three constructs were produced such that the insert was either in frame with the downstream coding sequence of β-galactosidase, or were out of frame (either −1 or −2). An additional three constructs were designed by mutating the frameshift sequence and then placing this insert into the three reading frames of the β-galactosidase gene. These six plasmids were i4 constructed as described below.

The upstream primer for the shifty sequences was 5'-gcg cgg atc cgg agg gag aaa aaa aaa gcc tca gcc ca-3' (SEQ. ID. No. 10). The BamHI site for cloning into pUC is underlined. Also, the stop codon, tga, has been mutated to tca (also underlined). The upstream primer for the mutant shifty sequence was: 5'-gcg cgg atc cgg agg gag aga aga aaa gcc tca gcc ca-3' (SEQ. ID. No. 11). The mutant sequence contains two substitutions of a G for an A residue in the polyA stretch (underlined). Three downstream primers were utilized with each upstream primer to create two sets of three inserts in the 0 frame, −1 frame and −2 frame. The sequence of these primers, and the length of insert (after cutting with EcoRI and BamHI and inserting into pUC19) are as follows: 5'-gaa tta aat tcg cgc ttc ggg agg tgg g-3' (0 frameshift, total 58 nucleotide insert) (SEQ. ID. No. 12); 5'-gcg cga att cgc gct tcg gga ggt ggg-3' (−1 frame, 54mer insert) (SEQ. ID. No. 13); and 5'-gcg cga att cgg gcg ctt cag gag gtg gg-3' (−2 frame, 56mer insert) (SEQ. ID. No. 14). The downstream primers have an EcoRI site (underlined); the EcoRI site of the 0 frame insert was blunt ended to produce the greater length insert (converting the EcoRI site to an aattaatt sequence). Also, the tcg sequence, which produces the tga stop codon (underlined) was mutated to tca in the −2 downstream primer so that readthrough would be allowed after the frameshift occurred.

In summary, a region surrounding the frameshift site and ending at least 5 nucleotides past the −1 frameshift stop codon was inserted into the β-galactosidase gene of pUC19 in the three different reading frames (stop codons were mutated to prevent stoppage following a frameshift). These three plasmids were introduced into *E. coli* and plated with X-gal. The results, in FIG. 8, show that blue colonies were observed after 24 h incubation with all three plasmids and therefore both −1 and −2 frameshifting had occurred.

To further these results, two γ residues were introduced into the polyA tract which should disrupt the ability of this sequence to direct frameshifts. The mutated slippery sequence was inserted into pUC19 followed by transformation into *E. coli* and plating on X-gal. The results showed that both −1 and −2 frameshifting was prevented, further supporting the fact that frameshifting requires the polyA tract as expected (FIG. 8).

EXAMPLE 3

Expression Vector for *T.th.* γ and τ

Figure 9:
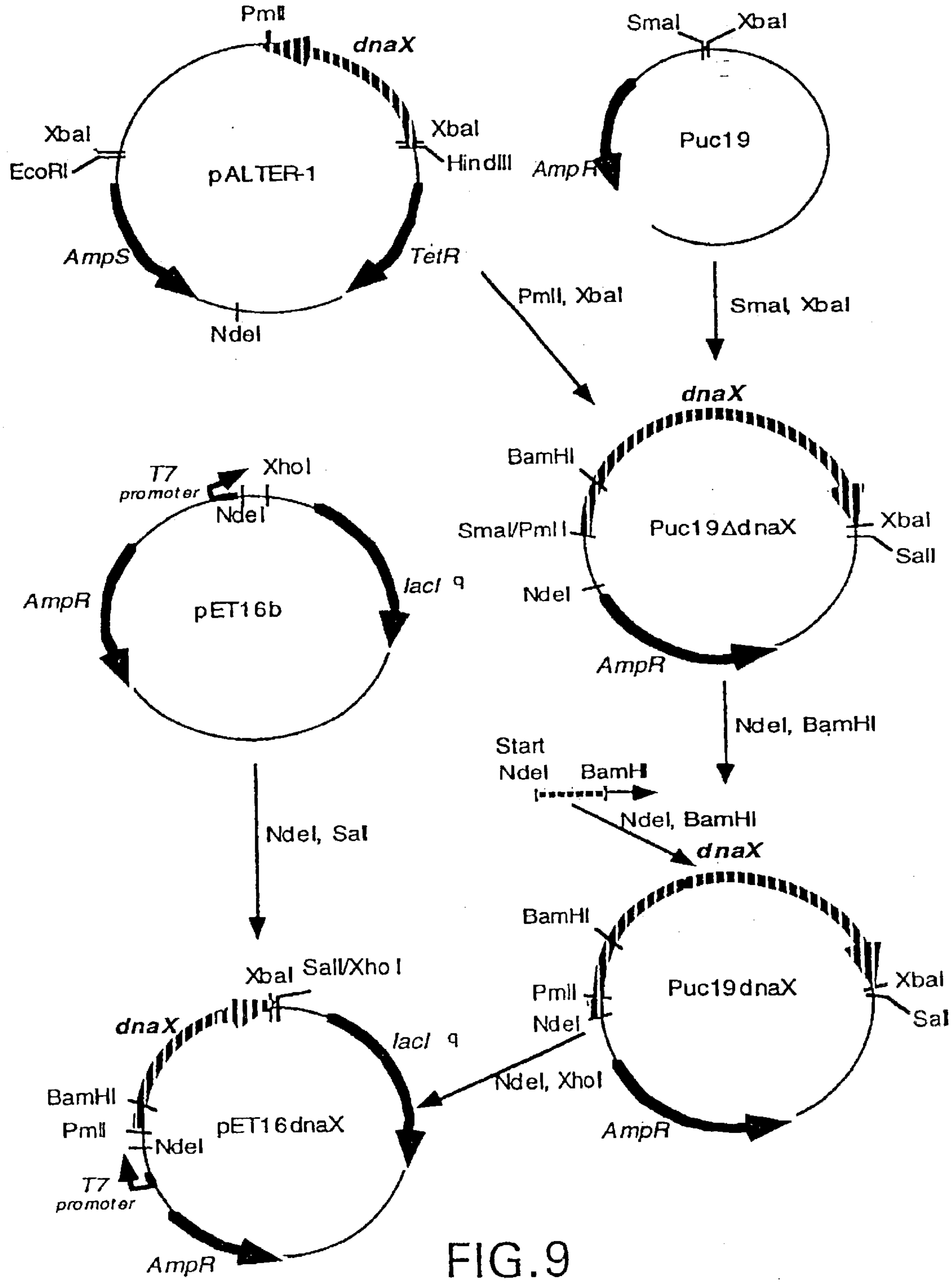
FIG. 9 shows the construction of the *T.th.* γ/τ expression vector. A genomic fragment containing a partial sequence of dnaX was cloned into pALTER-1. This fragment was subcloned into pUC19 (pUC19_dnaX). Then the N-terminal section of dnaX was amplified such that the fragment was flanked by NdeI (at the initiating codon) and the internal BamHI site. This fragment was inserted to form the entire coding sequence of the dnaX gene in pUC19 (pUC19dnaX). The dnaX gene was then cloned behind the polyhistidine leader in the T7 based expression vector pET16 to give pET16dnaX. Details are in "Experimental Procedures".

The dnaX gene was cloned into the pET16 expression vector in the steps shown in FIG. 9. First, the bulk of the gene was cloned into pET16 by removing the PmlI/XbaI fragment from pAlterdnaX, and placing it into SmaI/XbaI digested Puc19 to yield Puc19dnaXCterm. The N-terminal sequence of the dnaX gene was then reconstructed to position an NdeI site at the N-terminus. This was performed by amplifying the 5' region encoding the N-terminal section of γ/τ using an upstream primer containing an NdeI site that hybridizes to the dnaX gene at the initiating gtg codon (i.e. to encode Met where the Met is created by the PCR primer, and the Val is the initiating gtg start codon of dnaX). The primer sequence for this 5' end was: 5'-gtggtgcatatg gtg agc gcc ctc tac cgc c-3' (SEQ. ID. No. 15) (where the NdeI site is underlined, and the coding sequence of dnaX follows). The downstream primer hybridizes past the PmlI site at nucleotide positions 987–1004 downstream of the initiating gtg (primer sequence: 5'-gtggtggtcgac cca gga ggg cca cct cca g-3' (SEQ. ID. No. 16) where the initial 12 nucleotides contain a SalGI restriction site, followed by the sequence from the region downstream the stop codon). The 1.1 kb nucleotide PCR product was digested with PmlI/NdeI and the PmlI/NdeI fragment was ligated into NdeI/PmlI digested Puc19dnaXCterm to form Puc19dnaX. The Puc19dnaX plasmid was then digested with NdeI and SalI and the 1.9 kb fragment containing the dnaX gene was purified using the Sephaglas BandPrep Kit (Pharmacia-LKB). pET16b was digested with NdeI and XhoI. Then the full length dnaX gene was ligated into the digested pET16b to form pETdnaX.

EXAMPLE 4

Expression of *T.th.* γ and τ

Figures 10A, 10B, 10C:
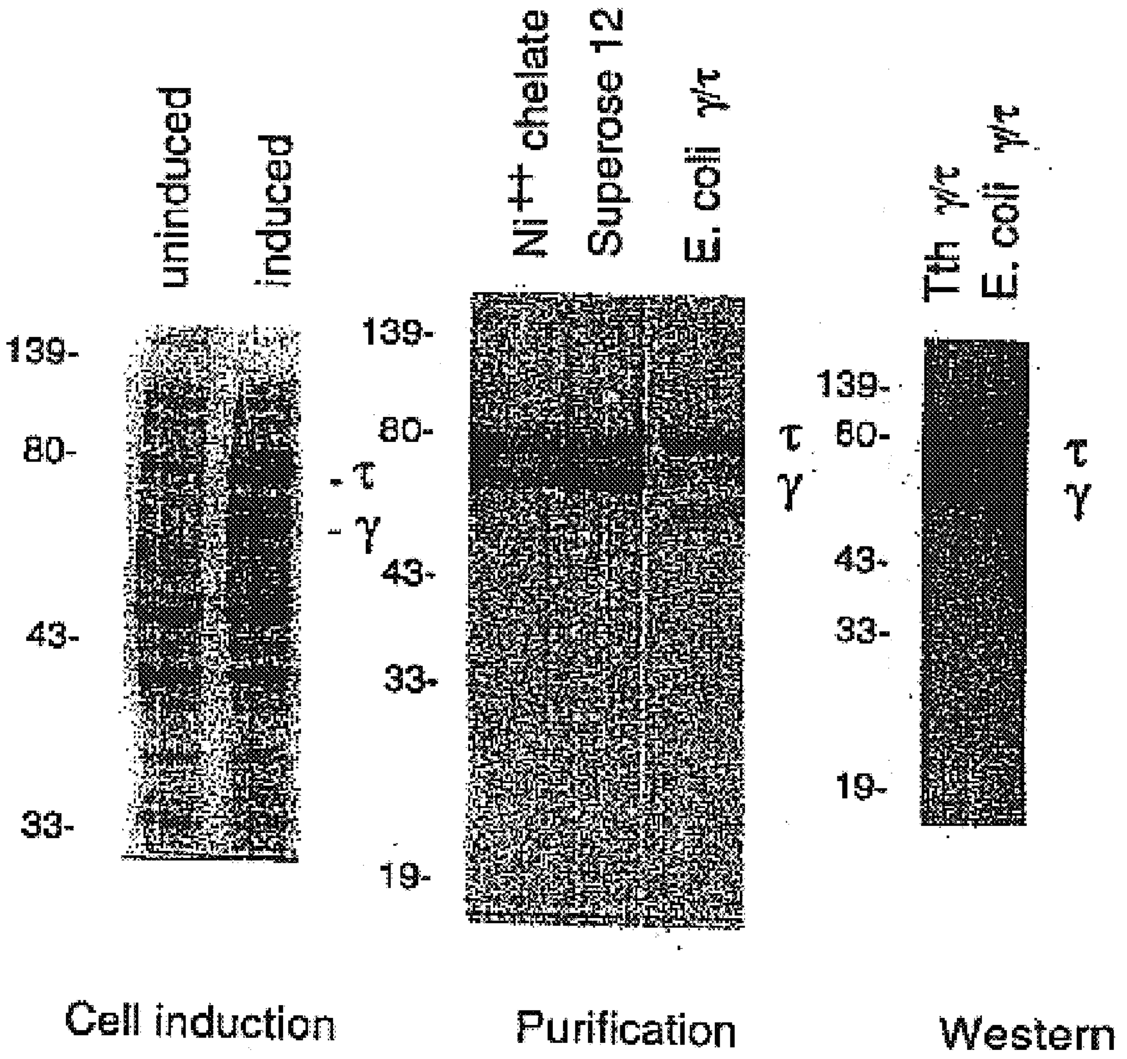
FIGS. 10A–C illustrate the purification of recombinant *T.th.* γ and τ subunits. *T.th.* γ and τ subunits were expressed in *E. coli* harboring pET16dnaX. Molecular size markers are shown to the left of the gels, and the two induced proteins are labeled as g and τ to the right of the gel. Panel A) 10% SDS gel of *E. coli* whole cell lysates before and after induction with IPTG. Panel B) 8% SDS gel of the purification two steps after cell lysis. First lane: the lysate was applied to a HiTrap Nickel chromatography column. Second lane: the *T.th.* γ/τ subunits were further purified on a Superose 12 gel filtration column. Third lane, the *E. coli* γ and τ subunits. Panel C) Western analysis of the pure *T.th.* γ and τ subunits (first lane) and *E. coli* γ and τ subunits (second lane).

As discussed in the previous example, the dnaX gene was engineered into the T7 based IPTG inducible pET16 vector such that the initiation codon was placed precisely following the Met residue N-terminal leader sequence (FIG. 9). This should produce a protein containing the entire sequence of γ and τ, along with a 21 residue leader containing 10 contiguous His residues (tagged-τ=60.6 kDa; tagged-γ=52.4 kDa for −2 frameshift). The pETdnaX plasmid was introduced into BL21(DE3)pLysS cells harboring the gene encoding T7 RNA polymerase under control of the lac repressor. Log phase cells were induced with IPTG and analyzed before and after induction in an SDS polyacrylamide gel (FIG. 10, lanes 1 and 2). The result shows that upon induction, two new proteins are expressed with the approximate sizes expected of the *T.th.* γ and τ subunits (larger than *E. coli* γ, and smaller than *E. coli* τ). The two proteins are produced in nearly equal amounts, similar to the case of the *E. coli* γ and τ subunits. Western analysis using antibodies against the *E. coli* γ and τ subunits cross-reacted with the induced proteins further supporting their identity as *T.th.* γ and τ (data not shown, but repeated with the pure subunits shown in FIG. 10, lane 6).

EXAMPLE 5

Purification of *T.th.* γ and τ

The His-tagged *T.th.* γ and τ proteins were purified from 6 L of induced *E. coli* cells containing the pETdnaX plasmid. Cells were lysed, clarified from cell debris by centrifugation and the supernatant was applied to a HiTrap chelate affinity column. Elution of the chelate affinity column yielded approximately 35 mg of protein in which the two predominant bands migrated in a region consistent with the molecular weight predicted from the dnaX gene (FIG. 10, lane 3), and produced a positive signal by Western analysis using polyclonal antibody directed against the *E. coli* γ and τ subunits (lane 4). The γ and τ subunits are present in nearly equal amounts consistent with the nearly equal expression of these proteins in *E. coli* cells harboring the pETdnaX plasmid.

Figure 11A:
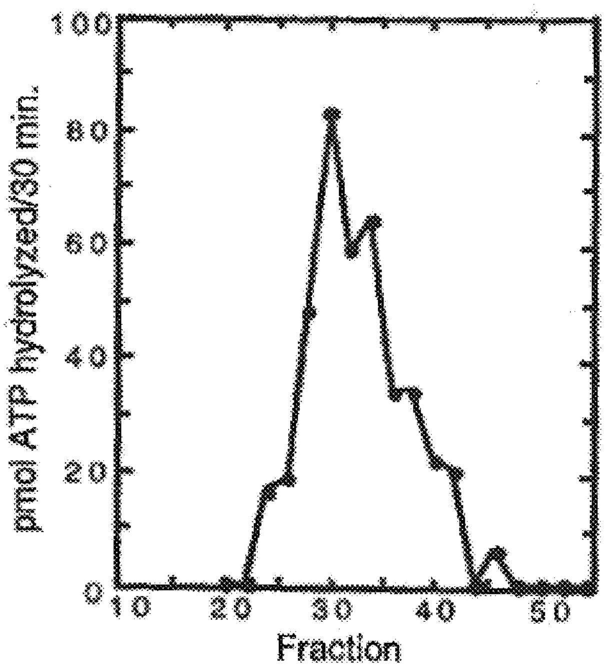
FIGS. 11A–B show the gel filtration of *T.th.* γ and τ. *T.th.* γ and τ were gel filtered on a Superose 12 column. Column fractions were analyzed for ATPase activity and in a Coomassie Blue stained 10% SDS polyacrylamide gel. Positions of molecular weight markers are shown to the left of the gel. The elution position of size standards analyzed in a parallel Superose 12 column under identical conditions are indicated above the gel. Thyroglobin (670 kDa), bovine gamma globin (150 kDa), chicken ovalbumin (44 kDa), equine myoglobin (17 kDa).
Figure 11B:
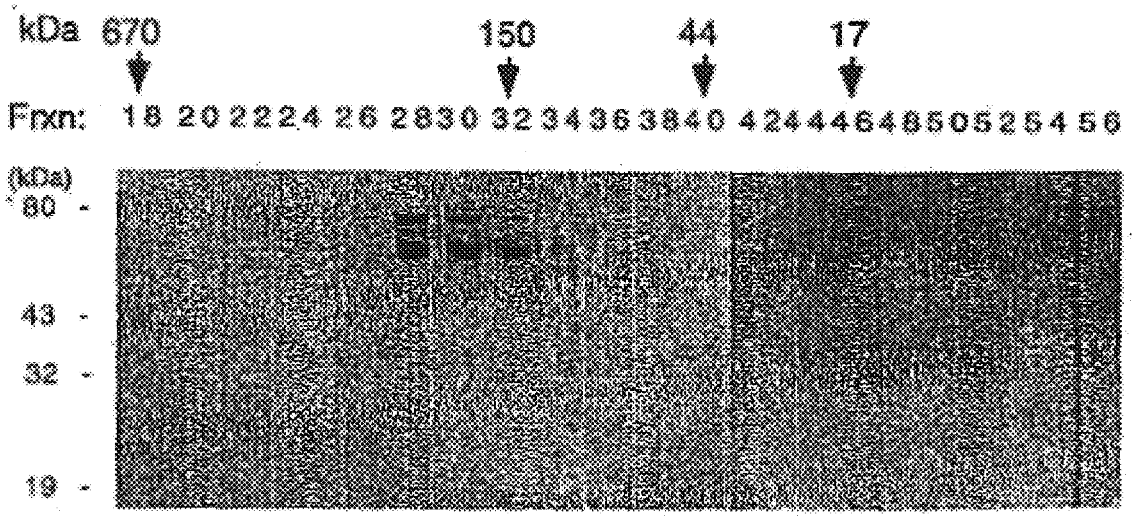

The γ and τ subunits were further purified by gel filtration on a Superose 12 column (FIG. 10, lane 4; FIG. 11). Recovery of *T.th.* γ and τ subunits through gel filtration was 81%. The *E. coli* γ and τ subunits, when separated from one another, elute during gel filtration as tetramers. A mixture of *E. coli* γ/τ results in a mixed tetramer of γ2τ2 along with γ4 and τ4 tetramers (Onrust et al., 1995). The mixture of *T.th.* γ/τ elutes ahead of the 150 kDa marker, and thus is consistent with the expected mass of a γ2τ2 tetramer (225 kDa) and γ4 and τ4 tetramers.

As described earlier, the dnaX frameshifting sequence could produce either a −1 or −2 frameshift to yield a His-tagged γ subunit of mass either 53.3 kDa or 52.4 kDa, respectively. The difference in these two possible products is too close to determine from migration in SDS gels. It also remains possible that two γ products are present and do not resolve under the conditions used. The exact protocol for this purification is described below.

Six liters of BL21(DE3)pLysSpETdnaX cells were grown in LB media containing 50 μg/ml ampicillin and 25 μg/ml chloramphenicol at 37° C. to an O.D. of 0.8 and then IPTG was added to a concentration of 2 mM. After a further 2 h at 37° C., cells were harvested by centrifugation and stored at −70° C. The following steps were performed at 4° C. Cells (15 g wet weight) were thawed and resuspended in 45 ml 1×binding buffer (5 mM imidizole, 0.5 M NaCl, 20 mM Tris HCl (final pH 7.5)) using a dounce homogenizer to complete cell lysis and 450 ml of 5% polyamine P (Sigma) was added. Cell debris was removed by centrifugation at 18,000 rpm for 30 min. in a Sorvall SS24 rotor at 4° C. The supernatant (Fraction 1, 40 ml, 376 mg protein) was applied to a 5 ml HiTrap Chelating Separose column (Pharmacia-LKB). The column was washed with 25 ml of binding buffer, then with 30 ml of binding buffer containing 60 mM imidizole, and then eluted with 30 ml of 0.5 M imidizole, 0.5 M NaCl, 20 mM Tris-HCl (pH 7.5). Fractions of 1 ml were collected and analyzed on an 8% Coomassie Blue stained SDS polyacrylamide gel. Fractions containing subunits migrating at the *T.th.* γ and τ positions, and exhibiting cross reactivity with antibody to *E. coli* γ and τ in a Western analysis, were pooled and dialyzed against buffer A (20 mM Tris-HCl (pH 7.5), 0.1 mM EDTA, 5 mM DTT and 10% glycerol) containing 0.5 M NaCl (Fraction II, 36 mg in 7 ml). Fraction II was diluted 2-fold with buffer A and passed through a 2 ml ATP agarose column equilibrated in buffer A containing 0.2 M NaCl to remove any *E. coli* γ complex contaminant. Then 0.18 mg (300 ml) Fraction II was gel filtered on a 24 ml Superose 12 column (Pharmacia-LKB) in buffer A containing 0.5 M NaCl. After the first 216 drops, fractions of 200 μl were collected (Fraction III) and analyzed by Western analysis (by procedures similar to those described in Example 6), by ATPase assays and by Coomassie Blue staining of an 8% Coomassie Blue stained SDS polyacrylamide gel. The Coomassie stained gels and Western analysis of recombinant *T.th.* gamma and tau for these purification steps are summarized in FIG. 10.

EXAMPLE 6

Western Analysis of *T.th.* Cells for Presence of γ and τ Subunits

Polyclonal antibody to *E. coli* γ/τ-*E. coli* γ subunit was prepared as described (Studwell-Vaughan and O'Donnell, 1991) Pure γ subunit (100 μg) was brought up in Freund's adjuvant and injected subcutaneously into a New Zealand Rabbit (Poccono Rabbit Farms). After two weeks, a booster consisting of 50 μg γ in Freund's adjuvant was administered, followed after two weeks by a third injection (50 μg).

Figure 7:
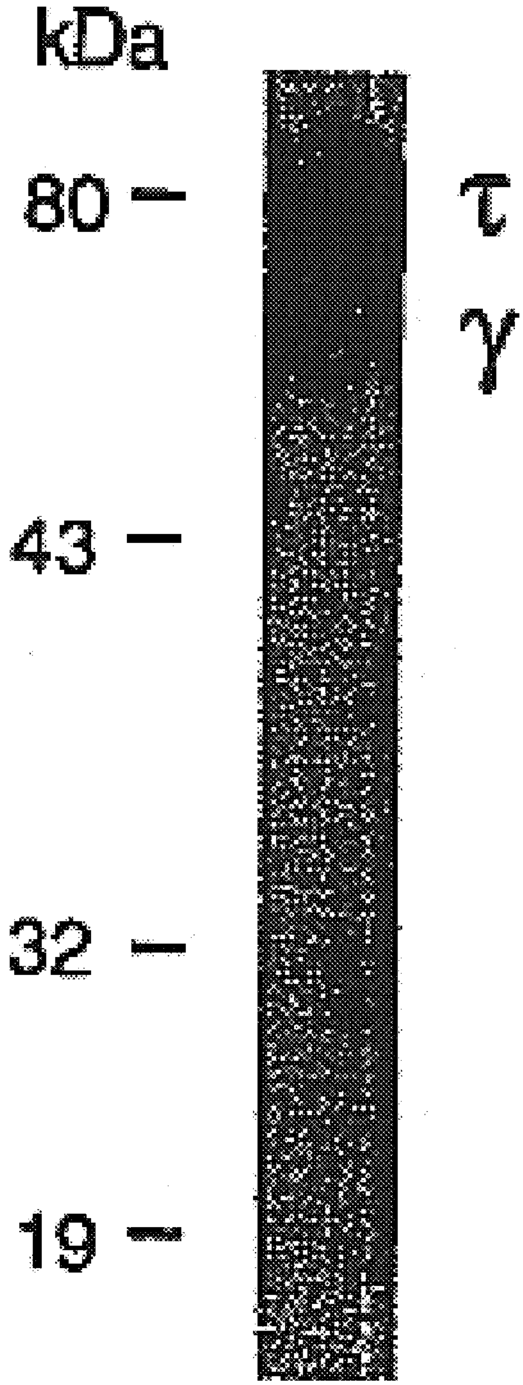
FIG. 7 is an image showing a Western analysis of γ and τ in *T.th.* cells. Whole cells were lysed in SDS and electrophoresed on a 10% SDS polyacrylamide gel then transferred to a membrane and probed with polyclonal antibody against *E. coli* γ/τ as described in Experimental Procedures. Positions of molecular weight size markers are shown to the left. Putative *T.th.* γ and τ are indicated to the right.

The homology between the amino terminal regions of *T.th.* and *E. coli* γ/τ subunits suggested that there may be some epitopes in common between them. Hence, polyclonal antibody directed against the *E. coli* γ/τ subunits was raised in rabbits for use in probing *T.th.* cells by Western analysis. FIG. 7 shows the results of a Western analysis of whole *T.th.* cells lysed in SDS. The results show that in *T.th.* cells, the antibody is rather specific for two high molecular proteins which migrate in the vicinity of the molecular masses of *E. coli* γ and τ subunits.

Procedure for Western Analysis

Samples were analyzed in duplicate 10% SDS polyacrylamide gels by the Western method (Towbin et al. 1979). One gel was Coomassie stained to evaluate the pattern of proteins present, and the other gel was then electroblotted onto a nitrocellulose membrane (Schleicher and Schuell). For molecular size markers, the kaliedoscope molecular weight markers (Bio-Rad) were used to verify by visualization that transfer of proteins onto the blotted membrane had occurred. The gel used in electroblotting was also stained after electroblotting to confirm that efficient transfer of protein had occured. Membranes were blocked using 5% non-fat milk, washed with 0.05% Tween in TBS (TBS-T) and then incubated for over 1 h with a 1/5000 dilution of rabbit polyclonal antibody directed against E. Coli γ and τ in 1% gelatin in TBS-T at room temperature. Membranes were washed using TBS-T buffer and then antibody was detected on X-ray film (Kodak) by using the ECL kit from (Amersham) and the manufactures recommended procedures.

Samples included: 1) a mixture of *E. coli* γ (15 ng) and τ (15 ng) subunits; 2) *T.th.* whole cells (100 μl) suspended in cracking buffer; and 3) purified *T.th.* γ and τ fraction II (0.6 μg as a mixture).

EXAMPLE 7

Characterization of the ATPase Activity of γ/τ

The *E. coli* τ subunit is a DNA dependent ATPase (Lee and Walker, 1987; Tsuchihashi and Kornberg, 1989). The γ subunit binds ATP but does not hydrolyze it even in the presence of DNA unless other subunits of the DNA polymerase III holoenzyme are also present (Onrust et al., 1991). Next we examined the *T.th.* γ/τ subunits for DNA dependent ATPase activity. The γ/τ preparation was, in fact, a DNA stimulated ATPase (FIG. 11, top panel). The specific activity of the *T.th.* γ/τ was 11.5 mol ATP hydrolyzed/mol γ/τ (as monomer and assuming an equal mixture of the two). Furthermore, analysis of the gel filtration column fractions shows that the ATPase activity coelutes with the *T.th.* γ/τ subunits, supporting evidence that the weak ATPase activity is intrinsic to the γ/τ subunits (FIG. 11). The specific activity of the γ/τ preparation before gel filtration was the same as after gel filtration (within 10%), further indicating that the DNA stimulated ATPase is an inherent activity of the γ/τ subunits. Presumably, only the τ subunit contains ATPase activity, as in the case of *E. coli*. Assuming only *T.th.* τ contains ATPase activity, its specific activity is twice the observed rate (after factoring out the weight of γ). This rate is still only one-fifth that of *E. coli* τ.

The *T.th.* γ/τ ATPase activity is lower at 37° C. than at 65° C. (middle panel), consistent with the expected behavior of protein activity from a thermophilic source. However, there is no apparent increase in activity in proceeding from 50° C. to 65° C. (the rapid breakdown of ATP above 65° C. precluded measurement of ATPase activity at temperatures above 65° C.). In contrast, the *E. coli* τ subunit lost most of its ATPase activity upon elevating the temperature to 50° C. (middle panel). These reactions contain no stabilizers such as a nonionic detergent or gelatin, nor did they include substrates such as ATP, DNA or magnesium.

Figure 12A:
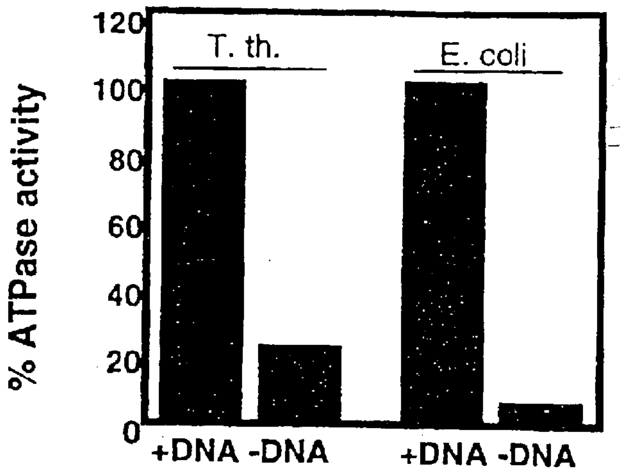
FIGS. 12A–C illustrate the characterization of the *T.th.* γ and τ ATPase activity. The *T.th.* γ/τ and *E. coli* τ subunits are compared in their ATPase activity characteristics. Due to the greater activity of *E. coli* τ, the values are plotted as percent for ease of comparison. Actual specific activities for 100% values are given below as pmol ATP hydrolyzed/30 min./pmol *T.th.* γ/τ (or pmol *E. coli* τ). Panel A) *T.th.* γ and τ ATPase is stimulated by the presence of ssDNA. *T.th.* γ/τ was incubated at 65° C. Specific activity was: 11.5 (+DNA); 2.5 (−DNA); *E. coli* τ was assayed at 37° C. Specific activity values were: 112.5 (+DNA); (7.3-DNA). Panel B) Temperature stability of DNA stimulated ATPase activity. *T.th.* γ/τ, 11.3 (65° C.); *E. coli* τ, 97.5 (37° C.). Panel C) Stability of *T.th.* γ/τ ATPase to NaCl. *T.th.* γ/τ, 8.1 (100 mM added NaCl and 65° C.); *E. coli* τ, 52.7 (0 M added NaCl and 37° C.).
Figure 12B:
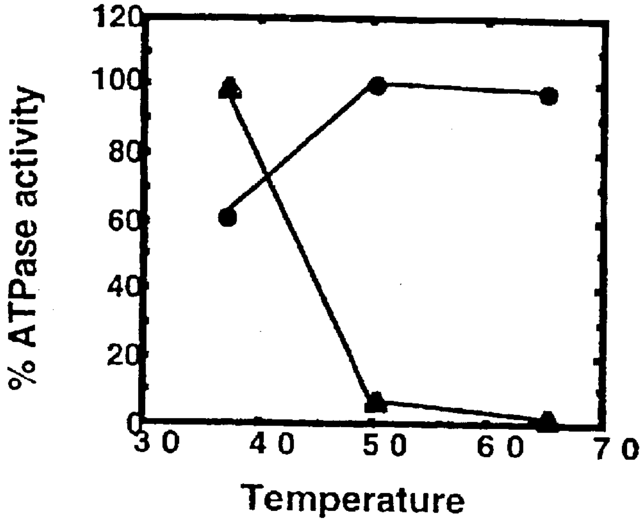
Figure 12C:
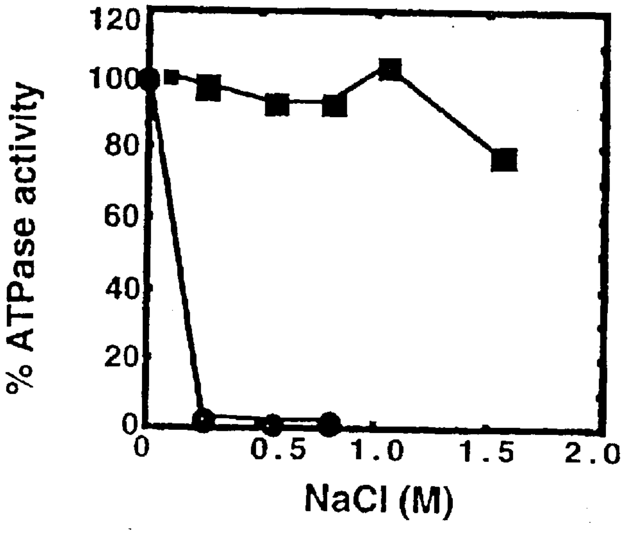

Last, the relative stability of *T.th.* γ/τ and *E. coli* γ/τ to addition of NaCl (FIG. 12, bottom panel) was examined. Whereas the *E. coli* τ subunit rapidly lost activity at even 0.2 M NaCl, the *T.th.* γ/τ retained full activity in 1.0 M NaCl and was still 80% active in 1.5 M NaCl. The detailed procedure for the ATPase activity assay is described below.

ATPase Assays

ATPase assays were performed in 20 μl of 20 mM Tris-HCl (pH 7.5), 8 mM $MgCl_2$ containing 0.72 μg of M13mp18 ssDNA (where indicated), 100 mM [γ-$^{32}$P]-ATP (specific activity of 2000–4000 cpm/pmol), and the indicated protein. Some reactions contained additional NaCl where indicated. Reactions were incubated at the temperatures indicated in the figure legends for 30 min. and then were quenched with an equal volume of 25 mM EDTA (final). The aliquots were analyzed by spotting them (1 μl each) onto thin layer chromatography (TLC) sheets coated with Cel-300 polyethyleneimine (Brinkmann Instruments Co.). TLC sheets were developed in 0.5 M lithium chloride, 1 M formic acid. An autoradiogram of the TLC chromatogram was used to visualize Pi at the solvent front and ATP near the origin which were then cut from the TLC sheet and quantitated by liquid scintillation. The extent of ATP hydrolyzed was used to calculate the mol of Pi released per mol of protein per min. One mol of *E. coli* τ was calculated assuming a mass of 71 kDa per monomer. The *T.th.* γ and τ preparation was treated as an equal mixture and thus one mole of protein as monomer was the average of the predicted masses of the γ and τ subunits (54 kDa).

EXAMPLE 8

Homolog of *T.th.* γ/τ to dnaX Gene Products of Other Organism

The XbaI insert encoded an open reading frame, starting with a GTG codon, of 529 amino acids in length (58.0 kDa), closer to the predicted length of the *B. subtilis* τ subunit (563 amino acids, 62.7 kDa mass)(Alonso et al., 1990) than the *E. coli* τ subunit (71.1 kDa)(Yin et al., 1986). The dnaX gene encoding the γ/τ subunits of *E. coli* DNA polymerase III holoenzyme is homologous to the holB gene encoding the δ' subunit of the γ complex clamp loader, and this homology extends to all 5 subunits of the eukaryotic RFC clamp loader as well as the bacteriophage gene protein 44 of the gp44/62 clamp loading complex (O'Donnell et al., 1993). These gene products show greatest homology over the N-terminal 166 amino acid residues (of *E. coli* dnaX); the C-terminal regions are more divergent. FIGS. 5A–B show an alignment of the amino acid sequence of the N-terminal regions of the *T.th.* dnaX gene product to those of several other bacteria. The consensus GXXGXGKT (SEQ. ID. No. 17) motif for nucleotide binding is conserved in all these protein products. Further, the *E. coli* δ' crystal structure reveals one atom of zinc coordinated to four Cys residues (Guenther, 1996). These four Cys residues are conserved in the *E. coli* dnaX gene, and the γ and τ subunits encoded by *E. coli* dnaX bind one atom of zinc. These Cys residues are also conserved in *T.th.* dnaX (shown in FIGS. 5A–B). Overall, the level of amino acid identity relative to *E. coli* dnaX in the N-terminal 165 residues of *T.th.* dnaX is 53%. The *T.th.* dnaX gene is just as homologous to the *B. subtilis* dnaX (53% identity) gene relative to *E. coli* dnaX. After this region of homology, the C-terminal region of *T.th.* dnaX shares 26% and 20% identity to *E. coli* and *B. subtilis* dnaX, respectively. A proline rich region, downstream of the conserved region, is also present in *T.th.* dnaX (residues 346–375), but not in the *B. subtilis* dnaX (see FIGS. 3A and 3B). The overall identity between *E. coli* dnaX and *T.th.* dnaX over the entire gene is 34%. Identity of *T.th.* dnaX to *B. subtilis* dnaX over the entire gene is 28%.

Comparison of dnaX Genes from *T.th.* and *E. coli*

The above identifies a homologue of the dnaX gene of *E. coli* in *Thermus thermophilus*. Like the *E. coli* gene, *T.th.* dnaX encodes two related proteins through use of a highly efficient translational frameshift. The *T.th.* γ/τ subunits are tetramers, or mixed tetramers, similar to the γ and τ subunits of *E. coli*. Further, the γ/τ subunit is a DNA stimulated ATPase like its *E. coli* counterpart. As expected for proteins from a thermophile, the *T.th.* γ/τ ATPase activity is thermostabile and resistant to added salt.

In *E. coli*, γ is a component of the clamp loader, and the τ subunit serves the function of holding the clamp loading apparatus together with two DNA polymerases for coordinated replication of duplex DNA. The presence of γ in *T.th.* suggests it has a clamp loading apparatus and thus a clamp as well. The presence of the τ subunit of *T.th.* implies that *T.th.* contains a replicative polymerase with a structure similar to that of *E. coli* DNA polymerase III holoenzyme.

A significant difference between *E. coli* and *T.th.* dnaX genes is in the translational frameshift sequence. In *E. coli*, the heptamer frameshift site contains six A residues followed by a G residue in the context A AAA AAG. This sequence satisfies the X XXY YYZ rule for −1 frameshifting. The frameshift is made more efficient by the absence of the AAG tRNA for Lys which presumably leads to stalling of the ribosome at the frameshift site and increases the efficiency of frameshifting (Tsuchihashi and Brown, 1992). Two additional aids to frameshifting include a downstream hairpin and an upstream Shine-Dalgarno sequence (Tsuchihashi and Kornberg, 1990; Larsen et al., 1994). The −1 frameshift leads to incorporation of one unique residue at the C-terminus of *E. coli* γ before encounter with a stop codon.

In *T.th.*, the dnaX frameshifting heptamer is AAAAAAA, and it is flanked by two other A residues, one on each side. There is also a downstream region of secondary structure. The nearest downstream stop codon is positioned such that gamma would contain only one unique amino acid, as in *E. coli*. However, the *T.th.* stop codon is in the −2 reading frame thus requires a −2 frameshift. No precedent exists in nature for −2 frameshifting, although −2 frameshifting has been shown to occur in test cases (Weiss et al., 1987). In vivo analysis of the *T.th.* frameshift sequence shows that this natural sequence promotes both −1 and −2 frameshifting in *E. coli*. Whereas the −2 frameshift results in only one unique C-terminal residue, a −1 frameshift would result in an extension of 12 C-terminal residues. At present, the results do not discriminate which path occurs in *T.th.*, a −1 or −2 frameshift, or a combination of the two.

There are two Shine-Dalgarno sequences just upstream of the frameshift site in *T.th.* dnaX. In two cases of frameshifting in *E. coli*, an upstream Shine-Dalgarno sequence has been shown to stimulate frameshifting (reviewed in Weiss et al., 1897). In release factor 2 (RF2), the Shine-Dalgarno is 3 nucleotides upstream of the shift site, and it stimulates a +1 frameshift event. In the case of *E. coli* dnaX, a Shine-Dalgarno sequence 10 nucleotides upstream of the shift sequence stimulates the −1 frameshift. One of the *T.th.* dnaX Shine-Dalgarno sequences is immediately adjacent to the frameshift sequence with no extra space, the other is 22 residues upstream of the frameshift site. Which of these Shine-Dalgarno sequences plays a role in *T.th.* dnaX frameshifting, if any, will require future study.

In *E. coli*, efficient separation of the two polypeptides, γ and τ, is achieved by mutation of the frameshift site such that only one polypeptide is produced from the gene (Tsuchihashi and Kornberg, 1990). Substitution of G-to-A in two positions of the heptamer of *T.th.* dnaX eliminates frameshifting and thus should be a source to obtain τ subunit free of γ. To produce pure γ subunit free of τ, the frameshifting site and sequence immediately downstream of it can be substituted for an in-frame sequence with a stop codon.

Examination of the *B. subtilis* dnaX gene shows no frameshift sequence that satisfies the X XXY YYZ rule. Hence, it would appear that dnaX does not make two proteins in this gram positive organism.

Rapid thermal motions associated with high temperature may make coordination of complicated processes more difficult. It seems possible that organizing the components of the replication apparatus may become yet more important at higher temperature. Hence, production of a τ subunit that could be used to crosslink two polymerases and a clamp loader into one organized particle may be most useful at elevated temperature.

As stated above, the following examples describe the continued isolation and purification of the substantial entirety of the Polymerase III from the extreme thermophile *Thermus thermophilus*. It is to be understood that the following exposition is reflective of the protocol and characteristics, both morphological and functional, of the Polymerase III-type enzymes that are the focus of the present invention, and that the invention is hereby illustrated and comprehends the entire class of enzymes of thermophilic origin.

EXAMPLE 9

Purification of the *Thermus thermophilus* DNA Polymerase III.

All steps in the purification assay were performed at 4° C. The following assay was used in the purification of DNA polymerase from *T.th.* cell extracts. Assays contained 2.5 mg activated calf thymus DNA (Sigma Chemical Company) in a final volume of 25 ml of 20 mM Tris-Cl (pH 7.5), 8 mM $MgCl_2$, 5 mM DTT, 0.5 mM EDTA, 40 mg/ml BSA, 4% glycerol, 0.5 mM ATP, 3 mM each dCTP, dGTP, dATP, and 20 mM [α-$^{32}$P]dTTP. An aliquot of the fraction to be assayed was added to the assay mixture on ice followed by incubation at 60° C. for 5 min. DNA synthesis was quantitated using DE81 paper followed by washing off unincorporated nucleotide. Incorporated nucleotide was determined by scintillation counting of the filters.

*Thermus thermophilus* cell extracts were prepared by suspending 35 grams of cell paste in 200 ml of 50 mM TRIS-HCl, pH=7.5, 30 mM spermidine, 100 mM NaCl, 0.5 mM EDTA, 5 mM DTT, 5% glycerol, followed by disruption by passage through a French pressure cell (15,000 PSI). Cell debris was removed by centrifugation (12,000 RPM, 60 min). DNA polymerase III in the clarified supernatant was precipitated by treatment with ammonium sulphate (0.226 gm/liter) and recovered by centrifugation. This fraction was then backwashed with the same buffer (but lacking spermidine) containing 0.20 gm/l ammonium sulfate. The pellet was then resuspended in buffer A and dialyzed overnight against 2 liters of buffer A; a precipitate which formed during dialysis was removed by centrifugation (17,000 RPM, 20 min).

Figures 13A, 13B:
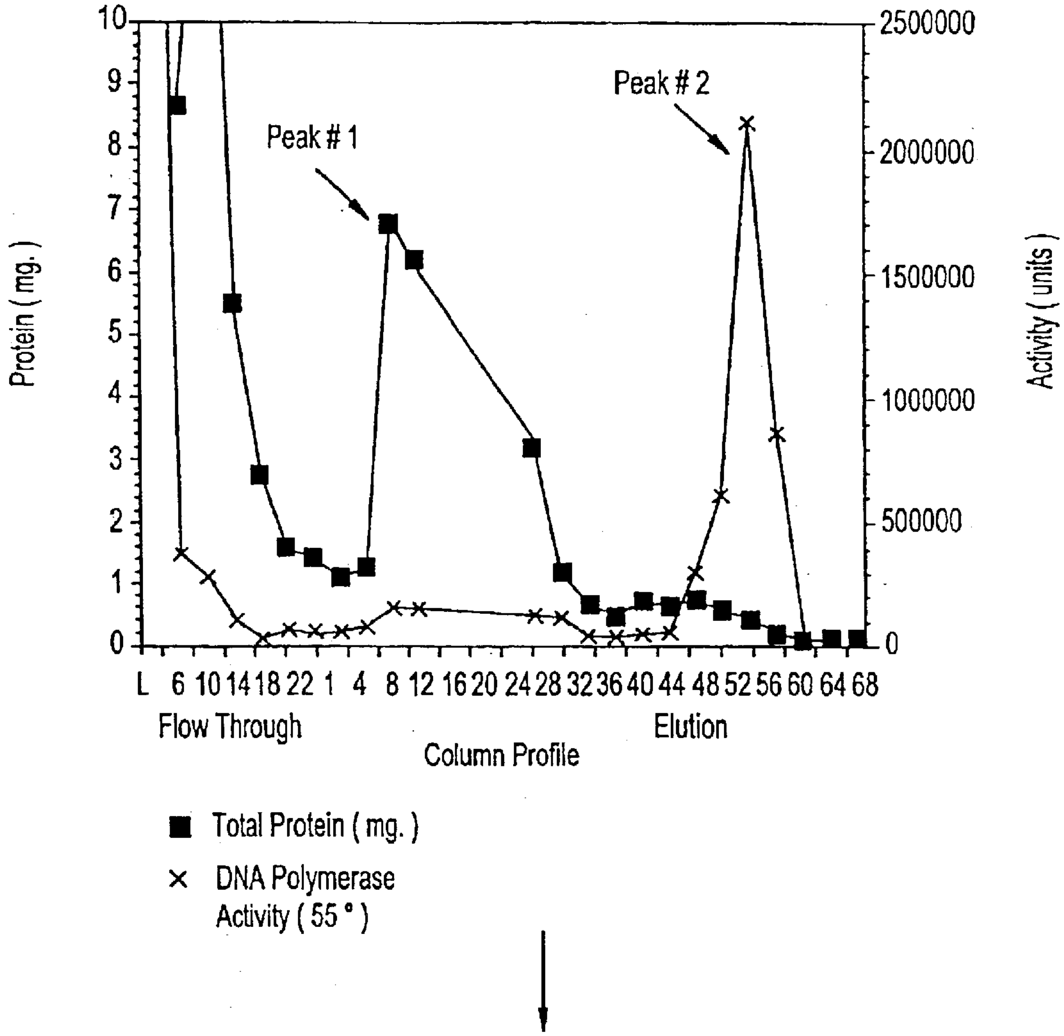
FIGS. 13A–13C are graphs that summarize the purification of the DNA polymerase III from *T.th.* extracts. Panel A) shows the activity and total protein in column fractions from the Heparin Agarose column. Peak 1 fractions were chromatographed on ATP agarose. Panel B) depicts the ATP-agarose column step, and Panel C) shows the total protein and DNA polymerase activity eluted from the MonoQ column.

The clarified dialysis supernatant, containing approximately 336 mg of protein, was applied onto a 60 ml heparin agarose column equilibrated in buffer A which was washed with the same buffer until A280 reached baseline. The column was developed with a 500 ml linear gradient of buffer A from 0 to 500 mM NaCl. More tightly adhered proteins were washed off the column by treatment with buffer A (20 mM Tris HCl, pH=7.5, 0.1 mM EDTA, 5 mM DTT, and 10% glycerol) and 1M NaCl. Some DNA polymerase activity flowed through the column. Two peaks (HEP.P1 and HEP.P2) of DNA polymerase activity eluted from the heparin agarose column containing 20 mg and 2 mg of total protein respectively (FIG. 13A). These were kept separate throughout the remainder of the purification protocol.

The Pol III resided in HEP.P1 as indicated by the following criteria: 1) Western analysis using antibody directed against the α subunit of *E. coli* Pol III indicated presence of Pol III in HEP.P 1; 2) Only the HEP.P1 fraction was capable of extending a single primer around an M13mp18 7.2 kb ssDNA circle (explained later in Example 16), such long primer extension being a characteristic of Pol III type enzymes; and 3) Only the HEP.P1 provided DNA polymerase activity that was retained on an ATP-agarose affinity column, which is indicative of a Pol III-type DNA polymerase since the γ and τ subunits are ATP interactive proteins.

The first peak of the heparin agarose column (HEP.P1: 20 mg in 127.5 ml) was dialyzed against buffer A and applied onto a 2 ml N6-linkage ATP agarose column pre-equilibrated in the same buffer. Bound protein was eluted by a slow (0.05 ml/min) wash with buffer A+2M NaCl and collected into 200 μl fractions. Chromatography of peak HEP.P1 yielded a flow-through (HEP.P1-ATP-FT) and a bound fraction (HEP.P1-ATP-Bound) (FIG. 13B). Binding of peak HEP.P2 to the ATP column could not be detected, though DNA polymerase activity was recovered in the flow-through.

Figure 13C:
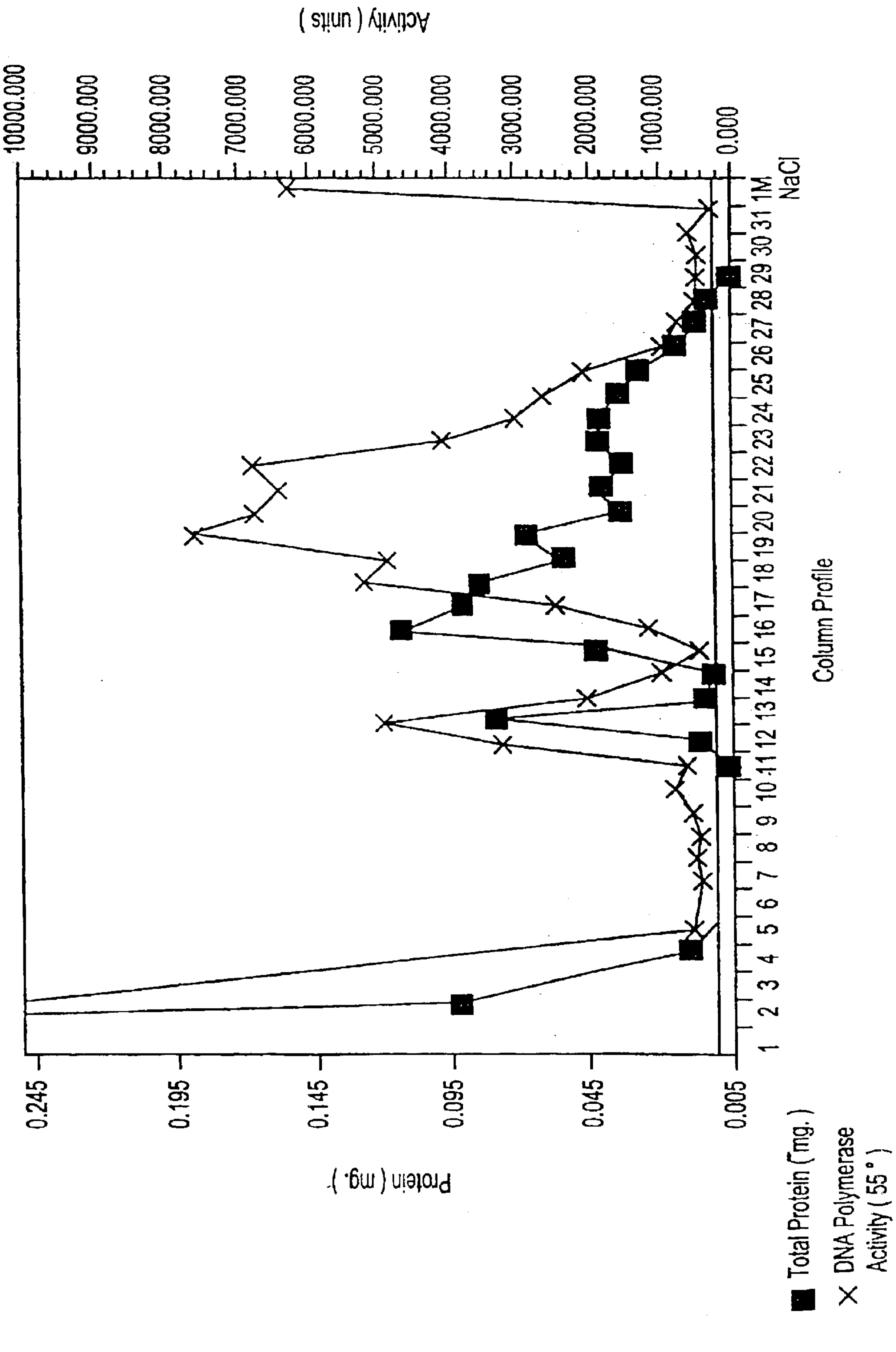
Figure 14A:
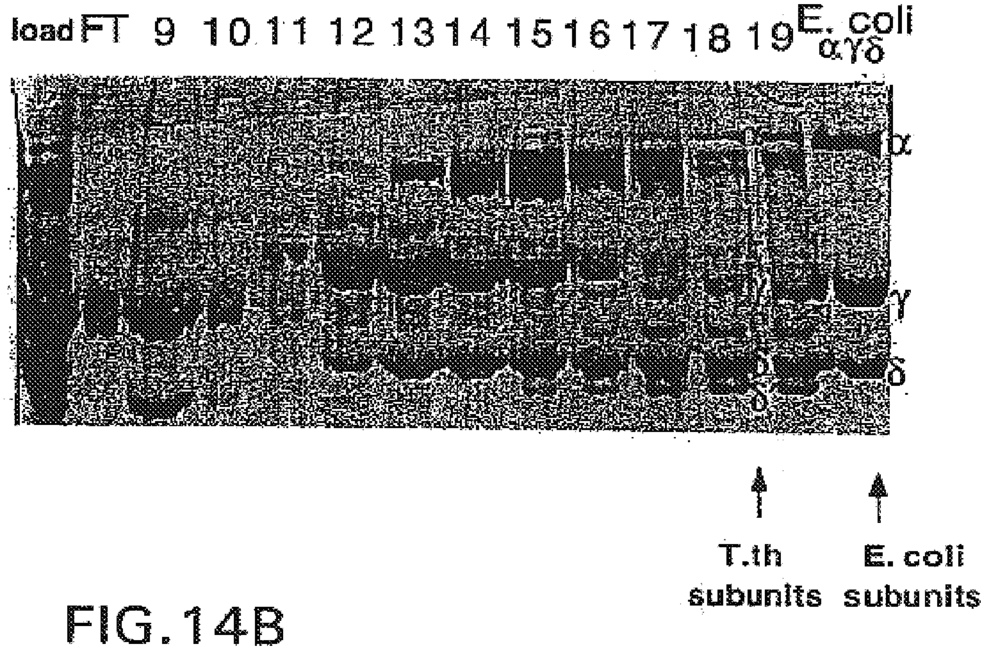
FIGS. 14A–B are SDS polyacrylamide gels of *T.th.* subunits.
Figure 14B:
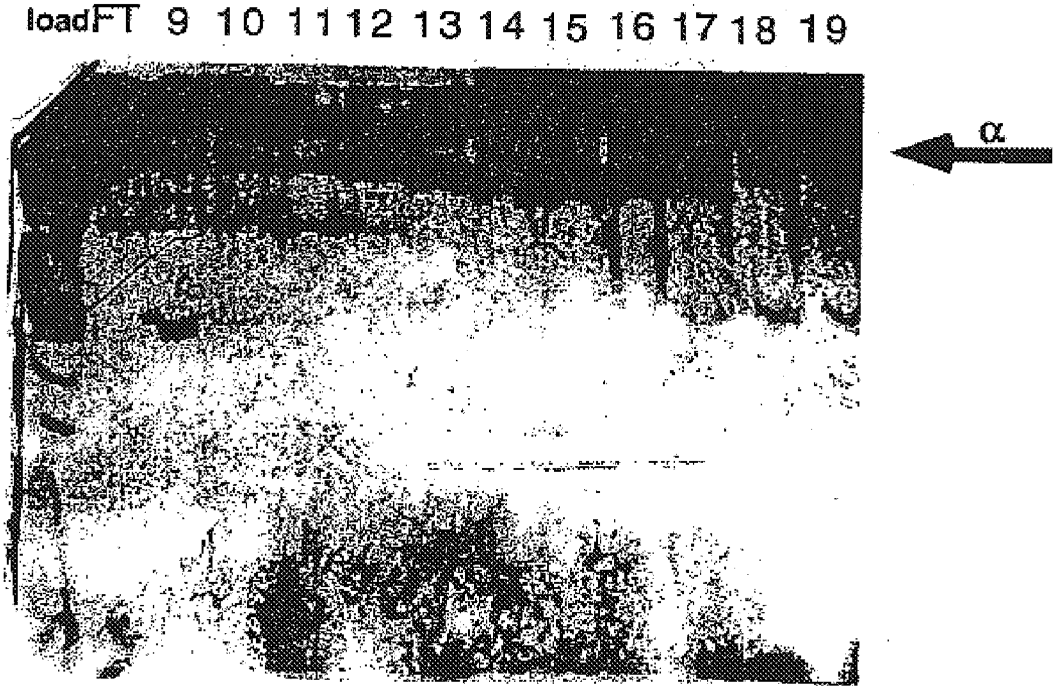

The HEP.P1-ATP-Bound fractions from the ATP agarose chromatographic step were further purified by anion exchange over monoQ. The HEP.P1-ATP-Bound fractions were diluted with buffer A to approximately the conductivity of buffer A plus 25 mM NaCl and applied to a 1 ml monoQ column equilibrated in Buffer A. DNA polymerase activity eluted in the flow-through and in two resolved chromatographic peaks (MONOQ peak 1 and peak 2) (FIG. 13C). Peak 2 was by far the major source of DNA polymerase activity. Western analysis using rabbit antibody directed against the *E. coli* α subunit confirmed presence of the α subunit in the second peak (see the Western analysis in FIG. 14B). Antibody against the *E. coli* τ subunit also confirmed the presence of the τ subunit in the second peak. Some reaction against α and τ was also present in the minor peak (first peak). The Coomassie Blue SDS polyacrylamide gel of the MonoQ fractions (FIG. 14A) showed a band that co-migrated with *E. coli* α and was in the same position as the antibody reactive material (antibody against *E. coli* α). Also present are bands corresponding to τ, γ, δ, and δ'. These subunits, along with β, are all that is necessary for rapid and processive synthesis and primer extension over a long (>7 kb) stretch of ssDNA in the case of*E. coli* DNA Polymerase III holoenzyme.

The Pol III-type enzyme purified from *T.th.* may be a Pol III*-like enzyme that contains the DNA polymerase and clamp loader subunits (i.e., like the Pol III* of *E. coli*). The evidence for this is: 1) the presence of dnaX and dnaE gene products in the same column fractions as indicated by Western analysis (see above); 2) the ability of this enzyme to extend a primer around a 7.2 kb circular ssDNA upon adding only β (see Example 16); 3) stimulation of Pol III by adding β on linear DNA, indicating β subunit is not present in saturating amounts (see Example 15); and 4) the presence of τ in *T.th.* which may glue the polymerase and clamp loader into a Pol III* as in *E. coli*; and 5) the comigration of α with subunits τ, γ, δ and δ' of the clamp loader in the column fractions of the last chromatographic step (MonoQ, FIG. 14A).

Micro-sequencing of *T. th* DNA Polymerase III α Subunit

The α subunit from the purified *T.th.* DNA polymerase III a (HEP.P1.ATP-Bound.MONOQ peak 2) was blotted onto PVDF membrane and was cut out of the SDS-PAGE gel and submitted to the Protein-Nucleic Acid Facility at Rockefeller University for N-terminal sequencing and proteolytic digestion, purification and microsequencing of the resultant peptides. Analysis of the α candidate band (Mw 130 kD) yielded four peptides, two of which (TTH1, TTH2) showed sequence similarity to α subunits from various bacterial sources (see FIG. 15).

EXAMPLE 10

Identification of the *Thermus thermophilus* dnaE Gene Encoding the α Subunit of DNA Polymerase III Replication Enzyme Cloning of the dnaE gene was started with the sequence of the TTH1 peptide from the purified α subunit (FFIEIQNHGLSEQK) (SEQ. ID. No. 61). The fragment was aligned to a region at approximately 180 amino acids downstream of the N-termini of several other known α subunits as shown in FIG. 15. The upstream 33mer (5'-GTG <u>GGATCC</u>GTGGTTCTGGATCTCGATGAAGAA-3') (SEQ. ID. No. 31) consists of a BamHI site within the first 9 nucleotides (underlined) and the sequence coding for the following peptide HGLSEQK on the complementary strand. The downstream 29mer (5'-GTG <u>GGATCC</u>ACGGSCTSTCSGAGCAGAAG-3') (SEQ. ID. No. 32) consists of a BamHI site within the first 9 nucleotides (underlined) and the following sequence coding for the peptide FFIEIQNH (SEQ. ID. No. 62).

These two primers were directed away from each other for the purpose of performing inverse PCR (also called circular PCR). The amplification reactions contained 10 ng *T.th.* genomic DNA (that had been cut and religated with XmaI), 0.5 mM of each primer, in a volume of 100 μl of Vent polymerase reaction mixture containing 10 μl ThermoPol Buffer, 0.5 mM of each dNTP and 0.25 mM $MgSO_4$. Amplification was performed using the following cycling scheme:

1. 4 cycles of: 95.5° C.—30 sec., 45° C.—30 sec., 75° C.—8 min.
2. 6 cycles of: 95.5° C.—30 sec., 50° C.—30 sec., 75° C.—6 min.
3. 30 cycles of: 95.5° C.—30 sec., 52.5° C.—30 sec., 75° C.—5 min.

A 1.4 kb fragment was obtained and cloned into pBS-SK:BamHI (i.e. pBS-SK (Stratragene) was cut with BamHI). This sequence was bracketted by the 29mer primer on both sides and contained the sequence coding for the N-terminal part of the subunit up to the peptide used for primer design.

To obtain further dnaE gene sequence, the TTH2 peptide was used. It was aligned to a region about 600 amino acids from the N-termini of the other known subunits (FIG. 15B). The upstream 34mer (5'-GCG <u>GGATCC</u>TCAACGAGGACCTCTCCATCTTCAA-3') (SEQ. ID. No. 33) consists of a BamHI site within the first 9 nucleotides (underlined) and the sequence from the end of the fragment previously obtained. The downstream 35mer (5'-GCG <u>GGATCC</u>TTGTCGTCSAGSGTSAGSGCGTCGTA-3') (SEQ. ID. No. 34) consists of a BamHI site within the first 9 nucleotides (underlined) and the following sequence coding for the peptide YDALTLDD (SEQ. ID. No. 63) on the complementary strand. The amplification reactions contained 10 ng *T.th.* genomic DNA, 0.5 mM of each primer, in a volume of 100 μl of Vent polymerase reaction mixture containing 10 μl ThermoPol Buffer, 0.5 mM of each dNTP and 0.25 mM $MgSO_4$. Amplification was performed using the following cycling scheme:

1. 4 cycles of: 95.5° C.—30 sec., 45° C.—30 sec., 75° C.—8 min.
2. 6 cycles of: 95.5° C.—30 sec., 50° C.—30 sec., 75° C.—6 min.
3. 30 cycles of: 95.5° C.—30 sec., 55° C.-30 sec., 75° C.—5 min.

A 1.2 kb PCR fragment was obtained and cloned into pUC19:BamHI. The fragment was bracketted by the downstream primer on both sides and contained the region overlapping in 56 bp with the fragment previously cloned.

To obtain yet more dnaE sequence, the following primers were used. The upstream 39mer (3'-GTGT <u>GGATCC</u>TCGTCCCCCTCATGCGCGACCAGGAAG GG-5') (SEQ. ID. Nos. 35 and 114) consists of a BamHI site within the first 10 nucleotides (underlined) and the sequence from the end of the fragment previously obtained. The downstream 27mer (5'-GTGT <u>GGATCC</u>TTCTTCTTSCCCATSGC-3') (SEQ. ID. No. 36) consists of a BamHI site within the first 10 nucleotides (underlined), and the sequence coding for the peptide AMGKKK (SEQ. ID. No. 64) (at position approximately 800 residues from the N terminus) on the complementary strand. The AMGKKK (SEQ. ID. No. 64) sequence was chosen for primer design as it is highly conserved among the known gram-negative α subunits. The amplification reactions contained 10 ng *T.th.* genomic DNA, 0.5 mM of each primer, in a volume of 100 μl of Taq polymerase reaction mixture containing 10 μl PCR Buffer, 0.5 mM of each dNTP and 2.5 mM $MgCl_2$. Amplification was performed using the following cycling scheme:

1.3 cycles of: 95.5° C.—30 sec., 45° C.—30 sec., 72° C.—8 min.
2. 6 cycles of: 94.5° C.—30 sec., 55° C.—30 sec., 72° C.—6 min.
3. 32 cycles of: 94.5° C.—30 sec., 50° C.—30 sec., 72° C.—5 min.

A 2.3 kb PCR fragment was obtained instead of the expected 0.6 kb fragment. BamHI digestion of the PCR product resulted in three fragments of 1.1 kb, 0.7 kb and 0.5 kb. The 1.1 kb fragment was cloned into pUC19:BamHI. It turned out to be the one adjacent to the fragment previously obtained and contained the dnaE sequence right up to the region coding for the AMGKKK (SEQ. ID. No. 64) peptide, but was disrupted by an intron just upstream of this region. The sequence that follows this was amplified from the 2.3 kb original PCR product using the same conditions and cycling scheme as for the 2.3 kb fragment. The downstream primer was the same as in the previous step. The upstream 27mer (3'-GTGTGGATCCGTGGTGACCTTAGCCAC-5') (SEQ. ID. Nos. 37 and 115) consisted of a BamHI site within the first 9 nucleotides (underlined) and the sequence from the end of the 1.1 kb fragment previously described.

The expected 1.2 kb PCR fragment was obtained and cloned into pUC19:SmaI. This fragment coded for the rest of the intein and the end of it was used to obtain the next sequence of dnaE downstream of this region. The upstream 30mer (3'-TTCGTGTCCGAGGACCTTGTGGTCCACAAC-5') (SEQ. ID. Nos. 38 and 116) was a sequence from the end of the intron. The downstream 23mer (5'-CCAGAATCGTCTGCTGGTCGTAG-3') (SEQ. ID. No. 39) was the sequence from the end of the dnaE gene of *D.rad.* (coding on the complementary strand for the region slightly homologous in the distantly related α subunits and possibly highly homologous between *T.th.* and *D.rad.* α subunits). The amplification reactions contained 10 ng *T.th.* genomic DNA, 0.5 mM of each primer, in a volume of 100 μl of Vent polymerase reaction mixture containing 10 μl ThermoPol Buffer, 0.5 mM of each dNTP and 0.1 mM $MgSO_4$. Amplification was performed using the following cycling scheme:

1. 3 cycles of: 95.5° C.—30 sec., 55° C.—30 sec., 75° C.—8 min.
2.32 cycles of: 94.5° C.—30 sec., 50° C.—30 sec., 75° C.—5 min.

A 2.5 kb PCR fragment was obtained and cloned into pUC19:SmaI. This fragment contained the dnaE sequence coding for the 300 mino acids next to the AMGKKK (SEQ. ID. No. 64) region disrupted by yet a second intein inside another sequence that is conserved among the known α subunits (FNKSHSAAY) (SEQ. ID. No. 65).

To obtain the rest of the dnaE gene the upstream 19mer (5'-AGCACCCTGGAGGAGCTTC-3') (SEQ. ID. No. 40) from the end of the known dnaE sequence was used. The downstream primer was: 5'-CATGTCGTACTGGGTGTAC-3' (SEQ. ID. No. 41). The amplification reactions contained 10 ng *T.th.* genomic DNA, 0.5 mM of each primer, in a volume of 100 μl of Vent polymerase reaction mixture containing 10 μl ThermoPol Buffer, 0.5 mM of each dNTP and 0.1 mM $MgSO_4$. Amplification was performed using the following cycling scheme:

1. 3 cycles of: 95.5° C.—30 sec., 55° C.—30 sec., 75° C.—8 min.
2. 32 cycles of: 94.5° C.—30 sec., 50° C.—30 sec., 75° C.—5 min.

A 1.0 kb fragment bracketed by this upstream primer was obtained. It contained the 3' end of the dnaE gene.

EXAMPLE 11

Cloning and Expression of the *Thermus thermophilus* dnaQ Gene Encoding the ε Subunit of DNA Polymerase III Replication Enzyme Cloning of dnaQ The dnaQ gene of *E. coli* and the corresponding region of PolC of *B. subtilis*, evolutionary divergent organisms, share approximately 30% identity. Comparison of the predicted amino acid sequences for DnaQ (ε) of *E. coli* and PolC of *B. subtilis* revealed two highly conserved regions (FIG. 17). Within each of these regions, a nine amino acid sequence was used to design two oligonucleotide primers for use in the polymerase chain reaction.

The regions highly conservative among Pol III exonucleases were chosen to design the degenerate primers for the amplification of a *T.th.* dnaQ internal fragment (see FIG. 17). DNA oligonucleotides for amplification of *T.th.* genomic DNA were as follows. The upstream 27mer (5'-GTSGTSNNSGACNNSGAGACSACSGGG-3' (SEQ. ID. No. 42)) encodes the following sequence (VVXDXETTG) (SEQ. ID. No. 66). The downstream 27mer (5'-GAASCCSNNGTCGAASNNGGCGTTGTG-3') (SEQ. ID. No. 43) encodes the sequence HNAXFDXGF (SEQ. ID. No. 67) on the complementary strand. The amplification reactions contained 10 ng *T.th.* genomic DNA, 0.5 mM of each primer, in a volume of 100 μl of Vent polymerase reaction mixture containing 10 μl ThermoPol Buffer, 0.5 mM of each dNTP and 0.5 mM $MgSO_4$. Amplification was performed using the following cycling scheme:

1. 5 cycles of: 95.5° C.—30 sec., 40° C.—30 sec., 72° C.—2 min.
2. 5 cycles of: 95.5° C.—30 sec., 45° C.—30 sec., 72° C.—2 min.
3. 30 cycles of: 95.5° C.—30 sec., 50° C.—30 sec., 72° C.—30 min.

Products were visualized in a 1.5% native agarose gel. A fragment of the expected size of 270 bp was cloned into the SmaI site of pUC19 and sequenced with the CircumVent Thermal Cycle DNA sequencing kit according to the manufacturer's instructions (New England Biolabs).

To obtain further sequence of the dnaQ gene, genomic DNA was digested with either mhoI, BamHI, KpnI or NcoI. These restriction enzymes were chosen because they cut *T.th.* genomic DNA frequently. Approximately 0.1 μg of DNA for each digest was ligated by T4 DNA ligase in 50 μl of ligation buffer (50 mM Tris-HCl (pH 7.8), 10 mM $MgCl_2$, 10 mM dithiothreitol, 1 mM ATP, 25 mg/ml bovine serum albumin) overnight at 20° C. The ligation mixtures were used for cicular PCR.

DNA oligonucleotides for amplification of *T.th.* genomic DNA were the following. The upstream 27mer (5'-CGG <u>GGATCC</u>ACCTCAATCACCTCGTGG-3') (SEQ. ID. No. 44) consists of a BamHI site within the first 9 nucleotides (underlined) and the sequence complementary to 42–61 bp region of the previously cloned dnaQ fragment. The downstream 30mer (5'-CGG <u>GGATCC</u>GCCACCTTGCGGCTCCGGGTG-3') (SEQ. ID. No. 45) consists of a BamHI site within the first 9 nucleotides (underlined) and the sequence corresponding to 240–261 bp region of the dnaQ fragment (see FIG. 17).

The amplification reactions contained 1 ng *T.th.* genomic DNA (that had been cut with NcoI and religated into circular DNA for circular PCR), 0.4 mM of each primer, in a volume of 100 μl of Vent polymerase reaction mixture containing 10 μl ThermoPol Buffer, 0.5 mM of each dNTP, 0.5 mM $MgSO_4$, and 10% DMSO. Circular amplification was performed using the following cycling scheme:

1. 5 cycles of: 95.5° C.—30 sec., 50° C.—30 sec., 72° C.—8 min.
2. 35 cycles of: 95.5° C.—30 sec., 55° C.—30 sec., 72° C.—6 min.
3. 72° C.—10 min.

A 1.5 kb fragment was obtained and cloned into the BamHI site of the pUC19 vector. Partial sequencing of the fragment revealed that it contained the dnaQ regions adjacent to sequences corresponding to the PCR primers and hence contained the sequences both upstream and downstream of the previously cloned dnaQ fragment. One of NcoI sites turned out to be approximately 300 bp downstream of the end of the first cloned dnaQ sequence and hence did not include the 3' end of dnaQ. To obtain the 3' end, another inverse PCR reaction was performed. Since an ApaI restriction site was recognized within this newly sequenced dnaQ fragment, the circular PCR procedure was performed using as template an ApaI digest of *T.th.* genomic DNA that was ligated (circularized) under the same conditions as described above.

DNA oligonucleotides for amplification of the ApaI/religated *T.th.* genomic DNA were as follows. The upstream 31mer (5'-GCGC TCTAGACGAGTTCCCAAAGCGTGCGGT-3') (SEQ. ID. No. 46) consists of a mbaI site within the first 10 nucleotides (underlined) and the sequence complementary to the region downstream of the ApaI restriction site in the newly sequenced dnaQ fragment. The downstream 25 mer (5'-CGCGTCTAGATCACCTGTATCCAGA-3') (SEQ. ID. No. 47) consists of a XbaI site within the first 10 nucleotides (underlined) and the sequence corresponding to another region downstream of the ApaI restriction site in the newly sequenced dnaQ fragment. The 1.7 kb PCR fragment was cloned into the XbaI site of the pUC19 vector and partially sequenced. The sequence of dnaQ, and the protein sequence of the ε subunit encoded by it, is shown in FIG. 18.

The dnaQ gene is encoded by an open reading frame of 209 (or 190 depending on which Val is used as the initiating residue) amino acids in length (23598.5 kDa- or 21383.8 kDa for shorter version), similar to the length of the *E. coli* ε subunit (243 amino acids, 27099.1 kDa mass) (see FIG. 17).

The entire amino acid sequence of the ε subunit predicted from the *T.th.* dnaQ gene aligns with the predicted amino acid sequence of the dnaQ genes of other organisms with only a few gaps and insertions (the first two amino acids, and four positions downstream) (FIG. 17). The consensus motifs VVXDXETTG (SEQ. ID. Nos. 66 and 68), HNAXFDXGF (SEQ. ID. No. 67), and HRALYD (SEQ. ID. No. 70), characteristic for exonucleases, are conserved. Overall, the level of amino acid identity relative to most of the known ε subunits, or corresponding proofreading exonuclease domains of gram positive PolC genes is approximately 30%. Upstream of start 1 (FIG. 17) there were stop codons in all three reading frames.

Expression of dnaQ

The dnaQ gene was cloned gene into the pET24-a expression vector in two steps. First, the PCR fragment encoding the N-terminal part of the gene was cloned into the pUC19 plasmid, containing the ApaI inverse PCR fragment into NdeI/ApaI sites. DNA oligonucleotides for amplification of *T.th.* genomic DNA were as follows. The upstream 33mer (5'-GCGGCG CATATGGTGGTGGTCCTGGACCTGGAG-3') (SEQ. ID. No. 48) consists of an NdeI site within the first 12 nucleotides (underlined) and the beginning of the dnaQ gene. The downstream 25 mer (5'-CGCG TCTAGATCACCTGTATCCAGA-3') (SEQ. ID. No. 49), already used for ApaI circular PCR, consists of an XbaI site within the first 10 nucleotides (underlined) and the sequence corresponding to the region downstream of the ApaI restriction site. The 2.2 kb NdeI/SalI fragment was then cloned into the NdeI/XhoI sites of the pET16 vector to produce pET24-a:dnaQ. The ε subunit was expressed in the BL21/LysS strain transformed by the pET24-a:dnaQ plasmid.

EXAMPLE 12

The *Thermus thermophilus* dnaN Gene Encoding the β subunit of DNA Polymerase III Replication Enzyme Strategy of Cloning dnaN by Use of dnaA DnaN proteins are highly divergent in bacteria making it difficult to clone them by homology. The level of identity between DnaN representatives from *E. coli* and *B. subtilis* is as low as 18%. These 18% of identical amino acid residues are dispersed through the proteins rather then clustering together in conservative regions, further complicating use of homology to design PCR primers. However, one feature of dnaN genes among widely different bacteria is their location in the chromosome. They appear to be near the origin, and immediately adjacent to the dnaA gene. The dnaA genes show good homology among different bacteria and, thus, dnaA was first cloned in order to obtain a DNA probe that is likely near dnaN.

Identification of dnaA and dnaN

The dnaA genes of *E. coli* and *B. subtilis* share 58% identity at the amino acid sequence level within the ATP-binding domain (or among the representatives of gram-positive and gram-negative bacteria, evolutionary divergent organisms). Comparison of the predicted amino acid sequences encoded by dnaA of *E. coli* and *B. subtilis* revealed two highly conserved regions (FIG. 19). Within each of these regions, a seven amino acid sequence was used to design two oligonucleotide primers for use in the polymerase chain reaction. The DNA oligonucleotides for amplification of *T.th.* genomic DNA were as follows. The upstream 20mer (5'-GTSCTSGTSAAGACSCACTT-3') (SEQ. ID. No. 50) encodes the following sequence: VLVKTHL (SEQ. ID. No. 69). The downstream 21mer (5'-SAGSAGSGCGTTGAASGTGTG-3', where S is G or C) (SEQ. ID. No. 51) encodes the sequence: HTFNALL (SEQ. ID. No. 71), on the complementary strand. The amplification reactions contained 10 ng *T.th.* genomic DNA, 0.5 mM of each primer, in a volume of 100 μl of Vent polymerase reaction mixture containing 10 μl ThermoPol Buffer, 0.5 mM of each dNTP and 0.5 mM $MgSO_4$. Amplification was performed using the following cycling scheme:

1. 5 cycles of: 95.5° C.—30 sec., 45° C.—30 sec., 75° C.—2 min.
2. 5 cycles of: 95.5° C.—30 sec., 50° C.—30 sec., 75° C.—2 min.
3. 30 cycles of: 95.5° C.—30 sec., 52° C.—30 sec., 75° C.—30 min.

Products were visualized in a 1.5% native agarose gel. A fragment of the expected size of 300 bp was cloned into the SmaI site of pUC19 and sequenced with the CircumVent Thermal Cycle DNA sequencing kit (New England Biolabs).

To obtain a larger section of the *T.th.* dnaA gene, genomic DNA was digested with either HaeII, HindIII, KasI, KpnI, MluI, NcoI, NgoMI, NheI, NsiI, PaeR71, PstI, SacI, SalI, SpeI, SphI, StuI, or XhoI, followed by Southern analysis in a native agarose gel. The filter was probed with the 300 bp PCR product radiolabeled by random priming. Four different restriction digests showed a single fragment of reasonable size for further cloning. These were, KasI, NgoMI, and StuI, all of which produced fragments of about 3 kb, and NcoI that produced a 2 kb fragment. Also, a KpnI digest resulted in two fragments of about 1.5 kb and 10 kb.

Genomic DNA digests using either NgoMI and StuI were used to obtain the dnaA gene by inverse PCR (also referred to as circular PCR). In this procedure, 0.1 μg of DNA from each digest was treated separately with T4 DNA ligase in 50 μl of ligation buffer (50 mM Tris-HCl (pH 7.8), 10 mM $MgCl_2$, 10 mM dithiothreitol, 1 mM ATP, 25 mg/ml bovine serum albumin) overnight at 20° C. This results in circularizing the genomic DNA fragments. The ligation mixtures were used as substrate in inverse PCR.

DNA oligonucleotides for amplification of recircularized *T.th.* genomic DNA were as follows. The upstream 22mer was (5'-CTCGTTGGTGAAAGTTTCCGTG-3') (SEQ. ID. No. 52), and the downstream 24mer was (5'-CGTCCAGTTCATCGCCGGAAAGGA-3') (SEQ. ID. No. 53). The amplification reactions contained 5 ng *T.th.* genomnic DNA, 0.5 μM of each primer, in a volume of 100 μl of Taq polymerase reaction mixture containing 10 μl PCR Buffer, 0.5 mM of each dNTP and 2.5 mM $MgCl_2$. Amplification was performed using the following cycling scheme:

1. 5 cycles of: 95.0° C.—30 sec., 55° C.—30 sec., 72° C.—10 min.
2. 35 cycles of: 95.5° C.—30 sec., 50° C.—30 sec., 72° C.—8 min.

The PCR fragments of the expected length for NgoMI and StuI treated and then ligated chromosomal DNA were digested with either BamHI or Sau3a and cloned into pUC19:BamHI and pUC19:(BamHI+SmaI) and sequenced with CircumVent Thermal Cycle DNA sequencing kit. The 1.6 kb (BamHI+BamH) fragment from the NgoMI PCR product contained a sequence coding for the N-terminal part of dnaN, followed by the gene for enolase. The 1 kb (Sau3a+Sau3a) fragment from the same PCR product included the start of dnaN gene and sequence characteristic of the origin of replication (i.e., 9mer DnaA-binding site sequences). The 0.6 kb (BamHI+BamHI) fragment from the StuI PCR reaction contained starts for dnaA and gidA genes in inverse orientation to each other. The 0.4 kb (Sau3a+Sau3a) fragment from the same PCR product contained the 3' end of the dnaA gene and DNA sequence characteristic for the origin of replication.

This sequence information provided the beginning and end of both the dnaA and the dnaN genes. Hence, these genes were easily cloned from this information. Further, the dnaN gene was readily cloned and expressed in a pET24-a vector. These steps are described below.

Cloning and Sequence of the dnaA Gene

The dnaA gene was cloned for sequencing in two parts: from the potential start of the gene up to its middle and from the middle up to the end. For the N-terminal part, the upstream 27mer (5'-TCTGGCAACACGTTCTGGAGCACATCC-3') (SEQ. ID. No. 54) was 20 bp downstream of the potential start codon of the gene. The downstream 23mer (5'-TGCTGGCGTTCATCTTCAGGATG-3') (SEQ. ID. No. 55) was approximately from the middle of the dnaA gene. For the C-terminal part, the upstream 23mer (5'-CATCCTGAAGATGAACGCCAGCA-3') (SEQ. ID. No. 56) was complementary to the previous primer. The downstream 25mer (5'-AGGTTATCCACAGGGGTCATGTGCA-3') (SEQ. ID. No. 57) was 20 bp upstream the potential stop codon for the dnaA gene. The amplification reactions contained 10 ng *T.th.* genomic DNA, 0.5 μM of each primer, in a volume of 100 μl of Vent polymerase reaction mixture containing 10 μl ThermoPol Buffer, 0.5 mM of each dNTP and 0.5 mM $MgSO_4$. Amplification was performed using the following cycling scheme:

1. 5 cycles of: 95.5° C.—30 sec., 55° C.—30 sec., 75° C.—3 min.
2. 30 cycles of: 95.5° C.—30 sec., 50° C.—30 sec., 75° C.—2 min.

Products were visualized in a 1.0% native agarose gel. Fragments of the expected sizes of 750 bp and 650 bp were produced, and were sequenced using CircumVent Thermal Cycle DNA sequencing method (New England Biolabs). The nucleotide and amino acid sequences of dnaA and its protein product are shown in FIG. 20. The DnaA protein is homologous to the DnaA proteins of several other bacteria as shown in FIG. 19.

Cloning and Expression of dnaN

The full length dnaN gene was obtained by PCR from *T.th.* total DNA. DNA oligonucleotides for amplification of *T.th.* dnaN were the following: the upstream 29mer (5'-GTGTGT<u>CATATG</u>AACATAACGGTTCCCAA-3') (SEQ. ID. No. 58) consists of an NdeI site within first 11 nucleotides (underlined), followed by the sequence for the start of the dnaN gene; the downstream 29mer (5'-GCGC <u>GAATTC</u>TCCCTTGTGGAAGGCTTAG-3') (SEQ. ID. No. 59) consists of an EcoRI site within the first 10 nucleotides (underlined), followed by the sequence complementary to a section just downstream of the dnaN stop codon. The amplification reactions contained 10 ng *T.th.* genomic DNA, 0.5 μM of each primer, in a volume of 100 μl of Vent polymerase reaction mixture containing 10 μl Thermopol Buffer, 0.5 mM of each dNTP and 0.2 mM $MgSO_4$. Amplification was performed using the following cycling scheme:

1. 5 cycles of: 95.0° C.—30 sec., 55° C.—30 sec., 75° C.—5 min.
2. 35 cycles of: 95.5° C.—30 sec., 50° C.—30 sec., 75° C.—4 min.

The nucleotide and amino acid sequences of dnaN and the β subunit, respectively, are shown in FIG. 21. The *T.th.* β subunit shows limited homology to the β subunit sequences of several other bacteria over its entire length (FIG. 22).

The approximately 1 kb dnaN gene was cloned into the pET24-a expression vector using the NdeI and EcoRI restriction sites both in the dnaN containing PCR product and in pET24-a (FIG. 23). Expression of *T.th.* β subunit was obtained under the following conditions: a fresh colony of B121(DE3) *E.coli* strain was transformed by the pET24-a:dnaN plasmid, and then was grown in LB broth containing 50 mg/ml kanamycin at 37° C. until the cell density reached 0.4 $OD_{600}$. The cell culture was then induced for dnaN expression upon addition of 2 mM IPTG. Cells were harvested after 4 additional hours of growth under 37° C. The induction of the *T.th.* β subunit is shown in FIG. 24.

Two liters of BL21(DE3)pETdnaN cells were grown in LB media containing 50 mg/ml ampicillin at 37° C. to an O.D. of 0.8 and then IPTG was added to a concentration of 2 mM. After a further 2 h at 37° C., cells were harvested by centrifugation and stored at −70° C. The following steps were performed at 4° C. Cells were thawed and resuspended in 40 ml of 5 mM Tris-HCl (pH 8.0), 1% sucrose, 1M NaCl, 5 mM DTT, and 30 mM spermidine. Cells were lysed using a French Pressure cell at 20,000 psi. The lysate was allowed to sit at 4° C. for 30 min. and then cell debris was removed by centrifugation (Sorvall SS-34 rotor, 45 min. 18,000 rpm). The supernatant was incubated at 65° C. for 20 minutes with occasional stirring. The resulting protein precipitate was removed by centrifugation as described above. The supernatant was dialyzed against 4 liters of buffer A containing 50 mM NaCl overnight. The dialyzed supernatant was clarified by centrifugation (35 ml, 150 mg total) and then loaded onto an 8 ml MonoQ column equilibrated in buffer A containing 50 mM NaCl. The column was washed with 5 column volumes of the same buffer and then eluted with a 120 ml gradient of buffer A plus 50 mM NaCl to buffer A plus 500 mM NaCl. Fractions of 2 ml were collected. Over 50 mg of *T.th.* β was recovered in fractions 5–21.

EXAMPLE 13

Identification and Cloning of *T. thermophilus* holA

A search of the incomplete *T.th.* genome database (www.g21.bio.unigoettingen.de) showed a match to *E. coli* β encoded by holA. The sequence obtained from the database was as follows (SEQ. ID. No. 185):

TPKGKDLVRHLENRAKRLGLRLPGGVAQYLA-SLEGDLEALERELEKLALLSP-PLTLE KVEKVVALRP-PLTGFDLVRSVLEKDPKEALLRLGR LKEEGEEPLR-LLGALSWQFALLARAFFLLREMPRPK EEDLARLEAHPYAAKKALL-EAARRLTEEALKEALDALMEAEKRAKG-GKDPWLALEAAVLRLAR-PAGQPRVD

Next, the following PCR primers were designed from the codon usage of *T.th.*: upstream 27mer (5'-GCC CAG TAC CTC GCC TCC CTC GAG GGG-3') (SEQ. ID. No. 186) and downstream 27mer (5'-GGC CCC CTT GGC CTT CTC GGC CTC CAT-3' (SEQ. ID. No. 187) to obtain a partial holA nucleotide sequence (SEQ. ID. No. 188):

1. 5 cycles of: 95° C.—30 sec., 65° C.—20 sec., 75° C.—5 min.
2. 5 cycles of: 95° C.—20 sec., 58° C.—10 sec., 75° C.—5 min.
3. 35 cycles of: 95° C.—20 sec., 50° C.—5 sec., 75° C.—4 min.

Products were visualized in a 1.0% native agarose gel. A fragment of 1.5 Kb was gel purified and partially sequenced.

A different set of primers were used to obtain the 3'-end of *T.th.* holA, including an upstream 25mer (5'-CTCCGTCCTGGAGAAGGACCCCAAG-3') (SEQ. ID. No. 192) which encoded the amino acid sequence SVLEKDPK from *T.th.* holA (aa residues 179–186 of SEQ. ID. No. 158), and a downstream 29mer (5'-CGCGAATTCAACGCSCTCCTCAAGACSCT-3' where S=C or G) (SEQ. ID. No. 193) was not related to the holA sequence. The amplification reactions contained 50 ng *T.th.* genomic DNA and 0.1 μM of each primer in a volume of 100 μl of Vent polymerase reaction mixture containing 10 μl ThermoPol Buffer, 2.5 mM of each dNTP, and 1–2 mM $MgSO_4$, and 10 μl of formamide. Amplification was performed using the following cycling scheme:

1. 5 cycles of: 95° C.—30 sec., 65° C.—20 sec., 75° C.—5 min.
2. 5 cycles of: 95° C.—20 sec., 55° C.—10 sec., 75° C.—5 min.
3. 35 cycles of: 95° C.—20 sec., 50° C.—5 sec., 75° C.—4 min.

Products were visualized in a 1.0% native agarose gel. A fragment of 1.2 Kb was gel purified and partially sequenced to obtain the remainder of the *T.th.* holA gene.

The *T.th.* holA gene was cloned into the NdeI/EcoRI sites in the pET24 vector using a pair of primers. The upstream

```
AGACTCGAGG CCCTGGAGCG GGAGCTGGAG AAGCTTGCCC TCCTCTCCCC ACCCCTCACC    60

CTGGAGAAGG TGGAGAAGGT GGTGGCCCTG AGGCCCCCCC TCACGGGCTT TGACCTGGTG   120

CGCTCCGTCC TGGAGAAGGA CCCCAAGGAG GCCCTCCTGC GCCTCAGGCG CCTCAGGGAG   180

GAGGGGGAGG AGCCCCTCAG GCTCCTCGGG GCCCTCTCCT GGCAGTTCGC CCTCCTCGCC   240

CGGGCCTTCT TCCTCCTCCG GGAAAACCCC AGGCCCAAGG AGGAGGACCT CGCCCGCCTC   300

GAGGCCCACC CCTACGCCGC CAAGAAGGCC A                                  331
```

This sequence codes for a partial amino acid sequence of the *T.th.* δ subunit (SEQ. ID. No. 189):

RLEALERELEKLALLSPPLTLEKVEKV-VALRPPLTGFDLVRSVLEKDPKEALLRL-RRLREEGEEPLRLLGALSWQFALLARAF-FLLRENPRPKEEDLARLEAHPYAAKKA

The DNA sequence obtained by PCR (SEQ. ID. No. 188) was used to design internal primers for inverted PCR. The upstream 31mer (5'-GTGGTGTCTAGACATCATAACGGTTCTGGCA-3') (SEQ. ID. NO. 190) introduced an XbaI site for cloning holA into a pGEX vector. The downstream 27mer (5'-GAGGGCCACCACCTTCTCCACCTTCTC-3') (SEQ. ID. No. 191) encodes holA sequence EKVEKVVAL (aa residues 159–167 of SEQ. ID. No. 158) on the complementary strand. The amplification reactions contained 50 ng *T.th.* genomic DNA and 0.1 uM of each primer in a volume of 100 μl of Vent polymerase reaction mixture containing 10 μl ThermoPol Buffer, 2.5 mM of each dNTP, 2 mM $MgSO_4$, and 10 μl of formamide. Amplification was performed using the following cycling scheme:

31 mer (5'-GACACTTAA <u>CATATG</u>GTCATCGCCTTCACCG-3') (SEQ. ID. No. 194) contains a NdeI site within the first 15 nucleotides (underlined) and has a sequence corresponding to 5' region of *T.th.* holA. The downstream 38 mer (5'-GTGTGT <u>GAATTC</u>GGGTCAACGGGCGAGGCGGAGGACCG-3') (SEQ. ID. No. 195) contains a EcoRI site within the first 12 nucleotides (underlined) and has a sequence complementary to the 3' end of holA gene.

EXAMPLE 14

Identification of *T.th.* holB Encoding δ' Subunit

To clone the ends of *T.th.* holB gene, it was assumed that the order of genes in *Thermus thermophilis* could be the same as in related *Deinococcus radiodurance*. Multiple alignment of the upstream neighbor (probable phosphoesterase, DNA repair Rad24c related protein) revealed a conservative region close to the C-terminus of the protein sequence:

*Deinococcus radiodurance* VILNPGSVGQ (SEQ. ID. No. 196)

*Methanococcus janaschii* YLINPGSVGQ (SEQ. ID. No. 197)

*Thermotoga maritima* LVLNPGSAGR (SEQ. ID. No. 198)

The *D.rad.* sequence was used to design an upstream 28mer primer (5'-CTGGTGAACCCGGGCTCCGTGGGCCAGC-3') (SEQ. ID. No. 199) that encodes the amino acid sequence LLVNPGSVGQ (SEQ. ID. No. 200) and a downstream 27mer (5'-CTCGAGGAGCTTGAGGAGGGTGTTGGC-3') (SEQ. ID. No. 201) encodes the sequence ANTLLKLLE (SEQ. ID. No. 202) on the complementary strand. The amplification reactions contained 50 ng *T.th.* genomic DNA and 0.1 μM of each primer in a volume of 100 μl of Deep Vent polymerase reaction mixture containing 10 μl ThermoPol Buffer, 2.5 mM of each dNTP, 1.5 mM $MgSO_4$, and 10 μl formamide. Amplification was performed using the following cycling scheme:

1. 5 cycles of: 95° C.—30 sec., 68° C.—20 sec., 75° C.—3 min.
2. 5 cycles of: 95° C.—20 sec., 63° C.—20 sec., 75° C.—3 min.
3. 35 cycles of: 95° C.—20 sec., 55° C.—10 sec., 75° C.—3 min.

Product was visualized in a 1.0% native agarose gel as a single band of 0.7 Kb. The fragment was purified and partially sequenced.

Multiple alignment of the gene downstream of *D.rad.* identified the following conservative region:

*Deinococcus radiodurans* GFGGVQLHAAHGYLLSQ-FLSPRHNVREDEYGG (SEQ. ID. No. 203)

*Caenorhabditis elegans* GFDGIQLHGAH-GYLLSQFTSPTTNKRVDKYGG (SEQ. ID. No. 204)

*Pseudomonas aeruginosa* GFSGVEIHAAHGYLLSQ-FLSPLSNRRSDAWGG (SEQ. ID. No. 205)

*Archaeoglobus fulgidus* GFDAVQLHAAHGYLLSE-FISPHVNRRKDEYGG (SEQ. ID. No. 206)

The fragment in bold was used to design primers, specifically the downstream primer, for cloning of the 3' region of the *T.th.* holB gene. The upstream 30mer (5'-CATCCTGGACTCGGCCCACCTCCTCACCGA-3') (SEQ. ID. No. 207) encodes the amino acid sequence ILDSAHLLT (SEQ. ID. No. 208). The downstream 33mer (5'-GAGGAGGTAGCCGTGGGCCGCGTGGAGCTCCAC-3') (SEQ. ID. No. 209) encodes the sequence VELHAAHGYLL (SEQ. ID. No. 210) on the complementary strand. The amplification reactions contained 50 ng *T.th.* genomic DNA and 0.1 μM of each primer in a volume of 100 μl of Deep Vent polymerase reaction mixture containing 10 μl ThermoPol Buffer, 2.5 mM of each dNTP, 2 mM $MgSO_4$, and 10 μl DMSO. Amplification was performed using the following cycling scheme:

1. 5 cycles of: 95° C.—30 sec., 70° C.—20 sec., 75° C.—4 min.
2. 5 cycles of: 95° C.—20 sec., 66° C.—20 sec., 75° C.—4 min.
3. 30 cycles of: 95° C.—20 sec., 60° C.—10 sec., 77° C.—4 min.

Products were visualized in a 1.0% native agarose gel as a single band of 1.1 kb. The Kb fragment was gel purified and sequenced to provide the remainder of the holB gene encoding *T.th.* δ'.

For protein expression, the *T.th.* holB gene was cloned into the pET24 vector at the Nde:EcoR sites using a pair of primers. The upstream 32mer (5'-GGCTTTCCCATATGGCTCTACACCCGGCTCAC-3') (SEQ. ID. No. 211) contains a NdeI site within the first 15 nucleotides (underlined) and the sequence corresponding to the 5' region of *T.th.* holB. The downstream 29 mer (5'-GCGTGGATCCACGGTCATGTCTCTAAGTC-3') (SEQ. ID. No. 212) contains a BamHI site within the first 10 nucleotides (underlined) and a sequence complementary to the 3' end of the holB gene.

EXAMPLE 15

Alternate Synthetic Path in Absence of Clamp Loader Activity

As discussed earlier, the Pol III-type enzyme of the present invention is capable of application and use in a variety of contexts, including a method wherein the clamp loader component that is traditionally involved in the initiation of enzyme activity, is not required. The clamp loader generally functions to increase the efficiency of ring assembly onto circular primed DNA, because both the ring and the DNA are circles and one must be broken transiently for them to become interlocked rings. In such a reaction, the clamp loader increases the efficiency of opening the ring.

The procedure described below illustrates the instance where the clamp loader need not be present. For example, the β clamp can be assembled onto DNA in the absence of the clamp loader. Particularly, the bulk of primed templates in PCR reactions are linear ssDNA fragments that are primed at the ends. On linear primed DNA, the ring need not open at all. Instead, the ring can simply thread onto the end of the linear primed template (Bauer and Burgers, 1988; Tan et al, 1986; O'Day et al., 1992; Burgers and Yoder, 1993). Hence, on linear primed templates, such as those generated in PCR, the beta clamp can simply slide over the DNA end. After the ring slides onto the end, the DNA polymerase can associate with the ring for enhanced DNA synthesis.

Such "end assembly" is common among Pol III-type enzymes and has been demonstrated in yeast and human systems. Rings assembling onto linear DNA for use by their respective DNA polymerases are shown in the following example demonstrated in the *E. coli* bacterial system, in the human system, and in the *T.th.* system.

The bulk of the primed templates in PCR reactions are linear ssDNA fragments that are primed at their ends. However, these end primed linear fragments are not generated until after the first step of PCR has already been performed. In the very first step, PCR primers generally anneal at internal sites in a heat denatured ssDNA template. Primed linear templates are then generated in subsequent steps enabling use of this alternate path. For this first step, the clamp may be assembled onto an internal site in the absence of the clamp loader using special conditions that allow clamp assembly in the absence of a clamp loader.

For example, a set of conditions that lead to assembly of the clamp onto circular DNA (i.e., internal primed sites) have been described in the protocol for the use of the bacteriophage T4 ring shaped clamp (gene 45 protein) without the clamp loader (Reddy et al., 1993). In this case, polyethylene glycol leads to "macromolecular crowding" such that the clamp and DNA are pushed together in close proximity, leading to the ring self assembling onto internal primed sites on circular DNA. Other possible conditions that may lead to assembly of rings onto internal sites include use of a high concentration of beta such that use of heat or denaturant to break the dimeric ring into two half rings (crescents) followed by lowering the heat (or dilution or removal of denaturant) leading to rings assembling around the DNA.

The ring shaped sliding clamps of *E. coli* and human slide over the end of linear DNA to activate their respective DNA polymerase in the absence of the clamp loader. This clamp loader independent assay is performed in the bacterial system in FIG. 25A. For this assay, the linear template is polydA primed with oligodT. The polydA is of average length 4500 nucleotides and was purchased from SuperTecs. OligodT35 was synthesized by Oligos etc. The template was prepared using 145 μl of 5.2 mM (as nucleotide) polydA and 22 μl of 1.75 mM (as nucleotide) oligodT. The mixture was incubated in a final volume of 2100 μl T.E. buffer (ratio as nucleotide was 21:1 polydA to oligodT). The mixture was heated to boiling in a 1 ml Eppendorf tube, then removed and allowed to cool to room temperature. Assays were performed in a final volume of 25 μl 20 mM Tris-Cl (pH 7.5), 8 mM $MgCl_2$, 5 mM DTT, 0.5 mM EDTA, 40 mg/ml BSA, 4% glycerol, containing 20 μM [α-$^{32}$P]dTTP, 0.1 μg polydA-oligodT, 25 ng Pol III and, where present, 5 μg of β subunit. Proteins were added to the reaction on ice, then shifted to 37° C. for 5 min. DNA synthesis was quantitated using DE81 paper as described (Rowen and Kornberg, 1978).

In the linear template assay, no ATP or dATP is provided and therefore, a clamp loader, even if present, is not active. Thus, the clamp (e.g., β) can only stimulate the DNA polymerase provided the clamp threads onto the DNA (see diagram in FIG. 25). Hence, threading of the clamp is shown by a stimulation of the DNA polymerase. In lane 1 of FIG. 25A, the DNA polymerase is incubated with the linear DNA in the absence of the clamp, and lane 2 shows the result of adding the clamp. The results show that the clamp is able to thread onto the DNA ends and stimulate the DNA polymerase in the absence of ATP and thus, in the absence of clamp loading as well.

This clamp loader independent assay is performed in the human system in FIG. 25B. The assay reaction (25 μl) contains 50 mM Tris-HCl (pH=7.8), 8 mM MgCl2, 1 mM DTT, 1 mM creatine phosphate, 40 μg/ml bovine serum albumin, 0.55 μg human SSB, 100 ng PCNA (where present), 7 units DNA polymerase delta (1 unit incorporates 1 pmol dTMP in 60 min.), 40 mM [α-$^{32}$P]dTTP and 0.1 μg polydA-oligodT. Proteins were added to the reaction on ice, then shifted to 37° C. for 60 min. DNA synthesis was quantitated using DE81 paper as described (Rowen and Kornberg, 1978). In lane 3, (FIG. 25) the DNA polymerase δ is incubated with the linear DNA in the absence of the clamp, and lane 4 shows the result of adding the PCNA clamp. The results demonstrate that the clamp is able to thread onto the DNA ends and stimulate the DNA polymerase in the absence of ATP and thus, the absence of clamp loading.

This clamp loader independent assay is performed in the *T.th.* system in FIG. 25C. The assay reaction is exactly as described above for use of the *E. coli* Pol III and beta system except the temperature is 60° C. and here the Pol III is HEP.P1 *T.th.* Pol III (0.5 μl, providing 0.1 units where one unit is equal to 1 pmol of dTTP incorporated in 1 minute under these conditions and in the absence of beta), and the beta subunit is 7 μg *T.th.* β (from the MonoQ column). Proteins were added to the reaction on ice, then shifted to 37° C. for 60 min. DNA synthesis was quantitated using DE81 paper as described (Rowen and Kornberg, 1978). In lane 3 (FIG. 25C), the *T.Th.* Pol III is incubated with the linear DNA in the absence of the clamp, and lane 4 shows the result of adding the *T.th.* β clamp. The results demonstrate that the clamp is able to thread onto the DNA ends and stimulate the DNA polymerase in the absence of clamp loader activity.

EXAMPLE 16

Use of *T.th.* Pol III in Long Chain Primer Extension

A characteristic of Pol III-type enzymes is their ability to extend a single primer for several kilobases around a long (e.g. 7 kb) circular single stranded DNA genome of a bacteriophage. This reaction uses the circular β clamp protein. For the circular β to be assembled onto a circular DNA genome, the circular β must be opened, positioned around the DNA, and then closed. This assembly of the circular beta around DNA requires the action of the clamp loader, which uses ATP to open and close the ring around DNA. In this example, the 7.2 kb circular single strand DNA genome of bacteriophage M13mp18 was used as a template. This template was primed with a single DNA 57mer oligonucleotide and the Pol III enzyme was tested for conversion of this template to a double strand circular form (RFII). The reaction was supplemented with recombinant *T.th.* β produced in *E. coli*. This assay is summarized in the scheme at the top of FIG. 26. M13mp18 ssDNA was phenol-extracted from phage purified as described (Turner and O'Donnell, 1995). M13mp18 ssDNA was primed with a 57mer DNA oligomer synthesized by Oligos etc. The replication assays contained 73 ng singly primed M13mp18 ssDNA and 100 ng *T.th.* β subunit in a 25 μl reaction containing 20 mM Tris-HCl (pH 7.5), 8 mM $MgCl_2$, 40 μg/ml BSA, 0.1 mM EDTA, 4% glycerol, 0.5 mM ATP, 60 μM each of dCTP, dGTP, dATP and 20 μM α-$^{32}$P-TTP (specific activity 2,000–4,000 cpm/pmol). Either *T.th.* Pol III from the Heparin, peak 1 (HEP.P1; 5 μl, 0.21 units where 1 unit equals 1 pmol nucleotide incorporated in 1 min.) or a non-Pol III from the Heparin peak 2 (HEP.P2; 5 μl, 2.6 units) were added to the reaction. Reactions were shifted to 60° C. for 5 min., and then DNA synthesis was quenched upon adding 25 μl of 1% SDS, 40 mM EDTA. One half of the reaction was analyzed in a 0.8% native agarose gel, and the other half was quantitated using DE81 paper as described (Studwell and O'Donnell, 1990).

The results of the assay are shown in FIG. 26. Lane 1 is the result obtained using the *T.th.* Pol III (HEP.P1) which was capable of extending the primer around the ssDNA circle to form RFII. Lane 2 shows the result of using the non-Pol III (HEP.P2) which was not capable of this extension and produced only incomplete DNA products (the result shown included 0.8 μg *E. coli* SSB which did not increase the chain length of the product). In the absence of SSB, the same product was observed, although the band contained more counts. The greater amount of total synthesis observed in lane 2 is due to the build up of immature products in a small region of the gel. The presence of immature products in lane 1 is likely due to a contaminating polymerase in the preparation that can not convert the single primer to the full length RFII form. Alternatively, the presence of incomplete products in lane 1 (Pol III type enzyme) is due to secondary structure in the DNA which causes the Pol III to pause. In this case it may be presumed that performing the reaction at higher temperature could remove the secondary structure barrier. Alternatively, SSB could be added to the assay (although *T.th.* SSB would be needed, because addition of *E. coli* SSB was tried and did not alter the quality of the product profile). Generally, SSB is needed to remove secondary structure elements from ssDNA at 37° C. for complete extension of primers by mesophilic Pol III-type enzymes.

The assay described above was performed at 60° C. The *T.th.* Pol III HEP.P1 gained activity as the temperature was increased from 37° C. to 60° C., as expected for an enzyme from a thermophilic source. The *E. coli* Pol III lost activity at 60° C. compared to 37° C., as expected for an enzyme from a mesophilic source.

EXAMPLE 17

Materials Used in Examples 18–29

Radioactive nucleotide were from Dupont NEN; unlabeled nucleotides were from Pharmacia Upjohn. DNA oligonucleotides were synthesized by Gibco BRL. M13mp18 ssDNA was purified from phage that was isolated by two successive bandings in cesium chloride gradients. M13mp18 ssDNA was primed with a 30-mer (map position 6817–6846) as described. The pET protein expression vectors and BL21(DE3) protein expression strain of *E. coli* were purchased from Novagen. DNA modification enzymes were from New England Biolabs. *Aquifex aeolicus* genomic DNA was a gift of Dr. Robert Huber and Dr. Karl Stetter (Regensburg University, Germany). Protein concentrations were determined by absorbance at 280 nm using extention coefficients calculated from their known Trp and Tyr content using the equation $\epsilon_{280}=Trp_m(5690\ M^{-1}\ cm^{-1})+Tyr_n(1280\ M^{-1}\ cm^{-1})$.

EXAMPLE 18

Purification of α Encoded by dnaE The *Aquifex aeolicus* dnaE gene was previously identified (Deckert et al., 1998). The dnaE was obtained by searching the *Aquifex aeolicus* genome with the amino acid sequence of *T.th.* α subunit (encoded by dnaE). The dnaE gene was amplified from *Aquifex aeolicus* genomic DNA by PCR using the following primers: the upstream 37mer (5'-GTGTGT CATATGAGTAAGGATTFCGTCCACCTFCACC-3') (SEQ. ID. No. 157) contains an NdeI site (underlined); the downstream 34mer (5'-GTGTGT GGATCCGGGGACTACTCGGAAGTAAGGG-3') (SEQ. ID. No. 158) contains a BamHI site (underlined). The PCR product was digested with NdeI and BamHI, purified, and ligated into the pET24 NdeI and BamHI sites to produce pETAadnaE.

The pETAadnaE plasmid was transformed into the BL21 (DE3) strain of *E. coli*. Cells were grown in 50L of LB containing 100 μl/ml of kanamycin, 5 mM $MgSO_4$ at 37° C. to $OD_{600}$=2.0, induced with 2 mM IPTG for 20 h at 20° C., then collected by centrifugation. Cells were resuspended in 400 ml 50 mM Tris-HCl (pH 7.5), 10% sucrose, 1M NaCl, 30 mM spermidine, 5 mM DTT and 2 mM EDTA. The following procedures were performed at 4° C. Cells were lysed by passing them twice through a French Press (15,000 psi) followed by centrifugation at 13,000 rpm for 90 min at 4° C. In this protein preparation, as well as each of those that follow, the induced *Aquifex aeolicus* protein was easily discernible as a large band in an SDS polyacrylamide gel stained with Coomassie Blue. Hence, column fractions were assayed for the presence of the *Aquifex aeolicus* protein by SDS PAGE analysis, which forms the basis for pooling column fractions.

The clarified cell lysate was heated to 65° C. for 30 min and the precipitate was removed by centrifugation at 13,000 rpm in a GSA rotor for 1 h. The supernatant (1.4 gm, 280 ml) was dialyzed against buffer A (20 mM Tris-HCl (pH 7.5)), 10% glycerol, 0.5 mM EDTA, 5 mM DTT) overnight, then diluted to 320 ml with buffer A to a conductivity equal to 100 mM NaCl. The dialysate was applied to a 150 ml Fast Flow Q (FFQ) Sepharose column (Pharmacia) equilibrated in buffer A, and eluted with a 1.5 L linear gradient of 0–500 mM NaCl in buffer A. Eighty fractions were collected. Fractions 38–58 (1 g, 390 ml) were pooled, dialyzed versus buffer A overnight, and applied to a 250 ml Heparin Agarose column (Bio-Rad) equilibrated with buffer A. Protein was eluted with a 1 L linear 0–5 mM NaCl gradient in buffer A. One hundred fractions were collected. Fractions 69–79 (320 mg in 200 ml) were pooled and dialyzed against buffer A containing 100 mM NaCl. The α preparation was aliquoted and stored frozen at −80° C. (see FIG. 27).

EXAMPLE 19

Purification of 8 Encoded by holA

The *Aquifex aeolicus* holA gene was not previously identified by the genome sequencing group at Diversa (Deckert et al., 1998). *Aquifex aeolicus* holA was identified by searching the *Aquifex aeolicus* genome with the amino acid sequence of the *T.th.* δ subunit (encoded by holA). The *Aquifex aeolicus* holA was amplified by PCR using the following primers: the upstream 36mer (5'-GTGTGT CATATGGAAACCACAATATTCCAGTTCCAG-3') (SEQ. ID. No. 159) contains an NdeI site (underlined); the downstream 39mer (5'-GTGTGT GGATCCTTATCCACCATGAGAAGTATTTTTCAC-3') (SEQ. ID. No. 160) contains a BamHI site (underlined). The PCR product τ was digested with NdeI and BamHI, purified, and ligated into the pET24 NdeI and BamHI sites to produce pETAaholA.

The pETAaholA plasmid was transformed into *E. coli* strain BL21(DE3). Cells were grown in 50 L of LB media containing 100 μg/ml kanamycin. Cells were grown at 37° C. to $OD_{600}$=2.0, induced for 20 h upon addition of 2 mM IPTG, then collected by centrifugation. Cells from 25 L of culture were lysed as described in Example 18.

The cell lysate was heated to 65° C. for 30 min and the precipatate was removed by centrifugation. The supernatant (650 mg, 240 ml) was dialyzed against buffer A, adjusted to a conductivity equal to 160 mM NaCl by addition of 40 ml of buffer A, and applied to a 220 ml Heparin Agarose column equilibrated in buffer A containing 100 mM NaCl. The column was eluted with 1.0 L linear gradient of 150–700 mM NaCl in buffer A. One hundred and four fractions were collected. Fractions 45–56 were pooled (250 mg, 210 ml), diluted with 230 ml buffer A to a conductivity equal to 230 mM NaCl, then loaded onto a 100 ml FFQ Sepharose column equilbrated in buffer A containing 150 mM NaCl. The column was eluted with 200 ml linear gradient of 150–750 mM NaCl in buffer A; seventy-three fractions were collected. Fractions 16–38 were pooled (95 mg, 40 ml), aliquoted, and stored at −80° C. (see FIG. 27).

EXAMPLE 20

Purification of δ' Encoded by holB

The *Aquifex aeolicus* holB gene was previously identified by the genome sequencing facility at Diversa (Deckert et al., 1998). The *Aquifex aeolicus* holB sequence was obtained by searching the *Aquifex aeolicus* genome with the sequence of the *T.th.* δ' (encoded by holB). The *Aquifex aeolicus* holB gene was amplified by PCR using the following primers: the upstream 39mer (5'-GTGTGT CATATGGAAAAGTTTTTTTTGGAAAAAACTCCAG-3') (SEQ. ID. No. 161) contains an NdeI site (underlined); the downstream 35mer (5'-GTGTGT GGATCCTTAATCCGCCTGAACGGCTAACG-3') (SEQ. ID. No. 162) contains a BamHI site (underlined). The PCR product was digested with NdeI and BamHI, purified, and ligated into the pET24 NdeI and BamHI site to produce pETAaholB.

The pETAaholB plasmid was transformed into *E. coli* strain BL21(DE3). Cells were grown at 37° C. in 50 L media containing 100 μ/ml kanamycin to $OD_{600}$ 2.0, then induced for 3 h upon addition of 0.2 mM IPTG. Cells were collected by centrifugation and were lysed using lysozyme by the heat lysis procedure (Wickner and Kornberg, 1974). The cell lystate was heated to 65° C. for 30 min and precipatate was removed by centrifugation. The supernatant (2.4 g, 400 ml)

was dialyzed versus buffer A, then applied to a 220 ml FFQ Sepharose column equilibrated in buffer A. Protein was eluted with a 1 L linear gradient of 0–500 mM NaCl in buffer A; eighty fractions were collected. Fractions 23–30 were pooled and diluted 2-fold with buffer A to a conductivity equal to 100 mM NaCl, then loaded onto a 200 ml Heparin Agarose column equilibrated in buffer A. Protein was eluted with a 1 L linear gradient of 0–1.0M NaCl in buffer A; eighty-four fractions were collected. Fractions 46–66 were pooled (1.3 g, 395 ml), dialyzed versus buffer A containing 100 mM NaCl, then aliquoted and stored frozen at –80° C. (see FIG. 27)

EXAMPLE 21

Purification of τ Encoded by dnaX

The *Aquifex aeolicus* dnaX gene was previously identified (Deckert et al., 1998). The dnaX gene sequence was obtained by searching the *Aquifex aeolicus* genome with the sequence of *T.th.* τ subunit (encoded by dnaX). The *Aquifex aeolicus* dnaX was amplified by PCR using the following primers: the upstream 41mer (5'-GTGTGT CATATGAACTACGTTCCCTTCGCGAGAAAGTACAG-3') (SEQ. ID. No. 163) contains an NdeI site (underlined); the downstream 36mer (5'-GTGTGT GGATCCTTAAAACAGCCTCGTCCCGCTGGA-3') (SEQ. ID. No. 164) contains a BamHI site (underlined). The PCR product was digested with NdeI and BamHI, purified, and ligated into the pET24 NdeI and BamHI sites to produce pETAadnaX.

The pETAadnaX plasmid was transformed into *E. coli* strain BL21(DE3). Cells were grown in 50 L LB containing 100 μg/ml kanamycin at 37° C. to $OD_{600}$=0.6, then induced for 20 h at 20° C. upon addition of IPTG to 0.2 mM. Cells were collected by centrifugation and lysed as described in Example 18. The clarified cell lysate was heated to 65° C. for 30 min and the protein precipitate was removed by centrifugation. The supernatant (1.1 g in 340 ml) was treated with 0.228 g/ml ammonium sulfate followed by centrifugation. The τ subunit remained in the pellet which was dissolved in buffer B (20 mM Hepes (pH 7.5), 0.5 mM EDTA, 2 mM DTT, 10% glycerol) and dialyzed versus buffer B to a conductivity equal to 87 mM NaCl. The dialysate (1073 mg, 570 ml) was applied to a 200 ml FFQ Sepharose column equilibrated in buffer A. The column was eluted with a 1.5 L linear gradient of 0–500 mM NaCl in buffer A; eighty fractions were collected. Fractions 28–37 were pooled (289 mg, 138 ml), dialyzed against buffer A to a conductivity equal to 82 mM NaCl, then loaded onto a 150 ml column of Heparin Agarose equilibrated in buffer A. The column was eluted with a 900 ml linear gradient of 0–500 mM NaCl in buffer A; thirty-two fractions were collected. Fractions 15–18 (187 mg, 110 ml) were dialyzed versus buffer A, then aliquoted and stored at –80° C. (see FIG. 27).

EXAMPLE 22

Purification of β Encoded by dnaN

The *Aquifex aeolicus* dnaN gene was previously identified (Deckert et al., 1998). The dnaN sequence was obtained by searching the *Aquifex aeolicus* genome with the sequence of *T.th.* β subunit (encoded by dnaN). The *Aquifex aeolicus* dnaN gene was amplified by PCR using the following primers: the upstream 33mer (5'-GTGTGT CATATGCGCGTTAAGGTGGACAGGGAG-3') (SEQ. ID. No. 165) contains an NdeI site (underlined); the downstream 36mer (5'-TGTGTCTCGAGTCATGGC TACACCCTCATCGGCAT-3') (SEQ. ID. No. 166) contains a XhoI site (underlined). The PCR product was digested with NdeI and BamHI, purified, and ligated into the pET24 NdeI and BamHI sites to produce pETAadnaN.

The pETAadnaN plasmid was transformed into *E. coli* strain BL21(DE3). Cells were grown in 1 L LB containing 100 mg/ml kanamycin at 37° C. to $OD_{600}$=1.0, then induced for 6 h upon addition of 2 mM IPTG. Cells were collected (7 g) and lysed as described in Example 18. The cell lysate was heated to 65° C. for 30 min and the protein precipitate was removed by centrifugation. The supernatant (39 mg, 45 ml) was applied to a 10 ml DEAE Sephacel column (Pharmacia) equilibrated in buffer A. The column was eluted with a 100 ml linear gradient of 0–500 mM NaCl in buffer A; seventy-five fractions were collected. Fractions 45–57 were pooled (18.7 mg), dialyzed versus buffer A, and applied to a 30 ml Heparin Agarose column equilibrated in buffer A. The column was eluted with a 300 ml linear gradient of 0–500 mM NaCl in buffer A; sixty-five fractions were collected. Fractions 27–33 were pooled (11 mg, 28 ml) and stored at –80° C. (see FIG. 27).

EXAMPLE 23

Purification of SSB Encoded by ssb

The *Aquifex aeolicus* ssb gene was previously identified (Deckert et al., 1998 g). The ssb gene sequence was obtained by searching the *Aquifex aeolicus* genome with the sequence of *T.th.* SSB (encoded by ssb). The *Aquifex aeolicus* ssb gene was amplified by PCR using the following primers: the upstream 47mer (5'-GTGTGTCATATGC TCAATAAGGTTTTTATAATAGGAAGACTTACGGG-3') (SEQ. ID. No. 167) contains an NdeI site (underlined); the downstream 39mer (5'-GTGTGGATCCTT AAAAAGGTATTTCGTCCTCTTCATCGG-3') (SEQ. ID. No. 168) contains a BamHI site (underlined). The PCR product was digested with NdeI and BamHI, purified, and ligated into the pET16 NdeI and BamHI sites to produce pETAassb.

The pETAassb plasmid was transformed into *E. coli* strain BL21(DE3). Cells were grown in 6 L of LB media containing 200 μg/ml ampicillin. Cells were grown at 37° C. to $OD_{600}$=0.6, then induced at 15° C. overnight in the presence of 2 mM IPTG and collected by centrifugation. Cells were lysed as described above in Example 18, except cells were resuspended in buffer C (20 mM Tris-HCl (pH 7.9), 500 mM NaCl).

The cell lysate was heated to 65° C. for 30 min, then the precipitate was removed by centrifugation. The supernatant (1.4 g, 190 ml) was applied to 25 ml Chelating Sepharose column (Pharmacia-Biotech) charged with 50 mM Nickel Sulfate and then equilibrated in buffer C containing 5 mM Imidazole. The column was eluted with a 300 ml linear gradient of 5–100 mM Imidazole in buffer C. Fractions of 4 ml were collected. Fractions 81–92 were pooled (~240 mg in 48 ml) and dialyzed overnight against 2 L of buffer B containing 200 mM NaCl. The dialysate was diluted to a conductivity equal to 92 mM NaCl using buffer A and then loaded onto an 8 ml MonoQ column equilibrated in buffer A containing 100 mM NaCl. The column was eluted with a 120 ml linear gradient of 100–500 mM Imidazole in buffer A. Seventy-four fractions were collected. Fractions 57–70 were pooled (100 mg, 25 ml), aliquoted, and stored at –80° C. (see FIG. 27).

EXAMPLE 24

MonoQ Preparation of τδδ'

The δ subunit (0.29 mg) purified in Example 19 and δ' subunit (0.31 mg) purified in Example 20 were mixed in a volume of 2.8 ml of buffer A at 15° C. After 30 min, the τ subunit (0.5 mg in 1.4 ml), purified in Example 21, was added and the reaction was incubated a further 1 h at 15° C. The reaction was applied to a 1 ml MonoQ column equilibrated in buffer A. The τδδ' complex elutes later than either τ, δ or δ' alone. Protein was eluted with a 32 ml linear gradient of 100–500 mM NaCl in buffer A; eighty fractions were collected. Analysis of the MonoQ fractions in a SDS polyacylamide gel shows a peak of τδδ' complex that elutes in fractions of 32–38 (see FIG. 28). The peak fractions 850 μg were stored at −80° C. This procedure can easily be scaled up. For example, a much larger amount of τδδ' was constituted by following a similar protocol and using a 8 ml MonoQ column, which yielded 9.6 mg of τδδ'.

EXAMPLE 25

Constitution of ατδδ' Complex

The reaction mixture contained 1.2 mg α subunit (9 nmol; 133,207 da) purified in Example 18, 0.41 mg τ subunit (7.5 nmol; 54,332 da) purified in Example 21, 0.41 mg δ subunit (10 nmol; 40,693 da) purified in Example 19, and 0.2 mg δ' subunit (9 nmol; 29,000 da) purified in Example 20 in 1.1 ml buffer A. The α and τ subunit solutions were premixed in 871 μl for 2 h at 15° C. before adding δ and δ' subunit solution, then the complete mixture was allowed to incubate an additional 12 h at 15° C. The reaction may not require an order of addition, or these extended incubation times. The reaction mixture was concentrated to 200 μl using a Centricon 30 at 4° C., then applied to an FPLC Superose 6 HR 10/30 column (25 ml) at 4° C. developed with a continuous flow of buffer A containing 100 mM NaCl. After the first 216 drops (6.6 ml), fractions of 7 drops each were collected. Fractions were analyzed on a SDS polyacrylamide gel stained with Coomassie Blue (FIG. 29). The analysis was repeated using the α subunit alone (FIG. 29). The results show that the peak fractions of α shift to a considerably earlier position when α, δ and δ' are present and α comigrates with τ, δ, and δ', when compared to the elution position of α alone, indicating that α assembles with τ, δ and δ' into a ατδδ' complex.

EXAMPLE 26

ατδδ' Functions with the β Clamp

Replication reactions were performed using circular M13mp18 ssDNA primed with a synthetic DNA 90 mer oligonucleotide. Reactions contained 8.6 μg primed M13mp18 ssDNA, 9.4 μg SSB purified in Example 23, 101 μg ατδδ' prepared in Example 25, and 2.0 μg β subunit purified in Example 22 (when present), in 230 μl of 20 mM Tris-HCl (pH 7.5), 5 mM DTT, 4% glycerol, 8 mM $MgCl_2$, 0.5 mM ATP, 60 μM each dATP and dGTP (buffer composition is for a final volume of 250 μl). Reactions were mixed on ice, then aliquoted into separate tubes containing 25 μl each. For each timed reaction, the mixture was brought to 65° C. for 2 min before initiating syntheses upon addition of 2 μl of dCTP and $\alpha^{32}$P-dTTP (final centrations, 60 and 40 μM, respectively). Aliquots were quenched at the times indicated in FIG. 30 upon adding 4 μl of 0.25M EDTA, 1% SDS. Quenched reactions were then analyzed in a 0.8% alkaline agarose gel. The results, illustrated in FIG. 30, demonstrate that efficient synthesis requires addition of the β subunit. Comparison with size standards in the same gel indicates an average speed of ~125 nucleotides; the leading edge of the product smear indicates a maximum speed of 375 nucleotides/s.

EXAMPLE 27

Purification of *T.th.* α Subunit

To obtain *T.th.* α subunit, 8 L of *E. coli* BL21(DE3) cells harboring pETtthalpha were grown to O.D.=0.3 and induced upon adding IPTG. Cells were collected by centrifugation and resuspended in 200 ml 50 mM Tris-HCl (pH 7.5), 10% sucrose, 1M NaCl, 30 mM spermidine, 5 mM DTT and 2 mM EDTA. The following procedures were performed at 4° C. Cells were lysed by passing them three times through a French Press (20,000 psi) followed by incubation at 4° C. for 30 min and then centrifugation at 18,000 rpm in an SS-34 rotor for 45 min at 4° C. Induced protein was less that 1% total cell protein but was discernible as a band that migrated in the appropriate position for its predicted molecular weight in an SDS polyacrylamide gel stained with Coomassie Blue. Hence, column fractions were assayed for the presence of the protein by SDS PAGE analysis, which forms the basis for pooling column fractions.

The clarified cell lysate was heated to 65° C. for 30 min and the precipitate was removed by centrifugation. The supernatant (1.4 gm, 280 ml) was dialyzed against buffer A (20 mM Tris-HCl (pH 7.5), 10% glycerol, 0.5 mM EDTA, 5 mM DTT) overnight, then diluted to 320 ml with buffer A to a conductivity equal to 100 mM NaCl. The dialysate (approximately 150 mg) was applied to a 60 ml DEAE Fast Flow Q (FFQ) Sepharose column (Pharmacia) equilibrated in buffer A, and eluted with a 600 ml linear gradient of 0–500 mM NaCl in buffer A. Fractions of 8 ml each were collected. The *T.th.* α subunit could be seen as a major band in several fractions, especially in fractions 26–30. In these peak fractions the *T.th.* α subunit was approximately 20–30 percent pure

EXAMPLE 28

Purification of *T.th.* ε Subunit

The dnaQ gene was cloned into the pET16 expression plasmid using the Val within the context "VGLWEW . . . " and transformed into *E. coli* (BL21(DE3).

This pET plasmid places an N-terminal leader containing six histidines onto the expressed protein to facilitate purification via use of chelate affinity chromatography. Twelve liters of cells were grown to an OD of 0.7 and induced with IPTG. Induced cells were collected by centrifugation and resuspended in 150 ml of buffer C (20 mM Tris-HCl (pH 7.9), 500 mM NaCl). Cells were lysed by passing them two times through a French Press (20,000 psi) followed by incubation at 4° C. for 30 min and then centrifugation at 13,800 rpm in an SLA-1500 rotor for 45 min at 4° C. Induced protein appeared greater than 5% total cell protein and was easily discernible as a band that migrated in the appropriate position for its predicted molecular weight in an SDS polyacrylamide gel stained with Coomassie Blue. Hence, column fractions were assayed for the presence of the protein by SDS PAGE analysis, which forms the basis for pooling column fractions.

Upon analyzing the precipitate from the cell lysis, and the supernatant, it was determined that the epsilon subunit was insoluble and appeared in the precipitate. Therefore the cell pellet was resuspended in 100 ml of binding buffer containing 6M freshly deionized urea. This resuspension was then placed in centrifuge bottles and spun at 13,800 rpm for 45 min in the SLA-1500 rotor. The epsilon was in the supernatant and was applied to a 25 ml Chelating Sepharose column (Pharmacia-Biotech) charged with 50 mM Nickel Sulfate and then equilibrated in buffer C containing 5 mM Imidazole. The column was washed with two column volumes of buffer C, then washed with 5 column volumes of buffer C containing 80 mM Imidazole (final). Then the *T.th.* epsilon was eluted with a 250 ml linear gradient of 60–1000 mM Imidazole in buffer C. Fractions of 4 ml were collected. Fractions 15–24 were pooled (~131 mg) and dialyzed overnight against 2 L of buffer A containing 6M urea, but no NaCl or glycerol. The dialysate was then loaded onto an 8 ml MonoQ column equilibrated in buffer A containing 6M urea. The column was eluted with a 120 ml linear gradient of 0–500 mM NaCl in buffer A containing urea. Sixty five fractions were collected. The epsilon is approximately 80–90 percent pure at this stage. Fractions 13–17 were stored at −80° C. The epsilon is in urea but is at a concentration of 5–10 mg/ml, and thus can be used with other proteins by diluting it such that the final urea concentration is less than 0.5 M. This level of urea does not generally denature protein, and should allow epsilon to renature for catalytic activity.

EXAMPLE 29

Temperature Optimum of Aquifex and Thermus α Subunit DNA Polymerases

The temperature optimum of the alpha subunits of the Aquifex and Thermus replicases was tested in the calf thymus DNA replication assay. In this experiment, the reactions were assembled on ice in 25 μl containing 2.5 μg calf thymus activated DNA, and either 0.88 ug Aquifex α, or 0.6 μg of the Thermus α DEAE pool of peak fractions (obtained from Examples 18 and 28, respectively) in 20 nM Tris-HCl (pH 8.8), 8 mM $MgCl_2$, 10 mM KCl, 10 mM $(NH_4)SO_4$, 2 mM $MgSO_4$, 0.1% Triton X-100, 60 μM each dATP, dCTP, dGTP, and 20 μM $\alpha^{32}$P-dTTP. Reactons were shifted to either 30, 40, 50, 60, 70, 80, or 90° C., then stopped after 5 minutes and spotted onto DE81 filters to quantitate DNA synthesis. The results, illustrated in FIGS. 31–32, show that these enzymes increase in activity as the temperature is raised. The Thermus α has a broad peak of activity from 70–80° C. (FIG. 31), while the Aquifex α is maximal at 80° C. (FIG. 32). The Aquifex α retains considerable activity at 90° C., whereas the Thermus α is nearly inactive at 90° C., a result that is consistent with the higher temperature at which the *Aquifex aeolicus* may live relative to the Thermus bacterium.

EXAMPLE 30

Temperature Optimum of Aquifex ατδδ'/β

Figures 33A, 33B, 33C, 33D, 33E:
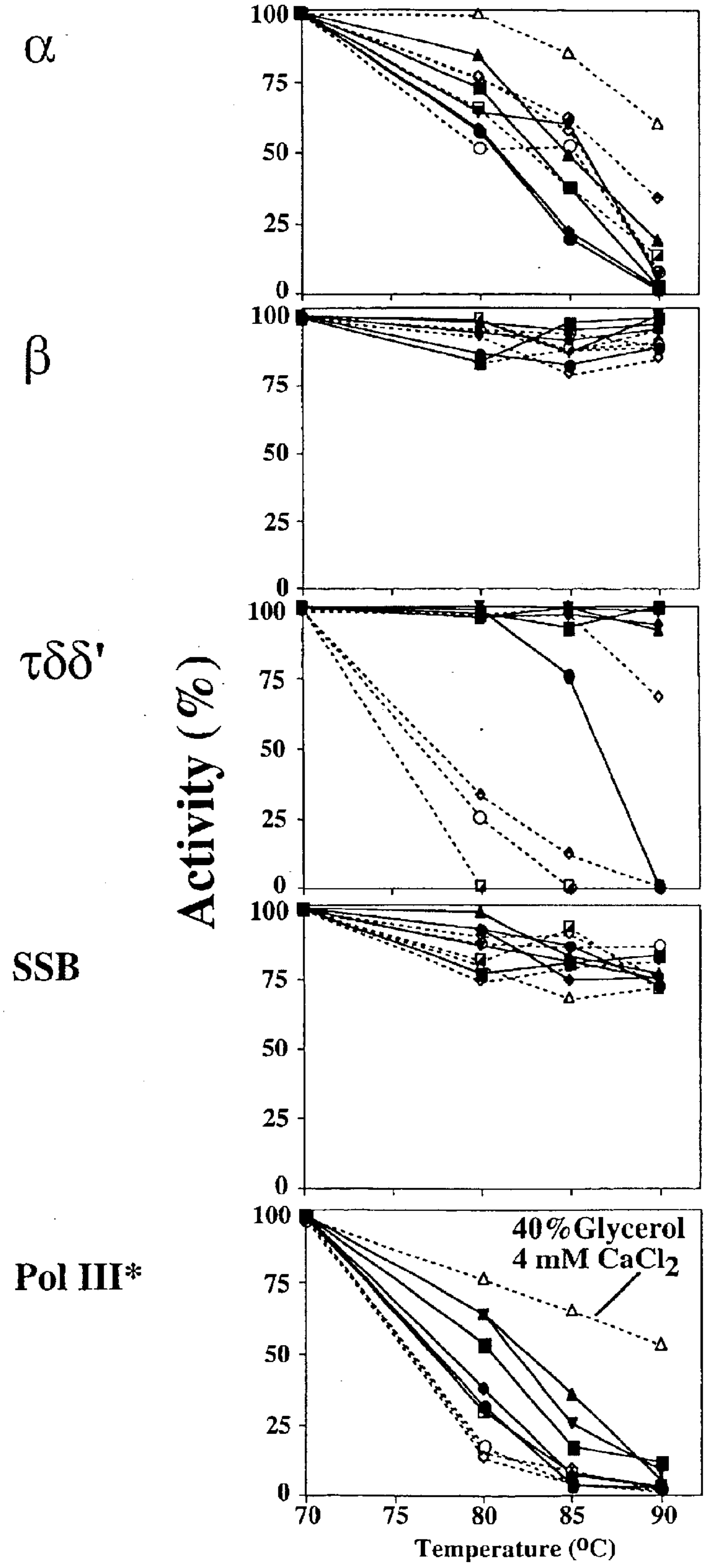

Aquifex α, β, τδδ', SSB and ατδδ' were tested for stability at different temperatures by incubating the protein in a solution, followed by performing a replication assay of the protein. Incubation was performed in 0.4 ml tubes under mineral oil. The 5 μl reaction mixture contained: buffer B (20 mM Tris-HCl (pH 7.5), 5 mM DTT, 5 mM EDTA), and either: 0.352 μg of α (FIG. 33A), 0.2 μg of β (FIG. 33B), 0.125 μg τ complex (FIG. 33C), 0.32 μg SSB and 0.042 μg primed M13mp18 ssDNA (FIG. 33D), 0.82 μg Pol III* (FIG. 33E). Reactions were incubated for 2 min. at either 70, 80, 85, or 90° C. in the presence of either 0.1% Triton X-100 (filled diamonds); 0.05% Tween-20 and 0.01% NP-40 (filled circles); 4 mM $CaCl_2$ (filled triangles); 40% Glycerol (inverted filled triangles); 0.01% Triton X-100, 0.05% Tween-20, 0.01% NP-40, 4 mM $CaCl_2$ (half-filled square); 40% Glycerol, 0.1% Triton X-100 (open diamonds); 40% Glycerol, 0.05% Tween-20, 0.01% NP-40 (open circles); 40% Glycerol, 4 mM $CaCl_2$ (open triangles); 40% Glycerol, 0.01% Triton X-100, 0.05% Tween-20, 0.01% NP-40, 4 mM $CaCl_2$ (half-filled diamonds). After heating, reactions were shifted to ice and 20 μl of replication assay buffer was added followed by incubation for 1.5 min at 70° C.; 15 μl was then spotted onto a DE81 filter and DNA synthesis was quantitated. The replication assay buffer contained: 60 mM Tris-HCl (pH 9.1 at 25° C.), 8 mM $MgCl_2$, 18 mM $(NH_4)_2SO_4$, 2 mM ATP, 60 μM each of dATP, dCTP, dGTP, and 20 μM [α-$^{32}$P]TTP (specific activity 10,000 cpm/pmol), and 0.264 μg primed M13mp18 ssDNA. To assay for β, 0.1 ng ατδδ' was added to the reaction. To assay τδδ', 0.9 ng β and 0.17 ng α were added to the reaction. To assay for SSB, 0.17 ng *E. coli* β and 0.1 ng *E. coli* ατδδ' were added to the reaction followed by incubation for 1.5 min at 37° C. To assay for ατδδ', 0.9 ng β was added to the reaction. To assay α, the calf thymus DNA replication assay was performed in the buffer as described above but 2.5 μg activated calf thymus DNA was used instead of primed M13mp18 ssDNA, no other replication proteins were added, and incubation was for 8 min at 70° C.

REFERENCES

The following is a list of documents related to the above disclosure and particularly to the experimental procedures and discussions. The documents should be considered as incorporated by reference in their entirety.

Alonso, J. C., Shirahige, K., and Ogasawara, N. (1990) Molecular cloning, genetic characterization and DNA sequence analysis of the recM region of *Bacillus subtilis. Nuc. Acids Res.* 18:6771–6777.

Altschul et al., (1997) Gapped BLAST and PSI-BLAST: A new generation of protein database search programs. *Nucl. Acids Res.* 25:3389–3402.

Ausubel, R. M., ed., *Current Protocols in Molecular Biology*, Vol. I–III (1994).

Bambara, R. A., and Jessee, C. B. (1991) Properties of DNA polymerases δ and ε, and their role in eukaryotic DNA replication. *Biochimica et Biophysica Acta* 1088:11–24.

Barnes, M. H., Tarantino, Jr., P. M., Spaccioappoli, P., Brown, N. C., Yu, H., and Dybvig, K. (1994) DNA polymerase III of Mycoplasma pulmonis: isolation of characterization of the enzyme and its structural gene, polC. *Molec Microbiol.* 13:843–854.

Barnes, W. M., (1994) PCR amplification of up to 35-kb DNA with high fidelity and high yield from lambda bacteriophage templates. *Proc. Natl. Acad. Sci. USA* 91:2216–2220.

Bauer, G. A., and Burgers, P. M. (1988) Protein-protein interactions of yeast DNA polymerase III with mammalian and yeast proliferating cell nuclear antigen (PCNA)/cyclin. *Biochim. Biophys. Acta* 951(2–3):274–9.

Blinkowa, A. L., and Walker, J. R., (1 990) Programmed ribosomal frameshifting generates the *Escherichia coli* DNA polymerase III gamma subunit from within the tau subunit reading frame. *Nucl. Acids Res.* 18(7):1725–1729.

Bonner, C. A., Stukenberg, P. T., Rajagopalan, M., Erija, R., O'Donnell, M., McEntee, K., Echols, H., and Goodman, M. F. (1992) Processive DNA synthesis by DNA polymerase II mediated by DNA polymerase III accessory proteins. *J. Biol Chem.*, 267:11431–11438.

Braithwaite, D. K., and Ito, J. (1993) Compilation, alignment, and phylogenetic relationships of DNA polymerases. *Nucl. Acids Res.* 21(4):787–802.

Brock, T. D., and Freeze, H., (1969) *Thermus aquaticus* gen. n. and sp. n., a nonsporulating extreme thermophile. *J. Bacteriol.* 98(1):289–297.

Burgers, P. M., Yoder, B. L. (1993) ATP-independent loading of the proliferating cell nuclear antigen requires DNA ends. *J. Biol. Chem.* 268(27):19923–19926.

Caetano-Anollés et al., (1991) DNA amplification fingerprinting using very short arbitrary oligonucleotide primers. *Bio/Technology* 9:553–557.

Carter, J. R., Franden, M. A., Aebersold, R., and McHenry, C. S. (1993) Identification, isolation, and characterization of the structural gene encoding the δ' subunit of *E. coli* DNA polymerase III holoenzyme. *J. Bacteriol.* 175:3812–3822.

Celis, J. E., ed., *Cell Biology: A Laboratory Handbook*, Vol. I–III (1994).

Chen, M., Pan, Z.-Q., and Hurwitz, J. (1992) Studies of the cloned 37-kDa subunit of activator 1 (replication factor C) of HeLa cells. *Proc. Natl. Acad. Sci. USA* 89(12) :5211–5215.

Cheng, S., Fockler, C., Barnes, W. M., and Higuchi, R., (1994) Effective amplification of long targets from cloned inserts and human genomic DNA. *Proc. Natl. Acad. Sci. USA* 91:5695–5699.

Coligan, J. E., ed., *Current Protocols in Immunology*, Vol, I–III (1994).

Cullman, G., Fien, K., Kobayashi, R., and Stillman, B. (1995) Characterization of the five replication factor C genes of *Saccharomyces cerevesiae. Mol. and Cell. Biol.* 15:4661–4671.

Davis, L. G., *Basic Methods In Molecular Biology*, Elsevier Edit., New York (1986).

Decket et al., (1998) The complete genome of the hyperthermophilic bacterium *Aquifex aeolicus. Nature* 392:353–358.

Dulbecco, R., et al. (1959) Plaque production by the polyoma virus. *Virol.* 8:396–397.

Edge, M. D., et al., (1981) Total synthesis of a human leukocyte interferon gene. *Nature* 292:756.

Flower, A. M. and McHenry, C. S. (1990) The γ subunit of DNA polymerase III holoenzyme of *Escherichia coli* is produced by ribosomal frameshifting. *Proc. Natl. Acad. Sci. USA* 87:3713–3717.

Freshney, R. I., ed., *Animal Cell Culture* (1986).

Gait, M. J., ed., *Oligonucleotide Synthesis* (1984).

Glover, ed., *DNA Cloning: A Practical Approach*, Vol. I & II, MRL Press, Ltd., Oxford, U.K. (1985).

Guenther, B. D. (1996) Structural studies on the DNA replication apparatus: X-ray crystal structure of the δ' subunit of *Escherichia coli* DNA Pol III. Ph.D. Thesis, Rockefeller University.

Guibus, J. M., Kelman, Z., Hurwitz, J., O'Donnell, M., and Kuriyan, J. (1996) Structure of the C-terminal region of p21waf1/cip1 complexed with human PCNA. *Cell* 87:297–306.

Hames, B. D., and Higgins, S. J., eds., *Nucleic Acid Hybridization* (1985).

Harnes, B. D., and Higgins, S. J., eds., *Transcription and Translation* (1984).

Hammerling et al., *Monoclonal Antibodies and T-cell Hybridomas* (1981).

Harlow and Lane, eds., *Antibodies—A Laboratory Manual*, Cold Spring Harbor, N.Y. (1988).

Heath, D. D., Iwama, G. K., and Devlin, R. H., (1993) PCR primed with VNTR core sequences yields species specific patterns and hypervariable probes. *Nucl. Acids Res.* 21(24):5782–5785.

Hughes, Jr., A. J., Bryan, S. K., Chen, H., Moses, R. E., and McHenry, C. S. (1991) *Escherichia coli* DNA polymerase II is stimulated by DNA polymerase III holoenzyme auxiliary subunits. *J. Biol. Chem.* 266:4568–4573.

IRL Press, Publ., *Immobilized Cells and Enzymes* (1986).

Ito, J., and Braithwaite, D., (1991) Compilation and alignment of DNA polymerase sequences. *Nucl. Acids Res.* 19(15):4045–4057 (1991).

Jacks, T., Madhami, H. D., Masiarz, F. R., and Varmus, H. E. (1988) Signals for ribosomal frameshifting in the Rous sarcoma virus gag-pol region. *Cell* 55:447–458.

Jay, E., et al., (1984) Chemical synthesis of a biologically active gene for human immune interferon-gamma. Prospect for site-specific mutagenesis and structure-function studies. *J. Biol. Chem.* 259:6311–6317.

Kelman Z., and O'Donnell, M. (1995) DNA Polymerase III holoenzyme: Structure and function of a chromosomal replicating machine, *Annu. Rev. Biochem.*, 64:171–200.

Kelman, Z., and O'Donnell, M. (1994) DNA replication: enzymology and mechanisms. *Current Opinions in Genetics and Development* 4:185–195.

Kennett et al., *Monoclonal Antibodies* (1980).

Kong, X. -P., Onrust, R., O'Donnell, M., and Kuriyan, J. (1992). Three dimensional structure of the β subunit of *Escherichia coli* DNA polymerase III holoenzyme: a sliding DNA clamp. *Cell* 69:425–437.

Kornberg, A., and Baker, T. (1992). *DNA Replication*, second edition. (New York:W. H. Freeman and Company), pp. 165–194.

Krishna, T. S., Kong, X.-P., Gary, S., Burgers, P. M., and Kuriyan, J. (1994 ) Crystal structure of the eukaryotic DNA polymerase processivity factor PCNA. Cell 79(7): 1233–1243.

Kuriyan, J. and O'Donnell, M. (1993) Sliding clamps of DNA polymerases. *J. Mol. Biol.* 234:915–925.

Larsen, B., Wills, N. M., Gesteland, R. F., and Atkins, J. F. (1994) rRNA-mRNA base pairing stimulates a programmed −1 ribosomal frameshift. *J. Bact.* 176: 6842–6851.

Lin, J. J., and Kuo, J. (1995) *Focus* 17(2):66–70.

Linn, S. (1991) How many pols does it take to replicate nuclear DNA? *Cell* 66:185–187.

Lee, S. H. and Walker, J. R. (1987) *Escherichia coli* dnaX product, the τ subunit of DNA polymerase III, is a multifunctional protein with single-stranded DNA-dependent ATPase activity. *Proc. Natl. Acad. Sci. USA* 84:2713–2717.

Low, R. L., Rashbaum, S. A., and Cozzarelli, N. R. (1976) Purification and characterization of DNA polymerase III from *Bacillus subtilis. J. Biol. Chem.*, 251:1311–1325.

Maki, H., Maki, S., and Kornberg, A. (1988) DNA polymerase III holoenzyme of *Escherichia coli IV.* The holoenzyme is an asymmetric dimer with twin active sites. *J. Biol. Chem.* 263:6570–6578.

Maniatis, T., Fritsch, E. F., and Sambrook, J. (1992) *Molecular Cloning: A Laboratory Manual*, Cold Spring Harbor Laboratory, Cold Spring Harbor, N.Y.

McHenry, C. S. (1991) DNA Polymerase III Holoenzyme. *J. Biol. Chem.*, 266:19127–19130.

McHenry, C. S., and Crow, W. (1979) DNA polymerase III of *Escherichia coli*: Purification and identification of Subunits. *J. Biol. Chem.* 254(5):1748–1753.

McHenry, C. S. (1982) Purification and characterization of DNA polymerase III'. Identification of τ as a subunit of the DNA polymerase III holoenzyme. *J. Biol. Chem.* 257:2657–2663.

Moarefi, I., Jeruzalmi, D., Turner, J., O'Donnell, M., and Kuriyan, J. (2000) Crystal structure of the DNA polymerase processivity factor of T4 bacteriophage. *J. Molec. Biol.*, 296:1215–1223.

Naktinis, V., Turner, J., and O'Donnell, M. (1996) A molecular switch in a replication machine defined by an internal competition for protein rings. *Cell* 84(1):137–145.

Naktinis, V., Onrust, R., Fang, L., O'Donnell, M. (1995) Assembly of a chromosomal replication machine: two DNA polymerases, a clamp loader, and sliding clamps in one holoenzyme particle. II. Intermediate complex between the clamp loader and its clamp. *J. Biol. Chem.* 270:13358–13365.

Nambair, K. P., et al., (1984) Total synthesis and cloning of a gene coding for the ribonuclease S protein. *Science* 223:1299–1300.

Nelson, K. E., et al., (1999) Evidence for lateral gene transfer between Archaea and bacteria from genome sequence of *Thermotoga maritima. Nature* 399:323–329.

Noren, C. J., et al., (1989) A general method for site-specific incorporation of unnatural amino acids into proteins. *Science* 244:182–188.

O'Day, C. L., Burgers, P. M., Taylor, J. S. (1992) PCNA-induced DNA synthesis past cis-syn and trans-syn-I thymine dimers by calf thymus DNA polymerase delta in vitro. *Nucl. Acids Res.* 20(20):5403–6.

O'Donnell, M., (1987) Accessory proteins bind a primed template and Mediate Rapid Cycling of DNA polymerase III Holoenzyme from *E. coli. J. Biol. Chem.* 262:16558–16565.

O'Donnell, M., Kuriyan, J., Kong, X-P., Stukenberg, P. T. and Onrust, R. (1992) The sliding clamp of DNA polymerase III holoenzyme encircles DNA. *Molec. Biol. Cell* 3:953–957.

O'Donnell, M., Onrust, R., Dean, F. B., Chen, M., and Hurwitz, J. (1993) Homology in accessory proteins of replicative polymerases-*E. coli* to humans. *Nucl. Acids Res.* 21:1–3.

Onrust, R., Finkelstein, J., Turner, J., Naktinis, V., and O'Donnell, M. (1995) Assembly of a chromosomal replication machine: two DNA polymerases, a clamp loader and sliding clamps in one holoenzyme particle. III) Interface between two polymerases and the clamp loader. *J. Biol. Chem.* 270:13366–13377.

Onrust, R. and O'Donnell, M. (1993) DNA polymerase III accessory proteins. I) holA and holB encoding δ and δ'. *J. Biol. Chem.* 268:11758–11765.

Onrust, R., Stukenberg, P. T., and O'Donnell, M. (1991) Analysis of the ATPase subassembly which initiates processive DNA synthesis by DNA polymerase III holoenzyme. *J. Biol. Chem.* 266:21681–21686.

Oshima, T., and Imahori, K, (1974) Description of *Thermus thermophilus* (Yoshida and Oshima) comb-nov, a nonsporulating bacterium from a Japanese spa. *Int. J. Syst. Bacteriol.* 24(1):102–112.

Pacitti, D. F., Barnes, M. H., Li, D. H., and Brown, N. C. (1995) Characterization and overexpression of the gene encoding *Staphylococcus aureus* DNA polymerase III. *Gene*, 1165:51–56.

Perbal, B., *A Practical Guide to Molecular Cloning* (1984).

Perrino, F. W., and Loeb, L. A. (1990) Hydrolysis of 3'-terminal mispairs in vitro by the 3'5' exonuclease of DNA polymerase δ permits subsequent extension by DNA polymerase α. *Biochem.* 29:5226–5231.

Reddy et al., (1993) Assembly of a functional replication complex without ATP hydrolysis: a direct interaction of bacteriophage T4 gp45 with T4 DNA polymerase. *Proc. Natl. Acad. Sci. USA* 90(8):3211–3215.

Rowen, L., and Kornberg, A. (1978) Primase, the DnaG protein of *Escherichia coli*. An enzyme which starts DNA chains. *J. Biol. Chem.* 253:758–764.

Ruttimann, C., Cotoras, M., Zaldivar, J., and Vicuna, R. (1985) DNA polymerases from the extremely thermophilic bacterium *Thermus thermophilus* HB-8. *European J. Biochem.* 149:41–46.

Sambrook et al., *Molecular Cloning: A Laboratory Manual* (1989).

Sanger, F., and Coulson, A. R., (1975) A rapid method for determining sequences in DNA by primed synthesis with DNA polymerase. *J. Mol. Biol.* 94:441–448.

Sanger, F., et al., (1977) DNA sequencing with chain-terminating inhibitors. *Proc. Natl. Acad. Sci. USA* 74:5463–5467

Schreier, M., et al., *Hybridoma Techniques* (1980).

Studwell-Vaughan, P. S. and O'Donnell, M. (1991) Constitution of the twin polymerase of DNA polymerase III holoenzyme. *J. Biol. Chem.* 266:19833–19841.

Studwell-Vaughan, P. S. and O'Donnell, M. (1990) Processive replication is contingent on the exonuclease subunit of DNA polymerase III holoenzyme. *J. Biol. Chem.* 265(2):1171–1178.

Stukenberg, P. T., Studwell-Vaughan, P. S., and O'Donnell, M. (1991) Mechanism of the sliding β-clamp of DNA polymerase III holoenzyme. *J. Biol. Chem.* 266:11328–11334.

Sugino, A. (1995) Yeast DNA polymerases and their role at the replication fork. Elsevier Science Ltd., 319–323.

Tabor, S. and Richardson, C. C. (1995) A single residue in DNA polymerases of the *Escherichia coli* DNA polymerase I family is critical for distinguishing between deoxy- and dideoxyribonucleotides. *Proc. Natl. Acad. Sci. USA*, 92(14):6339–6343.

Tan, C. K., Castillo, C., So, A. G., Downey, K. M. (1986) An auxiliary protein for DNA polymerase-delta from fetal calf thymus. *J. Biol. Chem.* 261(26):12310–6.

Towbin, H., Staehelin, T., Gordon, J. (1979) Electrophoretic transfer of proteins from polyacrylamide gels to nitrocellulose sheets: procedure and some applications. *Proc. Natl. Acad. Sci. USA* 76(9):4350–4354.

Tsuchihashi, Z., and Kornberg, A. (1989) ATP interactions of the tau and gamma subunits of DNA polymerase III holoenzyme of *Escherichia coli. J. Biol. Chem.* 264:17790–95.

Tsuchihashi, Z. and Kornberg, A. (1990) Translational frameshifting generates the γ subunit of DNA polymerase III holoenzyme. *Proc. Natl. Acad. Sci. USA* 87:2516–2520.

Tsuchihashi, Z., and Brown, P. O. (1992) Sequence requirements for efficient translational frameshifting in the *Escherichia coli* dnaX gene and the role of an unstable interaction between tRNALys and an AAG lysine codon. *Genes and Dev.* 6:511–519.

Turner, J., and O'Donnell, M. (1995) Cycling of *Escherichia coli* DNA polymerase III from one sliding clamp to another: model for lagging strand. *Methods Enzymol.* 262:442–449.

Vos, P., et al., (1995) AFLP: a new technique for DNA fingerprinting. *Nucl. Acids Res.* 23(21):4407–4414.

Weiss, R. B., Dunn, D. M., Atkins, J. F., and Gesteland, R. F., (1987) Slippery runs, shifty stops, backward steps, and forward hops: −2, −1, +2, +5 and +6 ribosomal frameshifting. in Cold Spring Harbor Symposia on Quantitative Biology 52: 687–693.

Welsh, J., and McClelland, M., (1990) Fingerprinting genomes using PCR with arbitrary primers. *Nucl. Acids Res.* 18(24):7213–7218.

Wickner, W., and Kornberg, A., (1974) A holoenzyme form of DNA Polymerase III. Isolation and Properties. *J. Biol. Chem.* 249(19):6244–6249.

Williams, J. G., et al., (1990) DNA polymorphisms amplified by arbitrary primers are 4: useful as genetic markers. *Nucl. Acids Res.* 18(22):6531–6535.

Yin, K-C., Blinkowa, A., and Walker, J. R. (1986) Nucleotide sequence of the Escherichia replication gene dnaZX. *Nuc. Acids. Res.* 14:6541–6549.

Young, M. C., Reddy, M. K., and von Hippel, P. H. (1992) Structure and function of the bacteriophage T4 DNA polymerase holoenzyme. *Biochem.*, 31:8675–8690.

Yuzhakov, A., Turner, J. and O'Donnell, M. (1996) Replisome assembly reveals the basis for asymmetric function in leading and lagging strand replication. *Cell* 86:877–886.

U.S. Pat. No. 5,668,004 to O'Donnell.

U.S. Pat. No. 5,583,026 to O'Donnell.

U.S. Pat. No. 5,545,552 to Mathur.
U.S. Pat. No. 5,498,523 to Tabor et al.
U.S. Pat. No. 5,455,166 to Walker.
U.S. Pat. No. 5,409,818 to Davey et al.
U.S. Pat. No. 5,374,553 to Gelfand et al.
U.S. Pat. No. 5,352,778 to Comb et al.
U.S. Pat. No. 5,322,785 to Comb et al.
U.S. Pat. No. 5,192,674 to Oshima et al.
U.S. Pat. No. 4,962,022 to Fleming et al.
U.S. Pat. No. 4,816,567 to Cabilly et al.
U.S. Pat. No. 4,816,397 to Boss et al.
U.S. Pat. No. 4,683,202 to Mullis.
U.S. Pat. No. 4,683,195 to Mullis et al.
U.S. Pat. No. 4,493,890 to Morris.
U.S. Pat. No. 4,493,795 to Nestor et al.
U.S. Pat. No. 4,491,632 to Wands et al.
U.S. Pat. No. 4,472,500 to Milstein et al.
U.S. Pat. No. 4,466,917 to Nussenzweig et al.
U.S. Pat. No. 4,451,570 to Royston et al.
U.S. Pat. No. 4,444,887 to Hoffman.
U.S. Pat. No. 4,427,783 to Newman et al.
U.S. Pat. No. 4,399,121 to Albarella et al.
U.S. Pat. No. 4,342,566 to Theofilopous et al.
U.S. Pat. No. 4,341,761 to Ganfield et al.
WO 96/10640 to Chatterjee et al.
EP 329,822 to Davey et al.
EP 534,858 to Vos et al.

This invention may be embodied in other forms or carried out in other ways without departing from the spirit or essential characteristics thereof The present disclosure is therefore to be considered as in all respects illustrative and not restrictive, the scope of the invention being indicated by the appended claims, and all changes which come within the meaning and range of equivalency are intended to be embraced therein.

What is claimed:

1. An isolated DNA molecule encoding a delta subunit of a DNA polymerase III-type enzyme, the isolated DNA molecule either:

(i) comprising the nucleotide sequence of SEQ ID NO: 157; or (ii) encoding a delta subunit comprising the amino acid sequence of SEQ ID NO: 158.

2. The isolated DNA molecule according to claim 1, wherein the DNA molecule comprises the nucleotide sequence of SEQ ID NO: 157.

3. An expression system comprising an expression vector into which is inserted a heterologous DNA molecule according to claim 1.

4. The expression system according to claim 3, wherein the heterologous DNA molecule is in sense orientation and correct reading frame.

5. A host cell comprising a heterologous DNA molecule according to claim 1.

6. A method of producing a recombinant unit of a DNA polymerase III-type enzyme said method comprising:

transforming a host cell with the DNA molecule according to claim 1 under conditions suitable for expression of the delta subunit, and isolating the delta subunit.

* * * * *